US008835387B2

(12) United States Patent
Chiang et al.

(10) Patent No.: US 8,835,387 B2
(45) Date of Patent: Sep. 16, 2014

(54) HISTIDYL-TRNA SYNTHETASES FOR TREATING AUTOIMMUNE AND INFLAMMATORY DISEASES

(71) Applicants: aTyr Pharma, Inc., San Diego, CA (US); Pangu BioPharma Limited

(72) Inventors: Kyle P. Chiang, Cardiff, CA (US); Elisabeth Gardiner, San Diego, CA (US); Ching-Fun Lau, New Territories (HK); Wing-Sze Lo, Chai Wan (HK); Jeffrey Greve, Berkeley, CA (US); Melissa Ashlock, Mount Vernon, NH (US); John D. Mendlein, Encinitas, CA (US)

(73) Assignees: aTyr Pharma, Inc., San Diego, CA (US); Pangu Biopharma Limited, Hong Kong (CN)

( * ) Notice: Subject to any disclaimer, the term of this patent is extended or adjusted under 35 U.S.C. 154(b) by 0 days.

(21) Appl. No.: 13/769,100

(22) Filed: Feb. 15, 2013

(65) Prior Publication Data

US 2013/0344096 A1    Dec. 26, 2013

Related U.S. Application Data

(60) Provisional application No. 61/725,414, filed on Nov. 12, 2012, provisional application No. 61/655,358, filed on Jun. 4, 2012, provisional application No. 61/599,802, filed on Feb. 16, 2012.

(51) Int. Cl.
| | |
|---|---|
| *A61K 38/00* | (2006.01) |
| *C07K 1/00* | (2006.01) |
| *A61K 38/17* | (2006.01) |
| *C12N 9/00* | (2006.01) |
| *A61K 38/16* | (2006.01) |
| *A61K 48/00* | (2006.01) |

(52) U.S. Cl.
CPC . *C12N 9/93* (2013.01); *A61K 38/17* (2013.01); *A61K 38/16* (2013.01); *A61K 48/00* (2013.01)
USPC .......................................... 514/12.1; 530/350

(58) Field of Classification Search
USPC ..................................... 514/12.1; 424/184.1
See application file for complete search history.

(56) References Cited

U.S. PATENT DOCUMENTS

| | | | |
|---|---|---|---|
| 5,155,214 A | 10/1992 | Baird et al. | |
| 5,484,703 A | 1/1996 | Raben et al. | |
| 5,556,645 A | 9/1996 | Bockman et al. | |
| 5,641,867 A | 6/1997 | Stern et al. | |
| 5,663,066 A | 9/1997 | Raben et al. | |
| 5,981,606 A | 11/1999 | Martin | |
| 6,013,483 A | 1/2000 | Coleman et al. | |
| 6,225,060 B1 | 5/2001 | Clark et al. | |
| 6,228,837 B1 | 5/2001 | Stern et al. | |
| 6,428,960 B1 | 8/2002 | Clark et al. | |
| 6,548,060 B1 | 4/2003 | Kim | |
| 6,743,619 B1 | 6/2004 | Tang et al. | |
| 6,800,286 B1 | 10/2004 | Olwin et al. | |
| 6,812,339 B1 | 11/2004 | Venter et al. | |
| 6,864,226 B1 | 3/2005 | Coleman et al. | |
| 6,875,749 B2 | 4/2005 | Schwarz et al. | |
| 6,903,189 B2 | 6/2005 | Schimmel et al. | |
| 6,916,648 B2 | 7/2005 | Goddard et al. | |
| 7,037,505 B2 | 5/2006 | Kim et al. | |
| 7,045,301 B2 | 5/2006 | Coleman et al. | |
| 7,067,126 B2 | 6/2006 | Schimmel et al. | |
| 7,144,984 B2 | 12/2006 | Schimmel et al. | |
| 7,196,068 B2 | 3/2007 | Kim et al. | |
| 7,273,844 B2 | 9/2007 | Schimmel et al. | |
| 7,282,208 B2 | 10/2007 | Kim | |
| 7,413,885 B2 | 8/2008 | Schimmel et al. | |
| 7,459,529 B2 | 12/2008 | Kim | |
| 7,476,651 B2 | 1/2009 | Schimmel et al. | |
| 7,482,326 B2 | 1/2009 | Coleman et al. | |
| 7,521,215 B2 | 4/2009 | Schimmel et al. | |
| 7,528,106 B2 | 5/2009 | Friedlander et al. | |
| 7,572,452 B2 | 8/2009 | Kim | |
| 7,842,467 B1 | 11/2010 | Heidbrink et al. | |
| 7,901,917 B2 | 3/2011 | Schimmel et al. | |
| 7,902,165 B2 | 3/2011 | Kim | |
| 7,981,426 B2 | 7/2011 | Kim | |
| 8,003,780 B2 | 8/2011 | Kim et al. | |
| 8,014,957 B2 | 9/2011 | Radich et al. | |
| 8,017,593 B2 | 9/2011 | Schimmel et al. | |
| 8,026,088 B2 | 9/2011 | Yang | |

(Continued)

FOREIGN PATENT DOCUMENTS

| | | |
|---|---|---|
| CN | 1341725 | 3/2002 |
| CN | 1341727 | 3/2002 |
| CN | 1352242 | 6/2002 |
| CN | 1352252 | 6/2002 |
| EP | 0307247 | 3/1989 |
| EP | 0893494 | 1/1999 |
| EP | 0893496 | 1/1999 |
| EP | 0897004 | 2/1999 |
| EP | 0575484 | 9/2000 |
| EP | 1275720 | 1/2003 |

(Continued)

OTHER PUBLICATIONS

International Preliminary Report on Patentability for International Application No. PCT/US2009/048915, dated Jan. 5, 2011.
International Search Report and Written Opinion for International Application No. PCT/US2009/048915, mailed Nov. 2, 2009.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
Supplementary European Search Report for European Application No. 10746935, mailed Oct. 26, 2012.

(Continued)

*Primary Examiner* — Maryam Monshipouri

(57) ABSTRACT

The present invention relates generally to compositions and methods comprising histidyl-tRNA synthetase polypeptides or other specific blocking agents for the treatment autoimmune diseases and other inflammatory diseases, including those related to Jo-1 antibodies.

30 Claims, 35 Drawing Sheets

(56) References Cited

U.S. PATENT DOCUMENTS

| | | |
|---|---|---|
| 8,101,566 B2 | 1/2012 | Schimmel et al. |
| 8,148,125 B2 | 4/2012 | Schimmel et al. |
| 8,404,242 B2 | 3/2013 | Zhou et al. |
| 2002/0128187 A1 | 9/2002 | Tang et al. |
| 2002/0160957 A1 | 10/2002 | Stern et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0158400 A1 | 8/2003 | Tang et al. |
| 2003/0165921 A1 | 9/2003 | Tang et al. |
| 2003/0215827 A1 | 11/2003 | Yue et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2005/0119175 A1 | 6/2005 | Kim |
| 2005/0181375 A1 | 8/2005 | Aziz et al. |
| 2005/0196754 A1 | 9/2005 | Drmanac et al. |
| 2006/0024288 A1 | 2/2006 | Glidden |
| 2006/0046250 A1 | 3/2006 | Kim |
| 2006/0078553 A1 | 4/2006 | Glidden |
| 2006/0134663 A1 | 6/2006 | Harkin et al. |
| 2006/0204508 A1 | 9/2006 | Champion et al. |
| 2006/0228715 A1 | 10/2006 | Shiffman et al. |
| 2006/0275794 A1 | 12/2006 | Carrino et al. |
| 2007/0037165 A1 | 2/2007 | Venter et al. |
| 2007/0042392 A1 | 2/2007 | Tang et al. |
| 2007/0048322 A1 | 3/2007 | Schimmel et al. |
| 2007/0054278 A1 | 3/2007 | Cargill |
| 2007/0061916 A1 | 3/2007 | Kovalic et al. |
| 2007/0072175 A1 | 3/2007 | Cooper et al. |
| 2007/0093440 A1 | 4/2007 | Champion et al. |
| 2007/0111238 A1 | 5/2007 | Jamieson et al. |
| 2007/0154931 A1 | 7/2007 | Radich et al. |
| 2009/0221437 A1 | 9/2009 | Harkin et al. |
| 2009/0221794 A1 | 9/2009 | Kim et al. |
| 2009/0227002 A1 | 9/2009 | Schultz et al. |
| 2009/0227662 A1 | 9/2009 | Schimmel et al. |
| 2009/0264453 A1 | 10/2009 | Shiffman et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0041608 A1 | 2/2010 | Kim |
| 2010/0048413 A1 | 2/2010 | Arcus et al. |
| 2010/0092434 A1 | 4/2010 | Belani et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0183924 A1 | 7/2011 | Beck et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0108630 A1 | 5/2013 | Watkins et al. |
| 2013/0202576 A1 | 8/2013 | Greene et al. |
| 2013/0243766 A1 | 9/2013 | Zhou et al. |

FOREIGN PATENT DOCUMENTS

| | | |
|---|---|---|
| EP | 1300468 | 4/2003 |
| EP | 1384486 | 1/2004 |
| EP | 1377305 | 1/2009 |
| EP | 1776138 | 10/2009 |
| EP | 1274834 | 7/2010 |
| KR | 10-2002-0092596 | 12/2002 |
| KR | 101067816 | 9/2011 |
| WO | WO 91/08291 | 6/1991 |
| WO | WO 96/39506 | 12/1996 |
| WO | WO 97/26351 | 7/1997 |
| WO | WO 97/39017 | 10/1997 |
| WO | WO 99/45130 | 9/1999 |
| WO | WO 00/73801 | 12/2000 |
| WO | WO 01/57190 | 8/2001 |
| WO | WO 01/74841 | 10/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 01/95927 | 12/2001 |
| WO | WO 02/055663 | 7/2002 |
| WO | WO 02/059323 | 8/2002 |
| WO | WO 02/067970 | 9/2002 |
| WO | WO 02/068579 | 9/2002 |
| WO | WO 03/009813 | 2/2003 |
| WO | WO 03/080648 | 10/2003 |
| WO | WO 03/094848 | 11/2003 |
| WO | WO 03/094862 | 11/2003 |
| WO | WO 2004/023973 | 3/2004 |
| WO | WO 2004/030615 | 4/2004 |
| WO | WO 2004/060262 | 7/2004 |
| WO | WO 2004/063355 | 7/2004 |
| WO | WO 2004/064863 | 8/2004 |
| WO | WO 2005/019258 | 3/2005 |
| WO | WO 2005/073250 | 8/2005 |
| WO | WO 2005/087953 | 9/2005 |
| WO | WO 2005/102395 | 11/2005 |
| WO | WO 2005/113812 | 12/2005 |
| WO | WO 2005/117954 | 12/2005 |
| WO | WO 2006/016217 | 2/2006 |
| WO | WO 2006/048219 | 5/2006 |
| WO | WO 2006/057500 | 6/2006 |
| WO | WO 2006/083087 | 8/2006 |
| WO | WO 2007/064941 | 6/2007 |
| WO | WO 2007/083853 | 7/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/094012 | 8/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2012/021249 | 2/2012 |
| WO | WO 2012/149247 | 11/2012 |
| WO | WO 2012/149252 | 11/2012 |
| WO | WO 2012/149259 | 11/2012 |
| WO | WO 2012/149265 | 11/2012 |
| WO | WO 2012/149282 | 11/2012 |
| WO | WO 2012/149301 | 11/2012 |
| WO | WO 2012/149405 | 11/2012 |
| WO | WO 2012/149411 | 11/2012 |
| WO | WO 2013/036293 | 3/2013 |
| WO | WO 2013/036294 | 3/2013 |
| WO | WO 2013/036295 | 3/2013 |
| WO | WO 2013/036296 | 3/2013 |
| WO | WO 2013/036299 | 3/2013 |
| WO | WO 2013/036300 | 3/2013 |

(56) References Cited

FOREIGN PATENT DOCUMENTS

| WO | WO 2013/036301 | 3/2013 |
|----|----------------|--------|
| WO | WO 2013/036302 | 3/2013 |

OTHER PUBLICATIONS

International Preliminary Report on Patentability for International Application No. PCT/US2010/025642, dated Aug. 30, 2011.
International Search Report and Written Opinion for International Application No. PCT/US2010/025642, mailed Oct. 29, 2010.
Supplementary European Search Report for European Application No. 10753998, mailed Nov. 21, 2012.
Office Action for U.S. Appl. No. 12/725,272,mailed Jul. 13, 2012.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
Office Action for U.S. Appl. No. 13/766,659, mailed Nov. 19, 2013.
Office Action for U.S. Appl. No. 13/766,659, mailed Sep. 16, 2013.
International Search Report and Written Opinion for International Application No. PCT/US2010/059964, mailed Aug. 25, 2011.
Communication Pursuant to Article 94(3) EPC for European Application No. 10793402.8, mailed Mar. 27, 2013.
International Preliminary Report on Patentability for International Application No. PCT/US2010/059963, dated Jun. 12, 2012.
International Search Report and Written Opinion for International Application No. PCT/US2010/059963, mailed May 12, 2011.
International Search Report and Written Opinion for International Application No. PCT/US2011/000210, mailed Aug. 12, 2011.
International Preliminary Report on Patentabiltity for International Application No. PCT/US2011/000210, dated Aug. 7, 2012.
International Search Report and Written Opinion for International Application No. PCT/US2011/043758, mailed on Mar. 2, 2012.
International Preliminary Report on Patentability for International Application No. PCT/US2011/043758, dated Jan. 15, 2013.
International Search Report and Written Opinion for International Application No. PCT/US2012/068282, mailed on Apr. 1, 2013.
International Search Report and Written Opinion for International Application No. PCT/US2012/068296, mailed on Apr. 19, 2013.
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Blechyden, L.M. et al., "Sequence and polymorphism analysis of the murine gene encoding histidyl-tRNA synthetase," Gene, 178:151-156 (1996).
Blechyden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Casciola-Rosen, L., et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Ewalt, K. L. et al., "Activation of Angiogenic Signaling Pathways by Two Human tRNA Synthetases," Biochemistry, 41(45):13344-13349 (2002).
Felden, B. et al., "Resected RNA pseudoknots and their recognition by histidyl-tRNA synthetase," Proc. Natl. Acad. Sci. USA, 95:10431-10436 (1998).
Francklyn, C. et al., "Histidyl-tRNA Synthetase," Eurekah Bioscience, 1(3):265-277 (2005).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA984229, published May 27, 1998.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK293531, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. BE872272, published Jan. 13, 2011.
GenBank Accession No. BF791754, published Jan. 13, 2011.
GenBank Accession No. BG108830, published Jun. 1, 2001.
GenBank Accession No. BP268250, published Feb. 10, 2011.
GenBank Accession No. DA083923, published Feb. 17, 2011.
GenBank Accession No. DB146646, published Feb. 16, 2011.
GenBank Accession No. Q7QD89, *Anopheles gambiae* Sequence Committee, submitted Apr. 2002, [Retrieved from the Internet Apr. 24, 2007], <URL: http://www.ncbi.nlm.nih.gov/entrez/viewerfcgi?db=protein&val=74803944>.
GenBank Accession No. Q9VV60, published May 1, 2000.
GenBank Accession No. Z11518, published Oct. 7, 2008.
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of *Bacillus stearothermophilus* Tyrosyl-tRNA Synthetase," Structure, 10:311-317 (2002).
Guo, M. et al., "Functional expansion of human tRNA synthetases achieved by structural inventions," FEBS Letters, 584(2):434-442 (2010).
Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).

(56) References Cited

OTHER PUBLICATIONS

Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11):4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26 (4):250-255 (2004).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into Human Aminoacyl-tRNA Synthetases as Autoantigens in Idiopathic Inflammatory Myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29:174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids, " Proc. Nat. Acad. Sci., 103(27):10180-10185 (2006).
Martin, A. et al., "Epitope studies indicate that histidyl-tRNA synthetase is a stimulating antigen in idiopathic myositis," The FASEB Journal, 9:1226-1233 (1995).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Miller, F. W. et al., "The role of an autoantigen, histidyl-tRNA synthetase, in the induction and maintenance of autoimmunity," Proc. Natl. Acad. Sci. USA, 87:9933-9937 (1990).

Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Mozaffar, T. et al., "Myopathy with anti-Jo-1 antibodies: pathology in perimysium and neighbouring muscle fibres," J. Neurol. Neurosurg. Psychiatry, 68:472-478 (2000).
Nackley, A. G. et al., "Human Caechol-O-Methytransferase haplotypes modulate protein expression by altering mRNA secondary structure," Science, 314:1930-1933 (2006).
Ngo, J. T. et al., "Computational complexity, protein structure prediction, and the Levinthal paradox," in the Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)", Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, C-K. et al., "Development of antisynthetase syndrome in a patient with rheumatoid arthritis," Rheumatol Int, 31:529-532 (2011).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Puffenberger, E. G. et al., "Genetic Mapping and Exome Sequencing Identify Variants Associated with Five Novel Diseases," PLoS, 7(1):e28936 (2012).
Quesniaux, V. F.J. et al., "Hematopoiesis, including lymphocyte developmet and maturation," Principles of Immunopharmacology, pp. 3-17, 2005.
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39): 24277-24283 (1994).
Reed, V. S. et al., "Characterization of a Novel N-terminal Peptide in Human Aspartyl-tRNA Synthetase," Journal of Biological Chemistry, 269(52):32937-32941 (1994).
Ribas de Pouplana, L. et al., "Not Just Because it is There: Aminoacyl-tRNA Synthetases Gain Control of the Cell," Molecular Cell, 30:3-4 (2008).
Richardson, R. M. et al., "Role of the cytoplasmic tails of CXCR1 and CXCR2 in mediating leukocyte migration, activation, and regulation," Journal of Immunology, 170(6):2904-2911 (2003).
Sauna, Z. E. et al., "Silent polymorhisms speak: How they affect pharmacogenomics and the treatment of cancer," Cancer Res., 67(20):9609-9612 (2007).
Schmutz, J. et al., "The DNA sequence and comparative analysis of human chromosome 5," Nature, 431:268-274 (2004).
Seburn, K. L. et al., "An active dominant mutation of glycyl-tRNA synthetase causes neuropathy in a Charcot-Marie-Tooth 2D mouse model," Neuron, 51(6):715-726 (2006).

(56) References Cited

OTHER PUBLICATIONS

Sen, S. et al., "Developments in directed evolution for improving enzyme functions," Appl. Biochem. Biotechnol., 143:212-223 (2007).
Shiba, K., "Intron positions delineate the evolutionary path of a pervasively appended peptide in five human aminoacyl-tRNA synthetases," Journal of Molecular Evolution, 55:727-733 (2002).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Sultan, S. M. et al., "Re-classifiyng myositis", Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," Proc. Natl. Acad. Sci., 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
Xie, W. et al., "Long-range structural effects of a Charcot-Marie-Tooth disease-causing mutation in human glycyl-tRNA synthetase," PNAS, 104(24):9976-9981 (2007).
Xu, Z. et al., "Internally Deleted Human tRNA Synthetase Suggest Evolutionary Pressure for Repurposing," Structure, 20(9):1470-1477 (2012).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14:1323-1333 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal Structure of Human Tryptophanyl-tRNA Synthetase Catalytic Fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the $42^{nd}$ Interscience Conference on Antimicrobial Agents and Chemotherapy, San Diego, California, Sep. 27-30, 2002, Session 156(B), p. 55.

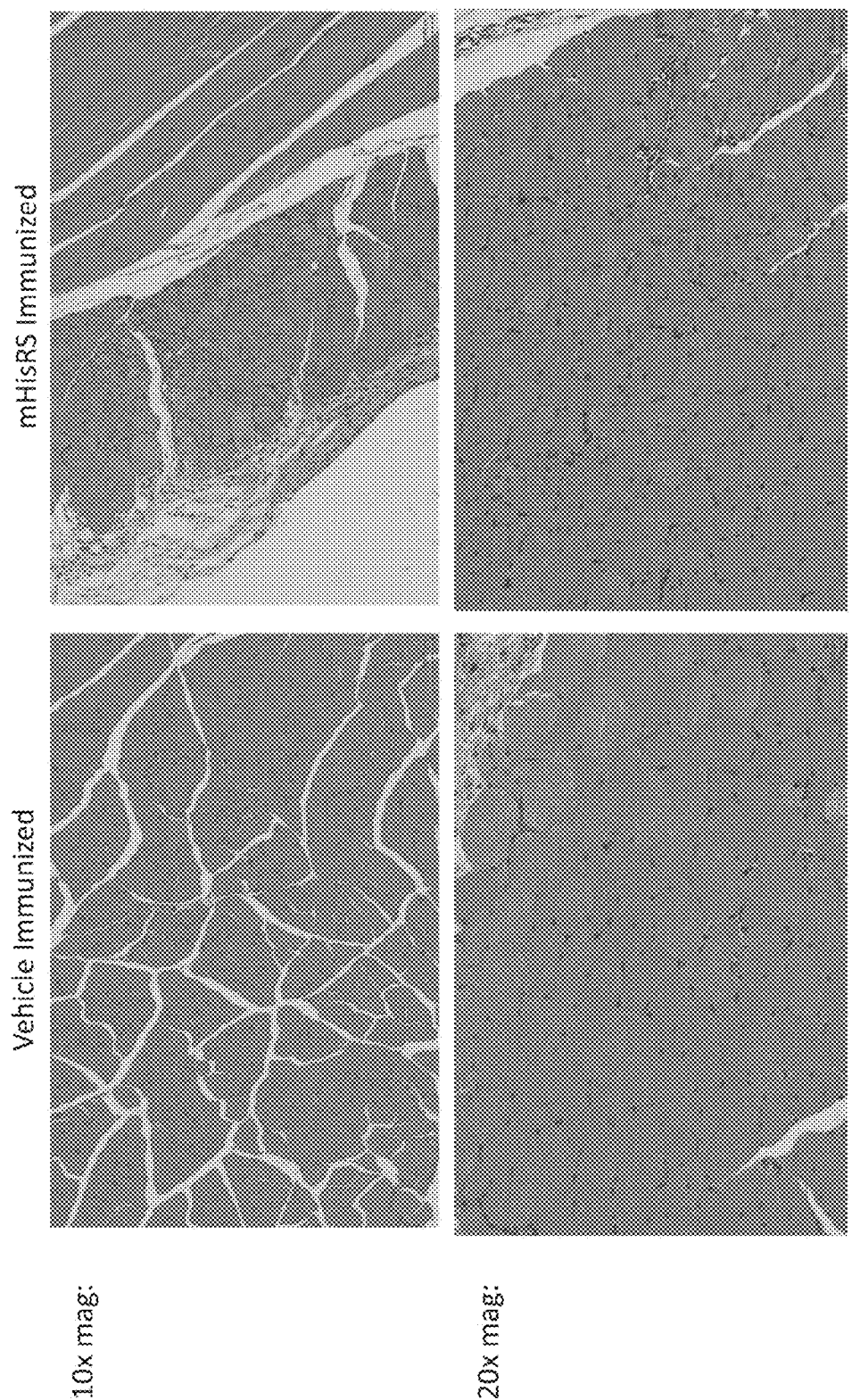

HISTIDYL-TRNA SYNTHETASES FOR TREATING AUTOIMMUNE AND INFLAMMATORY DISEASES

CROSS-REFERENCE TO RELATED APPLICATIONS

This application claims benefit under 35 U.S.C. §119(e) of U.S. Application No. 61/725,414, filed Nov. 12, 2012; U.S. Application No. 61/655,358, filed Jun. 4, 2012; and U.S. Application No. 61/599,802, filed Feb. 16, 2012, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_110_03US_ST25.txt. The text file is about 258 KB, was created on Feb. 15, 2013, and is being submitted electronically via EFS-Web.

BACKGROUND

1. Technical Field

Embodiments of the present invention relate generally to histidyl-tRNA synthetase polypeptides having improved characteristics, compositions comprising the HRS polypeptides, and related methods of using the HRS polypeptides or compositions to treat various inflammatory and autoimmune diseases, including methods of treating anti-Jo-1 antibody-related inflammatory and autoimmune diseases.

2. Description of the Related Art

Physiocrines are generally small, naturally-occurring, protein domains found in the aminoacyl-tRNA synthetases (AARSs) gene family of higher organisms, which are not required for the well-established role of aminoacyl-tRNA synthetases in protein synthesis. Until the Physiocrine paradigm was discovered, aminoacyl-tRNA synthetases, a family of about 20 enzymes, were known only for their ubiquitous expression in all living cells, and their essential role in the process of protein synthesis. More recent scientific findings however now suggest that aminoacyl-tRNA synthetases possess additional roles beyond protein synthesis and in fact have evolved in multicellular organisms to play important homeostatic roles in tissue physiology and disease.

Evidence for the existence of the non-canonical function of AARSs includes well defined sequence comparisons that establish that during the evolution from simple unicellular organisms to more complex life forms, AARSs have evolved to be more structurally complex through the addition of appended domains, without losing the ability to facilitate protein synthesis.

Consistent with this hypothesis, a rich and diverse set of expanded functions for AARSs have been found in higher eukaryotes, and in particular for human tRNA synthetases. This data, which is based both on the direct analysis of individual domains, as well as the discovery of mutations in genes for tRNA synthetases that are causally linked to disease, but do not affect aminoacylation or protein synthesis activity, suggests that these newly appended domains, or Physiocrines, are central to the newly acquired non-canonical functions of AARSs.

Additionally, there is now increasing recognition that specific tRNA synthetases such as histidyl-tRNA synthetase (HARS, HRS, or HisRS) can be released or secreted from living cells and can provide important locally acting signals with, inter alia, immunomodulatory, chemotactic, and angiogenic properties. Direct confirmation of the role of AARS as extracellular signaling molecules has been obtained through studies showing the secretion and extracellular release of specific tRNA synthetases, as well as the direct demonstration that the addition of fragments of the tRNA synthetases comprising the newly appended domains (Physiocrines), but not other fragments lacking these domains, are active in a range of extracellular signaling pathways. These Physiocrines, including those derived from HRS, represent a new and previously untapped opportunity to develop new first in class therapeutic proteins to treat human disease.

Recent studies have also established that some tRNA synthetases include novel regulatory genetic elements, including ALU elements (Rudinger-Thirion et al., *PNAS USA*. 108(40): E794-E802, 2011) that provide for increased cell type specific expression, or alternative splicing of specific tRNA synthetases in specific tissues, or in the context of specific diseases. Moreover some Physiocrines are proteolytically produced in response to particular stimuli in a cell type specific fashion. Consistent with the cell type specific over expression and extracellular release of Physiocrines, several autoimmune diseases, (generally referred to as ant-synthetase syndromes) are associated with the production of antibodies to a defined group of tRNA synthetases (Tzioufas Orphanet (2001) 1-5; Park et al., *Rheumatol. Int.* 31:529-532, 2011).

Autoimmune disorders arise when the immune system reacts against its own tissues. Autoimmune diseases are often classified on the basis of whether a single organ or tissue is involved or whether multiple organs or tissues are involved. Generalized or systemic autoimmune diseases, such as systemic lupus erythematosus (SLE), characterized by the involvement of multiple organs and tissues, are often associated with the presence of autoantibodies to fundamental cellular components. Other autoimmune diseases are characterized by autoantibodies to antigens associated with a single organ or tissue.

Systemic autoimmune diseases are typically characterized by the presence of autoantibodies. Some of the autoantibodies associated with the particular disease may be disease specific and others may be common to many autoimmune diseases. For example, SLE, which is a prototypical immune disorder, is characterized by the presence of autoantibodies that are detectable in other autoimmune disease, such as anti-single-strand DNA antibodies, anti-histones antibodies, and anti-ribonuclear particle (RNP) antibodies, and also by the presence of autoantibodies that are SLE-specific, such as the anti-double-stranded DNA antibodies. Other systemic autoimmune disorders, such as rheumatoid arthritis and (idiopathic) inflammatory myopathies, are also characterized by the presence of autoantibodies in the sera of patients that react with fundamental nuclear and cytoplasmic intracellular components. As with SLE, some of these autoantibodies are associated with other autoimmune disorders and some are specifically associated with autoimmune myositis.

The (idiopathic) inflammatory myopathies polymyositis, dermatomyositis and the related disorders, such as polymyositis-scleroderma overlap, are inflammatory myopathies that are characterized by chronic muscle inflammation and proximal muscle weakness. The muscle inflammation causes muscle tenderness, muscle weakness, and ultimately muscle atrophy and fibrosis as described by Plotz et al., *Annals of Internal Med.* 111:143-157, 1989; and Wallace et al., *J. Musculoskelat Med.* 27 (12) 470-479, 2010. Also associated with the muscle inflammation are elevated serum levels of aldolase, creatine kinase, transaminases (such as alanine aminotransferase and aspartate aminotransferase) and lactic dehydrogenase. Other systems besides muscle can be affected by these conditions, resulting in arthritis, Raynaud's phenomenon, and interstitial lung disease. Clinically, polymyositis and dermatomyositis are distinguished by the presence of a characteristic rash in patients with dermatomyositis. Differences in the myositis of these conditions can be distinguished in some studies of muscle pathology.

Interstitial lung disease (ILD) comprises a heterogeneous group of disorders in which fibrosis and inflammation occur within alveolar walls or in the loose tissue surrounding peribronchovascular sheaths, interlobular septa and the visceral pleura. Different forms of ILD are known which comprise, or are associated with, various autoimmune diseases in addition to myositis, including for example, hypersensitivity pneumonitis, scleroderma, systemic lupus erythematosus, rheumatoid arthritis, Churg-Strauss syndrome, Wegener's granulomatosis, and Good-pasture Syndrome.

Inflammatory muscle disease (IMD) and interstitial lung disease (ILD) are serious chronic potentially life threatening autoimmune diseases, for which the current standard of care includes non-specific anti-inflammatory drugs such as corticosteroids with the potential for important side effects. The cause of the on-set of these diseases has not yet been established, although autoantibodies can be detected in about 90% of patients with polymyositis and dermatomyositis according to Reichlin and Arnett, *Arthritis and Rheum.* 27:1150-1156, 1984. Sera from about 60% of these patients form precipitates with bovine thymus or human spleen extracts on Ouchterlony immunodiffusion (ID), while sera from about 80% of these patients stain tissue culture substrates, such as HEp-2 cells, by indirect immunofluorescence (IIF) (Targoff and Reichlin, *Arthritis and Rheum.* 28:796-803, 1985; Nishikai and Reichlin, *Arthritis and Rheum.* 23:881-888, 1980; and Reichlin et al., *J. Clin. Immunol.* 4:40-44, 1984). There are numerous precipitating autoantibody specificities in myositis patients, but each individual antibody specificity occurs in only a fraction of the patients.

Many autoantibodies associated with myositis or myositis-overlap syndrome have been defined and in some cases the antibodies have been identified (See U.S. Pat. No. 6,610,823, Antigens associated with polymyositis and with dermatomyositis). These include antibodies that are present in other disorders and also disease-specific antibodies as described by Targoff and Reichlin, *Mt. Sinai J. of Med.* 55:487-493, 1988.

For example, a group of myositis-associated autoantibodies have been identified which are directed at cytoplasmic proteins that are related to tRNA and protein synthesis, particularly aminoacyl-tRNA synthetases. These include anti-Jo-1, which is directed against histidyl-tRNA synthetase and is the most common autoantibody associated with myositis autoimmune disorders (about 20 to 40% of such patients according to Nishikai and Reichlin, *Arthritis Rheum.* 23:881-888, 1980); anti-PL-7, which is directed against threonyl-tRNA synthetase; anti-PL-12, which is directed against alanyl-tRNA synthetase, anti-OJ, which is directed against isoleucyl-tRNA synthetase, anti-EJ, which is directed against glycyl-tRNA synthetase, anti-KS which is directed against asparginyl-tRNA synthetase (see generally, Targoff, *Curr. Opin. Rheumatol.* 12 475-481, 2000) and against phenylalanine-tRNA synthetase (Betteridge et al., *Rheumat.* 46 1005-1008, 2007). A characteristic group of features is often associated with anti-synthetases (Love et al., *Medicine.* 70:360-374, 1991).

Anti-U1 RNP, which is frequently found in patients with SLE, may also be found in mixed connective tissue disease, overlap syndromes involving myositis, or in some cases of myositis alone. This antibody reacts with proteins that are uniquely present on the U1 small nuclear ribonucleoprotein, one of the nuclear RNPs that are involved in splicing mRNA. Autoantibodies that are associated with other conditions are sometimes found in patients with overlap syndrome such as anti-Sm, anti-Ro/SSA and anti-La/SSB. Anti-Ku has been found in myositis-scleroderma overlap syndrome and in SLE. The Ku antigen is a DNA binding protein complex with two polypeptide components, both of which have been cloned. Anti-Jo-1 and other anti-synthetases are disease-specific. Other myositis-associated antibodies are anti-PM-Scl, which is present in about 5-10% of myositis patients, many of whom have polymyositis-scleroderma overlap, and anti-Mi-2, which is present in about 8% of myositis patients, almost exclusively in dermatomyositis. Anti-Mi-2 is found in high titer in about 20% of all dermatomyositis patients and in low titer, by ELISA only, in less than 5% of polymyositis patients (Targoff and Reichlin, *Mt. Sinai J. of Med.* 55:487-493, 1988).

Typically patients with inflammatory muscle disease (IMD) and interstitial lung disease (ILD) present when relatively young and in otherwise in good health, unfortunately in a sub set of patients disease progression can result in significant disability and high morbidity. Moreover currently there are no drugs specifically approved for the treatment of the general population of IMD and ILD. The current standard of care, is to administer non-specific anti-inflammatory and immune modulatory drugs such as methotrexate or azathioprine, and if symptoms don't abate, cyclosporine (Wallace et al., *J. Musculoskelat Med.* 27:470-479, 2010). These drugs carry a substantive risk of side effects that can be severe with chronic administration. In severe progressive disease, individuals may be treated with intravenous immune globulin (IVIG). The burden and cost of care of treating patients with IVIG is high (as much as $10,000 per patient per monthly treatment), and a significant fraction of patients fail treatment and die.

Accordingly there remains a significant unmet need for improved methods of treatment of inflammatory muscle disease and related conditions that are both therapeutically and cost effective.

BRIEF DESCRIPTION OF THE DRAWINGS

FIG. 24B shows the results for MMP3, and FIG. 24C shows the results for MMP9.

FIGS. 27A-27B show the effects of immunization with full-length mouse HRS (mHRS) in SJL/J mice. These mice have an in-frame deletion of 171 bp in the 3' splice junction of exon 45 of dysferlin and develop spontaneous myopathy that is associated with muscle inflammation. The mice provide a genetic model of human dysferlin-deficient myopathies, such as Limb Girdle Muscular Dystrophy type 2B (LGMD2B). FIG. 27A shows that SJL/J mice immunized with mHisRS subcutaneously generated a robust antibody response to full-length HisRS. As shown in FIG. 27B, muscle tissue from HisRS-immunized mice showed regions of cellular infiltration and myositis, and consistent with this histopathology, two immunized mice displayed signs of myositis.

FIG. 28A shows that there were two thermal transitions for full-length HRS upon incubation at pH 7-7.5; the first transition occurred at 48° C. as indicated by the arrow, and the main transition occurred at ~54° C. FIG. 28B shows the thermal stability or melting temperature of HRS(1-506) over a range of concentrations of histidine buffer. The results demonstrate that the histidine buffer is capable of significantly stabilizing the conformation of HRS polypeptides such as HRS(1-506).

BRIEF SUMMARY OF THE INVENTION

Figure 1:
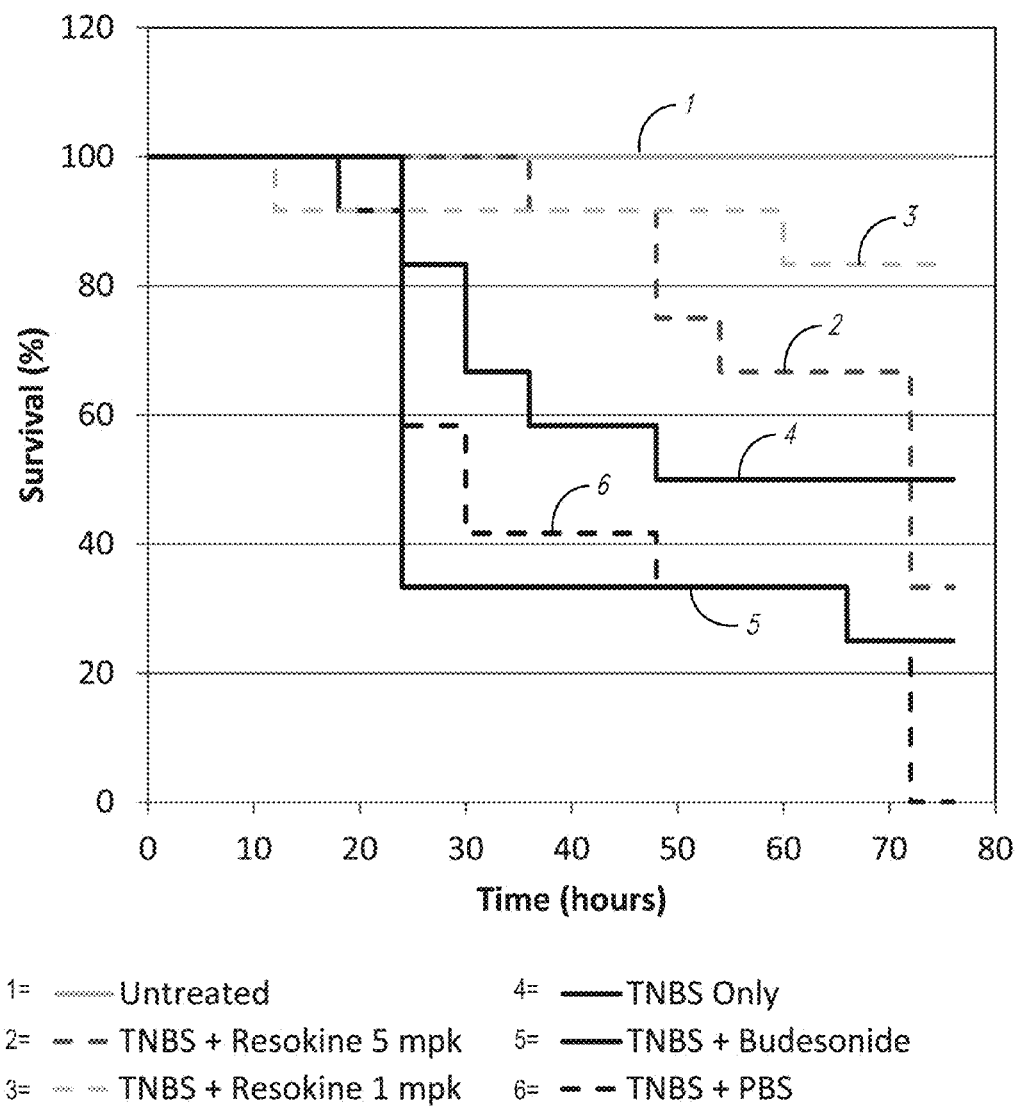
FIG. 1 shows the potential anti-inflammatory properties of exemplary HRS derived polypeptides in a TNBS induced model of colitis. Studies were performed in male BDF-1 mice, with 12 mice/group; TNBS and Budesonide was added at 5 mg/kg to the water. Resokine (HisRS$^{N4}$; HRS(1-60)) was administered daily by IV injection, starting 3 days prior to TNBS treatment, at a concentration of 1 or 5 mg/Kg.

Embodiments of the present invention are based in part on the surprising discovery that specifically blocking the activity, binding, or production of otherwise pathogenic anti-Jo-1 antibodies (also called Jo-1 antibodies), for example, with HRS polypeptides or other antibody-specific blocking agents, can be useful in treating subjects with inflammatory or autoimmune diseases, and can prevent, or significantly delay disease progression. One advantage to this discovery is that the negative impact of anti-Jo-1 antibodies can be overcome with little or no debilitation of the subject's immune system, resulting in significantly reduced side-effect profiles. Moreover, the approach is broadly applicable to other diseases including inflammatory diseases and related disorders where there is a local or temporal insufficiency of histidyl-tRNA synthetase.

Accordingly, certain embodiments relate to therapeutic compositions, comprising a histidyl-tRNA synthetase (HRS) polypeptide of about 20-90 amino acids in length that is at least 90% identical to SEQ ID NO:1, wherein the composition/HRS polypeptide is: a) at least about 95% pure; b) less than about 5% aggregated; and c) substantially endotoxin-free. In certain embodiments, at least 20 amino acids of the HRS polypeptide are from the region defined by residues 1-67 of SEQ ID NO:1. In some embodiments, at least 40 amino acids of the HRS polypeptide are from the region defined by residues 1-67 of SEQ ID NO:1. In some embodiments, at least 60 amino acids of the HRS polypeptide are from the region defined by residues 1-67 of SEQ ID NO:1.

Also included are therapeutic compositions, comprising a histidyl-tRNA synthetase (HRS) polypeptide of at least about 400 amino acids in length that comprises 80 or more contiguous amino acids that are at least 90% identical to SEQ ID NO:1, wherein the composition/HRS polypeptide is: a) at least about 95% pure; b) less than about 5% aggregated; and c) substantially endotoxin-free. In certain embodiments, the HRS polypeptide comprises 200 or more amino acids that are at least 90% identical to SEQ ID NO:1. In some embodiments, the HRS polypeptide comprises 400 or more amino acids that are at least 90% identical to SEQ ID NO:1. In certain embodiments, the HRS polypeptide is at least about 500 amino acids in length. In some embodiments, the HRS polypeptide comprises the sequence of full-length human HRS (SEQ ID NO:1). In some embodiments, the HRS polypeptide is truncated at residue 505 (HRS(1-505)) or 506 (HRS(1-506)) of SEQ ID NO:1.

Certain embodiments relate to therapeutic compositions, comprising a histidyl-tRNA synthetase (HRS) polypeptide of at least about 400 amino acids in length that is at least 90% identical to SEQ ID NO:1, wherein the composition/HRS polypeptide is: a) at least about 95% pure; b) less than about 5% aggregated; and c) substantially endotoxin-free. In some embodiments, the HRS polypeptide is at least about 500 amino acids in length that is at least 90% identical to SEQ ID NO:1. In certain embodiments, the HRS polypeptide comprises the sequence of SEQ ID NO:1 (full-length human HRS). In some embodiments, the HRS polypeptide is truncated at residue 505 (HRS(1-505)) or 506 (HRS(1-506)) of SEQ ID NO:1.

Also included are therapeutic compositions, comprising a histidyl-tRNA synthetase (HRS) polypeptide of 500-506 amino acids in length that is least 90% identical to SEQ ID NO:70 (HRS(1-506)) and lacks residues 507-509 of SEQ ID NO:1, wherein the composition/HRS polypeptide is: a) at least about 95% pure; b) less than about 5% aggregated; and c) substantially endotoxin-free. In certain embodiments, the HRS polypeptide is 505-506 amino acids in length is at least 90% identical to SEQ ID NO:70. In some embodiments, the HRS polypeptide is 506 amino acids in length. In some embodiments, the HRS polypeptide comprises SEQ ID NO:70. In some embodiments, the HRS polypeptide consists essentially of SEQ ID NO:70. In certain embodiments, the HRS polypeptide consists of SEQ ID NO:70. In some embodiments, the HRS polypeptide is 505 amino acids in length.

In some embodiments, the HRS polypeptide comprises residues 2-506 of SEQ ID NO:70 (HRS(2-506)). In some embodiments, the HRS polypeptide consists essentially of residues 2-506 of SEQ ID NO:70 (HRS(2-506)). In specific embodiments, the HRS polypeptide consists of residues 2-506 of SEQ ID NO:70 (HRS(2-506)).

In some embodiments, the HRS polypeptide has a mutation of at least one cysteine residue. In certain embodiments, the at least one cysteine residue is selected from Cys174, Cys191, Cys224, Cys235, and Cys455.

In some embodiments, the HRS polypeptide (e.g., lacking residues 507-509 of SEQ ID NO:1) has increased biological activity, stability, and/or homogeneity relative to a polypeptide of SEQ ID NO:1 (full-length human HRS) under comparable conditions, ranging from about 4-40° C., and a pH of about 6.0-8.0. In some embodiments, the conditions include a temperature of about 20-25° C. (room temperature) and a pH of about 7.0-7.5, optionally over a period of about 1, 2, 3, 4, 5, 6, or 7 days. In certain embodiments, the conditions include a temperature of about 37° C. and a pH of about 7.0-7.5, optionally over a period of about 1, 2, 3, 4, 5, 6, or 7 days.

In some embodiments, increased activity comprises an absolute increase in a non-canonical biological activity of at least about 10%. In some embodiments, the non-canonical activity is an anti-inflammatory activity or specific binding to an anti-Jo-1 antibody. In certain embodiments, the HRS polypeptide has reduced interchain disulfide formation under reducing conditions relative to the polypeptide of SEQ ID NO:1 (full-length HRS). In certain embodiments, the HRS polypeptide has reduced (charge) heterogeneity relative to the polypeptide of SEQ ID NO:1 (full-length HRS). In some embodiments, the HRS polypeptide has reduced formation of high molecular weight aggregates in solution relative to the polypeptide of SEQ ID NO:1 (full-length HRS). In certain embodiments, increased homogeneity comprises at least a 10% increase in the monodispersion of the HRS polypeptide relative to the polypeptide of SEQ ID NO:1. In some embodiments, the HRS polypeptide has increased yield of soluble protein upon recombinant production in $E.\ coli$ relative to the polypeptide of SEQ ID NO:1 (full-length HRS).

In certain embodiments, the HRS polypeptide is fused to a heterologous fusion partner, optionally a T-cell ligand. In particular embodiments, the HRS polypeptide comprises at least one D-amino acid.

In some embodiments, the therapeutic composition comprises a buffer at a concentration ranging from about 0.03 mM to about 100 mM. In some embodiments, the therapeutic composition comprises a buffer at a concentration ranging from about 2 mM to about 50 mM. In certain embodiments, the therapeutic composition comprises a buffer at a concentration ranging from about 40 mM to about 60 mM. In certain embodiments, the therapeutic composition comprises a comprising a buffer at a concentration ranging from about 45 mM to about 55 mM. In some embodiments, the therapeutic composition comprises a comprising a buffer at a concentration of about 50 mM. In some embodiments, the buffer is a histidine buffer, a citrate buffer, or a phosphate buffer.

In certain embodiments, the buffer is a histidine buffer, and wherein the HRS polypeptide has increased stability relative to a corresponding HRS polypeptide in a comparable composition without said histidine buffer, under comparable conditions, ranging from about 4-40° C., and a pH of about 7.0-7.5.

In certain embodiments, the buffer is a citrate buffer, and wherein the HRS polypeptide has increased stability relative to a corresponding HRS polypeptide in a comparable composition without said citrate buffer, under comparable conditions, ranging from about 4-40° C., and a pH of about 6.5-7.5.

In certain embodiments, the buffer is a phosphate buffer, and wherein the HRS polypeptide has increased stability relative to a corresponding HRS polypeptide in a comparable composition without said phosphate buffer, under comparable conditions, ranging from about 4-40° C., and a pH of about 7.0-7.5.

In some embodiments, the conditions (e.g., for comparison) include a temperature of about 5° C., optionally over a period of about 1, 2, 3, 4, 5, 6, or 7 days. In some embodiments, the conditions include a temperature of about 20-25° C. (room temperature), optionally over a period of about 1, 2, 3, 4, 5, 6, or 7 days. In certain embodiments, the conditions include a temperature of about 37° C., optionally over a period of about 1, 2, 3, 4, 5, 6, or 7 days.

In some embodiments, increased stability comprises thermal stability, wherein the melting temperature (Tm) of the HRS polypeptide is at least about 5° C. greater than that of the corresponding HRS polypeptide in the composition without said buffer and/or outside of said pH range. In some embodiments, increased stability comprises thermal stability, wherein the melting temperature of the HRS polypeptide unfolds at a rate that is at least 10% slower than that of the corresponding HRS polypeptide in the composition without said buffer and/or outside of said pH range.

In certain embodiments, the composition has reduced aggregation and/or precipitation relative to a composition without said buffer and/or outside of said pH range, under otherwise comparable conditions. In some embodiments, aggregation is reduced by at least about 10% as measured by absorbance at A340. In certain embodiments, the composition has reduced high molecular weight aggregates relative to a composition without said buffer and/or outside of said pH range, under otherwise comparable conditions.

In some embodiments, the buffer is a histidine buffer, and the HRS polypeptide is at least 90% identical to residues 1-506 or 2-506 of SEQ ID NO:1 and lacks residues 507-509 of SEQ ID NO:1. In certain embodiments, the buffer is a citrate buffer, and the HRS polypeptide is at least 90% identical to residues 1-506 or 2-506 of SEQ ID NO:1 and lacks residues 507-509 of SEQ ID NO:1. In some embodiments, the HRS polypeptide is HRS(1-506) or HRS(2-506).

In some embodiments, the composition comprises sodium chloride (NaCl) at a concentration ranging from about 100-300 mM, optionally at about 140 mM-240 mM, or optionally at about 140 mM. In certain embodiments, the HRS polypeptide is at least 90% identical to residues 1-506 or 2-506 of SEQ ID NO:1 and lacks residues 507-509 of SEQ ID NO:1, optionally wherein the HRS polypeptide has a melting temperature (Tm) of at least about 60° C. In certain embodiments, the HRS polypeptide is HRS(1-506) or HRS(2-506), optionally wherein the HRS polypeptide has a melting temperature (Tm) of at least about 60° C.

In certain embodiments, the composition comprises one or more pharmaceutically-acceptable excipients. In some embodiments, the one or more pharmaceutically-acceptable excipient(s) are selected from sucrose, mannitol, trehalose, sorbitol, arginine, glycine, and glycerol. In some embodiments, the one or more pharmaceutically-acceptable excipient(s) are at a concentration ranging from about 0.2-5.0%. In certain embodiments, the pharmaceutically-acceptable excipient is about 1-3% sucrose, optionally about 2% sucrose. In some embodiments, the pharmaceutically-acceptable excipient is about 1-3% trehalose, optionally about 2% trehalose.

In some embodiments, the composition comprises one or more surfactants. In some embodiments, the surfactant is a polysorbate or a poloxamer. In some embodiments, the polysorbate is polysorbate 20 (PS20), polysorbate 40 (PS40), polysorbate 60 (PS60), or polysorbate 80 (PS80). In certain embodiments, the polysorbate is PS20. In certain embodiments, the poloxamer is Pluronic F68. In some embodiments, the surfactant is present at a range of about 0.1-5.0% (w/v). In some embodiments, is about 0.05% (w/v) PS20.

In certain embodiments, the composition comprises one or more anti-oxidant compounds or reducing agents. In some embodiments, the anti-oxidant compound or reducing agent is selected from cysteine, methionine, and N-acetylcysteine (NAC). In some embodiments, the anti-oxidant compound or reducing agent is present at a concentration range of about 0.1-5.0 mM.

In certain embodiments, the composition comprises one or more chelating agents. In some embodiments, the chelating agent is ethylenediaminetetraacetate (EDTA). In some embodiments, the chelating agent is present at a concentration range of about 0.1-2.0 mM.

In certain compositions, the HRS polypeptide is present at a concentration of at least about 10 mg/ml. In some compositions, the HRS polypeptide is present at a concentration of at least about 25 mg/ml. In some compositions, the HRS polypeptide is present at a concentration of at least about 50 mg/ml.

In certain embodiments, the composition has a turbidity of less than about 0.5 as measured by absorbance at A340. In some embodiments, absorbance at A340 is measured after at least about 1, 2, 3, 4, 5, 6, or 7 days incubation at 37° C. In some embodiments, absorbance at A340 is measured after at least about 1, 2, 3, 4, 5, 6, or 7 days incubation at room temperature. In certain embodiments, absorbance at A340 is measured after freeze-thawing the composition at least 1, 2, 3, 4, or 5 times.

In some embodiments, the composition has an opalescence of less than about 0.6 as measured by absorbance at A580. In some embodiments, absorbance at A580 is measured after at least about 1, 2, 3, 4, 5, 6, or 7 days incubation at 37° C. In some embodiments, absorbance at A580 is measured after at least about 1, 2, 3, 4, 5, 6, or 7 days incubation at room temperature. In certain embodiments, absorbance at A580 is measured after freeze-thawing the composition at least 1, 2, 3, 4, or 5 times.

In some embodiments, the composition has less than about 3% high molecular weight aggregates. In some embodiments, high molecular weight (HMW) aggregation is measured after at least about 1, 2, 3, 4, 5, 6, or 7 days incubation at 37° C. In certain embodiments, high molecular weight (HMW) aggregation is measured after at least about 1, 2, 3, 4, 5, 6, or 7 days incubation at room temperature. In some embodiments, high molecular weight aggregation is measured after freeze-thawing the composition at least 1, 2, 3, 4, or 5 times.

In certain embodiments, the HRS polypeptide has a melting temperature (Tm) in the composition of at least about 50° C. In some embodiments, the HRS polypeptide has a melting temperature (Tm) in the composition of at least about 55° C. In some embodiments, the HRS polypeptide has a melting temperature (Tm) in the composition of at least about 60° C.

In certain embodiments, the HRS polypeptide is at least about 90% or 95% monodisperse.

In some embodiments, the composition comprises about 50 mM L-histidine, about 140 mM NaCl, about 2% trehalose, about 0.05% Polysorbate 20 (PS20), and has a pH of about 7.0-7.4. In some embodiments, the composition comprises about 50 mM L-histidine, about 140 mM NaCl, about 2% sucrose, about 0.05% Polysorbate 20 (PS20), and has a pH of about 7.0-7.4. In some embodiments, the HRS polypeptide is HRS(1-506) or HRS(2-506) and has a melting temperature (Tm) in the composition of at least about 60° C. In certain embodiments, the composition has a turbidity of less than about 0.1, or less than about 0.05, as measured by absorbance at A340. In some embodiments, the composition has opalescence of less than about 0.1, or less than about 0.05, as measured by absorbance at A580. In certain embodiments, the composition has less than about 2%, or less than about 1%, high molecular weight aggregates.

In certain embodiments the present invention includes a medically useful composition comprising a polypeptide between about 20 and 90 amino acids with at least 90% identity to human HRS (SEQ ID NO:1). In some embodiments, at least 20-40 amino acids are within amino acids 1-67 of human HRS (SEQ ID NO:1). In particular embodiments, at least one amino acid is a D amino acid. In some aspects, the polypeptide is: a) at least about 95% pure; b) less than about 5% aggregated; and c) substantially endotoxin free In another embodiment the present invention includes a medically useful composition comprising a polypeptide of at least about 400 amino acids of a HRS polypeptide; wherein the polypeptide is: a) at least about 95% pure; b) less than about 5% aggregated; and c) substantially endotoxin free.

In another embodiment the present invention includes a medically useful composition comprising a polypeptide of at least about 400 amino acids; wherein the polypeptide is: a) at least 80% identical to human HRS (SEQ ID NO:1); b) at least about 95% pure; c) less than about 5% aggregated; and d) substantially endotoxin free.

In some aspects, of any of these medically useful or therapeutic compositions, the polypeptide is comprises full-length HRS polypeptide. In some aspects, the HRS polypeptide is truncated at about residue 505 or 506. In some aspects, the HRS polypeptide has at least one mutation at a cysteine residue. In some aspects, the cysteine residue is selected from Cys174, Cys191, Cys224, Cys235, Cys455, Cys507 and Cys509. In some aspects, the polypeptide comprises at least one D amino acid. In some aspects, the polypeptide comprises a WHEP domain. In some aspects, the polypeptide, comprises an amino acid sequence at least 80% identical to any of SEQ ID NOS:1-23, 39, 41, 43, 70-71, 74-153, 160-172, or 176-182, or an amino acid sequence listed in or derivable from any of Tables 1-9. In some aspects, the polypeptide is fused to a heterologous protein. In some aspects, the heterologous protein comprises a T cell ligand. In some aspects, the composition is formulated for delivery via oral, intranasal, pulmonary or parental administration.

In some aspects, the medically useful or therapeutic composition is for use in treating a disease selected from the group consisting of autoimmune diseases, inflammatory diseases, inflammatory myopathies, including (idiopathic) inflammatory myopathies, polymyositis, dermatomyositis and related disorders, polymyositis-scleroderma overlap, inclusion body myositis (IBM), anti-synthetase syndrome, interstitial lung disease, arthritis, Reynaud's phenomenon, Perrault syndrome and Usher syndrome. In some aspects, the epitope is immunodominant epitope recognized by antibodies in sera from the subject. In some aspects, the HRS polypeptide binds to a human histocompatibility complex (MHC) class I or class II molecule. In some aspects, the nucleic acid is operatively coupled to expression control sequences, and wherein expression of the nucleic acid causes tolerization. In some aspects, the therapeutic composition comprises a delivery vehicle selected from the group consisting of liposomes, micelles, emulsions and cells.

In another embodiment the present invention includes a therapeutic composition for use in treating diseases associated with an insufficiency of histidyl tRNA synthetase, comprising at least one HRS polypeptide, wherein the HRS polypeptide is capable of replacing at least one canonical or non-canonical function of the histidyl tRNA synthetase. In some embodiments, the HRS polypeptide does not significantly compete for disease-associated autoantibody binding to histidyl-tRNA synthetase in a competitive ELISA up to a concentration of about $5 \times 10^{-7}$M.

In another embodiment the present invention includes a therapeutic composition for use in treating diseases associated with an autoantibody specific for histidyl tRNA synthetase, comprising at least one HRS polypeptide wherein the HRS polypeptide comprises at least one epitope specifically recognized by the autoantibody, and wherein the HRS polypeptide is capable of causing tolerization.

In another embodiment the present invention includes a therapeutic composition for use in treating diseases associated with an autoantibody specific for histidyl tRNA synthetase, the composition comprising a recombinant nucleic acid encoding a mammalian HRS polypeptide, wherein the HRS polypeptide comprises at least one epitope specifically recognized by the autoantibody, and wherein the nucleic acid is operatively coupled to expression control sequences, and wherein expression of the nucleic acid causes tolerization.

In another embodiment the present invention includes a therapeutic composition for use in treating diseases associated with an autoantibody specific for histidyl tRNA synthetase, the composition comprising a recombinant host cell, wherein the host cell expresses at least one heterologous HRS polypeptide comprising at least one epitope specifically recognized by the autoantibody, and wherein the nucleic acid is operatively coupled to expression control sequences to enable expression of the HRS in the host cell.

In another embodiment the present invention includes a therapeutic composition for use in treating diseases associated with an autoantibody specific for histidyl tRNA synthetase, the composition comprising an antibody or binding protein specific to the auto-antibody, wherein the antibody or binding protein blocks the binding of the auto-antibody to native histidyl tRNA synthetase.

Come embodiments relate to therapeutic compositions for use in treating an inflammatory disease comprising at least one HRS polypeptide, wherein the HRS polypeptide has at least one non-canonical activity.

Also included are therapeutic compositions for use in treating a muscular dystrophy comprising at least one HRS polypeptide, wherein the HRS polypeptide has at least one non-canonical activity. In some aspects, the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy, and congenital muscular dystrophy.

Certain embodiments include therapeutic compositions for use in treating rhabdomyolysis, muscle wasting, cachexia, muscle inflammation, or muscle injury comprising at least one HRS polypeptide, wherein the HRS polypeptide has at least one non-canonical activity.

In another embodiment the present invention includes the use of a HRS polypeptide in the preparation of a medicament for the treatment of an inflammatory or autoimmune disease. In another embodiment the current invention includes the use of a HRS polypeptide in the preparation of a medicament for the treatment of a disease associated with an insufficiency of histidyl tRNA synthetase.

In some aspects, of any of these therapeutic compositions or uses, the HRS polypeptide induces tolerance. In some aspects, the HRS polypeptide is about 10 to about 60 amino acids long. In some aspects, the HRS polypeptide is about 60 to about 120 amino acids long. In some aspects, the HRS polypeptide is about 120 to about 200 amino acids long. In some aspects, the HRS polypeptide is full-length. In some aspects, the HRS polypeptide is truncated at about residue 505 or 506. In some aspects, the HRS polypeptide has at least one mutation at a cysteine residue. In some aspects, the cysteine residue is selected from Cys174, Cys191, C224, Cys235, Cys455, Cys507 and Cys509. In some aspects, the HRS polypeptide comprises at least one D amino acid. In some aspects, the HRS polypeptide comprises a WHEP domain. In some aspects, the HRS polypeptide, comprises an amino acid sequence at least 80% identical to any of SEQ ID NOS: 1-23, 39, 41, 43, 70-71, 74-153, 160-172, or 176-182, or an amino acid sequence at least 80%, 90%, or 95% identical to any of the sequences in Tables D1, D3-D6, or D8. In some aspects, the HRS polypeptide is fused to a heterologous protein. In some aspects, the heterologous protein comprises a T cell ligand. In some aspects, the composition is formulated for delivery via oral, intranasal, pulmonary or parental administration. In some aspects, the therapeutic composition comprises a delivery vehicle selected from the group consisting of liposomes, micelles, emulsions and cells.

Also included are methods of treating a disease associated with an autoantibody comprising administering to a subject in need thereof a therapeutic composition comprising one or more of a) a HRS polypeptide, b) a recombinant nucleic acid encoding a heterologous HRS polypeptide, c) a recombinant host cell, wherein the host cell expresses at least one heterologous HRS polypeptide, or d) an antibody or binding protein specific to the auto-antibody.

In some aspects, the therapeutic composition is administered to the subject prior to the appearance of disease symptoms. In some aspects the autoantibody is specific for histidyl tRNA synthetase. In some aspects, the HRS polypeptide comprises at least one epitope of the histidyl tRNA synthetase recognized by the disease specific autoantibody. In some aspects, the HRS polypeptide blocks the binding of the autoantibody to native histidyl tRNA synthetase. In some aspects, the HRS polypeptide causes clonal deletion of autoreactive T-cells. In some aspects, the HRS polypeptide causes functional inactivation of the T cells involved in the autoimmune response. In some aspects, the HRS polypeptide results in reduced muscle or lung inflammation. In some aspects, the HRS polypeptide induces tolerance. In some aspects, the HRS polypeptide is about 10 to about 60 amino acids long. In some aspects, the HRS polypeptide is about 60 to about 120 amino acids long. In some aspects, the HRS polypeptide is about 120 to about 200 amino acids long. In some aspects, the HRS polypeptide is full-length. In some aspects, the HRS polypeptide is truncated at about residue 505 or 506. In some aspects, the HRS polypeptide has at least one mutation at a cysteine residue. In some aspects, the cysteine residue is selected from Cys174, Cys191, Cys224, Cys235, C455, Cys507 and Cys509. In some aspects, residues 507, 508, and 509 corresponding to full-length HRS (SEQ ID NO:1) are deleted. In some aspects, the HRS polypeptide comprises at least one D amino acid. In some aspects, the HRS polypeptide comprises a WHEP domain. In some aspects, the HRS polypeptide, comprises an amino acid sequence at least 80% identical to any of SEQ ID NOS: 1-23, 39, 41, 43, 70-71, 74-153, 160-172, or 176-182, or an amino acid sequence at least 80%, 90%, or 95% identical to any of the sequences in Tables D1, D3-D6, or D8. In some aspects, the HRS polypeptide is fused to a heterologous protein. In some aspects, the heterologous protein comprises a T cell ligand. In some aspects, the composition is formulated for delivery via oral, intranasal, pulmonary or parental administration.

In some aspects, the disease is selected from the group consisting of inflammatory myopathies, including inflammatory myopathies, polymyositis, dermatomyositis and related disorders, polymyositis-scleroderma overlap, inclusion body myositis (IBM), anti-synthetase syndrome, interstitial lung disease, arthritis, and Reynaud's phenomenon, among other disease or conditions described herein. In some aspects, the epitope is immunodominant epitope recognized by antibodies in sera from the subject. In some aspects, the HRS polypeptide binds to a human histocompatibility complex (MHC) class II molecule. In some aspects, the nucleic acid is operatively coupled to expression control sequences, and wherein expression of the nucleic acid causes tolerization. In some aspects, the therapeutic composition comprises a delivery vehicle selected from the group consisting of liposomes, micelles, emulsions and cells.

Also included are methods of reducing tissue inflammation comprising administering to a subject in need thereof a composition comprising one or more of a) a HRS polypeptide, b) a recombinant nucleic acid encoding a heterologous HRS polypeptide, or c) a recombinant host cell; wherein the host cell expresses at least one heterologous HRS polypeptide. In some aspects, the tissue is selected from muscle, lung, and skin Some embodiments relate to methods of reducing muscle or lung inflammation said method comprising administering to a subject a therapeutic composition comprising one or more of: a) a HRS polypeptide; b) a recombinant nucleic acid encoding a heterologous HRS polypeptide; or c) a recombinant host cell, wherein the host cell expresses at least one heterologous HRS polypeptide.

Also included are methods of treating a muscular dystrophy comprising administering to a subject in need thereof a composition comprising one or more of a) a HRS polypeptide, b) a recombinant nucleic acid encoding a heterologous HRS polypeptide, or c) a recombinant host cell, wherein the host cell expresses at least one heterologous HRS polypeptide. In some aspects, the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy, and congenital muscular dystrophy.

Some embodiments relate to methods of treating rhabdomyolysis, muscle wasting, cachexia, muscle inflammation, or muscle injury comprising administering to a subject in need thereof a composition comprising one or more of a) a HRS polypeptide, b) a recombinant nucleic acid encoding a heterologous HRS polypeptide, or c) a recombinant host cell, wherein the host cell expresses at least one heterologous HRS polypeptide.

Certain embodiments include methods of inducing tolerance to a histidyl tRNA synthetase (HisRS) autoantigen, said method comprising administering to a subject a therapeutic composition comprising one or more of: a) a HRS polypeptide, b) a recombinant nucleic acid encoding a heterologous HRS polypeptide; or c) a recombinant host cell, wherein the host cell expresses at least one heterologous HRS polypeptide, wherein the HRS polypeptide comprises at least one epitope specifically recognized by the autoantibody, and wherein administration of the composition causes tolerization to the autoantigen.

Some embodiments include methods for eliminating a set or subset of T cells involved in an autoimmune response to a histidyl tRNA synthetase (HisRS) autoantigen, the method comprising administering to a subject a therapeutic composition one or more of: a) a HRS polypeptide; b) a recombinant nucleic acid encoding a heterologous HRS polypeptide; or c) a recombinant host cell, wherein the host cell expresses at least one heterologous HRS polypeptide, wherein the HRS polypeptide comprises at least one epitope specifically recognized by the autoantibody, and wherein administration of the composition causes clonal deletion of auto-reactive T-cells.

Also included are methods for inducing anergy in T cells involved in an autoimmune response to a histidyl tRNA synthetase (HisRS) autoantigen, the method comprising administering to a subject a composition comprising one or more of: a) a HRS polypeptide; b) a recombinant nucleic acid encoding a heterologous HRS polypeptide; or c) a recombinant host cell, wherein the host cell expresses at least one heterologous HRS polypeptide, wherein the HRS polypeptide comprises at least one epitope specifically recognized by the autoantibody, and wherein administration of the composition causes functional inactivation of the T cells involved in the autoimmune response.

Some embodiments replacement therapies for treating a disease associated with an insufficiency of histidyl tRNA synthetase comprising administering to a subject in need thereof a therapeutic composition comprising one or more of: a) a HRS polypeptide; b) a recombinant nucleic acid encoding a heterologous HRS polypeptide; c) a recombinant host cell, wherein the host cell expresses at least one heterologous HRS polypeptide; or d) an antibody or binding protein specific to the auto-antibody; wherein the HRS polypeptide functionally compensates for the histidyl tRNA synthetase insufficiency.

Also included are methods for treating an inflammatory or autoimmune disease, comprising administering to a subject in need thereof a therapeutic composition comprising at least one HRS polypeptide.

In some aspects, the HRS polypeptide does not significantly compete for disease associated auto-antibody binding to histidyl-tRNA synthetase in a competitive ELISA up to a concentration of about $5 \times 10^{-7}$ M.

In some aspects, the HRS polypeptide is about 10 to about 60 amino acids long. In some aspects, the HRS polypeptide is about 60 to about 120 amino acids long. In some aspects, the HRS polypeptide is about 120 to about 200 amino acids long. In some aspects, the HRS polypeptide is about 200 to about 400 amino acids long. In some aspects, the HRS polypeptide is about 400 to about 500 amino acids long. In some aspects, the HRS polypeptide is full-length. In some aspects, the HRS polypeptide is truncated at about residue 505 or 506. In some aspects, the HRS polypeptide has at least one mutation at a cysteine residue. In some aspects, the cysteine residue is selected from Cys174, Cys191, Cys224, Cys235, C455, Cys507 and Cys509. In some aspects, the HRS polypeptide comprises at least one D amino acid. In some aspects, the HRS polypeptide comprises a WHEP domain. In some aspects, the HRS polypeptide, comprises an amino acid sequence at least 80% identical to any of SEQ ID NOS: 1-23, 39, 41, 43, 70-71, 74-153, 160-172, or 176-182, or an amino acid sequence at least 80%, 90%, or 95% identical to any of the sequences in Tables D1, D3-D6, or D8. In some aspects, the HRS polypeptide is fused to a heterologous protein. In some aspects, the heterologous protein comprises a T cell ligand. In some aspects, the composition is formulated for delivery via oral, intranasal, pulmonary or parental administration. In some aspects, the disease is selected from the group consisting of inflammatory myopathies, including inflammatory myopathies, polymyositis, dermatomyositis and related disorders, polymyositis-scleroderma overlap, inclusion body myositis (IBM), anti-synthetase syndrome, interstitial lung disease, arthritis, and Reynaud's phenomenon. In some aspects, the epitope is immunodominant epitope recognized by antibodies in sera from the subject. In some aspects, the HRS polypeptide binds to a human histocompatibility complex (MHC) class II molecule. In some aspects, the nucleic acid is operatively coupled to expression control sequences, and wherein expression of the nucleic acid causes tolerization. In some aspects, the therapeutic composition comprises a delivery vehicle selected from the group consisting of liposomes, micelles, emulsions and cells.

Also included are methods of determining presence or levels of a HRS polypeptide, or fragment thereof in a sample, comprising contacting the sample with one or more binding agents that specifically bind to the HRS polypeptide, and detecting the presence or absence of the binding agent, and thereby determining the presence or levels of the HRS polypeptide.

Some embodiments include methods of determining the epitope specificity of an anti-HRS polypeptide antibody to a specific HRS polypeptide, the method comprising contacting the antibody with one or more HRS polypeptides, and detecting the presence or absence of the binding agent, and thereby determining the epitope specificity of the antibody. In some aspects of this method, the HRS polypeptide is up to about 80 amino acids long and comprises the WHEP domain.

Some embodiments include methods for treating diseases associated with an autoantibody specific for histidyl tRNA synthetase, the method comprising administering to a subject in need thereof a therapeutic composition comprising at least one HRS polypeptide wherein the HRS polypeptide does not significantly compete for disease associated auto-antibody binding to histidyl-tRNA synthetase in a competitive ELISA up to a concentration of about $1 \times 10^{-7}$ M.

In another aspect of the invention, the HRS polypeptides may be used to profile patients to identify their Jo-1 antibody disease burden. Such profiles enable the selection of patients into subpopulations that would benefit from HRS polypeptide treatment, prognosticate the likely therapeutic outcome, and/or identify the HRS polypeptide(s) most suitable for use as therapeutic agents.

Accordingly, certain embodiments relate to methods for identifying a human subject at risk for having an adverse immune response to HRS polypeptide administration, comprising a) determining the antibody level, or epitope specificity of the anti-histidyl tRNA synthetase antibody in the subject; and b) and identifying the subject as being at risk of developing an adverse immune response to HRS polypeptide administration if the subject has detectable antibodies to histidyl tRNA synthetase, or the HRS polypeptide. In some aspects, the subject may be identified as being at risk of developing an adverse immune response to HRS polypeptide administration if the subject has a concentration of histidyl tRNA synthetase antibodies in their serum of greater than about 2 micromolar. In some aspects, the subject may be identified as being at high risk of developing an adverse immune response to HRS polypeptide administration if the subject has a concentration of histidyl tRNA synthetase antibodies in their serum of greater than about 4 micromolar.

Also included are methods for selecting a HRS polypeptide to treat a human subject with an autoimmune or inflammatory condition, comprising a) determining the antibody level, or epitope specificity of the anti-histidyl tRNA synthetase antibody in the subject; and b) and selecting a HRS polypeptide which has a reduced affinity for the anti-histidyl tRNA synthetase antibody compared to wild-type histidyl tRNA synthetase.

Some embodiments relate to methods for prognosticating a human subject's disease progression, comprising a) determining the antibody level, or epitope specificity of the anti-histidyl tRNA synthetase antibody in the subject; and b) and identifying the subject as being at risk of developing more severe disease if the subject has detectable antibodies to histidyl tRNA synthetase, or the HRS polypeptide.

Also included are methods for predicting subject responses to HRS polypeptide administration, comprising a) determining the antibody level, or epitope specificity of the anti-histidyl tRNA synthetase antibody in the subject; and b) and identifying the subject as suitable for HRS polypeptide administration if the subject has no detectable antibodies to histidyl tRNA synthetase, or the HRS polypeptide.

In some aspects, the subject may be identified as being as suitable for HRS polypeptide administration if the subject has a concentration of histidyl tRNA synthetase antibodies in their serum of less than about 1 micromolar.

In some aspects, the subject may be identified as being as suitable for HRS polypeptide administration if the subject has a concentration of histidyl tRNA synthetase antibodies in their serum of less than about 0.1 micromolar.

In some aspects, the subject may be identified as being as suitable for HRS polypeptide administration if the subject has a concentration of histidyl tRNA synthetase antibodies in their serum of greater than about 0.01 micromolar.

Also included are methods for extracorporeal immunoadsorption of anti-histidyl-tRNA synthetase (HRS) antibodies from an extracellular body fluid, comprising (a) providing the extracellular body fluid which has been obtained from a subject, contacting the extracellular body fluid with a biocompatible solid support having at least one histidyl-tRNA synthetase polypeptide attached thereto, thereby capturing the anti-HRS antibodies on the solid support, and (c) re-infusing the extracellular body fluid from step (b) into the subject. In some aspects, the anti-HRS antibodies include an anti-Jo-1 antibody.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3rd Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells*, a Manual of Basic Technique, 5th Ed. Hoboken N.J., John Wiley & Sons; B. Perbal, *A Practical Guide to Molecular Cloning* (3rd Edition 2010); Farrell, R., *RNA Methodologies: A Laboratory Guide for Isolation and Characterization* (3rd Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "*Use of functionalized Poly (Ethylene Glycols) for modification of polypeptides*" in Polyethylene Glycol Chemistry: Biotechnical and Biomedical Applications. The publications discussed above are provided solely for their disclosure before the filing date of the present application. Nothing herein is to be construed as an admission that the invention is not entitled to antedate such disclosure by virtue of prior invention.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "allergy" refers to the functional inactivation of a T-cell, or B-cell response to re-stimulation by antigen.

As used herein, the term "amino acid" is intended to mean both naturally-occurring and non-naturally-occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally-occurring amino acids include, for example, (D)-amino acids, norleucine, norvaline, p-fluorophenylalanine, ethionine and the like, which are known to a person skilled in the art. Amino acid analogs include modified forms of naturally and non-naturally-occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally-occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, a subject "at risk" of developing a disease, or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

An "autoimmune disease" as used herein is a disease or disorder arising from and directed against an individual's own tissues. Examples of autoimmune diseases or disorders include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, inflammatory myopathies, interstitial lung disease, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

The term "binding" refers to a direct association between two molecules, due to, for example, covalent, electrostatic, hydrophobic, and ionic and/or hydrogen-bond interactions, including interactions such as salt bridges and water bridges. Binding proteins include for example antibodies and antibody alternatives including binding agents, as described herein.

The term "clonal deletion" refers to the deletion (e.g., loss, or death) of auto-reactive T-cells. Clonal deletion can be achieved centrally in the thymus, or in the periphery, or both.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

By "continuous process" is meant a process that can be defined by a constant function being applied at the starting time point of the process and terminated at the end point of the process. Thus, in the present context a typical example of a continuous process is a procedure in which a certain type of body fluid, typically blood, is removed at a constant flow (i.e., substantially uninterrupted flow) from a patient and also reintroduced into the patient with a similar constant flow. This procedure is to be understood in contrast to any other "discontinuous" procedure wherein the body fluid is withdrawn from the patient in one independent procedure at one time, optionally stored and contacted with an adsorbent in a batch-wise manner at another time and reintroduced into the patient at still another time chosen largely independent of the two first procedures.

The term "endotoxin-free" or "substantially endotoxin-free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain microorganisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing HRS polypeptides in and isolating them from eukaryotic cells such as mammalian cells to reduce, if not eliminate, the risk of endotoxins being present in a composition of the invention. Preferred are methods of producing HRS polypeptides in and isolating them from serum free cells.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA). To be substantially endotoxin-free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

"Epitope" refers to that portion of an antigen or other macromolecule capable of forming a binding interaction that interacts with the variable region of an antibody (or like protein), antibody alternative, binding agent, or T cell receptor. In the case of antibodies, such binding interactions can be manifested as an intermolecular contact with one or more amino acid residues of a CDR. Antigen binding can involve a CDR3 or a CDR3 pair. An epitope can be a linear peptide sequence (e.g., "continuous") or can be composed of noncontiguous amino acid sequences (e.g., "conformational" or "discontinuous" sequences which may separately, or together form a recognizable shape). A binding protein can recognize one or more amino acid sequences; therefore an epitope can define more than one distinct amino acid sequence. Epitopes recognized by binding protein can be determined by peptide mapping and sequence analysis techniques well known to one of skill in the art. A "cryptic epitope" or a "cryptic binding site" is an epitope or binding site of a protein sequence that is not exposed or substantially protected from recognition within an unmodified polypeptide, or protein complex or multimer, but is capable of being recognized by a binding protein to the proteolyzed polypeptide, or non complexed, dissociated polypeptide Amino acid sequences that are not exposed, or are only partially exposed, in the unmodified, multimeric polypeptide structure are potential cryptic epitopes. If an epitope is not exposed, or only partially exposed, then it is likely that it is buried within the interior of the polypeptide, or masked in the polypeptide complex by the binding of other proteins or factors. Candidate cryptic epitopes can be identified, for example, by examining the three-dimensional structure of an unmodified polypeptide.

"Expression control sequences" are regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, that have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

The term "extracellular body fluids" refers to the extracellular fluids of the mammalian organism. Examples include blood, ascites, plasma, lymph, amnion fluid, urine, saliva, and cerebrospinal fluid.

The term "heterologous" refers to a nucleic acid or protein which has been introduced into an organism (such as a plant, animal, or prokaryotic cell), or a nucleic acid molecule (such as chromosome, vector, or nucleic acid construct), which are derived from another source, or which are from the same source, but are located in a different (i.e., non native) context.

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "half maximal effective concentration" or "$EC_{50}$" refers to the concentration of an agent (e.g., HRS polypeptide, or other agent) as described herein at which it induces a response halfway between the baseline and maximum after some specified exposure time; the $EC_{50}$ of a graded dose response curve therefore represents the concentration of a compound at which 50% of its maximal effect is observed. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an antibody blocking agent is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a biotherapeutic composition will have an $EC_{50}$ value of about 1 nM or less.

An "immunogenic composition" of the invention, as used herein, refers to any composition that elicits an immune response in an animal, such as a mammal. An "immune response" is the reaction of the body to foreign substances, without implying a physiologic or pathologic consequence of such a reaction, i.e., without necessarily conferring protective immunity on the animal. An immune response may include one or more of the following: (a) a cell mediated immune response, which involves the production of lymphocytes by the thymus (T cells) in response to exposure to the antigen; and/or (b) a humoral immune response, which involves production of plasma lymphocytes (B cells) in response to antigen exposure with subsequent antibody production.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "modulating" includes "increasing," "enhancing" or "stimulating," as well as "decreasing" or "reducing," typically in a statistically significant or a physiologically significant amount as compared to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the amount produced by no composition (e.g., in the absence of any of the HRS polypeptides of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between.

The terms "operably linked", "operatively linked," or "operatively coupled" as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more DNA or RNA nucleotide sequences chosen from: (a) a nucleotide sequence capable of increasing translation; (b) a nucleotide sequence capable of increasing secretion of the recombinant protein outside a cell; (c) a nucleotide sequence capable of increasing the mRNA stability, and (d) a nucleotide sequence capable of binding a trans-acting factor to modulate transcription or translation, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g., using PCR methodology, by ligation at suitable restrictions sites or by annealing. Synthetic oligonucleotide linkers or adaptors can be used in accord with conventional practice if suitable restriction sites are not present.

"Non-canonical" activity as used herein, refers generally to either i) a new non-aminoacylation biological activity possessed by HRS polypeptide of the invention that is not possessed to any significant degree by the intact native full-length parental protein, or ii) an activity that was possessed by the intact native full-length parental protein, where the HRS polypeptide either exhibits either a) a significantly higher (e.g., at least 20% greater) specific activity with respect to the non-canonical activity compared to the intact native full-length parental protein, or b) exhibits the activity in a new context; for example by isolating the activity from other activities possessed by the intact native full-length parental protein, or in the context of an extracellular environment, compared to the classical cytoplasmic intracellular compartment.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-RE$_x$™ system (Invitrogen Carlsbad, Calif.), LacSwitch® (Stratagene, (San Diego, Calif.) and the Cre-ER™ tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

In certain embodiments, the "purity" of any given agent (e.g., HRS polypeptide) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally-occurring amino acids, such as a chemical analogue of a corresponding naturally-occurring amino acid, as well as to naturally-occurring amino acid polymers.

The term "prognosis" is used herein to refer to the prediction of the likelihood of disease symptoms, including, for example, recurrence, flaring, and drug resistance, of a disease. The term "prediction" is used herein to refer to the likelihood that a subject or patient will respond either favorably or unfavorably to a drug or set of drugs, e.g., HRS polypeptides, or other agents. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

A "patient subpopulation," or alternatively "subject subpopulation" and grammatical variations thereof, as used herein, refers to a patient subset characterized as having one or more distinctive measurable and/or identifiable characteristics that distinguishes the patient or subject subset from others in the broader disease category to which it belongs. Such characteristics include disease subcategories, gender, lifestyle, health history, organs/tissues involved, treatment history, etc. In one embodiment, a patient or subject subpopulation is characterized by auto-antibody levels.

"Patient response" or alternatively "subject response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

The term "specific" is applicable to a situation in which one member of a specific binding pair will not show any significant binding to molecules other than its specific binding partner(s). The term is also applicable where e.g., an antigen binding domain is specific for a particular epitope which is carried by a number of antigens, in which case the specific binding member carrying the antigen binding domain will be able to bind to the various antigens carrying the epitope.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an antibody blocking agent provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a HRS polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject," as used herein, includes any animal that exhibits a symptom, or is at risk for exhibiting a symptom, which can be treated or diagnosed with a HRS polypeptide, or antibody blocking agent of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95% or greater of some given quantity.

"Therapeutic response" refers to improvement of symptoms (whether or not sustained) based on the administration of the therapeutic response (whether or not tolerance is induced).

The term "tolerance" refers to a sustained, (e.g., one month or more) specific reduced responsiveness of the immune system to an antigen (e.g., self-antigen) in the setting of an otherwise substantially normal immune system. Tolerance is distinct from generalized immunosuppression in which all, or all of a class of a class such as B cell mediated immune responses of immune responses are diminished. "Tolerization" refers to a process leading to the state of tolerance.

As used herein, the terms "therapeutically effective amount", "therapeutic dose", "prophylactically effective amount", or "diagnostically effective amount" is the amount of the drug, e.g., HRS polypeptide or antibody, needed to elicit the desired biological response following administration. Similarly the term "HRS polypeptide therapy" refers to a therapy that maintains the average steady state concentration a HRS polypeptide in the patient's plasma above the minimum effective therapeutic level.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "vaccine", as used herein, broadly refers to any compositions that may be administered to an animal to illicit a protective immune response to the vaccine or co-administered antigen. The terms "protect", "protective "immune response" or "protective immunity", as used herein describes the development of antibodies or cellular systems that specifically recognize the vaccine antigen.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Overview

The present invention relates to the development of improved therapeutic compositions, diagnostics and methods for treating inflammatory and autoimmune diseases, and in some aspects to the treatment of inflammatory myopathies, and related diseases and disorders, including lung diseases associated with the development of auto-antibodies to histidyl-tRNA synthetase, related proteins, and other antibodies.

The present invention also includes the development of improved therapeutic compositions, diagnostics, and methods for treating diseases having a secondary inflammatory component, which otherwise exacerbates, perpetuates, or drives disease progression, and which can be caused by an unrelated genetic defect or injury.

In some aspects, such treatments provide for improved efficacy relative to existing methods of treatment, and exhibit a significantly improved side effect profile.

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art.

Clinical signs of chronic inflammation are dependent upon duration of the illness, inflammatory lesions, cause and anatomical area affected. (see, e.g., Kumar et al., Robbins Basic Pathology-8th Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, autoimmunity, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, neurological disorders, diabetes, metabolic disorders, obesity, and psoriasis, among others described herein and known in the art. Accordingly, HRS polypeptides may be used to treat or manage chronic inflammation, modulate any of one or more of the individual chronic inflammatory responses, or treat any one or more diseases or conditions associated with acute or chronic inflammation.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Accordingly, some aspects include methods of reducing tissue inflammation, comprising administering to a subject in need thereof a composition comprising one or more of a) a HRS polypeptide, b) a recombinant nucleic acid encoding a heterologous HRS polypeptide, or c) a recombinant host cell; wherein the host cell expresses at least one heterologous HRS polypeptide. In some embodiments, the tissue is selected from muscle, lung, and skin.

Certain aspects include methods of reducing muscle or lung inflammation associated with an autoimmune disease comprising administering to a subject in need thereof a composition comprising one or more of a) a HRS polypeptide, b) a recombinant nucleic acid encoding a heterologous HRS polypeptide, or c) a recombinant host cell; wherein the host cell expresses at least one heterologous HRS polypeptide.

Also included are methods of treating a disease associated with an autoantibody comprising administering to a subject in need thereof a therapeutic composition comprising one or more of a) a HRS polypeptide, b) a recombinant nucleic acid encoding a heterologous HRS polypeptide, c) a recombinant host cell; wherein the host cell expresses at least one heterologous HRS polypeptide, or d) an antibody or binding protein specific to the auto-antibody; wherein the HRS polypeptide comprises at least one epitope specifically recognized by the autoantibody.

Some aspects include methods of inducing tolerance to a histidyl-tRNA synthetase (HisRS) antigen, said method comprising administering to a subject a composition comprising one or more of a) a HRS polypeptide, b) a recombinant nucleic acid encoding a heterologous HRS polypeptide, or c) a recombinant host cell; wherein the host cell expresses at least one heterologous HRS polypeptide; wherein the HRS polypeptide comprises at least one epitope specifically recognized by the autoantibody, and wherein administration of the composition causes tolerization to the autoantigen.

Certain aspects include methods for reducing or eliminating a set or subset of T cells involved in an autoimmune response to a histidyl-tRNA synthetase (HisRS) autoantigen, the method comprising administering to a subject a composition comprising one or more of a) a HRS polypeptide, b) a recombinant nucleic acid encoding a heterologous HRS polypeptide, or c) a recombinant host cell; wherein the host cell expresses at least one heterologous HRS polypeptide; wherein the HRS polypeptide comprises at least one epitope specifically recognized by the autoantibody, and wherein administration of the composition causes clonal deletion of auto-reactive T-cells.

Also included are methods for inducing anergy in T cells involved in an autoimmune response to a histidyl-tRNA synthetase (HisRS) autoantigen, the method comprising administering to a subject a composition comprising one or more of a) a HRS polypeptide, b) a recombinant nucleic acid encoding a heterologous HRS polypeptide, or c) a recombinant host cell, wherein the host cell expresses at least one heterologous HRS polypeptide; wherein the HRS polypeptide comprises at least one epitope specifically recognized by the autoantibody, and wherein administration of the composition causes functional inactivation of the T cells involved in the autoimmune response. Some of these and related embodiments include methods of reducing the presence or levels of histidyl-tRNA synthetase "autoantigen-activated T cells" and/or histidyl-tRNA synthetase "autoantigen-activated B cells."

In some embodiments, the subject having a disease associated with an autoantibody has a genetic predisposition to autoimmune diseases or disorders. For instance, in certain embodiments, the subject has an MHC class II allotype such as HLA DR2, HLA DR3, HLA DR4, mutations in protein tyrosine phosphatase, non-receptor type 22 (PTPN22), and dysregulation of pathways such as the pathogen recognition receptors of the innate immune system and the TNF supergene family (see, e.g., Rai and Wakeland, Semin. Immunology. 23:67-83, 2011), each of which has been correlated to certain autoimmune disorders.

Some aspects include replacement therapies for treating a disease associated with an insufficiency of histidyl-tRNA synthetase, comprising administering to a subject in need thereof a therapeutic composition comprising one or more of a) a HRS polypeptide, b) a recombinant nucleic acid encoding a heterologous HRS polypeptide, c) a recombinant host cell, wherein the host cell expresses at least one heterologous HRS polypeptide, or d) an antibody or binding protein specific to the auto-antibody; wherein the HRS polypeptide functionally compensates for the histidyl-tRNA synthetase insufficiency.

In some replacement therapies, the histidyl-tRNA synthetase insufficiency is caused by the presence of anti-Jo-1 antibodies. In some aspects of this replacement therapy, the histidyl-tRNA synthetase insufficiency is caused by mutations in an endogenous histidyl-tRNA synthetase which modulate the activity, expression or cellular distribution of the endogenous histidyl-tRNA synthetase. In some aspects the histidyl-tRNA synthetase insufficiency is associated with Perrault syndrome or Usher syndrome. In some aspects, the histidyl-tRNA synthetase insufficiency is associated with insufficient local production of histidyl-tRNA synthetase within a tissue or at the site of injury or inflammation. In certain aspects, the histidyl-tRNA synthetase insufficiency is associated with one or more of rhabdomyolysis, cachexia, and/or muscle injury.

The term "tolerance," as used herein, refers to the sustained reduction or absence of an immune response to a specific antigen in a mammal, particularly a human. Tolerance is distinct from generalized immunosuppression, in which all or all of a specific class of immune cells, such as B cell mediated immune responses, of an immune response are diminished, or eliminated. The development of tolerance may be routinely monitored by the absence, or a decrease, in the concentration of antibodies to HRS polypeptides in the serum of the host subject after administration, in single or successive doses of the treating HRS polypeptide. The development of tolerance will typically be sufficient to decrease the symptoms of the autoimmune disease in the patient, for example a patient may be sufficiently improved so as to maintain normal activities in the absence, or in the presence of reduced amounts, of general immunosuppressants, e.g., corticosteroids.

In any of these methods or compositions, tolerance will typically be sustained, meaning that it will have a duration of about one month, about two months, about three months, about 4 months, about 5 months, or about 6 months or longer. Tolerance may result in selective B-cell anergy, or T-cell anergy or both.

In any of these methods, treatments, and therapeutic compositions, the term "a disease associated with autoantibodies specific for histidyl-tRNA synthetase" refers to any disease or disorder in which antibodies to histidyl-tRNA synthetase are detected, or detectable, irrespective of whether other autoantibodies are also detected, or thought to play a role in disease progression or cause. Methods for detecting antibodies in patient samples may be carried out by any standard procedure including for example, by RIA, ELISA, by immunoprecipitation, by staining of tissues or cells (including transfected cells), antigen microarrays, mass spec analysis, specific neutralization assays or one of a number of other methods known in the art for identifying desired antigen specificity. In some aspects, antibody specificity can be further characterized by determining the ability of the antibodies to selectively bind to different splice variants and truncated or proteolytic forms of histidyl-tRNA synthetase. A relatively well known human auto-antibody to histidyl-tRNA synthetase includes for example antibodies to Jo-1.

In some embodiments, the HRS polypeptide comprises an epitope from histidyl-tRNA synthetase which specifically cross reacts with a disease associated auto-antibody to histidyl-tRNA synthetase. In some embodiments of any of the claimed methods, and compositions, the HRS polypeptide comprises an epitope from histidyl-tRNA synthetase which specifically cross reacts with a disease associated auto-reactive T cell to histidyl-tRNA synthetase. In some embodiments, the HRS polypeptide comprises an epitope which specifically cross reacts with a disease associated auto-antibody to either another tRNA synthetase, or to a non tRNA synthetase auto antibody.

In some embodiments, the HRS polypeptide comprises an immunodominant epitope which is specifically recognized by the majority of antibodies from the sera of a patient with a disease associated with auto antibodies to histidyl-tRNA synthetase. In some embodiments, the HRS polypeptide comprises an immunodominant epitope which is specifically recognized by the majority of autoreactive T cells from the sera of a patient with a disease associated with auto antibodies to histidyl-tRNA synthetase.

In some embodiments, the epitope is comprised within the WHEP domain of the HRS polypeptide (approximately amino acids 1-43 of SEQ ID NO:1); the aminoacylation domain (approximately amino acids 54-398 of SEQ ID NO:1); or the anticodon binding domain (approximately amino acids 406-501 of SEQ ID NO:1) or any combination thereof.

In some embodiments, the HRS polypeptide does not comprise an epitope which specifically cross reacts with a disease associated auto-antibody to histidyl-tRNA synthetase. In some embodiments, the HRS polypeptide does not significantly compete for disease associated auto-antibody binding to histidyl-tRNA synthetase in a competitive ELISA up to a concentration of about $1 \times 10^{-7}$M. In some embodiments, the HRS polypeptide does not significantly compete for disease associated auto-antibody binding to histidyl-tRNA synthetase in a competitive ELISA up to a concentration of about $5 \times 10^{-7}$M. In some embodiments, the HRS polypeptide does not significantly compete for disease associated auto-antibody binding to histidyl-tRNA synthetase in a competitive ELISA up to a concentration of about $1 \times 10^{-6}$M.

Accordingly in some embodiments, the HRS polypeptide has a lower affinity to a disease associated auto-antibody than wild-type histidyl-tRNA synthetase (SEQ ID NO:1) as measured in a competitive ELISA. In some embodiments, the HRS polypeptide has an apparent affinity for the disease associated auto-antibody which is at least about 10 fold less, or at least about 20 fold less, or at least about 50 fold less, or at least about 100 fold less than the affinity of the disease associated auto-antibody to wild-type human (SEQ ID NO:1). In some aspects, the auto-antibody to histidyl-tRNA synthetase is directed to the Jo-1 antigen.

Examples of diseases associated with autoantibodies specific for histidyl-tRNA synthetase (as well as diseases associated with an insufficiency of histidyl-tRNA synthetase) include without limitation, autoimmune diseases, inflammatory diseases, and inflammatory myopathies, including inflammatory myopathies, polymyositis, statin induced myopathies, dermatomyositis, interstitial lung disease (and other pulmonary fibrotic conditions) and related disorders, such as polymyositis-scleroderma overlap and inclusion body myositis (IBM) and conditions such as those found in anti-synthetase syndromes, including for example, interstitial lung disease, arthritis, esophageal dysmotility, cardiovascular disease and other vascular manifestations such as Reynaud's phenomenon; other examples of diseases associated with an insufficiency of histidyl-tRNA synthetase include genetic disorders that result in an insufficiency of active histidyl-tRNA synthetase including Usher syndrome and Perrault syndrome. Further examples of diseases of histidyl-tRNA synthetase insufficiency include inflammatory diseases and disorders associated with insufficient local production of histidyl-tRNA synthetase within a tissue, or at the site of injury or inflammation. In some aspects the histidyl-tRNA synthetase insufficiency is associated with one or more of rhabdomyolysis, cachexia, and/or muscle injury.

In certain embodiments, by blocking the binding, action, or production of ant-histidyl-tRNA synthetase antibodies, the compositions and methods described herein have utility to treat a broad range of auto-immune and inflammatory diseases and disorders associated with anti-histidyl-tRNA synthetase antibodies, other auto-antibodies, as well as diseases associated with histidyl-tRNA synthetase insufficiency.

Additionally the administration of HRS polypeptides of the invention, by restoring the concentration of histidyl-tRNA synthetase (in the absence of anti histidyl-tRNA synthetase antibodies)—can modulate local inflammatory responses which are effective both in the treatment of a broad range of inflammatory diseases and disorders, as well as diseases in inflammation is secondary to the primary disease, as in the case, for example with muscular dystrophies.

Certain embodiments include methods of treating a myositis comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide. In some embodiments, the myositis is polymyositis. In some embodiments, the myositis is dermatomyositis.

Some embodiments include methods of treating inclusion body myositis (IBM) comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Also included are methods of treating juvenile myositis comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Certain embodiments include methods of treating a statin-induced myopathy comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide. In some embodiments, the statin is cerivastatin.

Some embodiments include methods of treating an interstitial lung disease (ILD) comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Certain embodiments include methods of treating Usher Syndrome comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide. Certain embodiments include methods of treating type 1 Usher Syndrome. Some embodiments include methods of treating type 2 Usher Syndrome. Certain embodiments include methods of treating type 3 Usher Syndrome.

Some embodiments include methods of treating Perrault syndrome (PS) comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Also included are methods of treating a muscular dystrophy comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide. In some aspects, the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy and congenital muscular dystrophy.

Also included are methods of treating cachexia comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Also included are methods of treating rhabdomyolysis comprising administering to a subject in need thereof a composition comprising one or more of i) a HRS polypeptide, ii) a recombinant nucleic acid encoding a heterologous HRS polypeptide, or iii) a recombinant host cell; wherein the host cell expresses at least one heterologous HRS polypeptide.

Certain exemplary inflammatory or autoimmune disorders are described in greater detail below.

Polymyositis affects skeletal muscles (involved with making movement) on both sides of the body. It is rarely seen in persons under age 18; most cases are in people between the ages of 31 and 60. In addition to symptoms listed above, progressive muscle weakness leads to difficulty swallowing, speaking, rising from a sitting position, climbing stairs, lifting objects, or reaching overhead. People with polymyositis may also experience arthritis, shortness of breath, and heart arrhythmias.

Dermatomyositis is characterized by a skin rash that precedes or accompanies progressive muscle weakness. The rash looks patchy, with purple or red discolorations, and characteristically develops on the eyelids and on muscles used to extend or straighten joints, including knuckles, elbows, knees, and toes. Red rashes may also occur on the face, neck, shoulders, upper chest, back, and other locations, and there may be swelling in the affected areas. The rash sometimes occurs without obvious muscle involvement. Adults with dermatomyositis may experience weight loss or a low-grade fever, have inflamed lungs, and be sensitive to light. Adult dermatomyositis, unlike polymyositis, may accompany tumors of the breast, lung, female genitalia, or bowel. Children and adults with dermatomyositis may develop calcium deposits, which appear as hard bumps under the skin or in the muscle (called calcinosis). Calcinosis most often occurs 1-3 years after disease onset but may occur many years later. These deposits are seen more often in childhood dermatomyositis than in dermatomyositis that begins in adults. Dermatomyositis may be associated with collagen-vascular or autoimmune diseases.

In some cases of polymyositis and dermatomyositis, distal muscles (away from the trunk of the body, such as those in the forearms and around the ankles and wrists) may be affected as the disease progresses. Polymyositis and dermatomyositis may be associated with collagen-vascular or autoimmune diseases. Polymyositis may also be associated with infectious disorders.

Inclusion body myositis (IBM) is characterized by progressive muscle weakness and wasting. The onset of muscle weakness is generally gradual (over months or years) and affects both proximal and distal muscles. Muscle weakness may affect only one side of the body. Small holes called vacuoles are sometimes seen in the cells of affected muscle fibers. Falling and tripping are usually the first noticeable symptoms of IBM. For some individuals the disorder begins with weakness in the wrists and fingers that causes difficulty with pinching, buttoning, and gripping objects. There may be weakness of the wrist and finger muscles and atrophy (thinning or loss of muscle bulk) of the forearm muscles and quadricep muscles in the legs. Difficulty swallowing occurs in approximately half of IBM cases. Symptoms of the disease usually begin after the age of 50, although the disease can occur earlier. Unlike polymyositis and dermatomyositis, IBM occurs more frequently in men than in women.

Juvenile myositis has some similarities to adult dermatomyositis and polymyositis. It typically affects children ages 2 to 15 years, with symptoms that include proximal muscle weakness and inflammation, edema (an abnormal collection of fluids within body tissues that causes swelling), muscle pain, fatigue, skin rashes, abdominal pain, fever, and contractures (chronic shortening of muscles or tendons around joints, caused by inflammation in the muscle tendons, which prevents the joints from moving freely). Children with juvenile myositis may also have difficulty swallowing and breathing, and the heart may be affected. Approximately 20 to 30 percent of children with juvenile dermatomyositis develop calcinosis. Affected children may not show higher than normal levels of the muscle enzyme creatine kinase in their blood but have higher than normal levels of other muscle enzymes.

Statin-Induced Myopathies are associated with the long term use of statins which act via the inhibition of 3-hydroxy-3-methylglutaryl coenzyme A reductase (HMGCR). Generally well-tolerated, these medications have been described as inducers of myotoxicity. More recently, there have been reports of patients in whom statin myopathies persist even after drug cessation, which are hypothesized to have an autoimmune cause. The benefits of statins are undisputed in reducing the risk of coronary heart disease and the progression of coronary atherosclerosis. Nevertheless, associated complications can be life-threatening. More than 38 million people in the U.S. are currently estimated to be taking statins and up to 7% (>2.6 million) of these are predicted to develop muscle symptoms with up to 0.5% (>190,000) of these potentially going on to develop life-threatening myopathies.

All the statins can cause muscle problems and the risk increases along with increases in their lipophilicity, cholesterol-lowering potency, and dosage. Cerivastatin in particular has been implicated as having a higher risk and it has been withdrawn from the US market. Of the remaining statins, atorvastatin and simvastatin have higher myotoxicity rates. Other nonstatin lipid-lowering agents such as niacin and fibrates also carry risks of muscle problems, particularly when combined with statins. While it is not possible to predict what patients will have statin-induced muscle problems, prior muscle problems may be a risk factor and should be considered when initiating statin treatment. A family history of myopathy is relevant if a patient might be a carrier of a genetic myopathy because it could be unmasked by the added stress of statin treatment. Other risk factors may include age over 80 years, low body weight, female sex, hypothyroidism, certain genetic defects and Asian descent, as well as concomitant use of certain medications, including calcium channel blockers, macrolide antibiotics, omeprazole, amiodarone, azole antifungals, histamine $H_2$ receptor antagonists, nefazodone, cyclosporin, HIV protease inhibitors, warfarin, and grapefruit juice.

The most common muscle symptom caused by statins is muscle pain or myalgia and it occurs in about 7% of statin users. The myalgia can be anywhere from mild to severe and is often worsened by muscle activity. If the symptom is tolerable and the indication for statin treatment strong, for example, in a patient with hypercholesterolemia and a recent myocardial infarction, continued statin treatment may be appropriate.

Baseline creatine kinase (CK) levels are not uniformly recommended before initiation of statin treatment by the organizations guiding statin treatment, but CK levels can provide very useful information if muscle symptoms later develop. Muscle weakness can also occur, and it is often fatigable in quality and combined with pain and elevated CK. Like most myopathies, the weakness is most pronounced proximally. Rare episodes of rhabdomyolysis have also occurred with statin therapy; these are far less frequent but can possibly be fatal. The changes that can be seen on muscle histology that are most typical of a statin myopathy are cytochrome oxidase negative fibers, increased lipid content, and ragged red fibers. Autoimmune necrotizing myopathy is a rare form of statin myopathy. In these patients, discontinuation of the statin drug does not translate into recovery even after several months off the drug. Patients have a predominantly proximal, often painless weakness.

Diagnosis is based on the individual's medical history, results of a physical exam and tests of muscle strength, and blood samples that show elevated levels of various muscle enzymes and autoantibodies. Diagnostic tools include electromyography to record the electrical activity that controls muscles during contraction and at rest, ultrasound to look for muscle inflammation, and magnetic resonance imaging to reveal abnormal muscle and evaluate muscle disease. A muscle biopsy can be examined by microscopy for signs of chronic inflammation, muscle fiber death, vascular deformities, or the changes specific to the diagnosis of IBM. A skin biopsy can show changes in the skin layer in patients with dermatomyositis.

Interstitial lung disease (ILD) is a broad category of lung diseases that includes more than 130 disorders characterized by scarring (i.e., "fibrosis") and/or inflammation of the lungs. ILD accounts for 15 percent of the cases seen by pulmonologists. Interstitial lung disease (ILD) can develop from a variety of sources, ranging from other diseases to environmental factors. Some of the known causes of ILD include: connective tissue or autoimmune disease, including for example, scleroderma/progressive systemic sclerosis, Lupus (systemic lupus erythematosus), rheumatoid arthritis and polymyositis/dermatomyositis; occupational and environmental exposures, including for example, exposure to dust and certain gases, poisons, chemotherapy and radiation therapy.

In ILD, the tissue in the lungs becomes inflamed and/or scarred. The interstitium of the lung includes the area in and around the small blood vessels and alveoli (air sacs) where the exchange of oxygen and carbon dioxide takes place. Inflammation and scarring of the interstitium disrupts this tissue and leads to a decrease in the ability of the lungs to extract oxygen from the air.

The progression of ILD varies from disease to disease and from person to person. Because interstitial lung disease disrupts the transfer of oxygen and carbon dioxide in the lungs, its symptoms typically manifest as problems with breathing. The two most common symptoms of ILD are shortness of breath with exercise and a non-productive cough.

Usher Syndrome is the most common condition that affects both hearing and vision. The major symptoms of Usher syndrome are hearing loss and retinitis pigmentosa, (RP). RP causes night-blindness and a loss of peripheral vision (side vision) through the progressive degeneration of the retina. As RP progresses, the field of vision narrows until only central vision remains. Many people with Usher syndrome also have severe balance problems. Approximately 3 to 6 percent of all children who are deaf and another 3 to 6 percent of children who are hard-of-hearing have Usher syndrome. In developed countries such as the United States, about four babies in every 100,000 births have Usher syndrome. Usher syndrome is inherited as an autosomal recessive trait. Several genetic loci have been associated with Usher syndrome including histidyl-tRNA synthetase (Puffenberger et al., (2012) *PLoS ONE* 7 (1) e28936 doi: 10.1371/journal.pone.0028936)

There are three clinical types of Usher syndrome: type 1, type 2, and type 3. In the United States, types 1 and 2 are the most common types. Together, they account for approximately 90 to 95 percent of all cases of children who have Usher syndrome.

Children with type 1 Usher syndrome are profoundly deaf at birth and have severe balance problems. Because of the balance problems associated with type 1 Usher syndrome, children with this disorder are slow to sit without support and typically don't walk independently before they are 18 months old. These children usually begin to develop vision problems in early childhood, almost always by the time they reach age 10. Vision problems most often begin with difficulty seeing at night, but tend to progress rapidly until the person is completely blind.

Children with type 2 Usher syndrome are born with moderate to severe hearing loss and normal balance. Although the severity of hearing loss varies, most of these children can benefit from hearing aids and can communicate orally. The vision problems in type 2 Usher syndrome tend to progress more slowly than those in type 1, with the onset of RP often not apparent until the teens.

Children with type 3 Usher syndrome have normal hearing at birth. Although most children with the disorder have normal to near-normal balance, some may develop balance problems later on. Hearing and sight worsen over time, but the rate at which they decline can vary from person to person, even within the same family. A person with type 3 Usher syndrome may develop hearing loss by the teens, and he or she will usually require hearing aids by mid- to late adulthood. Night blindness usually begins sometime during puberty. Blind spots appear by the late teens to early adulthood, and, by mid-adulthood, the person is usually legally blind.

Perrault syndrome (PS) is characterized by the association of ovarian dysgenesis in females with sensorineural hearing impairment, and in some subjects, neurologic abnormalities, including progressive cerebellar ataxia and intellectual deficit. The exact prevalence for Perrault syndrome is unknown, and is probably under-diagnosed, particularly in males where hypogonadism is not a feature and the syndrome remains undetected. Mean age at diagnosis is 22 years following presentation with delayed puberty in females with sensorineural deafness. Hearing defects were noted in all but one of the reported cases (mean age at diagnosis of 8 years). The hearing loss is always sensorineural and bilateral but the severity is variable (mild to profound), even in affected patients from the same family. Ovarian dysgenesis has been reported in all female cases but no gonad defects are detected in males. Amenorrhea is generally primary but secondary amenorrhea has also been reported. Delayed growth (height below the third percentile) was reported in half the documented cases.

The exact frequency of the neurological abnormalities is unknown, but nine females and two males (16-37 years old) lacking neurological abnormalities have been reported. Neurological signs are progressive and generally appear later in life, however, walking delay or early frequent falls have been noted in young PS patients. Common neurological signs are ataxia, dyspraxia, limited extraocular movements, and polyneuropathy. Some cases with scoliosis have also been reported. Transmission of PS is autosomal recessive and mutations in mitochrondrial histidyl-tRNA synthetase have recently been identified to cause the ovarian dysgenesis and sensorineural hearing loss associated with Perrault syndrome. (Pierce et al., (2011) *PNAS USA*. 108(16) 6543-6548).

Muscular dystrophy refers to a group of inherited disorders in which strength and muscle bulk gradually decline. All of the muscular dystrophies are marked by muscle weakness that is driven by a primary genetic defect in one or more muscle specific genes. Additionally muscular dystrophies, typically have a variable inflammatory component that drives muscular inflammation and ultimately enhances the degeneration of muscular tissues. At least nine types of muscular dystrophies are generally recognized.

Duchenne Muscular Dystrophy (DMD):

DMD affects young boys, causing progressive muscle weakness, usually beginning in the legs. It is the most severe form of muscular dystrophy. DMD occurs in about 1 in 3,500 male births, and affects approximately 8,000 boys and young men in the United States. A milder form occurs in very few female carriers.

DMD is caused by mutations in the gene encoding dystrophin, a subsarcolemmal protein functioning within the dystrophin-associated glycoprotein complex (DGC) which prevent the production of functional protein. The amount of dystrophin correlates with the severity of the disease (i.e., the less dystrophin present, the more severe the phenotype). The DGC complex connects the intracellular cytoskeleton to the extracellular matrix. The DGC is concentrated at the Z-lines of the sarcomere and confers the transmission of force across the muscle fibre. Disruption of this link results in membrane instability, which eventually leads to sarcolemmal ruptures. Influx of extracellular calcium alters molecular processes like muscle contraction and activates proteolytic activity. Affected muscle fibres become necrotic or apoptotic, and release mitogenic chemoattractants, which initiate inflammatory processes. Cycles of degeneration and regeneration eventually lead to irreversible muscle wasting and replacement by fibrotic and adipose tissue.

A boy with Duchenne muscular dystrophy usually begins to show symptoms as a pre-schooler. The legs are affected first, making walking difficult and causing balance problems. Most patients walk three to six months later than expected and have difficulty running. Contractures (permanent muscle tightening) usually begin by age five or six, most severely in the calf muscles. Frequent falls and broken bones are common beginning at this age. Climbing stairs and rising unaided may become impossible by age nine or ten, and most boys use a wheelchair for mobility by the age of 12. Weakening of the trunk muscles around this age often leads to scoliosis (a side-to-side spine curvature) and kyphosis (a front-to back curvature).

One of the most serious weakness of DMD is weakness of the diaphragm, the sheet of muscles at the top of the abdomen that perform the main work of breathing and coughing. Diaphragm weakness leads to reduced energy and stamina, and increased lung infection because of the inability to cough effectively. Young men with DMD can live into their twenties and beyond, provided they have mechanical ventilation assistance and good respiratory hygiene.

In some embodiments, a subject having DMD is characterized by one or more of the following: a positive Gower's sign, reflecting impairment of the lower extremity muscles; high levels of creatine kinase (CPK-MM) in the blood; genetic errors in the Xp21 gene; or reduced levels of absence of dystrophin, for instance, as measured by muscle biopsy.

HRS compositions may be used in the treatment of DMD, either alone or in combination with other therapies, such as antisense oligonucleotides (e.g., exon-skipping therapies such as Eteplirsen), corticosteroids, beta2-agonists, physical therapy, respiratory support, stem cell therapies, and gene replacement therapies. In some embodiments, administration of HRS polypeptides leads to statistically significant improvements in the 6-minute walk test.

Becker Muscular Dystrophy (BMD):

BMD affects older boys and young men, following a milder course than DMD. BMD occurs in about 1 in 30,000 male births. Becker muscular dystrophy is a less severe variant of Duchenne muscular dystrophy and is caused by the production of a truncated, but partially functional form of dystrophin.

The symptoms of BMD usually appear in late childhood to early adulthood. Though the progression of symptoms may parallel that of DMD, the symptoms are usually milder and the course more variable. Scoliosis may occur, but is usually milder and progresses more slowly. Heart muscle disease (cardiomyopathy), occurs more commonly in BMD. Problems may include irregular heartbeats (arrhythmias) and congestive heart failure. Symptoms may include fatigue, shortness of breath, chest pain, and dizziness. Respiratory weakness also occurs, and may lead to the need for mechanical ventilation.

Emery-Dreifuss Muscular Dystrophy (EDMD):

EDMD affects young boys, causing contractures and weakness in the calves, weakness in the shoulders and upper arms, and problems in the way electrical impulses travel through the heart to make it beat (heart conduction defects). There are three subtypes of Emery-Dreifuss Muscular Dystrophy, distinguishable by their pattern of inheritance: X-Linked, autosomal dominant and autosomal recessive. The X-linked form is the most common Each type varies in prevalence and symptoms. The disease is caused by mutations in the LMNA gene, or more commonly, the EMD gene. Both genes encode for protein components of the nuclear envelope.

EDMD usually begins in early childhood, often with contractures preceding muscle weakness. Weakness affects the shoulder and upper arm originally, along with the calf muscles, leading to foot-drop. Most men with EDMD survive into middle age, although a defect in the heart's rhythm (heart block) may be fatal if not treated with a pacemaker.

Limb-Girdle Muscular Dystrophy (LGMD):

LGMD begins in late childhood to early adulthood and affects both men and women, causing weakness in the muscles around the hips and shoulders. It is the most variable of the muscular dystrophies, and there are several different forms of the disease now recognized. Many people with suspected LGMD have probably been misdiagnosed in the past, and therefore the prevalence of the disease is difficult to estimate. The number of people affected in the United States may be in the low thousands.

While there are at least a half-dozen genes that cause the various types of LGMD, two major clinical forms of LGMD are usually recognized. A severe childhood form is similar in appearance to DMD, but is inherited as an autosomal recessive trait.

Limb Girdle Muscular Dystrophy type 2B (LGMD2B) is caused by the loss of function mutations in the dysferlin gene. Dysferlin is primarily expressed in skeletal and cardiac muscle, but also in monocytes, macrophages, and other tissues where it is localized to cytoplasmic vesicles and the cell membrane. Dysferlin appears to be involved in membrane fusion and trafficking, as well as repair processes. LGMD2B is a late onset (teens/young adults) muscle disease that is characterized by progressive symmetrical muscle weakness, and notably aggressive immune/inflammatory pathology. Muscle biopsies typically show marked inflammatory cell infiltration, consisting primarily of macrophages/macrophage activation markers (HLA-DR, HLA-ABC, CD86), CD8$^+$ cytotoxic T cells, and CD4$^+$ T cells, together with muscle fiber degeneration/regeneration.

Symptoms of adult-onset LGMD usually appear in a person's teens or twenties, and are marked by progressive weakness and wasting of the muscles closest to the trunk. Contractures may occur, and the ability to walk is usually lost about 20 years after onset. Some people with LGMD develop respiratory weakness that requires use of a ventilator. Lifespan may be somewhat shortened. (Autosomal dominant forms usually occur later in life and progress relatively slowly.)

Facioscapulohumeral Muscular Dystrophy (FSH):

FSH, also known as Landouzy-Dejerine disease, begins in late childhood to early adulthood and affects both men and women, causing weakness in the muscles of the face, shoulders, and upper arms. The hips and legs may also be affected. FSH occurs in about 1 out of every 20,000 people, and affects approximately 13,000 people in the United States.

FSH varies in its severity and age of onset, even among members of the same family. Symptoms most commonly begin in the teens or early twenties, though infant or childhood onset is possible. Symptoms tend to be more severe in those with earlier onset. The disease is named for the regions of the body most severely affected by the disease: muscles of the face (facio-), shoulders (scapulo-), and upper arms (humeral). Hips and legs may be affected as well. Children with FSH often develop partial or complete deafness.

Two defects are needed for FSHD, the first is the deletion of D4Z4 repeats and the second is a "toxic gain of function" of the DUX4 gene. The first symptom noticed is often difficulty lifting objects above the shoulders. The weakness may be greater on one side than the other. Shoulder weakness also causes the shoulder blades to jut backward, called scapular winging.

Myotonic Dystrophy:

Myotonic dystrophy, also known as Steinert's disease, affects both men and women, causing generalized weakness first seen in the face, feet, and hands. It is accompanied by the inability to relax the affected muscles (myotonia). Symptoms may begin from birth through adulthood. Myotonic muscular dystrophy type 1 (DM1) is the most common form of muscular dystrophy, affecting more than 30,000 people in the United States. It results from the expansion of a short (CTG) repeat in the DNA sequence of the DMPK (myotonic dystrophy protein kinase) gene. Myotonic muscular dystrophy type 2 (DM2) is much rarer and is a result of the expansion of the CCTG repeat in the ZNF9 (zinc finger protein 9) gene.

Symptoms of myotonic dystrophy include facial weakness and a slack jaw, drooping eyelids (ptosis), and muscle wasting in the forearms and calves. A person with this dystrophy has difficulty relaxing his grasp, especially if the object is cold. Myotonic dystrophy affects heart muscle, causing arrhythmias and heart block, and the muscles of the digestive system, leading to motility disorders and constipation. Other body systems are affected as well: Myotonic dystrophy may cause cataracts, retinal degeneration, low IQ, frontal balding, skin disorders, testicular atrophy, sleep apnea, and insulin resistance. An increased need or desire for sleep is common, as is diminished motivation. Severe disability affects most people with this type of dystrophy within 20 years of onset, although most do not require a wheelchair even late in life. HRS compositions can be used to treat myotonic dystrophy, for instance, by reducing inflammation associated with muscle tissue, including skeletal muscle (e.g., quadricep muscles) and/or heart tissue, among other tissues.

Oculopharyngeal Muscular Dystrophy (OPMD):

OPMD affects adults of both sexes, causing weakness in the eye muscles and throat. It is most common among French Canadian families in Quebec, and in Spanish-American families in the southwestern United States.

OPMD usually begins in a person's thirties or forties, with weakness in the muscles controlling the eyes and throat. Symptoms include drooping eyelids, difficulty swallowing (dysphagia), and weakness progresses to other muscles of the face, neck, and occasionally the upper limbs. Swallowing difficulty may cause aspiration, or the introduction of food or saliva into the airways. Pneumonia may follow.

Distal Muscular Dystrophy (DD):

DD begins in middle age or later, causing weakness in the muscles of the feet and hands. It is most common in Sweden, and rare in other parts of the world. DD usually begins in the twenties or thirties, with weakness in the hands, forearms, and lower legs. Difficulty with fine movements such as typing or fastening buttons may be the first symptoms. Symptoms progress slowly, and the disease usually does not affect life span.

Congenital Muscular Dystrophy (CMD):

CMD is present from birth, results in generalized weakness, and usually progresses slowly. A subtype, called Fukuyama CMD, also involves mental retardation. Both are rare; Fukuyama CMD is more common in Japan.

CMD is marked by severe muscle weakness from birth, with infants displaying "floppiness" and very little voluntary movement. Nonetheless, a child with CMD may learn to walk, either with or without some assistive device, and live into young adulthood or beyond. In contrast, children with Fukuyama CMD are rarely able to walk, and have severe mental retardation. Most children with this type of CMD die in childhood.

Cachexia:

Cachexia (or wasting syndrome) is typically characterized by loss of weight, muscle atrophy, fatigue, weakness, and significant loss of appetite in someone who is not actively trying to lose weight. The formal definition of cachexia is the loss of body mass that cannot be reversed nutritionally. Even if the affected patient consumes more calories, lean body mass is lost, indicating the existence of a primary pathology.

Cachexia is experienced by patients with cancer, AIDS, chronic obstructive lung disease, multiple sclerosis, congestive heart failure, tuberculosis, familial amyloid polyneuropathy, mercury poisoning (acrodynia), and hormonal deficiency, among other disease.

Cachexia can also be a sign of various underlying disorders, including cancer, metabolic acidosis (i.e., decreased protein synthesis and increased protein catabolism), certain infectious diseases (e.g., tuberculosis, AIDS), chronic pancreatitis, autoimmune disorders, or addiction to amphetamines. Cachexia physically weakens patients to a state of immobility stemming from loss of appetite, asthenia, and anemia, and response to standard treatment is usually poor.

About 50% of all cancer patients suffer from cachexia. Those with upper gastrointestinal and pancreatic cancers have the highest frequency of developing a cachexic symptom. In addition to increasing morbidity and mortality, aggravating the side effects of chemotherapy, and reducing quality of life, cachexia is considered the immediate cause of death of a large proportion of cancer patients, ranging from 22% to 40% of the patients. Symptoms of cancer cachexia include progressive weight loss and depletion of host reserves of adipose tissue and skeletal muscle. Traditional treatment approaches include the use of appetite stimulants, 5-$HT_3$ antagonists, nutrient supplementation, and COX-2 inhibitors.

Although the pathogenesis of cachexia is poorly understood, multiple biologic pathways are expected to be involved, including pro-inflammatory cytokines such as TNF-α, neuroendocrine hormones, IGF-1, and tumor-specific factors such as proteolysis-inducing factor.

HRS compositions may thus be used to treat cachexia and any of its related, underlying, or secondary disorders or complications. HRS compositions can be used alone or in combination with other therapies, such as dietary supplementation with a combination of high protein, leucine and fish oil, antioxidants, progestogen (megestrol acetate, medroxyprogesterone acetate), and anticyclooxygenase-2 drugs, appetite stimulants, and 5-$HT_3$ antagonists, among others.

Rhabdomyolysis:

Rhabdomyolysis is the breakdown of muscle fibers in skeletal muscle tissue. The breakdown products are released into the bloodstream, and certain some of these products, such as myoglobin, are harmful to the kidneys and may lead to kidney failure.

Symptoms include muscle pain, vomiting, confusion, coma, or abnormal heart rate and rhythm and their severity usually depends on the extent of muscle damage and whether kidney failure develops. Damage to the kidneys may cause decreased or absent urine production, usually about 12 to 24 hours after the initial muscle damage. Swelling of the damaged muscle can cause compartment syndrome, or compression of surrounding tissues, such as nerves and blood vessels, in the same fascial compartment, and lead to blood loss and damage to (e.g., loss of function) the affected body parts. Symptoms of this complication include pain or reduced sensation in the affected limb. Other complications include disseminated intravascular coagulation (DIC), a severe disruption in blood clotting that may lead to uncontrollable bleeding.

The initial muscle damage may be caused, for instance, by physical factors (e.g. crush injury, strenuous exercise), altered blood supply (e.g., arterial thrombosis, embolism), altered metabolism (e.g., hyperglycemic hyperosmolar state, hyper- and hyponatremia, hypokalemia, hypocalcemia, hypophosphatemia, ketoacidosis, hypothyroidism), altered body temperature (hyperthermia, hypothermia), medications and toxins (e.g., statins, anti-psychotic medications, neuromuscular blocking agents, diuretics, heavy metals, hemlock, insect or snake venoms), drug abuse (e.g., alcohol, amphetamine, cocaine, heroin, ketamine, LDS, MDMA), infections (e.g., Coxsackie virus, influenza A virus, influenza B virus, Epstein-Barr virus, primary HIV infection, *Plasmodium falciparum*, herpes viruses, *Legionella pneumophila, salmonella*), and autoimmune muscle damage (e.g., polymyositis, dermatomyositis). Also, certain hereditary conditions increase the risk of rhabdomyolysis, including glycolysis and glycogenolysis defects (e.g., McArdle's disease, phosphofructokinase deficiency, glycogen storage diseases VIII, IX, X and XI), lipid metabolism defects (e.g., carnitine palmitoyltransferase I and II deficiency, deficiency of subtypes of acyl CoA dehydrogenase (e.g., LCAD, SCAD, MCAD, VLCAD, 3-hydroxyacyl-coenzyme A dehydrogenase deficiency), thiolase deficiency), mitochondrial myopathies (e.g., deficiency of succinate dehydrogenase, cytochrome c oxidase and coenzyme Q10), and others such as glucose-6-phosphate dehydrogenase deficiency, myoadenylate deaminase deficiency, and muscular dystrophies.

Rhabdomyolysis is usually diagnosed with blood tests and urinalysis, and can be indicated by abnormally raised or increasing creatinine and urea levels, falling urine output, or reddish-brown discoloration of the urine. The primary treatments include intravenous fluids, dialysis, and hemofiltration.

HRS compositions may thus be used to treat rhabdomyolysis and any of its related, secondary, or underlying disorders or complications. HRS compositions can be used alone or in combination with other therapies, including those meant to treat shock and preserve kidney function. Exemplary therapies include administration of intravenous fluids, usually isotonic saline (0.9% weight per volume sodium chloride solution) and renal replacement therapies (RRT) such as hemodialysis, continuous hemofiltration and peritoneal dialysis.

More generally, the HRS polypeptides described herein can reduce an inflammatory response, such as by reducing the migration or infiltration of immune cells into selected tissues, increasing the production of anti-inflammatory cytokines, or reducing the production or activity of pro-inflammatory cytokines, among other mechanisms.

Accordingly, the HRS polypeptides of the invention can be used to modulate acute inflammation, chronic inflammation, or both. Certain embodiments relate to increasing acute inflammation or acute inflammatory responses, and certain embodiments relate to increasing chronic inflammation or chronic inflammatory responses. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, lymphocytes, Kuppfer cells and T cells. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of preformed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, HRS polypeptides may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected, (see, e.g., Kumar et al, Robbins Basic Pathology-$S^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, HRS polypeptides may be used to treat or manage chronic inflammation, modulate any of one or more of the individual chronic inflammatory responses, or treat any one or more diseases or conditions associated with chronic inflammation.

HRS polypeptides may also modulate proliferative inflammation, an inflammatory process characterized by an increase in the number of tissue cells. These can encompass skin conditions such as psoriasis, seborrhea or eczema, or can also be thought of in terms of cancers and abnormal growths especially in light of accumulating evidence based on more efficient molecular methods to document even low grade chronic inflammation.

In certain embodiments, HRS polypeptides can modulate inflammatory responses at the cellular level, such as by modulating the activation, inflammatory molecule secretion (e.g., cytokine or kinin secretion), proliferation, activity, migration, or adhesion of various cells involved in inflammation. Examples of such cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including T 1 and T 2 cells), natural killer cells, γδ T-cells, dendritic cells, and mast cells. Examples of vascular cells include smooth muscle cells, endothelial cells, and fibroblasts. Also included are methods of modulating an inflammatory condition associated with one or more immune cells or vascular cells, including neutrophil-mediated, macrophage-mediated, and lymphocyte-mediated inflammatory conditions.

In certain embodiments, HRS polypeptides modulate local inflammation, systemic inflammation, or both. In certain embodiments, HRS polypeptide may reduce or maintain (i.e., prevent further increases) local inflammation or local inflammatory responses. In certain embodiments, depending on the needs of the subject, HRS polypeptides may increase local inflammation or local inflammatory responses. In certain embodiments, HRS polypeptides may reduce or maintain (i.e., prevent further increases) systemic inflammation or systemic inflammatory responses. In certain embodiments, depending on the needs of the subject, HRS polypeptides may increase systemic inflammation or systemic inflammatory responses.

In certain embodiments, the modulation of inflammation or inflammatory responses can be associated with one or more tissues or organs. Non-limiting examples of such tissues or organs include skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, HRS polypeptides may be used to modulate inflammation associated with any of these tissues or organs, such as to treat conditions or diseases that are associated with the inflammation of these tissues or organs.

As noted above, certain embodiments may employ HRS polypeptides to reduce or manage (i.e., prevent further increases) inflammation or inflammatory responses associated with particular tissues or organs. Included are inflammatory responses and conditions associated with the skin, including inflammation, infections, and cancers associated with the dermal, epidermal, and subcutaneous layers of the skin. Examples of skin-associated inflammatory conditions include, without limitation, dermatitis, such as psoriasis, irritant dermatitis, seborrheic dermatitis, atopic dermatitis (eczema), allergic contact dermatitis, thermal-induced dermatitis, drug-induced dermatitis, dyshidrotic dermatitis, urticaria, autoimmune dermatitis, skin cancer such as melanoma, and bullous dermatitis. Also included are bacterial, viral and parasitic infections, erythema multiforme, erythema nodosum, granuloma annulare, poison oak/poison ivy, and toxic epidermal necrolysis.

Certain embodiments relate to reducing inflammatory responses and conditions associated with the nervous system, including inflammation, infections, and cancer associated with the brain and spinal cord of the central nervous system, the peripheral nervous system, and the meninges. Expression of inflammatory mediators including complement, adhesion molecules, cyclooxygenase enzymes and their products and cytokines is increased in experimental and clinical neurodegenerative disease, and intervention studies in experimental animals suggest that several of these factors contribute directly to neuronal injury. For instance, specific cytokines, such as interleukin-1 (IL-1), have been implicated heavily in acute neurodegeneration, such as stroke and head injury.

Examples of nervous system associated inflammatory conditions include, without limitation, meningitis (i.e., inflammation of the protective membranes covering the brain and spinal cord), myelitis, encaphaloymyelitis (e.g., myalgic encephalomyelitis, acute disseminated encephalomyelitis, encephalomyelitis disseminata or multiple sclerosis, autoimmune encephalomyelitis), arachnoiditis (i.e., inflammation of the arachnoid, one of the membranes that surround and protect the nerves of the central nervous system), granuloma, drug-induced inflammation or meningitis, neurodegenerative diseases such as Alzheimer's disease, stroke, HIV-dementia, Sly syndrome, CMT, retinopathy, sensoriuenural hearing loss, Spinal muscular atrophy, ALS encephalitis such viral encephalitis and bacterial encephalitis, parasitic infections, inflammatory demyelinating disorders, and auto-immune disorders such as CD 8+ T Cell-mediated autoimmune diseases of the CNS. Additional examples include Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, and stiff-man syndrome.

As noted above, also included is inflammation associated with infections of the nervous system. Specific examples of bacterial infections associated with inflammation of the nervous system include, without limitation, streptococcal infection such as group B streptococci (e.g., subtypes III) and *Streptococcus pneumoniae* (e.g., serotypes 6, 9, 14, 18 and 23), *Escherichia coli* (e.g., carrying K1 antigen), *Listeria monocytogenes* (e.g., serotype IVb), neisserial infection such as *Neisseria meningitidis* (meningococcus), staphylococcal infection, *heamophilus* infection such as *Haemophilus influenzae* type B, *Klebsiella*, and *Mycobacterium tuberculosis*. Also included are infections by staphylococci and pseudomonas and other Gram-negative bacilli, mainly with respect to trauma to the skull, which gives bacteria in the nasal cavity the potential to enter the meningeal space, or in persons with cerebral shunt or related device (e.g., extraventricular drain, Ommaya reservoir). Specific examples of viral infections associated with inflammation of the nervous system include, without limitation, enteroviruses, herpes simplex virus type 1 and 2, human T-lymphotrophic virus, varicella zoster virus (chickenpox and shingles), mumps virus, human immunodeficiency virus (HIV), and lymphocytic choriomeningitis virus (LCMV). Meningitis may also result from infection by spirochetes such as *Treponema pallidum* (syphilis) and *Borrelia burgdorferi* (Lyme disease), parasites such as malaria (e.g., cerebral malaria), fungi such as *Cryptococcus neoformans*, and amoeba such as *Naegleria fowleri*.

Meningitis or other forms of nervous system inflammation may also associate with the spread of cancer to the meninges (malignant meningitis), certain drugs such as non-steroidal anti-inflammatory drugs, antibiotics and intravenous immunoglobulins, sarcoidosis (or neurosarcoidosis), connective tissue disorders such as systemic lupus erythematosus, and certain forms of vasculitis (inflammatory conditions of the blood vessel wall) such as Beliefs disease. Epidermoid cysts and dermoid cysts may cause meningitis by releasing irritant matter into the subarachnoid space. Accordingly, HRS polypeptides may be used to treat or manage any one or more of these conditions.

Certain embodiments relate to reducing inflammatory responses and conditions associated with the auditory system or balance organs, such as the inner ear, middle ear, and the outer ear. Examples of auditory system or balance organ associated inflammatory conditions include, without limitation, outer ear inflammation (e.g., ear infections), middle ear inflammation, which may lead to fluid build-up in the normally air-filled space and associated conductive hearing loss, labyrinthitis, an inner ear infection or inflammation causing both dizziness (vertigo) and hearing loss, vestibular neuronitis, an infection of the vestibular nerve, generally viral, causing vertigo, and cochlear neuronitis, an infection of the cochlear nerve, generally viral, causing sudden deafness but no vertigo. Recipients of cochlear implants for hearing loss are at an increased risk of pneumococcal meningitis and its associated inflammation.

Certain embodiments relate to reducing inflammatory responses and conditions associated with the respiratory system, including inflammation, infections, and cancer associated with the nose, trachea, and lungs. Examples of respiratory system associated inflammatory conditions include, without limitation, inflammatory lung diseases, atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema. Further examples include obstructive or inflammatory airways diseases such as chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, and adult respiratory distress syndrome (ARDS).

Further examples of conditions associated with pulmonary inflammation include conditions related to exacerbation of airways hyper-reactivity consequent to other drug therapy, airways disease that is associated with pulmonary hypertension, bronchitis such as acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury, and bronchiectasis such as cylindric bronchiectasis, sacculated bronchiectasis, fusiform bronchiectasis, capillary bronchiectasis, cystic bronchiectasis, dry bronchiectasis and follicular bronchiectasis.

COPD in particular refers to a group of lung diseases that block airflow and make it increasingly difficult for affected individuals to breathe normally. Emphysema and chronic bronchitis are the two main conditions within the group of COPD diseases, but COPD can also refer to damage caused by chronic asthmatic bronchitis, among other conditions known in the art. In most cases, damage to the airways eventually interferes with the exchange of oxygen and carbon dioxide in the lungs. Standard treatments focus mainly on controlling symptoms and minimizing further damage.

Emphysema represents one aspect of COPD. Emphysema leads to inflammation within the fragile walls of the alveoli, which may destroy some of the walls and elastic fibers, allowing small airways to collapse upon exhaling, and impairing airflow out of the lungs. Signs and symptoms of emphysema include, for instance, shortness of breath, especially during physical activities, wheezing, and chest tightness.

Chronic bronchitis represents another aspect of COPD. Chronic bronchitis is characterized by an ongoing cough, and leads to inflammation and narrowing of the bronchial tubes. This condition also causes increased mucus production, which can further block the narrowed tubes. Chronic bronchitis occurs mainly in smokers, and is typically defined as a cough that lasts for at least three months a year for two consecutive years. Signs and symptoms of chronic bronchitis include, for example, having to clear the throat first thing in the morning, especially for smokers, a chronic cough that produces yellowish sputum, shortness of breath in the later stages, and frequent respiratory infections. As noted above, COPD refers primarily to obstruction in the lungs resulting from the two above-noted chronic lung conditions. However, many individuals with COPD have both of these conditions.

Chronic asthmatic bronchitis represents another aspect of COPD which is usually characterized as chronic bronchitis combined with asthma (bronchospasm). Asthma may occur when inflamed and infected secretions irritate the smooth muscles in the airways. Symptoms are similar to those of chronic bronchitis, but also include intermittent, or even daily, episodes of wheezing.

In certain embodiments, COPD may also have an autoimmune component. For instance, lung and peripheral blood T cells in patients with severe emphysema secrete Th1 cytokines and chemokines when stimulated with elastin peptides in vitro, and these patients have increased anti-elastin antibody as compared to controls (see Goswami et al, The Journal of Immunology. 178: 130.41, 2007). Also, IgG autoantibodies with avidity for pulmonary epithelium, and the potential to mediate cytotoxicity, are prevalent in patients with COPD (see Feghali-Bostwick et al., Am J Respir Crit Care Med. 177: 156-63, 2008). Since autoreactive immune responses may be important in the etiology of this disease, including, for example, auto-reactive responses to self-antigens such as elastin, may play a role in COPD, the use of AARS polypeptides to desensitize immune cells to these antigens may reduce pulmonary inflammation.

As noted above, certain embodiments relate to the use of HRS polypeptides to desensitize immune cells to selected antigens, including self antigens and foreign antigens, irritants, allergens, or infectious agents related to pulmonary inflammation. By desensitizing these immune cells to a selected antigen, HRS polypeptides may reduce the migration or recruitment of these cells to the lungs, and thereby reduce inflammation. Examples of immune cells include lymphocytes, monocytes, macrophages, dendritic cells, and granulocytes, such as neutrophils, eosinophils, and basophils. Examples of antigens include, without limitation, smoke such as cigarette smoke, air pollution, fumes such as the fumes from welding, dust, including silica dust and workplace dust such as those found in coal mining and gold mining, chemicals such as cadmium and isocyanates. Also included are known allergens and infectious agents, such as bacterial and viral or antigens, including lipopolysaccharide (LPS), which may exacerbate COPD in sensitive individuals.

Certain embodiments relate to reducing inflammatory responses and conditions associated the gastrointestinal system, including inflammation, infections, and cancer associated with the mouth, esophagus, stomach, small intestines, large intestines, and rectum. "Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence.

"Mucosal layer of the gastrointestinal tract" is meant to include mucosa of the bowel (including the small intestine and large intestine), rectum, stomach (gastric) lining, oral cavity, and the like. "Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is often associated with infiltration or influx of mononuclear cells, and can be further associated with periods of spontaneous remission and spontaneous occurrence. "Chronic gastrointestinal inflammatory conditions" (also referred to as "chronic gastrointestinal inflammatory diseases") having such chronic inflammation include, but are not limited to, inflammatory bowel disease (IBD), colitis induced by environmental insults (e.g., gastrointestinal inflammation associated with a therapeutic regimen, such as chemotherapy, radiation therapy, and the like), colitis in conditions such as chronic granulomatous disease (see, e.g., Schappi et al, Arch Dis Child. 84: 147-151, 2001), celiac disease, celiac sprue (i.e., a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. The term IBD includes pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease; and within Crohn's disease all the subtypes including active, refractory, and fistulizing and Crohn's disease. Hence, HRS polypeptides may be employed to treat or manage any one or more of these conditions.

Certain embodiments relate to reducing inflammatory responses and conditions associated with the vascular system, or vascular inflammation, such as inflammation associated with the blood vessels and the heart. Examples of vascular system associated inflammatory conditions include, without limitation, myocarditis, pericarditis, occlusive disease, atherosclerosis, myocardial infarction, thrombosis, Autoimmune enteropathy, cardiomyopathy, Kawasaki disease, juvenile idiopathy arthritis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity in Chagas' disease, and anti-helper T lymphocyte autoimmunity. Also included are endocarditis, or infection of the heart valves with spread of small clusters of bacteria through the bloodstream, phlebitis or vasculitis, inflammation of one or more veins, and thrombophlebitis, vein inflammation related to a thrombus. Thrombophlebitis may occur repeatedly in different locations, and is then referred to as thrombophlebitis migrans, or migrating thrombophlebitis. Phlebitis may associate with a variety of causes, such as bacterial infection, exposure to chemical agents, such as irritating or vesicant solutions, physical trauma from skin puncture such as movement of a cannula into the vein during insertion, medications such as Celebrex, Olanzepine, antidepressants, and others, and alcohol abuse. Certain embodiments may relate to treating or managing heart inflammation caused by any one or more of acute rheumatic fever, congenital toxoplasmosis, enterovirus antenatal infection, lyme disease, and rheumatic fever.

Certain embodiments relate to reducing inflammatory responses and conditions associated with the liver or gallbladder, including acute and chronic liver inflammation, and acute and chronic cholecystis. Examples of liver or gallbladder associated inflammatory conditions include, without limitation, auto-immune hepatitis, viral hepatitis (e.g., Hepatitis A virus, Hepatitis B virus, Hepatitis C virus, Hepatitis D virus, Hepatitis E virus, mononucleosis, rubella, Epstein-Barr virus, and cytomegalovirus), other causes of hepatitis such as severe bacterial infection, amoebic infections, medicines (e.g., agomelatine, allopurinol, amitryptyline, amiodarone, asathioprine, paracetamol, halothane, ibuprofen, indomethacin, isoniazid, rifampicin, pyrazinamide, ketoconazole, loratadine, methotrexate, methyldopa, minocycline, nifedipine, nitrofurantoin, phenyloin, valproic acid, troglitazone, zidovudine), toxins (e.g., alcohol, fungal toxins), and metabolic disorders (e.g., Wilson's disease, a disorder of the body's copper metabolism, haemochromatosis, disorder of the body's iron metabolism, non-alcoholic steatohepatitis, alpha 1-antitrypsin deficiency). Additional examples include non-alcoholic fatty liver disease, cirrhosis such as primary biliary cirrhosis, obstructive jaundice, ischemic hepatitis, and gall bladder disease.

Certain embodiments relate to reducing inflammatory responses and conditions associated with the lymphatic/immune system. Examples of lymphatic/immune system associated inflammatory conditions include, without limitation, auto-immune diseases, such as Chagas disease, chronic obstructive pulmonary disorder (COPD), Crohn's disease, dermatomyositis, diabetes mellitus type I, endometriosis, Goodpasture's syndrome, Graves' disease, Guillain-Barre syndrome, Hashimoto's disease, hidradenitis suppurativa, Kawasaki disease, IgA nephropathy, (idiopathic) thrombocytopenia purpura, interstitial cystitis, lupus erythematosus, mixed connective tissue disease, morphea, myasthenia gravis, narcolepsy, neuromyotonia, pemphigus vulgaris, pernicous anemia, psoriasis, psoriatic arthritis, poliomyositis, primary biliary cirrhosis, rheumatoid arthritis, schizophrenia, scleroderma, Sjogren's syndrome, stiff person syndrome, temporal arteritis, ulcerative colitis, vitiligo, and Wegener's granulomatosis, in addition to autoimmune hemolytic anemia, and various lymphadenopathies.

Also included are immune-related inflammatory conditions associated with the transplantation of a graft, tissue, cell or organ, such as graft rejection, chronic graft rejection, subacute graft rejection, hyperacute graft rejection, acute graft rejection, and graft versus host disease. In certain embodiments, AARS polypeptides can be administered to a transplant donor before or during tissue removal. In certain embodiments, HRS polypeptides can be administered to a transplant recipient before, during, and/or after transplant therapy to reduce inflammation-related complications of transplant therapy. Examples of transplant therapies include bone marrow, stem cell, peripheral blood, liver, lung, heart, skin, and kidney, among others known in the art. Additional examples include inflammatory conditions associated with allergies, such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Certain embodiments relate to reducing inflammatory responses and conditions associated with the urogenital system. Examples of urogenital system associated inflammatory conditions include, without limitation, inflammations, infections or cancers of the ureter, bladder, urethra, cervix, Fallopian tubes, ovaries, uterus, womb, vulva, prostate, bulbourethral glands, epidiymis, prostate, seminal vesicles, testicles, or kidneys. Also included are auto-immune interstitial nephritis, renal abscess (intrarenal or extrarenal), acute prostatitis, hematuria, urethritis (e.g., *Chlamydia* and other sexually transmitted diseases), pelvic inflammatory disease (PID), and prostatic abscess. Also included is nephritis associated with one or more of glomerulonephritis, lupus nephritis, nephropathy, gout, poisons or chemicals (e.g., ether, thallium sulfate), certain medications (e.g., piroxicam, candyl, feldene gel, fensaid, pirox), Hellmann syndrome, yellow fever, immune complex diseases, typhoid fever, urethral stricture, renal tuberculosism, and post-streptococcal glomerulonephritis.

Certain embodiments relate to reducing inflammatory responses and conditions associated with the musculoskeletal system. Examples of musculoskeletal system associated inflammatory conditions include, without limitation, arthritis such as rheumatoid arthritis and psoriatic arthritis, ankylosing spondylitis, auto-immune myositis, primary Sjogren's syndrome, smooth muscle auto-immune disease, myositis, polymyositis, tendinitis, ligament inflammation, cartilage inflammation, joint inflammation, synovial inflammation, carpal tunnel syndrome, chronic muscle inflammation, and bone inflammation, including bone inflammation associated with osteoporosis and osteoarthritis. Also included are Tietze's syndrome, a benign, painful, nonsuppurative localized swelling of the costosternal, sternoclavicular, or costochondral joints, costochondritis, sternalis syndrome, xiphoidalgia, spontaneous sternoclavicular subluxation, sternocostoclavicular hyperostosis, fibromyalgia, shoulder tendinitis or bursitis, gouty arthritis, polymyalgia rheumatica, lupus erythematosus, bone spurs, fractures such as stress fractures, cachexia, sarcopenia, muscle weakness, muscle wasting disease, muscle injury, myalgia, sporadic inclusion body myopathy, hereditary inclusion body myopathy, and Sarcoglycan deficiency. Also included are muscular dystrophies (e.g., DMD), myotonic dystrophies, rhabdomyolysis, and other muscular inflammatory diseases described herein.

Certain embodiments relate to reducing inflammatory responses and conditions associated with the endocrine system. Examples of endocrine system associated inflammatory conditions include, without limitation, inflammation, infection, or cancer associated with the hypothalamus, pituitary, thyroid, pancreas, or adrenal glands, glandular diseases such as pancreatic disease, diabetes such as Type I diabetes, thyroid disease, Graves' disease, thyroiditis, spontaneous autoimmune thyroiditis, Hashimoto's thyroiditis, (idiopathic) myxedema, ovarian autoimmunity, autoimmune antisperm infertility, autoimmune prostatitis and Type I autoimmune polyglandular syndrome.

Certain embodiments relate to reducing inflammatory responses and conditions associated with adipose tissues, an active participant in regulating physiologic and pathologic processes, including immunity inflammation, As well as inflammatory states associated with lipodystrophies, Laminopathies, Kawasaki disease, Juvenile idiopathy arthritis, *Lysosome* storage diseases, and mucopolysaccharidoses.

Macrophages are components of adipose tissue and actively participate in its activities. Furthermore, cross-talk between lymphocytes and adipocytes can lead to immune regulation. Adipose tissue produces and releases a variety of pro-inflammatory and antiinflammatory factors, including the adipokines leptin, adiponectin, resistin, and visfatin, as well as cytokines and chemokines, such as TNF-alpha, IL-6, monocyte chemoattractant protein 1, and others. Proinflammatory molecules produced by adipose tissue have been implicated as active participants in the development of insulin resistance and the increased risk of cardiovascular disease associated with obesity. In contrast, reduced leptin levels may predispose to increased susceptibility to infection caused by reduced T-cell responses in malnourished individuals. Altered adipokine levels have been observed in a variety of inflammatory conditions (see, e.g., Fantuzzi, J Allergy Clin Immunol. 115:911-19, 2005; and Berg et al, Circulation Research. 96:939, 2005).

HRS polypeptides may also be employed to treat or manage inflammation associated with hypersensitivity. Examples of such conditions include type I hypersensitivity, type II hypersensitivity, type III hypersensitivity, type IV hypersensitivity, immediate hypersensitivity, antibody mediated hypersensitivity, immune complex mediated hypersensitivity, T-lymphocyte mediated hypersensitivity, and delayed type hypersensitivity.

HRS polypeptides may also be employed to treat or manage auto-inflammatory conditions. Examples of auto-inflammatory conditions include familial Mediterranean fever, TNF receptor associated periodic syndrome (TRAPS), Hyper-IgD syndrome (HIDS), CIASI-related diseases such as Muckle-Wells syndrome, familial cold auto-inflammatory syndrome, and neonatal onset multisystem inflammatory disease, PAPA syndrome (pyogenic sterile arthritis, pyoderma gangrenosum, acne), and Blau syndrome.

HRS polypeptides may be employed to treat or manage inflammation associated with a variety of cancers. Examples of such cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma.

As noted above, certain embodiments may employ HRS polypeptides to modulate systemic inflammation, such as to reduce or manage systemic inflammation. In certain embodiments, systemic inflammation may by associated with systemic inflammatory response syndrome (SIRS), a whole-body inflammatory condition with a variety of potential causes. SIRS may be characterized or identified according to routine diagnostic techniques. As one non-limiting example, SIRS may be identified by the presence of two or more of the following: (i) a body temperature that is less than 36° C. or greater than 38° C., (ii) a heart rate that is greater than 90 beats per minute, (iii) tachypnea (high respiratory rate), with greater than 20 breaths per minute; or, an arterial partial pressure of carbon dioxide less than 4.3 kPa (32 mmHg), and (iv) white blood cell count less than 4000 cells/mm$^3$ ($4 \times 10^9$ cells/L) or greater than 12,000 cells/mm$^3$ ($12 \times 10^9$ cells/L); or the presence of greater than 10% immature neutrophils (band forms).

SIRS is broadly classified as either infectious or non-infectious. Most generally, infectious SIRS is associated with sepsis, a whole-body inflammatory state combined with a known or suspected infection, which includes bacteremia, viremia, parasitemia, and toxic shock syndrome. Sepsis may be associated with a wide variety of infectious agents, including, without limitation, bacteria such as *Streptococcus agalactiae, Escherichia coli, Haemophilus influenzae, Listeria monocytogenes*, Coagulase-negative *Staphylococcus, Staphylococcus aureus, Klebsiella* species, *Pseudomonas aeruginosa, Enterobacter* species, *S. agalactiae, Serratia* species, *Acinetobacter* species, *Streptococcus pneumoniae, Salmonella* species, and *Neisseria meningitidis*; viruses such as rubella, cytomegalovirus, herpes simplex and the chickenpox virus; parasites such as in malarial infection {e.g., *Plasmodium falciparum*), trypanosomiasis, and filariasis; and fungi such as *Candida* species, *Aspergillus* species, *Histoplasma* species, *Cryptococcus neoformans, Coccidioides immitis, Blastomyces dermatitidis*, and *Pneumocystis carinii*. In certain instances, infections in the lungs (e.g., pneumonia), bladder and kidneys (e.g., urinary tract infections), skin (e.g., cellulitis), abdomen (e.g., appendicitis), and other areas (e.g., meningitis) can spread and lead to sepsis HRS polypeptides may be used to modulate inflammation associated with any of these infectious agents, whether sepsis is present or otherwise.

Noninfectious SIRS may be associated with trauma, burns, pancreatitis, ischemia, hemorrhage, surgical complications, adrenal insufficiency, pulmonary embolism, aortic aneurysm, cardiac tamponade, anaphylaxis, and drug overdose, among others. SIRS is often complicated by the failure of one or more organs or organ system, including those described herein. Specific examples include acute lung injury, acute kidney injury, shock, and multiple organ dysfunction syndrome, among others. Typically, SIRS is treated by focusing on the underlying problem (e.g., adequate fluid replacement for hypovolemia, IVF/NPO for pancreatitis, epinephrine/steroids/benadryl for anaphylaxis). In certain instances, selenium, glutamine, and eicosapentaenoic acid have shown effectiveness in improving symptoms of SIRS, and antioxidants such as vitamin E may also be helpful. Hence, HRS polypeptides may be used to treat or manage SIRS and the complications of SIRS, alone or in combination with other therapies.

Systemic inflammation may also be associated with "cytokine storm," a dangerous immune reaction caused by a positive feedback loop between cytokines and immune cells, resulting in highly elevated levels of various cytokines. In certain instances, cytokine storm (hypercytokinemia) includes the systemic release of numerous known inflammatory mediators such as cytokines, oxygen free radicals, and coagulation factors). Included are elevated levels of pro-inflammatory cytokines such as TNF-alpha, IL-1, and IL-6, and anti-inflammatory cytokines such as IL-10 and IL-1 receptor antagonist. Cytokine storms can occur in a number of infectious and non-infectious diseases including graft versus host disease (GVHD), acute respiratory distress syndrome (ARDS), sepsis, avian influenza, smallpox, and SIRS. Cytokine storm may also be induced by certain medications. Treatment includes OX40 IG, which reduces T-cell responses, ACE inhibitors, Angiotensin II receptor blockers, corticosteroids, gemfibrozil, free radical scavengers, and TNF-a blockers. Accordingly, HRS polypeptides may be employed to treat or manage cytokine storm, alone or in combination with other therapies.

Certain embodiments may employ HRS polypeptides to reduce any one or more of granulomatous inflammation, fibrinous inflammation, purulent inflammation, serous inflammation, or ulcerative inflammation. Granulomatous inflammation is characterized by the formation of granulomas, typically resulting from a response to infectious agents such as tuberculosis, leprosy, and syphilis. Fibrinous inflammation results from a large increase in vascular permeability, which allows fibrin to pass through the blood vessels. If an appropriate pro-coagulative stimulus is present, such as a cancer cell, a fibrinous exudate is deposited. This process is commonly seen in serous cavities, where the conversion of fibrinous exudate into a scar can occur between serous membranes, limiting their function. Purulent inflammation results from the formation of a large amount of pus, which consists of neutrophils, dead cells, and fluid. Infection by pyogenic bacteria such as staphylococci is characteristic of this kind of inflammation. Large, localized collections of pus enclosed by surrounding tissues are called abscesses. Serous inflammation is characterized by the copious effusion of non-viscous serous fluid, commonly produced by mesothelial cells of serous membranes, but may also be derived from blood plasma. Examples of this type of inflammation include skin blisters. Ulcerative inflammation, which typically occurs near an epithelium, results in the necrotic loss of tissue from the surface, thereby exposing lower layers of tissue. The subsequent excavation of the epithelium is known as an ulcer.

HRS polypeptides may also be employed in the treatment of physical injuries or wounds. Examples abrasions, bruises, cuts, puncture wounds, lacerations, impact wounds, concussions, contusions, thermal burns, frostbite, chemical burns, sunburns, gangrene, necrosis, desiccations, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves, ulcers, and gunshot or other traumatic wounds.

HRS polypeptides may also be employed to treat or manage idiopathic inflammation or inflammation of unknown etiology. Also included are combination therapies, in which one or more AARS polypeptides are administered or utilized in combination with one or more other therapies for any of the inflammatory diseases or conditions described herein, including those therapies that are commonly available and known in the art. Examples of combination therapies include the use of standard anti-inflammatory agents such as non-steroidal anti-inflammatory drugs (NSAIDs), immune selective anti-inflammatory derivatives (ImSAIDs), and steroids (e.g., corticosteroids), anti-infectives such as antibiotics and anti-viral agents, anti-oxidants, cytokines, chemotherapeutic agents and other anti-cancer therapies, and immunosuppressive therapies.

In some embodiments, the present invention relates generally to methods and compositions for facilitating the extracorporeal removal of endogenous antibodies using HRS polypeptides bound to a biocompatible solid support.

Specific removal of circulating antibodies by extracorporeal immunoadsorption employing an immobilized antigen has been described by various investigators. See generally Köhler et al., (2011) J Clin Apher. (6):347-55; Müller et al., (2012) Dermatology; 224(3):224-7; Koziolek et al., (2012) J Neuroinflammation. 9(1):80; Bontadi et al., (2012) J Clin Apher. doi: 10.1002/jca.21229; Westermann et al., (2012) J Dermatol. 39(2):168-71. Moreover this approach has been successfully commercialized as a viable system to specifically remove circulating antibodies, as exemplified by immunoadsorption columns sold under the trademarks Prosorba®, Immunosorba®, sold by Fresenius, St. Wendel, Germany, and Selesorb® sold by Kaneka, Wiesbaden, Germany.

In extracorporeal immunoadsorption, circulating antibodies are extracoporeally removed using an immunoadsorbent column specific for the endogenous antibody. Blood from the patient is withdrawn either continuously or discontinuously, separated into its cellular components and plasma, and the plasma is perfused through the immunoadsorbent material in order to remove the antibody. The treated plasma and cellular components of the blood are then reinfused into the patient, either separately or simultaneously. In some embodiments, extracorporeal immunoadsorption according to the present invention may be carried out immediately prior to administration of a HRS polypeptide.

Accordingly certain embodiments relate to methods for extracorporeal immunoadsorption of anti-histidyl-tRNA synthetase antibodies from an extracellular body fluid, comprising the steps of: (a) providing the extracellular body fluid which has been obtained from a subject, (b) contacting the extracellular body fluid with a biocompatible solid support having at least one HRS polypeptide attached thereto, thereby capturing the anti-HRS antibodies, and (c) reinfusing the extracellular body fluid from step (b) into the subject.

Also included are immunoadsorbent compositions for use in the removal of anti-HRS antibodies from the body fluid of a subject, comprising a biocompatible solid support having at least one HRS polypeptide attached thereto.

In general, in any of these immunoadsorbent methods and compositions, the body fluids are obtained, handled and re-infused under aseptic conditions using methods and systems that are well known to a person skilled in the art. For example, blood is withdrawn via a needle that is introduced into, for example, a peripheral vein connected via a suitable tube to the container containing the biocompatible solid support and re-infused into the patient via an inlet tube connected to a needle inserted into another vein. In situations where large volumes are to be withdrawn from the subject, blood may be withdrawn, for instance, from the vena subclavia.

The blood or plasma will be contacted with the biocompatible solid support under conditions that promote binding between the antibodies and HRS polypeptides bound to the support. Suitable columns and perfusion systems for extracorporeal adsorption are commercially available, for example from Fresenius, St. Wendel, Germany. Contact temperatures in the range of 35° C. to about 40° C. are typically used. The contact time will typically be in the range of about 1 to about 6 hours. The unbound portion of the blood or plasma is then collected for reintroduction into the patient or it can be reintroduced directly on a continuous basis. The subject's Jo-1 antibody titer may be monitored by immunoassay before and/or after the procedure to monitor the efficiency of the procedure.

Optionally, an anticoagulation substance such as sodium citrate, heparin, or dextran can be added to the blood when withdrawn from the body to prevent coagulation of the blood. Dextran reduces the viscosity of the blood and, in combination with addition of saline, ensures an increased distance between the blood cells and the blood platelets. Such anticoagulants may be added in quantities sufficient for non-coagulation of the blood. Before reinfusion of the treated blood into the subject the anticoagulation effect of e.g. heparin, may be reduced with the appropriate amount of heparinase, protamine and/or vitamin K etc.

To reduce the risk of embolism, precautions can be taken to avoid adsorption medium particles entering the patient upon reinfusion. Accordingly a particle capture device is typically employed downstream of the adsorption medium container to remove any residual particles from the remainder of the body fluid before it is returned to the patient. The particle capture device may be a filter or mesh having openings of a size that retain any particulate material of the adsorption medium while letting the non-adsorbed entities of the body fluid pass through. The extracorporeal blood perfusion may be performed continuously, or alternatively, discrete volumes of blood may be removed from the patient, treated as described above, and the treated plasma and cellular components of the blood returned to the patient after the treatment is complete.

A wide variety of materials will be suitable as biocompatible solid supports, for use in any of these immunoadsorbent methods and compositions, and ideally, the support matrix will be mechanically strong, sufficiently hydrophilic to avoid non-specific binding of proteins, stable and compatible with to blood and other aqueous solutions. Suitable biocompatible matrix materials include, for example, synthetic and natural polymers, polysaccharides, polyamides, glass beads, particulate silica, porous glass, silica, resins, synthetic matrixes including acrylamide derivatives, methacrylamide derivatives or polystyrene derivatives, etc, in various forms including beads, fibrous form, sheets or hollow fibers.

Exemplary polymers include natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses. Synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionality, and substituted derivatives thereof; and mixtures thereof.

In any of these extracorporeal methods and compositions, the HRS polypeptides are typically. covalently coupled to the biocompatible solid support, and standard methods for coupling proteins such as the HRS polypeptides are well known to those of skill in the art (see. e.g. Affinity Chromatography, Principles and Methods (Pharmacla-LKB), Dean, P. G., et al., eds., 1985, Affinity Chromatography: A practical approach, IRL Press, Oxford, and Scouten, W. H., 1981, Affinity Chromatography, Wiley Interscience, New York), "Immobilized Affinity Ligand Techniques" by Hermanson et al., Academic Press, Inc., San Diego, 1992). The biocompatible solid support may be derivatized (activated) to form a reactive substance that can react with one or more functional chemical groups within the HRS polypeptide, thereby forming a chemical covalent bond to couple the HRS polypeptide to the biocompatible solid support. Thus, materials comprising hydroxyl, amino, amide, carboxyl or thiol groups may be activated or derivatized using various activating chemicals, e.g., chemicals such as cyanogen bromide, divinyl sulfone, epichlorohydrin, bisepoxyranes, dibromopropanol, glutaric dialdehyde, carbodiimides, anhydrides, hydrazines, periodates, benzoquinones, triazines, tosylates, tresylates, and/or diazonium ions, etc.

Specific exemplary activated biocompatible solid supports for use in any of these methods and compositions include for example CNBr-Sepharose, celluloses, such as CNBr-activated Sepharose 4B (Amersham), or Epoxy-activated agarose (Sigma). Biocompatible spacers (like for example NHS-activated Sepharose 4 Fast Flow) or without (like for example CNBr-activated Sepharose 4B) may be employed and are commercially available, and methods for coupling such materials to HRS polypeptides are well known in the art, and can be optimized by routine experimentation based on the manufacturer's directions.

Suitable HRS polypeptides for use in any of these extracorporeal methods and compositions include any of the HRS polypeptides listed in or derivable from Tables 1-9, or any of SEQ ID NOS: 1-23, 39, 41, 43, 70-71, 74-153, 160-172, or 176-182, wherein the HRS polypeptide comprises at least one epitope recognized by an anti-Jo-1 antibody. In some embodiments, the HRS polypeptide is selected from full length HRS, HRS(1-506), HRS(2-506), and HRS(1-60).

Histidyl-tRNA Synthetase-Derived Polypeptides

Embodiments of the present invention relate generally to the use of histidyl-tRNA synthetase derived polypeptides (HRS polypeptides), for example, as anti-inflammatory agents, antibody blocking and/or immuno-regulatory agents, or replacement proteins. Histidyl-tRNA synthetases belong to the class II tRNA synthetase family, which has three highly conserved sequence motifs. Class I and II tRNA synthetases are widely recognized as being responsible for the specific attachment of an amino acid to its cognate tRNA in a 2 step reaction: the amino acid (AA) is first activated by ATP to form AA-AMP and then transferred to the acceptor end of the tRNA. The cytosolic full-length histidyl-tRNA synthetases typically exist either as a cytosolic homodimer, or an alternatively spliced mitochondrial form.

More recently it has been established that some biological fragments, or alternatively spliced isoforms of eukaryotic histidyl-tRNA synthetases (Physiocrines, or HRS polypeptides), or in some contexts the intact synthetase, modulate certain cell-signaling pathways, or have anti-inflammatory properties. These activities, which are distinct from the classical role of tRNA synthetases in protein synthesis, are collectively referred to herein as "non-canonical activities." These Physiocrines may be produced naturally by either alternative splicing or proteolysis, and can act in a cell autonomous fashion (i.e., within the host cell) or a non-cell autonomous fashion (i.e., outside the host cell) to regulate a variety of homeostatic mechanisms. For example, as provided in the present invention, HRS polypeptides such as the N-terminal fragment of histidyl-tRNA synthetase (e.g., HRS(1-48), HRS (1-60)) are capable, inter alia, of exerting an anti-inflammatory signal by blocking the migration of inflammatory cells to the sites of active inflammation in vivo. In addition, certain mutations or deletions (e.g., HRS(1-506)) relative to the full-length HRS polypeptide sequence confer increased activities and/or improved pharmacological properties, stability, and/or homogeneity compared to wild type histidyl-tRNA synthetase. The sequences of certain exemplary HRS polypeptides are provided in Table D1.

TABLE D1

Exemplary HRS polypeptides

| Name | Type/species/Residues | Amino acid and Nucleic Acid Sequences | SEQ ID NO: |
|---|---|---|---|
| N-terminal Physiocrines | | | |
| Full-length cytosolic wild-type | Protein/Human/ | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKLIYDLKDQGGELLSLR YDLTVPFARYLAMNKLTNIKRYHIAKVYRRDNPAMTRGRYR EFYQCDFDIAGNFDPMIPDAECLKIMCEILSSLQIGDFLVKVND RRILDGMFAICGVSDSKFRTICSSVDKLDKVSWEEVKNEMVG EKGLAPEVADRIGDYVQQHGGVSLVEQLLQDPKLSQNKQALE GLGDLKLLFEYLTLFGIDDKISFDLSLARGLDYYTGVIYEAVLL QTPAQAGEEPLGVGSVAAGGRYDGLVGMFDPKGRKVPCVGL SIGVERIFSIVEQRLEALEEKIRTTETQVLVASAQKKLLEERLKL VSELWDAGIKAELLYKKNPKLLNQLQYCEEAGIPLVAIIGEQE LKDGVIKLRSVTSREEVDVRREDLVEEIKRRTGQPLCIC | 1 |
| Full-length mitochondrial wild-type | Protein/Human/ | MPLLGLLPRRAWASLLSQLLRPPCASCTGAVRCQSQVAEAVL TSQLKAHQEKPNFIIKTPKGTRDLSPQHMVVREKILDLVISCFK RHGAKGMDTPAFELKETLTEKYGEDSGLMYDLKDQGGELLS LRYDLTVPFARYLAMNKVKKMKRYHVGKVWRRESPTIVQGR YREFCQCDFDIAGQFDPMIPDAECLKIMCEILSGLQLGDFLIKV NDRRIVDGMFAVCGVPESKFRAICSSIDKLDKMAWKDVRHE MVVKKGLAPEVADRIGDYVQCHGGVSLVEQMFQDPRLSQNK QALEGLGDLKLLFEYLTLFGIADKISFDLSLARGLDYYTGVIYE AVLLQTPTQAGEEPLNVGSVAAGGRYDGLVGMFDPKGHKVP CVGLSIGVERIFYIVEQRMKTKGEKVRTTETQVFVATPQKNFL QERLKLIAELWDSGIKAEMLYKNNPKLLTQLHYCESTGIPLVV IIGEQELKEGVIKIRSVASREEVAIKRENFVAEIQKRLSES | 39 |
| HisRS1$^{N1}$ | Protein/Human/1-141 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKLIYDLKDQGGELLSLR YDLTVPFARYLAM | 2 |
| HisRS1$^{N2}$ | Protein/Human/1-408 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKLIYDLKDQGGELLSLR YDLTVPFARYLAMNKLTNIKRYHIAKVYRRDNPAMTRGRYR EFYQCDFDIAGNFDPMIPDAECLKIMCEILSSLQIGDFLVKVND RRILDGMFAICGVSDSKFRTICSSVDKLDKVSWEEVKNEMVG EKGLAPEVADRIGDYVQQHGGVSLVEQLLQDPKLSQNKQALE GLGDLKLLFEYLTLFGIDDKISFDLSLARGLDYYTGVIYEAVLL QTPAQAGEEPLGVGSVAAGGRYDGLVGMFDPKGRKVPCVGL SIGVERIFSIVEQRLEALEEKIRTTE | 3 |

TABLE D1-continued

Exemplary HRS polypeptides

| Name | Type/species/Residues | Amino acid and Nucleic Acid Sequences | SEQ ID NO: |
|---|---|---|---|
| HisRS1[N3] | Protein/Human/1-113 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKL | 4 |
| HisRS1[N4] (Resokine; SV9; HRS(1-60)) | Protein/Human/1-60 | MAERAALEELVKLQGERVRGLKQQKASAELIEEEVAKLLKLK AQLGPDESKQKFVLKTPK | 5 |
| HisRS1[N5] | Protein/Human/1-243 + 27aa | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKLIYDLKDQGGELLSLR YDLTVPFARYLAMNKLTNIKRYHIAKVYRRDNPAMTRGRYR EFYQCDFDIAGNFDPMIPDAECLKIMCEILSSLQIGDFLVKVND RRILDGMFAICGVSDSKFRTICSSVDKLDKVGYPWWNSCSRIL NYPKTSRPWRAWET | 6 |

C-terminal Physiocrines

| Name | Type/species/Residues | Amino acid and Nucleic Acid Sequences | SEQ ID NO: |
|---|---|---|---|
| HisRS1[C1] | Protein/Human/405-509 | RTTETQVLVASAQKKLLEERLKLVSELWDAGIKAELLYKKNP KLLNQLQYCEEAGIPLVAIIGEQELKDGVIKLRSVTSREEVDVR REDLVEEIKRRTGQPLCIC | 7 |
| HisRS1[C2] | Protein/Human/1-60 + 175-509 | MAERAALEELVKLQGERVRGLKQQKASAELIEEEVAKLLKLK AQLGPDESKQKFVLKTPKDFDIAGNFDPMIPDAECLKIMCEILS SLQIGDFLVKVNDRRILDGMFAICGVSDSKFRTICSSVDKLDK VSWEEVKNEMVGEKGLAPEVADRIGDYVQQHGGVSLVEQLL QDPKLSQNKQALEGLGDLKLLFEYLTLFGIDDKISFDLSLARG LDYYTGVIYEAVLLQTPAQAGEEPLGVGSVAAGGRYDGLVG MFDPKGRKVPCVGLSIGVERIFSIVEQRLEALEEKIRTTETQVL VASAQKKLLEERLKLVSELWDAGIKAELLYKKNPKLLNQLQY CEEAGIPLVAIIGEQELKDGVIKLRSVTSREEVDVRREDLVEEI KRRTGQPLCIC | 8 |
| HisRS1[C3] | Protein/Human/1-60 + 211-509 | MAERAALEELVKLQGERVRGLKQQKASAELIEEEVAKLLKLK AQLGPDESKQKFVLKTPKVNDRRILDGMFAICGVSDSKFRTIC SSVDKLDKVSWEEVKNEMVGEKGLAPEVADRIGDYVQQHGG VSLVEQLLQDPKLSQNKQALEGLGDLKLLFEYLTLFGIDDKISF DLSLARGLDYYTGVIYEAVLLQTPAQAGEEPLGVGSVAAGGR YDGLVGMFDPKGRKVPCVGLSIGVERIFSIVEQRLEALEEKIRT TETQVLVASAQKKLLEERLKLVSELWDAGIKAELLYKKNPKL LNQLQYCEEAGIPLVAIIGEQELKDGVIKLRSVTSREEVDVRRE DLVEEIKRRTGQPLCIC | 9 |
| HisRS1[C4] | Protein/Human/1-100 + 211-509 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKVNDRRILDGMFAICGVSDSKFRTICSSVD KLDKVSWEEVKNEMVGEKGLAPEVADRIGDYVQQHGGVSLV EQLLQDPKLSQNKQALEGLGDLKLLFEYLTLFGIDDKISFDLSL ARGLDYYTGVIYEAVLLQTPAQAGEEPLGVGSVAAGGRYDG LVGMFDPKGRKVPCVGLSIGVERIFSIVEQRLEALEEKIRTTET QVLVASAQKKLLEERLKLVSELWDAGIKAELLYKKNPKLLNQ LQYCEEAGIPLVAIIGEQELKDGVIKLRSVTSREEVDVRREDLV EEIKRRTGQPLCIC | 10 |
| HisRS1[C5] | Protein/Human/1-174 + 211-509 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKETLMGKYGEDSKLIYDLKDQGGELLSLR YDLTVPFARYLAMNKLTNIKRYHIAKVYRRDNPAMTRGRYR EFYQCVNDRRILDGMFAICGVSDSKFRTICSSVDKLDKVSWEE VKNEMVGEKGLAPEVADRIGDYVQQHGGVSLVEQLLQDPKL SQNKQALEGLGDLKLLFEYLTLFGIDDKISFDLSLARGLDYYT GVIYEAVLLQTPAQAGEEPLGVGSVAAGGRYDGLVGMFDPK GRKVPCVGLSIGVERIFSIVEQRLEALEEKIRTTETQVLVASAQ KKLLEERLKLVSELWDAGIKAELLYKKNPKLLNQLQYCEEAG IPLVAIIGEQELKDGVIKLRSVTSREEVDVRREDLVEEIKRRTG QPLCIC | 11 |

TABLE D1-continued

Exemplary HRS polypeptides

| Name | Type/ species/ Residues | Amino acid and Nucleic Acid Sequences | SEQ ID NO: |
|---|---|---|---|
| HisRS1[C6] | Protein/ Human/ 1-60 + 101-509 | MAERAALEELVKLQGERVRGLKQQKASAELIEEEVAKLLKLK AQLGPDESKQKFVLKTPKETLMGKYGEDSKLIYDLKDQGGEL LSLRYDLTVPFARYLAMNKLTNIKRYHIAKVYRRDNPAMTRG RYREFYQCDFDIAGNFDPMIPDAECLKIMCEILSSLQIGDFLVK VNDRRILDGMFAICGVSDSKFRTICSSVDKLDKVSWEEVKNE MVGEKGLAPEVADRIGDYVQQHGGVSLVEQLLQDPKLSQNK QALEGLGDLKLLFEYLTLFGIDDKISFDLSLARGLDYYTGVIYE AVLLQTPAQAGEEPLGVGSVAAGGRYDGLVGMFDPKGRKVP CVGLSIGVERIFSIVEQRLEALEEKIRTTETQVLVASAQKKLLEE RLKLVSELWDAGIKAELLYKKNPKLLNQLQYCEEAGIPLVAII GEQELKDGVIKLRSVTSREEVDVRREDLVEEIKRRTGQPLCIC | 12 |
| HisRS1[C7] | Protein/ Human/ 1-100 + 175-509 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKDFDIAGNFDPMIPDAECLKIMCEILSSLQI GDFLVKVNDRRILDGMFAICGVSDSKFRTICSSVDKLDKVSWE EVKNEMVGEKGLAPEVADRIGDYVQQHGGVSLVEQLLQDPK LSQNKQALEGLGDLKLLFEYLTLFGIDDKISFDLSLARGLDYY TGVIYEAVLLQTPAQAGEEPLGVGSVAAGGRYDGLVGMFDP KGRKVPCVGLSIGVERIFSIVEQRLEALEEKIRTTETQVLVASA QKKLLEERLKLVSELWDAGIKAELLYKKNPKLLNQLQYCEEA GIPLVAIIGEQELKDGVIKLRSVTSREEVDVRREDLVEEIKRRT GQPLCIC | 13 |
| HisRS1[C8] | Protein/ Human/ 1-60 + 399-509 | MAERAALEELVKLQGERVRGLKQQKASAELIEEEVAKLLKLK AQLGPDESKQKFVLKTPKALEEKIRTTETQVLVASAQKKLLEE RLKLVSELWDAGIKAELLYKKNPKLLNQLQYCEEAGIPLVAII GEQELKDGVIKLRSVTSREEVDVRREDLVEEIKRRTGQPLCIC | 14 |
| HisRS1[C9] | Protein/ Human/ 1-100 + 399-509 | MAERAALEELVKLQGERVRGLKQQKASAELIEEEVAKLLKLK AQLGPDESKQKFVLKTPKGTRDYSPRQMAVREKVFDVIIRCFK RHGAEVIDTPVFELKALEEKIRTTETQVLVASAQKKLLEERLK LVSELWDAGIKAELLYKKNPKLLNQLQYCEEAGIPLVAIIGEQ ELKDGVIKLRSVTSREEVDVRREDLVEEIKRRTGQPLCIC | 15 |
| HisRS1[C10] | Protein/ Human/ 369-509 | MFDPKGRKVPCVGLSIGVERIFSIVEQRLEALEEKIRTTETQVL VASAQKKLLEERLKLVSELWDAGIKAELLYKKNPKLLNQLQY CEEAGIPLVAIIGEQELKDGVIKLRSVTSREEVDVRREDLVEEI KRRTGQPLCIC | 16 |
| | | Internal Physiocrines | |
| HisRS1[I1] | Protein/ Human/ 191-333 | CLKIMCEILSSLQIGDFLVKVNDRRILDGMFAICGVSDSKFRTI CSSVDKLDKVSWEEVKNEMVGEKGLAPEVADRIGDYVQQH GGVSLVEQLLQDPKLSQNKQALEGLGDLKLLFEYLTLFGIDD KISFDLSLARGLDYYTG | 17 |

A number of naturally-occurring histidyl-tRNA synthetase single nucleotide polymorphisms (SNPs) and naturally-occurring variants of the human gene have been sequenced, and are known in the art to be at least partially functionally interchangeable. Several such variants of histidyl-tRNA synthetase (i.e., representative histidyl-tRNA synthetase SNPs) are shown in Table D2.

TABLE D2

Human Histidyl-tRNA synthetase SNPs

| Gene Bank Accession Number | Nucleotide Change | Gene Bank Accession Number | Nucleotide Change |
|---|---|---|---|
| rs193103291 | A/G | rs186312047 | A/G |
| rs192923161 | C/T | rs186176857 | C/T |
| rs192784934 | A/G | rs186043734 | C/G |
| rs192164884 | A/G | rs185867584 | C/T |
| rs192090865 | A/C | rs185828130 | A/G |
| rs192015101 | A/T | rs185537686 | A/G |

TABLE D2-continued

Human Histidyl-tRNA synthetase SNPs

| Gene Bank Accession Number | Nucleotide Change | Gene Bank Accession Number | Nucleotide Change |
|---|---|---|---|
| rs191999492 | A/G | rs185440931 | C/T |
| rs191852363 | C/T | rs185100584 | A/C |
| rs191532032 | A/T | rs185077558 | C/T |
| rs191391414 | C/T | rs184748736 | C/G |
| rs191385862 | A/G | rs184591417 | C/T |
| rs191205977 | A/G | rs184400035 | C/G |
| rs191104160 | A/G | rs184098206 | C/T |
| rs190989313 | C/G | rs183982931 | C/T |
| rs190818970 | A/T | rs183942045 | A/G |
| rs190476138 | C/T | rs183854085 | A/G |
| rs190289555 | C/T | rs183430882 | G/T |
| rs190065567 | A/G | rs183419967 | A/C |
| rs189624055 | C/T | rs183366286 | A/G |
| rs189563577 | G/T | rs183084050 | C/T |
| rs189404434 | A/G | rs182948878 | C/T |
| rs189268935 | A/G | rs182813126 | A/G |
| rs189103453 | A/T | rs182498374 | A/G |
| rs188839103 | A/G | rs182161259 | A/T |
| rs188766717 | A/G | rs182119902 | C/T |
| rs188705391 | A/G | rs182106891 | C/T |
| rs188490030 | A/G | rs181930530 | A/G |
| rs188345926 | C/T | rs181819577 | A/G |
| rs188174426 | A/G | rs181706697 | C/T |
| rs187897435 | C/T | rs181400061 | G/T |
| rs187880261 | A/G | rs181240610 | G/T |
| rs187729939 | G/T | rs181150977 | A/C |
| rs187617985 | A/T | rs180848617 | A/G |
| rs187344319 | C/T | rs180765564 | A/G |
| rs187136933 | C/T | rs151330569 | C/G |
| rs186823043 | C/G | rs151258227 | C/T |
| rs186764765 | C/T | rs151174822 | C/T |
| rs186663247 | A/G | rs150874684 | C/T |
| rs186526524 | A/G | rs150589670 | A/G |
| rs150274370 | C/T | rs145059663 | C/T |
| rs150090766 | A/G | rs144588417 | C/T |
| rs149977222 | A/G | rs144457474 | A/G |
| rs149821411 | C/T | rs144322728 | C/T |

TABLE D2-continued

Human Histidyl-tRNA synthetase SNPs

| Gene Bank Accession Number | Nucleotide Change | Gene Bank Accession Number | Nucleotide Change |
|---|---|---|---|
| rs149542384 | A/G | rs143897456 | —/C |
| rs149336018 | C/G | rs143569397 | G/T |
| rs149283940 | C/T | rs143476664 | C/T |
| rs149259830 | C/T | rs143473232 | C/G |
| rs149241235 | C/T | rs143436373 | G/T |
| rs149018062 | C/T | rs143166254 | A/G |
| rs148935291 | C/T | rs143011702 | C/G |
| rs148921342 | —/A | rs142994969 | A/G |
| rs148614030 | C/T | rs142880704 | A/G |
| rs148584540 | C/T | rs142630342 | A/G |
| rs148532075 | A/C | rs142522782 | —/AAAC |
| rs148516171 | C/T | rs142443502 | C/T |
| rs148394305 | —/AA | rs142305093 | C/T |
| rs148267541 | C/T | rs142289599 | A/G |
| rs148213958 | C/T | rs142088963 | A/C |
| rs147637634 | A/G | rs141765732 | A/C |
| rs147372931 | A/C/G | rs141386881 | A/T |
| rs147350096 | A/C | rs141291994 | A/G |
| rs147288996 | C/T | rs141285041 | C/T |
| rs147194882 | G/T | rs141220649 | C/T |
| rs147185134 | C/T | rs141147961 | —/C |
| rs147172925 | A/G | rs141123446 | —/A |
| rs147011612 | C/T | rs140516034 | A/G |
| rs147001782 | A/G | rs140169815 | C/T |
| rs146922029 | C/T | rs140005970 | G/T |
| rs146835587 | A/G | rs139699964 | C/T |
| rs146820726 | C/T | rs139555499 | A/G |
| rs146801682 | C/T | rs139447495 | C/T |
| rs146571500 | G/T | rs139364834 | —/A |
| rs146560255 | C/T | rs139362540 | A/G |
| rs146205151 | —/A | rs139300653 | —/A |
| rs146159952 | A/G | rs139251223 | A/G |
| rs145532449 | C/G | rs139145072 | A/G |
| rs145446993 | A/G | rs138612783 | A/G |
| rs145112012 | G/T | rs138582560 | A/G |
| rs138414368 | A/G | rs111863295 | C/T |
| rs138377835 | A/G | rs111519226 | C/G |

TABLE D2-continued

Human Histidyl-tRNA synthetase SNPs

| Gene Bank Accession Number | Nucleotide Change | Gene Bank Accession Number | Nucleotide Change |
|---|---|---|---|
| rs138300828 | C/T | rs111314092 | C/T |
| rs138067637 | C/T | rs80074170 | A/T |
| rs138035024 | A/G | rs79408883 | A/C |
| rs137973748 | C/G | rs78741041 | G/T |
| rs137917558 | A/G | rs78677246 | A/T |
| rs117912126 | A/T | rs78299006 | A/G |
| rs117579809 | G/T | rs78085183 | A/T |
| rs116730458 | C/T | rs77844754 | C/T |
| rs116411189 | A/C | rs77585983 | A/T |
| rs116339664 | C/T | rs77576083 | A/G |
| rs116203404 | A/T | rs77154058 | G/T |
| rs115091892 | G/T | rs76999025 | A/G |
| rs114970855 | A/G | rs76496151 | C/T |
| rs114176478 | A/G | rs76471225 | G/T |
| rs113992989 | C/T | rs76085408 | G/T |
| rs113720830 | C/T | rs75409415 | A/G |
| rs113713558 | A/C | rs75397255 | C/G |
| rs113627177 | G/T | rs74336073 | A/G |
| rs113489608 | A/C | rs73791750 | C/T |
| rs113408729 | G/T | rs73791749 | A/T |
| rs113255561 | A/G | rs73791748 | C/T |
| rs113249111 | C/T | rs73791747 | A/T |
| rs113209109 | A/G | rs73273304 | C/T |
| rs113066628 | G/T | rs73271596 | C/T |
| rs112967222 | C/T | rs73271594 | C/T |
| rs112957918 | A/T | rs73271591 | A/G |
| rs112859141 | A/G | rs73271586 | A/T |
| rs112769834 | C/G | rs73271585 | A/G |
| rs112769758 | A/C | rs73271584 | A/G |
| rs112701444 | A/C | rs73271581 | C/T |
| rs112585944 | A/G | rs73271578 | A/T |
| rs112439761 | A/G | rs72800925 | G/T |
| rs112427345 | A/C | rs72800924 | C/T |
| rs112265354 | C/T | rs72800922 | A/T |
| rs112113896 | C/G | rs72432753 | —/A |
| rs112033118 | C/T | rs72427948 | —/A |
| rs112029988 | A/G | rs72388191 | —/A |

TABLE D2-continued

Human Histidyl-tRNA synthetase SNPs

| Gene Bank Accession Number | Nucleotide Change | Gene Bank Accession Number | Nucleotide Change |
|---|---|---|---|
| rs72317985 | —/A | rs6873628 | C/T |
| rs71583608 | G/T | rs5871749 | —/C |
| rs67251579 | —/A | rs4334930 | A/T |
| rs67180750 | —/A | rs3887397 | A/G |
| rs63429961 | A/T | rs3776130 | A/C |
| rs61093427 | C/T | rs3776129 | C/T |
| rs61059042 | —/A | rs3776128 | A/G |
| rs60936249 | —/AA | rs3177856 | A/C |
| rs60916571 | —/A | rs2563307 | A/G |
| rs59925457 | C/T | rs2563306 | A/G |
| rs59702263 | —/A | rs2563305 | C/T |
| rs58302597 | C/T | rs2563304 | A/G |
| rs57408905 | A/T | rs2530242 | C/G |
| rs35790592 | A/C | rs2530241 | A/G |
| rs35609344 | —/A | rs2530240 | A/G |
| rs35559471 | —/A | rs2530239 | A/G |
| rs35217222 | —/C | rs2530235 | A/C |
| rs34903998 | —/A | rs2230361 | C/T |
| rs34790864 | C/G | rs2073512 | C/T |
| rs34732372 | C/T | rs1131046 | C/T |
| rs34291233 | —/C | rs1131045 | C/G |
| rs34246519 | —/T | rs1131044 | C/T |
| rs34176495 | —/C | rs1131043 | C/G |
| rs13359823 | A/G | rs1131042 | A/C |
| rs13180544 | A/C | rs1131041 | C/G |
| rs12653992 | A/C | rs1131040 | A/G |
| rs12652092 | A/G | rs1131039 | C/T |
| rs11954514 | A/C | rs1131038 | A/G |
| rs11745372 | C/T | rs1131037 | A/G |
| rs11548125 | A/G | rs1131036 | A/G |
| rs11548124 | C/G | rs1131035 | C/T |
| rs11344157 | —/C | rs1131034 | A/G |
| rs11336085 | —/A | rs1131033 | A/G |
| rs11318345 | —/A | rs1131032 | A/G |
| rs11309606 | —/A | rs1089305 | A/G |
| rs10713463 | —/A | rs1089304 | A/C |
| rs7706544 | C/T | rs1065342 | A/C |

TABLE D2-continued

Human Histidyl-tRNA synthetase SNPs

| Gene Bank Accession Number | Nucleotide Change | Gene Bank Accession Number | Nucleotide Change |
|---|---|---|---|
| rs7701545 | A/T | rs1050252 | C/T |
| rs6880190 | C/T | rs1050251 | A/T |
| rs1050250 | A/G | rs145769024 | —/AAACAAAACAAAACA (SEQ ID NO: 154) |
| rs1050249 | C/T | rs10534452 | —/AAAC |
| rs1050248 | A/C/T | rs10534451 | —/AAACAAAACA (SEQ ID NO: 155) |
| rs1050247 | C/T | rs59554063 | —/CAAAACAAA (SEQ ID NO: 156) |
| rs1050246 | C/G | rs58606188 | —/CAAAACAAAACAAAA (SEQ ID NO: 157) |
| rs1050245 | C/T | rs71835204 | (LARGEDELETION)/— |
| rs1050222 | C/T | rs71766955 | (LARGEDELETION)/— |
| rs813897 | A/G | rs144998196 | —/AAACAAAACA (SEQ ID NO: 158) |
| rs812381 | C/G | rs68038188 | —/ACAAAACAAA (SEQ ID NO: 159) |
| rs811382 | C/T | rs71980275 | —/AAAC |
| rs801189 | C/T | rs71848069 | —/AAAC |
| rs801188 | A/C | rs60987104 | —/AAAC |
| rs801187 | A/T | rs801185 | C/T |
| rs801186 | A/G | rs702396 | C/G |

Additionally homologs and orthologs of the human gene exist in other species, as listed in Table D3, and it would thus be a routine matter to select a naturally-occurring amino acid, or nucleotide variant present in a SNP, or other naturally-occurring homolog in place of any of the human HRS polypeptide sequences listed in Tables D1, D4-D6, or D8.

TABLE D3

Homologs of Human Histidyl-tRNA synthetase

| Type/species/Residues | Amino acid Sequences | SEQ ID NO: |
|---|---|---|
| Mus musculus | MADRAALEELVRLQGAHVRGLKEQKASAEQIEEEVTKLLKLKAQLGQDE GKQKFVLKTPKGTRDYSPRQMAVREKVFDVIIRCFKRHGAEVIDTPVFEL KETLTGKYGEDSKLIYDLKDQGGELLSLRYDLTVPFARYLAMNKLTNIKR YHIAKVYRRDNPAMTRGRYREFYQCDFDIAGQFDPMIPDAECLKIMCEILS SLQIGNFLVKVNDRRILDGMFAVCGVPDSKFRTICSSVDKLDKVSWEEVK NEMVGEKGLAPEVADRIGDYVQQHGGVSLVEQLLQDPKLSQNKQAVEG LGDLKLLFEYLILFGIDDKISFDLSLARGLDYYTGVIYEAVLLQMPTQAGE EPLGVGSIAAGGRYDGLVGMFDPKGRKVPCVGLSIGVERIFSIVEQRLEAS EEKVRTTETQVLVASAQKKLLEERLKLVSELWDAGIKAELLYKKNPKLLN QLQYWEEAGIPLVAIIGEQELRDGVIKLRSVASREEVDVRREDLVEEIRRR TNQPLSTC | 18 |
| Canis lupus familiaris | MAERAALEELVRLQGERVRGLKQQKASAEQIEEEVAKLLKLKAQLGPDE GKQKFVLKTPKGTRDYSPRQMAVREKVFDVIISCFKRHGAEVIDTPVFEL KETLTGKYGEDSKLIYDLKDQGGELLSLRYDLTVPFARYLAMNKLTNIKR YHIAKVYRRDNPAMTRGRYREFYQCDFDIAGQFDPMIPDAECLEIMCEILR SLQIGDFLVKVNDRRILDGMFAICGVPDSKFRTICSSVDKLDKVSWEEVKN EMVGEKGLAPEVADHIGDYVQQHGGISLVEQLLQDPELSQNKQALEGLG DLKLLFEYLTLFGIADKISFDLSLARGLDYYTGVIYEAVLLQTPVQAGEEP LGVGSVAAGGRYDGLVGMFDPKGRKVPCVGLSIGVERIFSIVEQRLEATE EKVRTTETQVLVASAQKKLLEERLKLVSELWNAGIKAELLYKKNPKLLN | 19 |

TABLE D3-continued

Homologs of Human Histidyl-tRNA synthetase

| Type/species/Residues | Amino acid Sequences | SEQ ID NO: |
|---|---|---|
| | QLQYCEEAGIPLVAIIGEQELKDGVIKLRSVASREEVDVPREDLVEEIKRRT SQPFCIC | |
| Bos taurus | MADRAALEDLVRVQGERVRGLKQQKASAEQIEEEVAKLLKLKAQLGPDE GKPKFVLKTPKGTRDYSPRQMAVREKVFDVIISCFKRHGAEVIDTPVFELK ETLTGKYGEDSKLIYDLKDQGGELLSLRYDLTVPFARYLAMNKLTNIKRY HIAKVYRRDNPAMTRGRYREFYQCDFDIAGQFDPMLPDAECLKIMCEILS SLQIGDFLVKVNDRRILDGMFAICGVPDSKFRTICSSVDKLDKVSWEEVKN EMVGEKGLAPEVADRIGDYVQQHGGVSLVEQLLQDPKLSQNKQALEGLG DLKLLFEYLTLFGIADKISFDLSLARGLDYYTGVIYEAVLLQPPARAGEEPL GVGSVAAGGRYDGLVGMFDPKGRKVPCVGLSIGVERIFSIVEQRLEALEE KVRTTETQVLVASAQKKLLEERLKLISELWDAGIKAELLYKKNPKLLNQL QYCEETGIPLVAIIGEQELKDGVIKLRSVASREEVDVRREDLVEEIKR RTSQPLCIC | 20 |
| Rattus norvegicus | MADRAALEELVRLQGAHVRGLKEQKASAEQIEEEVTKLLKLKAQLGHDE GKQKFVLKTPKGTRDYSPRQMAVREKVFDVIIRCFKRHGAEVIDTPVFEL KETLTGKYGEDSKLIYDLKDQGGELLSLRYDLTVPFARYLAMNKLTNIKR YHIAKVYRRDNPAMTRGRYREFYQCDFDIAGQFDPMIPDAECLKIMCEILS SLQIGNFQVKVNDRRILDGMFAVCGVPDSKFRTICSSVDKLDKVSWEEVK NEMVGEKGLAPEVADRIGDYVQQHGGVSLVEQLLQDPKLSQNKQAVEG LGDLKLLFEYLTLFGIDDKISFDLSLARGLDYYTGVIYEAVLLQMPTQAGE EPLGVGSIAAGGRYDGLVGMFDPKGRKVPCVGLSIGVERIFSIVEQKLEAS EEKVRTTETQVLVASAQKKLLEERLKLISELWDAGIKAELLYKKNPKLLN QLQYCEEAGIPLVAIIGEQELKDGVIKLRSVTSREEVDVRREDLVEEIRR RTSQPLSM | 21 |
| Gallus gallus | MADEAAVRQQAEVVRRLKQDKAEPDEIAKEVAKLLEMKAHLGGDEGKH KFVLKTPKGTRDYGPKQMAIRERVFSAIIACFKRIIGAEVIDTPVFELKETL TGKYGEDSKLIYDLKDQGGELLSLRYDLTVPFARYLAMNKITNIKRYHIA KVYRRDNPAMTRGRYREFYQCDFDIAGQFDPMIPDAECLKIVQEILSDLQ LGDFLIKVNDRRILDGMFAVCGVPDSKFRTICSSVDKLDKMPWEEVRNEM VGEKGLSPEAADRIGEYVQLHGGMDLIEQLLQDPKLSQNKLVKEGLGDM KLLFEYLTLFGITGKISFDLSLARGLDYYTGVIYEAVLLQQNDHGEESVSV GSVAGGGRYDGLVGMFDPKGRKVPCVGISIGIERIFSILEQRVEASEEKIR TTETQVLVASAQKKLLEERLKLISELWDAGIKAEVLYKKNPKLLNQLQYC EDTGIPLVAIVGEQELKDGVVKLRVVATGEEVNIRRESLVEEIRRRTNQL | 22 |
| Danio rerio | MAALGLVSMRLCAGLMGRRSAVRLHSLRVCSGMTISQIDEEVARLLQLK AQLGGDEGKHVFVLKTAKGTRDYNPKQMAIREKVFNIIINCFKRHGAETI DSPVFELKETLTGKYGEDSKLIYDLKDQGGELLSLRYDLTVPFARYLAMN KITNIKRYHIAKVYRRDNPAMTRGRYREFYQCDFDIAGQYDAMIPDAECL KLVYEILSELDLGDFRIKVNDRRILDGMFAICGVPDEKFRTICSTVDKLDKL AWEEVKKEMVNEKGLSEEVADRIRDYVSMQGGKDLAERLLQDPKLSQS KQACAGITDMKLLFSYLELFQITDKVVFDLSLARGLDYYTGVIYEAILTQA NPAPASTPAEQNGAEDAGVSVGSVAGGGRYDGLVGMFDPKAGKCPVWG SALALRGSSPSWSRRQSCLQRRCAPLKLKCLWLQHRRTF | 23 |

Accordingly, in any of the methods, diagnostic compositions, therapeutic compositions and kits of the invention, the terms "HRS polypeptide," "HRS protein," or "HRS protein fragment" includes all naturally-occurring and synthetic forms of the histidyl-tRNA synthetase that comprise at least one epitope which specifically cross reacts with an auto-antibody or auto reactive T-cell from a disease associated with autoantibodies to histidyl-tRNA synthetase, or possesses a non canonical activity. Such HRS polypeptides include the full-length human protein, as well as the HRS peptides derived from the full-length protein listed in Table D1, as well as naturally-occurring, and other variants, for example as disclosed in or derivable from Tables D2-D9. In some embodiments, the term HRS polypeptide refers to a polypeptide sequence derived from human histidyl-tRNA synthetase (SEQ ID NO:1 in Table D1) of about 50 to about 250 amino acids in length.

In some embodiments, the HRS polypeptide does not significantly compete for disease associated auto-antibody binding to wild-type histidyl-tRNA synthetase in a competitive ELISA up to a concentration of about 1 to $5 \times 10^{-7}$M, or higher. Accordingly in some embodiments, the HRS polypeptide has a lower affinity to disease associated auto-antibody than wild-type histidyl-tRNA synthetase (SEQ ID NO:1) as measured in a competitive ELISA. In some embodiments, the HRS polypeptide has an apparent affinity for the disease associated auto-antibody which is at least about 10 fold less, or at least about 20 fold less, or at least about 50 fold less, or at least about 100 fold less than the affinity of the disease associated auto-antibody to wild-type human (SEQ ID NO:1).

Modified and Variant HRS Polypeptides

Thus all such homologues, orthologs, and naturally-occurring, or synthetic isoforms of histidyl-tRNA synthetase (e.g., any of the proteins or their corresponding nucleic acids listed in or derivable from Tables D1-D9) are included in any of the methods, kits and compositions of the invention. In some aspects, such HRS polypeptides retain at least one epitope which specifically cross reacts with an auto-antibody or auto reactive T-cell from a subject with a disease associated with autoantibodies to histidyl-tRNA synthetase and/or possess a non canonical activity. The HRS polypeptides may be in their native form, i.e., as different variants as they appear in nature in different species which may be viewed as functionally equivalent variants of human histidyl-tRNA synthetase, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of any HRS polypeptide, are also specifically included in any of the methods and compositions of the invention including, e.g., pyroglutamyl, isoaspartyl, proteolytic, phosphorylated, glycosylated, oxidatized, isomerized, and deaminated variants of a HRS polypeptide. HRS polypeptides can also be composed of naturally-occurring amino acids and/or non-naturally-occurring amino acids, as described herein.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound were termed "peptide mimetics" or "peptidomimetics" (Luthman, et al., *A Textbook of Drug Design and Development,* 14:386-406, 2nd Ed., Harwood Academic Publishers (1996); Joachim Grante, *Angew. Chem. Int. Ed. Engl.,* 33:1699-1720 (1994); Fauchere, J., *Adv. Drug Res.,* 15:29 (1986); Veber and Freidinger TINS, p. 392 (1985); and Evans, et al., *J. Med. Chem.* 30:229 (1987)). A peptidomimetic is a molecule that mimics the biological activity of a peptide but is no longer peptidic in chemical nature. Peptidomimetic compounds are known in the art and are described, for example, in U.S. Pat. No. 6,245,886. In certain embodiments, HRS polypeptides may be partially or fully composed of D-amino acids, for instance, to increase resistance to protein degradation in vivo (see, e.g., Wade et al., *PNAS USA.* 87:4761-4765, 1990; Hayry et al., *FASEB Journal.* 9:1336-44, 1995; Van Regenmortel and Muller, *Curr. Opin. Biotechol.* 9:377-82, 1998; Navab et al., *Circulation.* 105:290-292, 2002; Tugyi et al., *PNAS USA.* 102:412-418, 2005; and U.S. Application No. 2004/00086988; see also Taylor et al., *Biochemistry.* 49:3261-72, 2010; for retro-inverso-D-peptides; and see also Dedkova et al., *Biochemistry.* 45:15541-51, 2006 for modified bacterial ribosomes that are capable of producing recombinant proteins with increased D-amino acids).

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using a HRS polypeptide or variant thereof, e.g., by the use of automated computer recognition programs to identify potential T cell epitopes, and directed evolution approaches to identify less immunogenic forms.

As noted above, embodiments of the present invention include all homologues, orthologs, and naturally-occurring isoforms of histidyl-tRNA synthetase (e.g., any of the proteins listed in or derivable from Tables D1-D9, or their corresponding nucleic acids), and "variants" of these HRS reference polypeptides. The recitation polypeptide "variant" refers to polypeptides that are distinguished from a reference HRS polypeptide by the addition, deletion, and/or substitution of at least one amino acid residue, and which typically retain (e.g., mimic) or modulate (e.g., antagonize) one or more non-canonical activities of a reference HRS polypeptide. Variants also include polypeptides that have been modified by the addition, deletion, and/or substitution of at least one amino acid residue to have improved stability or other pharmaceutical properties.

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

Specific examples of HRS polypeptide variants useful in any of the methods and compositions of the invention include full-length HRS polypeptides, or truncations or splice variants thereof (e.g., any of the proteins listed in or derivable from Tables D1-D9) which i) retain detectable non canonical activity and/or retain at least one epitope which specifically cross reacts with an auto-antibody or auto reactive T-cell from a subject with a disease associated with autoantibodies to histidyl-tRNA synthetase, and ii) have one or more additional amino acid insertions, substitutions, deletions, and/or truncations. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a HRS reference polypeptide, as described herein, (e.g., SEQ ID NOS: 1-23, 39, 41, 43, 70-71, 74-153, 160-172, or 176-182, or any of the proteins listed in or derivable from Tables D1-D9) and substantially retains the non-canonical activity of that reference polypeptide. Also included are sequences differing from the reference HRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference HRS polypeptide. In certain embodiments, the amino acid additions or deletions occur at the C-terminal end and/or the N-terminal end of the HRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length HRS polypeptide) that are proximal to the C-terminal end and/or the N-terminal end of the HRS reference polypeptide.

In some embodiments, the HRS polypeptides comprise a polypeptide fragment of the full-length histidyl-tRNA synthetase of about 50 to 250 amino acids, which comprises, consists, or consists essentially of the amino acids of the HRS polypeptide sequence set forth in one or more of SEQ ID NOS: 1-23, 39, 41, 43, 70-71, 74-153, 160-172, or 176-182, or any of the proteins listed in or derivable from Tables D1-D9. In some embodiments, the HRS polypeptide comprises, consists, or consists essentially of residues 1-141, 1-408, 1-113, or 1-60 of SEQ ID NO:1. In some aspects, the HRS polypeptide is a splice variant that comprises, consists, or consists essentially of residues 1-60+175-509, 1-60+211-509 or 1-60+101-509 of SEQ ID NO:1. In particular aspects, the HRS polypeptide comprises, consists, or consists essentially of residues 1-48 or 1-506 of SEQ ID NO:1.

In certain embodiments, a HRS polypeptide of the invention comprises the minimal active fragment of a full-length HRS polypeptide capable of modulating an anti-inflammatory activity in vivo or having antibody or auto-reactive T-cell blocking activities. In some aspects, such a minimal active fragment comprises or consists essentially of the WHEP domain, (i.e., about amino acids 1-43 of SEQ ID NO:1). In some aspects, the minimal active fragment comprises or consists essentially of the aminoacylation domain, (i.e., about amino acids 54-398 of SEQ ID NO:1). In some aspects, the minimal active fragment comprises or consists essentially of the anticodon binding domain (i.e., about amino acids 406-501 of SEQ ID NO:1). Other exemplary active fragments are shown in Table D4 below.

TABLE D4

Exemplary HRS polypeptide fragments

| Name | Amino Acid Residue Range of SEQ ID NO: 1 | Amino acid sequence | SEQ ID NO: |
|---|---|---|---|
| HRS(1-500) | Protein/Human/1-500 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKR | 160 |
| HRS(1-501) | Protein/Human/1-501 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRR | 161 |
| HRS(1-502) | Protein/Human/1-502 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRT | 162 |
| HRS(1-503) | Protein/Human/1-503 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTG | 163 |
| HRS(1-504) | Protein/Human/1-504 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD | 164 |

TABLE D4-continued

Exemplary HRS polypeptide fragments

| Name | Amino Acid Residue Range of SEQ ID NO: 1 | Amino acid sequence | SEQ ID NO: |
|---|---|---|---|
| | | YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQ | |
| HRS(1-505) | Protein/ Human/ 1-505 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQP | 165 |
| HisRS1$^{N8}$ HRS(1-506) | Protein/ Human/ 1-506 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPL | 70 |
| HRS(2-506) | Protein/ Human/ 2-506 | AERAALEELVKLQGERVRGLKQQKASAELIEEEVAKLLKLK AQLGPDESKQKFVLKTPKGTRDYSPRQMAVREKVFDVIIRC FKRHGAEVIDTPVFELKETLMGKYGEDSKLIYDLKDQGGEL LSLRYDLTVPFARYLAMNKLTNIKRYHIAKVYRRDNPAMT RGRYREFYQCDFDIAGNFDPMIPDAECLKIMCEILSSLQIGDF LVKVNDRRILDGMFAICGVSDSKFRTICSSVDKLDKVSWEE VKNEMVGEKGLAPEVADRIGDYVQQHGGVSLVEQLLQDPK LSQNKQALEGLGDLKLLFEYLTLFGIDDKISFDLSLARGLDY YTGVIYEAVLLQTPAQAGEEPLGVGSVAAGGRYDGLVGMF DPKGRKVPCVGLSIGVERIFSIVEQRLEALEEKIRTTETQVLV ASAQKKLLEERLKLVSELWDAGIKAELLYKKNPKLLNQLQ YCEEAGIPLVAIIGEQELKDGVIKLRSVTSREEVDVRREDLV EEIKRRTGQPL | 166 |
| HRS(1-507) | Protein/ Human/ 1-507 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPLC | 167 |
| HRS(1-508) | Protein/ Human/ 1-508 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD | 168 |

TABLE D4-continued

Exemplary HRS polypeptide fragments

| Name | Amino Acid Residue Range of SEQ ID NO: 1 | Amino acid sequence | SEQ ID NO: |
|---|---|---|---|
| | | YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPLCI | |
| HRS(1-509) | Protein/ Human/ 1-509 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERKLVSELWDAGIKAELLYKKNPKLLNQL QYCEEAGIPLVAIIGEQELKDGVIKLRSVTSREEVDVRREDL VEEIKRRTGQPLCIC | 169 |
| HisRS1$^{N6}$ HRS(1-48) | Protein/ Human/ 1-48 | MAERAALEELVKLQGERVRGLKQQKASAELIEEEVAKLLK LKAQLGPD | 71 |

In certain embodiments, such minimal active fragments may comprise 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acids of a flexible linker connecting the minimum domain to a heterologous protein, or splice variant.

Without wishing to be bound by any one theory, the unique orientation, or conformation, of the WHEP domain in certain HRS polypeptides may contribute to the enhanced non canonical, and/or antibody blocking activities observed in these proteins.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (*Nucleic Acids Res.* 25:3389-3402, 1997). When utilizing BLAST and Gapped BLAST programs, the default parameters of the respective programs (e.g., XBLAST and NBLAST) can be used.

In certain embodiments, variant polypeptides differ from the corresponding HRS reference sequences by at least 1% but less than 20%, 15%, 10% or 5% of the residues. If this comparison requires alignment, the sequences should be aligned for maximum similarity. "Looped" out sequences from deletions or insertions, or mismatches, are considered differences. The differences are, suitably, differences or changes at a non-essential residue or a conservative substitution. In certain embodiments, the molecular weight of a variant HRS polypeptide differs from that of the HRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

Also included are biologically active "fragments" of the HRS reference polypeptides, i.e., biologically active fragments of the HRS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between a HRS polypeptide and a cellular binding partner, such as a cellular receptor or other host molecule that participates in the non-canonical activity of the HRS polypeptide.

A biologically active fragment of a HRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 410, 420, 430, 440, 450, 460, 470, 480, 490, 496, 497, 498, 499, 500, 501, 502, 503, 504, 505, 506, 507, 508 or more contiguous or non-contiguous amino acids, including all integers (e.g., 101, 102, 103) and ranges (e.g., 50-100, 50-150, 50-200) in between, of the amino acid sequences set forth in any one of the HRS reference polypeptides described herein. In certain embodiments, a biologically active fragment comprises a non-canonical activity-related sequence, domain, or motif. In certain embodiments, the C-terminal or N-terminal region of any HRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated HRS polypeptide retains the non-canonical activity of the reference polypeptide. Certain exemplary truncated HRS polypeptides are shown in Table D5 below.

TABLE D5

Exemplary truncated HRS polypeptides

| HRS range | Sequence | SEQ ID NO: |
|---|---|---|
| C-terminal truncations | | |
| 1-80 | MAERAALEELVKLQGERVRGLKQQKASAELIEEEVAKLLK LKAQLGPDESKQKFVLKTPKGTRDYSPRQMAVREKVFDVI | 74 |
| 1-79 | MAERAALEELVKLQGERVRGLKQQKASAELIEEEVAKLLK LKAQLGPDESKQKFVLKTPKGTRDYSPRQMAVREKVFDV | 75 |

TABLE D5-continued

Exemplary truncated HRS polypeptides

| HRS range | Sequence | SEQ ID NO: |
|---|---|---|
| 1-78 | MAERAALEELVKLQGERVRGLKQQKASAELIEEEVAKLLK LKAQLGPDESKQKFVLKTPKGTRDYSPRQMAVREKVFD | 76 |
| 1-77 | MAERAALEELVKLQGERVRGLKQQKASAELIEEEVAKLLK LKAQLGPDESKQKFVLKTPKGTRDYSPRQMAVREKVF | 77 |
| 1-76 | MAERAALEELVKLQGERVRGLKQQKASAELIEEEVAKLLK LKAQLGPDESKQKFVLKTPKGTRDYSPRQMAVREKV | 78 |
| 1-75 | MAERAALEELVKLQGERVRGLKQQKASAELIEEEVAKLLK LKAQLGPDESKQKFVLKTPKGTRDYSPRQMAVREK | 79 |
| 1-74 | MAERAALEELVKLQGERVRGLKQQKASAELIEEEVAKLLK LKAQLGPDESKQKFVLKTPKGTRDYSPRQMAVRE | 80 |
| 1-73 | MAERAALEELVKLQGERVRGLKQQKASAELIEEEVAKLLK LKAQLGPDESKQKFVLKTPKGTRDYSPRQMAVR | 81 |
| 1-72 | MAERAALEELVKLQGERVRGLKQQKASAELIEEEVAKLLK LKAQLGPDESKQKFVLKTPKGTRDYSPRQMAV | 82 |
| 1-71 | MAERAALEELVKLQGERVRGLKQQKASAELIEEEVAKLLK LKAQLGPDESKQKFVLKTPKGTRDYSPRQMA | 83 |
| 1-70 | MAERAALEELVKLQGERVRGLKQQKASAELIEEEVAKLLK LKAQLGPDESKQKFVLKTPKGTRDYSPRQM | 84 |
| 1-69 | MAERAALEELVKLQGERVRGLKQQKASAELIEEEVAKLLK LKAQLGPDESKQKFVLKTPKGTRDYSPRQ | 85 |
| 1-68 | MAERAALEELVKLQGERVRGLKQQKASAELIEEEVAKLLK LKAQLGPDESKQKFVLKTPKGTRDYSPR | 86 |
| 1-67 | MAERAALEELVKLQGERVRGLKQQKASAELIEEEVAKLLK LKAQLGPDESKQKFVLKTPKGTRDYSP | 87 |
| 1-66 | MAERAALEELVKLQGERVRGLKQQKASAELIEEEVAKLLK LKAQLGPDESKQKFVLKTPKGTRDYS | 88 |
| 1-65 | MAERAALEELVKLQGERVRGLKQQKASAELIEEEVAKLLK LKAQLGPDESKQKFVLKTPKGTRDY | 89 |
| 1-64 | MAERAALEELVKLQGERVRGLKQQKASAELIEEEVAKLLK LKAQLGPDESKQKFVLKTPKGTRD | 90 |
| 1-63 | MAERAALEELVKLQGERVRGLKQQKASAELIEEEVAKLLK LKAQLGPDESKQKFVLKTPKGTR | 91 |
| 1-62 | MAERAALEELVKLQGERVRGLKQQKASAELIEEEVAKLLK LKAQLGPDESKQKFVLKTPKGT | 92 |
| 1-61 | MAERAALEELVKLQGERVRGLKQQKASAELIEEEVAKLLK LKAQLGPDESKQKFVLKTPKG | 93 |
| 1-60 | MAERAALEELVKLQGERVRGLKQQKASAELIEEEVAKLLK LKAQLGPDESKQKFVLKTPK | 94 |
| 1-59 | MAERAALEELVKLQGERVRGLKQQKASAELIEEEVAKLLK LKAQLGPDESKQKFVLKTP | 95 |
| 1-58 | MAERAALEELVKLQGERVRGLKQQKASAELIEEEVAKLLK LKAQLGPDESKQKFVLKT | 96 |
| 1-57 | MAERAALEELVKLQGERVRGLKQQKASAELIEEEVAKLLK LKAQLGPDESKQKFVLK | 97 |
| 1-56 | MAERAALEELVKLQGERVRGLKQQKASAELIEEEVAKLLK LKAQLGPDESKQKFVL | 98 |
| 1-55 | MAERAALEELVKLQGERVRGLKQQKASAELIEEEVAKLLK LKAQLGPDESKQKFV | 99 |
| 1-54 | MAERAALEELVKLQGERVRGLKQQKASAELIEEEVAKLLK LKAQLGPDESKQKF | 100 |

TABLE D5-continued

Exemplary truncated HRS polypeptides

| HRS range | Sequence | SEQ ID NO: |
|---|---|---|
| 1-53 | MAERAALEELVKLQGERVRGLKQQKASAELIEEEVAKLLK LKAQLGPDESKQK | 101 |
| 1-52 | MAERAALEELVKLQGERVRGLKQQKASAELIEEEVAKLLK LKAQLGPDESKQ | 102 |
| 1-51 | MAERAALEELVKLQGERVRGLKQQKASAELIEEEVAKLLK LKAQLGPDESK | 103 |
| 1-50 | MAERAALEELVKLQGERVRGLKQQKASAELIEEEVAKLLK LKAQLGPDES | 104 |
| 1-49 | MAERAALEELVKLQGERVRGLKQQKASAELIEEEVAKLLK LKAQLGPDE | 105 |
| 1-48 | MAERAALEELVKLQGERVRGLKQQKASAELIEEEVAKLLK LKAQLGPD | 106 |
| 1-47 | MAERAALEELVKLQGERVRGLKQQKASAELIEEEVAKLLK LKAQLGP | 107 |
| 1-46 | MAERAALEELVKLQGERVRGLKQQKASAELIEEEVAKLLK LKAQLG | 108 |
| 1-45 | MAERAALEELVKLQGERVRGLKQQKASAELIEEEVAKLLK LKAQL | 109 |
| 1-44 | MAERAALEELVKLQGERVRGLKQQKASAELIEEEVAKLLK LKAQ | 110 |
| 1-43 | MAERAALEELVKLQGERVRGLKQQKASAELIEEEVAKLLK LKA | 111 |
| 1-42 | MAERAALEELVKLQGERVRGLKQQKASAELIEEEVAKLLK LK | 112 |
| 1-41 | MAERAALEELVKLQGERVRGLKQQKASAELIEEEVAKLLK L | 113 |
| 1-40 | MAERAALEELVKLQGERVRGLKQQKASAELIEEEVAKLLK | 114 |

N-terminal truncations

| HRS range | Sequence | SEQ ID NO: |
|---|---|---|
| 2-80 | AERAALEELVKLQGERVRGLKQQKASAELIEEEVAKLLK LKAQLGPDESKQKFVLKTPKGTRDYSPRQMAVREKVFDVI | 115 |
| 3-80 | ERAALEELVKLQGERVRGLKQQKASAELIEEEVAKLLK LKAQLGPDESKQKFVLKTPKGTRDYSPRQMAVREKVFDVI | 116 |
| 4-80 | RAALEELVKLQGERVRGLKQQKASAELIEEEVAKLLK LKAQLGPDESKQKFVLKTPKGTRDYSPRQMAVREKVFDVI | 117 |
| 5-80 | AALEELVKLQGERVRGLKQQKASAELIEEEVAKLLK LKAQLGPDESKQKFVLKTPKGTRDYSPRQMAVREKVFDVI | 118 |
| 6-80 | ALEELVKLQGERVRGLKQQKASAELIEEEVAKLLK LKAQLGPDESKQKFVLKTPKGTRDYSPRQMAVREKVFDVI | 119 |
| 7-80 | LEELVKLQGERVRGLKQQKASAELIEEEVAKLLK LKAQLGPDESKQKFVLKTPKGTRDYSPRQMAVREKVFDVI | 120 |
| 8-80 | EELVKLQGERVRGLKQQKASAELIEEEVAKLLK LKAQLGPDESKQKFVLKTPKGTRDYSPRQMAVREKVFDVI | 121 |
| 9-80 | ELVKLQGERVRGLKQQKASAELIEEEVAKLLK LKAQLGPDESKQKFVLKTPKGTRDYSPRQMAVREKVFDVI | 122 |
| 10-80 | LVKLQGERVRGLKQQKASAELIEEEVAKLLK LKAQLGPDESKQKFVLKTPKGTRDYSPRQMAVREKVFDVI | 123 |
| 11-80 | VKLQGERVRGLKQQKASAELIEEEVAKLLK LKAQLGPDESKQKFVLKTPKGTRDYSPRQMAVREKVFDVI | 124 |
| 12-80 | KLQGERVRGLKQQKASAELIEEEVAKLLK LKAQLGPDESKQKFVLKTPKGTRDYSPRQMAVREKVFDVI | 125 |
| 13-80 | LQGERVRGLKQQKASAELIEEEVAKLLK LKAQLGPDESKQKFVLKTPKGTRDYSPRQMAVREKVFDVI | 126 |
| 14-80 | QGERVRGLKQQKASAELIEEEVAKLLK LKAQLGPDESKQKFVLKTPKGTRDYSPRQMAVREKVFDVI | 127 |

TABLE D5-continued

Exemplary truncated HRS polypeptides

| HRS range | Sequence | SEQ ID NO: |
|---|---|---|
| 15-80 | GERVRGLKQQKASAELIEEEVAKLLK LKAQLGPDESKQKFVLKTPKGTRDYSPRQMAVREKVFDVI | 128 |
| 16-80 | RVRGLKQQKASAELIEEEVAKLLK LKAQLGPDESKQKFVLKTPKGTRDYSPRQMAVREKVFDVI | 129 |
| 17-80 | VRGLKQQKASAELIEEEVAKLLK LKAQLGPDESKQKFVLKTPKGTRDYSPRQMAVREKVFDVI | 130 |
| 18-80 | RGLKQQKASAELIEEEVAKLLK LKAQLGPDESKQKFVLKTPKGTRDYSPRQMAVREKVFDVI | 131 |
| 19-80 | GLKQQKASAELIEEEVAKLLK LKAQLGPDESKQKFVLKTPKGTRDYSPRQMAVREKVFDVI | 132 |
| 20-80 | LKQQKASAELIEEEVAKLLK LKAQLGPDESKQKFVLKTPKGTRDYSPRQMAVREKVFDVI | 133 |
| 21-80 | KQQKASAELIEEEVAKLLK LKAQLGPDESKQKFVLKTPKGTRDYSPRQMAVREKVFDVI | 134 |
| 22-80 | QQKASAELIEEEVAKLLK LKAQLGPDESKQKFVLKTPKGTRDYSPRQMAVREKVFDVI | 135 |
| 23-80 | QKASAELIEEEVAKLLK LKAQLGPDESKQKFVLKTPKGTRDYSPRQMAVREKVFDVI | 136 |
| 24-80 | KASAELIEEEVAKLLK LKAQLGPDESKQKFVLKTPKGTRDYSPRQMAVREKVFDVI | 137 |
| 25-80 | ASAELIEEEVAKLLK LKAQLGPDESKQKFVLKTPKGTRDYSPRQMAVREKVFDVI | 138 |
| 26-80 | SAELIEEEVAKLLK LKAQLGPDESKQKFVLKTPKGTRDYSPRQMAVREKVFDVI | 139 |
| 27-80 | AELIEEEVAKLLK LKAQLGPDESKQKFVLKTPKGTRDYSPRQMAVREKVFDVI | 140 |
| 28-80 | ELIEEEVAKLLK LKAQLGPDESKQKFVLKTPKGTRDYSPRQMAVREKVFDVI | 141 |
| 29-80 | LIEEEVAKLLK LKAQLGPDESKQKFVLKTPKGTRDYSPRQMAVREKVFDVI | 142 |
| 30-80 | IEEEVAKLLK LKAQLGPDESKQKFVLKTPKGTRDYSPRQMAVREKVFDVI | 143 |
| 31-80 | EEEVAKLLK LKAQLGPDESKQKFVLKTPKGTRDYSPRQMAVREKVFDVI | 144 |
| 32-80 | EEVAKLLKLKAQLGPDESKQKFVLKTPKGTRDYSPRQMAVREKVFDVI | 145 |
| 33-80 | EVAKLLKLKAQLGPDESKQKFVLKTPKGTRDYSPRQMAVREKVFDVI | 146 |
| 34-80 | VAKLLKLKAQLGPDESKQKFVLKTPKGTRDYSPRQMAVREKVFDVI | 147 |
| 35-80 | AKLLKLKAQLGPDESKQKFVLKTPKGTRDYSPRQMAVREKVFDVI | 148 |
| 36-80 | KLLKLKAQLGPDESKQKFVLKTPKGTRDYSPRQMAVREKVFDVI | 149 |
| 37-80 | LLKLKAQLGPDESKQKFVLKTPKGTRDYSPRQMAVREKVFDVI | 150 |
| 38-80 | LKLKAQLGPDESKQKFVLKTPKGTRDYSPRQMAVREKVFDVI | 151 |
| 39-80 | KLKAQLGPDESKQKFVLKTPKGTRDYSPRQMAVREKVFDVI | 152 |
| 40-80 | LKAQLGPDESKQKFVLKTPKGTRDYSPRQMAVREKVFDVI | 153 |

Typically, the biologically-active fragment has no less than about 1%, 10%, 25%, or 50% of an activity of the biologically-active (i.e., non-canonical activity) HRS reference polypeptide from which it is derived. Exemplary methods for measuring such non-canonical activities are described in the Examples.

In some embodiments, HRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, or 150 nM. In some embodiments, the binding affinity of a HRS protein fragment for a selected cellular binding partner, particularly a binding partner that participates in a non-canonical activity, can be stronger than that of the corresponding full-length HRS polypeptide or a specific alternatively spliced HRS polypeptide variant, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a HRS polypeptide may be altered in various ways including amino acid substitutions, deletions, truncations, and insertions. Methods for such manipulations are generally known in the art. For example, amino acid sequence variants of a HRS reference polypeptide can be prepared by mutations in the DNA. Methods for mutagenesis and nucleotide sequence alterations are well known in the art. See, for example, Kunkel (1985, *PNAS USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant HRS polypeptides may contain conservative amino acid substitutions at various locations along their sequence, as compared to a reference HRS amino acid residue, and such additional substitutions may further enhance the activity or stability of the HRS polypeptides with altered cysteine content. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxylcarbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant HRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser, Ala, Leu, Val | Ser, Ala |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

The NMR structure of the human HRS WHEP domain has been determined (see Nameki et al., Accession 1x59_A). Further, the crystal structures of full-length human HRS and an internal catalytic domain deletion mutant of HRS (HRSACD) have also been determined (see Xu et al., *Structure*. 20:1470-7, 2012; and U.S. Application No. 61/674,639). In conjunction with the primary amino acid sequence of HRS, these detailed physical descriptions of the protein provide precise insights into the roles played by specific amino acids within the protein. Persons skilled in the art can thus use this information to identify structurally-conserved domains, linking regions, secondary structures such as alpha-helices, surface or solvent-exposed amino acids, non-exposed or internal regions, catalytic sites, and ligand-interacting surfaces, among other structural features. Such persons can then use that and other information to readily engineer HRS variants that retain or improve the non-canonical activity of interest, for instance, by conserving or altering the characteristics of the amino acid residues within or adjacent to these and other structural features, such as by conserving or altering the polarity, hydropathy index, charge, size, and/or positioning (i.e., inward, outward) of selected amino acid side chain(s) relative to wild-type residues (see, e.g., Zaiwara et al., *Mol Biotechnol*. 51:67-102, 2012; Perona and Hadd, *Biochemistry*. 51:8705-29, 2012; Morin et al., *Trends Biotechol*. 29:159-66, 2011; Collins et al., *Annu. Rev. Biophys*. 40:81-98, 2011; and U.S. Application No. 61/674,639).

Thus, a predicted non-essential amino acid residue in a truncated and/or variant HRS polypeptide is typically replaced with another amino acid residue from the same side chain family. Alternatively, mutations can be introduced randomly along all or part of a HRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference HRS sequence. An "essential" amino acid residue is a residue that, when altered from the reference sequence of a HRS polypeptide, results in abolition of an activity of the parent molecule such that less than 20% of the reference activity is present. For example, such essential amino acid residues include those that are conserved in HRS polypeptides across different species, including those sequences that are conserved in the active binding site(s) or motif(s) of HRS polypeptides from various sources.

Assays to determine anti-inflammatory activity, including routine measurements of cytokine release from in vitro cell based, and animal studies are well established in the art (see, for example, Wittmann et al., *J Vis Exp*. (65):e4203. doi: 10.3791/4203, 2012; Feldman et al., *Mol Cell*. 47:585-95, 2012; Clutterbuck et al., *J Proteomics*. 74:704-15, 2011, Giddings and Maitra, *J Biomol Screen*. 15:1204-10, 2010; Wijnhoven et al., *Glycoconj J*. 25:177-85, 2008; and Frow et al., *Med Res Rev*. 24:276-98, 2004) and can be readily used to profile and optimize anti-inflammatory activity. At least one exemplary in vivo experimental system is described in the accompanying Examples.

Certain HRS polypeptides may have one or more cysteine substitutions, where one or more naturally-occurring (non-cysteine) residues are substituted with cysteine, for example, to alter stability or pK characteristics, facilitate thiol-based attachment of PEG molecules, etc. In some embodiments, cysteine substitutions are near the N-terminus and/or C-terminus of the HRS polypeptide (e.g., SEQ ID NOS: 1-23, 39, 41, 43, 70-71, 74-153, 160-172, or 176-182), or other surface exposed regions of a HRS polypeptide. Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of any one of SEQ ID NOS: 1-23, 39, 41, 43, 70-71, 74-153, 160-172, or 176-182 are substituted with a cysteine residue. In some embodiments, cysteine residues may be added to the HRS polypeptide through the creation of N, or C-terminal fusion proteins. Such fusion proteins may be of any length, but will typically be about 1-5, or about 5-10, about 10 to 20, or about 20 to 30 amino acids in length. In some embodiments, fusion to the C-terminus is preferred.

Specific exemplary embodiments of such cysteine modified proteins are shown in Table D6, based on the HRS polypeptide HRS(1-60). This approach is directly applicable to the HRS polypeptides of Table D5, and other HRS polypeptides described herein.

with the elimination of other surface exposed cysteine residues. Accordingly, in some embodiments, the HRS polypeptide may comprise one or more substitutions and/or deletions at Cys83, Cys174, Cys191, Cys196, Cys224, Cys235, Cys379, Cys455, Cys507, and/or Cys509 (as defined by SEQ ID NO:1), for instance, to remove naturally-occurring cysteine residues.

Specific embodiments include any one of SEQ ID NOS: 1-23, 39, 41, 43, 70-71, 74-153, 160-172, or 176-182, or variants thereof, having at mutation or deletion of any one or more of Cys83, Cys174, Cys191, Cys196, Cys224, Cys235, Cys379, Cys455, or the deletion of Cys507 and Cys509, for instance, by the deletion of the C-terminal 3 amino acids (4507-509). Exemplary mutations at these positions include for example the mutation of cysteine to serine, alanine, leucine, valine or glycine. In certain embodiments, amino acid residues for specific cysteine substitutions can be selected from naturally-occurring substitutions that are found in HRS

TABLE D6

| Name | Protein Sequences | SEQ ID NO: |
|---|---|---|
| HRS(1-60)-M1MC- | MCAERAALEE LVKLQGERVR GLKQQKASAE LIEEEVAKLL KLKAQLGPDE SKQKFVLKTP K | 170 |
| HRS(1-60)-A26C- | MAERAALEEL VKLQGERVRG LKQQKCSAEL IEEEVAKLLK LKAQLGPDES KQKFVLKTPK | 171 |
| HRS(1-60)-C61 | MAERAALEEL VKLQGERVRG LKQQKASAEL IEEEVAKLLK LKAQLGPDES KQKFVLKTPK C | 172 |

| | DNA sequences | |
|---|---|---|
| HRS(1-60)-M1MC- | ATGTGTGCAGAAAGAGCCGCCCTGGAAGAGTTAGTTAAGTTGCAAGGTG AACGTGTCCGTGGTCTGAAGCAGCAGAAGGCTAGCGCGGAGCTGATCGA AGAAGAGGTGGCCAAACTGCTGAAGCTGAAGGCGCAGCTGGGCCCGGAC GAGAGCAAACAAAAGTTCGTCCTGAAAACCCCGAAA | 173 |
| HRS(1-60)-A26C- | ATGGCAGAACGTGCGGCATTGGAAGAATTGGTTAAACTGCAAGGTGAAC GTGTTCGTGGTCTGAAGCAGCAGAAGTGCAGCGCGGAGCTGATCGAAGA AGAGGTGGCCAAACTGCTGAAGCTGAAGGCGCAGCTGGGCCCGGACGAG AGCAAACAAAAGTTCGTCCTGAAAACCCCGAAA | 174 |
| HRS(1-60)-C61 | ATGGCAGAACGTGCGGCATTGGAAGAATTGGTTAAACTGCAAGGTGAAC GTGTTCGTGGTCTGAAGCAGCAGAAGGCTAGCGCGGAGCTGATCGAAGA AGAGGTGGCCAAACTGCTGAAGCTGAAGGCGCAGCTGGGCCCGGACGAG AGCAAACAAAAGTTCGTCCTGAAAACCCCGAAATGC | 175 |

In some embodiments, the insertion or substitution of cysteine residue(s) into the HRS polypeptide may be combined orthologs from other species and organisms. Exemplary substitutions of this type are presented in Table D7.

TABLE D7

Naturally-occurring sequence variation at positions occupied by cysteine residues in human HRS

| H. sapiens cysteine residue # | P. troglodyte | M. mulatta | B. aturus | M. musculus | R. norvegicus | G. gallus | X. laevis | D. rerio | D. melanogaster | C. elegans | S. cerevisiae | E. coli |
|---|---|---|---|---|---|---|---|---|---|---|---|---|
| 83 | C | C | C | C | C | C | C | C | V | T | L | V |
| 174 | C | C | C | C | C | C | C | C | C | C | C | L |
| 191 | C | C | C | C | C | C | C | C | C | V | C | A/L |
| 196 | C | C | C | C | C | Q | H | Y | S | M | V | L/A |
| 224 | C | C | C | C | C | C | C | C | C | S | A | A |
| 235 | C | C | C | C | C | C | C | C | C | C | S | E |
| 379 | C | C | C | C | C | C | C | V | C | C | C | A |
| 455 | C | C | C | C | C | C | C | — | C | C | A | A |
| 507 | C | R | C | S | S | — | — | — | — | S/Q | S/E | — |
| 509 | C | C | C | C | — | — | — | — | — | — | I | I/G | — |

In some embodiments, the naturally-occurring cysteines residues selected for mutagenesis are identified or selected based on their surface exposure. Accordingly, in some aspects the cysteine residues selected for substitution are selected from Cys224, Cys235, Cys507 and Cys509. In some embodiments, the last three (C-terminal) residues of SEQ ID NO:1 are deleted so as to delete residues 507 to 509. In some embodiments, the cysteines are selected for mutation or deletion so as to eliminate an intramolecular cysteine pair, for example Cys174 and Cys191.

Specific additional examples of desired cysteine mutations/substitutions (indicated in bold underline) to reduce surface exposed cysteine residues include those listed below in Table D8.

TABLE D8

HRS polypeptides with Substitutions to Remove Surface Exposed Cysteines

| Name | Protein Sequence | SEQ ID NO: |
|---|---|---|
| HRS(1-506) C174A | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQADFDIAGNFDPMIPDAECLKIMCEIL SSLQIGDFLVKVNDRRILDGMFAICGVSDSKFRTICSSVDKLDKVSWEEVK NEMVGEKGLAPEVADRIGDYVQQHGGVSLVEQLLQDPKLSQNKQALEGL GDLKLLFEYLTLFGIDDKISFDLSLARGLDYYTGVIYEAVLLQTPAQAGEE PLGVGSVAAGGRYDGLVGMFDPKGRKVPCVGLSIGVERIFSIVEQRLEAL EEKIRTTETQVLVASAQKKLLEERLKLVSELWDAGIKAELLYKKNPKLLN QLQYCEEAGIPLVAIIGEQELKDGVIKLRSVTSREEVDVRREDLVEEIKRRT GQPL | 176 |
| HRS(1-506) C174V | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQVDFDIAGNFDPMIPDAECLKIMCEIL SSLQIGDFLVKVNDRRILDGMFAICGVSDSKFRTICSSVDKLDKVSWEEVK NEMVGEKGLAPEVADRIGDYVQQHGGVSLVEQLLQDPKLSQNKQALEGL GDLKLLFEYLTLFGIDDKISFDLSLARGLDYYTGVIYEAVLLQTPAQAGEE PLGVGSVAAGGRYDGLVGMFDPKGRKVPCVGLSIGVERIFSIVEQRLEAL EEKIRTTETQVLVASAQKKLLEERLKLVSELWDAGIKAELLYKKNPKLLN QLQYCEEAGIPLVAIIGEQELKDGVIKLRSVTSREEVDVRREDLVEEIKRRT GQPL | 177 |
| HRS(1-506) C191A | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQCDFDIAGNFDPMIPDAEALKIMCEIL SSLQIGDFLVKVNDRRILDGMFAICGVSDSKFRTICSSVDKLDKVSWEEVK NEMVGEKGLAPEVADRIGDYVQQHGGVSLVEQLLQDPKLSQNKQALEGL GDLKLLFEYLTLFGIDDKISFDLSLARGLDYYTGVIYEAVLLQTPAQAGEE PLGVGSVAAGGRYDGLVGMFDPKGRKVPCVGLSIGVERIFSIVEQRLEAL EEKIRTTETQVLVASAQKKLLEERLKLVSELWDAGIKAELLYKKNPKLLN QLQYCEEAGIPLVAIIGEQELKDGVIKLRSVTSREEVDVRREDLVEEIKRRT GQPL | 178 |
| HRS(1-506) C191S | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQCDFDIAGNFDPMIPDAESLKIMCEILS SLQIGDFLVKVNDRRILDGMFAICGVSDSKFRTICSSVDKLDKVSWEEVKN EMVGEKGLAPEVADRIGDYVQQHGGVSLVEQLLQDPKLSQNKQALEGLG DLKLLFEYLTLFGIDDKISFDLSLARGLDYYTGVIYEAVLLQTPAQAGEEP LGVGSVAAGGRYDGLVGMFDPKGRKVPCVGLSIGVERIFSIVEQRLEALE EKIRTTETQVLVASAQKKLLEERLKLVSELWDAGIKAELLYKKNPKLLNQ LQYCEEAGIPLVAIIGEQELKDGVIKLRSVTSREEVDVRREDLVEEIKRRTG QPL | 179 |
| HRS(1-506) C191V | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQCDFDIAGNFDPMIPDAEVLKIMCEIL SSLQIGDFLVKVNDRRILDGMFAICGVSDSKFRTICSSVDKLDKVSWEEVK NEMVGEKGLAPEVADRIGDYVQQHGGVSLVEQLLQDPKLSQNKQALEGL GDLKLLFEYLTLFGIDDKISFDLSLARGLDYYTGVIYEAVLLQTPAQAGEE PLGVGSVAAGGRYDGLVGMFDPKGRKVPCVGLSIGVERIFSIVEQRLEAL EEKIRTTETQVLVASAQKKLLEERLKLVSELWDAGIKAELLYKKNPKLLN QLQYCEEAGIPLVAIIGEQELKDGVIKLRSVTSREEVDVRREDLVEEIKRRT GQPL | 180 |
| HRS(1-506) C224S | MAERAALEELVKLQGERVRGLKQQKASAELIEEEVAKLLKLKAQLGPDE SKQKFVLKTPKGTRDYSPRQMAVREKVFDVIIRCFKRHGAEVIDTPVFELK ETLMGKYGEDSKLIYDLKDQGGELLSLRYDLTVPFARYLAMNKLTNIKR YHIAKVYRRDNPAMTRGRYREFYQCDFDIAGNFDPMIPDAECLKIMCEILS | 181 |

TABLE D8-continued

HRS polypeptides with Substitutions to
Remove Surface Exposed Cysteines

| | | |
|---|---|---|
| | SLQIGDFLVKVNDRRILDGMFAISGVSDSKFRTICSSVDKLDKVSWEEVKN<br>EMVGEKGLAPEVADRIGDYVQQHGGVSLVEQLLQDPKLSQNKQALEGLG<br>DLKLLFEYLTLFGIDDKISFDLSLARGLDYYTGVIYEAVLLQTPAQAGEEP<br>LGVGSVAAGGRYDGLVGMFDPKGRKVPCVGLSIGVERIFSIVEQRLEALE<br>EKIRTTETQVLVASAQKKLLEERLKLVSELWDAGIKAELLYKKNPKLLNQ<br>LQYCEEAGIPLVAIIGEQELKDGVIKLRSVTSREEVDVRREDLVEEIKRRTG<br>QPL | |
| HRS(1-506)<br>C235S | MAERAALEELVKLQGERVRGLKQQKASAELIEEEVAKLLKLKAQLGPDE<br>SKQKFVLKTPKGTRDYSPRQMAVREKVFDVIIRCFKRHGAEVIDTPVFELK<br>ETLMGKYGEDSKLIYDLKDQGGELLSLRYDLTVPFARYLAMNKLTNIKR<br>YHIAKVYRRDNPAMTRGRYREFYQCDFDIAGNFDPMIPDAECLKIMCEILS<br>SLQIGDFLVKVNDRRILDGMFAICGVSDSKFRTISSSVDKLDKVSWEEVKN<br>EMVGEKGLAPEVADRIGDYVQQHGGVSLVEQLLQDPKLSQNKQALEGLG<br>DLKLLFEYLTLFGIDDKISFDLSLARGLDYYTGVIYEAVLLQTPAQAGEEP<br>LGVGSVAAGGRYDGLVGMFDPKGRKVPCVGLSIGVERIFSIVEQRLEALE<br>EKIRTTETQVLVASAQKKLLEERLKLVSELWDAGIKAELLYKKNPKLLNQ<br>LQYCEEAGIPLVAIIGEQELKDGVIKLRSVTSREEVDVRREDLVEEIKRRTG<br>QPL | 182 |

| Name | DNA Sequence | SEQ ID NO: |
|---|---|---|
| HRS(1-506)<br>C174A | ATGGCGGAACGTGCCGCACTGGAAGAATTGGTTAAATTACAGGGAGA<br>ACGCGTACGTGGTCTTAAACAACAAAAAGCCTCTGCGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAGTATATCGCCGCGACAACC<br>CTGCAATGACTCGTGGACGCTATCGCGAATTCTATCAGGCTGATTTTGA<br>TATTGCCGGAAATTTCGACCCGATGATCCCGGATGCCGAGTGTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTGCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCCGCGGTCTTGATTATTATACCGGCGTGATTTACGAAGCT<br>GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTGAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA | 183 |
| HRS(1-506)<br>C174V | ATGGCGGAACGTGCCGCACTGGAAGAATTGGTTAAATTACAGGGAGA<br>ACGCGTACGTGGTCTTAAACAACAAAAAGCCTCTGCGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAGTATATCGCCGCGACAACC<br>CTGCAATGACTCGTGGACGCTATCGCGAATTCTATCAGGTTGATTTTGA<br>TATTGCCGGAAATTTCGACCCGATGATCCCGGATGCCGAGTGTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTGCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCCGCGGTCTTGATTATTATACCGGCGTGATTTACGAAGCT | 184 |

TABLE D8-continued

HRS polypeptides with Substitutions to
Remove Surface Exposed Cysteines

|  |  |  |
|---|---|---|
|  | GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA |  |
| HRS(1-506)<br>C191A | ATGGCGGAACGTGCCGCACTGGAAGAATTGGTTAAATTACAGGGAGA<br>ACGCGTACGTGGTCTTAAACAACAAAAAGCCTCTGCGGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAAGTATATCGCCGCGACAACC<br>CTGCAATGACTCGTGGACGCTATCGCGAATTCTATCAGTGTGATTTTGA<br>TATTGCCGGAAATTTCGACCCGATGATCCCGGATGCCGAGGCTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTGCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCGCGGTCTTGATTATTATACCGGCGTGATTTACGAAGCT<br>GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA | 185 |
| HRS(1-506)<br>C191S | ATGGCGGAACGTGCCGCACTGGAAGAATTGGTTAAATTACAGGGAGA<br>ACGCGTACGTGGTCTTAAACAACAAAAAGCCTCTGCGGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAAGTATATCGCCGCGACAACC<br>CTGCAATGACTCGTGGACGCTATCGCGAATTCTATCAGTGTGATTTTGA<br>TATTGCCGGAAATTTCGACCCGATGATCCCGGATGCCGAGAGTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTGCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCGCGGTCTTGATTATTATACCGGCGTGATTTACGAAGCT<br>GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA | 186 |

TABLE D8-continued

HRS polypeptides with Substitutions to
Remove Surface Exposed Cysteines

| HRS(1-506) C191V | ATGGCGGAACGTGCCGCACTGGAAGAATTGGTTAAATTACAGGGAGA<br>ACGCGTACGTGGTCTTAAACAACAAAAAGCCTCTGCGGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAAGTATATCGCCGCGACAACC<br>CTGCAATGACTCGTGGACGCTATCGCGAATTCTATCAGTGTGATTTTGA<br>TATTGCCGGAAATTTCGACCCGATGATCCCGGATGCCGAGGTTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTGCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCGCGGTCTTGATTATTATACCGGCGTGATTTACGAAGCT<br>GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTGAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA | 187 |
| HRS(1-506) C224S | ATGGCGGAACGTGCCGCACTGGAAGAATTGGTTAAATTACAGGGAGA<br>ACGCGTACGTGGTCTTAAACAACAAAAAGCCTCTGCGGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAAGTATATCGCCGCGACAACC<br>CTGCAATGACTCGTGGACGCTATCGCGAATTCTATCAGTGTGATTTTGA<br>TATTGCCGGAAATTTCGACCCGATGATCCCGGATGCCGAGTGTTTGAA<br>AATTATGTGTGAAATTCTGAGTTCGTTGCAGATCGGAGACTTTCTTGTA<br>AAAGTTAATGACCGCCGTATTCTGGATGGTATGTTTGCTATTTCCGGTG<br>TTTCTGATTCCAAATTCCGTACAATCTGCTCAAGCGTGGACAAATTGGA<br>TAAAGTGTCTTGGGAAGAAGTAAAAAATGAAATGGTGGGAGAAAAAG<br>GCCTGGCTCCAGAAGTAGCAGACCGTATTGGTGACTATGTTCAACAAC<br>ATGGCGGTGTGTCCTTAGTCGAACAGTTATTACAGGATCCTAAACTGA<br>GCCAAAATAAACAAGCACTTGAAGGACTGGGAGATCTGAAATTACTCT<br>TTGAATATCTGACCTTATTTGGGATTGATGATAAAATTAGCTTTGATCT<br>GAGCTTGGCCCGCGGTCTTGATTATTATACCGGCGTGATTTACGAAGCT<br>GTTCTCTTGCAAACCCCAGCCCAGGCGGGCGAAGAGCCTTTGGGAGTC<br>GGCAGTGTGGCAGCCGGTGGTCGTTATGATGGTTTGGTAGGAATGTTT<br>GACCCTAAAGGCCGTAAAGTACCATGTGTGGGGCTTTCTATCGGTGTC<br>GAACGTATCTTTTCTATTGTTGAACAACGTCTTGAAGCTTTGGAGGAAA<br>AGATCCGTACCACGGAAacCCAAGTCTTAGTTGCaAGTGCCCAAAAAAA<br>ACTGTTAGAAGAACGCCTGAAACTCGTATCAGAACTTTGGGACGCCGG<br>CATCAAGGCCGAACTGCTGTATAAAAAGAACCCGAAATTGTTAAACCA<br>ACTCCAGTATTGTGAAGAAGCTGGGATCCCACTCGTAGCTATTATTGG<br>TGAGCAAGAATTAAAAGATGGCGTGATTAAACTGCGTTCAGTAACAAG<br>CCGTGAAGAGGTAGATGTACGTCGCGAAGACTTAGTGGAAGAAATTA<br>AACGCCGCACCGGTCAACCGTTA | 188 |
| HRS(1-506) C235S | ATGGCGGAACGTGCCGCACTGGAAGAATTGGTTAAATTACAGGGAGA<br>ACGCGTACGTGGTCTTAAACAACAAAAAGCCTCTGCGGAATTGATTGA<br>AGAAGAAGTTGCCAAATTACTGAAACTGAAAGCTCAACTTGGACCCGA<br>TGAAAGTAAACAAAAATTTGTGTTGAAAACGCCCAAAGGAACCCGTG<br>ATTATAGTCCACGTCAAATGGCCGTTCGTGAAAAAGTGTTCGACGTTA<br>TTATTCGCTGTTTTAAACGTCACGGTGCTGAAGTAATCGATACCCCCGT<br>ATTTGAATTGAAAGAGACTCTGATGGGCAAATATGGTGAAGATTCTAA<br>ACTGATTTATGATTTGAAAGACCAAGGAGGTGAACTGCTGAGCCTGCG<br>CTACGACTTAACTGTGCCTTTTGCCCGTTACTTAGCCATGAATAAaTTaA<br>CCAACATCAAACGTTACCATATTGCAAAAGTATATCGCCGCGACAACC<br>CTGCAATGACTCGTGGACGCTATCGCGAATTCTATCAGTGTGATTTTGA | 189 |

TABLE D8-continued

HRS polypeptides with Substitutions to Remove Surface Exposed Cysteines

```
TATTGCCGGAAATTTCGACCCGATGATCCCGGATGCCGAGTGTTTGAA
AATTATGTGTGAAATTCTGAGTTCGTTGCAGATCGGAGACTTTCTTGTA
AAAGTTAATGACCGCCGTATTCTGGATGGTATGTTTGCTATTTGCGGTG
TTTCTGATTCCAAATTCCGTACAATCTCCTCAAGCGTGGACAAATTGGA
TAAAGTGTCTTGGGAAGAAGTAAAAAATGAAATGGTGGGAGAAAAAG
GCCTGGCTCCAGAAGTAGCAGACCGTATTGGTGACTATGTTCAACAAC
ATGGCGGTGTGTCCTTAGTCGAACAGTTATTACAGGATCCTAAACTGA
GCCAAAATAAACAAGCACTTGAAGGACTGGGAGATCTGAAATTACTCT
TTGAATATCTGACCTTATTTGGGATTGATGATAAAATTAGCTTTGATCT
GAGCTTGGCCCGCGGTCTTGATTATTATACCGGCGTGATTTACGAAGCT
GTTCTCTTGCAAACCCCAGCCCAGGCGGGCGAAGAGCCTTTGGGAGTC
GGCAGTGTGGCAGCCGGTGGTCGTTATGATGGTTTGGTAGGAATGTTT
GACCCTAAAGGCCGTAAAGTACCATGTGTGGGGCTTTCTATCGGTGTC
GAACGTATCTTTTCTATTGTTGAACAACGTCTTGAAGCTTTGGAGGAAA
AGATCCGTACCACGGAAacCCAAGTCTTAGTTGCaAGTGCCCAAAAAAA
ACTGTTAGAAGAACGCCTGAAACTCGTATCAGAACTTTGGGACGCCGG
CATCAAGGCCGAACTGCTGTATAAAAAGAACCCGAAATTGTTAAACCA
ACTCCAGTATTGTGAAGAAGCTGGGATCCCACTCGTAGCTATTATTGG
TGAGCAAGAATTAAAAGATGGCGTGATTAAACTGCGTTCAGTAACAAG
CCGTGAAGAGGTAGATGTACGTCGCGAAGACTTAGTGGAAGAAATTA
AACGCCGCACCGGTCAACCGTTA
```

In some embodiments, such cysteine substituted mutants are modified to engineer-in, insert, or otherwise introduce a new surface exposed cysteine residue at a defined surface exposed position, where the introduced residue does not substantially interfere with the non-canonical activity of the HRS polypeptide. Specific examples include for example the insertion (or re-insertion back) of additional cysteine residues at the N- or C-terminus of any of the reduced cysteine HRS polypeptides described above. In some embodiments, the insertion of such N- or C-terminal surface exposed cysteines involves the re-insertion of the last 1, last 2, or last 3 naturally-occurring C-terminal amino acids of the full-length human HRS to a reduced cysteine variant of a HRS polypeptide e.g., the re-insertion of all or part of the sequence CIC (Cys Ile Cys). Exemplary reduced cysteine mutants include for example any combination of mutations (or the deletion of) at residues Cys174, Cys191, Cys224, and Cys235, and or the deletion or substitution of Cys507 and Cys509 (based on the numbering of full-length human HRS (SEQ ID NO:1) in any of the HRS polypeptides of SEQ ID NOS:1-106, 131-133, 137-143, 178, 180, 182, 184, or 186-195 or any of the any of the HRS polypeptides listed in or derivable from Tables D1-D9.

In various embodiments, the present invention contemplates modifications at any amino acid position in a HRS polypeptide by virtue of substituting a non-naturally-occurring amino acid optionally comprising a functional group. Non-natural amino acids can be inserted or substituted at, for example, one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS: 1-23, 39, 41, 43, 70-71, 74-153, 160-172, or 176-182 (or any of the HRS polypeptides listed in or derivable from Tables D1-D9); at the N-terminus and/or C-terminus of any one of SEQ ID NOS: 1-23, 39, 41, 43, 70-71, 74-153, 160-172, or 176-182 (or any of the HRS polypeptides listed in or derivable from Tables D1-D9); or a solvent accessible surface amino acid residue as described herein.

In particular embodiments, non-naturally-occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

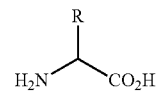

A non-natural amino acid is typically any structure having the foregoing formula wherein the R group is any substituent other than one used in the twenty natural amino acids. See, e.g., biochemistry texts such as Biochemistry by L. Stryer, 3rd ed. 1988, Freeman and Company, New York, for structures of the twenty natural amino acids. Note that the non-natural amino acids disclosed herein may be naturally-occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally-occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Accordingly, one may select a non-naturally-occurring amino acid comprising a functional group that forms a covalent bond with any preferred functional group of heterologous moiety, for example, a PEG moiety. Non-natural amino acids, once selected, can either be purchased from vendors, or chemically synthesized. Any number of non-natural amino acids may be incorporated into the target molecule and may vary according to the number of desired water soluble polymers, e.g., PEG moieties, that are to be attached. The moieties may be attached to all or only some of the non-natural amino acids. Further, the same or different non-natural amino acids may be incorporated into a HRS polypeptide, depending on the desired outcome. In certain embodiments, about 1, 2, 3, 4, 5, 6, 7, 8, 9, 10 or more non-natural amino acids are incorporated into a HRS polypeptide any or all of which may be conjugated to a heterologous moiety comprising a desired functional group.

Certain embodiments of the present invention also contemplate the use of modified HRS polypeptides, including modifications that improved the desired characteristics of a HRS polypeptide, as described herein. Modifications of HRS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of fusion proteins, carbohydrate or lipid moieties, cofactors, the substitution of D amino acids and the like. Exemplary modifications also include PEGylation of a HRS polypeptide (see, e.g., Veronese and Harris, *Advanced Drug Delivery Reviews* 54: 453-456, 2002; and Pasut et al., *Expert Opinion. Ther. Patents* 14(6) 859-894 2004, both herein incorporated by reference). In some embodiments, such PEGylated HRS polypeptides comprise a mutation to add or remove an endogenous cysteine, to enable selective coupling via an exogenous, or endogenous cysteine, or other residue.

PEG is a well-known polymer having the properties of solubility in water and in many organic solvents, lack of toxicity, and lack of immunogenicity. It is also clear, colorless, odorless, and chemically stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

In particular a wide variety of PEG derivatives are both available and suitable for use in the preparation of PEG-conjugates. For example, NOF Corp.'s PEG reagents sold under the trademark SUNBRIGHT® Series provides numerous PEG derivatives, including methoxypolyethylene glycols and activated PEG derivatives such as methoxy-PEG amines, maleimides, N-hydroxysuccinimide esters, and carboxylic acids, for coupling by various methods to the N-terminal, C-terminal or any internal amino acid of the AARS polypeptide. Nektar Therapeutics' Advanced PEGylation technology also offers diverse PEG-coupling technologies to potentially improve the safety and efficacy of a HRS polypeptide based therapeutic.

Patents, published patent applications, and related publications will also provide those skilled in the art reading this disclosure with significant possible PEG-coupling technologies and PEG-derivatives. See, e.g., U.S. Pat. Nos. 6,436,386; 5,932,462; 5,900,461; 5,824,784; and 4,904,584; the contents of which are incorporated by reference in their entirety, describe such technologies and derivatives, and methods for their manufacture.

In certain aspects, chemoselective ligation technology may be utilized to modify HRS polypeptides of the invention, such as by attaching polymers in a site-specific and controlled manner. Such technology typically relies on the incorporation of chemoselective anchors into the protein backbone by either chemical, or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

In other embodiments, fusion proteins of HRS polypeptide to other proteins are also included, and these fusion proteins may modulate the HRS polypeptide's biological activity, secretion, antigenicity, targeting, biological life, ability to penetrate cellular membranes, or the blood brain barrier, or pharmacokinetic properties. Examples of fusion proteins that improve pharmacokinetic properties ("PK modifiers") include without limitation, fusions to human albumin (Osborn et al.: *Eur. J. Pharmacol.* 456(1-3): 149-158, (2002)), antibody Fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the HRS polypeptide. This additional extension adopts a bulky random structure, which significantly increases the size of the resulting fusion protein. By this means the typically rapid clearance of smaller HRS polypeptides via kidney filtration is retarded by several orders of magnitude. Additionally use of IgG fusion proteins has also been shown to enable some fusion protein proteins to penetrate the blood brain barrier (Fu et al., (2010) Brain Res. 1352:208-13).

Examples of fusion proteins that modulate the antigenicity, or immunomodulatory properties of the HRS polypeptide include fusions to T cell binding ligands, including for example, MHC Class I and II proteins, b-2 microglobulin, portions of LFA-3, portions of the Fc region of the heavy chain, and conjugates and derivatives thereof; Examples of such fusion proteins are described in for example EP 1 964 854, U.S. Pat. Nos. 5,468,481; 5,130,297; 5,635,363; 6,451, 314 and US 2009/0280135.

Additionally in some embodiments, the HRS polypeptide can include synthetic, or naturally-occurring secretion signal sequences, derived from other well characterized secreted proteins. In some embodiments such proteins, may be processed by proteolytic cleavage to form the HRS polypeptide in situ. In some embodiments the HRS polypeptide can comprise heterologous proteolytic cleavage sites, to enable the in situ expression, and production of the HRS polypeptide either at an intracellular, or an extracellular location. Other fusions proteins may also include for example fusions of HRS polypeptide to ubiquitin to provide a new N-terminal amino acid, or the use of a secretion signal to mediate high level secretion of the HRS polypeptide into the extracellular medium, or N, or C-terminal epitope tags to improve purification or detection.

In certain aspects, the use of non-natural amino acids can be utilized to modify (e.g., increase) a selected non-canonical activity of a HRS polypeptide, or to alter the in vivo or in vitro half-life of the protein. Non-natural amino acids can also be used to facilitate (selective) chemical modifications (e.g., pegylation) of a HRS protein, as described elsewhere herein. For instance, certain non-natural amino acids allow selective attachment of polymers such as PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the HRS polypeptides of the present invention may be composed of naturally-occurring and non-naturally-occurring amino acids as well as amino acid analogs and mimetics.

In certain embodiments, the modified or variant HRS polypeptides described herein, for example, HRS polypeptides with reduced cysteine content, have altered (e.g., improved, increased, decreased, reduced) biochemical, physical, and/or pharmacokinetic properties relative to unmodified or non-variant HRS polypeptides (e.g., wild-type full-length human HRS (SEQ ID NO:1); a corresponding HRS fragment or sequence with wild-type cysteine residues) under identical or otherwise comparable conditions. In some embodiments, the modified or variant HRS polypeptide having altered biochemical, physical, and/or pharmacokinetic properties has a mutation (e.g., deletion, substitution) of any one or more of Cys174, Cys191, Cys224, Cys235, Cys455, Cys507 and Cys509, as described herein. In specific embodiments, the modified or variant HRS polypeptide has a mutation of Cys507 and Cys509, e.g., a deletion of residues 507-509 (Δ507-509). Some modified or variant HRS polypeptides comprise residues 1-506 or 2-506 of SEQ ID NO:1 (or a variant thereof) but lack residues 507-509 of SEQ ID NO:1 (also referred to as HRS(1-506), HRS(2-506)), and optionally have improved biochemical, physical, and/or pharmacokinetic properties relative to full-length human HRS (SEQ ID NO:1).

Examples of biochemical, physical, and pharmacokinetic properties include, without limitation, absolute biological activity (e.g., non-canonical activity), stability (e.g., half-life, kinetic or thermal stability, functional stability, susceptibility to oxidation), clarity (e.g., turbidity, opalescence) in solution, aggregate formation in solution, homogeneity or monodispersion in solution (e.g., altered ratio of monomeric/dimeric or monomeric/oligomeric forms, altered levels of interchain disulfide bond formation), immunogenicity, cross reactivity, non-specific binding, improved expression in bacteria such as E. coli, (e.g. reduced endotoxin contamination, improved homogeneity, improved charge homogeneity), improved yield of soluble protein, reduced endotoxin binding, degree of degradation in solution, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve (AUC; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state).

In some embodiments, the modified or variant HRS polypeptide has a plasma or sera pharmacokinetic AUC profile at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a corresponding unmodified or non-variant HRS polypeptide upon administration to a mammal.

In some aspects, these improved properties are achieved without significantly altering the secondary structure and/or reducing the non-canonical biological activity of the variant or modified HRS polypeptide. Indeed, some variant or modified HRS polypeptides have increased non-canonical biological activity. For instance, in some embodiments, a modified or variant HRS polypeptide has increased (e.g., absolute) biological activity relative to an unmodified or non-variant HRS polypeptide under comparable conditions. Exemplary activities include any of the non-canonical activities described herein, such as anti-inflammatory activities and the ability to bind to anti-Jo-1 antibodies or other cellular binding agents. In some embodiments, the modified or variant HRS polypeptide has at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater biological activity than an unmodified or non-variant HRS polypeptide under identical or otherwise comparable conditions.

In some embodiments, the modified or variant HRS polypeptide has a lower $IC_{50}$ (i.e., higher binding affinity) for binding to a Jo-1 antibody compared to the full-length unmodified protein (SEQ ID NO:1) in an ELISA assay. In some embodiments, the modified or variant HRS polypeptide has an IC$_{50}$ in a Jo-1 competitive ELISA which is at least about 10%, 20%, 30%, 40%, 50%, 60%, 70%, 80%, 90%, 100%, 200%, 300%, 400%, or 500% lower than an unmodified or non-variant HRS polypeptide under identical or otherwise comparable conditions. In some embodiments, the modified or variant HRS polypeptide has an $IC_{50}$ in a Jo-1 competitive ELISA which is less than about 0.2 nM, less than about 0.18 nM, less than about 0.16 nM, or less than or equal to about 0.15 nM.

In certain embodiments, the modified or variant HRS polypeptide has increased "stability" (e.g., as measured by half-life, rate of protein degradation) which is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than an unmodified or non-variant HRS polypeptide under identical or otherwise comparable conditions. In particular embodiments, a modified or variant HRS polypeptide has a half-life under a given set of conditions (e.g., temperature, pH) of at least about 30 minutes, about 1 hour, about 2 hour, about 3 hours, about 4 hours, about 5 hours, about 6 hours, about 12 hours, about 18 hours, about 24 hours, about 36 hours, about 48 hours, about 60 hours, about 72 hours, about 84 hours, about 96 hours, about 120 hours, about 144 hours, about 168 hours, about 192 hours, about 216 hours or more, about 240 hours or more, or any intervening half-life or range in between.

In some embodiments, the "stability" of a HRS polypeptide includes its "functional stability," or the rate at which at least one biological activity is reduced under a given set of conditions over time. Exemplary biological activities include any one or more of the non-canonical activities described herein, and the retention of at least one epitope which specifically cross reacts with an auto-antibody or auto reactive T-cell from a disease associated with autoantibodies to human HRS. In some embodiments, the biological activity of a modified or variant HRS polypeptide is reduced at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 10%, 20%, 30%, 40%, 50%, 60%, 70%, 80%, 90%, 100%, 200%, 300%, 400%, or 500% slower than an unmodified or non-variant HRS polypeptide under identical or otherwise comparable conditions.

In certain embodiments, the "stability" of a HRS polypeptide includes its "kinetic stability" or "thermal stability," including its rate of unfolding under a given set of conditions over time. A protein that is kinetically stable will unfold more slowly than a kinetically unstable protein. In a kinetically stable protein, a large free energy barrier to unfolding is required and the factors affecting stability are the relative free energies of the folded ($G_f$) and the transition state ($G_{ts}$) for the first committed step on the unfolding pathway. A protein can denature irreversibly if the unfolded protein rapidly undergoes some permanent change such as aggregation or proteolytic degradation. In particular embodiments, a modified or variant HRS polypeptide unfolds at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 10%, 20%, 30%, 40%, 50%, 60%, 70%, 80%, 90%, 100%, 200%, 300%, 400%, or 500% slower than an unmodified or non-variant HRS polypeptide under identical or otherwise comparable conditions. In some embodiments, the modified or variant HRS polypeptide has a melting temperature (Tm) that is at least about 5%, 10%, 20%, 30%, 40%, 50%, 60%, 70%, 80%, 90%, 100% greater than the melting temperature of an unmodified or non-variant HRS polypeptide under identical or otherwise comparable conditions. In some embodiments, the modified or variant HRS polypeptide has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than an unmodified or non-variant HRS polypeptide under identical or otherwise comparable conditions. Melting temperature can be measured, for instance, by differential scanning fluorimetry (DSF).

In some embodiments, a modified or variant HRS polypeptide has improved or increased homogeneity or monodispersion (e.g., ratio of monomers/oligomers, ratio of dimers/oligomers, ratio of monomers/dimers, ratio of dimers/monomers, ratio of interchain disulfide bond formation under reducing conditions, distribution of apparent molecular weights, including reduced high molecular weight or low molecular weight peaks detected by either SDS-PAGE or HPLC analysis) in solution relative to an unmodified or non-variant HRS polypeptide. In some embodiments, the homogeneity or monodispersion of a modified or variant HRS polypeptide is increased by at least about at least 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold or at least about 10%, 20%, 30%, 40%, 50%, 60%, 70%, 80%, 90%, 100%, 200%, 300%, 400%, or 500% relative to an unmodified or non-variant HRS polypeptide under identical or otherwise comparable conditions. In specific embodiments, the HRS polypeptide having a deletion (Δ507-509) or substitution of the C-terminal cysteine residues Cys507 and Cys509 has increased homogeneity (e.g., ratio of monomers/oligomers) in solution relative to a corresponding HRS polypeptide having one or both of Cys507/Cys509 (e.g., SEQ ID NO:1). Without wishing to be bound by any one theory, full-length human HRS oligomerizes via the C-terminal cysteine residues Cys507/Cys509, and substitution or deletion of one or both of these cysteine residues can increase the homogeneity of the HRS polypeptide in solution (e.g., physiological buffer, pharmaceutical/therapeutic composition, biological fluid such as blood or plasma). In specific embodiments, the variant HRS polypeptide is HRS(1-506) (SEQ ID NO:70) or HRS(2-506). Increased homogeneity of monomers in solution can also lead, for example, to increased biological activity, stability, and other properties described herein.

In some embodiments, a modified or variant HRS polypeptide has reduced turbidity (e.g., degree of particle or fiber formation) in solution relative to an unmodified or non-variant HRS polypeptide. In some embodiments, the turbidity of a modified or variant HRS polypeptide is reduced by about or at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold, or about or at least about 10%, 20%, 30%, 40%, 50%, 60%, 70%, 80%, 90%, 100%, 200%, 300%, 400%, or 500% relative to an unmodified or non-variant HRS polypeptide under identical or otherwise comparable conditions. Turbidity can be measured, for instance, by absorbance at A340.

In some embodiments, a modified or variant HRS polypeptide has reduced opalescence in solution relative to an unmodified or non-variant HRS polypeptide. In some embodiments, the opalescence of a modified or variant HRS polypeptide is reduced by at least about at least 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold or at least about 10%, 20%, 30%, 40%, 50%, 60%, 70%, 80%, 90%, 100%, 200%, 300%, 400%, or 500% relative to an unmodified or non-variant HRS polypeptide under identical or otherwise comparable conditions. Opalescence can be measured, for instance, by absorbance at A580.

In some embodiments, a modified or variant HRS polypeptide has reduced aggregates (e.g., high molecular weight aggregates, low molecular weight aggregates) in solution relative to an unmodified or non-variant HRS polypeptide. In some embodiments, the aggregate formation of a modified or variant HRS polypeptide is reduced by about or at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold, or about or at least about 10%, 20%, 30%, 40%, 50%, 60%, 70%, 80%, 90%, 100%, 200%, 300%, 400%, or 500% relative to an unmodified or non-variant HRS polypeptide under identical or otherwise comparable conditions. Aggregation can be measured, for instance, by size exclusion HPLC or SDS-PAGE analysis. Higher levels of aggregation can also be monitored by turbidity measurements, as described herein.

In some embodiments, a modified or variant HRS polypeptide has an improved yield in $E.$ $coli$ relative to an unmodified or non-variant HRS polypeptide. In some embodiments, the yield is improved by at least about 1.2, 1.5, 2, 3, 4, 5, 6, 7, 8, 9, or 10 fold, or at least about 10%, 20%, 30%, 40%, 50%, 60%, 70%, 80%, 90%, 100%, 200%, 300%, 400%, or 500% relative to an unmodified or non-variant HRS polypeptide produced under identical or otherwise comparable conditions.

In some embodiments, a modified or variant HRS polypeptide has increased purity and/or or reduced endotoxin content after expression and purification from $E.$ $coli$ relative to an unmodified or non-variant HRS polypeptide. In some embodiments, the endotoxin level is reduced by at least about 1.2, 1.5, 2, 3, 4, 5, 6, 7, 8, 9, or 10-fold, or at least about 5%, 10%, 20%, 30%, 40%, 50%, 60%, 70%, 80%, 90%, 100%, 200%, 300%, 400%, or 500% relative to an unmodified or non-variant HRS polypeptide produced under identical or otherwise comparable conditions.

In some embodiments, a modified or variant HRS polypeptide has reduced fragmentation in solution relative to an unmodified or non-variant HRS polypeptide. In some embodiments, the degree of fragmentation of a modified or variant HRS polypeptide is reduced by at least about at least 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold or at least about 10%, 20%, 30%, 40%, 50%, 60%, 70%, 80%, 90%, 100%, 200%, 300%, 400%, or 500% relative to an unmodified or non-variant HRS polypeptide under identical or otherwise comparable conditions. Fragmentation can be measured, for instance, by SDS-PAGE analysis and size exclusion HPLC.

Exemplary conditions for measuring any of the biochemical, physical, and/or pharmacokinetic properties described herein include "physiological conditions," such as a temperature range of ~20-40° C., atmospheric pressure of ~1, and pH of ~6-8. General examples of conditions include, without limitation, in vivo conditions upon administration to a mammal, in vitro or solution conditions in a biological fluid (e.g., blood, serum, tissue culture), and in vitro or solution conditions in a physiological buffer or a pharmaceutical/therapeutic composition. Exemplary pharmaceutical/therapeutic compositions are described elsewhere herein. In some embodiments, the conditions include a temperature of about −80, −60, −40, −20, −10, −5, −4, −3, −20, −2, −1, 0, 1, 2, 3, 4, 5, 6, 7, 8, 10, 11, 12, 13, 14, 15, 16, 17, 18, 19, 20, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 99 or 100° C., including all integers and ranges in between. In some embodiments, the conditions include a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0, including all integers and ranges in between.

The pharmacokinetic, biochemical, and/or physical properties described herein can be measured under any given condition or changing conditions (e.g., increasing temperature) for about 0.25, 0.5, 1, 2, 3, 4, 5, 6, 7, 8, 9, 10, 11, 12, 13, 14, 15, 16, 17, 18, 19, 20, 21, 22, 23, or 24 hours, or about 0.1, 0.25, 0.5, 0.75, 1, 1.5, 2, 2.5, 3, 4, 5, 6, 7, 8, 9, 10, 11, 12, 13, 14 days, or about 1, 2, 3, 4, 5, 6, 7, 8, 9, 10, 12, 14, 16, 18, 20, or 24 weeks, or about 1, 2, 3, 4, 5, 6, 7, 8, 9, 10, 11, or 12 months or so. In some embodiments, the pharmacokinetic, biochemical, and/or physical properties are measured after freeze-thawing a composition at least 1, 2, 3, 4, 5, 6, 7, 8, 9, 10 or more times.

HRS Polynucleotides

Certain embodiments relate to polynucleotides that encode a HRS polypeptide, including truncations and/or variants thereof, as well as compositions comprising such polynucleotides. Among other uses, these embodiments may be utilized to recombinantly produce a desired HRS polypeptide or variant thereof, or to express the HRS polypeptide in a selected cell or subject. Representative naturally-occurring nucleotide sequences encoding the native HRS polypeptides include for example GeneBank accession Nos. AK000498.1 and U18937.1.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an HRS polypeptide or a portion thereof) or may comprise a variant, or a biological functional equivalent of such a sequence. Polynucleotide variants may contain one or more substitutions, additions, deletions and/or insertions, as further described below, preferably such that the inflammatory response-modulating activity of the encoded polypeptide is not substantially diminished relative to the unmodified polypeptide. The effect on the inflammatory response-modulating activity of the encoded polypeptide may generally be assessed as described herein.

In some embodiments, the present invention provides isolated polynucleotides comprising various lengths of contiguous stretches of sequence identical to or complementary to HRS polypeptide, wherein the isolated polynucleotides encode a truncated HRS polypeptide as described herein.

It will be appreciated by those of ordinary skill in the art that, as a result of the degeneracy of the genetic code, there are many nucleotide sequences that encode a HRS polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

Therefore, multiple polynucleotides can encode the HRS polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., *Nuc. Acid. Res.* 28 (1): 292, 2000). In addition, silent mutations can be incorporated in order to introduce, or eliminate restriction sites, decrease the density of CpG dinucleotide motifs (see for example, Kameda et al., *Biochem. Biophys. Res. Commun.* 349(4): 1269-1277, 2006) or reduce the ability of single stranded sequences to form stem-loop structures: (see, e.g., Zuker M., *Nucl. Acid Res.* 31(13): 3406-3415, 2003). In addition, mammalian expression can be further optimized by including a Kozak consensus sequence [i.e., (a/g)cc(a/g)ccATGg; SEQ ID NO:130] at the start codon. Kozak consensus sequences useful for this purpose are known in the art (Mantyh et al. *PNAS.* 92: 2662-2666, 1995; Mantyh et al., *Prot. Exp. & Purif.* 6, 124, 1995). Exemplary codon-optimized polynucleotide sequences are provided in Table D9 below.

TABLE D9

Codon Optimized DNA Sequences

| Name | Amino Acid Residue Range of SEQ ID NO: 1 | Nucleic acid sequence | SEQ ID NO: |
|---|---|---|---|
| Wild-type (Full-length HisRS) | 1-509 | ATGGCAGAGCGTGCGGCGCTGGAGGAGCTGGTGAAACTTCA GGGAGAGCGCGTGCGAGGCCTCAAGCAGCAGAAGGCCAGC GCCCGAGCTGATCGAGGAGGAGGTGGCGAAACTCCTGAAACT GAAGGCACAGCTGGGTCCTGATGAAAGCAAACAGAAATTTG TGCTCAAAACCCCCAAGGGCACAAGAGACTATAGTCCCCGG CAGATGGCAGTTCGCGAGAAGGTGTTTGACGTAATCATCCG TTGCTTCAAGCGCCACGGTGCAGAAGTCATTGATACACCTGT ATTTGAACTAAAGGAAACACTGATGGGAAAGTATGGGGAAG ACTCCAAGCTTATCTATGACCTGAAGGACCAGGGCGGGGAG CTCCTGTCCCTTCGCTATGACCTCACTGTTCCTTTTGCTCGGT ATTTGGCAATGAATAAACTGACCAACATTAAACGCTACCAC ATAGCAAAGGTATATCGGCGGGATAACCCAGCCATGACCCG TGGCCGATACCGGGAATTCTACCAGTGTGATTTTGACATTGC TGGGAACTTTGATCCCATGATCCCTGATGCAGAGTGCCTGAA GATCATGTGCGAGATCCTGAGTTCACTTCAGATAGGCGACTT CCTGGTCAAGGTAAACGATCGACGCATTCTAGATGGGATGT TTGCTATCTGTGGTGTTTCTGACAGCAAGTTCCGTACCATCT GCTCCTCAGTAGACAAGCTGGACAAGGTGTCCTGGGAAGAG GTGAAGAATGAGATGGTGGGAGAGAAGGGCCTTGCACCTGA GGTGGCTGACCGCATTGGGGACTATGTCCAGCAACATGGTG GGGTATCCCTGGTGGAACAGCTGCTCCAGGATCCTAAACTAT CCCAAAACAAGCAGGCCTTGGAGGGCCTGGGAGACCTGAAG TTGCTCTTTGAGTACCTGACCCTATTTGGCATTGATGACAAA ATCTCCTTTGACCTGAGCCTTGCTCGAGGGCTGGATTACTAC ACTGGGGTGATCTATGAGGCAGTGCTGCTACAGACCCCAGC CCAGGCAGGGGAAGAGCCCCTGGGTGTGGGCAGTGTGGCTG CTGGAGGACGCTATGATGGGCTAGTGGGCATGTTCGACCCC AAAGGGCGCAAGGTGCCATGTGTGGGGCTCAGCATTGGGGT GGAGCGGATTTTCTCCATCGTGGAACAGAGACTAGAGGCTT TGGAGGAGAAGATACGGACCACGGAGACACAGGTGCTTGTG GCATCTGCACAGAAGAAGCTGCTAGAGGAAAGACTAAAGCT TGTCTCAGAACTGTGGGATGCTGGGATCAAGGCTGAGCTGC TGTACAAGAAGAACCCAAAGCTACTGAACCAGTTACAGTAC TGTGAGGAGGCAGGCATCCCACTGGTGGCTATCATCGGCGA GCAGGAACTCAAGGATGGGGTCATCAAGCTCCGTTCAGTGA CGAGCAGGGAAGAGGTGGATGTCCGAAGAGAAGACCTTGTG GAGGAAATCAAAAGGAGAACAGGCCAGCCCCTCTGCATCTGC | 24 |
| HisRS1^N1 | 1-141 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGGAACCCGTGACTATTCTCCTCGTCA AATGGCCGTCCGTGAAAAAGTGTTCGACGTGATCATTCGCTG CTTTAAACGCCATGGTGCCGAAGTGATTGATACCCCGGTGTT TGAGCTGAAAGAGACACTGATGGGCAAATATGGTGAGGACA GCAAACTGATTTATGACCTGAAAGATCAGGGTGGTGAACTG CTGAGTCTGCGCTATGATCTGACAGTTCCGTTTGCCCGTTAT CTGGCAATG | 25 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| HisRS1$^{N2}$ | 1-408 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGT<br>CCTGAAAACTCCGAAAGGAACCCGTGACTATTCTCCTCGTCA<br>AATGGCCGTCCGTGAAAAAGTGTTCGACGTGATCATTCGCTG<br>CTTTAAACGCCATGGTGCCGAAGTGATTGATACCCCGGTGTT<br>TGAGCTGAAAGAGACACTGATGGGCAAATATGGTGAGGACA<br>GCAAACTGATTTATGACCTGAAAGATCAGGGTGGTGAACTG<br>CTGAGTCTGCGCTATGATCTGACAGTTCCGTTTGCCCGTTAT<br>CTGGCAATGAATAAACTGACCAACATTAAACGCTATCACAT<br>TGCTAAAGTCTATCGCCGTGACAATCCTGCTATGACCCGTGG<br>TCGTTATCGTGAGTTCTATCAGTGTGACTTCGATATTGCCGG<br>CAACTTTGATCCGATGATCCCGGATGCTGAATGCCTGAAAAT<br>CATGTGTGAGATCCTGAGCAGTCTGCAGATTGGCGATTTCCT<br>GGTGAAAGTCAACGATCGCCGTATTCTGGATGGCATGTTCGC<br>CATCTGTGGTGTTAGCGACTCCAAATTCCGTACCATCTGTAG<br>TAGTGTGGACAAACTGGATAAAGTGAGCTGGGAGGAGGTGA<br>AAAACGAAATGGTGGGCGAGAAAGGTCTGGCTCCTGAAGTG<br>GCTGACCGTATTGGTGATTATGTCCAGCAGCACGGTGGAGT<br>ATCACTGGTTGAGCAACTGCTGCAAGACCCTAAACTGAGTC<br>AGAATAAACAGGCCCTGGAGGGACTGGGAGATCTGAAACTG<br>CTGTTCGAGTATCTGACCCTGTTCGGTATCGATGACAAAATC<br>TCCTTTGACCTGTCACTGGCTCGTGGACTGGACTATTATACC<br>GGCCGTGATCTATGAAGCTGTACTGCAAACTCCAGCACA<br>AGCAGGTGAAGAGCCTCTGGGTGTGGGTAGTGTAGCCGCTG<br>GGGGACGTTATGATGGACTGGTGGGATGTTCGACCCTAAA<br>GGCCGTAAAGTTCCGTGTGTGGGTCTGAGTATCGGTGTTGAG<br>CGTATCTTTTCCATCGTCGAGCAACGTCTGGAAGCACTGGAG<br>GAAAAAAATCCGTACGACCGAA | 26 |
| HisRS1$^{N3}$ | 1-113 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGT<br>CCTGAAAACTCCGAAAGGAACCCGTGACTATTCTCCTCGTCA<br>AATGGCCGTCCGTGAAAAAGTGTTCGACGTGATCATTCGCTG<br>CTTTAAACGCCATGGTGCCGAAGTGATTGATACCCCGGTGTT<br>TGAGCTGAAAGAGACACTGATGGGCAAATATGGTGAGGACA<br>GCAAACTG | 27 |
| HisRS1$^{N4}$ | HRS(1-60) | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGT<br>CCTGAAAACTCCGAAG | 28 |
| HisRS1$^{N8}$ | HRS(1-506) | ATGGCAGAGCGTGCGGCGCTGGAGGAGCTGGTGAAACTTCA<br>GGGAGAGCGCGTGCGAGGCCTCAAGCAGCAGAAGGCCAGC<br>GCCGAGCTGATCGAGGAGGAGGTGGCGAAACTCCTGAAACT<br>GAAGGCACAGCTGGGTCCTGATGAAAGCAAACAGAAATTTG<br>TGCTCAAAACCCCCAAGGGCACAAGAGACTATAGTCCCCGG<br>CAGATGGCAGTTCGCGAGAAGGTGTTTGACGTAATCATCCG<br>TTGCTTCAAGCGCCACGGTGCAGAAGTCATTGATACACCTGT<br>ATTTGAACTAAAGGAAACACTGATGGGAAAGTATGGGGAAG<br>ACTCCAAGCTTATCTATGACCTGAAGGACCAGGGCGGGGAG<br>CTCCTGTCCCTTCGCTATGACCTCACTGTTCCTTTTGCTCGGT<br>ATTTGGCAATGAATAAACTGACCAACATTAAACGCTACCAC<br>ATAGCAAAGGTATATCGGCGGGATAACCCAGCCATGACCCG<br>TGGCCGATACCGGGAATTCTACCAGTGTGATTTTGACATTGC<br>TGGGAACTTTGATCCCATGATCCCTGATGCAGAGTGCCTGAA<br>GATCATGTGCGAGATCCTGAGTTCACTTCAGATAGGCGACTT<br>CCTGGTCAAGGTAAACGATCGACGCATTCTAGATGGGATGT<br>TTGCTATCTGTGGTGTTTCTGACAGCAAGTTCCGTACCATCT<br>GCTCCTCAGTAGACAAGCTGGACAAGGTGTCCTGGGAAGAG<br>GTGAAGAATGAGATGGTGGGAGAGAAGGGCCTTGCACCTGA<br>GGTGGCTGACCGCATTGGGGACTATGTCCAGCAACATGGTG<br>GGGTATCCCTGGTGGAACAGCTGCTCCAGGATCCTAAACTAT<br>CCCAAAACAAGCAGGCCTTGGAGGGCCTGGGAGACCTGAAG<br>TTGCTCTTTGAGTACCTGACCCTATTTGGCATTGATGACAAA<br>ATCTCCTTTGACCTGAGCCTTGCTCGAGGGCTGGATTACTAC<br>ACTGGGGTGATCTATGAGGCAGTGCTGCTACAGACCCCAGC | 72 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | CCAGGCAGGGGAAGAGCCCCTGGGTGTGGGCAGTGTGGCTG<br>CTGGAGGACGCTATGATGGGCTAGTGGGCATGTTCGACCCC<br>AAAGGGCGCAAGGTGCCATGTGTGGGGCTCAGCATTGGGGT<br>GGAGCGGATTTTCTCCATCGTGGAACAGAGACTAGAGGCTT<br>TGGAGGAGAAGATACGGACCACGGAGACACAGGTGCTTGTG<br>GCATCTGCACAGAAGAGCTGCTAGAGGAAAGACTAAAGCT<br>TGTCTCAGAACTGTGGGATGCTGGGATCAAGGCTGAGCTGC<br>TGTACAAGAAGAACCCAAAGCTACTGAACCAGTTACAGTAC<br>TGTGAGGAGGCAGGCATCCCACTGGTGGCTATCATCGGCGA<br>GCAGGAACTCAAGGATGGGGTCATCAAGCTCCGTTCAGTGA<br>CGAGCAGGGAAGAGGTGGATGTCCGAAGAGAAGACCTTGTG<br>GAGGAAATCAAAAGGAGAACAGGCCAGCCCCTC | |
| HisRS1$^{N6}$ | HRS(1-48) | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGAT | 73 |
| HisRS1$^{I1}$ | 191-333 | TGCCTGAAAATCATGTGTGAGATCCTGAGTAGTCTGCAAATT<br>GGCGACTTTCTGGTCAAAGTGAACGATCGCCGTATTCTGGAT<br>GGCATGTTCGCCATCTGTGGTGTTAGCGACTCCAAATTCCGT<br>ACAATCTGTAGCAGCGTGGACAAACTGGATAAAGTGTCCTG<br>GGAAGAGGTGAAAAACGAAATGGTGGGTAAAAAGGTCTG<br>GCTCCGGAGGTTGCTGACCGTATCGGTGATTATGTTCAGCAG<br>CACGGCGGTGTTAGTCTGGTTGAACAACTGCTGCAAGACCC<br>GAAACTGTCTCAGAACAAACAGGCCCTGGAAGGACTGGGAG<br>ATCTGAAACTGCTGTTCGAGTATCTGACGCTGTTCGGCATTG<br>ATGACAAAATTTCTTTCGACCTGTCACTGGCACGTGGACTGG<br>ACTATTATACCGGT | 29 |
| HisRS1$^{C1}$ | 405-509 | CGTACCACCGAAACCCAAGTTCTGGTTGCCTCAGCTCAGAA<br>AAAACTGCTGGAAGAACGCCTGAAACTGGTTAGCGAACTGT<br>GGGATGCTGGCATTAAAGCCGAACTGCTGTATAAAAAAAAC<br>CCGAAACTGCTGAATCAGCTGCAGTATTGTGAGGAAGCGGG<br>TATTCCTCTGGTGGCCATTATCGGAGAACAGGAACTGAAAG<br>ACGGCGTTATTAAACTGCTGTAGCGTGACCTCTCGTGAAGAA<br>GTTGACGTTCGCCGTGAAGATCTGGTCGAGGAAATCAAACG<br>TCGTACCGGTCAACCTCTGTGTATTTGC | 30 |
| HisRS1$^{N5}$ | 1-243 + 27aa | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGT<br>CCTGAAAACTCCGAAAGGAACCCGTGACTATTCTCCTCGTCA<br>AATGGCCGTCCGTGAAAAAGTGTTCGACGTGATCATTCGCTG<br>CTTTAAACGCCATGGTGCCGAAGTGATTGATACCCCGGTGTT<br>TGAGCTGAAAGAGACACTGATGGGCAAATATGGTGAGGACA<br>GCAAACTGATCTATGACCTGAAAGACCAAGGCGGTGAACTG<br>CTGTCCCTGCGTTATGATCTGACTGTGCCGTTTGCCCGTTATC<br>TGGCCATGAATAAACTGACGAACATTAAACGCTATCACATT<br>GCCAAAGTGTATCGCCGTGACAATCCTGCTATGACTCGTGGA<br>CGTTATCGTGAATTCTATCAGTGTGACTTCGATATTGCCGGC<br>AACTTCGACCCTATGATTCCGGATGCTGAATGCCTGAAAATC<br>ATGTGTGAGATCCTGAGCAGCCTGCAAATTGGTGACTTCCTG<br>GTGAAAGTGAATGACCGTCGTATCCTGGATGGCATGTTTGCC<br>ATTTGTGGTGTGAGCGATTCCAAATTCCGTACCATCTGTAGT<br>AGTGTGGACAAACTGGATAAAGTGGGCTATCCGTGGTGGAA<br>CTCTTGTAGCCGTATTCTGAACTATCCTAAAACCAGCCGCCC<br>GTGGCGTGCTTGGGAAACT | 31 |
| HisRS1$^{C2}$ | 1-60 + 175-509 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGT<br>CCTGAAAACTCCGAAAGACTTCGATATTGCCGGGAATTTTGA<br>CCCTATGATCCCTGATGCCGAATGTCTGAAAATCATGTGTGA<br>GATCCTGAGCAGTCTGCAGATTGGTGACTTCCTGGTGAAAGT<br>GAACGATCGCCGTATTCTGGATGGAATGTTTGCCATTTGTGG<br>CGTGTCTGACAGCAAATTTCGTACGATCTGTAGCAGCGTGGA<br>TAAACTGGATAAAGTGAGCTGGAGGAGGTGAAAAATGAG<br>ATGGTGGGCGAAAAAGGTCTGGCACCTGAAGTGGCTGACCG<br>TATCGGTGATTATGTTCAGCAACATGGCGGTGTTTCTCTGGT | 32 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | CGAACAGCTGCTGCAAGACCCAAAACTGAGCCAGAACAAAC AGGCACTGGAAGGACTGGGTGATCTGAAACTGCTGTTTGAG TATCTGACGCTGTTTGGCATCGATGACAAAATCTCGTTTGAC CTGAGCCTGGCACGTGGTCTGGATTATTATACCGGCGTGATC TATGAAGCCGTCCTGCTGCAAACTCCAGCACAAGCAGGTGA AGAACCTCTGGGTGTTGGTAGTGTAGCGGCAGGCGGACGTT ATGATGGACTGGTGGGGATGTTTGATCCGAAAGGCCGTAAA GTTCCGTGTGTCGGTCTGAGTATCGGGGTTGAGCGTATCTTT AGCATTGTGGAGCAACGTCTGGAAGCTCTGGAGGAAAAAAT CCGTACCACCGAAACCCAAGTTCTGGTTGCCTCAGCTCAGAA AAAACTGCTGGAAGAACGCCTGAAACTGGTTAGCGAACTGT GGGATGCTGGCATTAAAGCCGAACTGCTGTATAAAAAAAAC CCGAAACTGCTGAATCAGCTGCAGTATTGTGAGGAAGCGGG TATTCCTCTGGTGGCCATTATCGGAGAACAGGAACTGAAAG ACGGCGTTATTAAACTGCGTAGCGTGACCTCTCGTGAAGAA GTTGACGTTCGCCGTGAAGATCTGGTCGAGGAAATCAAACG TCGTACCGGTCAACCTCTGTGTATTTGC | |
| HisRS1<sup>C3</sup> | 1-60 + 211-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGTGAATGATCGCCGTATCCTGGATG GCATGTTTGCCATTTGTGGTGTGAGCGACTCGAAATTCCGTA CGATTTGCTCTAGCGTCGATAAACTGGACAAAGTGTCCTGGG AAGAGGTGAAAAACGAGATGGTGGGTGAGAAAGGTCTGGC TCCTGAAGTTGCCGACCGTATTGGTGATTATGTTCAGCAGCA TGGCGGTGTTTCACTGGTTGAACAACTGCTGCAAGACCCGA AACTGTCTCAGAATAAACAGGCGCTGGAAGGACTGGGAGAT CTGAAACTGCTGTTTGAGTATCTGACCCTGTTCGGCATTGAT GACAAAATCAGCTTCGACCTGAGCCTGGCACGTGGTCTGGA TTATTATACCGGCGTGATCTATGAAGCCGTTCTGCTGCAGAC ACCAGCACAAGCAGGCGAAGAACCTCTGGGTGTTGGTTCTG TGGCAGCCGGTGGTCGTTATGATGGACTGGTAGGCATGTTCG ATCCGAAAGGCCGTAAAGTTCCGTGTGTGGGACTGAGTATC GGTGTTGAGCGTATCTTTAGCATCGTGGAACAACGTCTGGAA GCGCTGGAGGAGAAAATTCGTACCACCGAAACCCAAGTTCT GGTTGCCTCAGCTCAGAAAAAACTGCTGGAAGAACGCCTGA AACTGGTTAGCGAACTGTGGGATGCTGGCATTAAAGCCGAA CTGCTGTATAAAAAAAACCCGAAACTGCTGAATCAGCTGCA GTATTGTGAGGAAGCGGGTATTCCTCTGGTGGCCATTATCGG AGAACAGGAACTGAAAGACGGCGTTATTAAACTGCGTAGCG TGACCTCTCGTGAAGAAGTTGACGTTCGCCGTGAAGATCTGG TCGAGGAAATCAAACGTCGTACCGGTCAACCTCTGTGTATTT GC | 33 |
| HisRS1<sup>C4</sup> | 1-100 + 211-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGGAACTCGTGATTATAGCCCTCGCC AGATGGCTGTCCGTGAAAAAGTGTTCGATGTGATCATTCGCT GCTTCAAACGTCATGGTGCCGAAGTCATTGATACCCCGGTGT TCGAGCTGAAAGTGAACGATCGCCGTATTCTGGATGGCATG TTCGCCATTTGTGGTGTTAGCGATAGCAAATTCCGTACAATC TGCTCTAGCGTGGACAAACTGGACAAAGTGAGCTGGGAAGA GGTGAAAAACGAGATGGTGGGTGAGAAAGGCCTGGCTCCTG AAGTTGCCGACCGTATCGGAGATTATGTTCAGCAGCATGGC GGAGTTTCACTGGTTGAACAACTGCTGCAAGACCCGAAACT GTCTCAGAACAAACAGGCACTGGAAGGTCTGGGAGATCTGA AACTGCTGTTCGAGTATCTGACGCTGTTCGGTATTGACGACA AAATTTCCTTCGACCTGTCGCTGGCACGTGGTCTGGATTATT ATACAGGCGTGATCTATGAGGCTGTACTGCTGCAGACACCA GCACAAGCAGGTGAAGAGCCTCTGGGTGTTGGTTCAGTTGC TGCCGGTGGACGTTATGACGGACTGGTAGGGATGTTTGACC CAAAAGGCCGTAAAGTCCCGTGTGTAGGACTGTCTATTGGC GTTGAGCGTATCTTTAGCATCGTGGAGCAACGTCTGGAAGCT CTGGAGGAGAAAATCCGTACCACCGAAACCCAAGTTCTGGT TGCCTCAGCTCAGAAAAAACTGCTGGAAGAACGCCTGAAAC TGGTTAGCGAACTGTGGGATGCTGGCATTAAAGCCGAACTG CTGTATAAAAAAAACCCGAAACTGCTGAATCAGCTGCAGTA TTGTGAGGAAGCGGGTATTCCTCTGGTGGCCATTATCGGAGA | 34 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | ACAGGAACTGAAAGACGGCGTTATTAAACTGCGTAGCGTGA CCTCTCGTGAAGAAGTTGACGTTCGCCGTGAAGATCTGGTCG AGGAAATCAAACGTCGTACCGGTCAACCTCTGTGTATTTGC | |
| HisRS1[C5] | 1-174 + 211-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGGAACTCGTGATTATAGCCCTCGCC AGATGGCTGTCCGTGAAAAAGTGTTCGATGTGATCATTCGCT GCTTCAAACGTCATGGTGCCGAAGTCATTGATACCCCGGTGT TCGAGCTGAAAGAAACCCTGATGGGCAAATATGGGGAAGAT TCCAAACTGATCTATGACCTGAAAGACCAGGGAGGTGAACT GCTGTCTCTGCGCTATGACCTGACTGTTCCTTTTGCTCGCTAT CTGGCCATGAATAAACTGACCAACATCAAACGCTATCATAT CGCCAAAGTGTATCGCCGTGACAATCCAGCAATGACCCGTG GTCGTTATCGTGAATTTTATCAGTGTGTGAACGATCGCCGTA TTCTGGACGGCATGTTCGCCATTTGTGGTGTGTCTGACTCCA AATTTCGTACGATCTGCTCAAGCGTGGACAAACTGGACAAA GTGAGCTGGGAAGAGGTGAAAAACGAGATGGTGGGTGAGA AAGGCCTGGCTCCTGAAGTTGCCGACCGTATCGGAGATTAT GTTCAGCAGCATGGCGGAGTTTCACTGGTTGAACAACTGCTG CAAGACCCGAAACTGTCACAGAACAAACAGGCACTGGAAG GTCTGGGGGATCTGAAACTGCTGTTCGAGTATCTGACGCTGT TCGGTATTGACGACAAATCAGCTTCGATCTGAGCCTGGCAC GTGGTCTGGACTATTATACCGGCGTGATTTATGAAGCCGTTC TGCTGCAGACTCCAGCACAAGCAGGTGAAGAGCCTCTGGGT GTTGGAAGTGTGGCAGCCGGTGGCCGTTATGATGGTCTGGTT GGCATGTTTGACCCGAAAGGCCGTAAAGTCCCGTGTGTAGG ACTGTCTATCGGCGTGGAGCGTATTTTTAGCATCGTGGAACA ACGCCTGGAAGCTCTGAAGAGAAAATCCGTACCACCGAAA CCCAAGTTCTGGTTGCCTCAGCTCAGAAAAAACTGCTGGAA GAACGCCTGAAACTGGTTAGCGAACTGTGGGATGCTGGCAT TAAAGCCGAACTGCTGTATAAAAAAAACCCGAAACTGCTGA ATCAGCTGCAGTATTGTGAGGAAGCGGGTATTCCTCTGGTGG CCATTATCGGAGAACAGGAACTGAAAGACGGCGTTATTAAA CTGCGTAGCGTGACCTCTCGTGAAGAAGTTGACGTTCGCCGT GAAGATCTGGTCGAGGAAATCAAACGTCGTACCGGTCAACC TCTGTGTATTTGC | 35 |
| HisRS1[C6] | 1-60 + 101-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGAAACCCTGATGGGCAAATATGGCG AAGATTCCAAACTGATCTATGACCTGAAAGACCAAGGCGGT GAACTGCTGTCCCTGCGTTATGACCTGACTGTTCCGTTTGCT CGTTATCTGGCCATGAATAAACTGACCAACATTAAACGCTAT CACATTGCCAAAGTGTATCGCCGTGACAATCCTGCTATGACT CGTGGACGTTATCGTGAATTCTATCAGTGTGACTTCGATATT GCCGGCAACTTCGACCCTATGATTCCGGATGCTGAATGCCTG AAAATCATGTGTGAGATCCTGAGCAGCCTGCAAATTGGTGA CTTCCTGGTGAAAGTGAATGACCGTCGTATCCTGGATGGCAT GTTCGCCATTTGTGGTGTTAGCGATTCCAAATTCCGTACCAT CTGTAGTAGTGTGGACAAACTGGATAAAGTGAGCTGGGAAG AGGTGAAAAACGAAATGGTGGGCGAAAAAGGTCTGGCACCT GAGGTTGCTGATCGTATCGGTGACTATGTCCAGCAGCATGG AGGTGTTTCACTGGTTGAGCAACTGCTGCAAGATCCGAAACT GTCTCAGAACAAACAGGCCCTGGAAGGACTGGGTGATCTGA AACTGCTGTTCGAGTATCTGACGCTGTTCGGTATTGATGACA AAATCTCGTTGACCTGTCTCTGGCTCGTGGACTGGATTATT ATACGGGCGTAATCTATGAAGCTGTCCTGCTGCAGACACCA GCACAAGCAGGTGAAGAGCCTCTGGGTGTTGGAAGTGTTGC TGCCGGTGGTCGCTATGACGGACTGGTTGGCATGTTCGATCC GAAAGGCCGTAAAGTTCCGTGTGTAGGACTGAGCATTGGCG TTGAGCGTATCTTTTCCATCGTTGAGCAACGTCTGGAAGCAC TGGAAGAGAAAATCCGTACCACCGAAACCCAAGTTCTGGTT GCCTCAGCTCAGAAAAAACTGCTGGAAAACGCCTGAAACT GGTTAGCGAACTGTGGGATGCTGGCATTAAAGCCGAACTGC TGTATAAAAAAAACCCGAAACTGCTGAATCAGCTGCAGTAT TGTGAGGAAGCGGGTATTCCTCTGGTGGCCATTATCGGAGA | 36 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | ACAGGAACTGAAAGACGGCGTTATTAAACTGCGTAGCGTGA CCTCTCGTGAAGAAGTTGACGTTCGCCGTGAAGATCTGGTCG AGGAAATCAAACGTCGTACCGGTCAACCTCTGTGTATTTGC | |
| HisRS1[C7] | 1-100 + 175-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGT CCTGAAAACTCCGAAAGGAACTCGTGATTATAGCCCTCGCC AGATGGCTGTCCGTGAAAAAGTGTTCGATGTGATCATTCGCT GCTTCAAACGTCATGGTGCCGAAGTCATTGATACCCCGGTGT TCGAGCTGAAAGATTTCGATATTGCCGGCAACTTTGATCCGA TGATTCCGGATGCTGAGTGTCTGAAAATCATGTGTGAGATCC TGAGTAGTCTGCAGATTGGGGATTTCCTGGTGAAAGTGAAC GATCGCCGTATTCTGGACGGCATGTTTGCCATTTGTGGCGTT AGCGATAGCAAATTCCGTACGATCTGTAGCAGTGTGGACAA ACTGGATAAAGTCTCTTGGGAAGAGGTCAAAAACGAGATGG TTGGTGAGAAAGGCCTGGCTCCTGAAGTGGCTGACCGTATT GGTGATTATGTCCAGCAGCATGGTGGTGTTTCACTGGTTGAA CAACTGCTGCAAGACCCGAAACTGTCTCAGAACAAACAGGC ACTGGAAGGTCTGGGTGATCTGAAACTGCTGTTCGAGTATCT GACGCTGTTCGGTATTGACGACAAAATTTCCTTCGACCTGTC ACTGGCACGTGGTCTGGATTATTATACAGGCGTAATCTATGA GGCTGTACTGCTGCAAACTCCAGCACAAGCAGGTGAAGAAC CTCTGGGAGTTGGTAGTGTAGCGGCAGGGGGTCGTTATGAT GGGCTGGTCGGGATGTTCGATCCAAAAGGCCGTAAAGTCCC GTGTGTTGGTCTGTCTATTGGCGTTGAGCGTATCTTCTCCATC GTGGAGCAACGTCTGGAAGCTCTGGAAGAAAAAATCCGTAC CACCGAAACCCAAGTTCTGGTTGCCTCAGCTCAGAAAAAAC TGCTGGAAGAACGCCTGAAACTGGTTAGCGAACTGTGGGAT GCTGGCATTAAAGCCGAACTGCTGTATAAAAAAAAACCCGAA ACTGCTGAATCAGCTGCAGTATTGTGAGGAAGCGGGTATTC CTCTGGTGGCCATTATCGGAGAACAGGAACTGAAAGACGGC GTTATTAAACTGCGTAGCGTGACCTCTCGTGAAGAAGTTGAC GTTCGCCGTGAAGATCTGGTCGAGGAAATCAAACGTCGTAC CGGTCAACCTCTGTGTATTTGC | 37 |
| HisRS1[C10] | 369-509 | ATGTTCGACCCAAAAGGCCGTAAAGTTCCGTGTGTAGGGCT GTCTATCGGTGTTGAGCGTATCTTCTCCATCGTTGAGCAGCG TCTGGAAGCACTGGAGGAAAAAATCCGTACGACCGAGACTC AAGTCCTGGTTGCTAGTGCCCAGAAAAAACTGCTGGAAGAG CGCCTGAAACTGGTTAGTGAGCTGTGGGATGCCGGTATTAA AGCCGAACTGCTGTATAAAAAAAAACCCGAAACTGCTGAATC AGCTGCAGTATTGTGAAGAAGCGGGCATTCCGCTGGTAGCG ATTATCGGGGAACAAGAACTGAAAGATGGCGTTGATCAAACT GCGTAGCGTTACAAGCCGTGAGGAAGTGGACGTCCGCCGTG AGGATCTGGTTGAAGAGATTAAACGCCGTACAGGTCAGCCT CTGTGTATTTGC | 38 |

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with and operatively coupled to other DNA or RNA sequences, such as expression control sequences, including for example, promoters, polyadenylation signals. Additionally, the polynucleotides can further comprise restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of a HRS reference polynucleotide (e.g., base number X-Y, in which X is about 1-3000 or more and Y is about 10-3000 or more), or its complement.

Embodiments of the present invention also include "variants" of the HRS polypeptide-encoding reference polynucleotide sequences. Polynucleotide "variants" may contain one or more substitutions, additions, deletions and/or insertions in relation to a reference polynucleotide. Generally, variants of a HRS polypeptide reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence (Such as for example, SEQ ID NOS:24-38, 40, 42, 72-73, 173-175, or 183-189) as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100 (including all integers in between) or more bases. In certain embodiments, such as when the polynucleotide variant encodes a HRS polypeptide having a non-canonical activity, the desired activity of the encoded HRS polypeptide is not substantially diminished relative to the unmodified polypeptide. The effect on the activity of the encoded polypeptide may generally be assessed as described herein, including for example the methods described herein. In some embodiments, the variants can alter the aggregation state of the HRS polypeptides, for example, to provide for HRS polypeptides that exist in different embodiments primarily as a monomer, dimer or multimer.

Certain embodiments include polynucleotides that hybridize to a reference HRS polynucleotide sequence, (such as for example, any of SEQ ID NOS: 24-38, 40, 42, 72-73, 173-175, or 183-189) or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2× SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the T$_m$ for formation of a DNA-DNA hybrid. It is well known in the art that the T$_m$ is the melting temperature, or temperature at which two complementary polynucleotide sequences dissociate. Methods for estimating T$_m$ are well known in the art (see Ausubel et al., supra at page 2.10.8).

In general, the T$_m$ of a perfectly matched duplex of DNA may be predicted as an approximation by the formula: T$_m$=81.5+16.6 (log$_{10}$ M)+0.41 (% G+C)−0.63 (% formamide)−(600/length) wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The T$_m$ of a duplex DNA decreases by approximately 1° C. with every increase of 1% in the number of randomly mismatched base pairs. Washing is generally carried out at T$_m$−15° C. for high stringency, or T$_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Production of HRS Polypeptides

HRS polypeptide may be prepared by any suitable procedure known to those of skill in the art for example, by using standard solid-phase peptide synthesis (Merrifield, *J. Am. Chem. Soc.* 85:2149-2154 (1963)), or by recombinant technology using a genetically modified host. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

HRS polypeptides can also be produced by expressing a DNA sequence encoding the HRS polypeptide in question) in a suitable host cell by well-known techniques. The polynucleotide sequence coding for the HRS polypeptide may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3:801-805. According to the phosphoramidite method, oligonucleotides are synthesized, e.g., in an automatic DNA synthesizer, purified, duplexed and ligated to form the synthetic DNA construct. Alternatively the DNA construct can be constructed using standard recombinant molecular biological techniques including restriction enzyme mediated cloning and PCR based gene amplification.

The polynucleotide sequences may also be of mixed genomic, cDNA, and synthetic origin. For example, a genomic or cDNA sequence encoding a leader peptide may be joined to a genomic or cDNA sequence encoding the HRS polypeptide, after which the DNA sequence may be modified at a site by inserting synthetic oligonucleotides encoding the desired amino acid sequence or by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors.

Such expression vectors can comprise expression control sequences, including for example, enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ *E. coli*-based expression systems (see, e.g., Structural Genomics Consortium et al., *Nature Methods*. 5:135-146, 2008). These and related embodiments may rely partially or totally on ligation-independent cloning (LIC) to produce a suitable expression vector.

In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. In some embodiments other *E. coli* strains may be utilized, including other *E. coli* K-12 strains such as W3110 (F$^-$ lambda$^-$ IN(rrnD-rrnE)1 rph-1), which can result in reduced levels of post-translational modifications during fermentation. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags, or other affinity or purification tags, followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology*. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L. In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol*. 153:516-544 (1987). Also included are *Pichia pandoris* expression systems (see, e.g., L1 et al., *Nature Biotechnology*. 24, 210-215, 2006; and Hamilton et al., *Science,* 301:1244, 2003). Certain embodiments include yeast systems that are engineered to selectively glycosylate proteins, including yeast that have humanized N-glycosylation pathways, among others (see, e.g., Hamilton et al., *Science*. 313:1441-1443, 2006; Wildt et al., *Nature Reviews Microbiol*. 3:119-28, 2005; and Gerngross et al., *Nature-Biotechnology*. 22:1409-1414, 2004; U.S. Pat. Nos. 7,629, 163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., Science 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology, pp.* 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *Proc. Natl. Acad. Sci. U.S.A.* 91:3224-3227 (1994)). Also included are baculovirus expression systems, including those that utilize SF9, SF21, and *T. ni* cells (see, e.g., Murphy and Piwnica-Worms, *Curr Protoc Protein Sci.* Chapter 5:Unit 5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659, 1984). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NS0 and Sp2/0. For a review of certain mammalian host cell lines suitable for antibody production, see, e.g., Yazaki and Wu, *Methods in Molecular Biology, Vol.* 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included are methods of cell-free protein expression. These and related embodiments typically utilize purified RNA polymerase, ribosomes, tRNA, and ribonucleotides. Such reagents can be produced, for example, by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally-occurring amino acids (see generally U.S. Pat. No. 7,939,496; U.S. Pat. No. 7,816,320; U.S. Pat. No. 7,947,473; U.S. Pat. No. 7,883,866; U.S. Pat. No. 7,838,265; U.S. Pat. No. 7,829,310; U.S. Pat. No. 7,820,766; U.S. Pat. No. 7,820,766; U.S. Pat. No. 7,7737,226, U.S. Pat. No. 7,736,872; U.S. Pat. No. 7,638,299; U.S. Pat. No. 7,632,924; and U.S. Pat. No. 7,230,068). Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The HRS polypeptides produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Several exemplary methods are also disclosed in the Examples sections.

Recombinant Vectors and Polynucleotides

Another embodiment of the invention provides for recombinant polynucleotides, recombinant vectors, and recombinant viral vectors comprising a polynucleotide whose sequence comprises a nucleotide sequence which encodes for any of the HRS polypeptides disclosed herein.

Also included are formulations comprising modified and enhanced mRNAs encoding the HRS polypeptides which are capable of reducing the innate immune activity of a population of cells into which they are introduced, thus increasing the efficiency of protein production in that cell population. Such modified mRNAs include for example a 5'Cap1 structure and a polyA tail of approximately 160 nucleotides in length, and which are optionally formulated in a lipid formulation such as a liposome, lipoplexe, or lipid nanoparticle, as described for example in, US Application publication no. 2012/0251618, and International Application Nos. PCT/US2011/046861 and PCT/US2011/054636, the contents of which are incorporated by reference in their entirety.

The selection of recombinant vectors suitable for expressing the HRS polypeptides of the invention, methods for inserting nucleic acid sequences for expressing the HRS polypeptides into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; Paul C P et al. (2002), Nat. Biotechnol. 20: 505-508, Conese et al., Gene Therapy 11: 1735-1742 (2004), and Fjord-Larsen et al., (2005) Exp Neurol 195:49-60 the entire disclosures of which are herein incorporated by reference.

Representative commercially available recombinant expression vectors include, for example, pREP4, pCEP4, pREP7 and pcDNA3.1 and pcDNA™5/FRT from Invitrogen, and pBK-CMV and pExchange-6 Core Vectors from Stratagene. Representative commercially available viral expression vectors include, but are not limited to, the adenovirus-based systems, such as the Per.C6 system available from Crucell, Inc., lentiviral-based systems such as pLP1 from Invitrogen, and retroviral vectors such as Retroviral Vectors pFB-ERV and pCFB-EGSH from Stratagene (US).

In general, any recombinant or viral vector capable of accepting the coding sequences for the HRS polypeptides to be expressed can be used, for example vectors derived from adenovirus (AV); adeno-associated virus (AAV); retroviruses (e.g., lentiviruses (LV), Rhabdoviruses, murine leukemia virus); herpes virus, papillomavirus (U.S. Pat. Nos. 6,399, 383,& 7,205,126) and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like. Non infectious pseudovirions, for example of Papillomavirus, may also be used to enable the efficient delivery of genes to mucosal membranes (U.S. Pat. No. 7,205,126, Peng et al., Gene Ther. 2010 Jul. 29 epub).

In some aspects, viral vectors derived from AV and AAV may be used in the present invention. Suitable AAV vectors for expressing the HRS polypeptides of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Typically the recombinant vectors and recombinant viral vectors include expression control sequences that direct the expression of the polynucleotide of the invention in various systems, both in vitro and in vivo. For instance, one set of regulatory elements will direct expression in certain mammalian cells or tissues and another set of regulatory elements will direct expression to bacterial cells and yet a third set of regulatory elements will direct expression in baculovirus systems. Some vectors are hybrid vectors that contain regulatory elements necessary for expression in more than one system. Vectors containing these various regulatory systems are commercially available and one skilled in the art will readily be able to clone the polynucleotides of the invention into such vectors.

In some instances, the polynucleotides or vectors will possess promoters for expression of the HRS polypeptides in a wide variety of cells. In other instances, the vectors will possess promoters that are tissue specific. For example, the promoters direct expression only in immune cells, muscle cells. In some aspects, the vector of the invention comprises a polynucleotide whose nucleotide sequence encodes a HRS polypeptide of any of SEQ ID NOS: 1-23, 39, 41, 43, 70-71, 74-153, 160-172, or 176-182.

Recombinant polynucleotides and vectors can be administered to a patient directly or in conjunction with a suitable delivery reagent, including the Minis Transit LT1 lipophilic reagent; lipofectin; lipofectamine; cellfectin; polycations (e.g., polylysine) or liposomes. Selection of recombinant viral vectors suitable for use in the invention, methods for inserting nucleic acid sequences for expressing the HRS polypeptides into the vector, and methods of delivering the viral vector to the cells of interest are within the skill in the art. See, for example, Dornburg R (1995), Gene Therap. 2: 301-310; Eglitis M A (1988), *Biotechniques* 6: 608-614; Miller A D (1990), Hum Gene Therap. 1: 5-14; and Anderson W F (1998), *Nature* 392: 25-30, the entire disclosures of which are herein incorporated by reference.

Host Cells

Some embodiments include a host cell transformed with a vector or polynucleotide described herein. In some aspects, the HRS polypeptides described herein are expressed by the host cell in order to produce or manufacture the HRS polypeptide. Such host cells include bacteria, insect cells, yeast cells, and mammalian cells.

In some aspects, the host cells may be used to express and deliver a HRS polypeptide via cell therapy. Accordingly, certain aspects include a cell therapy for treating an autoimmune or inflammatory disease or disorder, comprising administering a host cell expressing, or capable of expressing, a HRS polypeptide of the invention. In some aspects the disease or disorder is selected from inflammatory myopathies, including, for example, polymyositis, dermatomyositis, polymyositis-scleroderma overlap, interstitial lung disease, hypersensitivity pneumonitis, scleroderma, systemic lupus erythematosus, rheumatoid arthritis, Churg-Strauss syndrome, Wegener's granulomatosis, Goodpasture Syndrome, asthma, muscular dystrophies, cachexia, and rhabdomyolysis, among others described herein.

Cell therapy involves the administration of cells which have been selected, multiplied and pharmacologically treated or altered (e.g., genetically modified) outside of the body (Bordignon, C. et al, Cell Therapy: Achievements and Perspectives (1999), Haematologica, 84, pp. 1110-1149). Such host cells include for example, primary cells, including muscle cells, PBMCs, macrophages, and stem cells which have been genetically modified to express a HRS polypeptide of the invention. The aim of cell therapy is to replace, repair or enhance the biological function of damaged tissues or organs (Bordignon, C. et al, (1999), Haematologica, 84, pp. 1110-1149).

In some aspects of such methods the host cell secretes the HRS polypeptide and thus provides a sustainable source of the HRS polypeptide within the tissue or organ into which the host cell is implanted.

Other Therapeutic Agents

In some embodiments, the compositions and methods described herein may employ antibodies, antibody fragments, or non-HRS polypeptide binding proteins to block the activity of anti-histidyl-tRNA synthetase auto-antibodies. In some aspects, the antibody or binding protein is directed to the antigen binding domain of the auto-antibody, i.e., the antibodies represent anti-idiotype antibodies, thereby selectively blocking the activity of the autoantibody. Accordingly, such binding agents may be used to diagnose, treat, or prevent diseases, disorders or other conditions that are mediated by autoantibodies to a histidyl-tRNA synthetase associated with autoimmune disease.

The term "antibody" describes an immunoglobulin whether natural or partly or wholly synthetically produced. The term also covers any polypeptide or protein having a binding domain which is, or is homologous to, an antigen-binding domain. CDR grafted antibodies, including bi-specific antibodies, and humanized antibodies, in which one or more of the CDRs are derived from antibodies obtained from B-cells identified, cloned, or selected using any of the methods disclosed or claimed herein are also contemplated by this term.

"Native IgG antibodies" and "native IgG immunoglobulins" are typically heterotetrameric glycoproteins of about 150,000 daltons, composed of two identical light (L) chains and two identical heavy (H) chains. Each light chain is, in some cases, linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable domain" refers to protein domains that differ extensively in sequence among family members (i.e., among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR." The variable domains of unmodified heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647 669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs," which directly bind, in a complementary manner, to an antigen and are known as CDR1, CDR2, and CDR3 respectively.

In the light chain variable domain, the CDRs correspond to approximately residues 24-34 (CDRL1), 50-56 (CDRL2) and 89-97 (CDRL3), and in the heavy chain variable domain the CDRs correspond to approximately residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J., Mol. Biol. 196:901-917 (1987)).

As used herein, "variable framework region" or "VFR" refers to framework residues that form a part of the antigen binding pocket and/or groove that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) can be less diversified. The three-dimensional structure of the antibody variable domain can be derived from a crystal structure or protein modeling. In some embodiments, the VFR comprises, consists essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. Preferably, VFR forms a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known. The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably in the present invention to mean one or more fragments of an antibody that retain the ability to specifically bind to an antigen (see, e.g., Holliger et al., Nature Biotech. 23 (9): 1126-1129 (2005)). Non-limiting examples of antibody fragments included within, but not limited to, the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *PNAS USA*. 85:5879-5883; and Osbourn et al. (1998) *Nat. Biotechnol.* 16:778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed.

"F(ab')$_2$" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_{H\gamma1}$ (γ1 region in the constant region of H chain) are connected at their C terminal regions through a disulfide bond. Each of these two homologous antibody fragments is called Fab'. Pepsin cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFv molecules, see, e.g., Pluckthun in The Pharmacology of Monoclonal Antibodies, Vol. 113, Rosenburg and Moore eds. Springer-Verlag, New York, pp. 269-315 (1994).

As used herein, "natural" or "naturally-occurring" antibodies or antibody variable domains, refers to antibodies or antibody variable domains having a sequence of an antibody or antibody variable domain identified from a non-synthetic source, for example, from a germline sequence, or differentiated antigen-specific B cell obtained ex vivo, or its corresponding hybridoma cell line, or from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database.

Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VELOCIMMUNE® platform by REGERNEREX® (see, e.g., U.S. Pat. No. 6,596, 541). Antibodies can also be generated or identified by the use of phage display or yeast display libraries (see, e.g., U.S. Pat. No. 7,244,592; Chao et al., *Nature Protocols*. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

According to another aspect, the present invention further provides antibody alternatives or other binding agents, such as soluble receptors, adnectins, peptides, peptide mimetics, aptamers, etc., that exhibit binding specificity for an autoantibody to a histidyl-tRNA synthetase, and compositions and methods of using same. Binding agents can be used in any of the therapeutic methods and compositions described herein. Biologic-based binding agents such as adnectins, soluble receptors, avimers, and trinectins are particularly useful.

In certain embodiments, such binding agents are effective for blocking the autoantibodies to a histidyl-tRNA synthetase associated with autoimmune disease. Accordingly, such binding agents may be used to diagnose, treat, or prevent diseases, disorders or other conditions that are mediated by autoantibodies to a histidyl-tRNA synthetase associated with autoimmune disease, such as by antagonizing or agonizing its activity partially or fully.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with one or more autoantibodies to a histidyl-tRNA synthetase associated with autoimmune disease. Peptides can be composed of naturally-occurring amino acids and/or non-naturally-occurring amino acids, as described herein.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Luthman, et al., *A Textbook of Drug Design and Development*, 14:386-406, 2nd Ed., Harwood Academic Publishers (1996); Joachim Grante, *Angew. Chem. Int. Ed. Engl.*, 33:1699-1720 (1994); Fauchere, J., *Adv. Drug Res.*, 15:29 (1986); Veber and Freidinger TINS, p. 392 (1985); and Evans, et al., *J. Med. Chem.* 30:229 (1987)). A peptidomimetic is a molecule that mimics the biological activity of a peptide but is no longer peptidic in chemical nature. Peptidomimetic compounds are known in the art and are described, for example, in U.S. Pat. No. 6,245,886.

The present invention also includes peptoids. Peptoid derivatives of peptides represent another form of modified peptides that retain the important structural determinants for biological activity, yet eliminate the peptide bonds, thereby conferring resistance to proteolysis (Simon, et al., *PNAS USA*. 89:9367-9371, 1992). Peptoids are oligomers of N-substituted glycines. A number of N-alkyl groups have been described, each corresponding to the side chain of a natural amino acid. The peptidomimetics of the present invention include compounds in which at least one amino acid, a few amino acids or all amino acid residues are replaced by the corresponding N-substituted glycines. Peptoid libraries are described, for example, in U.S. Pat. No. 5,811,387.

Aptamers are also included as binding agents (see, e.g., Ellington et al., *Nature*. 346, 818-22, 1990; and Tuerk et al., *Science*. 249, 505-10, 1990). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620. Hence, included are nucleic acid aptamers that bind to the AARS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys-loop in the wild protein), with the two cysteines lateral chains being able to form a disulfide bridge. Methods for identifying peptide aptamers are described, for example, in U.S. Application No. 2003/0108532. Hence, included are peptide aptamers that bind to the AARS polypeptides described herein and/or their cellular binding partners. Peptide aptamer selection can be performed using different systems known in the art, including the yeast two-hybrid system.

Also included are ADNECTINS™, AVIMERS™, anaphones and anticalins that specifically bind to an AARS protein fragment of the invention. ADNECTINS™ refer to a class of targeted biologics derived from human fibronectin, an abundant extracellular protein that naturally binds to other proteins. See, e.g., U.S. Application Nos. 2007/0082365; 2008/0139791; and 2008/0220049. ADNECTINS™ typically consists of a natural fibronectin backbone, as well as the multiple targeting domains of a specific portion of human fibronectin. The targeting domains can be engineered to enable an ADNECTINT™ to specifically recognize autoantibodies to a histidyl-tRNA synthetase associated with autoimmune disease.

AVIMERS™ refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., *Nature Biotechnology*. 23:1556-1561, 2005; U.S. Pat. No. 7,166, 697; and U.S. Application Nos. 2004/0175756, 2005/0048512, 2005/0053973, 2005/0089932 and 2005/0221384.

Also included are designed ankyrin repeat proteins (DARPins), which include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins. See, e.g., Stumpp et al., *Curr Opin Drug Discov Devel.* 10:153-159, 2007; U.S. Application No. 2009/0082274; and PCT/EP2001/10454.

Certain embodiments include "monobodies," which typically utilize the 10th fibronectin type III domain of human fibronectin (FNfn10) as a scaffold to display multiple surface loops for target binding. FNfn10 is a small (94 residues) protein with a β-sandwich structure similar to the immunoglobulin fold. It is highly stable without disulfide bonds or metal ions, and it can be expressed in the correctly folded form at a high level in bacteria. The FNfn10 scaffold is compatible with virtually any display technologies. See, e.g., Baton et al., *Protein Eng.* 15:1015-20, 2002; and Wojcik et al., *Nat Struct Mol Biol.*, 2010; and U.S. Pat. No. 6,673,901.

Anticalins refer to a class of antibody mimetics, which are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, *FEBS J.* 275:2677-83, 2008, herein incorporated by reference.

Therapeutic Compositions, Pharmaceutical Formulations, Administration, and Kits

Embodiments of the present invention include therapeutic or pharmaceutical compositions for treating inflammatory disease(s), muscular dystrophies, rhabdomyolysis, cachexia, and other diseases described herein, comprising at least one HRS polypeptide, wherein the HRS polypeptide possesses one or more non-canonical activities.

Also included are therapeutic or pharmaceutical compositions for treating autoimmune disease(s), comprising at least one HRS polypeptide, wherein the HRS polypeptide possesses one or more non-canonical activities.

Some embodiments relate to therapeutic or pharmaceutical compositions for treating autoimmune diseases, inflammatory disease(s), muscular dystrophies, rhabdomyolysis, cachexia, and other diseases described herein, comprising at least one HRS polypeptide, wherein the HRS polypeptide comprises at least one epitope which specifically cross reacts with an auto-antibody or auto reactive T-cell from a disease associated with autoantibodies to histidyl-tRNA synthetase, and/or possesses one or more non-canonical activities. In certain embodiments, the HRS polypeptide comprises at least one Th epitope of the histidyl-tRNA synthetase.

Some embodiments include therapeutic or pharmaceutical compositions for treating autoimmune diseases, inflammatory disease(s), muscular dystrophies, rhabdomyolysis, cachexia, and other diseases described herein, comprising a recombinant nucleic acid encoding a mammalian HRS polypeptide, wherein the HRS polypeptide comprises at least one epitope of the histidyl-tRNA synthetase and/or possesses one or more non-canonical activities, and wherein the nucleic acid is operatively coupled to expression control sequences to enable expression of the HRS in a cell.

Certain embodiments include therapeutic or pharmaceutical compositions for treating diseases associated with autoantibodies specific for histidyl-tRNA synthetase, comprising a recombinant host cell, wherein the host cell expresses at least one heterologous HRS polypeptide which comprises at least one epitope of the histidyl-tRNA synthetase, and wherein the nucleic acid is operatively coupled to expression control sequences to enable expression of the HRS in a cell. Also included are therapeutic or pharmaceutical compositions for treating diseases associated with an insufficiency of histidyl-tRNA synthetase, comprising at least one HRS polypeptide, wherein the HRS polypeptide is capable of replacing at least one canonical or non-canonical function of the histidyl-tRNA synthetase.

Some embodiments include therapeutic or pharmaceutical compositions for treating diseases associated with an autoantibody specific for histidyl-tRNA synthetase, comprising at least one HRS polypeptide, wherein the HRS polypeptide does not significantly compete for disease associated auto-antibody binding to histidyl-tRNA synthetase in a competitive ELISA up to a concentration of about $1\times10^{-7}$M.

Some embodiments include therapeutic or pharmaceutical compositions which enhance, optimize or prolong the stability, homogeneity, monodispersion or activity of the HRS polypeptides.

Also included in the invention are medically-useful, therapeutic, or pharmaceutical compositions comprising a polypeptide of at least about 400 amino acids of a HRS polypeptide; wherein the polypeptide is;
a) at least about 95% pure;
b) less than about 5% aggregated; and
c) substantially endotoxin-free.

In another embodiment the medically useful, therapeutic, or pharmaceutical compositions comprises a HRS polypeptide of between about 40 and 80 amino acids; wherein the polypeptide is;
a) at least about 95% pure;
b) less than about 5% aggregated; and
c) substantially endotoxin-free.

Also included are new medical uses of the HRS polypeptides in the preparation of a medicament for the treatment of an autoimmune disease.

In any of these therapeutic compositions and uses, the compositions can be formulated in pharmaceutically-acceptable, physiologically-acceptable, and/or pharmaceutical grade solutions for administration to a cell, subject, or an animal, either alone, or in combination with one or more other modalities of therapy. It will also be understood that, if desired, the compositions of the invention may be administered in combination with other agents as well, such as, e.g., other proteins or polypeptides or pharmaceutically-active agents. In this context "administered in combination" includes (1) part of the same unitary dosage form; and (2) administration separately, but as part of the same therapeutic treatment program or regimen, typically, but not necessarily, on the same day.

In some embodiments, the compositions comprise a mixture of 2 or more HRS polypeptides. In some aspects the compositions may comprise about 2 to about 50, or about 2 to about 25, or about 2 to about 15, or 1, 2, 3, 4, 5, 6, 7, 8, 9, 10, 11, 12, 13, 14, 15 or more HRS polypeptides described herein.

Therapeutic or pharmaceutical compositions comprising a therapeutic dose of a HRS polypeptide include any one or more homologues, orthologs, variants, fragments, modified polypeptides, and/or naturally-occurring isoforms of histidyl-tRNA synthetase described herein (e.g., any of SEQ ID NOS: 1-23, 39, 41, 43, 70-71, 74-153, 160-172, or 176-182, or any of the HRS polypeptides or nucleic acids listed in or derivable from Tables D1-D9).

In some embodiments, the HRS polypeptide does not significantly compete for disease associated auto-antibody binding to wild-type histidyl-tRNA synthetase in a competitive ELISA up to a concentration of about $1\times10^{-7}$M. Accordingly in some embodiments, the HRS polypeptide has a lower affinity to disease associated auto-antibody than wild-type histidyl-tRNA synthetase (SEQ ID NO:1) as measured in a competitive ELISA. In some embodiments, the HRS polypeptide has an apparent affinity for the disease associated auto-antibody which is at least about 10-fold less, or at least about 20-fold less, or at least about 50-fold less, or at least about 100-fold less than the affinity of the disease associated auto-antibody to wild-type human (SEQ ID NO:1).

For pharmaceutical production, the HRS polypeptide compositions will typically be substantially endotoxin-free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA).

To be substantially endotoxin-free, endotoxin levels may be about or less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, a composition has an endotoxin content of about or less than about 10 EU/mg of HRS polypeptide, about or less than about 9 EU/mg of HRS polypeptide, about or less than about 8 EU/mg of HRS polypeptide, about or less than about 7 EU/mg of HRS polypeptide, about or less than about 6 EU/mg of HRS polypeptide, about or less than about 5 EU/mg of HRS polypeptide, about or less than about 4 EU/mg of HRS polypeptide, about or less than about 3 EU/mg of HRS polypeptide, about or less than about 2 EU/mg of HRS polypeptide, about or less than about 1 EU/mg of HRS polypeptide, about or less than about 1 EU/mg of HRS polypeptide, about or less than about 0.1 EU/mg of HRS polypeptide, about or less than about 0.1 EU/mg of HRS polypeptide, or about or less than about 0.01 EU/mg of HRS polypeptide. In certain embodiments, as noted above, a composition is at least about 95%, 96%, 97%, or 98% endotoxin-free, at least about 99% endotoxin-free, at least about 99.5% endotoxin-free, or at least about 99.99% endotoxin-free on a wt/wt protein basis.

In some embodiments, a composition comprises one or more pH buffering agents, i.e., buffers. Exemplary buffers include histidine (e.g., L-histidine, D-histidine), citrate buffers (e.g., sodium citrate, citric acid, mixtures thereof), and phosphate buffers (e.g., sodium phosphate, phosphate buffered saline (PBS)).

In some embodiments, the buffer is present at a concentration ranging from about 0.3 mM to about 100 mM, or about 0.3 mM to about 95 mM, or about 0.3 mM to about 90 mM, or about 0.3 mM to about 85 mM, or about 0.3 mM to about 80 mM, or about 0.3 mM to about 75 mM, or about 0.3 mM to about 70 mM, or about 0.3 mM to about 65 mM, or about 0.3 mM to about 60 mM, or about 0.3 mM to about 55 mM, or about 0.3 mM to about 50 mM, or about 0.3 mM to about 45 mM, or about 0.3 mM to about 40 mM, or about 0.3 mM to about 35 mM, or about 0.3 mM to about 30 mM, or about 0.3 mM to about 25 mM, or about 0.3 mM to about 20 mM, or about 0.3 mM to about 15 mM, or about 0.3 mM to about 10 mM, or about 0.3 mM to about 5 mM.

In some embodiments, the buffer is present at a concentration ranging from about 1 mM to about 100 mM, or about 1 mM to about 95 mM, or about 1 mM to about 90 mM, or about 1 mM to about 85 mM, or about 1 mM to about 80 mM, or about 1 mM to about 75 mM, or about 1 mM to about 70 mM, or about 1 mM to about 65 mM, or about 1 mM to about 60 mM, or about 1 mM to about 55 mM, or about 1 mM to about 50 mM, or about 1 mM to about 45 mM, or about 1 mM to about 40 mM, or about 1 mM to about 35 mM, or about 1 mM to about 30 mM, or about 1 mM to about 25 mM, or about 1 mM to about 20 mM, or about 1 mM to about 15 mM, or about 1 mM to about 10 mM, or about 1 mM to about 5 mM.

In some embodiments, the buffer is present at a concentration ranging from about 2 mM to about 100 mM, or about 2 mM to about 95 mM, or about 2 mM to about 90 mM, or about 2 mM to about 85 mM, or about 2 mM to about 80 mM, or about 2 mM to about 75 mM, or about 2 mM to about 70 mM, or about 2 mM to about 65 mM, or about 2 mM to about 60 mM, or about 2 mM to about 55 mM, or about 2 mM to about 50 mM, or about 2 mM to about 45 mM, or about 2 mM to about 40 mM, or about 2 mM to about 35 mM, or about 2 mM to about 30 mM, or about 2 mM to about 25 mM, or about 2 mM to about 20 mM, or about 2 mM to about 15 mM, or about 2 mM to about 10 mM, or about 2 mM to about 5 mM.

In some embodiments, the buffer is present at a concentration ranging from about 5 mM to about 100 mM, or about 5 mM to about 95 mM, or about 5 mM to about 90 mM, or about 5 mM to about 85 mM, or about 5 mM to about 80 mM, or about 5 mM to about 75 mM, or about 5 mM to about 70 mM, or about 5 mM to about 65 mM, or about 5 mM to about 60 mM, or about 5 mM to about 55 mM, or about 5 mM to about 50 mM, or about 5 mM to about 45 mM, or about 5 mM to about 40 mM, or about 5 mM to about 35 mM, or about 5 mM to about 30 mM, or about 5 mM to about 25 mM, or about 5 mM to about 20 mM, or about 5 mM to about 15 mM, or about 5 mM to about 10 mM.

In some embodiments, the is present at a concentration ranging from about 10 mM to about 100 mM, or about 10 mM to about 95 mM, or about 10 mM to about 90 mM, or about 10 mM to about 85 mM, or about 10 mM to about 80 mM, or about 10 mM to about 75 mM, or about 10 mM to about 70 mM, or about 10 mM to about 65 mM, or about 10 mM to about 60 mM, or about 10 mM to about 55 mM, or about 10 mM to about 50 mM, or about 10 mM to about 45 mM, or about 10 mM to about 40 mM, or about 10 mM to about 35 mM, or about 10 mM to about 30 mM, or about 10 mM to about 25 mM, or about 10 mM to about 20 mM, or about 10 mM to about 15 mM.

In some embodiments, the buffer is present at a concentration ranging from about 15 mM to about 100 mM, or about 15 mM to about 95 mM, or about 15 mM to about 90 mM, or about 15 mM to about 85 mM, or about 15 mM to about 80 mM, or about 15 mM to about 75 mM, or about 15 mM to about 70 mM, or about 15 mM to about 65 mM, or about 15 mM to about 60 mM, or about 15 mM to about 55 mM, or about 15 mM to about 50 mM, or about 15 mM to about 45 mM, or about 15 mM to about 40 mM, or about 15 mM to about 35 mM, or about 15 mM to about 30 mM, or about 15 mM to about 25 mM, or about 15 mM to about 20 mM.

In some embodiments, the buffer is present at a concentration ranging from about 20 mM to about 100 mM, or about 20 mM to about 95 mM, or about 20 mM to about 90 mM, or about 20 mM to about 85 mM, or about 20 mM to about 80 mM, or about 20 mM to about 75 mM, or about 20 mM to about 70 mM, or about 20 mM to about 65 mM, or about 20 mM to about 60 mM, or about 20 mM to about 55 mM, or about 20 mM to about 50 mM, or about 20 mM to about 45 mM, or about 20 mM to about 40 mM, or about 20 mM to about 35 mM, or about 20 mM to about 30 mM, or about 20 mM to about 25 mM.

In some embodiments, the buffer is present at a concentration ranging from about 25 mM to about 100 mM, or about 25 mM to about 95 mM, or about 25 mM to about 90 mM, or about 25 mM to about 85 mM, or about 25 mM to about 80 mM, or about 25 mM to about 75 mM, or about 25 mM to about 70 mM, or about 25 mM to about 65 mM, or about 25 mM to about 60 mM, or about 25 mM to about 55 mM, or about 25 mM to about 50 mM, or about 25 mM to about 45 mM, or about 25 mM to about 40 mM, or about 25 mM to about 35 mM, or about 25 mM to about 30 mM.

In some embodiments, the buffer is present at a concentration ranging from about 30 mM to about 100 mM, or about 30 mM to about 95 mM, or about 30 mM to about 90 mM, or about 30 mM to about 85 mM, or about 30 mM to about 80 mM, or about 30 mM to about 75 mM, or about 30 mM to about 70 mM, or about 30 mM to about 65 mM, or about 30 mM to about 60 mM, or about 30 mM to about 55 mM, or about 30 mM to about 50 mM, or about 30 mM to about 45 mM, or about 30 mM to about 40 mM, or about 30 mM to about 35 mM.

In some embodiments, the buffer is present at a concentration ranging from about 35 mM to about 100 mM, or about 35 mM to about 95 mM, or about 35 mM to about 90 mM, or about 35 mM to about 85 mM, or about 35 mM to about 80 mM, or about 35 mM to about 75 mM, or about 35 mM to about 70 mM, or about 35 mM to about 65 mM, or about 35 mM to about 60 mM, or about 35 mM to about 55 mM, or about 35 mM to about 50 mM, or about 35 mM to about 45 mM, or about 35 mM to about 40 mM.

In some embodiments, the buffer is present at a concentration ranging from about 40 mM to about 100 mM, or about 40 mM to about 95 mM, or about 40 mM to about 90 mM, or about 40 mM to about 85 mM, or about 40 mM to about 80 mM, or about 40 mM to about 75 mM, or about 40 mM to about 70 mM, or about 40 mM to about 65 mM, or about 40 mM to about 60 mM, or about 40 mM to about 55 mM, or about 40 mM to about 50 mM, or about 40 mM to about 45 mM.

In some embodiments, the buffer is present at a concentration ranging from about 45 mM to about 100 mM, or about 45 mM to about 95 mM, or about 45 mM to about 90 mM, or about 45 mM to about 85 mM, or about 45 mM to about 80 mM, or about 45 mM to about 75 mM, or about 45 mM to about 70 mM, or about 45 mM to about 65 mM, or about 45 mM to about 60 mM, or about 45 mM to about 55 mM, or about 45 mM to about 50 mM.

In some embodiments, the buffer is present at a concentration ranging from about 50 mM to about 100 mM, or about 50 mM to about 95 mM, or about 50 mM to about 90 mM, or about 50 mM to about 85 mM, or about 50 mM to about 80 mM, or about 50 mM to about 75 mM, or about 50 mM to about 70 mM, or about 50 mM to about 65 mM, or about 50 mM to about 60 mM, or about 50 mM to about 55 mM.

In some embodiments, the buffer is present at a concentration ranging from about 55 mM to about 100 mM, or about 55 mM to about 95 mM, or about 55 mM to about 90 mM, or about 55 mM to about 85 mM, or about 55 mM to about 80 mM, or about 55 mM to about 75 mM, or about 55 mM to about 70 mM, or about 55 mM to about 65 mM, or about 55 mM to about 60 mM.

In some embodiments, the buffer is present at a concentration ranging from about 60 mM to about 100 mM, or about 60 mM to about 95 mM, or about 60 mM to about 90 mM, or about 60 mM to about 85 mM, or about 60 mM to about 80 mM, or about 60 mM to about 75 mM, or about 60 mM to about 70 mM, or about 60 mM to about 65 mM. In some embodiments, the buffer is present at a concentration ranging from about 65 mM to about 100 mM, or about 65 mM to about 95 mM, or about 65 mM to about 90 mM, or about 65 mM to about 85 mM, or about 65 mM to about 80 mM, or about 65 mM to about 75 mM, or about 65 mM to about 70 mM.

In some embodiments, the buffer is present at a concentration ranging from about 70 mM to about 100 mM, or about 70 mM to about 95 mM, or about 70 mM to about 90 mM, or about 70 mM to about 85 mM, or about 70 mM to about 80 mM, or about 70 mM to about 75 mM. In some embodiments, the buffer is present at a concentration ranging from about 75 mM to about 100 mM, or about 75 mM to about 95 mM, or about 75 mM to about 90 mM, or about 75 mM to about 85 mM, or about 75 mM to about 80 mM.

In some embodiments, the buffer is present at a concentration ranging from about 80 mM to about 100 mM, or about 80 mM to about 95 mM, or about 80 mM to about 90 mM, or about 80 mM to about 85 mM. In some embodiments, the buffer is present at a concentration ranging from about 85 mM to about 100 mM, or about 85 mM to about 95 mM, or about 85 mM to about 90 mM. In some embodiments, the buffer is present at a concentration ranging from about 90 mM to about 100 mM, or about 90 mM to about 95 mM, or about 95 mM to about 100 mM.

In some embodiments, the buffer is present at a concentration ranging from about 40-60, 41-60, 42-60, 43-60, 44-60, 45-60, 46-60, 47-60, 48-60, 49-60, 50-60, 51-60, 52-60, 53-60, 54-60, 55-60, 56-60, 57-60, 58-60, 59-60 mM, or about 40-59, 41-59, 42-59, 43-59, 44-59, 45-59, 46-59, 47-59, 48-59, 49-59, 50-59, 51-59, 52-59, 53-59, 54-59, 55-59, 56-59, 57-59, 58-59 mM, or about 40-58, 41-58, 42-58, 43-58, 44-58, 45-58, 46-58, 47-58, 48-58, 49-58, 50-58, 51-58, 52-58, 53-58, 54-58, 55-58, 56-58, 57-58 mM, or about 40-57, 41-57, 42-57, 43-57, 44-57, 45-57, 46-57, 47-57, 48-57, 49-57, 50-57, 51-57, 52-57, 53-57, 54-57, 55-57, 56-57 mM, or about 40-56, 41-56, 42-56, 43-56, 44-56, 45-56, 46-56, 47-56, 48-56, 49-56, 50-56, 51-56, 52-56, 53-56, 54-56, 55-56 mM, or about 40-55, 41-55, 42-55, 43-55, 44-55, 45-55, 46-55, 47-55, 48-55, 49-55, 50-55, 51-55, 52-55, 53-55, 54-55 mM, or about 40-54, 41-54, 42-54, 43-54, 44-54, 45-54, 46-54, 47-54, 48-54, 49-54, 50-54, 51-54, 52-54, 53-54 mM, or about 40-53, 41-53, 42-53, 43-53, 44-53, 45-53, 46-53, 47-53, 48-53, 49-53, 50-53, 51-53, 52-53 mM, or about 40-52, 41-52, 42-52, 43-52, 44-52, 45-52, 46-52, 47-52, 48-52, 49-52, 50-52, 51-52 mM, or about 40-51, 41-51, 42-51, 43-51, 44-51, 45-51, 46-51, 47-51, 48-51, 49-51, 50-51 mM, or about 40-50, 41-50, 42-50, 43-50, 44-50, 45-50, 46-50, 47-50, 48-50, 49-50 mM, or about 40-49, 41-49, 42-49, 43-49, 44-49, 45-49, 46-49, 47-49, 48-49 mM, or about 40-48, 41-48, 42-48, 43-48, 44-48, 45-48, 46-48, 47-48 mM, or about 40-47, 41-47, 42-47, 43-47, 44-47, 45-47, 46-47 mM, or about 40-46, 41-46, 42-46, 43-46, 44-46, 45-46 mM, or about 40-45, 41-45, 42-45, 43-45, 44-45 mM, or about 40-44, 41-44, 42-44, 43-44 mM, or about 40-43, 41-43, 42-43 mM, or about 40-42, 41-42 mM, or about 40-42 mM.

In some embodiments, the composition comprises a buffer at a concentration of about 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mM, including all ranges in between.

In some embodiments, the presence of the buffer alters (e.g., improves, increases, decreases, reduces) one or more biochemical, physical, and/or pharmacokinetic properties of the HRS polypeptide relative to a composition without the buffer or with a different buffer.

For instance, in certain embodiments, the HRS polypeptide in the presence of the buffer has increased biological activity relative to a corresponding HRS polypeptide in an otherwise identical or comparable composition without the buffer or with a different buffer. Exemplary activities include any of the non-canonical activities described herein, such as anti-inflammatory activities and other biological activities, including antibody binding (e.g., binding to anti-Jo-1 antibodies). In some embodiments, the HRS polypeptide in the buffer has at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater biological activity than a corresponding HRS polypeptide in an otherwise identical or comparable composition without the buffer or with a different buffer. In specific aspects, the buffer is a histidine buffer.

In certain embodiments, the HRS polypeptide in the presence of the buffer has increased "stability" (e.g., as measured by half-life), which is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a corresponding HRS polypeptide in an otherwise identical or comparable composition without the buffer or with a different buffer. In specific aspects, the buffer is a histidine buffer.

In some embodiments, the "stability" of the HRS polypeptide includes its "functional stability," or the rate at which at least one biological activity of the HRS polypeptide is reduced under a given set of conditions over time. Exemplary biological activities include any one or more of the canonical or non-canonical activities described herein, including, for example, the retention of at least one epitope which specifically cross reacts with an anti-Jo-1 antibody. In some embodiments, the biological activity of the HRS polypeptide in the presence of the buffer is reduced at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 10%, 20%, 30%, 40%, 50%, 60%, 70%, 80%, 90%, 100%, 200%, 300%, 400%, or 500% slower than a corresponding HRS polypeptide in an otherwise identical or comparable composition without the buffer or with a different buffer. In specific aspects, the buffer is a histidine buffer.

In certain embodiments, the "stability" of the HRS polypeptide includes its "kinetic stability" or "thermal stability," including its rate of unfolding, aggregation, or precipitation under a given set of conditions over time. In certain embodiments, the HRS polypeptide in the presence of the buffer unfolds, aggregates, or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide in an otherwise identical or comparable composition without the buffer or with a different buffer.

In certain embodiments, the HRS polypeptide in the presence of the buffer unfolds, aggregates, or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the buffer or with a different buffer.

In some embodiments, the HRS polypeptide in the presence of the buffer has a melting temperature (Tm) that is at least about 5%, 10%, 20%, 30%, 40%, 50%, 60%, 70%, 80%, 90%, 100% greater than the melting temperature of a corresponding HRS polypeptide in an otherwise identical or comparable composition without the buffer or with a different buffer. In some embodiments, the HRS polypeptide in the presence of the buffer has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than a corresponding HRS polypeptide in an otherwise identical or comparable composition without the buffer or with a different buffer. In specific aspects, the buffer is a histidine buffer.

In some embodiments, the HRS polypeptide has improved or increased homogeneity or monodispersion (e.g., ratio of monomers/oligomers, ratio of dimers/oligomers, ratio of monomers/dimers, ratio of dimers/monomers, ratio of interchain disulfide bond formation under reducing conditions, distribution of apparent molecular weights, including reduced high molecular weight and/or low molecular weight peaks as detected by either SDS-PAGE or HPLC analysis) in the presence of the buffer relative to a corresponding HRS polypeptide in an otherwise identical or comparable composition without the buffer or with a different buffer. In some embodiments, the homogeneity or monodispersion of the HRS polypeptide in the buffer is increased by at least about at least 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold or at least about 5%, 10%, 20%, 30%, 40%, 50%, 60%, 70%, 80%, 90%, 100%, 200%, 300%, 400%, or 500% relative to a corresponding HRS polypeptide in an otherwise identical or comparable composition without the buffer or with a different buffer. In specific aspects, the buffer is a histidine buffer at a pH within the range of about pH 7.0 to about pH 7.5, or a citrate buffer at a pH within the range of about pH 7.5 to about pH 6.5.

In certain embodiments, the HRS polypeptide composition in the presence of the histidine or citrate buffer has decreased high molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the buffer or with a different buffer. In some aspects, the HRS composition has a high molecular weight peak content by SE-HPLC analysis which is less than about 2% of the main peak after 2 days storage at 37° C. In some aspects, the HRS composition has a high molecular weight peak content which is less than about 1% of the main peak after 2 days storage at 37° C.

In certain embodiments, the HRS polypeptide composition in the presence of the histidine or citrate buffer has decreased low molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the buffer or with a different buffer.

In certain embodiments, the HRS polypeptide composition in the presence of the histidine or citrate buffer has a decreased turbidity (A340) that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the buffer or with a different buffer. In some aspects, the HRS composition comprises a histidine buffer of about pH 7.0 to 7.5 and has a turbidity (A340) which is less than about 0.5 after 2 days storage at 37° C. In specific aspects, the HRS composition has a turbidity (A340) which is less than about 0.05 after 2 days storage at 37 C. In some aspects, the HRS composition comprises a citrate buffer of about pH 7.0 to 7.5 and has a turbidity (A340) which is less than about 0.5 after 2 days storage at 37° C. In specific aspects, the HRS composition has a turbidity (A340) which is less than about 0.05 after 2 days storage at 37° C.

In certain embodiments, the pH of the composition (e.g., in the presence of the buffering agent or buffer) is about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. In some embodiments, the pH of the composition ranges from about 6.0-6.1, 6.0-6.2, 6.0-6.3, 6.0-6.4, 6.0-6.5, 6.0-6.6, 6.0-6.7, 6.0-6.8, 6.0-6.9, 6.0-7.0, 6.0-7.1, 6.0-7.2, 6.0-7.3, 6.0-7.4, 6.0-7.5, 6.0-7.6, 6.0-7.7, 6.0-7.8, 6.0-7.9, 6.0-8.0, or from about 6.5-6.6, 6.5-6.7, 6.5-6.8, 6.5-6.9, 6.5-7.0, 6.5-7.1, 6.5-7.2, 6.5-7.3, 6.5-7.4, 6.5-7.5, 6.5-7.6, 6.5-7.7, 6.5-7.8, 6.5-7.9, 6.5-8.0, or from about 7.0-7.1, 7.0-7.2, 7.0-7.3, 7.0-7.4, 7.0-7.5, 7.0-7.6, 7.0-7.7, 7.0-7.8, 7.0-7.9, 7.0-8.0, or from about 7.2-7.3, 7.2-7.4, 7.2-7.5, 7.2-7.6, 7.2-7.7, 7.2-7.8, 7.2-7.9, 7.2-8.0, or from about 7.4-7.5, 7.4-7.6, 7.4-7.7, 7.4-7.8, 7.4-7.9, 7.4-8.0, or from about 7.5-7.6, 7.5-7.7, 7.5-7.8, 7.5-7.9, 7.5-8.0, or from about 7.6-7.7, 7.6-7.8, 7.6-7.9, or 7.6-8.0.

In some embodiments, the pH of the composition or buffer alters (e.g., improves, increases, decreases, reduces) one or more biochemical, physical, and/or pharmacokinetic properties of the HRS polypeptide relative to a composition having a pH outside of the ranges above. In specific embodiments, the buffer is histidine and the pH of the composition ranges from about 7.0-7.5. In other embodiments, the buffer is a citrate buffer and the pH of the composition ranges from about 6.5-7.5. In other embodiments, the buffer is a sodium phosphate buffer and the pH of the composition ranges from about 7.0-7.5.

For instance, in certain embodiments, the HRS polypeptide in a composition comprising (a) a histidine buffer and a pH of about 7.0-7.5, (b) a citrate buffer and a pH of about 6.5-7.5, or (c) a phosphate buffer and a pH of about 7.0-7.5 has increased biological activity relative to a comparable composition having a pH outside of said ranges in (a), (b), or (c) above. Exemplary activities include any of the non-canonical activities described herein, such as anti-inflammatory activities and other biological activities, including antibody binding (e.g., binding to anti-Jo-1 antibodies). In some embodiments, the HRS polypeptide has at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater biological activity than a corresponding HRS polypeptide in a comparable composition having a pH outside of said ranges in (a), (b), or (c) above.

In certain embodiments, the HRS polypeptide in a composition comprising (a) a histidine buffer and a pH of about 7.0-7.5, (b) a citrate buffer and a pH of about 6.5-7.5, or (c) a phosphate buffer and a pH of about 7.0-7.5 has increased "stability" (e.g., as measured by half-life), which is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a corresponding HRS polypeptide in a comparable composition having a pH outside of said ranges in (a), (b), or (c) above.

In some embodiments, the "stability" of the HRS polypeptide includes its "functional stability," or the rate at which at least one biological activity of the HRS polypeptide is reduced under a given set of conditions over time. Exemplary biological activities include any one or more of the canonical or non-canonical activities described herein, including, for example, the retention of at least one epitope which specifically cross reacts with an anti-Jo-1 antibody. In some embodiments, the biological activity of the HRS polypeptide is reduced at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 10%, 20%, 30%, 40%, 50%, 60%, 70%, 80%, 90%, 100%, 200%, 300%, 400%, or 500% slower than a corresponding HRS polypeptide in a comparable composition having a pH outside of said ranges in (a), (b), or (c) above.

In certain embodiments, the "stability" of the HRS polypeptide includes its "kinetic stability" or "thermal stability," including its rate of unfolding under a given set of conditions over time. In certain embodiments, the HRS polypeptide unfolds at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide in a comparable composition having a pH outside of said ranges. In some embodiments, the HRS polypeptide has a melting temperature (Tm) that is at least about 5%, 10%, 20%, 30%, 40%, 50%, 60%, 70%, 80%, 90%, 100% greater than the melting temperature of a corresponding HRS polypeptide in a comparable composition having a pH outside of said ranges in (a), (b), or (c) above. In some embodiments, the HRS polypeptide has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than a corresponding HRS polypeptide in a comparable composition having a pH outside of said ranges in (a), (b), or (c) above.

In some embodiments, the HRS polypeptide has improved or increased homogeneity or monodispersion (e.g., ratio of monomers/oligomers, ratio of dimers/oligomers, ratio of monomers/dimers, ratio of dimers/monomers, ratio of interchain disulfide bond formation under reducing conditions, distribution of apparent molecular weights e.g. reduced high molecular weight or low molecular weight peaks detected by either SDS-PAGE or HPLC analysis) relative to a corresponding HRS polypeptide in a comparable composition having a pH outside of said ranges in (a), (b), or (c) above. In some embodiments, the homogeneity or monodispersion of the HRS polypeptide is increased by at least about at least 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold or at least about 5%, 10%, 20%, 30%, 40%, 50%, 60%, 70%, 80%, 90%, 100%, 200%, 300%, 400%, or 500% relative to a corresponding HRS polypeptide in a comparable composition having a pH outside of said ranges in (a), (b), or (c) above.

In certain embodiments, the HRS polypeptide composition within the pH ranges in (a), (b), or (c) above has decreased high molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days relative to a corresponding HRS polypeptide in a comparable composition having a pH outside of said ranges in (a), (b), or (c) above.

In certain embodiments, the HRS polypeptide composition in the pH ranges (a), (b), or (c) above has decreased low molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days relative to a corresponding HRS polypeptide in a comparable composition having a pH outside of said ranges in (a), (b), or (c) above.

In certain embodiments, the HRS polypeptide composition in the pH ranges (a), (b), or (c) above has a decreased turbidity (A340) that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days relative to a corresponding HRS polypeptide in a comparable composition having a pH outside of said ranges in (a), (b), or (c) above.

In some embodiments, a composition has a defined ionic strength, for example, a defined concentration of sodium chloride (NaCl) or other salt. For instance, a composition may have about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mM NaCl or other salt, including all integers and ranges in between. In some embodiments, a composition has about 50-300, 100-300, 150-300, 200-300, 250-300, 50-250, 100-250, 150-250, 200-250, 50-200, 100-200, 150-200, 50-150, 100-150, or 50-100 mM NaCl or other salt. In certain embodiments, the composition has a high salt concentration, e.g., about or ≥about 140 mM NaCl, about or ≥about 280 mM NaCl.

In some embodiments, the presence of NaCl at any one or more of these concentrations or ranges alters (e.g., improves, increases, decreases, reduces) one or more biochemical, physical, and/or pharmacokinetic properties of the HRS polypeptide relative to a composition without the NaCl, or relative to a composition with a concentration of NaCl that lies outside of the above amounts or ranges. In certain embodiments, the HRS polypeptide in the presence of the defined concentration of NaCl unfolds, aggregates, or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide in an otherwise identical or comparable composition without the defined concentration of NaCl.

In certain embodiments, the HRS polypeptide in the presence of the NaCl unfolds, aggregates, or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the NaCl or with a concentration of NaCl that lies outside of the above amounts or ranges.

In some embodiments, the HRS polypeptide in the presence of the defined concentration of NaCl has a melting temperature (Tm) that is at least about 5%, 10%, 20%, 30%, 40%, 50%, 60%, 70%, 80%, 90%, 100% greater than the melting temperature of a corresponding HRS polypeptide in an otherwise identical or comparable composition without the defined concentration of NaCl. In some embodiments, the HRS polypeptide in the presence of the defined concentration of NaCl has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than a corresponding HRS polypeptide in an otherwise identical or comparable composition without the defined concentration of NaCl or with a concentration of NaCl that lies outside of the above amounts or ranges. In certain embodiments, the composition also comprises a buffer, as described above. In specific embodiments, the buffer is a histidine buffer. In other embodiments, the buffer is a citrate buffer.

In certain embodiments, the HRS polypeptide composition has a concentration of NaCl ranging from about 140 mM to about 240 mM and has decreased high molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the NaCl. In some aspects, the HRS composition comprises about 140 mM to about 280 mM NaCl, a histidine buffer having a pH of about 7.0-7.5, and has a high molecular weight peak content by SE-HPLC analysis which is less than about 2% of the main peak after 2 days storage at 37° C. In specific aspects, the HRS composition has a high molecular weight peak content which is less than about 1% of the main peak after 2 days storage at 37° C.

In certain embodiments, the HRS polypeptide composition has a concentration of NaCl ranging from about 140 mM to about 240 mM and has decreased low molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the NaCl or with a concentration of NaCl that lies outside of about 140 mM to about 240 mM.

In certain embodiments, the HRS polypeptide composition has a concentration of NaCl ranging from about 140 mM to about 240 mM and has decreased turbidity (A340) that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the NaCl or with a concentration of NaCl that lies outside of about 140 mM to about 240 mM. In some aspects, the HRS composition comprises about 140 mM to about 280 mM NaCl, a histidine buffer having a pH of about 7.0-7.5 and has a turbidity (A340) which is less than about 0.5 after 2 days storage at 37° C. In specific aspects, the HRS composition has a turbidity (A340) which is less than about 0.05 after 2 days storage at 37 C.

In some embodiments, the composition comprises one or more pharmaceutically-acceptable excipients. Exemplary excipients include, without limitation, sucrose, mannitol, trehalose, sorbitol, arginine, glycine, and glycerol. In certain embodiments, the excipient is present at about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10% (w/v), including all ranges in between. In some embodiments, the excipient is present at a range of about 0.1-5.0, 0.1-4.5, 0.1-4.0, 0.1-3.5, 0.1-3.0, 0.1-2.5, 0.1-2.0, 0.1-1.5, 0.1-1.0, 0.1-0.5% (w/v), or in a range of about 0.2-5.0, 0.2-4.5, 0.2-4.0, 0.2-3.5, 0.2-3.0, 0.2-2.5, 0.2-2.0, 0.2-1.5, 0.2-1.0, 0.2-0.5% (w/v), or at a range of about 0.5-5.0, 0.5-4.5, 0.5-4.0, 0.5-3.5, 0.5-3.0, 0.5-2.5, 0.5-2.0, 0.5-1.5, 0.5-1.0% (w/v), or at a range of about 1.0-5.0, 1.0-4.5, 1.0-4.0, 1.0-3.5, 1.0-3.0, 1.0-2.5, 1.0-2.0, 1.0-1.5% (w/v), or at a range of about 1.5-5.0, 1.5-4.5, 1.5-4.0, 1.5-3.5, 1.5-3.0, 1.5-2.5, 1.5-2.0% (w/v), or at a range of about 2.0-5.0, 2.0-4.5, 2.0-4.0, 2.0-3.5, 2.0-3.0, 2.0-2.5% (w/v), or at a range of about 2.5-5.0, 2.5-4.5, 2.5-4.0, 2.5-3.5, 2.5-3.0% (w/v), or at a range of about 3.0-5.0, 3.0-4.5, 3.0-4.0, 3.0-3.5% (w/v), or in a range of about 3.5-5.0, 3.5-4.5, 3.5-4.0% (w/v), or at a range of about 4.0-5.0, 4.0-4.5, or 4.5-5.0% (w/v). In some embodiments, the excipient is present at a concentration of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mM, including all ranges in between. In some embodiments, the excipient is present at a concentration range of about 50-400, 100-400, 150-400, 200-400, 250-400, 300-400, 350-400, 50-350, 100-350, 150-350, 200-350, 250-350, 300-350, 50-300, 100-300, 150-300, 200-300, 250-300, 50-250, 100-250, 150-250, 200-250, 50-200, 100-200, 150-200, 50-150, 100-150, or 50-100 mM.

In some embodiments, the presence of one or more excipients alters (e.g., improves, increases, decreases, reduces) one or more biochemical, physical, and/or pharmacokinetic properties of the HRS polypeptide relative to a composition without the excipient(s), or relative to a composition with a concentration of excipient(s) that lies outside of the above amounts or ranges. In certain embodiments, the HRS polypeptide in the presence of the excipient(s) unfolds at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide in an otherwise identical or comparable composition without the excipient(s). In some embodiments, the HRS polypeptide in the presence of the excipient(s) has a melting temperature (Tm) that is at least about 5%, 10%, 20%, 30%, 40%, 50%, 60%, 70%, 80%, 90%, 100% greater than the melting temperature of a corresponding HRS polypeptide in an otherwise identical or comparable composition without the excipient(s). In some embodiments, the HRS polypeptide in the presence of the excipient(s) has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than a corresponding HRS polypeptide in an otherwise identical or comparable composition without the excipient(s). In certain embodiments, the composition also comprises a buffer, as described above, and optionally has a defined concentration of NaCl, as described above. In specific embodiments, the buffer is a histidine buffer. In other embodiments, the buffer is a citrate buffer.

In certain embodiments, a composition comprises one or more surfactants. Exemplary surfactants include, without limitation, polysorbates and poloxamers. Polysorbates are oily liquids derived from PEGylated sorbitan (a derivative of sorbitol) that are esterified with fatty acids. Some polysorbates are sold under the trade names Alkest™, Canarcel™, and Tween™. Exemplary polysorbates include Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate). Poloxamers are nonionic triblock copolymers that comprise a central hydrophobic chain of polyoxypropylene (poly(propylene oxide)) flanked by two hydrophilic chains of polyoxyethylene (poly(ethylene oxide)). Some poloxamers are sold under the trade names Synperonics™, Pluronics™, and Kolliphor™. In certain embodiments, the surfactant is present at about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% (w/v), including all ranges in between. In some embodiments, the surfactant is present at a range of about 0.01-3.0, 0.01-2.5, 0.01-2.0, 0.01-1.5, 0.01-1.0, 0.01-1.5, 0.01-1.0, 0.01-0.5, 0.01-0.1% (w/v), or at a range of about 0.05-3.0, 0.05-2.5, 0.05-2.0, 0.05-1.5, 0.05-1.0, 0.05-1.5, 0.05-1.0, 0.05-0.5, 0.05-0.1% (w/v), or at a range of about 0.1-3.0, 0.1-2.5, 0.1-2.0, 0.1-1.5, 0.1-1.0, 0.1-1.5, 0.1-1.0, 0.1-0.5% (w/v), or at a range of about 0.5-3.0, 0.5-2.5, 0.5-2.0, 0.5-1.5, 0.5-1.0, 0.5-1.5, 0.5-1.0% (w/v), or at a range of about 1.0-3.0, 1.0-2.5, 1.0-2.0, 1.0-1.5% (w/v), or at a range of about 1.5-3.0, 1.5-2.5, 1.5-2.0% (w/v), or at a range of about 2.0-3.0, 2.0-2.5% (w/v), or at a range of about 2.5-3.0% (w/v). In some embodiments, the surfactant is Polysorbate 20 (PS20). In certain embodiments, the surfactant is the poloxamer Pluronic F68.

In some embodiments, the presence of one or more surfactants alters (e.g., improves, increases, decreases, reduces) one or more biochemical, physical, and/or pharmacokinetic properties of the HRS polypeptide relative to a composition without the surfactant(s), or relative to a composition with a concentration of surfactant(s) that lies outside of the above amounts or ranges. In certain embodiments, the HRS polypeptide in the presence of the surfactant(s) unfolds, aggregates or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide in an otherwise identical or comparable composition without the surfactant(s).

In certain embodiments, the HRS polypeptide in the presence of the surfactant(s) unfolds, aggregates, or precipitates at a rate that is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold slower or at least about 5%, 10%, 20%, 30%, 40%, 50%, 60%, 70%, 80%, 90%, 100%, 200%, 300%, 400%, or 500% slower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the surfactant(s).

In some embodiments, the HRS polypeptide in the presence of the surfactant(s) has a melting temperature (Tm) that is at least about 5%, 10%, 20%, 30%, 40%, 50%, 60%, 70%, 80%, 90%, 100% greater than the melting temperature of a corresponding HRS polypeptide in an otherwise identical or comparable composition without the surfactant(s). In some embodiments, the HRS polypeptide in the presence of the surfactant(s) has a melting temperature ($T_m$) that is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. higher than a corresponding HRS polypeptide in an otherwise identical or comparable composition without the surfactant(s). In certain embodiments, the composition also comprises a buffer, as described above, and optionally has a defined concentration of NaCl, as described above, and optionally comprises one or more excipients, as described above. In specific embodiments, the buffer is a histidine buffer. In other embodiments, the buffer is a citrate buffer.

In certain embodiments, the HRS polypeptide composition in the presence of the surfactant(s) has decreased high molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the surfactant(s).

In some aspects, the HRS composition comprises PS20, a histidine buffer having a pH of about 7.0-7.5, and about 140 mM NaCl, and has a high molecular weight peak content which is less than about 1% of the main peak by SE-HPLC analysis after 7 days storage at 37° C. In some aspects, the HRS composition has a high molecular weight peak content which is less than about 0.5% of the main peak after 7 days storage at 37° C.

In some aspects, the HRS composition comprises PS80, a histidine buffer having a pH of about 7.0-7.5, and about 140 mM NaCl, and has a high molecular weight peak content which is less than about 2% of the main peak by SE-HPLC analysis after 7 days storage at 37° C. In some aspects, the HRS composition has a high molecular weight peak content which is less than about 0.5% of the main peak after 7 days storage at 37° C.

In some aspects, the HRS composition comprises pluronic F68, a histidine buffer having a pH of about 7.0-7.5, and about 140 mM NaCl, and has a high molecular weight peak content which is less than about 1% of the main peak by SE-HPLC analysis after 7 days storage at 37° C. In some aspects, the HRS composition has a high molecular weight peak content which is less than about 0.5% of the main peak after 7 days storage at 37° C.

In certain embodiments, the HRS polypeptide composition in the presence of the surfactant(s) has decreased low molecular weight peak(s) by SE-HPLC analysis that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the surfactant(s).

In certain embodiments, the HRS polypeptide composition in the surfactant(s) has a decreased turbidity (A340) that is at least about 1.5, 2, 3, 4, 5, 6, 7, 8, 9, or 10-fold lower or at least about 5%, 10%, 20%, 30%, 40%, 50%, 60%, 70%, 80%, 90%, 100%, 200%, 300%, 400%, or 500% lower than a corresponding HRS polypeptide when incubated at about 5° C., or at about room temperature (e.g., ~20-25° C.), or at about 37° C. for about or at least about 3 hours, or about or at least about 3 days, or about or at least about 7 days in an otherwise identical or comparable composition without the surfactant(s).

In some aspects, the HRS composition comprises PS20, a histidine buffer having a pH of about 7.0-7.5, and about 140 mM NaCl, and has a turbidity (A340) which is less than about 0.5 after 7 days storage at 37 C. In some aspects, the HRS composition has a turbidity (A340) which is less than about 0.2 after 7 days storage at 37° C.

In some aspects, the HRS composition comprises PS80, a histidine buffer having a pH of about 7.0-7.5, and about 140 mM NaCl, and has a turbidity (A340) which is less than about 0.5 after 7 days storage at 37 C. In some aspects, the HRS composition has a turbidity (A340) which is less than about 0.2 after 7 days storage at 37° C.

In some aspects, the HRS composition comprises pluronic F68, a histidine buffer having a pH of about 7.0-7.5, and about 140 mM NaCl, and has a turbidity (A340) which is less than about 0.5 after 7 days storage at 37° C. In some aspects, the HRS composition has a turbidity (A340) which is less than about 0.2 after 7 days storage at 37° C.

In certain embodiments, a composition comprises one or more anti-oxidant compounds. Exemplary anti-oxidants include, without limitation, cysteine, methionine, N-acetyl-cysteine (NAC), and glutathione, tocopherols, carotenes, ubiquinol, and ascorbic acid. In some embodiments, the anti-oxidant compound is present at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 mM, including all ranges in between. In some embodiments, the anti-oxidant compound is present at a concentration range of about 0.1-5.0, 0.1-4.5, 0.1-4.0, 0.1-3.5, 0.1-3.0, 0.1-2.5, 0.1-2.0, 0.1-1.5, 0.1-1.0, 0.1-0.5 mM, or a concentration range of about 0.2-5.0, 0.2-4.5, 0.2-4.0, 0.2-3.5, 0.2-3.0, 0.2-2.5, 0.2-2.0, 0.2-1.5, 0.2-1.0, 0.2-0.5 mM, or a concentration range of about 0.5-5.0, 0.5-4.5, 0.5-4.0, 0.5-3.5, 0.5-3.0, 0.5-2.5, 0.5-2.0, 0.5-1.5, 0.5-1.0 mM, or a concentration range of about 1.0-5.0, 1.0-4.5, 1.0-4.0, 1.0-3.5, 1.0-3.0, 1.0-2.5, 1.0-2.0, 1.0-1.5 mM, or a concentration range of about 1.5-5.0, 1.5-4.5, 1.5-4.0, 1.5-3.5, 1.5-3.0, 1.5-2.5, 1.5-2.0 mM, or a concentration range of about 2.0-5.0, 2.0-4.5, 2.0-4.0, 2.0-3.5, 2.0-3.0, 2.0-2.5 mM, or a concentration range of about 2.5.0-5.0, 2.5-4.5, 2.5-4.0. 2.5-3.5, 2.5-3.0 mM, or a concentration range of about 3.0-5.0, 3.0-4.5, 3.0-4.0, 3.0-3.5 mM, or a concentration range of about 3.5-5.0, 3.5-4.5, 3.5-4.0 mM, or a concentration range of about 4.0-5.0, 4.0-4.5, or 4.5-5.0 mM.

In some embodiments, the composition comprises a chelating agent. Exemplary chelating agents include, without limitation, ethylene diamine tetraacetate (EDTA), ethylene glycol tetraacetic acid (EGTA), 1,2-bis(o-aminophenoxy) ethane-N,N,N',N'-tetraacetic acid (BAPTA), and 2,3-dimer-capto-1-propanesulfonic acid (DMPS). In certain embodiments, the chelating agent is present at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mM, including all ranges in between. In some embodiments, the chelating agent is present at a concentration range of about 0.1-5.0, 0.1-4.5, 0.1-4.0. 0.1-3.5, 0.1-3.0, 0.1-2.5, 0.1-2.0, 0.1-1.5, 0.1-1.0, 0.1-0.5 mM, or a concentration range of about 0.2-5.0, 0.2-4.5, 0.2-4.0, 0.2-3.5, 0.2-3.0, 0.2-2.5, 0.2-2.0, 0.2-1.5, 0.2-1.0, 0.2-0.5 mM, or a concentration range of about 0.5-5.0, 0.5-4.5, 0.5-4.0, 0.5-3.5, 0.5-3.0, 0.5-2.5, 0.5-2.0, 0.5-1.5, 0.5-1.0 mM, or a concentration range of about 1.0-5.0, 1.0-4.5, 1.0-4.0, 1.0-3.5, 1.0-3.0, 1.0-2.5, 1.0-2.0, 1.0-1.5 mM, or a concentration range of about 1.5-5.0, 1.5-4.5, 1.5-4.0, 1.5-3.5, 1.5-3.0, 1.5-2.5, 1.5-2.0 mM, or a concentration range of about 2.0-5.0, 2.0-4.5, 2.0-4.0, 2.0-3.5, 2.0-3.0, 2.0-2.5 mM, or a concentration range of about 2.5.0-5.0, 2.5-4.5, 2.5-4.0, 2.5-3.5, 2.5-3.0 mM, or a concentration range of about 3.0-5.0, 3.0-4.5, 3.0-4.0, 3.0-3.5 mM, or a concentration range of about 3.5-5.0, 3.5-4.5, 3.5-4.0 mM, or a concentration range of about 4.0-5.0, 4.0-4.5, or 4.5-5.0 mM.

In some embodiments, a composition and/or the HRS polypeptide(s) contained therein are characterized by one or more absolute physical properties, such as the degree of high molecular weight aggregation (or aggregate formation), appearance or clarity (e.g., turbidity, opalescence), degree of homogeneity or monodispersion, solubility, protein purity, melting temperature, protein concentration, and/or degree of protein fragmentation.

In certain aspects, a composition has an aggregate content of about or less than about 10% relative to the total amount of protein present, or in some embodiments a composition has an aggregate content of about or less than about 9%, 8%, 7%, 6%, or 5%, or in some aspects a composition has an aggregate content of about or less than about 4%, 3%, or 2%, or in specific aspects a composition has an aggregate content of about or less than about 1%, 0.5%, 0.4%, 0.3%, 0.2%, or 0.1%. In some embodiments, the aggregate content is high molecular weight aggregate content. High molecular weight aggregate content can be determined by a variety of analytical techniques, including, for example, size exclusion chromatography (SE-HPLC), dynamic light scattering, SDS-PAGE analysis, and analytical ultracentrifugation.

In some aspects, the appearance of a composition is clear and lacks significant particle or fiber formation. The clarity of a composition can be characterized, for example, by turbidity, opalescence, or both. Turbidity can be measured by absorbance at A340, and opalescence can be measured by absorbance at A580. In some embodiments, the turbidity of a composition as measured by absorbance at A340 is about or less than about 1.0, 0.9, 0.8, 0.7, 0.6, 0.5, 0.4, 0.3, 0.2, 0.1, 0.09, 0.08, 0.09, 0.07, 0.06, 0.05, 0.04, 0.03, 0.02, 0.01, 0.009, 0.008, 0.007, 0.006, 0.005, 0.004, 0.003, 0.002, or 0.001. In certain embodiments, the opalescence of a composition as measured by absorbance at A580 is about or less than about 1.0, 0.9, 0.8, 0.7, 0.6, 0.5, 0.4, 0.3, 0.2, 0.1, 0.09, 0.08, 0.09, 0.07, 0.06, 0.05, 0.04, 0.03, 0.02, 0.01, 0.009, 0.008, 0.007, 0.006, 0.005, 0.004, 0.003, 0.002, or 0.001.

In some aspects, a composition comprises one or more HRS polypeptides that are substantially homogenous or monodisperse, meaning that the HRS polypeptide composition exist substantially (e.g., at least about 90%, 91%, 92%, 93%, 94%, 95%, 96%, 97%, 98%, 99%, 99.5% or greater) in one apparent molecular weight form when assessed, for example, by size exclusion chromatography, dynamic light scattering, SDS-PAGE, or analytical ultracentrifugation. In some aspects, the HRS polypeptide exists substantially as a monomer. In certain aspects, the HRS polypeptide exists substantially as a dimer. In some aspects, such compositions may comprise DTT, or other suitable reducing agents to reduce disulfide bond formation.

In certain embodiments, the HRS polypeptides have a solubility that is desirable for the particular mode of administration, such intravenous administration, subcutaneous administration, etc. Examples of desirable solubilities include about or at least about 1, 2, 3, 4, 5, 6, 7, 8, or 9 mg/ml, or about or at least about 10, 11, 12, 13, 14, 15, 16, 17, 18, 19, 20, 21, 22, 23, or 24 mg/ml, or about or at least about 25, 26, 27, 28, 29, 30, 31, 32, 33, 34, 35, 36, 37, 38, 39, 40, 41, 42, 43, 44, 45, 46, 47, 48, or 49 mg/ml, or about or at least about 50, 51, 52, 53, 54, 55, 56, 57, 58, 59, or 60 mg/ml.

In some aspects, a composition has a purity on a protein basis (e.g., HRS polypeptide relative to other cellular proteins) of about or at least about 90%, or in some aspects has a purity on a protein basis of about or at least about 95%, 96%, 97%, or 98%, or in some aspects has a purity on a protein basis of about or at least about 99% or 99.5%. Purity may be determined via any routine analytical method as known in the art.

In some aspects, the HRS polypeptide in a given composition has a defined thermal stability, as characterized, for example, by melting temperature (Tm). In some aspects, the HRS polypeptide in a composition has a Tm of about or at least about 45, 46, 47, 48, 49, 50, 51, 52, 53, 54, 55, 56, 57, 58, 59, 60, 61, 62, 63, 64, 65, 66, 67, 68, 69, or 70° C. In certain aspects, the HRS polypeptide in a composition has a Tm that ranges from about 45-70, 46-70, 47-70, 48-70, 49-70, 50-70, 51-70, 52-70, 53-70, 54-70, 55-70, 56-70, 57-70, 58-70, 59-70, 60-70, 61-70, 62-70, 63-70, 64-70, 65-70, 66-70, 67-70, 68-70, or 69-70° C., or ranges from about 45-69, 46-69, 47-69, 48-69, 49-69, 50-69, 51-69, 52-69, 53-69, 54-69, 55-69, 56-69, 57-69, 58-69, 59-69, 60-69, 61-69, 62-69, 63-69, 64-69, 65-69, 66-69, 67-69, 68-69° C., or ranges from about 45-68, 46-68, 47-68, 48-68, 49-68, 50-68, 51-68, 52-68, 53-68, 54-68, 55-68, 56-68, 57-68, 58-68, 59-68, 60-68, 61-68, 62-68, 63-68, 64-68, 65-68, 66-68, 67-68° C., or ranges from about 45-67, 46-67, 47-67, 48-67, 49-67, 50-67, 51-67, 52-67, 53-67, 54-67, 55-67, 56-67, 57-67, 58-67, 59-67, 60-67, 61-67, 62-67, 63-67, 64-67, 65-67, 66-67° C., or ranges from about 45-66, 46-66, 47-66, 48-66, 49-66, 50-66, 51-66, 52-66, 53-66, 54-66, 55-66, 56-66, 57-66, 58-66, 59-66, 60-66, 61-66, 62-66, 63-66, 64-66, 65-66° C., or ranges from about 45-65, 46-65, 47-65, 48-65, 49-65, 50-65, 51-65, 52-65, 53-65, 54-65, 55-65, 56-65, 57-65, 58-65, 59-65, 60-65, 61-65, 62-65, 63-65, 64-65° C., or ranges from about 45-64, 46-64, 47-64, 48-64, 49-64, 50-64, 51-64, 52-64, 53-64, 54-64, 55-64, 56-64, 57-64, 58-64, 59-64, 60-64, 61-64, 62-64, 63-64° C., or ranges from about 45-63, 46-63, 47-63, 48-63, 49-63, 50-63, 51-63, 52-63, 53-63, 54-63, 55-63, 56-63, 57-63, 58-63, 59-63, 60-63, 61-63, 62-63° C., or ranges from about 45-62, 46-62, 47-62, 48-62, 49-62, 50-62, 51-62, 52-62, 53-62, 54-62, 55-62, 56-62, 57-62, 58-62, 59-62, 60-62, 61-62° C., or ranges from about 45-61, 46-61, 47-61, 48-61, 49-61, 50-61, 51-61, 52-61, 53-61, 54-61, 55-61, 56-61, 57-61, 58-61, 59-61, 60-61° C., or ranges from about 45-60, 46-60, 47-60, 48-60, 49-60, 50-60, 51-60, 52-60, 53-60, 54-60, 55-60, 56-60, 57-60, 58-60, 59-60° C., or ranges from about 45-59, 46-59, 47-59, 48-59, 49-59, 50-59, 51-59, 52-59, 53-59, 54-59, 55-59, 56-59, 57-59, 58-59° C., or ranges from about 45-58, 46-58, 47-58, 48-58, 49-58, 50-58, 51-58, 52-58, 53-58, 54-58, 55-58, 56-58, 57-58° C., or ranges from about 45-57, 46-57, 47-57, 48-57, 49-57, 50-57, 51-57, 52-57, 53-57, 54-57, 55-57, 56-57° C., or ranges from about 45-56, 46-56, 47-56, 48-56, 49-56, 50-56, 51-56, 52-56, 53-56, 54-56, 55-56° C., or ranges from about 45-55, 46-55, 47-55, 48-55, 49-55, 50-55, 51-55, 52-55, 53-55, 54-55° C., or ranges from about 45-54, 46-54, 47-54, 48-54, 49-54, 50-54, 51-54, 52-54, 53-54° C., or ranges from about 45-53, 46-53, 47-53, 48-53, 49-53, 50-53, 51-53, 52-53° C., or ranges from about 45-52, 46-52, 47-52, 48-52, 49-52, 50-52, 51-52° C., or ranges from about 45-51, 46-51, 47-51, 48-51, 49-51, 50-51° C., or ranges from about 45-50, 46-50, 47-50, 48-50, 49-50° C., or ranges from about 45-49, 46-49, 47-49, 48-49° C., or ranges from about 45-48, 46-48, 47-48, 45-47, 46-47, or 45-46° C. Melting temperature can be determined by a variety of analytical methods, including, for instance, differential scanning fluorimetry (DSF).

In some aspects, the HRS polypeptide is present in a composition at a defined protein concentration. For instance, certain compositions have a concentration of the HRS polypeptide(s) of about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, or 100 mg/ml. Some compositions have a concentration of the HRS polypeptide(s) that ranges from about 5-100, 10-100, 15-100, 20-100, 25-100, 30-100, 35-100, 40-100, 45-100, 50-100, 55-100, 60-100, 70-100, 80-100, 90-100 mg/ml, or from about 5-90, 10-90, 15-90, 20-90, 25-90, 30-90, 35-90, 40-90, 45-90, 50-90, 55-90, 60-90, 70-90, 80-90 mg/ml, or from about 5-80, 10-80, 15-80, 20-80, 25-80, 30-80, 35-80, 40-80, 45-80, 50-80, 55-80, 60-80, 70-80 mg/ml, or from about 5-70, 10-70, 15-70, 20-70, 25-70, 30-70, 35-70, 40-70, 45-70, 50-70, 55-70, 60-70 mg/ml, or from about 5-60, 10-60, 15-60, 20-60, 25-60, 30-60, 35-60, 40-60, 45-60, 50-60, 55-60 mg/ml, or from about 5-50, 10-50, 15-50, 20-50, 25-50, 30-50, 35-50, 40-50, 45-50 mg/ml, or from about 5-45, 10-45, 15-45, 20-45, 25-45, 30-45, 35-45, 40-45 mg/ml, or from about 5-40, 10-40, 15-40, 20-40, 25-40, 30-40, 35-40 mg/ml, or from about 5-35, 10-35, 15-35, 20-35, 25-35, 30-35 mg/ml, or from about 5-30, 10-30, 15-30, 20-30, 25-30 mg/ml, or from about 5-25, 10-25, 15-25, 20-25, 5-20, 10-20, 15-20, 5-15, 10-15, or 5-10 mg/ml of protein.

In certain aspects, a composition has a degree of protein fragmentation of less than about 10% relative to the total amount of protein present, or in some embodiments a composition has a degree of protein fragmentation of less than about 9%, 8%, 7%, 6%, or 5%, or in some aspects a composition has a degree of protein fragmentation of less than about 4%, 3%, or 2%, or in specific aspects a composition has a degree of protein fragmentation of less than about 1%, 0.5%, 0.4%, 0.3%, 0.2%, or 0.1%. Protein fragmentation can be measured by a variety of analytical techniques, including, for example, size exclusion chromatography, SDS-PAGE analysis, and analytical ultracentrifugation.

In specific embodiments, the therapeutic composition comprises at least one substantially pure HRS polypeptide, optionally at a concentration of at least about 10-50 mg/ml, about 40-50 mM histidine (e.g., L-histidine), about 140-240 mM NaCl, about 1-2% trehalose, about 0.20-0.05% Polysorbate 20 (PS20), has a pH of about 7.0-7.5, and is substantially endotoxin-free. In some aspects, the therapeutic composition is characterized by a high molecular weight peak content which is less than about 1% of the main peak by SE-HPLC analysis after 7 days storage at 37° C. In some aspects, the therapeutic composition has a high molecular weight peak content which is less than about 0.5% of the main peak by SE-HPLC analysis after 7 days storage at 37° C. In some aspects, the therapeutic composition is characterized by a turbidity (A340) which is less than about 0.5 after 7 days storage at 37 C. In some aspects, the therapeutic composition has a turbidity (A340) which is less than about 0.2 after 7 days storage at 37° C.

In other embodiments, the composition comprises at least one substantially pure HRS polypeptide, optionally at a concentration of at least about 10-50 mg/ml, about 40-50 mM histidine (e.g., L-histidine), about 140-240 mM NaCl, about 1-2% sucrose, about 0.01-0.05% Polysorbate 20 (PS20), has a pH of about 7.3, and is substantially endotoxin-free. In some aspects, the therapeutic composition is characterized by a high molecular weight peak content which is less than about 1% of the main peak by SE-HPLC analysis after 7 days storage at 37° C. In some aspects, the therapeutic composition has a high molecular weight peak content by SE-HPLC analysis which is less than about 0.5% of the main peak after 7 days storage at 37° C. In some aspects, the therapeutic composition is characterized by a turbidity (A340) which is less than about 0.5 after 7 days storage at 37° C. In some aspects, the therapeutic composition has a turbidity (A340) which is less than about 0.2 after 7 days storage at 37° C.

In certain embodiments, the HRS polypeptide comprises, consists, or consists essentially of any of SEQ ID NOS: 1-23, 39, 41, 43, 70-71, 74-153, 160-172, or 176-182, or a HRS polypeptide listed in or derivable from any of Tables 1-9, including variants thereof. In some embodiments, the HRS polypeptide is HRS(1-506) or HRS(2-506), or a variant thereof, which has a Tm in the composition of at least about 58, 59, 60, or 61° C.

The biochemical, physical, and/or pharmacokinetic properties of the HRS polypeptide compositions described herein can be characterized under any defined set of conditions, such as temperature, pH, or other condition, and optionally at any given time or over a period of time. For instance, in certain embodiments, such properties are characterized at a temperature of about −80, −60, −40, −20, −10, −5, −4, −3, −20, −2, −1, 0, 1, 2, 3, 4, 5, 6, 7, 8, 10, 11, 12, 13, 14, 15, 16, 17, 18, 19, 20, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 99 or 100° C., including all integers and ranges in between. In some embodiments, such properties are characterized at about room temperature (e.g., 20-25° C.). Such properties can also be characterized over a period of time, for instance, over a period of about 0.25, 0.5, 1, 2, 3, 4, 5, 6, 7, 8, 9, 10, 11, 12, 13, 14, 15, 16, 17, 18, 19, 20, 21, 22, 23, or 24 hours, or over a period of about 0.1, 0.25, 0.5, 0.75, 1, 1.5, 2, 2.5, 3, 4, 5, 6, 7, 8, 9, 10, 11, 12, 13, 14 days, or over a period of about 1, 2, 3, 4, 5, 6, 7, 8, 9, 10, 12, 14, 16, 18, 20, or 24 weeks, or about 1, 2, 3, 4, 5, 6, 7, 8, 9, 10, 11, or 12 months or so. In some embodiments, such properties are characterized after freeze-thawing the composition at least 1, 2, 3, 4, 5, 6, 7, 8, 9, 10 or more times.

Pharmaceutical compositions may include pharmaceutically-acceptable salts of a HRS polypeptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In particular embodiments, the carrier may include water. In some embodiments, the carrier may be an aqueous solution of saline, for example, water containing physiological concentrations of sodium, potassium, calcium, magnesium, and chloride at a physiological pH. In some embodiments, the carrier may be water and the formulation may further include NaCl. In some embodiments, the formulation may be isotonic. In some embodiments, the formulation may be hypotonic. In other embodiments, the formulation may be hypertonic. In some embodiments, the formulation may be isosmotic. In some embodiments, the formulation is substantially free of polymers (e.g., gel-forming polymers, polymeric viscosity-enhancing agents, etc.). In some embodiments, the formulation is substantially-free of viscosity-increasing agents (e.g., carboxymethylcellulose, polyanionic polymers, etc.). In some embodiments, the formulation is substantially free of gel-forming polymers. In some embodiments, the viscosity of the formulation is about the same as the viscosity of a saline solution containing the same concentration of a HRS polypeptide (or a pharmaceutically acceptable salt thereof).

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

Pharmaceutical compositions suitable for the delivery of HRS polypeptides and methods for their preparation will be readily apparent to those skilled in the art. Such compositions and methods for their preparation may be found, e.g., in *Remington's Pharmaceutical Sciences*, 19th Edition (Mack Publishing Company, 1995).

Administration of a therapeutic dose of a HRS polypeptide may be by any suitable method known in the medicinal arts, including for example, oral, rectal, intranasal, parenteral administration include intravitreal, subconjuctival, sub-tenon, retrobulbar, suprachoroidal intravenous, intra-arterial, intraperitoneal, intrathecal, intraventricular, intraurethral, intrasternal, intracranial, intramuscular, intrasynovial, intraocular, topical and subcutaneous. Suitable devices for parenteral administration include needle (including microneedle) injectors, needle-free injectors, and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, substantially pyrogen-free or pyrogen-free water. The preparation of parenteral formulations under sterile conditions, e.g., by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus a HRS polypeptide may be formulated as a suspension or as a solid, semi-solid, or thixotropic liquid for administration as an implanted depot providing sustained release of HRS polypeptides. Examples of such formulations include without limitation, drug-coated stents and semi-solids and suspensions comprising drug-loaded poly(DL-lactic-co-glycolic)acid (PGLA), poly(DL-lactide-co-glycolide) (PLG) or poly(lactide) (PLA) lamellar vesicles or microparticles, hydrogels (Hoffman A S: *Ann. N.Y. Acad. Sci.* 944: 62-73 (2001)), poly-amino acid nanoparticles systems, such as the Medusa system developed by Flamel Technologies Inc., non-aqueous gel systems such as Atrigel developed by Atrix, Inc., and SABER (Sucrose Acetate Isobutyrate Extended Release) developed by Durect Corporation, and lipid-based systems such as DepoFoam developed by SkyePharma.

As noted above, solutions of the active compounds as free base or pharmacologically acceptable salts may be prepared in water suitably mixed with a surfactant, such as hydroxypropylcellulose, Polysorbate (e.g., Polysorbate 20, Polysorbate 80), or Pluronic F68. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can include a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, excipients, ionic strength modifiers, surfactants, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regimen. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises a biodegradable polymer such as that sold under the tradename Atrigel® (QLT, Inc., Vancouver, B.C.). The Atrigel® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

In particular embodiments, the amount of a HRS composition the agent administered will generally range from a dosage of from about 0.1 to about 100 mg/kg/day, and typically from about 0.1 to 10 mg/kg where administered orally or intravenously. In particular embodiments, a dosage is 1 mg/kg or 5.0 mg/kg. For humans, the daily dosage used may range from, about 0.1 mg/kg to 0.5 mg/kg, about 1 mg/kg to 5 mg/kg, about 5 mg/kg to 10 mg/kg, about 10 mg/kg to 20 mg/kg, about 20 mg/kg to 30 mg/kg, about 30 mg/kg to 50 mg/kg, and about 50 mg/kg to 100 mg/kg/24 hours.

In certain embodiments, a composition or agent is administered in a single dosage of 0.1 to 10 mg/kg or 0.5 to 15 mg/kg. In other embodiments, a composition or agent is administered in a dosage of 0.1 to 1 mg/kg/day, 0.5 to 2 mg/kg/day, or 5 to 20 mg/kg/day, or about 20 to 80 mg/kg/day, or about 80 to 150 mg/kg/day.

In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 200 mg bid, 300 mg bid, 400 mg bid, 500 mg bid, 600 mg bid, or 700 mg bid, 800 mg bid, 900 mg bid, or 1000 mg bid. In various embodiments, the composition or agent is administered in single or repeat dosing. The initial dosage and subsequent dosages may be the same or different.

In some embodiments, the total dose administered may be about 0.001 mg, about 0.005 mg, about 0.01 mg, about 0.05 mg, about 0.1 mg, 0.5 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 500 mg, 1,000 mg, about 2,000 mg, about 3,000 mg, about 4,000 mg, about 5,000 mg, about 6,000 mg, about 7,000 mg, about 8,000 mg, about 9,000 mg, about 10,000 mg,/dosing interval (e.g., every 24 hours). In some embodiments, the dosing interval may be once every day, once every two days, once every three days, once every four days, once every five days, once per week, or once per two weeks. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

It will be further appreciated that for sustained delivery devices and compositions the total dose of HRS contained in such delivery system will be correspondingly larger depending upon the release profile of the sustained release system. Thus, a sustained release composition or device that is intended to deliver HRS polypeptide over a period of 5 days will typically comprise at least about 5 to 10 times the daily dose of HRS polypeptide; a sustained release composition or device that is intended to deliver a HRS peptide over a period of 365 days will typically comprise at least about 400 to 800 times the daily dose of the HRS polypeptide (depending upon the stability and bioavailability of the HRS polypeptide when administered using the sustained release system).

In certain embodiments, a composition or agent is administered intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 µg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 ng/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain embodiments, the amount of polypeptide administered will typically be in the range of about 0.1 mg/kg to about 15 mg/kg or to about 15 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 mg/kg to about 20 mg/kg to 100 mg/kg or more, depending on the factors mentioned above. For repeated administrations over several days or longer, depending on the condition, the treatment is sustained until a desired suppression of disease symptoms occurs. In particular embodiments, the effective dosage achieves the blood plasma levels or mean trough concentration of a composition or agent described herein. These may be readily determined using routine procedures.

In particular embodiments, the effective dosage achieves the blood plasma levels or mean trough concentration of a composition or agent described herein. These may be readily determined using routine procedures.

In some embodiments, the composition may also include one or more adjuvants, for instance, when employing the therapeutic immunogenic compositions as vaccines. Adjuvants are substances that non-specifically enhance or potentiate the immune response (e.g., immune responses mediated by CTLs and helper-T ($T_H$) cells to an antigen, and would thus be considered useful in the therapeutic compositions of the present invention. Suitable adjuvants include, but are not limited to 1018 ISS, aluminium salts, Amplivax, AS15, BCG, CP-870,893, CpG7909, CyaA, dSLIM, flagellin or TLR5 ligands derived from flagellin, FLT3 ligand, GM-C SF, IC30, IC31, Imiquimod (ALDARA), ImuFact IMP321, Interferon-alpha or -beta, or pegylated derivatives thereof, IS Patch, ISS, ISCOMATRIX, ISCOMs, Juvlmmune, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, PLG microparticles, resiquimod, SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Dupuis M et al. 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha, IFN-beta) (Gabrilovich et al. 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T-cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, JUNE 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, Germany), which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g., CpR, Idera), Poly (I:C), such as AmpliGen, non-CpG bacterial DNA or RNA as well as immunoactive small molecules and antibodies such as cyclophosphamide, sunitinib, Bavacizumab, celebrex, NCX-4016, sildenafil, tadalafil, vardenafil, sorafinib, XL-999, CP-547632, pazopanib, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation.

Combination Therapies

The present invention also includes combination therapies comprising administering to a patient a therapeutic dose of a HRS polypeptide, or antibody blocking reagent in combination with a second active agent, or a device or a procedure for treating autoimmune diseases, inflammatory disease(s), muscular dystrophies, rhabdomyolysis, cachexia, and other diseases described herein. In this context "administered in combination" means: (1) part of the same unitary dosage form; (2) administration separately, but as part of the same therapeutic treatment program or regimen, typically but not necessarily, on the same day.

In some aspects of these combination therapies, the second active agent is selected from one or more anti-histamines, one or more anti-inflammatory agents, one or more anti-neoplastic agents, one or more immunosuppressive agents, one or more antiviral agents, one or more agents that inhibit B cells, block B cell differentiation, or the activation of memory B cells, or one or more antioxidant agents. Pharmacologic or therapeutic agents which may find use in combination with the HRS polypeptides of the invention, include, without limitation, those disclosed in U.S. Pat. No. 4,474,451, columns 4-6 and U.S. Pat. No. 4,327,725, columns 7-8.

Examples of antihistamines include, but are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antineoplastic agents include, but are not limited to Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g., folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of anti-inflammatory agents include but are not limited to steroidal anti-inflammatory agents and non-steroidal anti-inflammatory agents. Exemplary steroidal anti-inflammatory agents include acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Exemplary non-steroidal anti-inflammatory agents include aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of immunosuppressive agents include without limitation, 2-amino-6-aryl-5-substituted pyrimidines (see U.S. Pat. No. 4,665,077); azathioprine; cyclophosphamide; bromocryptine; danazol; dapsone; glutaraldehyde (which masks the MHC antigens, as described in U.S. Pat. No. 4,120, 649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies, anti-tumor necrosis factor-α antibodies, anti-tumor necrosis factor-43 antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); and T cell receptor antibodies (EP 340,109) such as T10139; anti-CD19 antibodies as described in Hekman et al. Cancer Immunol. Immunother. 32:364-372 (1991) and Vlasveld et al. Cancer Immunol. Immunother. 40:37-47 (1995); the B4 antibody in Kiesel et al. Leukemia Research II, 12: 1119 (1987); anti-CD22 antibodies including epratuzmab; anti-BLyS (CD257) antibodies including Belimumab (benalysta); anti-CD20 antibodies including Ocrelizumab, rituximab, and ofatumumab. "Rituximab" or "RITUXAN®" refers to the genetically engineered chimeric murine/human monoclonal antibody directed against the CD20 antigen and designated "C2B8" in U.S. Pat. No. 5,736,137. The antibody is an IgG$_1$ kappa immunoglobulin containing murine light and heavy chain variable region sequences and human constant region sequences. Rituximab has a binding affinity for the CD20 antigen of approximately 8.0 nM.

Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of agents that inhibit B cells, block B cell differentiation, or the activation of memory B cells, include anti-CD19 antibodies, anti-CD22 antibodies including epratuzmab; anti-BLyS (CD257) antibodies including Belimumab (benalysta); anti-CD20 antibodies including Ocrelizumab, rituximab, ofatumumab and "Rituximab" or "RITUXAN®"

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof. Other therapeutic agents include squalamine, carbonic anhydrase inhibitors, alpha-2 adrenergic receptor agonists, antiparasitics, antifungals, and derivatives thereof.

Preferably, the HRS polypeptide may be administered at a fixed daily dosage, and the other active agents taken on an as needed basis. When the HRS polypeptide is administered as adjuvant therapy with a second active agent, a preferred daily dosage is about 0.1 mg/kg/24 hours to about 55 mg/kg/24 hours, more preferably about 2 mg/kg/24 hours to about 20 mg/kg/24 hours.

The exact dose of each component administered will, of course, differ depending on the specific components prescribed, on the subject being treated, on the severity of the disease, e.g., severity of the inflammatory reaction, on the manner of administration and on the judgment of the prescribing physician. Thus, because of patient-to-patient variability, the dosages given above are a guideline and the physician may adjust doses of the compounds to achieve the treatment that the physician considers appropriate.

Kits

Embodiments of the present invention, in other aspects, provide kits comprising one or more containers filled with one or more of the isolated HRS polypeptides, polynucleotides, antibodies, and binding proteins of the invention, as described herein. The kits can include written instructions on how to use such compositions (e.g., to modulate cellular signaling, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

In another aspect of the invention, kits, comprising: a) a container comprising a HRS polypeptide component; and b) instructions for use. Instructions may include steps of how to handle the HRS polypeptides, how to store the HRS polypeptides, and what to expect from using the HRS polypeptides.

In another aspect of the invention, kits, comprising: a) a container comprising a recombinant vector or polynucleotide comprising a nucleic acid encoding a HRS polypeptide component; and b) instructions for use. Instructions may include steps of how to handle the vectors or polynucleotides, how to store the vectors or polynucleotides, or how to transfect cells with the vectors or polynucleotides.

In another aspect of the invention, kits for treating a disease or disorder are provided, comprising: a) a container comprising a pharmaceutical composition comprising a HRS polypeptide component in a pharmaceutically acceptable formulation and b) instructions, and/or a product insert.

Diagnostics

HRS polypeptides, and the corresponding polynucleotides (HRS polynucleotides), can be used in diagnostic assays and diagnostic compositions. Included are biochemical, histological, and cell-based methods and compositions, among others.

These and related embodiments include the detection of the HRS polynucleotide sequence(s) or corresponding HRS polypeptide sequence(s) or portions thereof, or antibodies thereto. For instance, certain aspects include detection of the HRS polynucleotide sequence(s) or corresponding polypeptide sequence(s) or portions thereof of one or more newly identified HRS splice variants, and/or one or more splice junctions of those splice variants. In certain embodiments, the polynucleotide or corresponding polypeptide sequence(s) of at least one of the splice junctions is unique to that particular HRS splice variant. In some embodiments such HRS splice variants can indicate a susceptibility to a disease, including for example, autoimmune diseases, inflammatory disease(s), muscular dystrophies, rhabdomyolysis, cachexia, and other diseases described herein.

Also included is the direct detection of HRS protein fragments, including splice variants, proteolytic fragments, and others. In certain embodiments, the presence or levels of one or more newly identified HRS protein fragments associate or correlate with one or more cellular types or cellular states, including for example specific auto-antibodies. Hence, the presence or levels of a HRS polypeptide or polynucleotide can be used to distinguish between different cellular types or different cellular states. The presence or levels of HRS protein fragments or their related polynucleotides can be detected according to polynucleotide and/or polypeptide-based diagnostic techniques, as described herein and known in the art.

Certain aspects can employ the HRS protein fragments, or HRS polynucleotides as part of a companion diagnostic method, typically to assess whether a subject or population subjects will respond favorably to a specific medical treatment. For instance, a given HRS polypeptide based therapeutic agent (e.g., protein fragment, antibody, binding agent) could be identified as suitable for a subject or certain populations of subjects based on whether the subject(s) have one or more selected biomarkers, or antibodies for a given disease or condition. Examples of biomarkers include serum/tissue markers, pre-existing antibodies to histidyl-tRNA synthetase, as well as markers that can be identified by medical imaging techniques. In certain embodiments, a naturally-occurring HRS protein, or fragment thereof (or its corresponding polynucleotide) may itself provide a serum and/or tissue biomarker that can be utilized to measure anti-HRS polypeptide levels, or free HRS polypeptide levels in a specific subject or a specific population of subjects. In certain aspects, the identification of a HRS polypeptide or polynucleotide reference sequence may include characterizing the differential expression of that sequence, whether in a selected subject, selected tissue, or otherwise, as described herein and known in the art.

Certain of the methods provided herein rely on the differential expression of a HRS polypeptide or polynucleotide to characterize the condition or state of a cell, tissue, or subject, and to distinguish it from another cell, tissue, or subject. Non-limiting examples include methods of detecting the presence or levels of a HRS polypeptide or polynucleotide in a biological sample to distinguish between cells or tissues of different species, cells of different tissues or organs, cellular developmental states such as neonatal and adult, cellular differentiation states, conditions such as healthy, diseased and treated, intracellular and extracellular fractions, in addition to primary cell cultures and other cell cultures, such as immortalized cell cultures.

Differential expression includes a statistically significant difference in one or more gene expression levels of a HRS polynucleotide or polypeptide reference sequence compared to the expression levels of the same sequence in an appropriate control. The statistically significant difference may relate to either an increase or a decrease in expression levels, as measured by RNA levels, protein levels, protein function, or any other relevant measure of gene expression such as those described herein. Also included is a comparison between a HRS polynucleotide or polypeptide of the invention and a full-length or wild-type cytosolic or mitochondrial HRS sequence, typically of the same or corresponding type. Differential expression can be detected by a variety of techniques in the art and described herein, including polynucleotide and polypeptide based techniques, such as real-time PCR, subtractive hybridization, polynucleotide and polypeptide arrays, and others.

A result is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med* 130:1005-13, 1999).

In more complicated, but practically important cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, statistically significant differential expression may include situations wherein the expression level of a given HRS sequence provides at least about a 1.2×, 1.3×, 1.4×, 1.5×, 1.6×, 1.7×, 1.8×, 1.9×. 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in expression (i.e., differential expression that may be higher or lower expression) in a suspected biological sample as compared to an appropriate control, including all integers and decimal points in between (e.g., 1.24×, 1.25×, 2.1×, 2.5×, 60.0×, 75.0×, etc.). In certain embodiments, statistically significant differential expression may include situations wherein the expression level of a given HRS sequence provides at least about 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in expression (i.e., differential expression that may be higher or lower) in a suspected biological sample as compared to an appropriate control, including all integers and decimal points in between.

As an additional example, differential expression may also be determined by performing Z-testing, i.e., calculating an absolute Z score, as described herein and known in the art. Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that p<0.01, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarly relates generally to the lack of a statistically significant difference in the expression levels between the biological sample and the reference control. Examples of substantially similar expression levels may include situations wherein the expression level of a given SSCIGS provides less than about a 0.05×, 0.1×, 0.2×, 0.3×, 0.4×, 0.5×, 0.6×, 0.7×, 0.8×, 0.9×. 1.0×, 1.1×, 1.2×, 1.3×, or 1.4× difference in expression (i.e., differential expression that may be higher or lower expression) in a suspected biological sample as compared to a reference sample, including all decimal points in between (e.g., 0.15×, 0.25×, 0.35×, etc.). In certain embodiments, differential expression may include situations wherein the expression level of a given HRS sequence provides less than about 0.25, 0.5, 1, 2, 3, 4, 5, 6, 7, 8, 9, 10, 11, 12, 13, 14, 15, 16, 17, 18, 19, 20, 30, 40, 50 percent (%) difference in expression (i.e., differential expression that may be higher or lower) in a suspected biological sample as compared to a reference sample, including all decimal points in between.

In certain embodiments, such as when using an Affymetrix Microarray to measure the expression levels of a HRS polynucleotide or polypeptide reference sequence, differential expression may also be determined by the mean expression value summarized by Affymetrix Microarray Suite 5 software (Affymetrix, Santa Clara, Calif.), or other similar software, typically with a scaled mean expression value of 1000.

Embodiments of the present invention include methods of detecting the presence or levels of a HRS polynucleotide or polypeptide reference sequence to characterize or diagnose the condition or a cell, tissue, organ, or subject, in which that condition may be characterized as healthy, diseased, at risk for being diseased, or treated. For such diagnostic purposes, the term "diagnostic" or "diagnosed" includes identifying the presence or nature of a pathologic condition, characterizing the risk of developing such a condition, and/or measuring the change (or no change) of a pathologic condition in response to therapy. Diagnostic methods may differ in their sensitivity and specificity. In certain embodiments, the "sensitivity" of a diagnostic assay refers to the percentage of diseased cells, tissues or subjects which test positive (percent of "true positives"). Diseased cells, tissues or subjects not detected by the assay are typically referred to as "false negatives." Cells, tissues or subjects that are not diseased and which test negative in the assay may be termed "true negatives." In certain embodiments, the "specificity" of a diagnostic assay may be defined as one (1) minus the false positive rate, where the "false positive" rate is defined as the proportion of those samples or subjects without the disease and which test positive. While a particular diagnostic method may not provide a definitive diagnosis of a condition, it suffices if the method provides a positive indication that aids in diagnosis.

In certain instances, the presence or risk of developing a pathologic condition can be diagnosed by comparing the presence or levels of one or more selected HRS polynucleotide or polypeptide reference sequences or portions thereof, or antibodies thereto, that correlate with the condition, whether by increased or decreased levels, as compared to a suitable control. A "suitable control" or "appropriate control" includes a value, level, feature, characteristic, or property determined in a cell or other biological sample of a tissue or organism, e.g., a control or normal cell, tissue or organism, exhibiting, for example, normal traits, such as the absence of the condition. In certain embodiments, a "suitable control" or "appropriate control" is a predefined value, level, feature, characteristic, or property. Other suitable controls will be apparent to persons skilled in the art. Examples of diseases and conditions, for example, diseases associated with autoantibodies specific for histidyl-tRNA synthetase, are described elsewhere herein.

Embodiments of the present invention include HRS polynucleotide or nucleic acid-based detection techniques, which offer certain advantages due to sensitivity of detection. Hence, certain embodiments relate to the use or detection of HRS polynucleotides as part of a diagnostic method or assay. The presence and/or levels of HRS polynucleotides may be measured by any method known in the art, including hybridization assays such as Northern blot, quantitative or qualitative polymerase chain reaction (PCR), quantitative or qualitative reverse transcriptase PCR (RT-PCR), microarray, dot or slot blots, or in situ hybridization such as fluorescent in situ hybridization (FISH), among others. Certain of these methods are described in greater detail below.

HRS polynucleotides such as DNA and RNA can be collected and/or generated from blood, biological fluids, tissues, organs, cell lines, or other relevant sample using techniques known in the art, such as those described in Kingston. (2002 *Current Protocols in Molecular Biology*, Greene Publ. Assoc. Inc. & John Wiley & Sons, Inc., NY, N.Y. (see, e.g., as described by Nelson et al. *Proc Natl Acad Sci USA*, 99: 11890-11895, 2002) and elsewhere. Further, a variety of commercially available kits for constructing RNA are useful for making the RNA to be used in the present invention. RNA may be constructed from organs/tissues/cells procured from normal healthy subjects; however, this invention also contemplates construction of RNA from diseased subjects. Certain embodiments contemplate using any type of organ from any type of subject or animal. For test samples RNA may be procured from an individual (e.g., any animal, including mammals) with or without visible disease and from tissue samples, biological fluids (e.g., whole blood) or the like.

In certain embodiments, amplification or construction of cDNA sequences may be helpful to increase detection capabilities. The instant disclosure, as well as the art, provides the requisite level of detail to perform such tasks. In one exemplary embodiment, whole blood is used as the source of RNA and accordingly, RNA stabilizing reagents are optionally used, such as PAX tubes, as described, for example, in Thach et al., *J. Immunol. Methods*. December 283(1-2):269-279, 2003 and Chai et al., *J. Clin. Lab Anal*. 19(5):182-188, 2005 (both of which are incorporated by reference). Complementary DNA (cDNA) libraries can be generated using techniques known in the art, such as those described in Ausubel et al. (2001 *Current Protocols in Molecular Biology*, Greene Publ. Assoc. Inc. & John Wiley & Sons, Inc., NY, N.Y.); Sambrook et al. (1989 *Molecular Cloning*, Second Ed., Cold Spring Harbor Laboratory, Plainview, N.Y.); Maniatis et al. (1982 *Molecular Cloning*, Cold Spring Harbor Laboratory, Plainview, N.Y.) and elsewhere. Further, a variety of commercially available kits for constructing cDNA libraries are useful for making the cDNA libraries of the present invention. Libraries can be constructed from organs/tissues/cells procured from normal, healthy subjects.

Certain embodiments may employ hybridization methods for detecting HRS polynucleotide sequences. Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, *PNAS*. 80: 1194 (1983). Methods and apparatus for carrying out repeated and controlled hybridization reactions have been described in U.S. Pat. Nos. 5,871,928, 5,874,219, 6,045,996 and 6,386,749, 6,391,623, each of which are incorporated herein by reference Certain embodiments may employ nucleic acid amplification methods for detecting HRS polynucleotide sequences. The term "amplification" or "nucleic acid amplification" refers to the production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

"Selective amplification" or "specific amplification," as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

The term "amplification conditions" refers to conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention typically hybridize under stringent hybridization conditions. Acceptable conditions to carry out nucleic acid amplifications according to the present invention can be easily ascertained by someone having ordinary skill in the art depending on the particular method of amplification employed.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

As noted above, the term "PCR" refers to multiple amplification cycles that selectively amplify a target nucleic acid species. Included are quantitative PCR (qPCR), real-time PCR), reverse transcription PCR (RT-PCR) and quantitative reverse transcription PCR (qRT-PCR) is well described in the art. The term "pPCR" refers to quantitative polymerase chain reaction, and the term "qRT-PCR" refers to quantitative reverse transcription polymerase chain reaction. qPCR and qRT-PCR may be used to amplify and simultaneously quantify a targeted cDNA molecule. It enables both detection and quantification of a specific sequence in a cDNA pool, such as a selected AARS gene or transcript.

The term "real-time PCR" may use DNA-binding dye to bind to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

Certain embodiments may employ the ligase chain reaction (Weiss, *Science*. 254: 1292, 1991), commonly referred to as LCR, which uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Another method is strand displacement amplification (Walker et al., 1992, *PNAS USA* 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315).

Other amplification methods include, for example: nucleic acid sequence based amplification (U.S. Pat. No. 5,130,238), commonly referred to as NASBA; one that uses an RNA replicase to amplify the probe molecule itself (Lizardi et al., 1988, *BioTechnol*. 6: 1197-1202), commonly referred to as Qβ replicase; a transcription based amplification method (Kwoh, D. et al., 1989, *Proc. Natl. Acad. Sci. USA* 86:1173-1177); self-sustained sequence replication (Guatelli, J. et al., 1990, *Proc. Natl. Acad. Sci. USA* 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

Illustrative transcription-based amplification systems of the present invention include TMA, which employs an RNA polymerase to produce multiple RNA transcripts of a target region (U.S. Pat. Nos. 5,480,784 and 5,399,491). TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In an illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer." From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

In certain embodiments, other techniques may be used to evaluate RNA transcripts of the transcripts from a particular cDNA library, including microarray analysis (Han et al., *Nat Biotechnol,* 19: 631-635, 2001; Bao et al., *Anal Chem,* 74: 1792-1797, 2002; Schena et al., *PNAS.* USA 93:10614-19, 1996; and Heller et al., *Proc. Natl. Acad. Sci. USA* 94:2150-55, 1997) and SAGE (serial analysis of gene expression). Like MPSS, SAGE is digital and can generate a large number of signature sequences. (see e.g., Velculescu, V. E., et al., *Trends Genet,* 16: 423-425, 2000; Tuteja R. and Tuteja N. *Bioessays.* 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci. USA* 97(4): 1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, the disclosures of which are incorporated by reference.

Additional examples include nucleic acid arrays that are commercially available from Affymetrix (Santa Clara, Calif.) under the brand name GENECHIP™. Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394.

The present invention as related to arrays and microarrays also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Application No. 2003/0036069), and U.S. Pat. Nos. 5,925,525, 6,268,141, 5,856,092, 6,267,152, 6,300,063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

As will be apparent to persons skilled in the art, certain embodiments may employ oligonucleotides, such as primers or probes, for amplification or detection, as described herein. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. In certain embodiments, an oligonucleotide does not consist solely of wild-type chromosomal DNA or the in vivo transcription products thereof.

Oligonucleotides or primers may be modified in any way, as long as a given modification is compatible with the desired function of a given oligonucleotide. One of ordinary skill in the art can easily determine whether a given modification is suitable or desired for any given oligonucleotide of the present invention. Relevant AARS oligonucleotides are described in greater detail elsewhere herein.

While the design and sequence of oligonucleotides depends on their function as described herein, several variables are generally taken into account. Among the most relevant are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

Certain embodiments therefore include methods for detecting a target AARS polynucleotide in a sample, the polynucleotide comprising the sequence of a reference AARS polynucleotide, as described herein, comprising a) hybridizing the sample with a probe comprising a sequence complementary to the target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. Also included are methods for detecting a target HRS polynucleotide in a sample, the polynucleotide comprising the sequence of a reference HRS polynucleotide, as described herein, comprising a) amplifying the target polynucleotide or fragment thereof, and b) detecting the presence or absence of said amplified target polynucleotide or fragment thereof, and, optionally, if present, the amount thereof. Specific embodiments relate to the detection of AARS splice variants, such as by detecting a unique splice junction of the splice variant, whether by hybridization, amplification, or other detection method.

Embodiments of the present invention include a variety of HRS polypeptide-based detection techniques, including antibody-based detection techniques. Included in these embodiments are the use of HRS polypeptides to detect, quantitate, or epitope map anti-HRS antibodies in a biological sample, such as serum, whole blood or plasma. Certain embodiments may employ standard methodologies and detectors such as western blotting and immunoprecipitation, enzyme-linked immunosorbent assays (ELISA), flow cytometry, and immunofluorescence assays (IFA), which utilize an imaging device.

Such human HRS polypeptides possess surprisingly superior antibody binding characteristics compared to pre-existing antibody detection methodologies which rely upon non human, and or crude preparations of histidyl-tRNA synthetase.

In some embodiments of these assays the HRS polypeptide is a HRS polypeptides listed in or derivable from Tables D1-D9. In some embodiments the HRS polypeptide comprises a tag to facilitate attachment to a solid surface. In one embodiment the tag is a poly-his tag.

Accordingly in some embodiments the HRS polypeptides may be used to profile patients to identify their Jo-1 antibody disease burden. Such profiles enable the selection of patients into subpopulations that would benefit from HRS polypeptide treatment, prognosticate the likely therapeutic outcome, and or identify the HRS polypeptide(s) most suitable for use as therapeutic agents.

In one embodiment the invention includes a method for identifying a human subject at risk for having an adverse immune response to HRS polypeptide administration, comprising a) determining the antibody level, or epitope specificity of the anti-histidyl-tRNA synthetase antibody in the subject; and b) and identifying the subject as being at risk of developing an adverse immune response to HRS polypeptide administration if the subject has detectable antibodies to histidyl-tRNA synthetase, or the HRS polypeptide.

In some aspects, the subject may be identified as being at risk of developing an adverse immune response to HRS polypeptide administration if the subject has a concentration of histidyl-tRNA synthetase antibodies in their serum of greater than about 1 micromolar.

In some aspects, the subject may be identified as being at risk of developing an adverse immune response to HRS polypeptide administration if the subject has a concentration of histidyl-tRNA synthetase antibodies in their serum of greater than about 2 micromolar.

In some aspects, the subject may be identified as being at high risk of developing an adverse immune response to HRS polypeptide administration if the subject has a concentration of histidyl-tRNA synthetase antibodies in their serum of greater than about 4 micromolar.

In another embodiment the invention includes a method for selecting a HRS polypeptide to treat a human subject with an autoimmune or inflammatory condition, comprising a) determining the antibody level, or epitope specificity of the anti-histidyl-tRNA synthetase antibody in the subject; and b) and selecting a HRS polypeptide which has a reduced affinity for the anti-histidyl-tRNA synthetase antibody compared to wild-type histidyl-tRNA synthetase.

In one embodiment the invention includes a method for prognosticating a human subject's disease progression, comprising a) determining the antibody level, or epitope specificity of the anti-histidyl-tRNA synthetase antibody in the subject; and b) and identifying the subject as being at risk of developing more severe disease if the subject has detectable antibodies to histidyl-tRNA synthetase, or the HRS polypeptide.

In some aspects, the subject may be identified as being at risk of developing more severe disease if the subject has a concentration of histidyl-tRNA synthetase antibodies in their serum of greater than about 1 micromolar.

In some aspects, the subject may be identified as being at risk of developing more severe disease if the subject has a concentration of histidyl-tRNA synthetase antibodies in their serum of greater than about 2 micromolar.

In some aspects, the subject may be identified as being at high risk of developing more severe disease if the subject has a concentration of histidyl-tRNA synthetase antibodies in their serum of greater than about 4 micromolar.

In another embodiment the invention includes a method for predicting subject responses to HRS polypeptide administration, comprising a) determining the antibody level, or epitope specificity of the anti-histidyl-tRNA synthetase antibody in the subject; and b) and identifying the subject as suitable for HRS polypeptide administration if the subject has no detectable antibodies to histidyl-tRNA synthetase, or the HRS polypeptide.

In some aspects, the subject may be identified as being as suitable for HRS polypeptide administration if the subject has a concentration of histidyl-tRNA synthetase antibodies in their serum of less than about 1 micromolar.

In some aspects, the subject may be identified as being as suitable for HRS polypeptide administration if the subject has a concentration of histidyl-tRNA synthetase antibodies in their serum of less than about 0.1 micromolar.

In some aspects, the subject may be identified as being as suitable for HRS polypeptide administration if the subject has a concentration of histidyl-tRNA synthetase antibodies in their serum of greater than about 0.01 micromolar.

Certain embodiments may employ "arrays," such as "microarrays." In certain embodiments, a "microarray" may also refer to a "peptide microarray" or "protein microarray" having a substrate-bound collection or plurality of polypeptides, the binding to each of the plurality of bound polypeptides being separately detectable. Alternatively, the peptide microarray may have a plurality of binders, including but not limited to monoclonal antibodies, polyclonal antibodies, phage display binders, yeast 2 hybrid binders, and aptamers, which can specifically detect the binding of the HRS polypeptides described herein. The array may be based on autoantibody detection of these HRS polypeptides, as described, for example, in Robinson et al., *Nature Medicine* 8(3):295-301 (2002). Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507 and U.S. Pat. Nos. 6,268,210, 5,766,960, and 5,143,854, each of which are incorporated by reference.

Certain embodiments may employ MS or other molecular weight-based methods for diagnostically detecting HRS polypeptide sequences. Mass spectrometry (MS) refers generally to an analytical technique for determining the elemental composition of a sample or molecule. MS may also be used for determining the chemical structures of molecules, such as peptides and other chemical compounds.

Generally, the MS principle consists of ionizing chemical compounds to generate charged molecules or molecule fragments, and then measuring their mass-to-charge ratios. In an illustrative MS procedure: a sample is loaded onto the MS instrument, and undergoes vaporization, the components of the sample are ionized by one of a variety of methods (e.g., by impacting them with an electron beam), which results in the formation of positively charged particles, the positive ions are then accelerated by a magnetic field, computations are performed on the mass-to-charge ratio (m/z) of the particles based on the details of motion of the ions as they transit through electromagnetic fields, and, detection of the ions, which in step prior were sorted according to m/z.

An illustrative MS instruments has three modules: an ion source, which converts gas phase sample molecules into ions (or, in the case of electrospray ionization, move ions that exist in solution into the gas phase); a mass analyzer, which sorts the ions by their masses by applying electromagnetic fields; and a detector, which measures the value of an indicator quantity and thus provides data for calculating the abundances of each ion present.

The MS technique has both qualitative and quantitative uses, including identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). Included are gas chromatography-mass spectrometry (GC/MS or GC-MS), liquid chromatography mass spectrometry (LC/MS or LC-MS), and ion mobility spectrometry/mass spectrometry (IMS/MS or IMMS) Accordingly, MS techniques may be used according to any of the methods provided herein to measure the presence or levels of an AARS polypeptide of the invention in a biological sample, and to compare those levels to a control sample or a pre-determined value.

Certain embodiments may employ cell-sorting or cell visualization or imaging devices/techniques to detect or quantitate the presence or levels of AARS polynucleotides or polypeptides. Examples include flow cytometry or FACS, immunofluorescence analysis (IFA), and in situ hybridization techniques, such as fluorescent in situ hybridization (FISH).

Certain embodiments may employ conventional biology methods, software and systems for diagnostic purposes. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

Certain embodiments may employ various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The whole genome sampling assay (WGSA) is described, for example in Kennedy et al., Nat. Biotech. 21, 1233-1237 (2003), Matsuzaki et al., Gen. Res. 14: 414-425, (2004), and Matsuzaki, et al., Nature Methods 1:109-111 (2004). Algorithms for use with mapping assays are described, for example, in Liu et al., Bioinformatics. 19: 2397-2403 (2003) and Di et al. Bioinformatics. 21:1958 (2005). Additional methods related to WGSA and arrays useful for WGSA and applications of WGSA are disclosed, for example, in U.S. Patent Application No. 60/676,058 filed Apr. 29, 2005, 60/616,273 filed Oct. 5, 2004, Ser. No. 10/912,445, Ser. No. 11/044,831, Ser. No. 10/442,021, Ser. No. 10/650,332 and Ser. No. 10/463,991.

Genome wide association studies using mapping assays are described in, for example, Hu et al., Cancer Res.; 65(7): 2542-6 (2005), Mitra et al., Cancer Res., 64(21):8116-25 (2004), Butcher et al., Hum Mol Genet., 14(10):1315-25 (2005), and Klein et al., Science. 308(5720):385-9 (2005).

Additionally, certain embodiments may include methods for providing genetic information over networks such as the Internet as shown, for example, in U.S. application Ser. Nos. 10/197,621, 10/063,559 (United States Publication Number 2002/0183936), 10/065,856, 10/065,868, 10/328,818, 10/328,872, 10/423,403, and 60/482,389.

EXAMPLES

Example 1

Production of His-Tagged Resokine (HRS(1-60))

Codon Optimization and Gene Synthesis

DNA encoding Resokine (HRS(1-60)) was codon-optimized for E. coli expression using the algorithm developed by DNA2.0 (Menlo Park, Calif.). The gene was synthesized with a C-terminal 6×His tag and subcloned into pJexpress411 vector where the T7 promoter was used to drive the transcription and the kanamycin resistance was used for antibiotic selection. The codon-optimized DNA sequence is as follows:

```
                                             (SEQ ID NO: 40)
ATGGCAGAACGTGCGGCATTGGAAGAATTGGTTAAACTGCAAGGTGAA

CGTGTTCGTGGTCTGAAGCAGCAGAAGGCTAGCGCGGAGCTGATCGAA

GAAGAGGTGGCCAAACTGCTGAAGCTGAAGGCGCAGCTGGGCCCGGAC

GAGAGCAAACAAAAGTTCGTCCTGAAAACCCCGAAACACCACCATCACC

ATCAC
```

The translated protein sequence is as follows:

```
                                             (SEQ ID NO: 41)
MAERAALEELVKLQGERVRGLKQQKASAELIEEEVAKLLKLKAQLGPDES

KQKFVLKTPKHHHHHH
```

Expression Strain.

BL21(DE3) competent cells (Novagen, cat. no. 69450) were transformed with the codon-optimized expression construct. Briefly, the plasmid (1 µL) was added into 50 µL of the competent cells. The reaction was mixed and incubated on ice for 30 minutes. The reaction was heat-shocked for at 42° C. for 30 seconds followed by a cold-shock on ice for 2 minutes. Then the SOC medium (500 µL) was added and the tube was incubated at 37° C., 250 rpm for 1 hour. Finally, an aliquot of the culture (50 µL) was spread on the Kanamycin plate (Teknova 59641) and incubated at 37° C. overnight. A single colony was picked and used for expression scale-up.

Medium.

The M9YE medium was prepared by mixing 200 mL sterile M9 minimal salt 5× (BD248510), 778 mL of 30 g/L yeast extract in sterile purified water (BD212750), 20 mL sterilized 20% glucose (Sigma G7021) and 2 mL sterile 1.0 M $MgSO_4$ (Sigma M7506). The feeding solution contains 5% yeast extract, 50% glucose, trace elements and 2 g/L magnesium sulfate. Kanamycin sulfate (Invitrogen 15160) was added to a final concentration of 100 µg/mL in both M9YE and feeding solution.

Fed-Batch Fermentation.

A 4 L fermentor (Sartorius Biostat B plus) with MFCS/DA software was used for the fed-batch fermentation. The agitation was set at 1000 rpm. The pH value was controlled at 7.0 automatically by the addition of 30% ammonium hydroxide (Sigma 221228) and 30% phosphoric acid (Sigma P5811).

The air was provided at a flow rate of 4 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3 L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 mL/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000×g for 1 hour. The cell pellet was stored at −20° C. until purification. The expression of Resokine was confirmed on the SDS-PAGE.

Purification of Resokine.

Frozen cell paste (70 g) was resuspended in 280 mL (i.e., 4 mL/g cell paste) of Lysis Buffer (50 mM Tris, 300 mM NaCl, 10 mM Imidazole, 5 mM β-ME, pH 7.5). Complete EDTA-FREE protease inhibitor tablets (Roche) were added to the suspension at a ratio of 1 tablet/50 mL. The suspension was passed through a microfluidizer (Microfluidics) twice at 15,000 psi with cooling by ice. The lysate was centrifuged at 15,000×g for 30 min at 4° C. The supernatant was filtered through 0.45+0.22 μm Acropak 400 capsule filters (Pall).

The clarified lysate was bound to the Ni-NTA resin (Qiagen), pre-equilibrated with Ni-NTA Binding Buffer (50 mM Tris, 300 mM NaCl, 10 mM Imidazole, pH 7.5). The column was washed with 50 column volumes of Ni-NTA Binding Buffer+0.1% Triton X-114 followed by 20 column volumes of the Ni-NTA Binding Buffer. The bound protein, Resokine, was eluted with 4 column volumes of Ni-NTA Elution Buffer (50 mM Tris, 300 mM NaCl, 300 mM Imidazole, pH 7.5).

The Ni-NTA eluate was further purified by a cation exchange column. Specifically, the Ni-NTA eluate was diluted 20-fold with the SP Binding Buffer (10 mM Na phosphate, pH 7.0) and loaded onto a 33 mL SP-sepharose HP column, pre-equilibrated with the SP Binding Buffer. The column dimension was 2.6 cm diameter at a height of 6.2 cm. The desired product was eluted off the column with a linear gradient of 0-0.5 M NaCl in the SP Binding Buffer over 10 column volumes. The purified protein was concentrated to 6 mg/mL, buffer exchanged into PBS (Invitrogen product #10010), and filtered through a 0.22 μm sterile filter. The yield of purified protein was 150 mg (from 70 g of cell paste), and its endotoxin level was <1.7 EU/mg.

Example 2

Production of His Tagged Full-Length Histidyl-TRNA Synthetase (HRS)

Codon Optimization and Gene Synthesis.

The full-length HisRS gene was codon-optimized for *E. coli* expression and sub-cloned into pET21a vector where the T7 promoter was used to drive the transcription. In addition, a 5-amino acid linker and 6×His tag were attached to the C-terminus The DNA sequence is as follows:

```
                                          (SEQ ID NO: 42)
ATGGCGGAACGTGCCGCACTGGAAGAATTGGTTAAATTACAGGGAGAAC

GCGTACGTGGTCTTAAACAACAAAAAGCCTCTGCGGAATTGATTGAAGA

AGAAGTTGCCAAATTACTGAAACTGAAAGCTCAACTTGGACCCGATGAA

AGTAAACAAAAATTTGTGTTGAAAACGCCCAAAGGAACCCGTGATTATA

GTCCACGTCAAATGGCCGTTCGTGAAAAAGTGTTCGACGTTATTATTCG

CTGTTTTAAACGTCACGGTGCTGAAGTAATCGATACCCCCGTATTTGAA

TTGAAAGAGACTCTGATGGGCAAATATGGTGAAGATTCTAAACTGATTT

ATGATTTGAAAGACCAAGGAGGTGAACTGCTGAGCCTGCGCTACGACTT

AACTGTGCCTTTTGCCCGTTACTTAGCCATGAATAAaTTaACCAACATC

AAACGTTACCATATTGCAAAAGTATATCGCCGCGACAACCCTGCAATGA

CTCGTGGACGCTATCGCGAATTCTATCAGTGTGATTTTGATATTGCCGG

AAATTTCGACCCGATGATCCCGGATGCCGAGTGTTTGAAAATTATGTGT

GAAATTCTGAGTTCGTTGCAGATCGGAGACTTTCTTGTAAAAGTTAATG

ACCGCCGTATTCTGGATGGTATGTTTGCTATTTGCGGTGTTTCTGATTC

CAAATTCCGTACAATCTGCTCAAGCGTGGACAAATTGGATAAAGTGTCT

TGGGAAGAAGTAAAAAATGAAATGGTGGGAGAAAAAGGCCTGGCTCCAG

AAGTAGCAGACCGTATTGGTGACTATGTTCAACAACATGGCGGTGTGTCC

TTAGTCGAACAGTTATTACAGGATCCTAAACTGAGCCAAAATAAACAAG

CACTTGAAGGACTGGGAGATCTGAAATTACTCTTTGAATATCTGACCTT

ATTTGGGATTGATGATAAAATTAGCTTTGATCTGAGCTTGGCCCGCGGT

CTTGATTATTATACCGGCGTGATTTACGAAGCTGTTCTCTTGCAAACCC

CAGCCCAGGCGGGCGAAGAGCCTTTGGGAGTCGGCAGTGTGGCAGCCGG

TGGTCGTTATGATGGTTTGGTAGGAATGTTTGACCCTAAAGGCCGTAAA

GTACCATGTGTGGGCTTTCTATCGGTGTCGAACGTATCTTTTCTATTG

TTGAACAACGTCTTGAAGCTTTGGAGGAAAAGATCCGTACCACGGAAac

CCAAGTCTTAGTTGCaAGTGCCCAAAAAAAACTGTTAGAAGAACGCCTG

AAACTCGTATCAGAACTTTGGGACGCCGGCATCAAGGCCGAACTGCTGT

ATAAAAGAACCCGAAATTGTTAAACCAACTCCAGTATTGTGAAGAAGC

TGGGATCCCACTCGTAGCTATTATTGGTGAGCAAGAATTAAAAGATGGC

GTGATTAAACTGCGTTCAGTAACAAGCCGTGAAGAGGTAGATGTACGTC

GCGAAGACTTAGTGGAAGAAATTAAACGCCGCACCGGTCAACCGTTATG

TATTTGCGCGGCCGCACTCGAGCACCACCACCACCACCACTGA
```

The sequence of the translated protein is as follows:

```
                                          (SEQ ID NO: 43)
MAERAALEELVKLQGERVRGLKQQKASAELIEEEVAKLLKLKAQLGPDE

SKQKFVLKTPKGTRDYSPRQMAVREKVFDVIIRCFKRHGAEVIDTPVFE

LKETLMGKYGEDSKLIYDLKDQGGELLSLRYDLTVPFARYLAMNKLTNI

KRYHIAKVYRRDNPAMTRGRYREFYQCDFDIAGNFDPMIPDAECLKIMC

EILSSLQIGDFLVKVNDRRILDGMFAICGVSDSKFRTICSSVDKLDKVS
```

-continued

```
WEEVKNEMVGEKGLAPEVADRIGDYVQQHGGVSLVEQLLQDPKLSQNKQ

ALEGLGDLKLLFEYLTLFGIDDKISFDLSLARGLDYYTGVIYEAVLLQT

PAQAGEEPLGVGSVAAGGRYDGLVGMFDPKGRKVPCVGLSIGVERIFSI

VEQRLEALEEKIRTTETQVLVASAQKKLLEERLKLVSELWDAGIKAELL

YKKNPKLLNQLQYCEEAGIPLVAIIGEQELKDGVIKLRSVTSREEVDVR

REDLVEEIKRRTGQPLCICAAALEHHHHHH
```

Expression Strain.

BL21(DE3) competent cells (Novagen, cat. no. 69450) were transformed with the codon-optimized expression construct. Briefly, the plasmid (1 µL) was added into 50 µL of the competent cells. The reaction was mixed and incubated on ice for 30 minutes. The reaction was heat-shocked for at 42° C. for 30 seconds followed by a cold-shock on ice for 2 minutes. Then the SOC medium (500 µL) was added and the tube was incubated at 37° C., 250 rpm for 1 hour. Finally, an aliquot of the culture (50 µL) was spread on the Ampicillin plate (Teknova 59641) and incubated at 37° C. overnight. Single colony was picked and used for expression scale-up.

Medium.

M9YE medium was prepared by mixing 200 mL sterile M9 minimal salt 5× (BD248510), 778 mL of 30 g/L yeast extract in sterile purified water (BD212750), 20 mL sterilized 20% glucose (Sigma G7021) and 2 mL sterile 1.0 M MgSO4 (Sigma M7506). The feeding solution contains 5% yeast extract, 50% glucose, trace elements and 2 g/L magnesium sulfate. Ampicillin was added to a final concentration of 100 µg/mL in both M9YE and feeding solution.

Fed-Batch Fermentation.

A 4 L fermentor (Sartorius Biostat B plus) with MFCS/DA software was used for the fed-batch fermentation. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 µm Midisart 2000 filter (Sartorius 17805). The pure oxygen (WestAir) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3 L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 mL/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000×g for 1 hour. The cell pellet was stored at −20° C. until purification. The expression of HisRS was confirmed on the SDS-PAGE.

Purification of HisRS.

Frozen cell paste (40 g) were resuspended in 160 mL (i.e., 4 mL/g cell paste) of Lysis Buffer (20 mM Tris, 400 mM NaCl, 20 mM Imidazole, 14 mM β-ME, pH 8.0 at 4° C.). Complete EDTA-FREE protease inhibitor tablets (Roche) were added to the suspension at a ratio of 1 tablet/50 mL. The suspension was passed through a microfluidizer (Microfluidics) twice at 15,000 psi with cooling by ice. The lysate was centrifuged at 35,000×g for 45 min at 4° C. The supernatant was filtered through 0.22 µm Acropak 200 capsule filters (Pall).

The clarified lysate was bound to the Ni-NTA resin (Qiagen), pre-equilibrated with Ni-NTA Binding Buffer (20 mM Tris, 400 mM NaCl, 20 mM Imidazole, 5 mM β-ME, pH 8.0 at 4° C.). The column was washed with 500 column volumes of Ni-NTA Binding Buffer+0.1% Triton X-114 followed by 50 column volumes of the Ni-NTA Binding Buffer. The bound protein, HisRS, was eluted with 5 column volumes of Ni-NTA Elution Buffer (20 mM Tris, 400 mM NaCl, 500 mM Imidazole, 5 mM β-ME, pH 8.0 at 4° C.).

The Ni-NTA eluate was further purified by an anion exchange column. Specifically, the Ni-NTA eluate was dialyzed against Q Binding Buffer (20 mM Tris, 50 mM NaCl, 1 mM DTT, pH 7.4) and loaded onto a 5 mL Q-sepharose column, pre-equilibrated with the Q Binding Buffer. The desired product was eluted off the column with a linear gradient of 0-1 M NaCl in the Q Binding Buffer over 10 column volumes. The purified HisRS was concentrated and buffer exchanged into PBS (Invitrogen product #10010)+1 mM DTT, and filtered through a 0.22 µm sterile filter.

Example 3

Evaluation of Resokine (HRS(1-60)) as an Anti-Inflammatory Agent

To evaluate the potential anti-inflammatory property of HRS derived polypeptides, an N-terminal, naturally-occurring splice variant comprising amino acids 1-60 of HRS (Resokine) was tested in a TNBS induced model of colitis (Epistem, Ltd, UK).

The most common forms of inflammatory bowel disease (IBD), Crohn's disease and ulcerative colitis, are chronic and progressive inflammatory disorders of the digestive tract. Crohn's disease usually affects both ileum and colon while ulcerative colitis usually affects only the innermost lining of the colon and rectum. The symptoms for Crohn's disease and ulcerative colitis are generally similar with abdominal pain and diarrhea. In moderate to severe ulcerative colitis, bloody stool is often observed. There is currently no cure for IBD. Drugs and biologics are commonly used to treat symptoms, induce remission and prevent relapse. Anti-inflammatory drugs such as sulfasalazine, mesalamine and corticosteroids are often the first line medications for the treatment of IBD to induce remission, while immune system suppressors are generally used to help maintain remission. The most common immune system modulators used for treating IBD are azathioprine, mercaptopurine and biological therapies such as anti-tumor necrosis factor (anti-TNF-α).

Development of animal models of IBD has contributed to the understanding and discovery of therapies for IBD. Dextran sulfate (DSS) and the trinitrobenzene sulfonic acid (TNBS) colitis rodent models have demonstrated that the severity of weight loss, colon histopathology and endoscopy scores corresponded to the degree of changes in proinflammatory cytokines and chemokines that preferentially attract infiltration of neutrophils and matrix metalloproteinases. These IBD rodent models have also been used to validate a computational approach to identify potential new drug therapies for IBD.

Studies were performed in male BDF-1 mice, with 12 mice/group; All mice in the treatment groups received 3 mg TNBS in 50% ethanol/saline by colonic instillation on study day 0 in order to induce colitis, and Budesonide was added at 5 mg/kg orally as a positive control.

In this study Resokine was administered daily by IV injection, starting 3 hours prior to TNBS treatment, at a concentration of 1 or 5 mg/Kg. The data, shown in FIG. 1 demonstrates that treatment with Resokine (HRS(1-60)) at either concentration resulted in a significant increase in survival. Accordingly Resokine appears to have potent anti-inflammatory effects, consistent with the hypothesis that HRS polypeptides are involved in the local control of inflammatory processes.

To directly compare HRS(1-60) directly to HRS (1-506) a repeat TNBS study was conducted by Biomodels (MA, USA in C57BL/6 mice.).

Study Design:

A no treatment control group consisted of 5 mice with intra-rectal administration of vehicle for TNBS (Group 1). TNBS (4 mg/100 μL, 50% ethanol) was administered to Group 2 (15 mice/group) and 10 mice/group for Groups 3-7 on Day 0. Groups 2 and 4-7 received intravenous administration q.d. of vehicle, HRS(1-506), 3 and 1 mg/kg, and aTyr1920 5 and 1 mg/kg, respectively, from Days −1 to 5. Group 3 received oral administration of 2 mg/kg of Prednisolone q.d. from Days −1 to 5. Animals were weighed daily. All animals underwent video endoscopy on Days 3 and 5 to assess the extent of colitis and whether any beneficial treatment effects could be observed. All surviving animals were euthanized on Day 5 to obtain colon tissues for weight and length measurements and for pathology examination.

Methods:

Endoscopy was performed in a blinded fashion using a small animal endoscope (Karl Storz Endoskope, Germany). To evaluate colitis severity, animals were anesthetized with isoflurane and subjected to video endoscopy of the lower colon. Colitis was scored visually on a 5 point scale that ranges from 0 for normal, to 4 for severe ulceration. In descriptive terms, this scale is defined as depicted in Table E1. Each mouse was assigned a single score that corresponded to the most severe damage observed throughout the entire length of the colon. On Day 5, animals were euthanized and their colons were removed, rinsed, weighed, and their lengths were measured.

TABLE E1

Endoscopy Colitis Scoring Scale

| Score | Description: |
|---|---|
| 0 | Normal |
| 1 | Loss of vascularity |
| 2 | Loss of vascularity and friability |
| 3 | Friability and erosions |
| 4 | Ulcerations and bleeding |

Histology was assessed by examining the colon spanning the lower 5 cm of each animal which was trimmed and the 2 cm sections from each end fixed in 10% formalin, embedded, sectioned at approximately 5 microns and stained with hematoxylin and eosin (H & E) for histological analysis. The middle 1 cm section of the colon was snap frozen, and stored at −80° C. Tissue sections were examined by a board certified veterinary pathologist with particular expertise in GI pathology in a blinded fashion. Each section was scored for inflammation, edema and epithelial necrosis/loss using a 5 point scale according to the criteria listed in Table E2. Scores for each of the 4 sections were averaged to obtain a single mean score per mouse per parameter. The mean sum score which is the sum of the three parameter scores was also reported.

TABLE E2

Histology Colitis Scoring Scale

| Score | Description |
|---|---|
| | Inflammation |
| 0 | None present |
| 1 | Rare foci; minimal |
| 2 | Scattered aggregates or mild diffuse inflammation |
| 3 | Numerous aggregates or moderate diffuse inflammation |
| 4 | Marked diffuse inflammation |
| | Edema |
| 0 | None present |
| 1 | Rare foci; minimal |
| 2 | Scattered regions or mild diffuse edema |
| 3 | Numerous regions or moderate diffuse edema |
| 4 | Marked diffuse edema |
| | Epithelial Necrosis/Loss |
| 0 | None present |
| 1 | <25% of the mucosa affected |
| 2 | 26-50% of the mucosa affected |
| 3 | 51-75% of the mucosa affected |
| 4 | >76% of the mucosa affected |

Results:

All TNBS-treated animals lost notable body weight on Day 1 and began to gain weight again on Days 3 or 4. On Days 3 and 5, treatment with 1 and 3 mg/kg of HRS(1-506) or 1 and 5 mg/kg of HRS(1-60) produced a mild to moderate decrease in colitis scores (Table E3). Treatment with 3 mg/kg of HRS (1-506) consistently produced the largest decrease in colitis scores compared to other treatment groups on both Days 3 and 5. (Table E3). Treatment with 2 mg/kg of Prednisolone produced a mild decrease in colitis scores on Day 5 but had no effect on Day 3. Treatment with 1 and 3 mg/kg of a HRS(1-506) or 1 and 5 mg/kg of HRS(1-60) resulted insignificant decreases of inflammation, edema, epithelial necrosis/loss, and sum scores compared to treatment with TNBS+vehicle (Table E3).

TABLE E3

Summary of Pathology Scores

| | | Mean Score ± SEM | | | |
|---|---|---|---|---|---|
| Group | Treatment | Inflammation | Edema | Necrosis | Sum |
| 1 | — | 0.00 ± 0.00 | 0.04 ± 0.04 | 0.00 ± 0.00 | 0.04 ± 0.04 |
| 2 | Vehicle (i.v.) | 0.68 ± 0.08 | 0.79 ± 0.10 | 0.43 ± 0.09 | 1.89 ± 0.20 |
| 3 | Prednisolone 2 mg/kg (p.o.) | 0.72 ± 0.14 | 0.71 ± 0.16 | 0.61 ± 0.15 | 2.05 ± 0.42 |
| 4 | HRS (1-506) 3 mg/kg (i.v.) | 0.37 ± 0.06 | 0.38 ± 0.08 | 0.27 ± 0.06 | 1.02 ± 0.15 |

TABLE E3-continued

Summary of Pathology Scores

| | | Mean Score ± SEM | | | |
|---|---|---|---|---|---|
| Group | Treatment | Inflammation | Edema | Necrosis | Sum |
| 5 | HRS (1-506) 1 mg/kg (i.v.) | 0.47 ± 0.08 | 0.48 ± 0.10 | 0.37 ± 0.07 | 1.32 ± 0.23 |
| 6 | HRS (1-60) 5 mg/kg (i.v.) | 0.50 ± 0.10 | 0.65 ± 0.16 | 0.35 ± 0.08 | 1.50 ± 0.30 |
| 7 | HRS (1-60) 1 mg/kg (i.v.) | 0.49 ± 0.08 | 0.52 ± 0.15 | 0.33 ± 0.06 | 1.34 ± 0.27 |

Conclusion:

In a mouse model of TNBS-induced colitis, intravenous treatment with HRS(1-60) at 1 and 5 mg/kg and HRS(1-506) at 1 and 3 mg/kg, resulted in significant decreases in endoscopic colitis scores and pathology scores of inflammation, edema, epithelial necrosis/loss and sum score. There were no adverse effects attributed to treatment with HRS(1-60), HRS (1-506), or prednisolone. These results confirm previous studies and further establish an anti-inflammatory role for HRS polypeptides in inflammatory diseases and disorders such as IBD.

Example 4

Active Site Titration of the Cysteine Residues in Full-Length HARS

To determine the location and identity of the surface exposed cysteine residues in full-length HARS, purified recombinant protein was incubated with iodoacetamide under native and denatured conditions to alkylate any surface exposed cysteine residues. Samples were then analyzed by limiting proteolysis followed by LC-mass analysis to determine the location and identity of the modified cysteine residues.

To perform the alkylation studies, full-length, polyhistidine-tagged HRS (6.65 mg/ml in PBS, 10% glycerol, 2 mM DTT, pH7.4, (Example 2) was first fully reduced by incubation with 10 mM DTT for 45 minutes at room temperature. Incubations with iodoacetamide were conducted with an iodoacetamide concentration at either 30 mM ("Low") or a 100 mM ("High") for 30 minutes in the dark, and were conducted on native and denatured samples of HARS to confirm that the reaction was successful. Denatured HARS was prepared by pre-incubation of the protein with 4M guanidine for 45 min at 50 C. After incubation with iodoacetamide, samples were dialyzed in PBS pH 7.4 at 4 C using 10 KDa molecular weight cutoff dialysis membrane, and with at least 3 buffer exchanges, and then used for mass spectroscopy analysis as described below.

In brief, samples were prepared by diluting the proteins into 0.1% formic acid to a final concentration of 1 m/ml and 5 µg samples of the proteins were injected and analyzed by reverse phase HPLC followed by mass spectrum analysis using an Agilent TOF mass spectrometer. Samples were first separated on a C3 HPLC column (Agilent ZORBAX 300SB-C3, 5 µm, 2.1×150 mm column) using a linear gradient of (mobile phase B of 2-60%) over 18 min (mobile phase A: 0.1% formic acid; mobile phase B: 0.1% formic acid in acetonitrile). Mass spectrometry analysis of the samples was in profile mode. Data was acquired and analyzed by MassHunter (Agilent). Measured molecular weight was calculated by MassHunter Bioconfirm Agilent).

The results (data not shown) demonstrated that under native conditions only 3 or 4 cysteine residues are readily modified, whereas by comparison when the protein is first denatured to disrupt its native conformation all 10 cysteines were readily denatured.

To identify the identity of the modified cysteine residues, samples before and after incubation with iodoacetamide were subjected to denaturation in 4 M Guanidine HCl at 37° C. for 30 min followed by proteolytic cleavage with LysC using a by a 10:1 ratio (w/w) at room temperature for 20 h. Protein digests were analyzed by LC/MS/MS using Dionex HPLC and Thermo LTQ XL mass spectrometer. Samples were first separated on C18 HPLC column (Agilent ZORBAX 300SB-C18, 5 µm, 2.1×150 mm) using a gradient of mobile phase B (mobile phase A: 0.1% formic acid; mobile phase B: 0.1% formic acid in acetonitrile). The gradient start off with 1-3% B in 10 min and then to 40% B in 76 min. Separated protein digests were analyzed either by full MS in profile mode or by a full MS scan were analyzed by tandem MS/MS scan on the top three identified ions. Data was acquired and analyzed by Xcalibur (Thermo). Peptide sequencing was based on the MS/MS spectra of each peptide, in which b- and y-ion peaks match their theoretical ions. Identification of the peptides and mapping of the modification sites are based on the molecular weight and confirmed by peptide sequencing using MS/MS spectra, and are listed in Table E4.

TABLE E4

LC-MS Peptide mapping results after limiting trypsin digestion

| Cys res. | From-To | Sequence | RT (min) | MH+ |
|---|---|---|---|---|
| Cys83 | 76-85 | VFDVIIRCFK (SEQ ID NO: 190) | 56.24 | 1239.68 |
| Cys174 Cys191 | 155-193 | VYRRDNPAMTRGRYREFYQCDFDIAGNFDPMIPDAECLK (SEQ ID NO: 191) | 61.27 | 4673.14 |

TABLE E4-continued

LC-MS Peptide mapping results after limiting trypsin digestion

| Cys res. | From-To | Sequence | RT (min) | MH+ |
|---|---|---|---|---|
| Cys196 | 194-210 | IMCEILSSLQIGDFLVK (SEQ ID NO: 192) | 73.14 | 1909.01 |
| Cys224 | 211-230 | VNDRRILDGMFAICGVSDSK (SEQ ID NO: 193) | 58.53 | 2196.08 |
| Cys235 | 231-240 | FRTICSSVDK (SEQ ID NO: 194) | 22.8 | 1155.57 |
| Cys235 | 231-243 | FRTICSSVDKLDK (SEQ ID NO: 195) | 28.77 | 1511.79 |
| Cys379 | 377-403 | VPCVGLSIGVERIFSIVEQRLEALEEK (SEQ ID NO: 196) | 81.00 | 3013.63 |
| Cys445 | 448-472 | LLNQLQYCEEAGIPLVAIIGEQELK (SEQ ID NO: 197) | 72.46 | 2784.48 |
| Cys505 Cys509 | 500-509 | RRTGQPLCIC (SEQ ID NO: 198) | 27.17 | 1146.57 |

The results revealed (data not shown) that Cys235, Cys507 and Cys509 are readily modified by iodoacetamide treatment and are thus likely to be surface-exposed residues that are readily amenable to chemical modification.

Example 5

Creation of Modified HRS Polypeptides with Altered Cysteine Content

To determine whether any of the 10 naturally-occurring cysteine residues in full-length HRS could be mutated to alternative naturally-occurring amino acid residues, or deleted, primers were designed to selectively mutate each cysteine residue. To accomplish this, primers based on the following may be used (see Table E5).

TABLE E5

| Mutation | Oligo sequence | SEQ ID NO: |
|---|---|---|
| C83 | 5'-GTTTGACGTAATCATCCGTTGCTTCAAGCGCCACGGTGCAG-3' (Forward) | 199 |
| C83 | 5'-CTGCACCGTGGCGCTTGAAGCAACGGATGATTACGTCAAAC-3' (Reverse) | 200 |
| C174 | 5'-GCCGATACCGGGAATTCTACCAGTGTGATTTTGACATTGCTGGG-3' (Forward) | 201 |
| C174 | 5'-CCCAGCAATGTCAAAATCACACTGGTAGAATTCCCGGTATCGGC-3' (Reverse) | 202 |
| C191 | 5'-CCATGATCCCTGATGCAGAGTGCCTGAAGATCATGTGCGAG-3' (Forward) | 203 |
| C191 | 5'-CTCGCACATGATCTTCAGGCACTCTGCATCAGGGATCATGG-3' (Reverse) | 204 |
| C196 | 5'-GCAGAGTGCCTGAAGATCATGTGCGAGATCCTGAGTTCACTTC-3' (Forward) | 205 |
| C196 | 5'-GAAGTGAACTCAGGATCTCGCACATGATCTTCAGGCACTCTGC-3' (Reverse) | 206 |
| C224 | 5'-CTAGATGGGATGTTTGCTATCTGTGGTGTTTCTGACAGCAAGTTC-3' (Forward) | 207 |
| C224 | 5'-GAACTTGCTGTCAGAAACACCACAGATAGCAAACATCCCATCTAG-3' (Reverse) | 208 |
| C235 | 5'-CAGCAAGTTCCGTACCATCTGCTCCTCAGTAGACAAGCTGG-3' (Forward) | 209 |

TABLE E5-continued

| Mutation | Oligo sequence | SEQ ID NO: |
|---|---|---|
| C235 | 5'-CCAGCTTGTCTACTGAGGAGCAGATGGTACGGAACTTGCTG-3' | 210 |
| C379 | 5'-GGGCGCAAGGTGCCATGTGTGGGGCTCAGCATTGGGG-3' (Forward) | 211 |
| C379 | 5'-CCC CAA TGC TGA GCC CCA CAC ATG GCA CCT TGC GCC C-3' (Reverse) | 212 |
| C455 | 5'-CTGAACCAGTTACAGTACTGTGAGGAGGCAGGCATCCC-3' (Forward) | 213 |
| C455 | 5'-GGGATGCCTGCCTCCTCACAGTACTGTAACTGG TTCAG-3' (Reverse) | 214 |
| C507 | 5'-GAGAACAGGCCAGCCCCTCTGCATCTGCTAGAACCCAGC-3' (Forward) | 215 |
| C507 | 5'-GCTGGGTTCTAGCAGATGCAGAGGGGCTGGCCTGTTCTC-3' (Reverse) | 216 |
| C509 | 5'-CCAGCCCCTCTGCATCTGCTAGAACCCAGCTTTCTTG-3' (Forward) | 217 |
| C509 | 5'-CAAGAAAGCTGGGTTCTAGCAGATGCAGAGGGGCTGG-3' (Reverse) | 218 |
| Last 3 codon removal | 5' GAACAGGCCAGCCCCTCTAGAACCCAGCTTTCTTG 3' (Forward) | 219 |
| Last 3 codon removal | 5'-CAAGAAAGCTGGGTTCTAGAGGGGCTGGCCTGTTC-3' (Reverse) | 220 |

To confirm the active site titration data, the crystal structure of full-length HRS was analyzed using the program Getareal.1 to assess the relative location of the 10 cysteine residues. The results (data not shown) suggest that in addition to Cys235, Cys507 and Cys509, the cysteines at positions Cys174, Cys191 and Cys224 of SEQ ID NO:1, are at least partially exposed to the surface and could likely be modified via standard reagents. Additionally analysis of the crystal structure of HRS suggests that Cys174 and Cys191 are capable of making an internal disulfide bond, while Cys507 and Cys509 are capable of making interchain disulfide bonds within the HRS dimer, both potentially contributing to micro-heterogeneity that could be beneficially eliminated.

Figure 2:
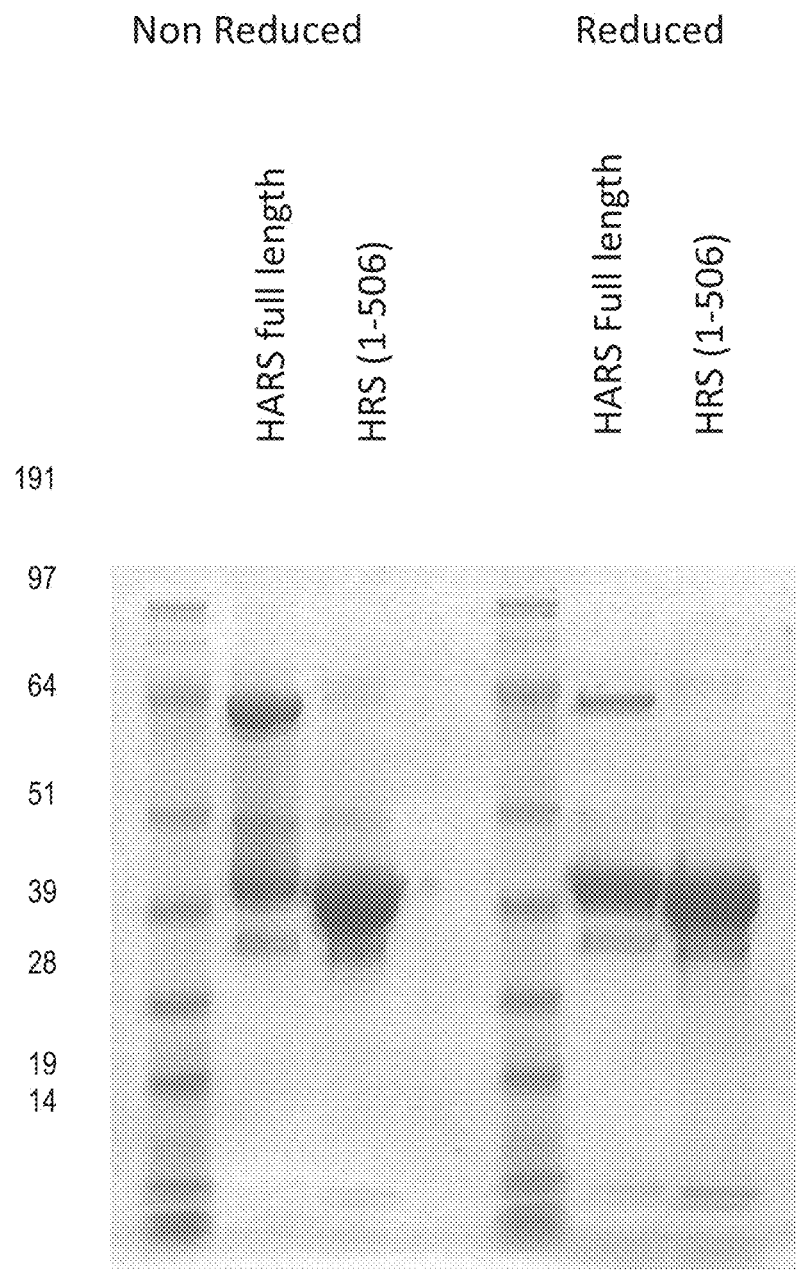
FIG. 2 shows an SDS-PAGE analysis full-length HRS and HRS(1-506) under non-reduced and reduced conditions. The gels show that full-length HRS is a ~50:50 mixture of non-covalent and SS-linked dimer under both normal and reduced conditions, and that HRS(1-506) shows significantly reduced formation of the SS-linked dimer, increased homogeneity, and monodispersity relative to the full-length protein.

To directly assess the significance of the two C-terminal cysteine residues in contributing to interchain disulfide bond formation, His-tagged versions of the full-length and the C-terminally deleted versions of HRS(HRS(1-506)) were compared by SDSPAGE analysis before and after reduction, as described below. The results, shown in FIG. 2, demonstrate that full-length HRS is a ~50:50 mixture of non-covalent and SS-linked dimer, while HRS(1-506) dramatically reduces the SS-linked dimer. Comparison of the two proteins by competitive ELISA, as described below, revealed that both proteins had comparable IC50 values with respect to Jo-1 antibody binding (data not shown). The dramatically reduced inter-chain disulfide bond formation associated with HRS(1-506) suggests that this variant is a suitable starting point for the development of improved next generation product forms.

To determine whether any of the remaining four partially exposed cysteine residues in full-length HRS could be mutated to alternative naturally-occurring amino acid residues, primers were designed to selectively mutate C174, C191, C224, and C235 residues. To accomplish this, the following primers were used as listed in Table E6.

TABLE E6

| Mutation | Oligo sequence | SEQ ID NO: |
|---|---|---|
| C191A | CCCGGATGCCGAGGCTTTGAAAATTATGTG (Forward) | 221 |
| C191A | CAC ATA ATT TTC AAA GCC TCG GCA TCC GGG (Reverse) | 222 |
| C191S | GATCCCGGATGCCGAGAGTTTGAAAATTATGTGTG (Forward) | 223 |
| C191S | CAC ACA TAA TTT TCA AAC TCT CGG CAT CCG GGA TC (Reverse) | 224 |
| C191V | GATCCCGGATGCCGAGGTTTTGAAAATTATGTGTG (Forward) | 225 |
| C191V | CAC ACA TAA TTT TCA AAA CCT CGG CAT CCG GGA TC (Reverse) | 226 |
| C174A | CGCGAATTCTATCAGGCTGATTTTGATATTGCCGG (Forward) | 227 |

TABLE E6-continued

| Mutation | Oligo sequence | SEQ ID NO: |
|---|---|---|
| C174A | CCG GCA ATA TCA AAA TCA GCC TGA TAG AAT TCG CG (Reverse) | 228 |
| C174V | CGCGAATTCTATCAGGTTGATTTTGATATTGCCG (Forward) | 229 |
| C174V | CGG CAA TAT CAA AAT CAA CCT GAT AGA ATT CGC G (Reverse) | 230 |
| C224S | GGTATGTTTGCTATTTCCGGTGTTTCTGATTCC (Forward) | 231 |
| C224S | GGA ATC AGA AAC ACC GGA AAT AGC AAA CAT ACC (Reverse) | 232 |
| C235S | CCAAATTCCGTACAATCTCCTCAAGCGTGGACAAATTGG (Forward) | 233 |
| C235S | CCA ATT TGT CCA CGC TTG AGG AGA TTG TAC GGA ATT TGG (Reverse) | 234 |
| C191A | CCCGGATGCCGAGGCTTTGAAAATTATGTG (Forward) | 235 |
| C191A | CAC ATA ATT TTC AAA GCC TCG GCA TCC GGG (Reverse) | 236 |

Mutations were introduced by mutagenesis using the QuikChange Lightning Site-Directed Mutagenesis Kit (Agilent, cat. no. 210518) following the manufacturer's instructions. After mutagenesis, the samples were treated with Dpn I enzyme at 37° C. and transformed into XL10 gold competent cells using routine procedures. Multiple colonies were grown in terrific broth overnight at 37° C. and the resulting plasmids were purified with QIAprep Spin Miniprep Kit (Qiagen cat. no. 27106). The plasmids were sequenced to confirm the identity of the amino acid substitution of each clone. Representative clones were transformed into NovaBlue competent cells (Novagen cat. no. 70181) and grown in 250 ml M9YE medium at 37° C. overnight. Maxipreps were performed using the HiSpeed Plasmid Maxi Kit (Qiagen cat. no. 12663) to create a plasmid stock of mutant for further analysis. The concentration and purity were determined by measuring A260, A280 and A230. The purified plasmids were stored at −20° C. before transfection into E. coli or mammalian cells following standard protocols.

To assess the impact of the mutation of the mutation of each residue, representative clones were transformed into E. coli, or mammalian cells, and the production yields, endotoxin contents, stability and relative activity in an ELISA assay to determine Jo-1 antibody binding as described below.

Protein Production.

BL21(DE3) competent cells (Novagen, cat. no. 69450) or W3110 cells (ATTC) were transformed with the codon-optimized expression constructs encoding the reduced cysteine constructs as described above. The expression system, fermentation media, fermentation conditions and purification steps used to produce recombinant protein were essentially the same as those described in Example 6 below, after adjusting for the production scale, and amount of cell paste used. Table E7 below shows the purification yields, and endotoxin levels for the proteins made.

TABLE E7

Purification yields and endotoxin levels of reduced cysteine variants

| Name | Yield (mg/g cell paste) | Endotoxin (EU/mg) |
|---|---|---|
| Full-length HRS | ++ | 3.2 |
| HRS(1-506) | +++ | 0.32 |
| HRS(1-506)C174V | ++ | 0.71 |
| HRS(1-506)C174A | ++ | 0.30 |
| HRS(1-506)C191A | ++ | 0.46 |
| HRS(1-506)C191V | +++ | 0.33 |

TABLE E7-continued

Purification yields and endotoxin levels of reduced cysteine variants

| Name | Yield (mg/g cell paste) | Endotoxin (EU/mg) |
|---|---|---|
| HRS(1-506)C191S | +++ | 0.32 |
| HRS(1-506)C224S | ++ | 0.54 |
| HRS(1-506)C235S | +++ | 0.60 |

+++ greater than 7 mg protein/g cell paste;
++ greater than 5 mg/g cell paste
+ less than 5 mg/g cell paste.

The results show that all of the reduced Cys variants were relatively well expressed, and were successfully purified with low endotoxin levels. In particular the reduced cysteine variants based on the mutation of Cys191, and Cys235 displayed favorable expression levels; though all clones exhibited reasonable levels of expression, and low endotoxin levels. Compared to the expression of full-length HRS, all of the cysteine modified proteins exhibited significantly less endotoxin content. Moreover, the reduced cysteine mutants HRS(1-506), HRS(1-506)C191V, HRS(1-506)C191S and HRS(1-506) C235S all showed improved expression relative to full-length wild type HARS.

To assess the impact of the cysteine mutations on the charge heterogeneity of the purified proteins, samples of each clone were analyzed by isoelectric focusing. Samples (10 µg) were loaded onto an isoelectric focusing gel (pH 3-10) using a Life Technologies Novex pH 3-10 IEF gel 1.0 mm (Cat No. P/N EC6645BOX), Novex IEF Marker 3-10 (Cat No. P/N 391201), Novex pH 3-10IEF buffer kit (Cat. No. P/N LC5317), run with 1× cathode buffer (upper chamber) and lx anode buffer (lower chamber) at 100V for 1 hour, 200V for 1 hour, and 500V for 30 minutes. Gels were fixed with 12% TCA with 3.5% sulfosalicylic acid for 30 minutes and stained with Expedeon InstantBlue (Cat No. P/N ISB1L). The data, (results not shown) demonstrate that the mutation of the cysteine at position 174 significantly reduced isoelectric point heterogeneity, consistent with the possibility that this cysteine residue undergoes an intramolecular disulfide bond formation with cysteine 191.

To assess the impact of the cysteine modifications on the thermal stability, aggregation propensity, structure, and tRNA synthetase activity of the resultant proteins, the proteins were assessed by differential scanning fluorimetry, size exclusion HPLC (SE-HPLC), competitive ELISA and active site titration. The results are shown in Table E8 below.

Differential scanning fluorimetry was performed on protein samples by monitoring fluorescence as a function of the fluorescence intensity of a lipophilic dye during thermal denaturation. Studies were carried out on samples after they were diluted to 0.5 mg/mL into 100 μL final volume of PBS pH 7.0 (150 mM NaCl, 20 mM phosphate) and mixed with a thermal shift dye solution, which was prepared by diluting the stock solution (Applied Biosystems/Life Technologies, P/N 4461146) 20-fold in ultrapure distilled water (Gibco, P/N 10977). Five μL of the diluted dye was added to 100 μL of sample. The mixture was plated into a 384 well clear optical reaction plate (Applied Biosystems/Life Technologies P/N 4309849) at 20 μL each well and 4 well replicates per sample. The plate was read by the ViiA 7 Real Time PCR Instrument (Applied Biosystems/Life Technologies, P/N 4453552). The thermal denaturation protocol commenced with a rate of change of 1.6° C./s, until a temperature of 25° C. was attained, at which point the instrument held this temperature for 2 minutes, before further increasing the temperature to 99° C., at a rate of 0.5° C./s at which point this temperature was held for a further 2 minutes.

Size exclusion HPLC analysis was completed on the purified protein samples using a TSKgel Super SW3000, 4.6 mm ID×30 cm, 4 μm particle size, 250 U column (Tosoh, 18675) using a mobile phase of 200 mM NaPhosphate, 150 mM NaCl pH 7.0, at a flow rate of 0.3 ml/min, with an Agilent 1260 HPLC system equipped with a vacuum degasser, binary/quaternary pump, thermostatted autosampler, thermostatted column compartment, diode array detector (DAD), and Chemstation chromatography software). Un-diluted samples (40 μg) of each protein were injected after brief centrifugation. System suitability sample (bovine serum albumin, BSA, Thermo Scientific, P/N: 23209) and internal control (wild-type HRS) were used to bracket samples to ensure the validity of the test.

Competitive ELISAs were performed in 96-well plates (Immulon 4HBX) which had been coated with a 50 μL solution of full-length his-tagged HARS, adjusted to a concentration of 2 μg/mL with PBS. Plates were sealed and incubated overnight at 4° C. Prior to use, plates were washed five times with PBST and subsequently blocked with 100 μl 1% BSA in PBS for one hour at room temperature. While the ELISA plates were blocking, the reduced cysteine competition molecules (over a concentration range of $1\times10^{-6}$M to $1\times10^{-13}$M) were incubated with α-Jo-1 antibodies (GenWay GWB-FB7A3D or Immunovision HJO-0100) at 1:10,000 dilution in 1% BSA PBS in a separate incubation plate (Costar 3357 96-well) for one hour at 4° C. After blocking was finished, the ELISA plates were washed three times with PBST and 50 μL of solution containing antibody and competitor was added to the ELISA plate and the samples incubated at room temperature for 1.5 hours. Following initial binding incubation, plates were washed five times with PBST. Next, 50 μL of detection antibody (AbD Serotec Goat Anti-human IgG F(ab')$_2$:HRP 0500-0099) was added a 1:5,000 dilution and incubated for one hour at room temperature. Following secondary binding incubation, plates were washed with five times PBST and 50 μL TMB substrate (Thermo Scientific Pierce TMB Substrate PI-34021) was added. Reactions proceeded for 8 minutes at which point 50 μL of 2M sulfuric acid stop solution was added. Colorimetric quantification was performed using a SpectraMax plate reader at 450 nM.

To determine the number of catalytic active sites in each HARS506 cysteine variant the active site titration assay (as described in Fersht et al., (1975) Biochemistry) was employed. Briefly, assays were performed at room temperature with 5 μM HARS, 10 mM MgCl2, 50 μM ATP, 20 mM L-histidine, 2 ug/mL inorganic pyrophosphatase, 1.65 μM [γ-32P]ATP in standard buffer (100 mM HEPES pH 7.5, 20 mM KCl). Reactions were initiated with enzyme in low profile PCR plates and time points were quenched in 96-well PVDF multiScreen filter plates Millipore containing HClO4/charcoal slurry (1:4 7% HClO4:10% charcoal slurry) at 30 s, 1 min, 2 min, 4 min, 6 min and 10 min. After mixing up and down by pipetting and samples were spun into a collection plate with Supermix scintillant, and counted in a Microbetae plate reader.

TABLE E8

Effect of cysteine modification on thermal stability, aggregation and activity of HARS

| Name | Tm | % Low molecular weight aggregates | % High molecular weight aggregates | IC50 by ELISA Assay | Active site titration |
|---|---|---|---|---|---|
| Full-length HRS |  | 1.2 | 7.0 | 0.2 | ND |
| HRS(1-506) | 49.0 | 2.0 | 0.2 | 0.15 | 63.3 |
| HRS(1-506)C174V | 47.8 | 7.8 | 0.4 | 0.39 | 55.5 |
| HRS(1-506)C174A | 49.2 | 3.0 | 0.8 | 0.19 | 59.8 |
| HRS(1-506)C191A | 44.7 | 5.1 | 0.3 | 0.14 | 66.2 |
| HRS(1-506)C191V | 47.8 | 1.8 | 0.2 | 0.16 | 60.8 |
| HRS(1-506)C191S | 45.8 | 2.3 | 0.3 | 0.16 | 63.2 |
| HRS(1-506)C224S | 48.9 | 4.9 | 0.5 | 0.14 | 60.5 |
| HRS(1-506)C235S | 48.8 | 3.1 | 0.42 | 0.14 | 64.6 |

The results from these studies confirm that all of the cysteine mutants are active, with little or no loss in activity, stability, or conformation as measured by active site titration, ELISA binding and Tm determinations for thermal denaturation. Active site titration of tRNA synthetase activity revealed that all of the reduced cysteine mutants are active, and thus suitable for use in any of the compositions, methods and kits of the invention. In general the Cys191 substitutions displayed overall lower thermostability, while the Cys174 mutants exhibited significantly less heterogeneity as determined by isoelectric focusing.

Example 6

Creation of Modified Hrs Polypeptides with a C-Terminal Truncation (HisRS$^{N8}$)

To delete the last three amino acids and the linker between wild-type HisRS and the His tag, primers were designed for use with QuikChange Lightning Site-Directed Mutagenesis Kit (Agilent, cat no 210519). To accomplish this, the following primers are used as listed in Table E9:

TABLE E9

| Mutation | Oligo sequence | SEQ ID NO: |
|---|---|---|
| Delete CICAAALE For | 5'-CGCCGCACCGGTCAACCGTTACACCACCACCAC CACCACTG-3' | 66 |
| Delete CICAAALE Rev | 5'-CAG TGG TGG TGG TGG TGG TGT AAC GGT TGA CCG GTG CGG CG-3' | 67 |

The deletion was made per the QuikChange Lightning Site-Directed Mutagenesis Kit manufacturer's instructions. After mutagenesis, the sample was treated with Dpn I enzyme at 37° C. and transformed into XL10 gold competent cells using routine procedures. Multiple colonies were grown in luria-bertani broth overnight at 37° C. and the resulting plasmids were purified with QIAprep Spin Miniprep Kit (Qiagen cat. no. 27106). The plasmids were sequenced to confirm the identity of the amino acid substitution of each clone. To delete the His tag, primers were designed for use with QuikChange Lightning Site-Directed Mutagenesis Kit (Agilent, cat no 210519). To accomplish this, the following primers were used as listed in Table E10:

TABLE E10

| Mutation | Oligo sequence | SEQ ID NO: |
|---|---|---|
| Delete His-tag For | 5'-CGC CGC ACC GGT CAA CCG TTA TGA GAT CCG GCT GCT AAC-3' | 68 |
| Delete His-tag Rev | 5'-GTT AGC AGC CGG ATC TCA TAA CGG TTG ACC GGT GCG GCG-3' | 69 |

The deletion was made per the QuikChange Lightning Site-Directed Mutagenesis Kit manufacturer's instructions, as described above.

Protein Production.

BL21(DE3) competent cells (Novagen, cat. no. 69450) or W3110 cells (ATTC) were transformed with the codon-optimized expression construct encoding HisRS$^{N8}$ (HRS(1-506)) as described in Example 2. The expression system, fermentation media, and fermentation conditions used to produce recombinant protein were essentially same as described in Example 2.

Purification of Tag-Free HisRS$^{N8}$ (HisRS(1-506)).

Frozen cell paste (400 g) was resuspended in 4-volumes (1600 mL) of Lysis Buffer (50 mM Tris, 50 mM NaCl, 5 mM MgCl$_2$, 2 mM L-Cysteine, pH7.4). Complete EDTA-FREE protease inhibitor tablets (Roche, Cat #05 056 489 001) were added to the suspension at a ratio of 1 tablet/50 mL. The suspension was passed through a microfluidizer (Microfluidics) twice at 18,000 psi with cooling by ice. The lysate was centrifuged at 15,000×g for 45 min at 4° C. The supernatant was filtered through 2-3 AcroPak 1500 capsules (0.8/0.2 μm, Pall, PN12675).

The clarified lysate was loaded onto a 382 ml Q HP column (5×19.5 cm) pre-equilibrated with Q Buffer A (50 mM Tris, 50 mM NaCl, pH 7.4). The product was eluted with a linear gradient of 0-30% Q Buffer B (50 mM Tris, 1 M NaCl, pH 7.4) over 10 column volumes (CV). Fractions were collected at ½ CV/fraction and analyzed by SDS-PAGE. Pooling was based on gel analysis.

A 3.5 M ammonium sulfate solution was added to the Q HP pool above to a final concentration of 1.2 M. The mixture was filter through an AcroPak 200 (0.2 um) and loaded onto a 481 ml Phenyl HP column (5×24.5 cm) pre-equilibrated with 20 mM Tris, 1.2 M ammonium sulfate, pH 7.0. The product was eluted with a linear gradient of 1.2-0 M ammonium sulfate in 20 mM Tris/pH 7.0 over 10 CV. Fractions (½ CV/fraction) containing the product based on SDS-PAGE analysis were pooled.

The Phenyl Pool from above was concentrated to 0.5 L via a TFF system, consisting of a Pellicon Mini cassette holder (Millipore Cat#XX42PMINI), a Mastedlex I/P pump, and 2×0.1 m$^2$ cassette (30 kD MWCO, Novasep Cat#PP030M01L). The concentrated solution was then buffer exchanged with 6 diavolumes (3 L) of CHT Buffer A (10 mM sodium phosphate, 150 mM NaCl, pH 7.0). The retentate was filtered through a 0.2 μm Millex GP-50 filter (Millipore part #SLGP 05010) before proceeding to the next step.

The above solution was loaded onto a 380 ml ceramic hydroxyapatite (CHT) column (5×19.4 cm) pre-equilibrated with CHT Buffer A. The column was washed with Buffer A and followed by 6% Buffer B (500 mM sodium phosphate, 150 mM NaCl, pH 7.0). The product was eluted with a linear gradient of 6-56% Buffer B over 10 CV. Fractions (½ CV/fraction) containing the product based on SDS-PAGE analysis were pooled.

Using the same TFF system, the CHT Pool was concentrated to ~0.2 L, buffer exchanged with 6 diavolumes of the current formulation buffer (20 mM sodium phosphate, 150 mM NaCl, pH 7.0), and concentrated to a target concentration of ~10 mg/ml. The product solution was filtered through a 0.2 μm Millex GP-50 filter (Millipore part #SLGP 05010), and stored in −80° C. freezer.

Example 7

Evaluation of HRS Polypeptides to Bind to Anti-Jo-1 Antibodies from Human Patient Samples 96-well plates (Immulon 4HBX) were coated with a 50 μL solution of protein, adjusted to a concentration of 2 μg/mL with PBS. Plates were sealed and incubated overnight at 4° C. Prior to use, plates were washed five times with PBST and subsequently blocked with 100 μl 1% BSA in PBS for one hour at room temperature. While the ELISA plates were blocking, the competition molecule was incubated with commercially available α-Jo-1 antibodies (GenWay GWB-FB7A3D, Immunovision HJO-0100 or RDL) at various dilutions in 1% BSA PBS in a separate incubation plate (Costar 3357 96-well) for one hour at 4° C. After blocking was finished, the ELISA plates were washed three times with PBST and 50 μL of solution containing antibody and competitor was added to the ELISA plate and the samples incubated at room temperature for 1.5 hours. Following initial binding incubation, plates were washed five times with PBST. Next, 50 μL of detection antibody (AbD Serotec Goat Anti-human IgG F(ab')2:HRP 0500-0099) was added a 1:5,000 dilution and incubated for one hour at room temperature. Following secondary binding incubation, plates were washed with five times PBST and 50 μL TMB substrate (Thermo Scientific Pierce TMB Substrate PI-34021) was added. Reactions proceeded for 8 minutes at which point 50 μL of 2M sulfuric acid stop solution was added. Colorimetric quantification was performed using a SpectraMax plate reader at 450 nM.

Figure 3:
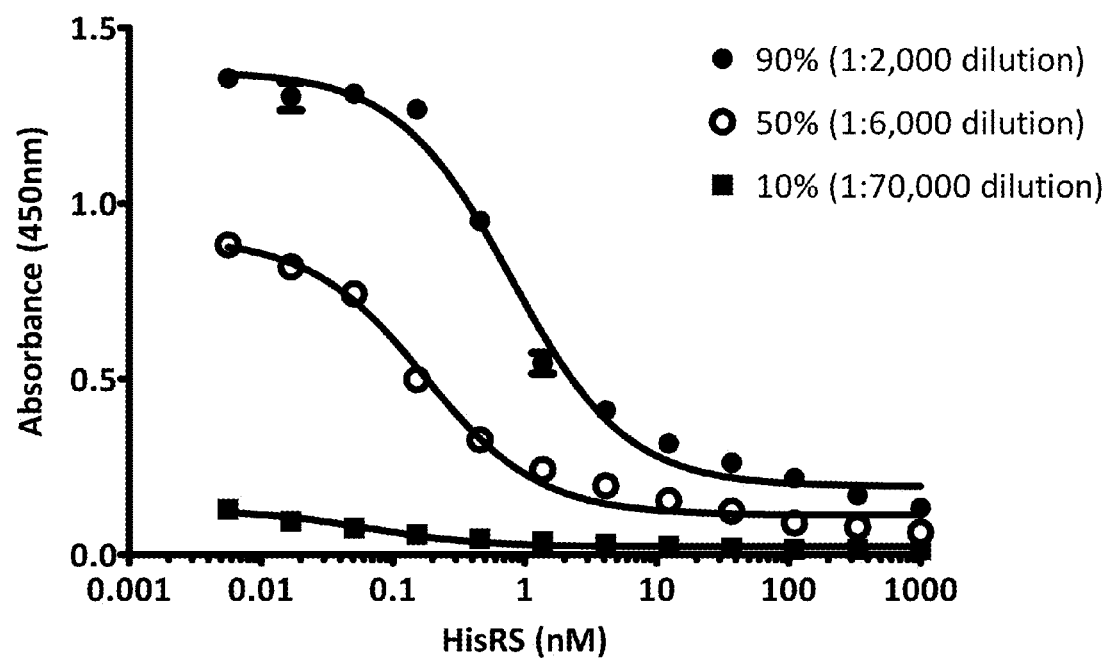
FIG. 3 shows the competition of anti-Jo-1 antibody containing serum with full-length HRS via an ELISA assay in which full-length wild-type HisRS is attached to the surface of a 96 well plate. The figure shows data from three dilutions of sera obtained from a human serum sample.
Figure 4:
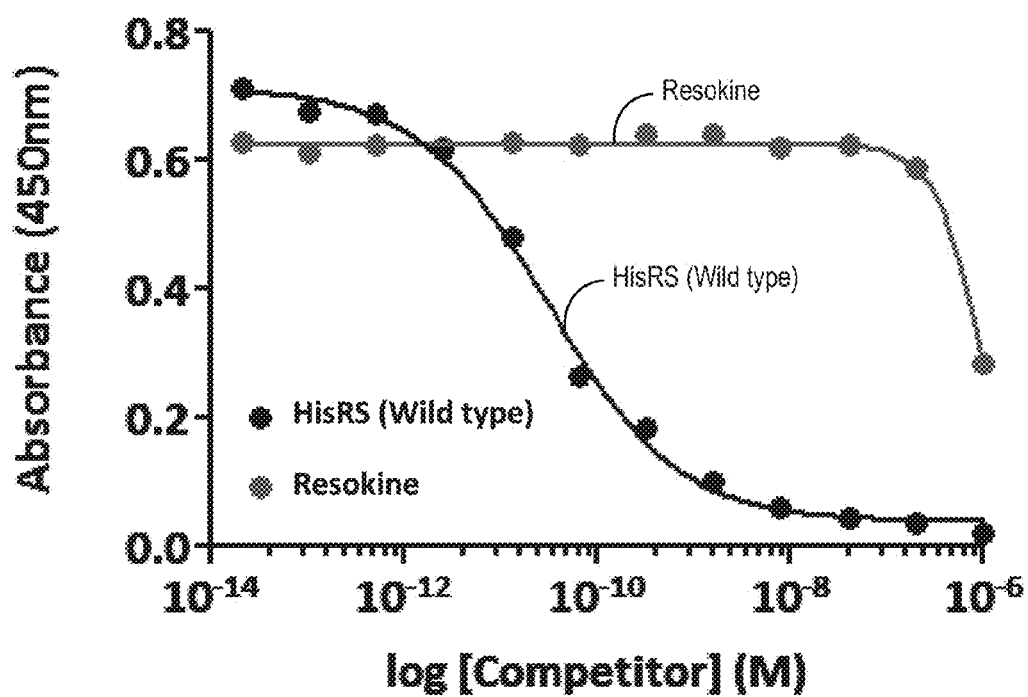
FIG. 4 shows the competition of anti-Jo-1 antibody containing serum with Resokine (HisRS$^{N4}$; HRS(1-60)), compared to full-length human HisRS (FL-hu HisRS) via an ELISA assay in which full-length wild-type HisRS is attached to the surface of a 96 well plate. The data shows that Resokine does not significantly compete for antibody binding to full-length HisRS until present at concentrations greater than about $1 \times 10^{-7}$ M, when full-length histidyl-tRNA synthetase is attached to the surface of the plate.
Figure 5:
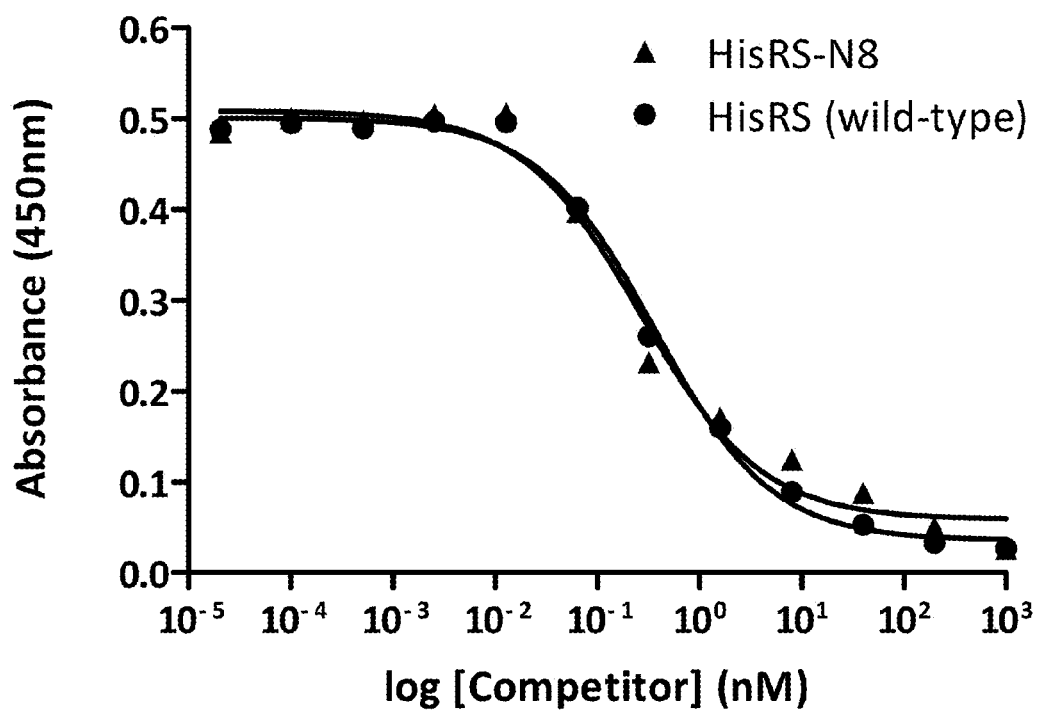
FIG. 5 shows the competition of anti-Jo-1 antibody containing serum with HisRS$^{N8}$ (HRS(1-506)), compared to full-length human HisRS via an ELISA assay in which full-length human wild-type HisRS is attached to the surface of a 96 well plate. The data shows that HisRS$^{N8}$ and the full-length HisRS share virtually identical competition binding curves to anti-Jo-1 antibodies.

Representative results are shown for competitive ELISAs for HisRS$^{N8}$ (HRS1-506) compared to full-length HRS (FIG. 5), Resokine (HisRS$^{N4}$: HRS(1-60)) compared to full-length HRS (FIG. 4), and full-length HRS incubated with serum over a range of dilutions (FIG. 3). The data shows that HisRS$^{N8}$ and full-length HRS, but not Resokine, are capable of competing for the binding of anti-Jo-1 antibodies from human patient samples with inflammatory myopathy and or interstitial lung disease who have anti-Jo-1 antibodies. Thus both HisRS$^{N8}$ and full-length HRS provides for a viable strategy to compete with and block the activity of anti-Jo-1 antibodies from human clinical samples having a disease associated with autoantibodies specific for histidyl-tRNA synthetase.

Additionally the data shows surprisingly that Resokine (HisRS$^{N4}$) under these conditions does not significantly cross react with anti-Jo-1 antibodies and does not significantly compete until present at concentrations greater than about $1 \times 10^{-7}$ M, when full-length histidyl t RNA synthetase is attached to the surface of the plate. Resokine (HisRS$^{N4}$) may thus be administered to patients to mediate an anti-inflammatory effect potentially without causing significant cross reactivity with circulating anti-Jo-1 antibodies.

Figure 6:
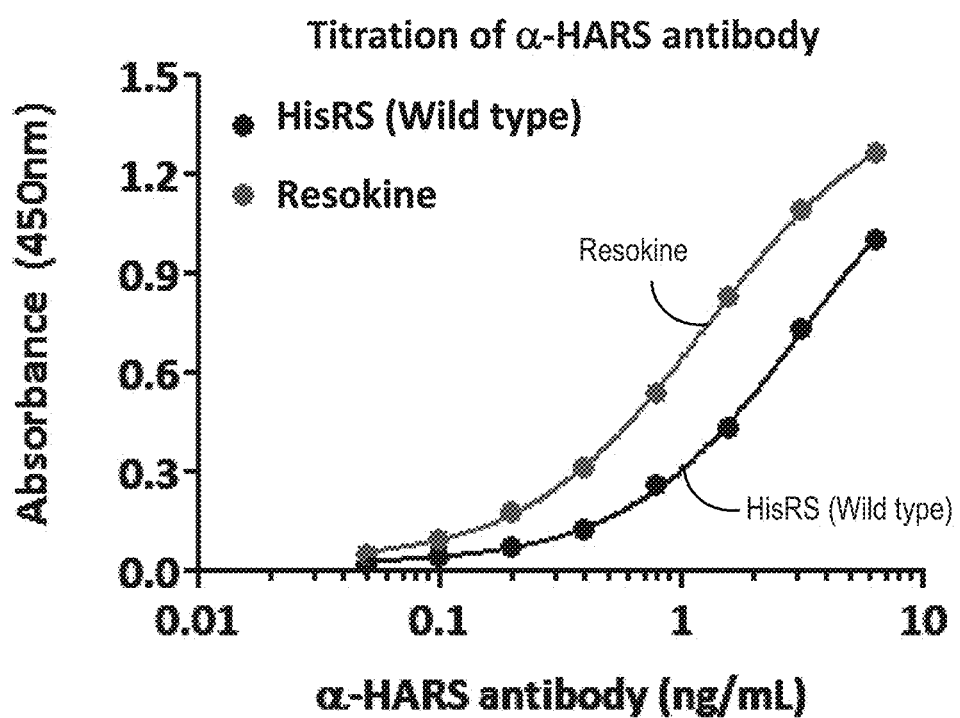
FIG. 6 shows a standard titering ELISA of anti-Jo-1 antibodies using either essentially full-length HARS, or HisRS$^{N4}$ (HRS(1-60)) attached to the plate surface. The data shows that when the assay is run under these conditions the apparent titers for antibodies to HisRS$^{N4}$ in anti-Jo-1 antibody containing serum is comparable to full-length HisRS.

To further explore this observation additional competition studies were conducted using traditional titering ELISAs (FIG. 6). The results show that when HisRS$^{N4}$ or essentially full-length histidyl-tRNA synthetase is attached to the surface of the plate the binding curves of anti-Jo-1 antibodies are roughly comparable, suggesting that avidity or other effects may contribute significantly to the apparent differences observed in the competitive ELISA assay.

Example 8

Evaluation of Anti-Jo-1 Antibody Epitope Specificity

To evaluate the epitope specificity of the anti-Jo-1 antibodies from a variety of patients, serum samples were obtained from RDL (California) and screened by a depletion ELISA approach to identify the relative antibody specificity of the samples.

Figure 7:
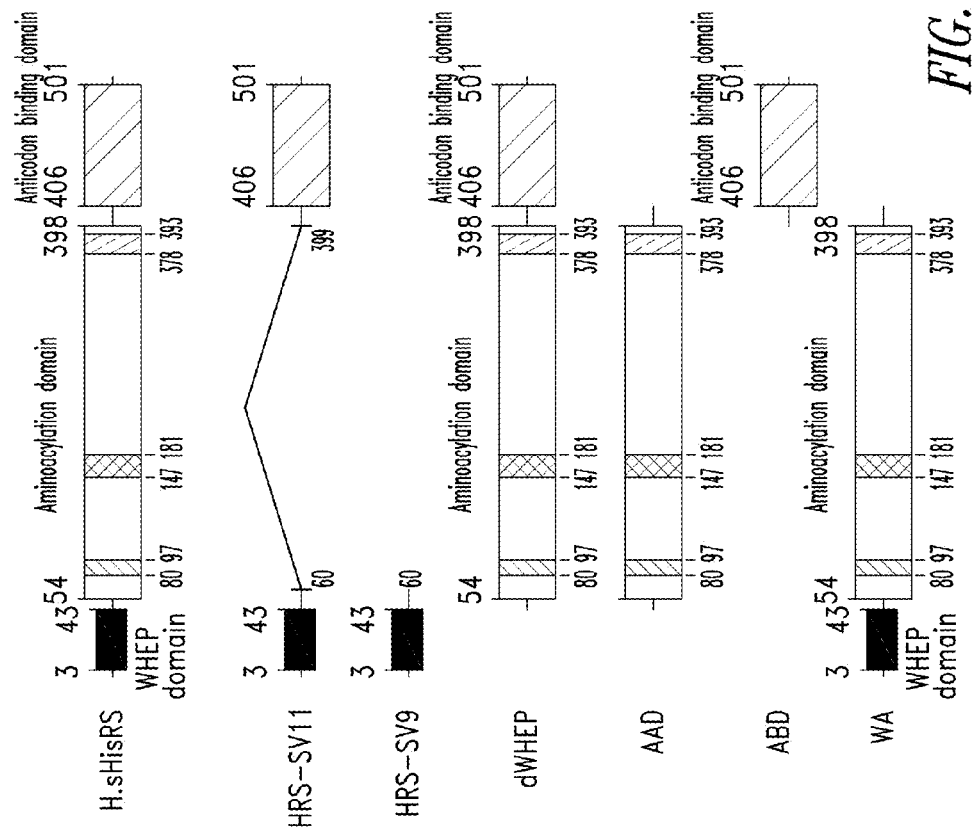
FIG. 7 shows a schematic representation of the HRS splice variant and other HRS constructs used in the epitope mapping studies.

In brief ELISA plates were set up with the His-tagged protein samples listed in FIG. 7, as described previously, which were expressed and purified in *E. coli*, as described in Example 2. Samples were first incubated in ELISA plates containing the proteins listed above (see Example 5), and the supernatants then transferred to a new ELISA plate to which was bound essentially full-length histidyl-tRNA synthetase. By comparing the antibody titers before and after depletion it is possible to calculate the portion of anti-Jo-1 antibody binding which is specific to each protein construct.

Figure 8:
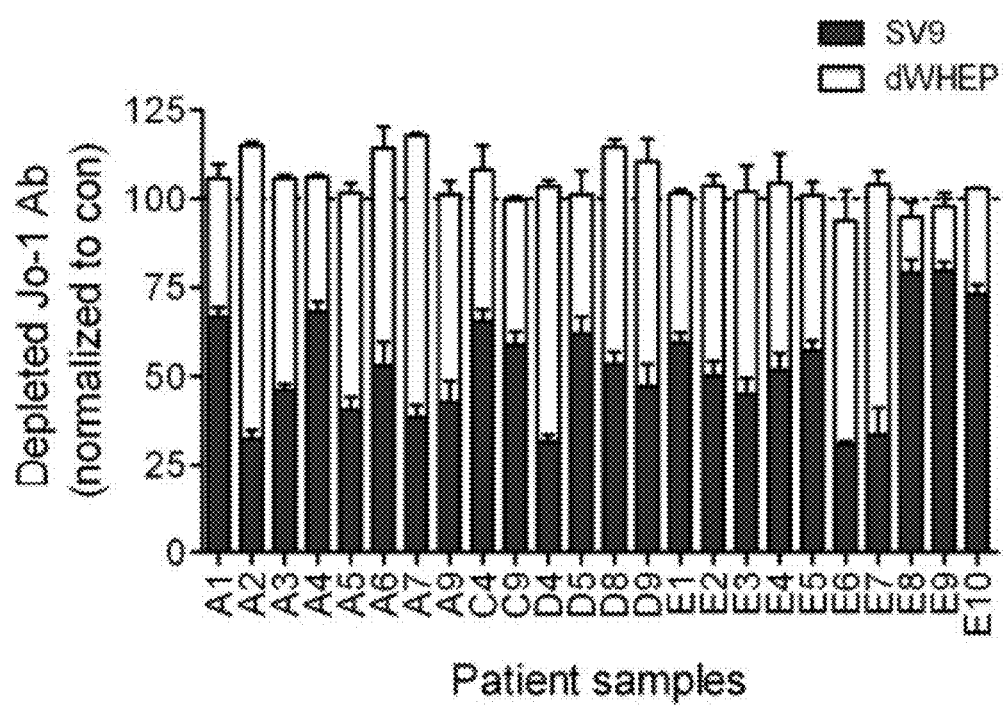
FIG. 8 shows the results of the epitope mapping studies and displays the antibody selectivity of a range of Jo-1 positive antibodies samples with respect to binding to the WHEP domain (HisRS$^{N4}$; SV9; or HRS(1-60)), or a deleted HisRS (comprising amino acids 54-506 of SEQ ID NO:1) (dWHEP) construct that lacks the WHEP domain.

The data, shown in FIG. 8, shows a broad a range of antibody specificities to both the WHEP domain region (1-60) as well as the remaining portion of the protein (dWHEP).

Example 9

Extracorporeal Removal of Jo-1 Antibodies with HRS Polypeptides

To evaluate whether HRS polypeptides could be used to effectively immunodeplete anti-HRS antibodies (e.g., anti-Jo-1 antibodies) from patient serum, samples of HRS(1-506) and HRS(1-60) were immobilized onto a solid support, and then contacted with sera to determine if there were capable of immunodepleting the serum samples of anti-HRS antibodies. Anti-Jo-1 antibody titers were measured before and after application to the affinity column to assess the ability of each of the HRS polypeptides to remove anti-Jo-1 antibodies.

Immobilization of HRS Polypeptides and Jo-1 Antibody Depletion.

Full-length HARS, HRS(1-506), HRS(1-60), and bovine serum albumin were immobilized to agarose gel using N-hydroxy-succinimide (NHS) crosslinking chemistry as per manufacturer's recommendations (Bio-Rad Affi-gel 10 catalog #153-6046). A ratio of 2 mg of protein per 1 mL of resin was used for conjugation. Human anti-Jo-1 antibodies, obtained from a commercial provider (RDL, Los Angeles Calif.), were diluted to 1:1,000 and then samples flowed through a column made with each of the immobilized HRS polypeptide agarose conjugates prepared as described above. Jo-1 antibody titers were determined before and after passage through the affinity column as described below.

Jo-1 Antibody Titering.

96-well plates (Thermo scientific Immulon 4 HBX plates, catalog #6484) were coated with HisRS1 at a concentration of 2 mcg/mL in PBS overnight at 4° C. The next day plates were washed with PBST and blocked with 1% BSA (Invitrogen, catalog #15260) diluted in PBS for 1 hour at room temperature. Plates were then washed three times with PBST and incubated with samples containing Jo-1 antibodies for 1.5 hours at 37° C. Plates were then washed again three times with PBST and incubated with secondary antibody (AbD Serotec goat anti-human IgG, catalog #0500-0099) and incubated for 1 hour at room temperature. Plates were then washed again three times with PBST and incubated with 3,3',5,5'-tetramethylbenzidine (TMB) substrate (Thermo scientific, catalog #34021) for 5 minutes and 2M sulfuric acid is added and mixed to stop the reaction. Plates are then read at 450 nM and relative antibody titer was determined.

Figure 9:
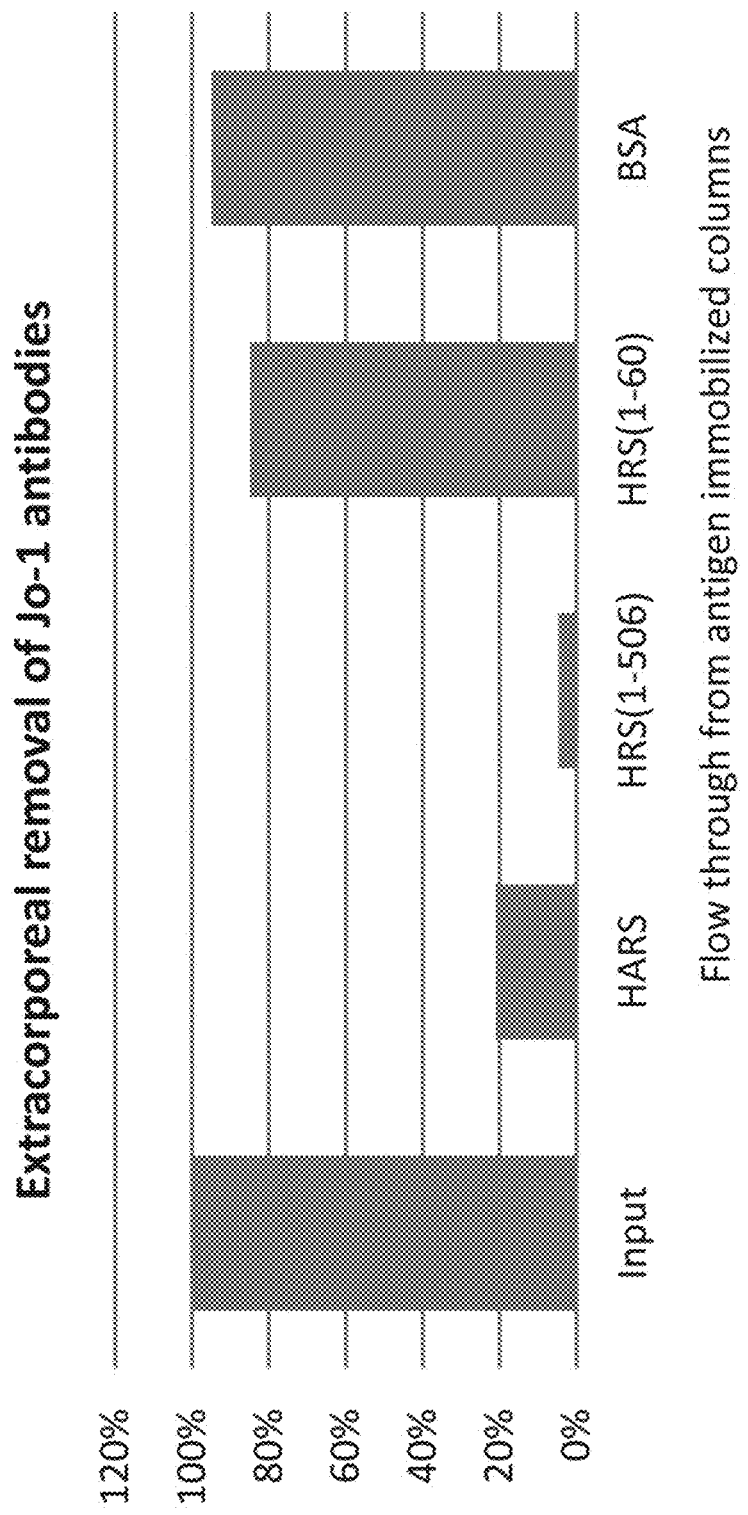
FIG. 9 shows the results of immuno-depletion studies using full-length HRS and HRS(1-506). The results show that both full-length HARS and HRS(1-506) were effective in immuno-depleting Jo-1 antibodies from human serum samples, and that HRS(1-506) was capable of removing up to 99% of the detectable Jo-1 antibodies.

The results (FIG. 9) revealed that both full-length HARS and HRS(1-506) were effective in immuno-depleting Jo-1 antibodies from human serum samples. Surprisingly HRS(1-506) was capable of removing up to 99% of the detectable Jo-1 antibodies, with a single pass through the affinity resin, whereas full-length HARS was capable of removing only about 93% of the detectable antibodies under the same conditions. Consistent with previous studies, the use of a smaller fragment of HARS, HRS(1-60) was capable of depleting only about 20% of the detectable Jo-1 antibodies, suggesting that this HRS polypeptide could be useful for the selective removal of specific sub-populations of circulating Jo-1 antibodies.

Example 10

Evaluation of Hrs Polypeptides for the Treatment of Statin-Induced Myositis and Rhabdomyolysis Statins are HMG CoA Reductase inhibitors which inhibit the synthesis of mevalonate, the rate limiting step in cholesterol synthesis. Statin therapy has proved beneficial in lowering cholesterol levels in patients. However, side-effects and complications of statin therapy include muscle weakness, myositis and Rhabdomyolysis. Muscle myopathy is a complication with several statins on the market and patients are often removed from their statin-therapy if they exhibit any of these symptoms. Like many other myopathies, muscular dystrophies and inflammatory disorders of muscle, disease progression in statin induced myopathy appears to occur as the result of an initial chemical, genetic or physical injury, which becomes increasingly inflamed as a result of immune cell invasion into the damaged muscle cells.

Accordingly statin induced myopathy represents a broadly applicable model system to study drug induced myositis, which is directly applicable to other myopathies and muscular dystrophies, all of which all share a common inflammatory component which mediates disease progression by promoting immune cell invasion of the damaged muscle tissue.

The purpose of this study was to evaluate the efficacy of HRS(1-506) in reversing the effects of statin-induced muscular myositis, as indicated by altered circulating enzyme levels, and changes in gene expression of muscle function and inflammatory markers in response to treatment with HRS(1-506).

To achieve this, rats were dosed daily with 1 mg/kg Cerivastatin and then switched to an every other day (qod) dosing with Cerivastatin. The goal of this dosing regimen was to maintain a sustained disease state in the animals, but not to have such severe disease that rat survival is greatly impacted. The efficacy of a dose range of HRS(1-506) was then evaluated in rats after statin-dosing had already initiated measureable changes in circulating markers of myositis.

Protocol and Methods.

Figure 10A:
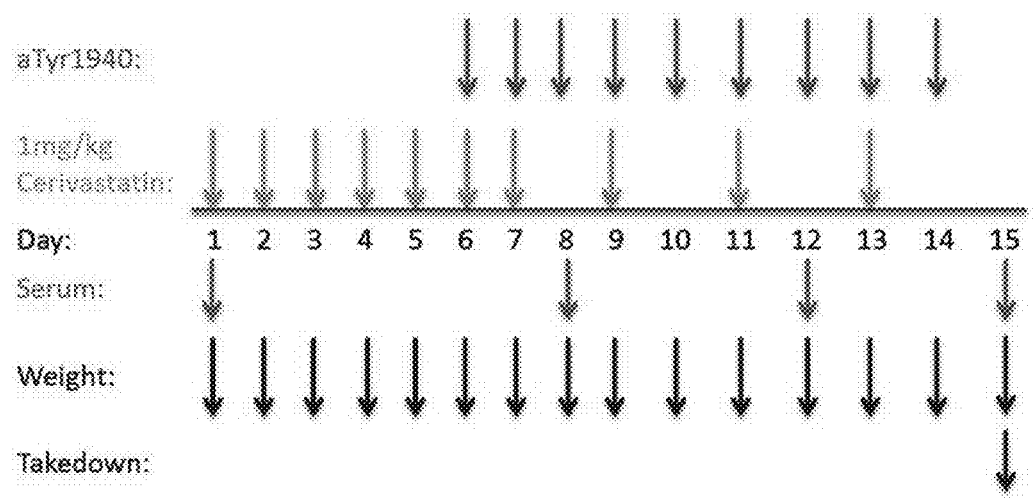
FIG. 10A shows the schematic of the dosing strategy used to evaluate the effects of HRS(1-506) (or ATYR1940) in a rat model of statin-induced myositis.

In this study, 10 week old female Sprague-Dawley rats were treated with 1 mg/kg Cerivastatin ((Sigma, Cat No. SML0005) in 0.5% methylcellulose, starting on day 1 via oral gavage. After 7 days of daily administration, rats were switched to an every other day dosing strategy (qod) on days 9, 11 and 13. HRS(1-506) and vehicle administration were initiated on day 6 through intravenous injection and rats were dosed daily to day 14 (shown schematically in FIG. 10A). All rats were taken down on day 15, 24 hours after the final test article dosing and 48 hours after the last statin administration. HRS(1-506) was administered at 3 doses (0.3, 1.0 and 3.0 mg/kg) in 20 mM NaPO4, 0.15M NaCl, pH 7.0 daily.

To address the primary objective of this study, the following study measurements and endpoints were performed: rat survival, weight, circulating serum CK levels at days 12 and 15, H&E staining on day 15 hamstring samples, Troponin-I ELISA, CBC on day 15 blood, qPCR on hamstring samples and serum endogenous HARS levels.

qPCR Methods.

Mouse hamstring was excised from the animals and stored at −80° C. until analysis. Tissue was prepped in groups of 10 hamstrings using Qiagen's RNeasy Fibrous Tissue Midi Kit (Catalog #75742). Once RNA was eluted from the Qiagen column, it was run on an Agilent's Bioanalyzer 2100 to test RNA integrity and NanoDrop to determine RNA concentration and purity. RNA was then stored at −80° C.

Reverse transcription (RT) of RNA to cDNA was performed in a 96 well PCR plate format in Eppendorf s Mastercycler PCR machine with the following program: 37° C. for 60 minutes, 95° C. for 5 minutes. The edge wells of the 96 well plate were not used and filled with 50 mcL water to prevent evaporation of inside wells. 20 mcL RNA and 30 mcL of reverse transcription master mix (Ambion's TaqMan PreAmp Cells to CT Kit catalog #4387299) was used per sample RT. Once RT was completed, next step was to pre-amplify genes of interest in the sample cDNA. Primers of genes of interest (DELTAgene primers designed by Fluidigm) were combined to a final concentration of 200 nM. Using these primers, genes of interest were pre-amplified in each sample. Pre-amplification was performed in 10 mcL reactions (2.5 mcL cDNA, 7.5 mcL Pre-Amp mastermix) in 384-well format using an Applied Biosystems ViiA7 PCR machine with the following program: 95° C. for 10 minutes, 14 cycles of 95° C. for 15 seconds and 60° C. for 4 minutes. After pre-amplification step, exonuclease (New England BioLabs catalog #M0293L) was added to remove unincorporated primers from each sample. This exonuclease reaction was also completed in the ViiA7 PCR machine with the following program: 37° C. for 30 minutes, 80° C. for 15 minutes. After exonuclease, the RT sample was further diluted 1:5 (7 mcL exonuclease sample+18 mcL low EDTA buffer).

The chip used to run qPCR on Fluidigm's Biomark system was a 96.96 Dynamic Array IFC for Gene Expression. The chip was first primed with the IFC controller HX as per manufacturer's recommendations before sample and assays were loaded. To prepare assays to be loaded on a chip, 4.4 mcL assay master mix (Fluidigm's 2× Assay Loading Reagent catalog #8500736 and low EDTA TE) to 3.6 mcL 20 mcM forward and reverse primers for each gene of interest were prepared in a 96 well plate. To prepare samples, 4.5 mcL sample master mix (Ambion's 2× TaqMan Gene Expression Master Mix, Fluidigm's 20×DNA Binding Dye Sample Loading Reagent catalog number 100-0388, and Biotium's 20× EvaGreen catalog #31000) was added to 3 mcL diluted pre-amplified/exonuclease sample in a 96 well plate. Once the chip had been primed, 5 mcL sample or assay prepared above were loaded onto the chip. The chip was them returned to the IFC controller for the samples to be loaded into the chip. After the chip had finished loading, qPCR could then be run on the Biomark using preset program for 96.96 Dynamic Array for Gene Expression with a melt curve to determine primer specificity. Relative gene expression was determined by the delta-delta Ct method.

Quantification of Extracellular HARS.

A 96 well based ELISA was developed in-house using 2 mouse anti-HARS monoclonal antibodies M03 (Sigma #SAB1403905, and Abnova #H00003035-M03) and M01 (Abgent #AT2317a) in a sandwich format to detect HARS in rat serum. Assays were run in 96 well Costar plates (Costar 96-well plate #3369) using a seven point standard curve which was generated ranging from 75 to 0.1 ng/ml using a stock solution of HRS(1-506); (7.5 mg/ml in 20 mM NaPO4, 0.15 M NaCl pH 7.0, using 1×PBST (0.05% Tween-20) as a diluent). The: M01 mouse monoclonal, clone 1C8 (Abgent #AT2317a) was biotinylated in house and used as the detection antibody, and the M03 mouse monoclonal antibody (Sigma #SAB1403905, lot #11238, 0.5 mg/mL and Abnova #H00003035-M03, lot #11238, 0.5 mg/mL) was used as a capture antibody. Casein (Thermo Scientific #37528) was used as a blocking agent, and 1×PBST (0.05% Tween-20) was used as a wash buffer. Antibody binding was quantified using Streptavidin-HRP (Invitrogen cat #434323, Lot #816755A) using TMB Substrate (Thermo #34021) and with 2M sulfuric acid as the stop solution.

ELISA assays were run by Coating plates overnight with 0.6 to 2 µg/ml M03 antibody in 1×PBS, which were then blocked by incubation with casein for one hour, and washed 3× with PBST. Plates were then incubated with standards and samples for 1 hour, washed 3×PB ST, and then incubated with 500 ng/ml biotinylated-M01 diluted in PBST, 1 hour, washed 3×PBST, incubated with 200 ng/ml streptavidin-HRP for one hour, washed 3× with PBST, and then the TMB substrate was added for 4 minutes. Reactions were stopped with stop solution and absorbance read at 450 nm.

The results were quantified based on the standard curve based on the average raw absorbance values without background subtraction. Prism was used for standard curve fitting. Model: Log(agonist) vs. response fit [4-parameter logistic regression] Percent recovery was calculated for each individual concentration point (not averaged) by:

$$\frac{(\text{measured} - \text{actual}) \times 100\%}{(\text{actual})}$$

Other Readouts.

Rats were weighed daily. Serum samples were taken on days 1, 8, 12 (via tail vein) and day 15 (terminal) to be used for circulating enzyme analysis (Idexx) and serum skeletal muscle Troponin-I measurements, were measured using a commercial ELISA kit. Urinalysis was performed on days 3, 5, 8, 10, 12 and 15 prior to dosing on that day. CBC analysis was run on blood isolated on day 15 prior to euthanizing rats. On day 15, the rats were euthanized and a portion of the hamstring muscle and lung (not inflated) was placed in 10% NBF for paraffin embedding and H&E staining of sections (Premier Laboratory). Another portion of hamstring muscle and lung was placed at −80 C to use for RNA extraction and profiling. Liver, kidney and heart were also isolated on day 15 and placed in zinc-formalin for paraffin embedding (TSRI Histology) for long-term tissue storage.

Results.

There was 100% survival in this study, and all rats survived to the scheduled takedown on day 15. Statin-dosed rats had lower average weights than control rats not dosed with statin. On day 15, the statin+vehicle group had the lowest average rat weight of all the groups, whereas the Statin+3 mg/kg HRS(1-506)-dosed group had the highest weight average of all the statin-treated animals (data not shown). CBC analysis showed overall similar patterns of changes between different animal treatment groups (data not shown).

Figure 10B:
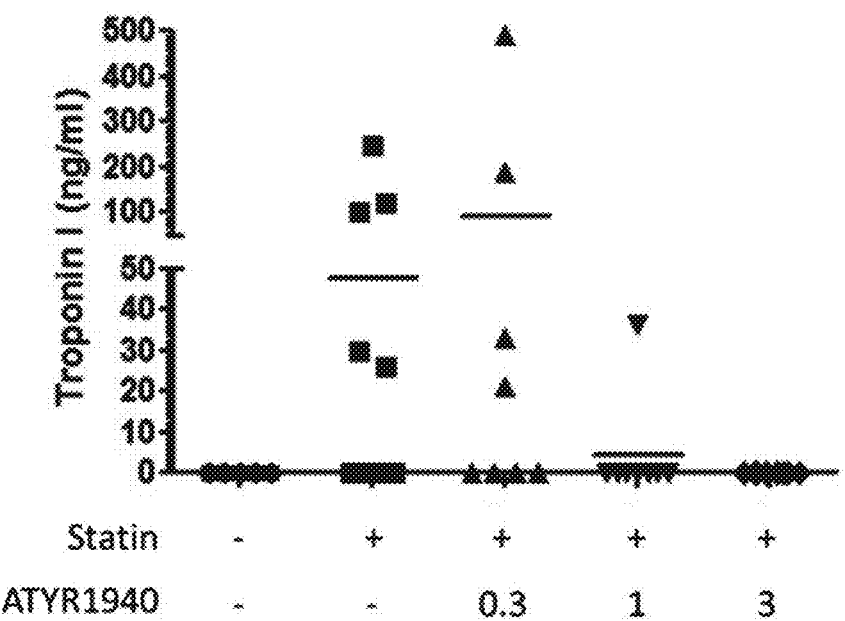
FIG. 10B shows the effects of HRS(1-506) on reducing muscle troponin levels in the rat model of statin-induced myositis.
Figure 11A:
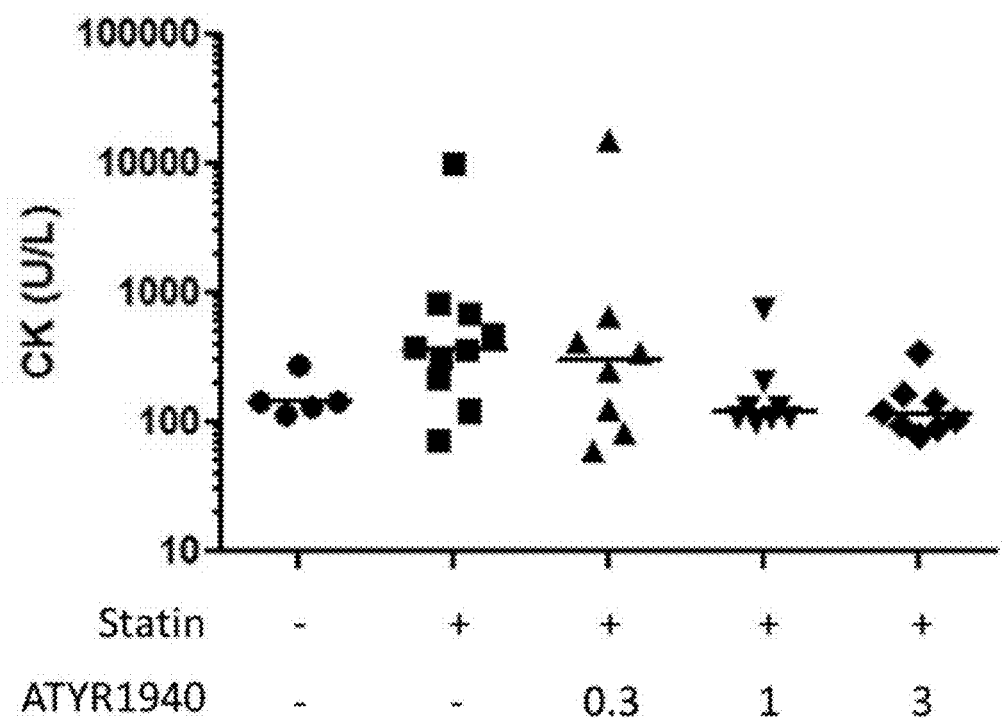
FIGS. 11A-11B show the effects of HRS(1-506) on CK levels in the rat model of statin-induced myositis.
Figure 11B:
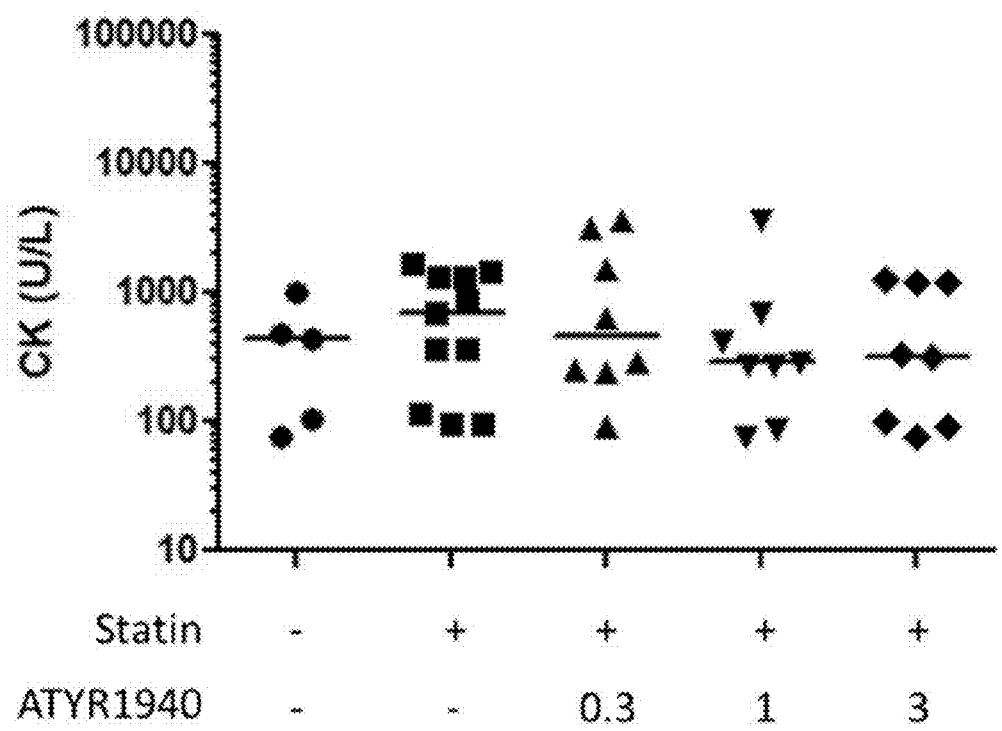
Figure 12:
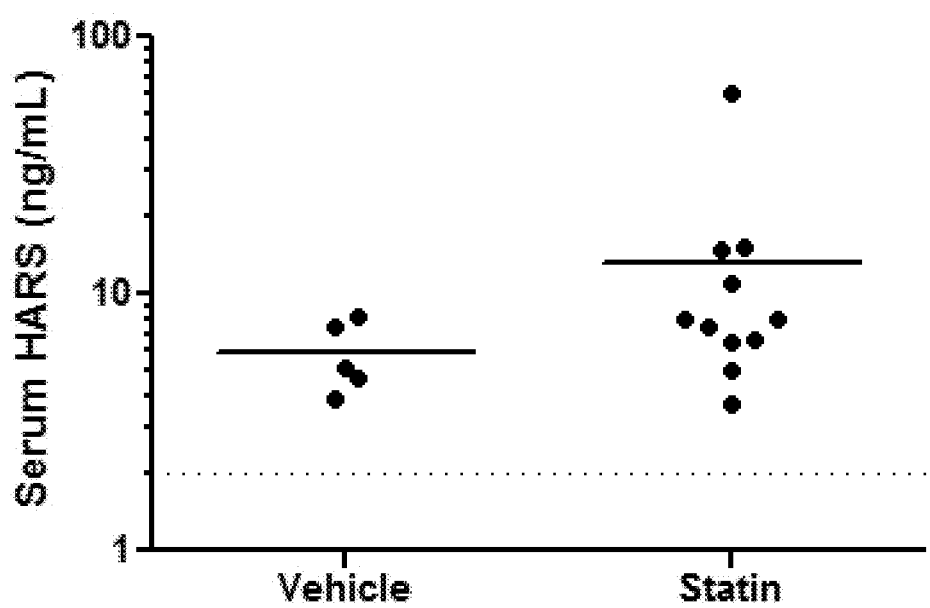
FIG. 12 shows that endogenous serum HRS levels were elevated in statin-treated rats relative to untreated rats. This result suggests that the release of endogenous HRS may play a role in regulating muscle inflammation.
Figure 13:
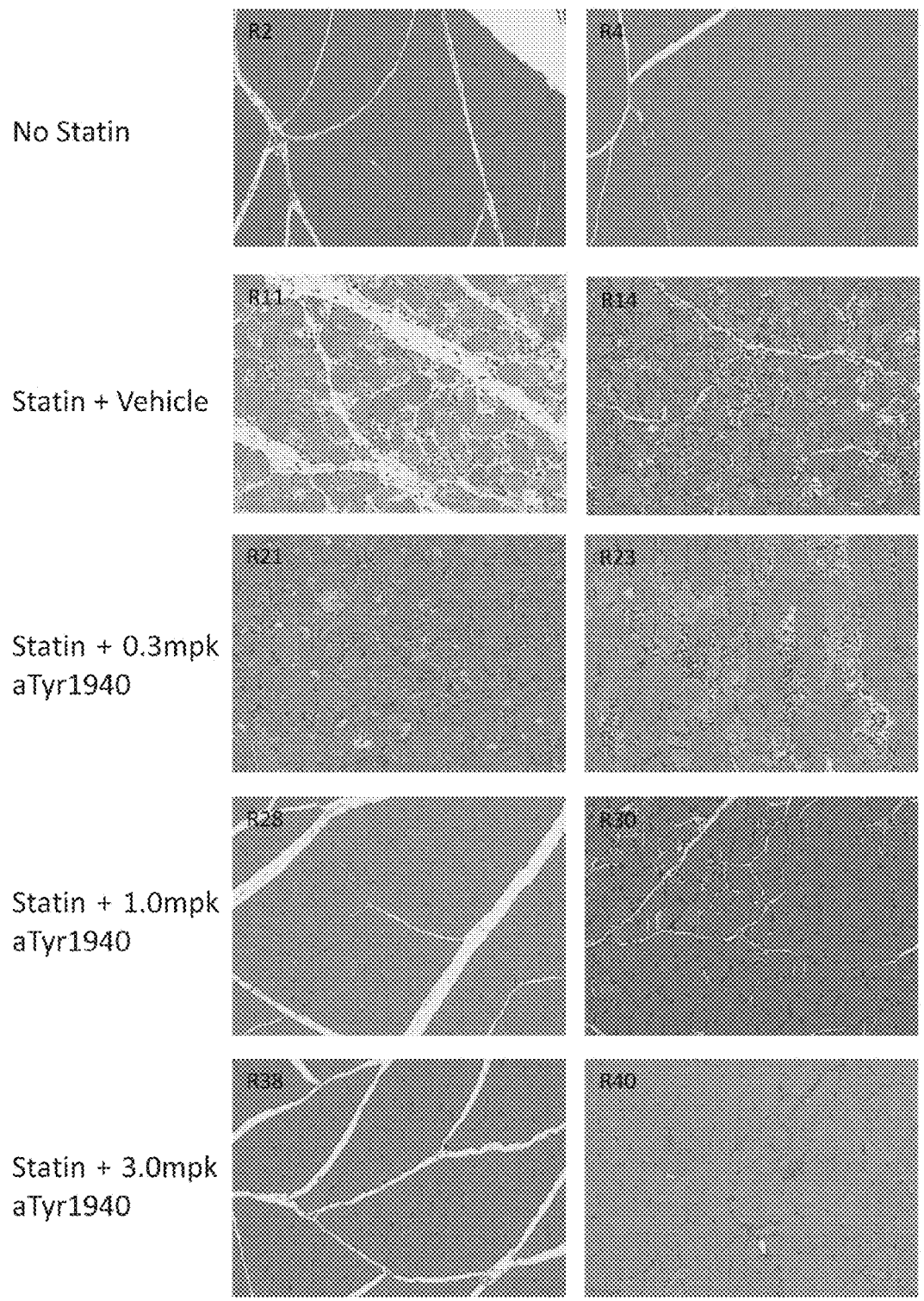
FIG. 13 shows H&E staining of hamstrings in the rat model of statin-induced myositis. These results show reduced muscle degeneration/necrosis and inflammation scores in statin-induced rats that were treated with 1 mg/kg and 3 mg/kg HRS(1-506) relative to vehicle-treated and 0.3 mg/kg HRS (1-506)-treated rats.

A small increase in serum CK was observed in statin treated rats over untreated controls on days 12 and 15. On day 12, rats dosed with 1 mg/kg and 3 mg/kg HRS(1-506) had smaller, tighter CK averages compared to Statin+Vehicle treated animals. (FIG. 11) consistent with a positive impact of HRS(1-506) treatment on statin induced myositis, also consistent with a positive effect of HRS(1-506) on muscle function, muscle troponin C levels were also reduced in HRS(1-506) treated animals (FIG. 10B). Moreover endogenous serum HRS levels were elevated in statin-treated rats compared to rats not receiving statin (FIG. 12), suggesting that the release of HRS may play a role as an endogenous regulator of muscle inflammation. H&E staining on hamstrings demonstrated reduced muscle degeneration/necrosis and inflammation scores in statin-treated rats dosed with 1 mg/kg and 3 mg/kg HRS(1-506) compared to vehicle-dosed and 0.3 mg/kg HRS(1-506)-dosed rats (FIG. 13).

Figure 14:
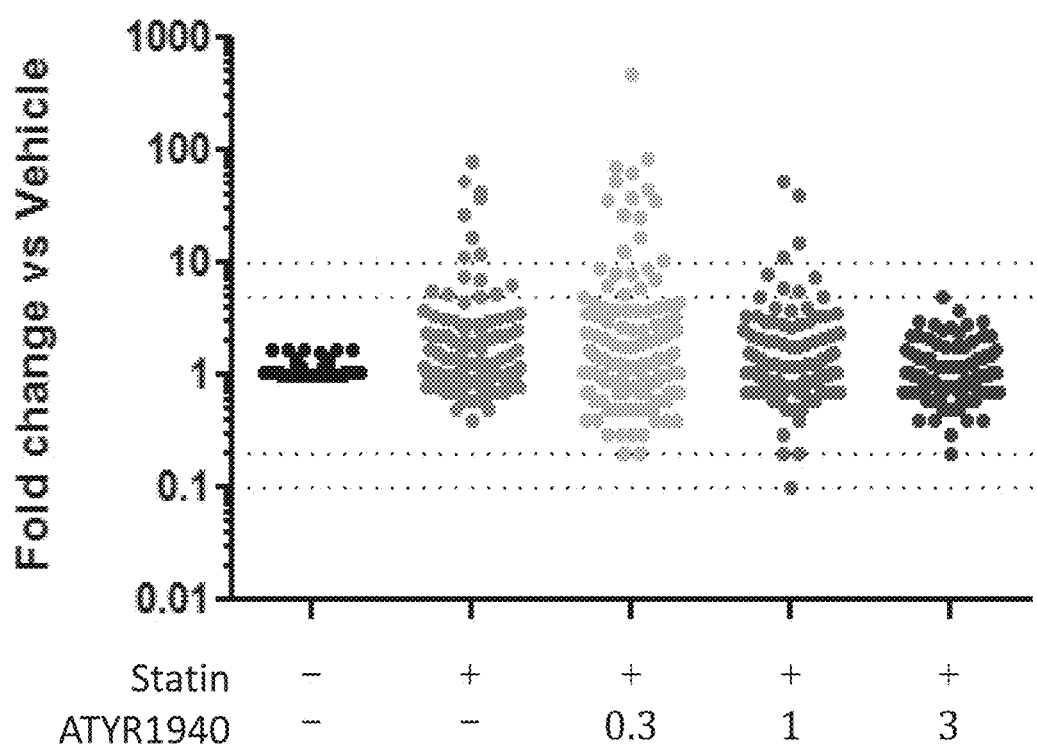
FIG. 14 shows the results of RNA profiling performed on hamstring muscles from statin-induced rats, which were treated with increasing amounts of HRS(1-506). These results demonstrated that all 13 genes that were elevated by more than 5-fold in response to statin treatment were reduced by treatment with HRS(1-506).
Figure 15A:
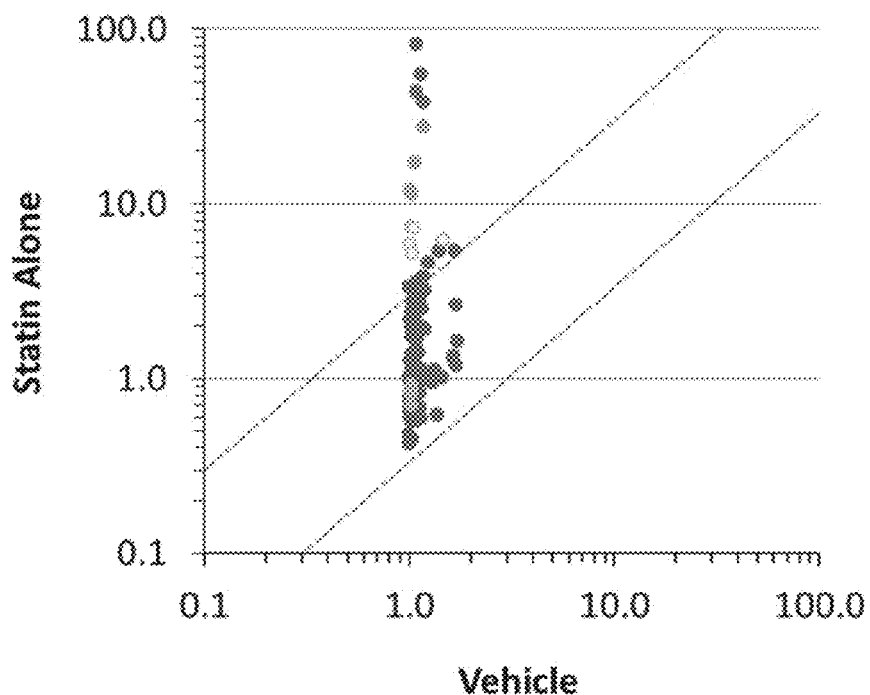
FIG. 15A shows the results of RNA profiling performed on hamstring muscles from statin-induced rats.
Figure 15B:
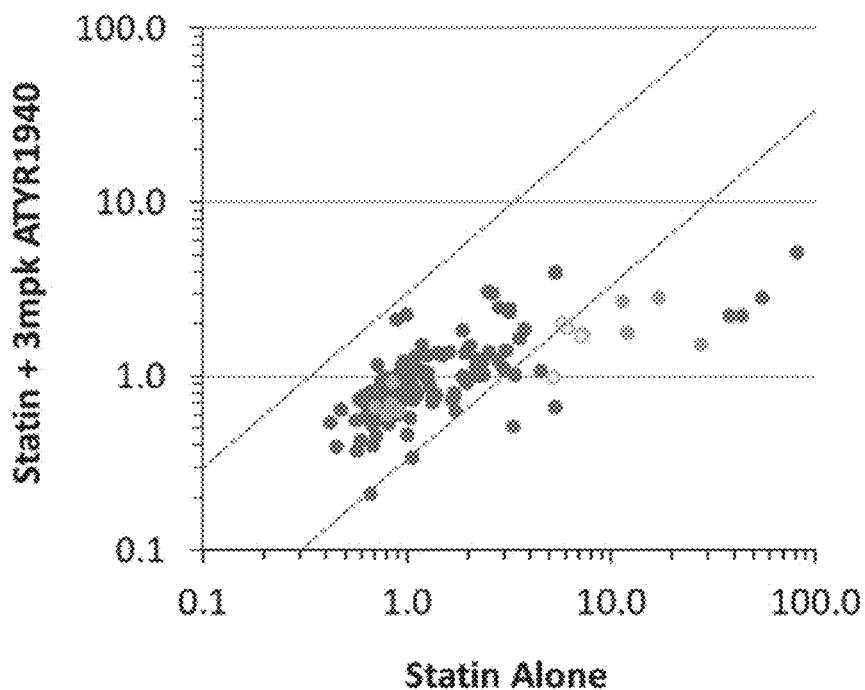
FIG. 15B shows the results for statin-induced rats treated with HRS(1-506).

To further investigate the mechanistic basis for the effects of HRS on statin-induced myopathy, changes in gene expression in the hamstrings from treated animals was examined after the completion of the study. RNA profiling was performed on hamstring muscles isolated from the rats on day 15 as described above. The results from these studies demonstrated that all 13 genes that were elevated by more than 5 fold in response to statin treatment were reduced by treatment with HRS(1-506) (see Table E11; and FIGS. 14-15)

TABLE E11

| Gene regulated by more than 25 fold | Gene regulated by more than 10 fold | Gene regulated by more than 4 fold | No Change |
|---|---|---|---|
| CD8a | MCP1 | CD11a | HARS |
| MMP9 | CD8b | CD11b | HARS2 |
| IL6 | CCR5 | CD45 | DARS |
| IL10 | CD18 | SDC1 | GARS |
|  |  | IFN-g | QARS |

Figure 16:
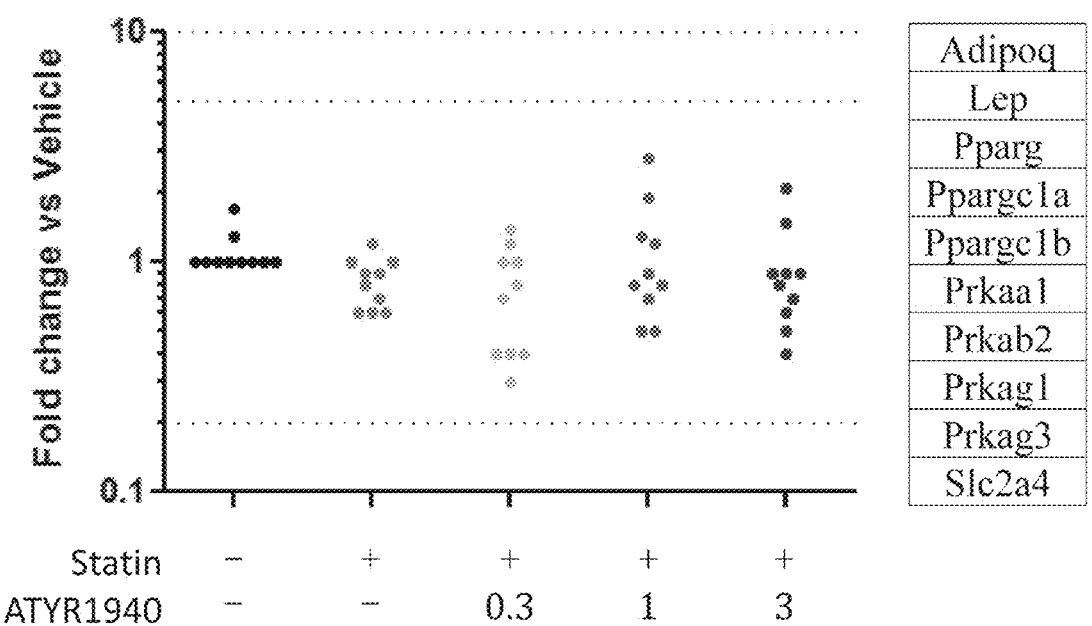
FIG. 16 shows the transcriptional profiling of hamstrings from statin-induced rats. These results revealed that expression of 10 diabetes/metabolic syndrome related genes and several housekeeping genes (data not shown) were not significantly impacted by HRS(1-506) treatment.
Figure 17:
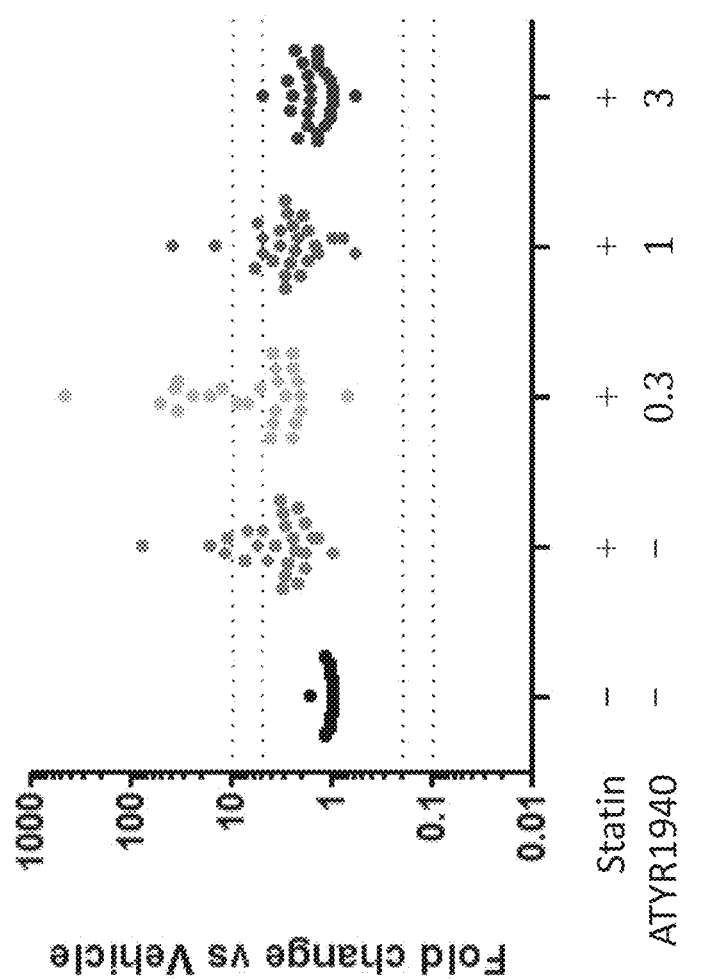
FIG. 17 shows the transcriptional profiling of hamstrings from statin-induced rats. These results revealed that expression of numerous immune cell marker genes was reduced by HRS(1-506) treatment.
Figures 18A, 18B:
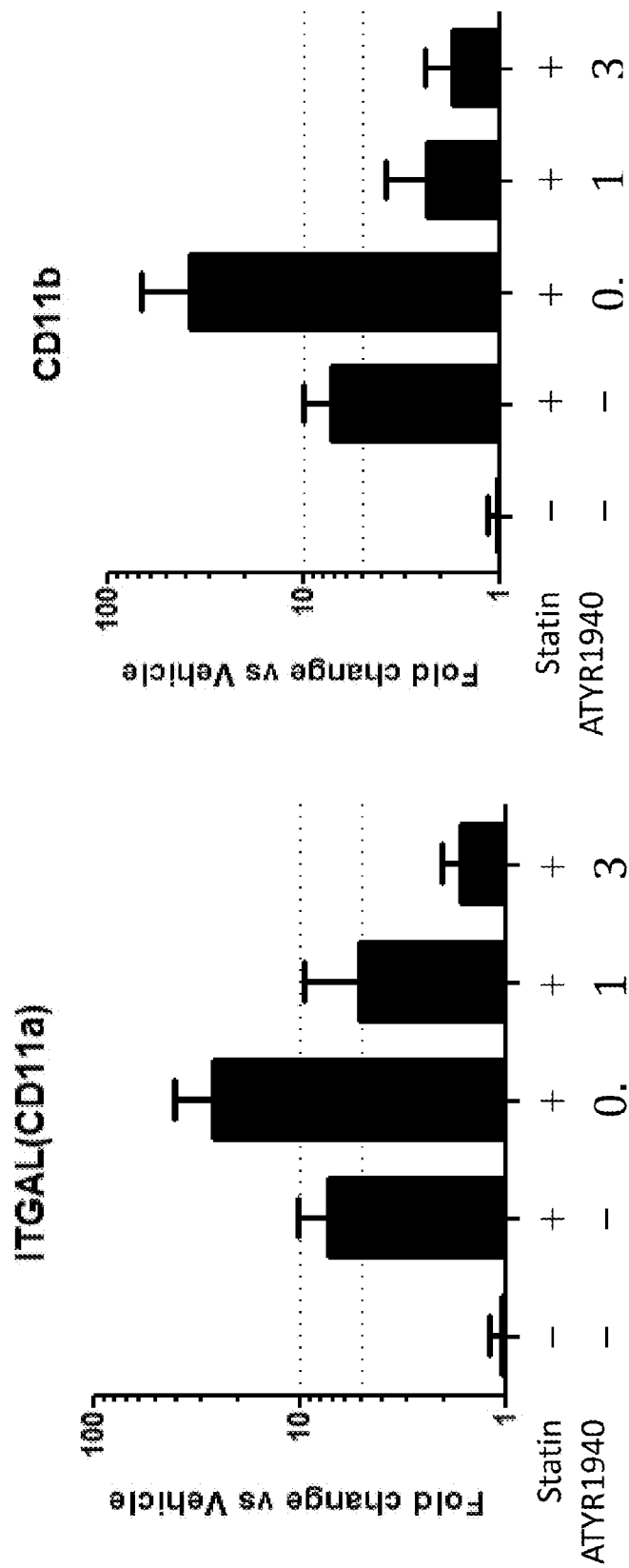
FIGS. 18A-18D show that HRS(1-506) treatment reduced the expression of immune cell marker genes ITGAL (CD11a) (FIG. 18A), CD11b (FIG. 18B), CD8a (FIG. 18C), CD8b (FIG. 18D).
Figures 18C, 18D:
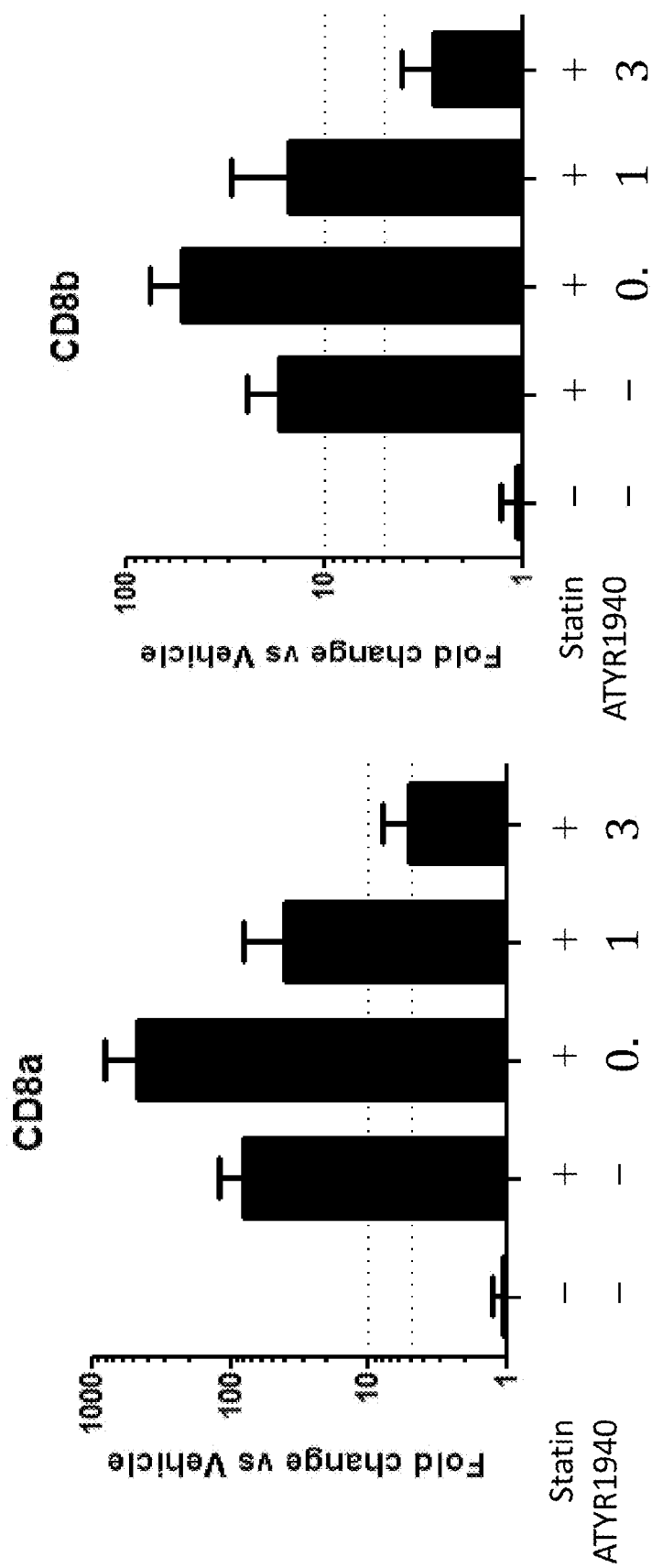
Figure 19B:
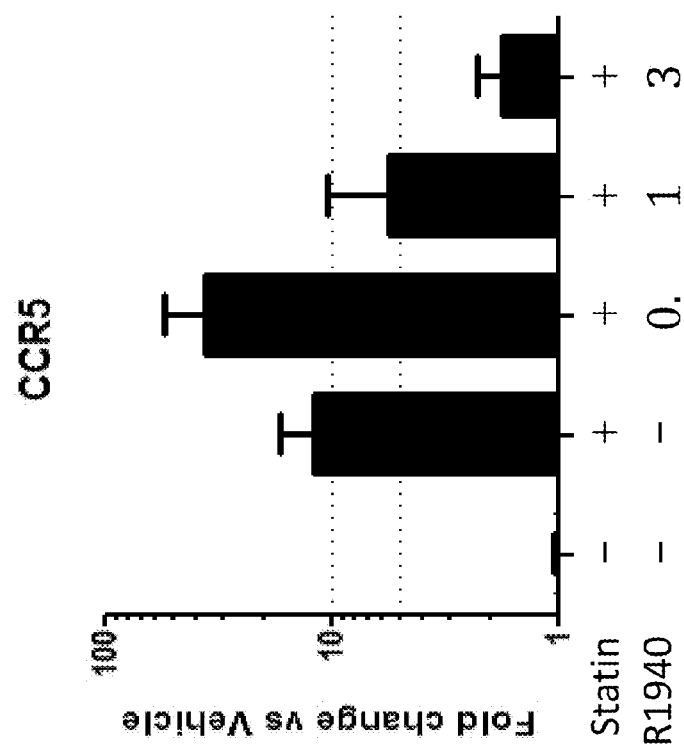
FIGS. 19A-19C show that HRS(1-506) treatment reduced the expression of immune cell marker genes CD18 (FIG. 19A), CCR5 (FIG. 19B), and PTPPC (CD45R) (FIG. 19C).
Figure 19A:
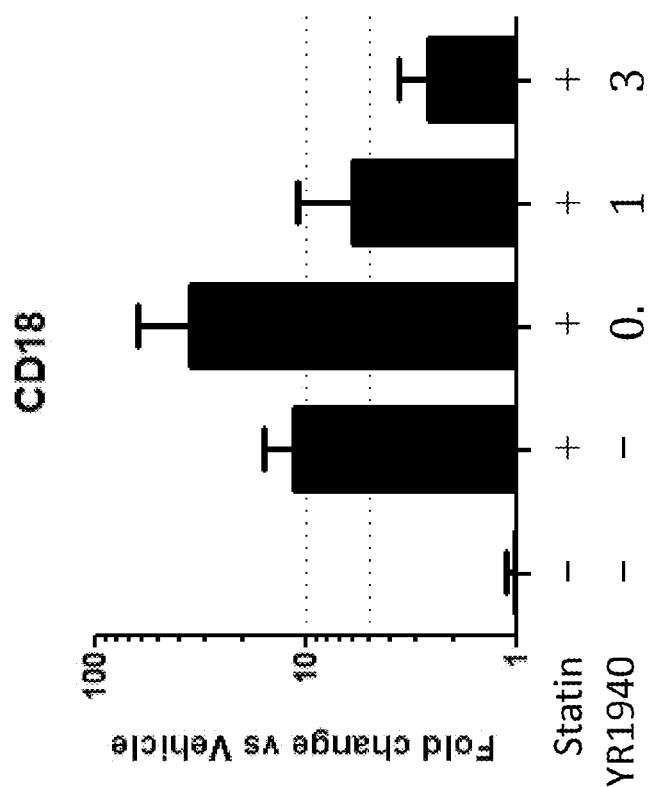
Figure 19C:
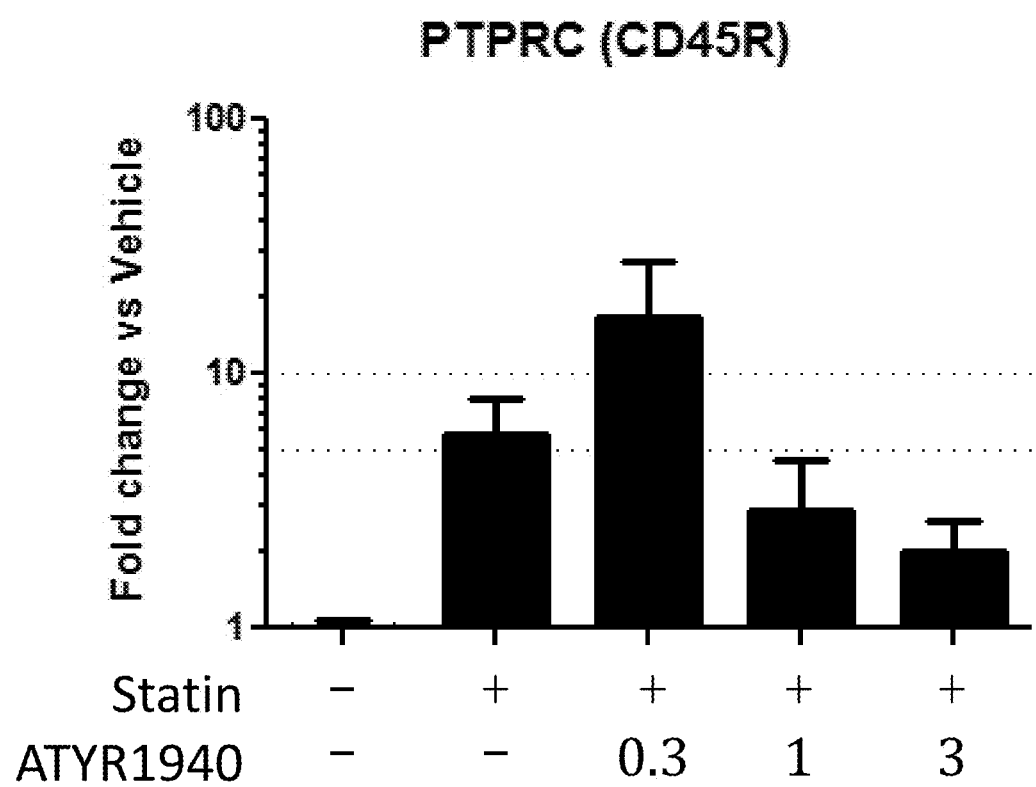
Figure 20:
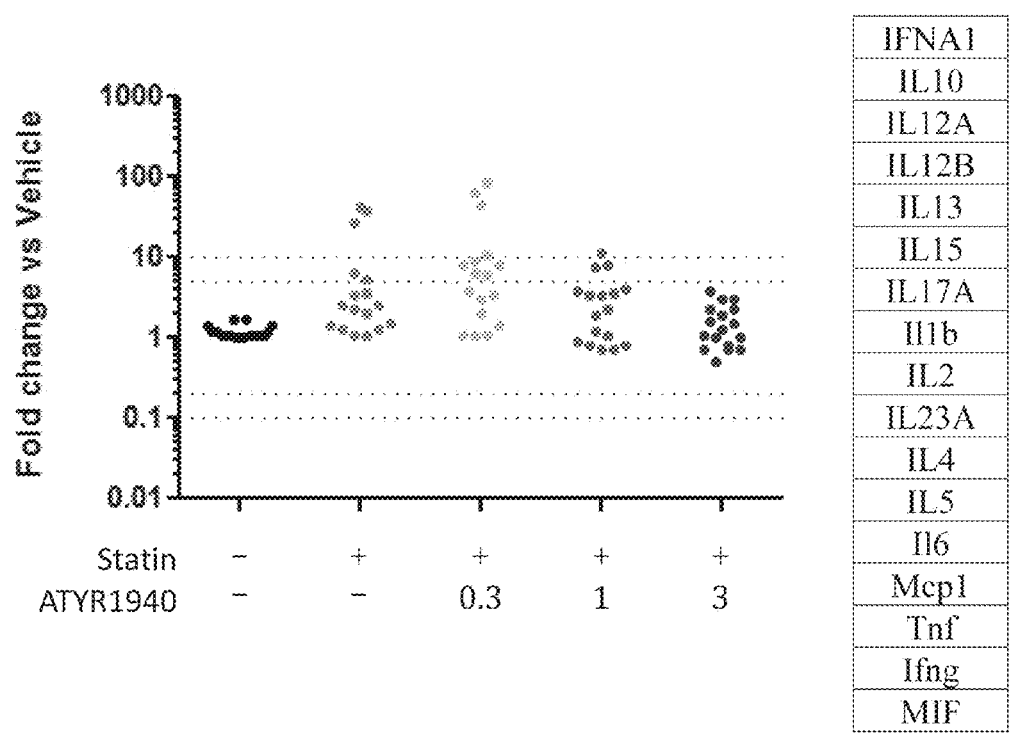
FIG. 20 shows the transcriptional profiling of hamstrings from statin-induced rats. These results revealed that expression of numerous inflammatory marker genes was reduced by HRS(1-506) treatment.
Figure 21B:
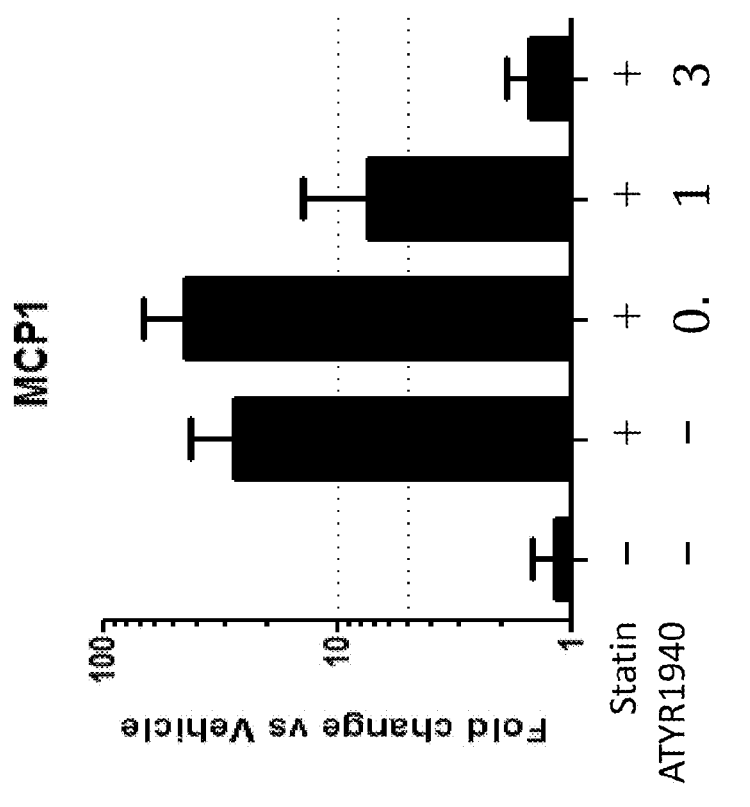
FIGS. 21A-21D show that HRS(1-506) treatment reduced the expression of inflammatory marker genes IL-6 (FIG. 21A), MCP1 (FIG. 21B), IL-10 (FIG. 21C) and IFN-gamma (FIG. 21D).
Figure 21A:
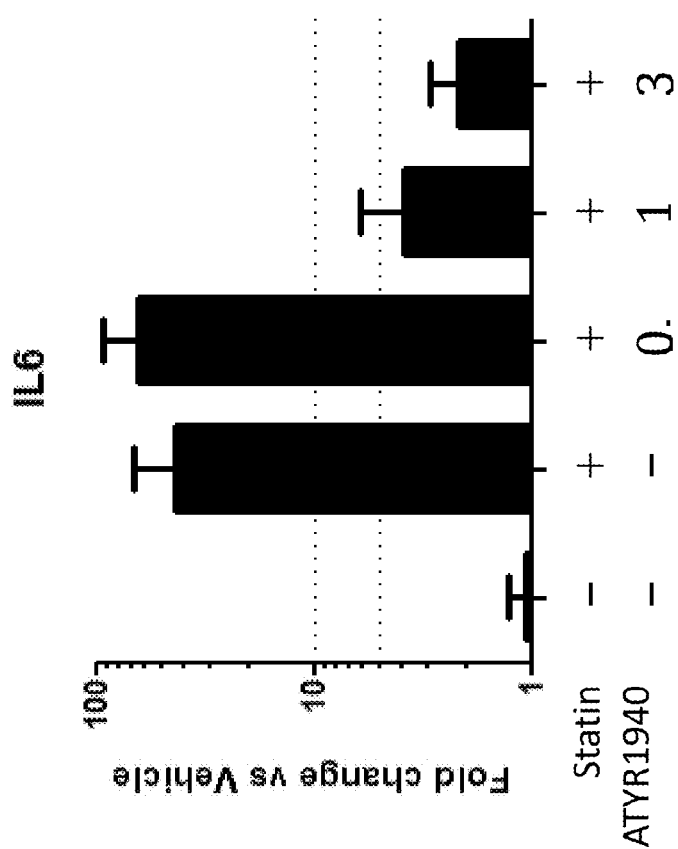
Figure 21D:
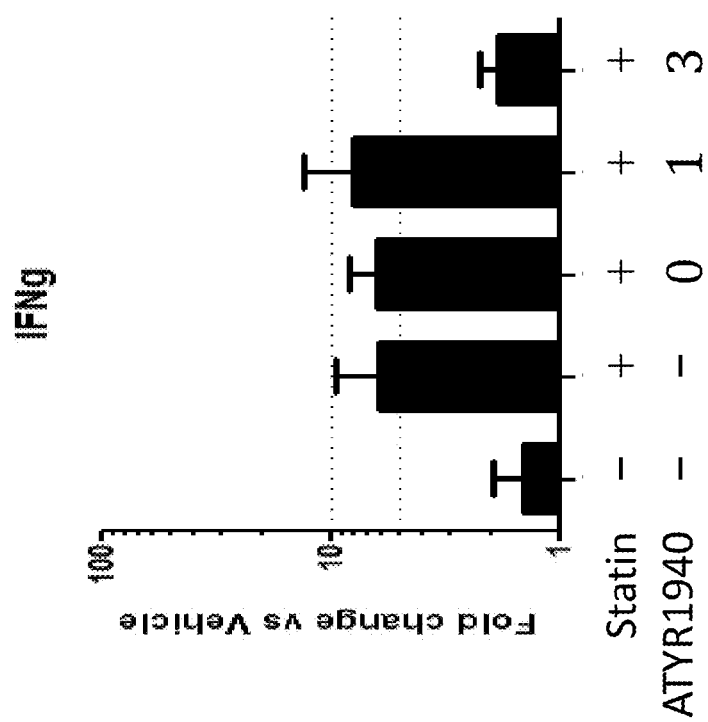
Figure 21C:
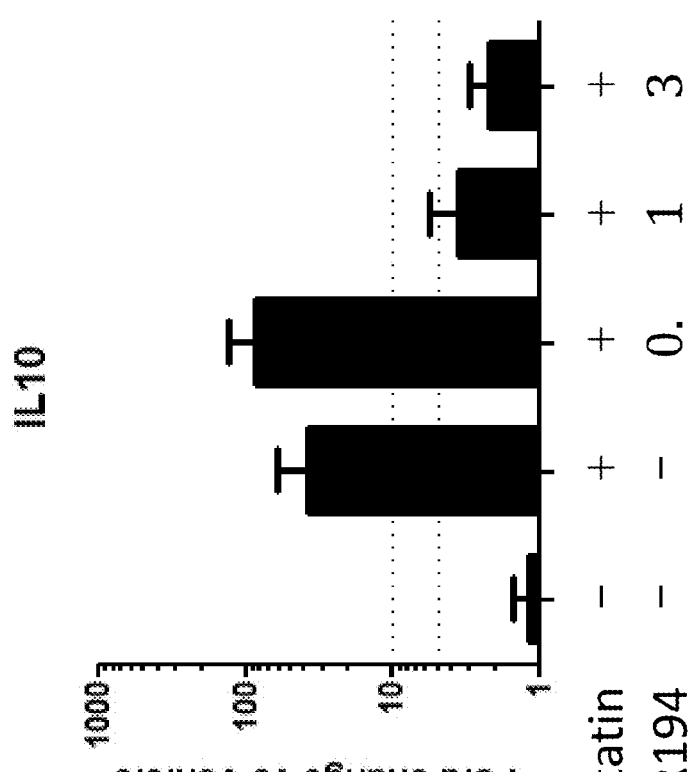
Figure 22:
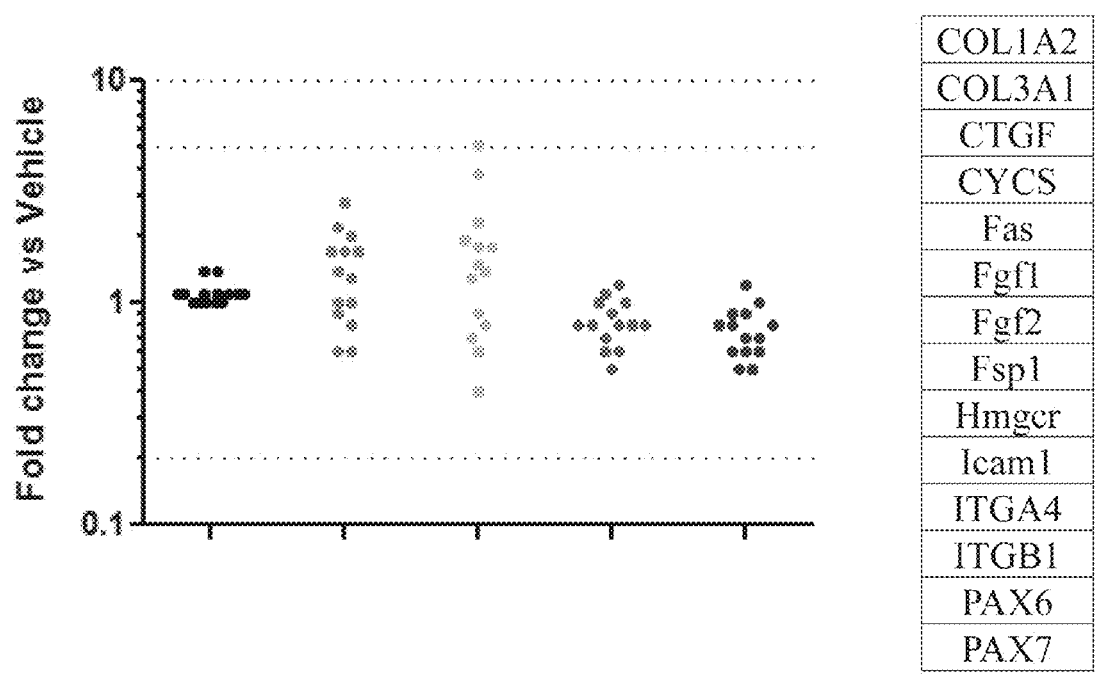
FIGS. 22-23 show the transcriptional profiling of hamstrings from statin-induced rats. These results revealed that expression of various adhesion, development, and fibrosis-related genes was altered by HRS(1-506) treatment.
Figure 23:
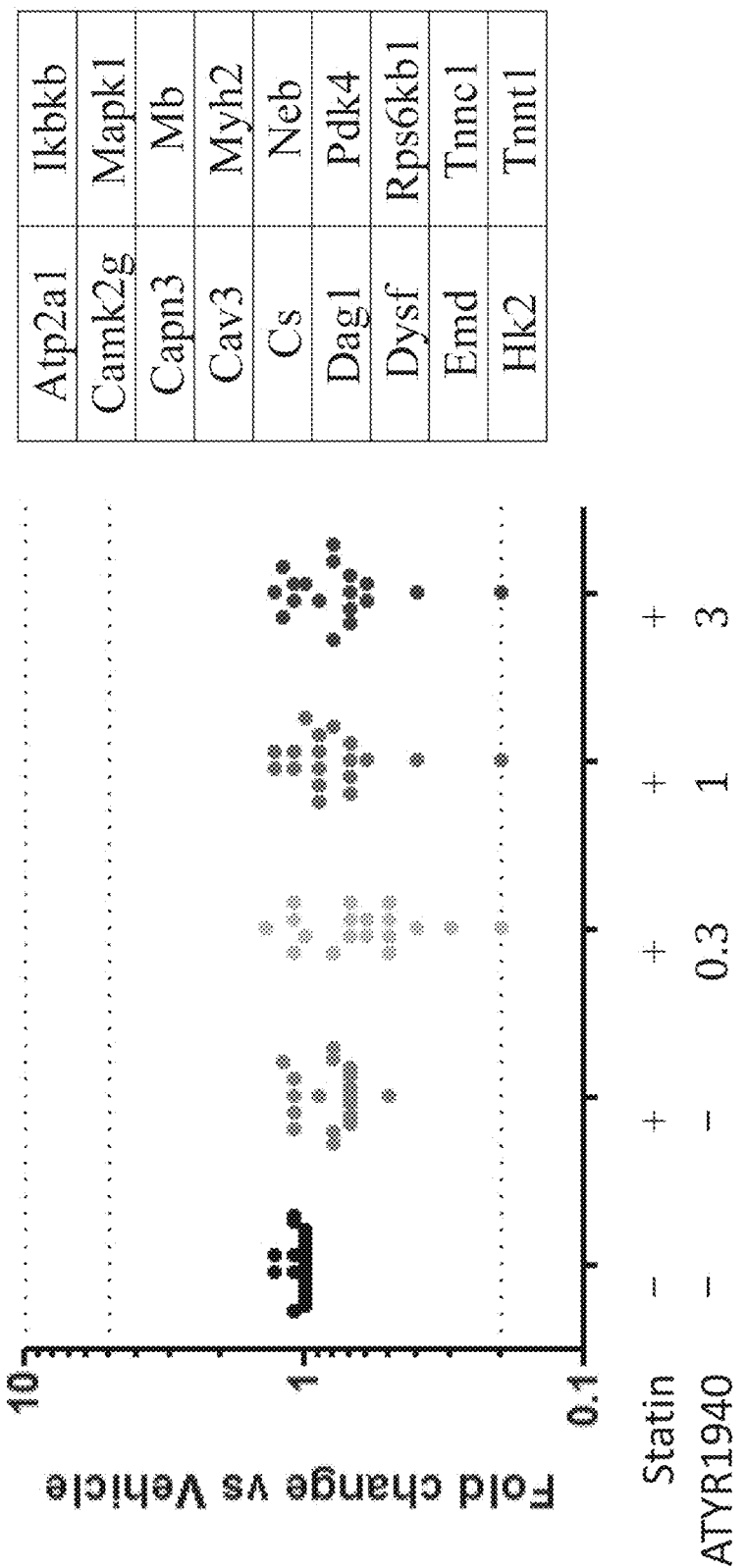
Figure 24A:
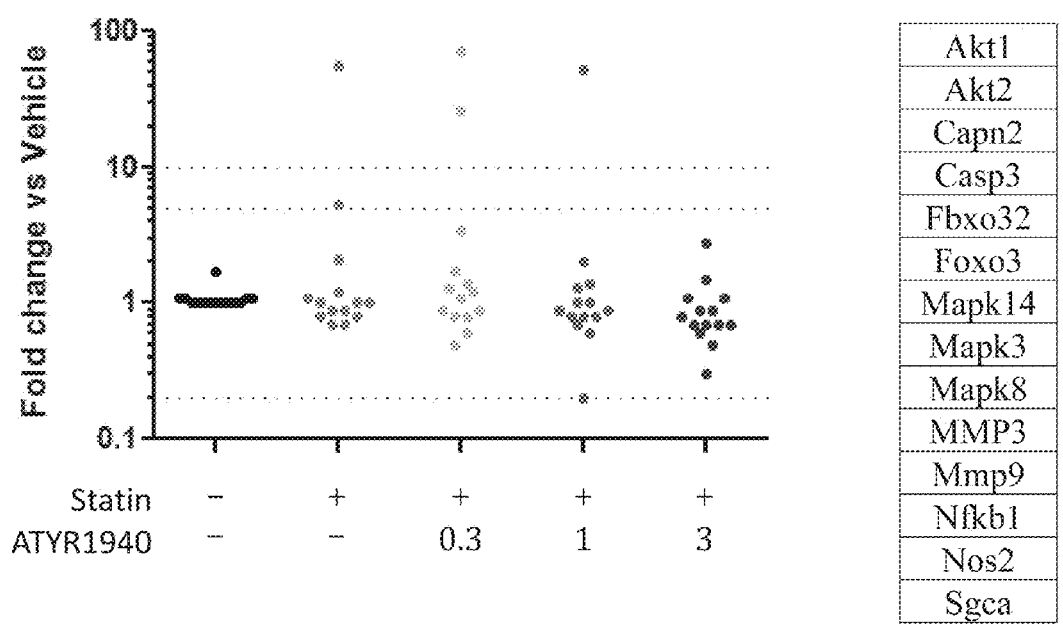
FIGS. 24A-C and 25 show the transcriptional profiling of hamstrings from statin-induced rats. These results revealed that expression of various genes associated with muscular wasting, atrophy, and myogenesis was altered by HRS(1-506) treatment.
Figure 24C:
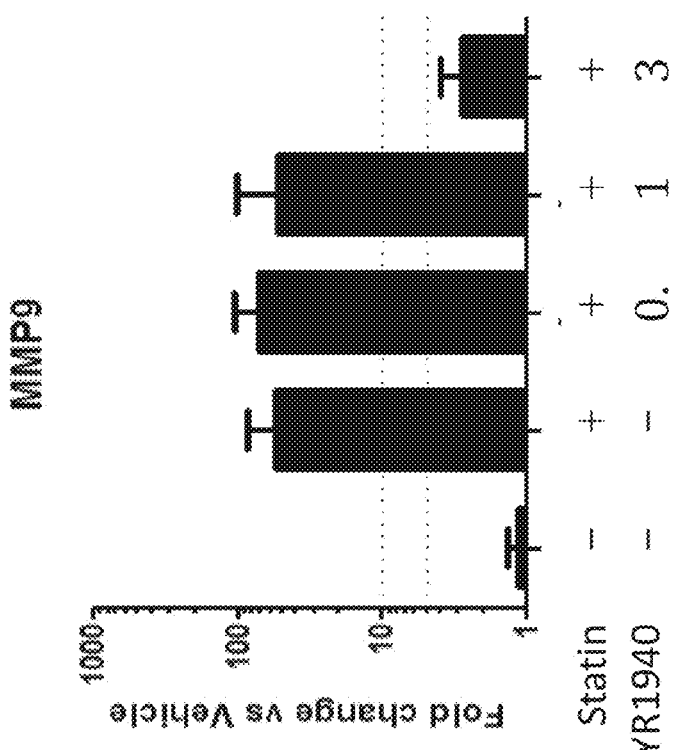
Figure 24B:
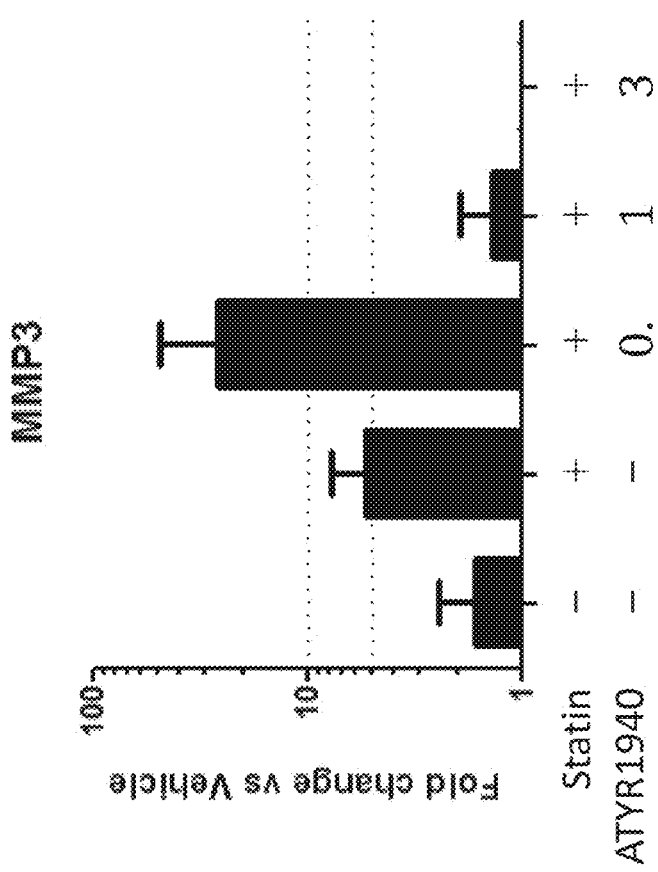
Figure 25:
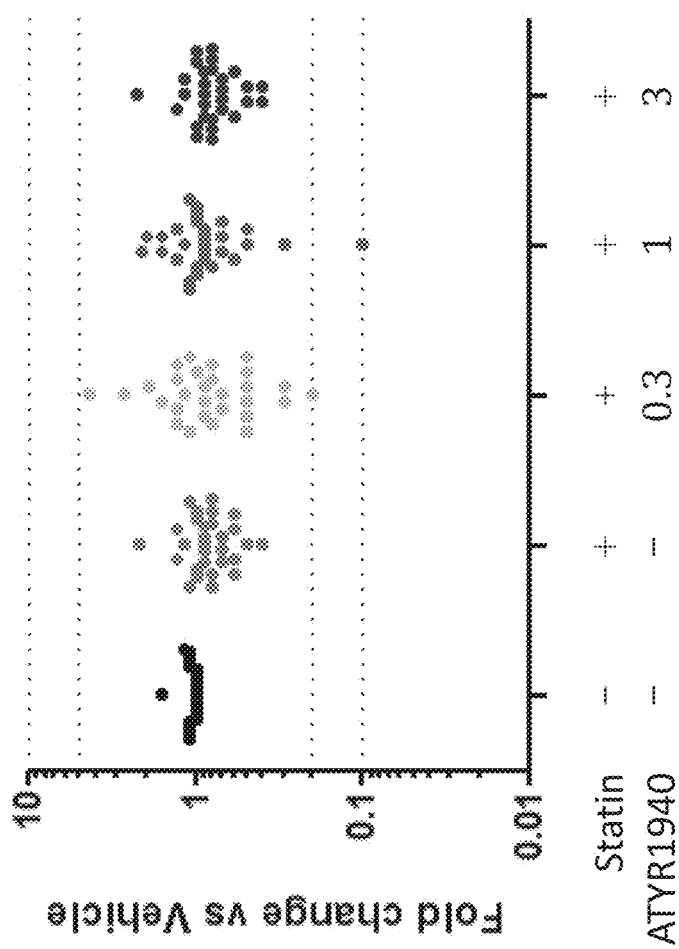

Transcriptional profiling of statin treated rat hamstrings: revealed that 10 diabetes/metabolic syndrome related genes (FIG. 16) and several housekeeping genes (data not shown) were not significantly impacted by HRS treatment. By contrast, transcriptional profiling of statin treated rat hamstrings of 26 immune cell marker genes revealed significant changes in a larger number of genes (see FIGS. 17-19), including the dose dependent inhibition of ITGAL (CD11a), CD11b, CD8a, CD8b, CD18, CCR5, and PTPPC(CD45R) expression. Additionally HRS(1-506) was effective in reducing the expression of a number of inflammatory marker genes including IL6, MCP1, IL10 and IFN-gamma (see FIGS. 20-21). Transcriptional changes were also observed in 14 adhesion, development, and fibrosis related genes (see FIGS. 22-23), the muscle contractility gene Neb (data not shown), and in genes associated with muscular wasting, atrophy, and myogenesis (see FIGS. 24-25).

Conclusions.

Decreased CK, serum Troponin-I and muscle cell degeneration/necrosis and muscle inflammation were all observed in animals receiving higher doses of HRS(1-506), either at 1.0 mg/kg or 3.0 mg/kg in contrast to animals receiving either Vehicle or low dose 0.3 mg/kg HRS(1-506). RNA profiling data supported these results by demonstrating reduced CD8a, IL-6, MCP-1 and MMP-9 expression in hamstrings of statin-treated rats dosed with higher doses of HRS(1-506). Up-regulation of these genes is most likely due to increased immune cell infiltrate into damaged muscle tissue. Based on the identity of the expressed genes, the infiltrating immune cells are likely to be made up of one of more of the following cell types, T cells, dendritic cell, NK cells, and macrophage/monocytes. All of these cell types have been associated with muscle inflammation, and the ability of the HRS polypeptides, including HRS(1-506) to mediate a dramatic inhibition of this immune cell influx suggests that HRS polypeptides such as HRS(1-506) represent potent immuno-regulators, which are capable of acting as potent immunomodulators in a broad range of inflammatory and autoimmune diseases and disorders.

Example 11

Evaluation of HRS Polypeptides for the Treatment of Muscular Dystrophy

Duchenne muscular dystrophy (DMD) is caused by mutations in the gene encoding dystrophin, a subsarcolemmal protein functioning within the dystrophin-associated glycoprotein complex (DGC). This complex connects the intracellular cytoskeleton to the extracellular matrix. The DGC is concentrated at the Z-lines of the sarcomere and confers the transmission of force across the muscle fibre. Disruption of this link results in membrane instability, which eventually leads to sarcolemmal ruptures. Influx of extracellular calcium alters molecular processes like muscle contraction and activates proteolytic activity. Affected muscle fibres become necrotic or apoptotic, and release mitogenic chemoattractants, which initiate inflammatory processes. Cycles of degeneration and regeneration eventually lead to irreversible muscle wasting and replacement by fibrotic and adipose tissue.

Muscle has the potential to regenerate by activation of undifferentiated myogenic precursor cells (satellite cells), which are normally quiescent and situated between the basal membrane and the myofibers. Upon activation, satellite cells proliferate and divide asymmetrically, with the daughter cells having divergent cell fates. Only one of the daughter cells differentiates, progresses towards the myoblast-stadium, and subsequently fuses with other myoblasts or with damaged muscle fibres to induce muscle fibre repair. The other daughter cell remains in a proliferating state or returns to quiescence. Genetic mutations responsible for DMD are also present in satellite cells. Hence, the ability to restore normal muscle function remains obstructed. A small number of muscle fibres are able to produce functional dystrophin, mostly due to secondary mutations in myogenic precursor cells which restore the reading frame. However, these so-called revertant fibres are in a too small minority to alleviate the pathology of the dystrophin-deficiency. Exhaustion of the satellite cell pool due to degeneration and regeneration cycles is thought to critically contribute to the disease.

The mdx mouse model for DMD has a spontaneous mutation in exon 23 of the Dmd gene, introducing a premature stop codon. The pathology of the mdx mouse is characterized by histologically well-defined stages with similarity to the human pathology. Neonatal muscle tissue appears to be unaffected. Necrotic or apoptotic processes in combination with inflammation emerge at approximately 3 weeks of age. Regeneration processes are initiated around the age of 6 weeks and continue while alternating with ongoing degeneration until 12 weeks of age. Mdx mice show a decline in their regeneration capacity at advanced age (>65 weeks), while necrotic processes persist. Since the degeneration processes are similar to those seen in human pathology, the regenerational differences may hold one of the clues of restoration of proper muscle function.

Accordingly this mouse model provides an in vivo model system to test the impact of HRS polypeptides on muscle cell degeneration, regeneration and inflammation in a genetic background of direct relevance to human disease, and the treatment of muscular dystrophies.

The purpose of this study was to evaluate the efficacy of HRS(1-506) in reversing the age related effects of the genetic defect of the dystrophin gene on the progressive loss of muscle function in the mdx mouse model, as indicated by altered circulating enzyme levels, and changes in gene expression of muscle function and inflammatory markers in response to treatment with HRS(1-506).

To achieve this, groups of 8 animals (C57B:/10ScSn-Dm-d$^{mdx}$/J mice; six weeks old at start of study) were administered by IV injection vehicle, HRS(1-506) (3 mg/Kg) or a positive control (Dexamethasone) (1 mg/Kg) once daily for 14 days.

Protocol and Methods.

Mice were weighed on days 1, 8, and 15 of the study. A wire hang muscle function test was performed to assess muscle strength on days 1, 8 and 15. Serum samples were taken on days 1, 8, (via tail vein) and day 15 (terminal) to be used for circulating enzyme analysis (Idexx). CBC analysis was run on blood isolated on day 15 prior to euthanizing rats. On day 15, the rats were euthanized and a portion of the tibialis anterior muscle and diaphragms was placed in 10% NBF for paraffin embedding and H&E staining of sections (Premier Laboratory).

Figure 26B:
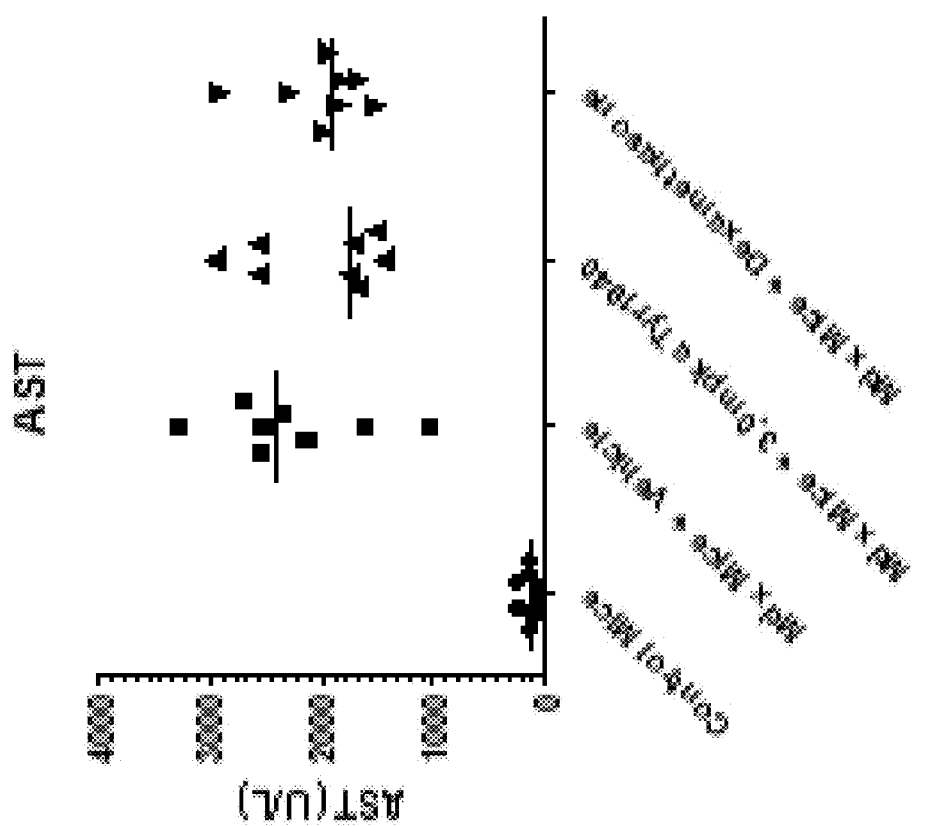
FIGS. 26A-26B show the effects of HRS(1-506) in the mdx mouse model of Duchenne muscular dystrophy (DMD). Reductions in serum CK (FIG. 26A), AST (FIG. 26B), and LDH (FIG. 26C) were observed in mice treated with HRS(1-506) or dexamethasone relative to the vehicle controls.
Figure 26A:
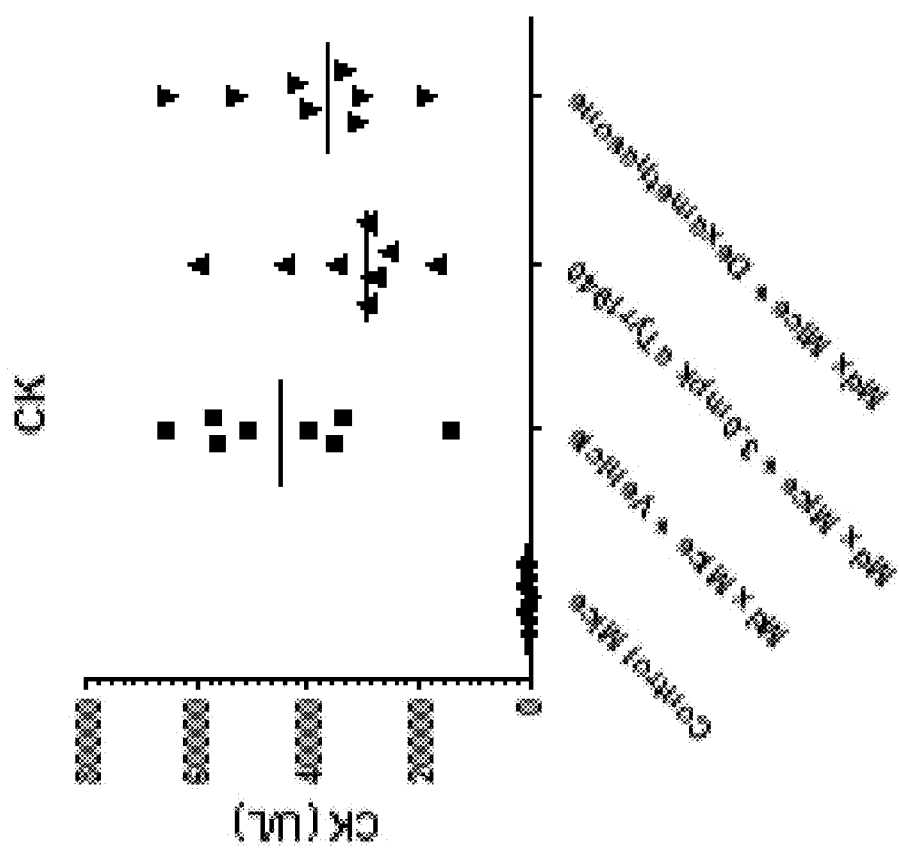
Figure 26C:
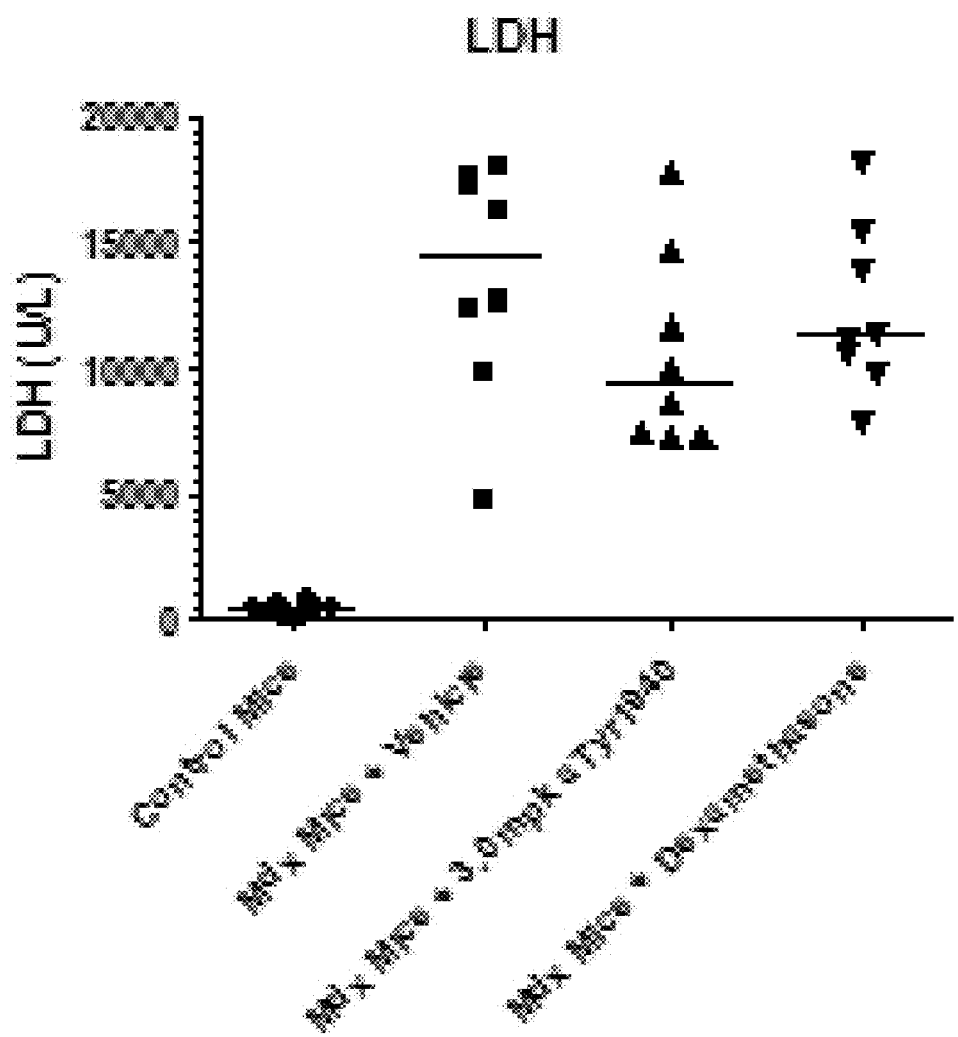

Results:

No significant differences were observed in the weights, hang times or CBC data of animals treated with HRS(1-506) or Dexamethasone (DEX) compared to the untreated controls at either day 8 or 15 of the study (data not shown). However, reductions in serum CK, AST, and LDH were observed in mice treated with HRS(1-506) and dexamethasone compared to the vehicle controls (FIG. 26).

The results demonstrate that with dosing only for 14 days consistent reductions in the circulating levels of a variety of serum markers of muscle inflammation, including CK, AST and LDH levels were observed, indicating that HRS(1-506) has therapeutic efficacy in the mdx mouse model of Duchenne muscular dystrophy (DMD).

Example 12

Evaluation of the Impact of Antibodies to HRS in the Development of Limb Girdle Muscular Dystrophy Limb Girdle Muscular Dystrophy type 2B (LGMD2B) is caused by the loss of function mutations in the dysferlin gene. Dysferlin is primarily expressed in skeletal and cardiac muscle, but also in monocytes, macrophages, and other tissues where it is localized to cytoplasmic vesicles and the cell membrane. Dysferlin appears to be involved in membrane fusion and trafficking, as well as repair processes. LGMD2B is a late onset (teens/young adults) muscle disease that is characterized by progressive symmetrical muscle weakness, and notably aggressive immune/inflammatory pathology. Muscle biopsies typically show marked inflammatory cell infiltration, consisting primarily of macrophages/macrophage activation markers (HLA-DR, HLA-ABC, CD86), CD8$^+$ cytotoxic T cells, and CD4$^+$ T cells, together with muscle fiber degeneration/regeneration.

SJL/J mice have an in-frame deletion of 171 bp in the 3' splice junction of exon 45 of dysferlin. They develop spontaneous myopathy that is associated with obvious muscle inflammation as they age. Together, these features make SJL/J mice a genetic homologue of human dysferlin deficient myopathies. Inflammatory changes in SJL/J mouse muscles typically begin around 4-6 weeks of age, and are characterized by infiltration of activated macrophages, followed by CD4+ T cells. At 6 months, the infiltrate consists primarily of macrophages, along with some muscle fiber necrosis. By 16 months, muscle fibers completely degenerate and are replaced by fat and collagen.

Although biochemical and histological features of the SJL/J strain have been relatively well documented, the functional causes of the progressing myopathy have not been fully characterized, particularly during the early stages of disease, which are most likely to be useful for evaluation of potential treatment strategies. To directly evaluate the potential role of endogenous HRS polypeptides in regulating the inflammatory processes at work in the SJL/J strain, mice were immunized with full-length HRS to sequester any endogenous HRS. If HRS is involved in regulating the inflammatory processes in muscle, then this approach should result in the induction of muscle inflammation. Accordingly this mouse model provides additional support for a role of HRS polypeptides in modulating muscle cell degeneration, regeneration and inflammation in a genetic background of direct relevance to human disease, and the treatment of muscular dystrophies.

To generate antibodies to full-length HARS, SJL/J mice were immunized with a subcutaneous immunization with complete Freunds adjuvant (CFA) at Day 1 and a boost of antigen with IFA was given on days 15 and 29 to further stimulate antibody production.

Protocol and Methods.

Groups of 8 animals SLJ/J male mice (JAX labs); (eight weeks old at start of study) were immunized with 0.2 mg full-length mouse HRS (mHRS) via subcutaneous administration, with complete Freunds adjuvant on days 1, 15 and 29. Serum was isolated on Days 10, 25 and 43 to determine antibody production. Mice were sacrificed on Day 43 and both hamstrings and lungs (lungs were inflated) were harvested for histology (H&E staining of sections (Premier Laboratory). Circulating enzyme levels were examined in serum isolated on Day 43 (Idexx).

Figure 27A:
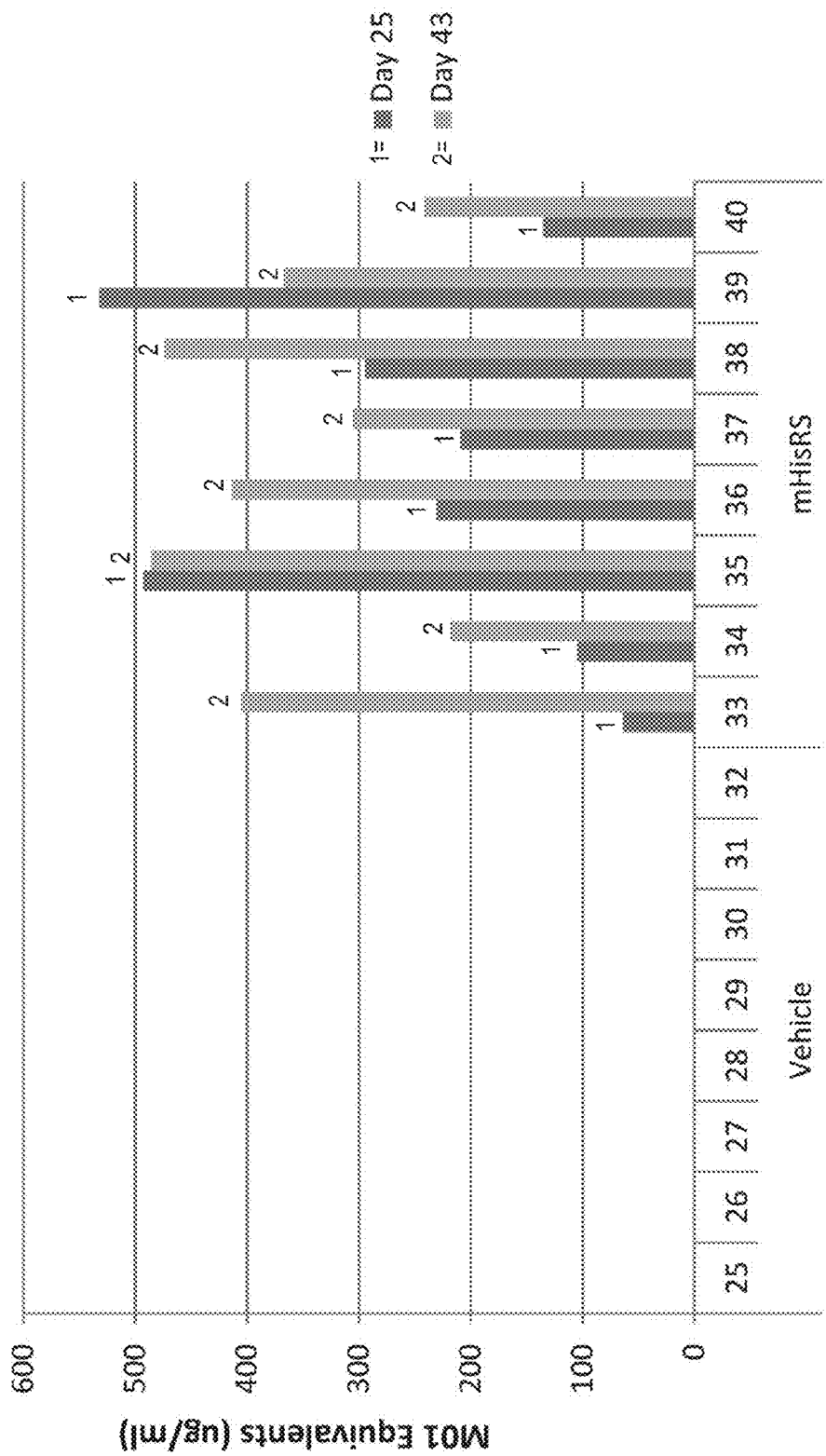

Results:

SJL/J mice immunized with mHisRS subcutaneously generated a robust antibody response to full-length HisRS (FIG. 27A). No significant changes in circulating enzyme levels were observed in immunized mice compared to vehicle controls, although aCK levels were slightly elevated in the HRS immunized group (data not shown). However, muscle tissue from HisRS-immunized mice clearly showed some regions of cellular infiltration and myositis (FIG. 27B), and consistent with this histopathology, two immunized mice displayed signs of myositis.

Example 13

Development of Stabilized Formulation for HRS Polypeptides

To determine the optimal buffer conditions to store HRS polypeptides a step-wise approach was used to optimize the basic formulation conditions. These studies involved the determination of the optimal pH range, preferred stabilizing buffer, and excipient(s) to maintain protein stability and solubility.

Studies were carried out with proteins stored in "control buffer" (20 mM Sodium Phosphate, 150 mM NaCl, pH 7.0) at a concentration of 2 mg/ml. Working stock solutions of HRS (1-506) were prepared by diluting the stock protein concentration (12.5 mg/ml stored at −80° C.) to a concentration of 2 mg/ml into the respective buffers to a final volume of 9.1 ml. The diluted proteins were then dialyzed against 2 L of desired buffer overnight with 10 kDa MWCO Slide-A-Lyzers (Thermo Fisher) at 2-8° C. (P/N: 66810), and then dialyzed into 2 L fresh buffer for 4 hours the next day.

After dialysis, samples were tested to determine the zero time values of the measured parameters and distributed into 5 ml polystyrene tubes (BD Falcon, #352859) at a volume of 1 ml/condition. The tubes were capped, and the caps were wrapped with Parafilm. Visual inspection was performed pre- and post-dialysis. The assays conducted for each sample included appearance, pH, differential scanning fluorimetry, turbidity and opalescence, size exclusion HPLC analysis (SE-HPLC) and SDS-PAGE analysis.

Analytical Methods:

Appearance:

The appearance of proteins was evaluated by visual examination in two categories: A) opalescence and B) particles. Category A: 1=Clear; 2=Slightly opalescent; 3=Opalescent; Category B: 1=No particles; 2=Particles present; 3=Fiber(s). Results are expressed as "category A, followed by category B". For example, a result of "1,1" means clear solution without particles.

pH:

Sample pH was measured using the Accumet Basic AB15 plus pH meter (Fisher Scientific) with a microprobe (Accumet electrode, cat #13-620-292). Calibration and measurement were performed according to manufacturer's instruction manual.

Absorbance:

Absorbance at 280 nm, 340 nm, and 580 nm was measured using the SpectraMax M2 spectrophotometer (Molecular Devices). At each time point, 100 pt of non-treated (neat) samples were used for A340 (turbidity) and A580 (opalescence) readings. The remaining samples were spun for 5 min at 14,000 rcf, and supernatants were diluted 4-fold in corresponding buffers and measured for A280 absorption.

Differential scanning fluorimetry (DSF) was performed on protein samples by monitoring fluorescence as a function of the fluorescence intensity of a lipophilic dye during thermal denaturation. Studies were carried on samples after they were diluted to 0.5 mg/mL into 100 µL final volume of PBS pH 7.0 (150 mM NaCl, 20 mM phosphate) and mixed with a thermal shift dye solution, which was prepared by diluting the stock solution (Applied Biosystems/Life Technologies, P/N 4461146) 20-fold in ultrapure distilled water (Gibco, P/N 10977). Five µL of the diluted dye was added to 100 µL of sample. The mixture was plated into a 384 well clear optical reaction plate (Applied Biosystems/Life Technologies P/N 4309849) at 20 µL each well and 4 well replicates per sample. The plate was read by the ViiA 7 Real Time PCR Instrument (Applied Biosystems/Life Technologies, P/N 4453552). The thermal denaturation protocol commenced with a rate of change of 1.6° C./s, until a temperature of 25° C. was attained, at which point the instrument held this temperature for 2 minutes, before further increasing the temperature to 99° C., at a rate of 0.5° C./s at which point this temperature was held for a further 2 minutes.

Size exclusion HPLC (SE-HPLC) analysis was completed on the purified protein samples using a TSKgel Super SW3000, 4.6 mm ID×30 cm, 4 µm particle size, 250 Å column (Tosoh, 18675) using a mobile phase of 200 mM NaPhosphate, 150 mM NaCl pH 7.0, at a flow rate of 0.3 ml/min, with an Agilent 1260 HPLC system equipped with a vacuum degasser, binary/quaternary pump, thermostatted autosampler, thermostatted column compartment, diode array detector (DAD), and Chemstation chromatography software). Un-diluted samples (40 µg) of each protein were injected after brief centrifugation. System suitability sample (bovine serum albumin, BSA, Thermo Scientific, P/N: 23209) and internal control (wild-type HRS) were used to bracket samples to ensure the validity of the test.

SDS-PAGE Analysis:

To assess fragmentation and aggregation, reduced and non-reduced SDS-gels were run for each time point. Ten µg samples of each protein were loaded per lane, and analyzed using an XCell Surelock Mini-Cell system (Invitrogen) using 4-12% Bis-Tris NuPAGE precast gels, 1.5 mm×10-well (Invitrogen PN NP0335BOX) and NuPAGE MES SDS Running Buffer (Invitrogen PN NP0002) or NuPAGE MOPS SDS Running Buffer (Invitrogen PN NP001) following the manufactures instructions. Reducing Sample Buffer was prepared from a 4× stock (0.25M Tris, 8% SDS, 40% Glycerol, 0.008% Bromophenol blue, 20% 14.3M βME); Non-Reducing Sample Buffer was prepared without mercaptoethanol. Pre-Stained Molecular Weight Markers were obtained from Invitrogen (See Blue Plus2, Invitrogen PN LC5925). Gels were stained with InstantBlue (Expedeon PN ISB1L) following the manufacturer's instructions.

Preliminary Studies on the Effects of pH and Histidine on Thermal Stability.

Figure 28A:
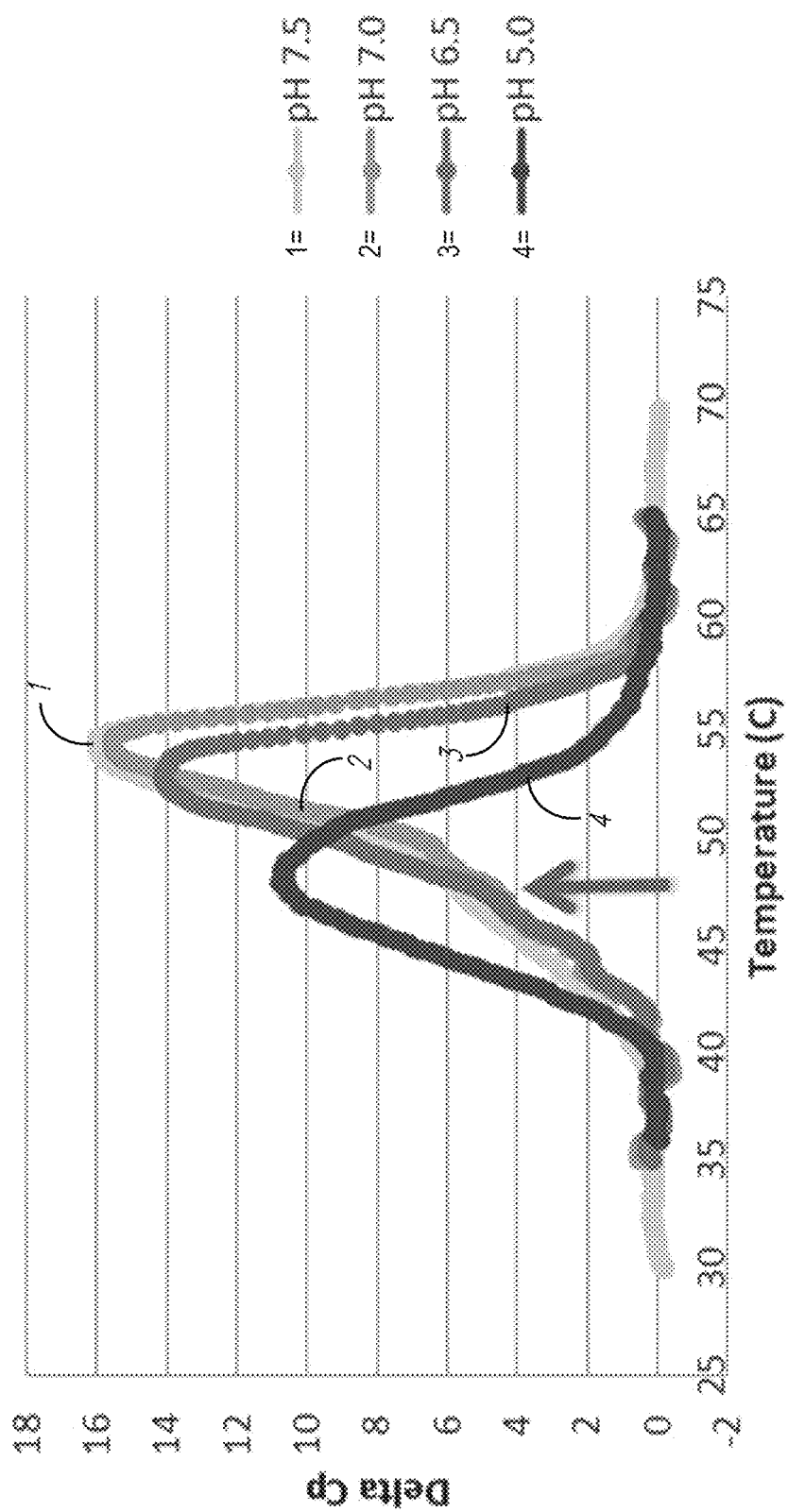
FIGS. 28A-28B show differential scanning fluorimetry (DSF) analysis of full-length HRS and HRS(1-506).

Exploratory stability studies were performed using 6×His-tagged full-length HARS and 6×His-tagged HRS(1-506). Full-length protein was dialyzed into 20 mM sodium phosphate buffer at the indicated pH (pH 5.5, 6.0, 6.5, 7.0 or 7.5) by dialysis overnight into buffers at the respective pH. The results of the DSF analysis demonstrated that there are two thermal transitions for HRS when incubated at pH 7-7.5. The first transition occurred at 48° C. as indicated by the arrow, in FIG. 28A, and the main transition at this pH range occurred at around 54° C. The main transitions temperatures for each pH incubation condition are summarized in Table E12. SE-HPLC analysis revealed comparable levels of high molecular weight (HMW) peaks for samples stored at pH 6.5-7.5, and significantly higher HMW content with samples stored at around pH 5.5 (data not shown). Precipitation was also observed with the sample stored at pH5.5 buffer and this sample was not evaluated further.

TABLE E12

Main thermal transition temperatures for full-length HARS

| pH | Tm |
|---|---|
| 7.5 | 54.2 |
| 7.0 | 54.2 |
| 6.5 | 52.9 |
| 6.0 | 47.7 |
| 5.5 | n.d |

The results from these preliminary studies therefore suggested that the optimal pH was in the range of about 6.5 to pH 7.5, and further more detailed studies were conducted within this pH range, as outlined in more detail below.

Figure 28B:
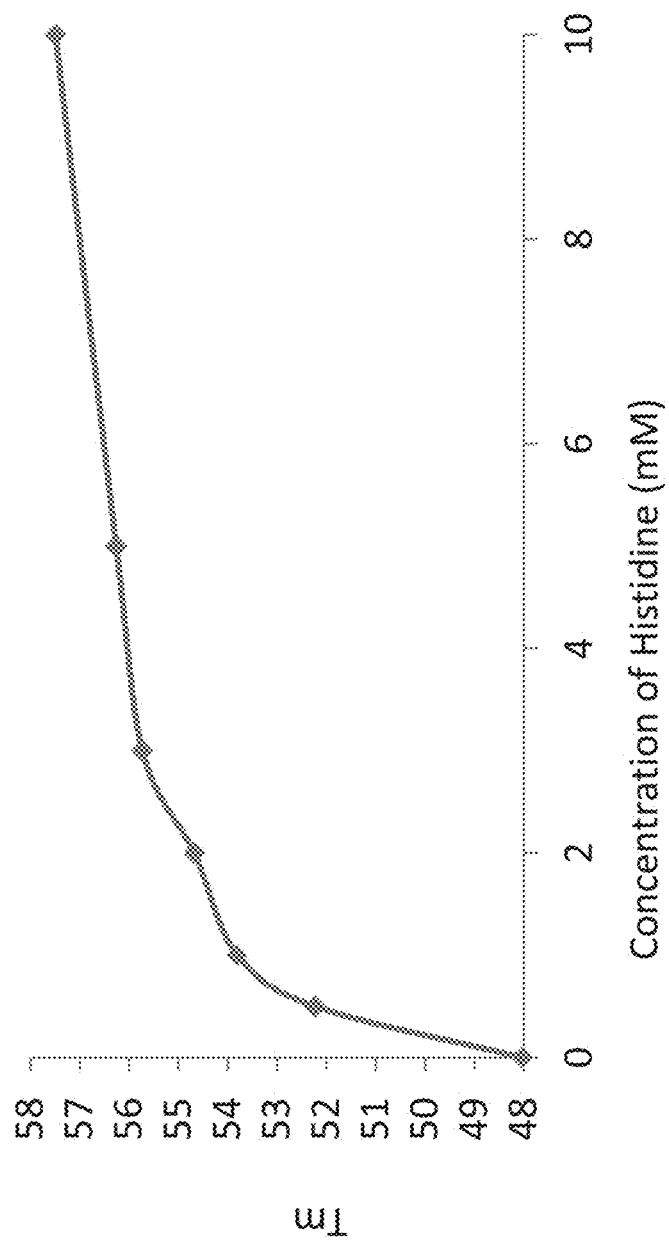

To determine if the addition of exogenous histidine could impact the stability of HARS, preliminary stability studies were conducted over a range of histidine concentrations within the range of 0.1 to 50 mM. The results for the experiments in the range of 0.5 to 10 mM histidine are shown in FIG. 28B, and the effect of a wider range of concentrations is shown in Table E13.

TABLE E13

Impact of histidine on the thermal stability of HRS(1-506)

| Concentration of His (mM) | $T_m$ |
|---|---|
| Low range (0.01 to 0.5 mM) | |
| 0 | 48.03 |
| 0.01 | 48.03 |
| 0.03 | 48.21 |
| 0.05 | 48.38 |
| 0.08 | 49.08 |
| 0.1 | 49.08 |
| 0.2 | 49.96 |
| 0.3 | 50.31 |
| 0.4 | 50.83 |
| 0.5 | 51 |
| High range (0.5 to 50 mM) | |
| 0 | 48.03 |
| 0.5 | 52.23 |
| 1 | 53.81 |
| 2 | 54.68 |
| 3 | 55.73 |

TABLE E13-continued

Impact of histidine on the thermal stability of HRS(1-506)

| Concentration of His (mM) | $T_m$ |
|---|---|
| 5 | 56.26 |
| 10 | 57.49 |
| 50 | 56.94 |

The results from these experiments demonstrate that the addition of exogenous histidine is effective over a broad range of concentrations in stabilizing the structure of HRS polypeptides. This effect is apparent at a concentration of histidine as low as 0.03 mM, and starts to reach its maximum at concentrations around 5 mM and above. Accordingly histidine concentrations within the range of about 0.03 mM to 50 mM are effective in stabilizing HRS polypeptides, and concentrations of histidine within the range of about 2 mM to about 50 mM provide for significantly improved thermal stabilization of HRS polypeptides.

Detailed Characterization of the Influence of pH on HRS Polypeptide Stability.

The impact of pH on the stability of HRS(1-506) was evaluated over a broader range of incubation conditions, and with more detailed analytical characterization within the range of pH 6.0 to 7.5. These studies were performed using the analytical methods described above, and with samples incubated at SC, room temperature and 37° C. for up to one week. The results from these studies are summarized in Table E14.

TABLE E14

Evaluation of Optimal pH

| Buffer conditions | Appearance | Absorbance A340 | A580 | A280 | Concentration (mg/ml) | SE-HPLC % HMW | % Main | % LMW |
|---|---|---|---|---|---|---|---|---|
| 20 mM NaPhosphate, 150 mM NaCl, pH 7.0 | | | | | | | | |
| T zero | 1,1 | 0 | −0.001 | 0.338 | 2.1 | 0.3 | 97.0 | 2.7 |
| 3 hours 5 C. | | 0 | ND | ND | ND | 0 | ND | ND |
| 3 days 5 C. | | 0 | ND | ND | ND | 0 | ND | ND |
| 7 days 5 C. | | 0 | ND | ND | ND | 0 | ND | ND |
| 3 hours RT | | 0 | ND | ND | ND | 0 | ND | ND |
| 3 days RT | | 0 | ND | ND | ND | 0 | ND | ND |
| 7 days RT | | 0 | ND | ND | ND | 0 | ND | ND |
| 3 hours 37 C. | | 0 | ND | ND | ND | + | ND | ND |
| 3 days 37 C. | | ++ | ND | ND | ND | 0 | ND | ND |
| 50 mM NaPhosphate, pH 7.5 | | | | | | | | |
| T zero | 1,1 | 0 | −0.008 | 0.313 | 2.0 | 0.3 | 96.9 | 2.8 |
| 3 hours 5 C. | | 0 | ND | ND | ND | 0 | ND | ND |
| 3 days 5 C. | | 0 | ND | ND | ND | 0 | ND | ND |
| 7 days 5 C. | | 0 | ND | ND | ND | 0 | ND | ND |
| 3 hours RT | | 0 | ND | ND | ND | 0 | ND | ND |
| 3 days RT | | 0 | ND | ND | ND | + | ND | ND |
| 7 days RT | | + | ND | ND | ND | 0 | ND | ND |
| 3 hours 37 C. | | 0 | ND | ND | ND | ++ | ND | ND |
| 3 days 37 C. | | ++++ | ND | ND | ND | 0 | ND | ND |
| 50 mM NaPhosphate, pH 7.0 | | | | | | | | |
| T zero | 1,1 | + | 0.069 | 0.343 | 2.2 | 0.7 | 96.3 | 3.0 |
| 3 hours 5 C. | | + | ND | ND | ND | 0 | ND | ND |
| 3 days 5 C. | | 0 | ND | ND | ND | + | ND | ND |
| 7 days 5 C. | | 0 | ND | ND | ND | 0 | ND | ND |
| 3 hours RT | | + | ND | ND | ND | 0 | ND | ND |
| 3 days RT | | + | ND | ND | ND | 0 | ND | ND |
| 7 days RT | | + | ND | ND | ND | + | ND | ND |
| 3 hours 37 C. | | + | ND | ND | ND | + | ND | ND |
| 3 days 37 C. | | +++ | ND | ND | ND | ++ | ND | ND |

TABLE E14-continued

Evaluation of Optimal pH

| Buffer conditions | Appearance | Absorbance A340 | A580 | A280 | Concentration (mg/ml) | SE-HPLC % HMW | % Main | % LMW |
|---|---|---|---|---|---|---|---|---|
| 50 mM NaPhosphate, pH 6.5 ||||||||
| T zero | 1,3 | 0 | 0.000 | 0.320 | 2.0 | 0.6 | 96.4 | 3.0 |
| 3 hours 5 C. |  | 0 | ND | ND | ND | 0 | ND | ND |
| 3 days 5 C. |  | 0 | ND | ND | ND | + | ND | ND |
| 7 days 5 C. |  | 0 | ND | ND | ND | 0 | ND | ND |
| 3 hours RT |  | 0 | ND | ND | ND | 0 | ND | ND |
| 3 days RT |  | + | ND | ND | ND | 0 | ND | ND |
| 7 days RT |  | ++ | ND | ND | ND | 0 | ND | ND |
| 3 hours 37 C. |  | + | ND | ND | ND | 0 | ND | ND |
| 3 days 37 C. |  | +++ | ND | ND | ND | ++++ | ND | ND |
| 50 mM NaPhosphate, pH 6.0 ||||||||
| T zero | 1,1 | 0 | 0.006 | 0.327 | 2.1 | 0.4 | 96.4 | 3.1 |
| 3 hours 5 C. |  | 0 | ND | ND | ND | 0 | ND | ND |
| 3 days 5 C. |  | 0 | ND | ND | ND | + | ND | ND |
| 7 days 5 C. |  | 0 | ND | ND | ND | 0 | ND | ND |
| 3 hours RT |  | 0 | ND | ND | ND | 0 | ND | ND |
| 3 days RT |  | + | ND | ND | ND | 0 | ND | ND |
| 7 days RT |  | + | ND | ND | ND | 0 | ND | ND |
| 3 hours 37 C. |  | ++ | ND | ND | ND | + | ND | ND |
| 3 days 37 C. |  | +++++ | ND | ND | ND | +++++ | ND | ND |

For A340: "+++++" = A340 > 2.0; "++++" = A340 > 1.5, but < 2.0; "+++" = A340 > 1.0, but < 1.5; "++" = A340 > 0.5, but < 1.0; "+" = A340 > 0.05, but < 0.5; and "0" = A340 < 0.05
For % HMW: "+++++" = % HMW > 5.0; "++++" = % HMW > 4.0, but < 5.0; "+++" = % HMW > 3.0, but < 4.0; "++" % HMW > 2.0, but < 3.0; "+" = % HMW > 1.0, but < 2.0; and "0" = % HMW < 1.0

The results in totality suggest that the protein was relatively stable when incubated in a buffer at a pH within the range of about pH 7.0 to about pH 7.5, but that potential degradation and aggregation issues start to appear at lower pHs. Based on the conditions tested and the assay results obtained it is concluded that, the optimal pH range for the storage of HRS polypeptides is within the range of about pH7.0 to about 7.5.

Detailed Characterization of the Influence of Different Buffer Compositions on HRS Polypeptide Stability.

The impact of buffer composition on the stability of HRS (1-506) was evaluated using three alternative buffer systems, based around a phosphate buffer, a citrate buffer and a histidine buffer, at three pH values, 7.3, 7.0 and 6.5. These studies were performed using the analytical methods described above, and with samples incubated at 5° C., room temperature and 37° C. for up to one week, and the results are summarized in Table E15.

TABLE E15

Evaluation of Optimal Buffer

| Buffer conditions | Appearance | Absorbance A340 | A580 | A280 | Concentration (mg/ml) | SE-HPLC % HMW | % Main | % LMW |
|---|---|---|---|---|---|---|---|---|
| 50 mM NaPhosphate, pH 7.3 ||||||||
| T zero | 1,1 | 0 | −0.008 | 0.292 | 1.8 | 0.3 | 96.4 | 3.3 |
| 2 days 5 C. |  | 0 | ND | ND | ND | 0 | ND | ND |
| 7 days 5 C. |  | 0 | ND | ND | ND | 0 | ND | ND |
| 2 days RT |  | + | ND | ND | ND | 0 | ND | ND |
| 7 days RT |  | 0 | ND | ND | ND | + | ND | ND |
| 2 days 37 C. |  | 0 | ND | ND | ND | 0 | ND | ND |
| 7 days 37 C. |  | +++ | ND | ND | ND | 0 | ND | ND |
| 50 mM NaPhosphate, pH 7.0 ||||||||
| T zero | 1,1 |  | 0.009 | 0.001 | 0.291 | 1.8 | 0.3 | 96.4 |
| 2 days 5 C. |  | 0 | ND | ND | ND | 0 | ND | ND |
| 7 days 5 C. |  | 0 | ND | ND | ND | 0 | ND | ND |
| 2 days RT |  | 0 | ND | ND | ND | 0 | ND | ND |
| 7 days RT |  | 0 | ND | ND | ND | + | ND | ND |
| 3 hours 37 C. |  | 0 | ND | ND | ND | 0 | ND | ND |
| 2 days 37 C. |  | ++ | ND | ND | ND | 0 | ND | ND |
| 50 mM NaPhosphate, pH 6.5 ||||||||
| T zero |  | 0.009 | 0.001 | 0.290 | 1.8 | 0.5 | 96.0 | 3.5 |
| 2 days 5 C. |  | 0 | ND | ND | ND | 0 | ND | ND |
| 7 days 5 C. |  | 0 | ND | ND | ND | 0 | ND | ND |
| 2 days RT |  | 0 | ND | ND | ND | 0 | ND | ND |

TABLE E15-continued

Evaluation of Optimal Buffer

| Buffer conditions | Appearance | Absorbance | | | Concentration (mg/ml) | SE-HPLC | | |
|---|---|---|---|---|---|---|---|---|
| | | A340 | A580 | A280 | | % HMW | % Main | % LMW |
| 7 days RT | | 0 | ND | ND | ND | + | ND | ND |
| 3 hours 37 C. | | + | ND | ND | ND | 0 | ND | ND |
| 2 days 37 C. | | ++ | ND | ND | ND | 0 | ND | ND |
| 50 mM Citrate, pH 7.3 | | | | | | | | |
| T zero | 1,1 | | −0.011 | 0.287 | 1.8 | | 96.4 | 3.2 |
| 2 days 5 C. | | + | ND | ND | ND | 0 | ND | ND |
| 7 days 5 C. | | 0 | ND | ND | ND | 0 | ND | ND |
| 2 days RT | | 0 | ND | ND | ND | 0 | ND | ND |
| 7 days RT | | 0 | ND | ND | ND | 0 | ND | ND |
| 3 hours 37 C. | | 0 | ND | ND | ND | 0 | ND | ND |
| 3 hours 37 C. | | 0 | ND | ND | ND | 0 | ND | ND |
| 2 days 37 C. | | + | ND | ND | ND | 0 | ND | ND |
| 50 mM Citrate, pH 7.0 | | | | | | | | |
| T zero | | −0.001 | −0.008 | 0.294 | 1.8 | 0.2 | 96.6 | 3.2 |
| 2 days 5 C. | | 0 | ND | ND | ND | 0 | ND | ND |
| 7 days 5 C. | | 0 | ND | ND | ND | 0 | ND | ND |
| 2 days RT | | 0 | ND | ND | ND | 0 | ND | ND |
| 7 days RT | | 0 | ND | ND | ND | 0 | ND | ND |
| 3 hours 37 C. | | 0 | ND | ND | ND | 0 | ND | ND |
| 2 days 37 C. | | + | ND | ND | ND | 0 | ND | ND |
| 50 mM Citrate, pH 6.5 | | | | | | | | |
| T zero | | −0.001 | −0.010 | 0.287 | 1.8 | 0.3 | 96.6 | 3.1 |
| 2 days 5 C. | | 0 | ND | ND | ND | 0 | ND | ND |
| 7 days 5 C. | | 0 | ND | ND | ND | 0 | ND | ND |
| 2 days RT | | 0 | ND | ND | ND | 0 | ND | ND |
| 7 days RT | | 0 | ND | ND | ND | 0 | ND | ND |
| 3 hours 37 C. | | 0 | ND | ND | ND | 0 | ND | ND |
| 3 hours 37 C. | | 0 | ND | ND | ND | 0 | ND | ND |
| 2 days 37 C. | | + | ND | ND | ND | 0 | ND | ND |
| 50 mM L-histidine pH 7.3 | | | | | | | | |
| T zero | | −0.008 | −0.016 | 0.242 | 1.5 | 0.4 | 96.1 | 3.5 |
| 2 days 5 C. | | 0 | ND | ND | ND | 0 | ND | ND |
| 7 days 5 C. | | 0 | ND | ND | ND | 0 | ND | ND |
| 2 days RT | | 0 | ND | ND | ND | 0 | ND | ND |
| 7 days RT | | 0 | ND | ND | ND | + | ND | ND |
| 3 hours 37 C. | | 0 | ND | ND | ND | 0 | ND | ND |
| 2 days 37 C. | | 0 | ND | ND | ND | + | ND | ND |
| 50 mM L-histidine pH 7.0 | | | | | | | | |
| T zero | | −0.003 | −0.014 | 0.253 | 1.6 | 0.4 | 96.3 | 3.3 |
| 2 days 5 C. | | 0 | ND | ND | ND | 0 | ND | ND |
| 7 days 5 C. | | 0 | ND | ND | ND | 0 | ND | ND |
| 2 days RT | | 0 | ND | ND | ND | 0 | ND | ND |
| 7 days RT | | 0 | ND | ND | ND | 0 | ND | ND |
| 3 hours 37 C. | | 0 | ND | ND | ND | 0 | ND | ND |
| 2 days 37 C. | | 0 | ND | ND | ND | + | ND | ND |
| 50 mM L-histidine pH 6.5 | | | | | | | | |
| T zero | | 0.327 | 0.080 | 0.269 | 1.7 | 0.4 | 96.4 | 3.2 |
| 2 days 5 C. | | + | ND | ND | ND | 0 | ND | ND |
| 7 days 5 C. | | + | ND | ND | ND | 0 | ND | ND |
| 2 days RT | | ++ | ND | ND | ND | + | ND | ND |
| 7 days RT | | ++ | ND | ND | ND | + | ND | ND |
| 3 hours 37 C. | | ++++ | ND | ND | ND | 0 | ND | ND |
| 2 days 37 C. | | +++++ | ND | ND | ND | ++ | ND | ND |

For A340: "+++++" = A340 > 2.0; "++++" = A340 > 1.5, but < 2.0; "+++" = A340 > 1.0, but < 1.5; "++" = A340 > 0.5, but < 1.0; "+" = A340 > 0.05, but < 0.5; and "0" = A340 < 0.05
For % HMW: "+++++" = % HMW > 5.0; "++++" = % HMW > 4.0, but < 5.0; "+++" = % HMW > 3.0, but < 4.0; "++" % HMW > 2.0, but < 3.0; "+" = % HMW > 1.0, but < 2.0; and "0" = % HMW < 1.0

Results and Conclusions:

Histidine buffer within the range of about pH 7.0 to pH 7.4 had the best performance in these studies. Histidine buffer also improved HRS polypeptide folding stability by ~8° C. (data not shown). HRS polypeptides also displayed good stability in citrate buffers within a broad range of pH values (pH 6.7-7.3).

The larger range of acceptable pHs observed with the citrate buffers compared to the histidine buffers, suggests that both histidine and citrate based buffers are potentially attractive candidate buffer systems to further evaluate as storage buffers for HRS polypeptides.

Detailed Characterization of the Influence of Different Excipients on HRS Polypeptide Stability.

The impact of buffer composition on the stability of HRS (1-506) was evaluated using a variety of potential excipients including sucrose, mannitol, trehalose, sorbitol, arginine, glycine, glycerol and high salt (280 mM NaCl). These studies were performed using the analytical methods described above, and with samples incubated at 5° C., room temperature and 37° C. for up to one week, and the results are summarized in Tables E16 and E17.

TABLE E16

Evaluation of optimal excipients

| Buffer conditions | Appearance | Absorbance A340 | A580 | A280 | Concentration (mg/ml) | SE-HPLC % HMW | % Main | % LMW | Tm |
|---|---|---|---|---|---|---|---|---|---|
| | | | | | 50 mM L-Histidine pH 7.3 | | | | |
| T zero | 1,1 | 0.024 | 0.010 | 0.300 | 1.9 | 0.8 | 97.2 | 2.0 | 56.94 |
| 3 days 5 C. | | 0 | ND | ND | ND | 0 | ND | ND | |
| 7 days 5 C. | | 0 | ND | ND | ND | + | ND | ND | |
| 3 days RT | | 0 | ND | ND | ND | 0 | ND | ND | |
| 7 days RT | | 0 | ND | ND | ND | ++ | ND | ND | |
| 3 hrs 37 C. | | 0 | ND | ND | ND | + | ND | ND | |
| 7 days 37 C. | | + | ND | ND | ND | ++ | ND | ND | |
| | | | | | 50 mM L-Histidine + 280 mM Sucrose pH 7.3 | | | | |
| T zero | 1,1 | 0.005 | −0.008 | 0.318 | 2.0 | 0.7 | 97.3 | 2.0 | 57.64 |
| 3 days 5 C. | | 0 | ND | ND | ND | 0 | ND | ND | |
| 7 days 5 C. | | + | ND | ND | ND | 0 | ND | ND | |
| 3 days RT | | 0 | ND | ND | ND | 0 | ND | ND | |
| 7 days RT | | 0 | ND | ND | ND | + | ND | ND | |
| 3 hrs 37 C. | | 0 | ND | ND | ND | + | ND | ND | |
| 3 days 37 C. | | 0 | ND | ND | ND | ++ | ND | ND | |
| | | | | | 50 mM L-Histidine + 280 mM Mannitol pH 7.3 | | | | |
| T zero | | 0.017 | 0.001 | 0.321 | 2.0 | 0.8 | 97.4 | 1.7 | 57.46 |
| 3 days 5 C. | | 0 | ND | ND | ND | + | ND | ND | |
| 7 days 5 C. | | + | ND | ND | ND | 0 | ND | ND | |
| 3 days RT | | 0 | ND | ND | ND | 0 | ND | ND | |
| 7 days RT | | + | ND | ND | ND | + | ND | ND | |
| 3 hrs 37 C. | | 0 | ND | ND | ND | 0 | ND | ND | |
| 3 days 37 C. | | + | ND | ND | ND | + | ND | ND | |
| | | | | | 50 mM L-Histidine + 280 mM Trehalose pH 7.3 | | | | |
| T zero | 1,1 | 0.013 | 0.000 | 0.342 | 2.2 | 0.8 | 97.5 | 1.7 | 57.64 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | + | ND | ND | |
| 3 hrs 37 C. | | 0 | ND | ND | ND | + | ND | ND | |
| 3 days 37 C. | | 0 | ND | ND | ND | + | ND | ND | |
| | | | | | 50 mM L-Histidine + 280 mM Sorbitol pH 7.3 | | | | |
| T zero | | −0.035 | −0.051 | 0.263 | 1.7 | 0.8 | 97.4 | 1.8 | 57.64 |
| 3 days 5 C. | | 0 | ND | ND | ND | 0 | ND | ND | |
| 7 days 5 C. | | 0 | ND | ND | ND | + | ND | ND | |
| 3 days RT | | 0 | ND | ND | ND | 0 | ND | ND | |
| 7 days RT | | 0 | ND | ND | ND | + | ND | ND | |
| 3 hrs 37 C. | | 0 | ND | ND | ND | + | ND | ND | |
| 3 days 37 C. | | 0 | ND | ND | ND | + | ND | ND | |
| | | | | | 50 mM L-Histidine + 280 mM Arginine pH 7.3 | | | | |
| T zero | | 0.007 | 0.001 | 0.344 | 2.2 | 0.7 | 97.3 | 1.9 | 58.34 |
| 3 days 5 C. | | 0 | ND | ND | ND | 0 | ND | ND | |
| 7 days 5 C. | | 0 | ND | ND | ND | 0 | ND | ND | |
| 3 days RT | | 0 | ND | ND | ND | 0 | ND | ND | |
| 7 days RT | | 0 | ND | ND | ND | 0 | ND | ND | |
| 3 hrs 37 C. | | 0 | ND | ND | ND | 0 | ND | ND | |
| 3 days 37 C. | | 0 | ND | ND | ND | 0 | ND | ND | |
| | | | | | 50 mM L-Histidine + 280 mM Glycine pH 7.3 | | | | |
| T zero | | 0.037 | 0.022 | 0.333 | 2.1 | 0.8 | 97.3 | 1.8 | 57.29 |
| 3 days 5 C. | | 0 | ND | ND | ND | 0 | ND | ND | |

TABLE E16-continued

Evaluation of optimal excipients

| Buffer conditions | Appearance | Absorbance A340 | A580 | A280 | Concentration (mg/ml) | SE-HPLC % HMW | % Main | % LMW | Tm |
|---|---|---|---|---|---|---|---|---|---|
| 7 days 5 C. | | + | ND | ND | ND | 0 | ND | ND | |
| 3 days RT | | 0 | ND | ND | ND | 0 | ND | ND | |
| 7 days RT | | 0 | ND | ND | ND | + | ND | ND | |
| 3 hrs 37 C. | | 0 | ND | ND | ND | 0 | ND | ND | |
| 3 days 37 C. | | 0 | ND | ND | ND | + | ND | ND | |
| 50 mM L-Histidine + 280 mM Glycerol pH 7.3 | | | | | | | | | |
| T zero | | 0.033 | 0.017 | 0.284 | 1.8 | 0.9 | 97.3 | 1.8 | 57.29 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | +++ | ND | ND | |
| 3 hrs 37 C. | | + | ND | ND | ND | + | ND | ND | |
| 3 days 37 C. | | +++ | ND | ND | ND | +++++ | ND | ND | |
| 50 mM L-Histidine + 280 mM NaCl pH 7.3 | | | | | | | | | |
| T zero | | 0.060 | 0.046 | 0.353 | 2.2 | 0.7 | 97.5 | 1.9 | 59.74 |
| 3 days 5 C. | | 0 | ND | ND | ND | 0 | ND | ND | |
| 7 days 5 C. | | 0 | ND | ND | ND | 0 | ND | ND | |
| 3 days RT | | 0 | ND | ND | ND | 0 | ND | ND | |
| 7 days RT | | 0 | ND | ND | ND | + | ND | ND | |
| 3 hrs 37 C. | | 0 | ND | ND | ND | 0 | ND | ND | |
| 3 days 37 C. | | 0 | ND | ND | ND | 0 | ND | ND | |

For A340: "+++++" = A340 > 2.0; "++++" = A340 > 1.5, but < 2.0; "+++" = A340 > 1.0, but < 1.5; "++" = A340 > 0.5, but < 1.0; "+" = A340 > 0.05, but < 0.5; and "0" = A340 < 0.05
For % HMW: "+++++" = % HMW > 5.0; "++++" = % HMW > 4.0, but < 5.0; "+++" = % HMW > 3.0, but < 4.0; "++" % HMW > 2.0, but < 3.0; "+" = % HMW > 1.0, but < 2.0; and "0" = % HMW < 1.0

These results demonstrate significant improvements in the stability of HRS polypeptides in the presence of a histidine buffer, within the range of pH 7.0 to pH 7.5, and in the presence of sodium chloride, arginine, sucrose, trehalose, sorbitol, and/or glycine. To further evaluate the potential for the development of formulations with additional stabilizing characteristics, the combinations listed in Table E17 were evaluated.

TABLE E17

Evaluation of further optimal excipients

| Buffer conditions | Appearance | Absorbance A340 | A580 | A280 | Concentration (mg/ml) | SE-HPLC % HMW | % Main | % LMW | Tm |
|---|---|---|---|---|---|---|---|---|---|
| 50 mM L-Histidine + 280 mM Sucrose + 0.05% PS80 pH 7.3 | | | | | | | | | |
| T zero | 1,1 | 0.020 | 0.004 | 0.380 | 2.4 | 1.3 | 97.0 | 1.7 | 58.35 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | + | ND | ND | |
| 3 days 37 C. | | + | ND | ND | ND | +++++ | ND | ND | |
| 7 days 37 C. | | + | ND | ND | ND | +++++ | ND | ND | |
| 5X freeze thaw | | 0 | ND | ND | ND | + | ND | ND | |
| 50 mM L-Histidine + 280 mM Arginine + 0.05% PS80 pH 7.3 | | | | | | | | | |
| T zero | 1,1 | 0.010 | 0.001 | 0.361 | 2.3 | 1.1 | 97.2 | 1.7 | 56.08 |
| 3 days 5 C. | | 0 | ND | ND | ND | + | ND | ND | |
| 7 days 5 C. | | 0 | ND | ND | ND | 0 | ND | ND | |
| 3 days RT | | 0 | ND | ND | ND | + | ND | ND | |
| 7 days RT | | 0 | ND | ND | ND | + | ND | ND | |
| 3 days 37 C. | | 0 | ND | ND | ND | ++ | ND | ND | |
| 7 days 37 C. | | 0 | ND | ND | ND | ++++ | ND | ND | |
| 5X freeze thaw | | 0 | ND | ND | ND | + | ND | ND | |
| 50 mM L-Histidine + 280 mM NaCl + 0.05% PS80 pH 7.3 | | | | | | | | | |
| T zero | | 0.012 | 0.002 | 0.372 | 2.3 | 1.3 | 97.0 | 1.7 | 62.03 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | + | ND | ND | |
| 3 days 37 C. | | 0 | ND | ND | ND | + | ND | ND | |

TABLE E17-continued

Evaluation of further optimal excipients

| Buffer conditions | Appearance | Absorbance A340 | A580 | A280 | Concentration (mg/ml) | % HMW | SE-HPLC % Main | % LMW | Tm |
|---|---|---|---|---|---|---|---|---|---|
| 7 days 37 C. | | 0 | ND | ND | ND | + | ND | ND | |
| 5X freeze thaw | | 0 | ND | ND | ND | + | ND | ND | |
| *50 mM L-Histidine + 140 mM NaCl + 0.05% PS80 pH 7.3* | | | | | | | | | |
| T zero | 1,1 | 0.015 | 0.005 | 0.376 | 2.4 | 1.2 | 97.1 | 1.7 | 61.15 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | + | ND | ND | |
| 3 days 37 C. | | 0 | ND | ND | ND | + | ND | ND | |
| 7 days 37 C. | | 0 | ND | ND | ND | ++ | ND | ND | |
| 5X freeze thaw | | 0 | ND | ND | ND | + | ND | ND | |
| *50 mM L-Histidine + 140 mM NaCl + 2% Trehalose + 0.05% PS80 pH 7.3* | | | | | | | | | |
| T zero | | 0.009 | −0.001 | 0.357 | 2.2 | 1.2 | 97.1 | 1.8 | 61.15 |
| 3 days 5 C. | | 0 | ND | ND | ND | + | ND | ND | |
| 7 days 5 C. | | 0 | ND | ND | ND | + | ND | ND | |
| 3 days RT | | 0 | ND | ND | ND | + | ND | ND | |
| 7 days RT | | 0 | ND | ND | ND | + | ND | ND | |
| 3 days 37 C. | | 0 | ND | ND | ND | + | ND | ND | |
| 7 days 37 C. | | 0 | ND | ND | ND | + | ND | ND | |
| 5X freeze thaw | | 0 | ND | ND | ND | + | ND | ND | |
| *50 mM L-Histidine + 140 mM NaCl + 2% Sucrose + 0.05% PS80 pH 7.3* | | | | | | | | | |
| T zero | | 0.005 | −0.004 | 0.366 | 2.3 | 1.1 | 97.2 | 1.8 | 61.15 |
| 3 days 5 C. | | 0 | ND | ND | ND | + | ND | ND | |
| 7 days 5 C. | | 0 | ND | ND | ND | 0 | ND | ND | |
| 3 days RT | | 0 | ND | ND | ND | 0 | ND | ND | |
| 7 days RT | | 0 | ND | ND | ND | 0 | ND | ND | |
| 3 days 37 C. | | + | ND | ND | ND | + | ND | ND | |
| 7 days 37 C. | | + | ND | ND | ND | +++++ | ND | ND | |
| 5X freeze thaw | | 0 | ND | ND | ND | + | ND | ND | |
| *50 mM L-Histidine + 140 mM NaCl + 2% Sucrose + 0.05% PS20 pH 7.3* | | | | | | | | | |
| T zero | | 0.007 | −0.001 | 0.385 | 2.4 | 0.1 | 97.9 | 1.9 | 60.98 |
| 3 days 5 C. | | 0 | ND | ND | ND | 0 | ND | ND | |
| 7 days 5 C. | | 0 | ND | ND | ND | 0 | ND | ND | |
| 3 days RT | | 0 | ND | ND | ND | 0 | ND | ND | |
| 7 days RT | | 0 | ND | ND | ND | 0 | ND | ND | |
| 3 days 37 C. | | + | ND | ND | ND | + | ND | ND | |
| 7 days 37 C. | | + | ND | ND | ND | + | ND | ND | |
| 5X freeze thaw | | 0 | ND | ND | ND | 0 | ND | ND | |
| *50 mM L-Histidine + 140 mM NaCl + 2% Sucrose + 0.1% Pluronic F68 pH 7.3* | | | | | | | | | |
| T zero | | 0.015 | 0.008 | 0.352 | 2.2 | 0.2 | 97.9 | 1.9 | 60.10 |
| 3 days 5 C. | | 0 | ND | ND | ND | 0 | ND | ND | |
| 7 days 5 C. | | 0 | ND | ND | ND | 0 | ND | ND | |
| 3 hours RT | | 0 | ND | ND | ND | 0 | ND | ND | |
| 7 days RT | | 0 | ND | ND | ND | 0 | ND | ND | |
| 3 days 37 C. | | + | ND | ND | ND | 0 | ND | ND | |
| 7 days 37 C. | | + | ND | ND | ND | + | ND | ND | |
| 5X freeze thaw | | 0 | ND | ND | ND | 0 | ND | ND | |

For A340: "+++++" = A340 > 2.0; "++++" = A340 > 1.5, but < 2.0; "+++" = A340 > 1.0, but < 1.5; "++" = A340 > 0.5, but < 1.0; "+" = A340 > 0.05, but < 0.5; and "0" = A340 < 0.05

For % HMW: "+++++" = % HMW > 5.0; "++++" = % HMW > 4.0, but < 5.0; "+++" = % HMW > 3.0, but < 4.0; "++" % HMW > 2.0, but < 3.0; "+" = % HMW > 1.0, but < 2.0; and "0" = % HMW < 1.0

Results:

Using these buffer systems there little or no changes in turbidity or HMW aggregate formation when samples were incubated at 5° C. or at room temperature. However time-dependent increases were observed in these parameter for all samples when incubated at 37° C. All formulations had very little change upon 5 cycles of freeze-thaw.

Overall, PS20 (Histidine/Sucrose/PS20) and F68 (Histidine/Sucrose/F68) conditions performed the best based on the SE-HPLC analysis of high molecular weight aggregate formation, and these agents were able to significantly reduce the formation of HMW peaks when the HRS polypeptides were incubated at 37° C. for up to 7 days With respect to turbidity formation (A340), the addition of arginine performed the best, followed by high salt (280 mM NaCl and 140 mM NaCl conditions). suggesting that these agents effectively reduce or prevent aggregation and denaturation of the HRS polypeptides when incubated for extended periods of time at 37° C. Under these conditions, Polysorbate 80, Polysorbate 20, and Pluronic F68, also effectively reduced both turbidity and HMW aggregate formation as determined by HPLC analysis. In these studies, sucrose and trehalose appear to roughly comparable, and both agents significantly inhibited protein denaturation, and aggregation, as determined by reduced turbidity and HMW formation upon extended incubation at 37° C.

Based on these studies, the stabilization of HRS polypeptides can be readily obtained through the utilization of histidine buffers within a pH range of about 7.0 to 7.5. Surprisingly the further addition of sodium chloride within the range of about 100 mM to about 300 mM, provided additional stabilization of these buffers, leading to a further increase in the Tm to 61° C. (data not shown) and reduced denaturation upon extended incubation at 37° C. Stability can be further enhanced via the addition of sugars such as trehalose within the range of about 0.2% to 5%, or sucrose within the range of about 0.2% to 5%. Also, the addition of surfactants including polysorbate 20 or 80 or pluronic F68 within the range of about 0.01 to 1% further improved overall stability, particularly when incubated for extended periods at 37° C. Further improvements in overall protein stability are also likely through the addition of reducing agents (anti-oxidant agents) and/or and chelating agents, as described herein Based on these studies exemplary formulations for the HRS polypeptides exhibiting enhanced stability include buffers comprising one or more of the components listed in Table E18.

TABLE E18

Exemplary buffer components for stabilizing HRS polypeptides

| Component | Function | Exemplary Range |
|---|---|---|
| Histidine | pH buffering | 2 mM to 50 mM; pH 7.0 to 7.5 |
| Citrate | pH buffering | 2 mM to 50 mM; pH 6.5 to 7.5 |
| Phosphate | pH buffering | 2 mM to 50 mM; pH 7.0 to 7.5 |
| NaCl | Ionic strength | 100 mM-300 mM |
| trehalose | Excipient | 0.2% to 5% |
| Sucrose | Excipient | 0.2% to 5% |
| Arginine | Excipient | 0.2% to 5% |
| Polysorbate 20 | Surfactant | 0.01 to 1% |
| Polysorbate 20 | Surfactant | 0.01 to 1% |
| Pluronic F68 | Surfactant | 0.01 to 1% |
| Cysteine | Anti-oxidant | 0.1 to 5 mM |
| Methionine | Anti-oxidant | 0.1 to 5 mM |
| N-acetylcysteine | Anti-oxidant | 0.1 to 5 mM |
| EDTA | Chelating agent | 0.1 to 2 mM |

The invention claimed is:

1. A therapeutic composition, comprising a histidyl-tRNA synthetase (HRS) polypeptide of 500-506 amino acids in length that is least 90% identical to SEQ ID NO:70 (HRS(1-506)) and lacks residues 507-509 of SEQ ID NO:1, wherein the composition is: a) at least about 95% pure; b) less than about 5% aggregated; and c) substantially endotoxin-free, and wherein the HRS polypeptide has reduced interchain disulfide formation under reducing conditions relative to the polypeptide of SEQ ID NO:1 (full-length HRS).

2. The composition of claim 1, wherein the HRS polypeptide is 505-506 amino acids in length is at least 90% identical to SEQ ID NO:70.

3. The composition of claim 1, wherein the HRS polypeptide is 506 amino acids in length.

4. The composition of claim 1, wherein the HRS polypeptide comprises SEQ ID NO:70.

5. The composition of claim 1, wherein the HRS polypeptide consists of SEQ ID NO:70.

6. The composition of claim 1, where the HRS polypeptide is 505 amino acids in length.

7. The composition of claim 6, where the HRS polypeptide comprises residues 2-506 of SEQ ID NO:70 (HRS(2-506)).

8. The composition of claim 7, where the HRS polypeptide consists of residues 2-506 of SEQ ID NO:70 (HRS(2-506)).

9. The composition of claim 1, wherein the HRS polypeptide has a mutation of at least one cysteine residue.

10. The composition of claim 9, wherein the at least one cysteine residue is selected from Cys174, Cys191, Cys224, Cys235, and Cys455.

11. The composition of claim 1, wherein the HRS polypeptide has increased biological activity, stability, and/or homogeneity relative to a polypeptide of SEQ ID NO:1 (full-length human HRS) under comparable conditions, ranging from about 4-40° C., and a pH of about 6.0-8.0.

12. The composition of claim 11, wherein the conditions include a temperature of about 20-25° C. (room temperature) or about 37° C. and a pH of about 7.0-7.5, optionally over a period of about 1, 2, 3, 4, 5, 6, or 7 days.

13. The composition of claim 11, wherein increased activity comprises an absolute increase in an anti-inflammatory activity or specific binding to an anti-Jo-1 antibody of at least about 10%.

14. The composition of claim 11, wherein the HRS polypeptide has reduced charge heterogeneity relative to the polypeptide of SEQ ID NO:1 (full-length HRS).

15. The composition of claim 11, wherein the HRS polypeptide has reduced formation of high molecular weight aggregates in solution relative to the polypeptide of SEQ ID NO:1 (full-length HRS).

16. The composition of claim 11, wherein increased homogeneity comprises at least a 10% increase in the monodispersion of the HRS polypeptide relative to the polypeptide of SEQ ID NO:1.

17. The composition of claim 1, wherein the HRS polypeptide has increased yield of soluble protein upon recombinant production in E. coli relative to the polypeptide of SEQ ID NO:1 (full-length HRS).

18. The composition of claim 1, where the HRS polypeptide is fused to a heterologous fusion partner, optionally a T-cell ligand.

19. A method of treating a disease associated with an autoantibody comprising administering to a subject in need thereof a therapeutic composition of claim 1.

20. The method of claim 19, wherein the therapeutic composition is administered to the subject prior to the appearance of disease symptoms.

21. The method of claim 19, wherein the HRS polypeptide results in reduced muscle or lung inflammation.

22. The method of claim 19, wherein the HRS polypeptide induces tolerance.

23. The method of claim 19, wherein the disease is selected from the group consisting of inflammatory myopathies, including inflammatory myopathies, polymyositis, dermatomyositis and related disorders, polymyositis-scleroderma overlap, inclusion body myositis (IBM), anti-synthetase syndrome, interstitial lung disease, arthritis, and Reynaud's phenomenon.

24. A method of reducing tissue inflammation comprising administering to a subject in need thereof a composition comprising of claim 1.

25. The method of claim 24, wherein the tissue is selected from muscle, gastrointestinal tissue, lung, and skin.

26. A method of treating a muscular dystrophy comprising administering to a subject in need thereof a composition of claim 1.

27. The method of claim 26, wherein the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy, and congenital muscular dystrophy.

28. A method of treating rhabdomyolysis, muscle wasting, cachexia, muscle inflammation, or muscle injury comprising administering to a subject in need thereof a composition of claim 1.

29. The method of claim 27, where the muscular dystrophy is facioscapulohumeral muscular dystrophy.

30. The method of claim 29, where the facioscapulohumeral muscular dystrophy is infant or child onset.

* * * * *

SEQUENCE LISTING

```
<160> NUMBER OF SEQ ID NOS: 236

<210> SEQ ID NO 1
<211> LENGTH: 509
<212> TYPE: PRT
<213> ORGANISM: Homo sapiens

<400> SEQUENCE: 1

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205
```

```
Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505

<210> SEQ ID NO 2
<211> LENGTH: 141
<212> TYPE: PRT
<213> ORGANISM: Homo sapiens

<400> SEQUENCE: 2

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
```

```
                65                  70                  75                  80
Ile Arg Cys Phe Lys Arg His Gly Ala Glu Val Ile Asp Thr Pro Val
                    85                  90                  95

Phe Glu Leu Lys Glu Thr Leu Met Gly Lys Tyr Gly Glu Asp Ser Lys
                    100                 105                 110

Leu Ile Tyr Asp Leu Lys Asp Gln Gly Gly Glu Leu Leu Ser Leu Arg
                    115                 120                 125

Tyr Asp Leu Thr Val Pro Phe Ala Arg Tyr Leu Ala Met
                    130                 135                 140

<210> SEQ ID NO 3
<211> LENGTH: 408
<212> TYPE: PRT
<213> ORGANISM: Homo sapiens

<400> SEQUENCE: 3

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
                35                  40                  45

Glu Ser Lys Gln Lys Phe Val Leu Lys Thr Pro Lys Gly Thr Arg Asp
                50                  55                  60

Tyr Ser Pro Arg Gln Met Ala Val Arg Glu Lys Val Phe Asp Val Ile
65              70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
                115                 120                 125

Tyr Asp Leu Thr Val Pro Phe Ala Arg Tyr Leu Ala Met Asn Lys Leu
                130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
                180                 185                 190

Lys Ile Met Cys Glu Ile Leu Ser Ser Leu Gln Ile Gly Asp Phe Leu
                195                 200                 205

Val Lys Val Asn Asp Arg Arg Ile Leu Asp Gly Met Phe Ala Ile Cys
                210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
                290                 295                 300
```

```
Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu
                405

<210> SEQ ID NO 4
<211> LENGTH: 113
<212> TYPE: PRT
<213> ORGANISM: Homo sapiens

<400> SEQUENCE: 4

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu

<210> SEQ ID NO 5
<211> LENGTH: 60
<212> TYPE: PRT
<213> ORGANISM: Homo sapiens

<400> SEQUENCE: 5

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 6
<211> LENGTH: 270
<212> TYPE: PRT
<213> ORGANISM: Homo sapiens

<400> SEQUENCE: 6
```

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Gly Tyr Pro Trp Trp Asn Ser Cys Ser Arg Ile Leu
                245                 250                 255

Asn Tyr Pro Lys Thr Ser Arg Pro Trp Arg Ala Trp Glu Thr
            260                 265                 270

<210> SEQ ID NO 7
<211> LENGTH: 105
<212> TYPE: PRT
<213> ORGANISM: Homo sapiens

<400> SEQUENCE: 7

Arg Thr Thr Glu Thr Gln Val Leu Val Ala Ser Ala Gln Lys Lys Leu
1               5                   10                  15

Leu Glu Glu Arg Leu Lys Leu Val Ser Glu Leu Trp Asp Ala Gly Ile
            20                  25                  30

Lys Ala Glu Leu Leu Tyr Lys Lys Asn Pro Lys Leu Leu Asn Gln Leu
        35                  40                  45

Gln Tyr Cys Glu Glu Ala Gly Ile Pro Leu Val Ala Ile Ile Gly Glu
50                  55                  60

Gln Glu Leu Lys Asp Gly Val Ile Lys Leu Ser Val Thr Ser Arg
65                  70                  75                  80

Glu Glu Val Asp Val Arg Arg Glu Asp Leu Val Glu Glu Ile Lys Arg
                85                  90                  95

Arg Thr Gly Gln Pro Leu Cys Ile Cys 100          105

<210> SEQ ID NO 8
<211> LENGTH: 395
<212> TYPE: PRT
<213> ORGANISM: Homo sapiens

<400> SEQUENCE: 8

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Asp Phe Asp Ile
    50                  55                  60

Ala Gly Asn Phe Asp Pro Met Ile Pro Asp Ala Glu Cys Leu Lys Ile
65                  70                  75                  80

Met Cys Glu Ile Leu Ser Ser Leu Gln Ile Gly Asp Phe Leu Val Lys
                85                  90                  95

Val Asn Asp Arg Arg Ile Leu Asp Gly Met Phe Ala Ile Cys Gly Val
            100                 105                 110

Ser Asp Ser Lys Phe Arg Thr Ile Cys Ser Ser Val Asp Lys Leu Asp
        115                 120                 125

Lys Val Ser Trp Glu Glu Val Lys Asn Glu Met Val Gly Glu Lys Gly
    130                 135                 140

Leu Ala Pro Glu Val Ala Asp Arg Ile Gly Asp Tyr Val Gln Gln His
145                 150                 155                 160

Gly Gly Val Ser Leu Val Glu Gln Leu Gln Asp Pro Lys Leu Ser
                165                 170                 175

Gln Asn Lys Gln Ala Leu Glu Gly Leu Gly Asp Leu Lys Leu Leu Phe
            180                 185                 190

Glu Tyr Leu Thr Leu Phe Gly Ile Asp Asp Lys Ile Ser Phe Asp Leu
        195                 200                 205

Ser Leu Ala Arg Gly Leu Asp Tyr Tyr Thr Gly Val Ile Tyr Glu Ala
    210                 215                 220

Val Leu Leu Gln Thr Pro Ala Gln Ala Gly Glu Glu Pro Leu Gly Val
225                 230                 235                 240

Gly Ser Val Ala Ala Gly Gly Arg Tyr Asp Gly Leu Val Gly Met Phe
                245                 250                 255

Asp Pro Lys Gly Arg Lys Val Pro Cys Val Gly Leu Ser Ile Gly Val
            260                 265                 270

Glu Arg Ile Phe Ser Ile Val Glu Gln Arg Leu Glu Ala Leu Glu Glu
        275                 280                 285

Lys Ile Arg Thr Thr Glu Thr Gln Val Leu Val Ala Ser Ala Gln Lys
    290                 295                 300

Lys Leu Leu Glu Glu Arg Leu Lys Leu Val Ser Glu Leu Trp Asp Ala
305                 310                 315                 320

Gly Ile Lys Ala Glu Leu Leu Tyr Lys Lys Asn Pro Lys Leu Leu Asn
                325                 330                 335

Gln Leu Gln Tyr Cys Glu Glu Ala Gly Ile Pro Leu Val Ala Ile Ile
            340                 345                 350

Gly Glu Gln Glu Leu Lys Asp Gly Val Ile Lys Leu Arg Ser Val Thr
        355                 360                 365

Ser Arg Glu Glu Val Asp Val Arg Glu Asp Leu Val Glu Ile
370                 375                 380

Lys Arg Arg Thr Gly Gln Pro Leu Cys Ile Cys
385                 390                 395

<210> SEQ ID NO 9
<211> LENGTH: 359
<212> TYPE: PRT
<213> ORGANISM: Homo sapiens

<400> SEQUENCE: 9

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Val Asn Asp Arg
    50                  55                  60

Arg Ile Leu Asp Gly Met Phe Ala Ile Cys Gly Val Ser Asp Ser Lys
65                  70                  75                  80

Phe Arg Thr Ile Cys Ser Ser Val Asp Lys Leu Asp Lys Val Ser Trp
                85                  90                  95

Glu Glu Val Lys Asn Glu Met Val Gly Glu Lys Gly Leu Ala Pro Glu
            100                 105                 110

Val Ala Asp Arg Ile Gly Asp Tyr Val Gln Gln His Gly Gly Val Ser
        115                 120                 125

Leu Val Glu Gln Leu Leu Gln Asp Pro Lys Leu Ser Gln Asn Lys Gln
    130                 135                 140

Ala Leu Glu Gly Leu Gly Asp Leu Lys Leu Phe Glu Tyr Leu Thr
145                 150                 155                 160

Leu Phe Gly Ile Asp Asp Lys Ile Ser Phe Asp Leu Ser Leu Ala Arg
                165                 170                 175

Gly Leu Asp Tyr Tyr Thr Gly Val Ile Tyr Glu Ala Val Leu Leu Gln
            180                 185                 190

Thr Pro Ala Gln Ala Gly Glu Glu Pro Leu Gly Val Gly Ser Val Ala
        195                 200                 205

Ala Gly Gly Arg Tyr Asp Gly Leu Val Gly Met Phe Asp Pro Lys Gly
    210                 215                 220

Arg Lys Val Pro Cys Val Gly Leu Ser Ile Gly Val Glu Arg Ile Phe
225                 230                 235                 240

Ser Ile Val Glu Gln Arg Leu Glu Ala Leu Glu Glu Lys Ile Arg Thr
                245                 250                 255

Thr Glu Thr Gln Val Leu Val Ala Ser Ala Gln Lys Lys Leu Leu Glu
            260                 265                 270

Glu Arg Leu Lys Leu Val Ser Glu Leu Trp Asp Ala Gly Ile Lys Ala
        275                 280                 285

Glu Leu Leu Tyr Lys Lys Asn Pro Lys Leu Leu Asn Gln Leu Gln Tyr
    290                 295                 300

Cys Glu Glu Ala Gly Ile Pro Leu Val Ala Ile Ile Gly Glu Gln Glu
305                 310                 315                 320

Leu Lys Asp Gly Val Ile Lys Leu Arg Ser Val Thr Ser Arg Glu Glu
                325                 330                 335

Val Asp Val Arg Arg Glu Asp Leu Val Glu Glu Ile Lys Arg Arg Thr
            340                 345                 350

Gly Gln Pro Leu Cys Ile Cys
        355

<210> SEQ ID NO 10
<211> LENGTH: 399
<212> TYPE: PRT
<213> ORGANISM: Homo sapiens

<400> SEQUENCE: 10

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Val Asn Asp Arg Arg Ile Leu Asp Gly Met Phe Ala
            100                 105                 110

Ile Cys Gly Val Ser Asp Ser Lys Phe Arg Thr Ile Cys Ser Ser Val
        115                 120                 125

Asp Lys Leu Asp Lys Val Ser Trp Glu Glu Val Lys Asn Glu Met Val
    130                 135                 140

Gly Glu Lys Gly Leu Ala Pro Glu Val Ala Asp Arg Ile Gly Asp Tyr
145                 150                 155                 160

Val Gln Gln His Gly Gly Val Ser Leu Val Glu Gln Leu Leu Gln Asp
                165                 170                 175

Pro Lys Leu Ser Gln Asn Lys Gln Ala Leu Glu Gly Leu Gly Asp Leu
            180                 185                 190

Lys Leu Leu Phe Glu Tyr Leu Thr Leu Phe Gly Ile Asp Asp Lys Ile
        195                 200                 205

Ser Phe Asp Leu Ser Leu Ala Arg Gly Leu Asp Tyr Tyr Thr Gly Val
    210                 215                 220

Ile Tyr Glu Ala Val Leu Leu Gln Thr Pro Ala Gln Ala Gly Glu Glu
225                 230                 235                 240

Pro Leu Gly Val Gly Ser Val Ala Ala Gly Gly Arg Tyr Asp Gly Leu
                245                 250                 255

Val Gly Met Phe Asp Pro Lys Gly Arg Lys Val Pro Cys Val Gly Leu
            260                 265                 270

Ser Ile Gly Val Glu Arg Ile Phe Ser Ile Val Glu Gln Arg Leu Glu
        275                 280                 285

Ala Leu Glu Glu Lys Ile Arg Thr Thr Glu Thr Gln Val Leu Val Ala
    290                 295                 300

Ser Ala Gln Lys Lys Leu Leu Glu Glu Arg Leu Lys Leu Val Ser Glu
305                 310                 315                 320

Leu Trp Asp Ala Gly Ile Lys Ala Glu Leu Leu Tyr Lys Lys Asn Pro
                325                 330                 335

Lys Leu Leu Asn Gln Leu Gln Tyr Cys Glu Glu Ala Gly Ile Pro Leu
            340                 345                 350

Val Ala Ile Ile Gly Glu Gln Glu Leu Lys Asp Gly Val Ile Lys Leu

```
                355                 360                 365
Arg Ser Val Thr Ser Arg Glu Glu Val Asp Val Arg Arg Glu Asp Leu
    370                 375                 380

Val Glu Glu Ile Lys Arg Arg Thr Gly Gln Pro Leu Cys Ile Cys
385                 390                 395

<210> SEQ ID NO 11
<211> LENGTH: 473
<212> TYPE: PRT
<213> ORGANISM: Homo sapiens

<400> SEQUENCE: 11

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Val Asn
                165                 170                 175

Asp Arg Arg Ile Leu Asp Gly Met Phe Ala Ile Cys Gly Val Ser Asp
            180                 185                 190

Ser Lys Phe Arg Thr Ile Cys Ser Ser Val Asp Lys Leu Asp Lys Val
        195                 200                 205

Ser Trp Glu Glu Val Lys Asn Glu Met Val Gly Glu Lys Gly Leu Ala
    210                 215                 220

Pro Glu Val Ala Asp Arg Ile Gly Asp Tyr Val Gln Gln His Gly Gly
225                 230                 235                 240

Val Ser Leu Val Glu Gln Leu Leu Gln Asp Pro Lys Leu Ser Gln Asn
                245                 250                 255

Lys Gln Ala Leu Glu Gly Leu Gly Asp Leu Lys Leu Leu Phe Glu Tyr
            260                 265                 270

Leu Thr Leu Phe Gly Ile Asp Asp Lys Ile Ser Phe Asp Leu Ser Leu
        275                 280                 285

Ala Arg Gly Leu Asp Tyr Tyr Thr Gly Val Ile Tyr Glu Ala Val Leu
    290                 295                 300

Leu Gln Thr Pro Ala Gln Ala Gly Glu Glu Pro Leu Gly Val Gly Ser
305                 310                 315                 320

Val Ala Ala Gly Gly Arg Tyr Asp Gly Leu Val Gly Met Phe Asp Pro
                325                 330                 335
```

```
Lys Gly Arg Lys Val Pro Cys Val Gly Leu Ser Ile Gly Val Glu Arg
                340                 345                 350

Ile Phe Ser Ile Val Glu Gln Arg Leu Glu Ala Leu Glu Glu Lys Ile
            355                 360                 365

Arg Thr Thr Glu Thr Gln Val Leu Val Ala Ser Ala Gln Lys Lys Leu
        370                 375                 380

Leu Glu Glu Arg Leu Lys Leu Val Ser Glu Leu Trp Asp Ala Gly Ile
385                 390                 395                 400

Lys Ala Glu Leu Leu Tyr Lys Lys Asn Pro Lys Leu Leu Asn Gln Leu
                405                 410                 415

Gln Tyr Cys Glu Glu Ala Gly Ile Pro Leu Val Ala Ile Ile Gly Glu
            420                 425                 430

Gln Glu Leu Lys Asp Gly Val Ile Lys Leu Arg Ser Val Thr Ser Arg
        435                 440                 445

Glu Glu Val Asp Val Arg Arg Glu Asp Leu Val Glu Glu Ile Lys Arg
450                 455                 460

Arg Thr Gly Gln Pro Leu Cys Ile Cys
465                 470

<210> SEQ ID NO 12
<211> LENGTH: 469
<212> TYPE: PRT
<213> ORGANISM: Homo sapiens

<400> SEQUENCE: 12

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Glu Thr Leu Met
    50                  55                  60

Gly Lys Tyr Gly Glu Asp Ser Lys Leu Ile Tyr Asp Leu Lys Asp Gln
65              70                  75                  80

Gly Gly Glu Leu Leu Ser Leu Arg Tyr Asp Leu Thr Val Pro Phe Ala
                85                  90                  95

Arg Tyr Leu Ala Met Asn Lys Leu Thr Asn Ile Lys Arg Tyr His Ile
            100                 105                 110

Ala Lys Val Tyr Arg Arg Asp Asn Pro Ala Met Thr Arg Gly Arg Tyr
        115                 120                 125

Arg Glu Phe Tyr Gln Cys Asp Phe Asp Ile Ala Gly Asn Phe Asp Pro
    130                 135                 140

Met Ile Pro Asp Ala Glu Cys Leu Lys Ile Met Cys Glu Ile Leu Ser
145                 150                 155                 160

Ser Leu Gln Ile Gly Asp Phe Leu Val Lys Val Asn Asp Arg Arg Ile
                165                 170                 175

Leu Asp Gly Met Phe Ala Ile Cys Gly Val Ser Asp Ser Lys Phe Arg
            180                 185                 190

Thr Ile Cys Ser Ser Val Asp Lys Leu Asp Lys Val Ser Trp Glu Glu
        195                 200                 205

Val Lys Asn Glu Met Val Gly Glu Lys Gly Leu Ala Pro Glu Val Ala
    210                 215                 220

Asp Arg Ile Gly Asp Tyr Val Gln Gln His Gly Gly Val Ser Leu Val
225                 230                 235                 240
```

```
Glu Gln Leu Leu Gln Asp Pro Lys Leu Ser Gln Asn Lys Gln Ala Leu
                245                 250                 255

Glu Gly Leu Gly Asp Leu Lys Leu Leu Phe Glu Tyr Leu Thr Leu Phe
            260                 265                 270

Gly Ile Asp Asp Lys Ile Ser Phe Asp Leu Ser Leu Ala Arg Gly Leu
        275                 280                 285

Asp Tyr Tyr Thr Gly Val Ile Tyr Glu Ala Val Leu Leu Gln Thr Pro
    290                 295                 300

Ala Gln Ala Gly Glu Glu Pro Leu Gly Val Gly Ser Val Ala Ala Gly
305                 310                 315                 320

Gly Arg Tyr Asp Gly Leu Val Gly Met Phe Asp Pro Lys Gly Arg Lys
                325                 330                 335

Val Pro Cys Val Gly Leu Ser Ile Gly Val Glu Arg Ile Phe Ser Ile
            340                 345                 350

Val Glu Gln Arg Leu Glu Ala Leu Glu Glu Lys Ile Arg Thr Thr Glu
        355                 360                 365

Thr Gln Val Leu Val Ala Ser Ala Gln Lys Lys Leu Leu Glu Glu Arg
    370                 375                 380

Leu Lys Leu Val Ser Glu Leu Trp Asp Ala Gly Ile Lys Ala Glu Leu
385                 390                 395                 400

Leu Tyr Lys Lys Asn Pro Lys Leu Leu Asn Gln Leu Gln Tyr Cys Glu
                405                 410                 415

Glu Ala Gly Ile Pro Leu Val Ala Ile Ile Gly Glu Gln Glu Leu Lys
            420                 425                 430

Asp Gly Val Ile Lys Leu Arg Ser Val Thr Ser Arg Glu Glu Val Asp
        435                 440                 445

Val Arg Arg Glu Asp Leu Val Glu Glu Ile Lys Arg Arg Thr Gly Gln
    450                 455                 460

Pro Leu Cys Ile Cys
465

<210> SEQ ID NO 13
<211> LENGTH: 435
<212> TYPE: PRT
<213> ORGANISM: Homo sapiens

<400> SEQUENCE: 13

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Asp Phe Asp Ile Ala Gly Asn Phe Asp Pro Met Ile
            100                 105                 110

Pro Asp Ala Glu Cys Leu Lys Ile Met Cys Glu Ile Leu Ser Ser Leu
        115                 120                 125

Gln Ile Gly Asp Phe Leu Val Lys Val Asn Asp Arg Arg Ile Leu Asp
```

```
                130                 135                 140
Gly Met Phe Ala Ile Cys Gly Val Ser Asp Ser Lys Phe Arg Thr Ile
145                 150                 155                 160

Cys Ser Ser Val Asp Lys Leu Asp Lys Val Ser Trp Glu Glu Val Lys
                165                 170                 175

Asn Glu Met Val Gly Glu Lys Gly Leu Ala Pro Glu Val Ala Asp Arg
            180                 185                 190

Ile Gly Asp Tyr Val Gln Gln His Gly Gly Val Ser Leu Val Glu Gln
        195                 200                 205

Leu Leu Gln Asp Pro Lys Leu Ser Gln Asn Lys Gln Ala Leu Glu Gly
210                 215                 220

Leu Gly Asp Leu Lys Leu Leu Phe Glu Tyr Leu Thr Leu Phe Gly Ile
225                 230                 235                 240

Asp Asp Lys Ile Ser Phe Asp Leu Ser Leu Ala Arg Gly Leu Asp Tyr
                245                 250                 255

Tyr Thr Gly Val Ile Tyr Glu Ala Val Leu Leu Gln Thr Pro Ala Gln
            260                 265                 270

Ala Gly Glu Glu Pro Leu Gly Val Gly Ser Val Ala Ala Gly Gly Arg
        275                 280                 285

Tyr Asp Gly Leu Val Gly Met Phe Asp Pro Lys Gly Arg Lys Val Pro
290                 295                 300

Cys Val Gly Leu Ser Ile Gly Val Glu Arg Ile Phe Ser Ile Val Glu
305                 310                 315                 320

Gln Arg Leu Glu Ala Leu Glu Glu Lys Ile Arg Thr Thr Glu Thr Gln
                325                 330                 335

Val Leu Val Ala Ser Ala Gln Lys Lys Leu Leu Glu Glu Arg Leu Lys
            340                 345                 350

Leu Val Ser Glu Leu Trp Asp Ala Gly Ile Lys Ala Glu Leu Leu Tyr
        355                 360                 365

Lys Lys Asn Pro Lys Leu Leu Asn Gln Leu Gln Tyr Cys Glu Glu Ala
370                 375                 380

Gly Ile Pro Leu Val Ala Ile Ile Gly Glu Gln Glu Leu Lys Asp Gly
385                 390                 395                 400

Val Ile Lys Leu Arg Ser Val Thr Ser Arg Glu Val Asp Val Arg
                405                 410                 415

Arg Glu Asp Leu Val Glu Glu Ile Lys Arg Arg Thr Gly Gln Pro Leu
            420                 425                 430

Cys Ile Cys
        435

<210> SEQ ID NO 14
<211> LENGTH: 171
<212> TYPE: PRT
<213> ORGANISM: Homo sapiens

<400> SEQUENCE: 14

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ala Leu Glu Glu
50                  55                  60
```

```
Lys Ile Arg Thr Thr Glu Thr Gln Val Leu Val Ala Ser Ala Gln Lys
 65                  70                  75                  80

Lys Leu Leu Glu Glu Arg Leu Lys Leu Val Ser Glu Leu Trp Asp Ala
                 85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
            115                 120                 125

Gly Glu Gln Glu Leu Lys Asp Gly Val Ile Lys Leu Arg Ser Val Thr
130                 135                 140

Ser Arg Glu Glu Val Asp Val Arg Arg Glu Asp Leu Val Glu Glu Ile
145                 150                 155                 160

Lys Arg Arg Thr Gly Gln Pro Leu Cys Ile Cys
                165                 170

<210> SEQ ID NO 15
<211> LENGTH: 211
<212> TYPE: PRT
<213> ORGANISM: Homo sapiens

<400> SEQUENCE: 15

Met Ala Glu Arg Ala Ala Leu Glu Glu Leu Val Lys Leu Gln Gly Glu
  1               5                  10                  15

Arg Val Arg Gly Leu Lys Gln Gln Lys Ala Ser Ala Glu Leu Ile Glu
                 20                  25                  30

Glu Glu Val Ala Lys Leu Leu Lys Leu Lys Ala Gln Leu Gly Pro Asp
             35                  40                  45

Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Ala Leu Glu Glu Lys Ile Arg Thr Thr Glu Thr Gln
            100                 105                 110

Val Leu Val Ala Ser Ala Gln Lys Leu Leu Glu Glu Arg Leu Lys
            115                 120                 125

Leu Val Ser Glu Leu Trp Asp Ala Gly Ile Lys Ala Glu Leu Leu Tyr
130                 135                 140

Lys Lys Asn Pro Lys Leu Leu Asn Gln Leu Gln Tyr Cys Glu Glu Ala
145                 150                 155                 160

Gly Ile Pro Leu Val Ala Ile Ile Gly Glu Gln Glu Leu Lys Asp Gly
                165                 170                 175

Val Ile Lys Leu Arg Ser Val Thr Ser Arg Glu Glu Val Asp Val Arg
            180                 185                 190

Arg Glu Asp Leu Val Glu Glu Ile Lys Arg Arg Thr Gly Gln Pro Leu
            195                 200                 205

Cys Ile Cys
210

<210> SEQ ID NO 16
<211> LENGTH: 141
<212> TYPE: PRT
<213> ORGANISM: Homo sapiens

<400> SEQUENCE: 16
```

```
Met Phe Asp Pro Lys Gly Arg Lys Val Pro Cys Val Gly Leu Ser Ile
1               5                   10                  15

Gly Val Glu Arg Ile Phe Ser Ile Val Glu Gln Arg Leu Glu Ala Leu
            20                  25                  30

Glu Glu Lys Ile Arg Thr Thr Glu Thr Gln Val Leu Val Ala Ser Ala
        35                  40                  45

Gln Lys Lys Leu Leu Glu Arg Leu Lys Leu Val Ser Glu Leu Trp
    50                  55                  60

Asp Ala Gly Ile Lys Ala Glu Leu Leu Tyr Lys Asn Pro Lys Leu
65                  70                  75                  80

Leu Asn Gln Leu Gln Tyr Cys Glu Glu Ala Gly Ile Pro Leu Val Ala
                85                  90                  95

Ile Ile Gly Glu Gln Glu Leu Lys Asp Gly Val Ile Lys Leu Arg Ser
            100                 105                 110

Val Thr Ser Arg Glu Glu Val Asp Val Arg Arg Glu Asp Leu Val Glu
            115                 120                 125

Glu Ile Lys Arg Arg Thr Gly Gln Pro Leu Cys Ile Cys
130                 135                 140
```

<210> SEQ ID NO 17
<211> LENGTH: 143
<212> TYPE: PRT
<213> ORGANISM: Homo sapiens

<400> SEQUENCE: 17

```
Cys Leu Lys Ile Met Cys Glu Ile Leu Ser Ser Leu Gln Ile Gly Asp
1               5                   10                  15

Phe Leu Val Lys Val Asn Asp Arg Arg Ile Leu Asp Gly Met Phe Ala
            20                  25                  30

Ile Cys Gly Val Ser Asp Ser Lys Phe Arg Thr Ile Cys Ser Ser Val
            35                  40                  45

Asp Lys Leu Asp Lys Val Ser Trp Glu Glu Val Lys Asn Glu Met Val
    50                  55                  60

Gly Glu Lys Gly Leu Ala Pro Glu Val Ala Asp Arg Ile Gly Asp Tyr
65                  70                  75                  80

Val Gln Gln His Gly Val Ser Leu Val Glu Gln Leu Leu Gln Asp
                85                  90                  95

Pro Lys Leu Ser Gln Asn Lys Gln Ala Leu Gly Leu Gly Asp Leu
            100                 105                 110

Lys Leu Leu Phe Glu Tyr Leu Thr Leu Phe Gly Ile Asp Asp Lys Ile
            115                 120                 125

Ser Phe Asp Leu Ser Leu Ala Arg Gly Leu Asp Tyr Tyr Thr Gly
130                 135                 140
```

<210> SEQ ID NO 18
<211> LENGTH: 509
<212> TYPE: PRT
<213> ORGANISM: Mus musculus

<400> SEQUENCE: 18

```
Met Ala Asp Arg Ala Ala Leu Glu Glu Leu Val Arg Leu Gln Gly Ala
1               5                   10                  15

His Val Arg Gly Leu Lys Glu Gln Lys Ala Ser Ala Glu Gln Ile Glu
            20                  25                  30

Glu Glu Val Thr Lys Leu Leu Lys Leu Lys Ala Gln Leu Gly Gln Asp
        35                  40                  45
```

```
Glu Gly Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
                100                 105                 110

Leu Ile Tyr Asp Leu Lys Asp Gln Gly Glu Leu Leu Ser Leu Arg
            115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Lys Ile Met Cys Glu Ile Leu Ser Ser Leu Gln Ile Gly Asn Phe Leu
            195                 200                 205

Val Lys Val Asn Asp Arg Arg Ile Leu Asp Gly Met Phe Ala Val Cys
    210                 215                 220

Gly Val Pro Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
            275                 280                 285

Leu Ser Gln Asn Lys Gln Ala Val Glu Gly Leu Gly Asp Leu Lys Leu
    290                 295                 300

Leu Phe Glu Tyr Leu Ile Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
            340                 345                 350

Gly Val Gly Ser Ile Ala Ala Gly Gly Arg Tyr Asp Gly Leu Val Gly
            355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Ser
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Tyr Lys Lys Asn Pro Lys Leu
            435                 440                 445

Leu Asn Gln Leu Gln Tyr Trp Glu Glu Ala Gly Ile Pro Leu Val Ala
    450                 455                 460

Ile Ile Gly Glu Gln Glu Leu Arg Asp Gly Val Ile Lys Leu Arg Ser
```

```
                465                 470                 475                 480
Val Ala Ser Arg Glu Glu Val Asp Val Arg Arg Glu Asp Leu Val Glu
                    485                 490                 495

Glu Ile Arg Arg Arg Thr Asn Gln Pro Leu Ser Thr Cys
                500                 505

<210> SEQ ID NO 19
<211> LENGTH: 509
<212> TYPE: PRT
<213> ORGANISM: Canis lupus familiaris

<400> SEQUENCE: 19

Met Ala Glu Arg Ala Ala Leu Glu Glu Leu Val Arg Leu Gln Gly Glu
1               5                   10                  15

Arg Val Arg Gly Leu Lys Gln Gln Lys Ala Ser Ala Glu Gln Ile Glu
                20                  25                  30

Glu Glu Val Ala Lys Leu Leu Lys Leu Lys Ala Gln Leu Gly Pro Asp
            35                  40                  45

Glu Gly Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Glu Ile Met Cys Glu Ile Leu Arg Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp His Ile Gly Asp Tyr Val Gln
            260                 265                 270

Gln His Gly Gly Ile Ser Leu Val Glu Gln Leu Leu Gln Asp Pro Glu
        275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Ala Asp Lys Ile Ser Phe
305                 310                 315                 320

Asp Leu Ser Leu Ala Arg Gly Leu Asp Tyr Tyr Thr Gly Val Ile Tyr
                325                 330                 335
```

```
Glu Ala Val Leu Leu Gln Thr Pro Val Gln Ala Gly Glu Glu Pro Leu
                340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Thr
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asn Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
            450                 455                 460

Ile Ile Gly Glu Gln Glu Leu Lys Asp Gly Val Ile Lys Leu Arg Ser
465                 470                 475                 480

Val Ala Ser Arg Glu Glu Val Asp Val Pro Arg Glu Asp Leu Val Glu
                485                 490                 495

Glu Ile Lys Arg Arg Thr Ser Gln Pro Phe Cys Ile Cys
                500                 505

<210> SEQ ID NO 20
<211> LENGTH: 509
<212> TYPE: PRT
<213> ORGANISM: Bos taurus

<400> SEQUENCE: 20

Met Ala Asp Arg Ala Ala Leu Glu Asp Leu Val Arg Val Gln Gly Glu
1               5                   10                  15

Arg Val Arg Gly Leu Lys Gln Gln Lys Ala Ser Ala Glu Gln Ile Glu
            20                  25                  30

Glu Glu Val Ala Lys Leu Leu Lys Leu Lys Ala Gln Leu Gly Pro Asp
        35                  40                  45

Glu Gly Lys Pro Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Leu Pro Asp Ala Glu Cys Leu
            180                 185                 190

Lys Ile Met Cys Glu Ile Leu Ser Ser Leu Gln Ile Gly Asp Phe Leu
        195                 200                 205
```

```
Val Lys Val Asn Asp Arg Arg Ile Leu Asp Gly Met Phe Ala Ile Cys
    210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Ala Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Pro Pro Ala Arg Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Ile Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Thr Gly Ile Pro Leu Val Ala
    450                 455                 460

Ile Ile Gly Glu Gln Glu Leu Lys Asp Gly Val Ile Lys Leu Arg Ser
465                 470                 475                 480

Val Ala Ser Arg Glu Glu Val Asp Val Arg Arg Glu Asp Leu Val Glu
                485                 490                 495

Glu Ile Lys Arg Arg Thr Ser Gln Pro Leu Cys Ile Cys
            500                 505
```

<210> SEQ ID NO 21
<211> LENGTH: 508
<212> TYPE: PRT
<213> ORGANISM: Rattus norvegicus

<400> SEQUENCE: 21

```
Met Ala Asp Arg Ala Ala Leu Glu Glu Leu Val Arg Leu Gln Gly Ala
1               5                   10                  15

His Val Arg Gly Leu Lys Glu Gln Lys Ala Ser Ala Glu Gln Ile Glu
            20                  25                  30

Glu Glu Val Thr Lys Leu Leu Lys Leu Lys Ala Gln Leu Gly His Asp
        35                  40                  45

Glu Gly Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
```

```
             65                  70                  75                  80
Ile Arg Cys Phe Lys Arg His Gly Ala Glu Val Ile Asp Thr Pro Val
                     85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Leu Leu Ser Leu Arg
            115                 120                 125

Tyr Asp Leu Thr Val Pro Phe Ala Arg Tyr Leu Ala Met Asn Lys Leu
            130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                    165                 170                 175

Asp Ile Ala Gly Gln Phe Asp Pro Met Ile Pro Asp Ala Glu Cys Leu
                180                 185                 190

Lys Ile Met Cys Glu Ile Leu Ser Ser Leu Gln Ile Gly Asn Phe Gln
                195                 200                 205

Val Lys Val Asn Asp Arg Arg Ile Leu Asp Gly Met Phe Ala Val Cys
            210                 215                 220

Gly Val Pro Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                    245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
            275                 280                 285

Leu Ser Gln Asn Lys Gln Ala Val Glu Gly Leu Gly Asp Leu Lys Leu
            290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
                340                 345                 350

Gly Val Gly Ser Ile Ala Ala Gly Gly Arg Tyr Asp Gly Leu Val Gly
                355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Lys Leu Glu Ala Ser
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Ile Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
            450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495
```

```
Glu Ile Arg Arg Arg Thr Ser Gln Pro Leu Ser Met
            500                 505
```

<210> SEQ ID NO 22
<211> LENGTH: 500
<212> TYPE: PRT
<213> ORGANISM: Gallus gallus

<400> SEQUENCE: 22

```
Met Ala Asp Glu Ala Ala Val Arg Gln Gln Ala Glu Val Val Arg Arg
1               5                   10                  15

Leu Lys Gln Asp Lys Ala Glu Pro Asp Glu Ile Ala Lys Glu Val Ala
            20                  25                  30

Lys Leu Leu Glu Met Lys Ala His Leu Gly Gly Asp Glu Gly Lys His
        35                  40                  45

Lys Phe Val Leu Lys Thr Pro Lys Gly Thr Arg Asp Tyr Gly Pro Lys
    50                  55                  60

Gln Met Ala Ile Arg Glu Arg Val Phe Ser Ala Ile Ile Ala Cys Phe
65                  70                  75                  80

Lys Arg His Gly Ala Glu Val Ile Asp Thr Pro Val Phe Glu Leu Lys
                85                  90                  95

Glu Thr Leu Thr Gly Lys Tyr Gly Glu Asp Ser Lys Leu Ile Tyr Asp
            100                 105                 110

Leu Lys Asp Gln Gly Gly Glu Leu Leu Ser Leu Arg Tyr Asp Leu Thr
        115                 120                 125

Val Pro Phe Ala Arg Tyr Leu Ala Met Asn Lys Ile Thr Asn Ile Lys
    130                 135                 140

Arg Tyr His Ile Ala Lys Val Tyr Arg Arg Asp Asn Pro Ala Met Thr
145                 150                 155                 160

Arg Gly Arg Tyr Arg Glu Phe Tyr Gln Cys Asp Phe Asp Ile Ala Gly
                165                 170                 175

Gln Phe Asp Pro Met Ile Pro Asp Ala Glu Cys Leu Lys Ile Val Gln
            180                 185                 190

Glu Ile Leu Ser Asp Leu Gln Leu Gly Asp Phe Leu Ile Lys Val Asn
        195                 200                 205

Asp Arg Arg Ile Leu Asp Gly Met Phe Ala Val Cys Gly Val Pro Asp
    210                 215                 220

Ser Lys Phe Arg Thr Ile Cys Ser Ser Val Asp Lys Leu Asp Lys Met
225                 230                 235                 240

Pro Trp Glu Glu Val Arg Asn Glu Met Val Gly Glu Lys Gly Leu Ser
                245                 250                 255

Pro Glu Ala Ala Asp Arg Ile Gly Glu Tyr Val Gln Leu His Gly Gly
            260                 265                 270

Met Asp Leu Ile Glu Gln Leu Leu Gln Asp Pro Lys Leu Ser Gln Asn
        275                 280                 285

Lys Leu Val Lys Glu Gly Leu Gly Asp Met Lys Leu Leu Phe Glu Tyr
    290                 295                 300

Leu Thr Leu Phe Gly Ile Thr Gly Lys Ile Ser Phe Asp Leu Ser Leu
305                 310                 315                 320

Ala Arg Gly Leu Asp Tyr Tyr Thr Gly Val Ile Tyr Glu Ala Val Leu
                325                 330                 335

Leu Gln Gln Asn Asp His Gly Glu Glu Ser Val Ser Val Gly Ser Val
            340                 345                 350

Ala Gly Gly Gly Arg Tyr Asp Gly Leu Val Gly Met Phe Asp Pro Lys
```

```
                355                 360                 365
Gly Arg Lys Val Pro Cys Val Gly Ile Ser Ile Gly Ile Glu Arg Ile
370                 375                 380

Phe Ser Ile Leu Glu Gln Arg Val Glu Ala Ser Glu Lys Ile Arg
385                 390                 395                 400

Thr Thr Glu Thr Gln Val Leu Val Ala Ser Ala Gln Lys Lys Leu Leu
                405                 410                 415

Glu Glu Arg Leu Lys Leu Ile Ser Glu Leu Trp Asp Ala Gly Ile Lys
                420                 425                 430

Ala Glu Val Leu Tyr Lys Lys Asn Pro Lys Leu Leu Asn Gln Leu Gln
                435                 440                 445

Tyr Cys Glu Asp Thr Gly Ile Pro Leu Val Ala Ile Val Gly Glu Gln
                450                 455                 460

Glu Leu Lys Asp Gly Val Val Lys Leu Arg Val Val Ala Thr Gly Glu
465                 470                 475                 480

Glu Val Asn Ile Arg Arg Glu Ser Leu Val Glu Glu Ile Arg Arg Arg
                485                 490                 495

Thr Asn Gln Leu
            500

<210> SEQ ID NO 23
<211> LENGTH: 437
<212> TYPE: PRT
<213> ORGANISM: Danio rerio

<400> SEQUENCE: 23

Met Ala Ala Leu Gly Leu Val Ser Met Arg Leu Cys Ala Gly Leu Met
1               5                   10                  15

Gly Arg Arg Ser Ala Val Arg Leu His Ser Leu Arg Val Cys Ser Gly
                20                  25                  30

Met Thr Ile Ser Gln Ile Asp Glu Glu Val Ala Arg Leu Leu Gln Leu
                35                  40                  45

Lys Ala Gln Leu Gly Gly Asp Glu Gly Lys His Val Phe Val Leu Lys
            50                  55                  60

Thr Ala Lys Gly Thr Arg Asp Tyr Asn Pro Lys Gln Met Ala Ile Arg
65                  70                  75                  80

Glu Lys Val Phe Asn Ile Ile Asn Cys Phe Lys Arg His Gly Ala
                85                  90                  95

Glu Thr Ile Asp Ser Pro Val Phe Glu Leu Lys Glu Thr Leu Thr Gly
                100                 105                 110

Lys Tyr Gly Glu Asp Ser Lys Leu Ile Tyr Asp Leu Lys Asp Gln Gly
            115                 120                 125

Gly Glu Leu Leu Ser Leu Arg Tyr Asp Leu Thr Val Pro Phe Ala Arg
        130                 135                 140

Tyr Leu Ala Met Asn Lys Ile Thr Asn Ile Lys Arg Tyr His Ile Ala
145                 150                 155                 160

Lys Val Tyr Arg Arg Asp Asn Pro Ala Met Thr Arg Gly Arg Tyr Arg
                165                 170                 175

Glu Phe Tyr Gln Cys Asp Phe Asp Ile Ala Gly Gln Tyr Asp Ala Met
                180                 185                 190

Ile Pro Asp Ala Glu Cys Leu Lys Leu Val Tyr Glu Ile Leu Ser Glu
            195                 200                 205

Leu Asp Leu Gly Asp Phe Arg Ile Lys Val Asn Asp Arg Arg Ile Leu
        210                 215                 220
```

```
Asp Gly Met Phe Ala Ile Cys Gly Val Pro Asp Glu Lys Phe Arg Thr
225                 230                 235                 240

Ile Cys Ser Thr Val Asp Lys Leu Asp Lys Leu Ala Trp Glu Glu Val
            245                 250                 255

Lys Lys Glu Met Val Asn Glu Lys Gly Leu Ser Glu Glu Val Ala Asp
        260                 265                 270

Arg Ile Arg Asp Tyr Val Ser Met Gln Gly Gly Lys Asp Leu Ala Glu
    275                 280                 285

Arg Leu Leu Gln Asp Pro Lys Leu Ser Gln Ser Lys Gln Ala Cys Ala
    290                 295                 300

Gly Ile Thr Asp Met Lys Leu Leu Phe Ser Tyr Leu Glu Leu Phe Gln
305                 310                 315                 320

Ile Thr Asp Lys Val Val Phe Asp Leu Ser Leu Ala Arg Gly Leu Asp
            325                 330                 335

Tyr Tyr Thr Gly Val Ile Tyr Glu Ala Ile Leu Thr Gln Ala Asn Pro
            340                 345                 350

Ala Pro Ala Ser Thr Pro Ala Glu Gln Asn Gly Ala Glu Asp Ala Gly
        355                 360                 365

Val Ser Val Gly Ser Val Ala Gly Gly Arg Tyr Asp Gly Leu Val
370                 375                 380

Gly Met Phe Asp Pro Lys Ala Gly Lys Cys Pro Val Trp Gly Ser Ala
385                 390                 395                 400

Leu Ala Leu Arg Gly Ser Ser Pro Ser Trp Ser Arg Gln Ser Cys
            405                 410                 415

Leu Gln Arg Arg Cys Ala Pro Leu Lys Leu Lys Cys Leu Trp Leu Gln
        420                 425                 430

His Arg Arg Thr Phe
        435

<210> SEQ ID NO 24
<211> LENGTH: 1527
<212> TYPE: DNA
<213> ORGANISM: Artificial Sequence
<220> FEATURE:
<223> OTHER INFORMATION: Codon optimized nucleic acid sequence for wild
      type HisRs

<400> SEQUENCE: 24
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat tgtgctcaa aaccccccaag     180 ggcacaagag actatagtcc ccggcagatg gcagttcgcg agaaggtgtt tgacgtaatc     240
atccgttgct tcaagcgcca cggtgcagaa gtcattgata cacctgtatt tgaactaaag     300
gaaacactga tgggaaagta tgggaagac tccaagctta tctatgacct gaaggaccag     360
ggcggggagc tcctgtccct tcgctatgac ctcactgttc cttttgctcg gtatttggca     420
atgaataaac tgaccaacat taaacgctac cacatagcaa aggtatatcg gcgggataac     480
ccagccatga cccgtggccg ataccgggaa ttctaccagt gtgattttga cattgctggg     540
aactttgatc ccatgatccc tgatgcagag tgcctgaaga tcatgtgcga gatcctgagt     600
tcacttcaga taggcgactt cctggtcaag gtaaacgatc gacgcattct agatgggatg     660
tttgctatct gtggtgtttc tgacagcaag ttccgtacca tctgctcctc agtagacaag     720
ctggacaagg tgtcctggga agaggtgaag aatgagatgg tgggagagaa gggccttgca     780
```

| | |
|---|---|
| cctgaggtgg ctgaccgcat tggggactat gtccagcaac atggtggggt atccctggtg | 840 |
| gaacagctgc tccaggatcc taaactatcc caaaacaagc aggccttgga gggcctggga | 900 |
| gacctgaagt tgctctttga gtacctgacc ctatttggca ttgatgacaa atctcctttt | 960 |
| gacctgagcc ttgctcgagg gctggattac tacactgggg tgatctatga ggcagtgctg | 1020 |
| ctacagaccc cagcccaggc aggggaagag ccctgggtg tgggcagtgt ggctgctgga | 1080 |
| ggacgctatg atgggctagt gggcatgttc gaccccaaag gcgcaaggt gccatgtgtg | 1140 |
| gggctcagca ttgggtgga gcggatttc tccatcgtgg aacagagact agaggctttg | 1200 |
| gaggagaaga tacggaccac ggagacacag gtgcttgtgg catctgcaca gaagaagctg | 1260 |
| ctagaggaaa gactaaagct tgtctcagaa ctgtgggatg ctgggatcaa ggctgagctg | 1320 |
| ctgtacaaga gaacccaaa gctactgaac cagttacagt actgtgagga ggcaggcatc | 1380 |
| ccactggtgg ctatcatcgg cgagcaggaa ctcaaggatg gggtcatcaa gctccgttca | 1440 |
| gtgacgagca gggaagaggt ggatgtccga agagaagacc ttgtggagga aatcaaaagg | 1500 |
| agaacaggcc agcccctctg catctgc | 1527 |

<210> SEQ ID NO 25
<211> LENGTH: 423
<212> TYPE: DNA
<213> ORGANISM: Artificial Sequence
<220> FEATURE:
<223> OTHER INFORMATION: Codon optimized nucleic acid sequence for
      N-terminal fragment of HisRS1

<400> SEQUENCE: 25

| | |
|---|---|
| atggcagaac gtgccgccct ggaagagctg gtaaaactgc aaggcgagcg tgttcgtggt | 60 |
| ctgaaacagc agaaagcaag cgctgaactg atcgaagaag aagtggcgaa actgctgaaa | 120 |
| ctgaaagcac agctgggtcc tgatgaatca aaacaaaaat tcgtcctgaa aactccgaaa | 180 |
| ggaacccgtg actattctcc tcgtcaaatg gccgtccgtg aaaaagtgtt cgacgtgatc | 240 |
| attcgctgct ttaaacgcca tggtgccgaa gtgattgata ccccggtgtt tgagctgaaa | 300 |
| gagacactga tgggcaaata tggtgaggac agcaaactga tttatgacct gaaagatcag | 360 |
| ggtggtgaac tgctgagtct gcgctatgat ctgacagttc cgtttgcccg ttatctggca | 420 |
| atg | 423 |

<210> SEQ ID NO 26
<211> LENGTH: 1224
<212> TYPE: DNA
<213> ORGANISM: Artificial Sequence
<220> FEATURE:
<223> OTHER INFORMATION: Codon optimized nucleic acid sequence for
      N-terminal fragment of HisRS1

<400> SEQUENCE: 26

| | |
|---|---|
| atggcagaac gtgccgccct ggaagagctg gtaaaactgc aaggcgagcg tgttcgtggt | 60 |
| ctgaaacagc agaaagcaag cgctgaactg atcgaagaag aagtggcgaa actgctgaaa | 120 |
| ctgaaagcac agctgggtcc tgatgaatca aaacaaaaat tcgtcctgaa aactccgaaa | 180 |
| ggaacccgtg actattctcc tcgtcaaatg gccgtccgtg aaaaagtgtt cgacgtgatc | 240 |
| attcgctgct ttaaacgcca tggtgccgaa gtgattgata ccccggtgtt tgagctgaaa | 300 |
| gagacactga tgggcaaata tggtgaggac agcaaactga tttatgacct gaaagatcag | 360 |
| ggtggtgaac tgctgagtct gcgctatgat ctgacagttc cgtttgcccg ttatctggca | 420 |
| atgaataaac tgaccaacat taaacgctat cacattgcta aagtctatcg ccgtgacaat | 480 |

```
cctgctatga cccgtggtcg ttatcgtgag ttctatcagt gtgacttcga tattgccggc    540
aactttgatc cgatgatccc ggatgctgaa tgcctgaaaa tcatgtgtga gatcctgagc    600
agtctgcaga ttggcgattt cctggtgaaa gtcaacgatc gccgtattct ggatggcatg    660
ttcgccatct gtggtgttag cgactccaaa ttccgtacca tctgtagtag tgtggacaaa    720
ctggataaag tgagctggga ggaggtgaaa aacgaaatgg tgggcgagaa aggtctggct    780
cctgaagtgg ctgaccgtat tggtgattat gtccagcagc acggtggagt atcactggtt    840
gagcaactgc tgcaagaccc taaactgagt cagaataaac aggccctgga gggactggga    900
gatctgaaac tgctgttcga gtatctgacc ctgttcggta tcgatgacaa atctcctttt    960
gacctgtcac tggctcgtgg actggactat tataccggcg tgatctatga agctgtactg    1020
ctgcaaactc cagcacaagc aggtgaagag cctctgggtg tgggtagtgt agccgctggg    1080
ggacgttatg atggactggt ggggatgttc gaccctaaag gccgtaaagt tccgtgtgtg    1140
ggtctgagta tcggtgttga gcgtatcttt ccatcgtcg agcaacgtct ggaagcactg    1200
gaggaaaaaa tccgtacgac cgaa                                          1224
```

<210> SEQ ID NO 27
<211> LENGTH: 339
<212> TYPE: DNA
<213> ORGANISM: Artificial Sequence
<220> FEATURE:
<223> OTHER INFORMATION: Codon optimized nucleic acid sequence for
      N-terminal fragment of HisRS1

<400> SEQUENCE: 27

```
atggcagaac gtgccgccct ggaagagctg gtaaaactgc aaggcgagcg tgttcgtggt    60
ctgaaacagc agaaagcaag cgctgaactg atcgaagaag aagtggcgaa actgctgaaa    120
ctgaaagcac agctgggtcc tgatgaatca aaacaaaaat tcgtcctgaa aactccgaaa    180
ggaacccgtg actattctcc tcgtcaaatg gccgtccgtg aaaaagtgtt cgacgtgatc    240
attcgctgct ttaaacgcca tggtgccgaa gtgattgata ccccggtgtt tgagctgaaa    300
gagacactga tgggcaaata tggtgaggac agcaaactg                          339
```

<210> SEQ ID NO 28
<211> LENGTH: 180
<212> TYPE: DNA
<213> ORGANISM: Artificial Sequence
<220> FEATURE:
<223> OTHER INFORMATION: Codon optimized nucleic acid sequence for
      N-terminal fragment of HisRS

<400> SEQUENCE: 28

```
atggcagaac gtgccgccct ggaagagctg gtaaaactgc aaggcgagcg tgttcgtggt    60
ctgaaacagc agaaagcaag cgctgaactg atcgaagaag aagtggcgaa actgctgaaa    120
ctgaaagcac agctgggtcc tgatgaatca aaacaaaaat tcgtcctgaa aactccgaag    180
```

<210> SEQ ID NO 29
<211> LENGTH: 429
<212> TYPE: DNA
<213> ORGANISM: Artificial Sequence
<220> FEATURE:
<223> OTHER INFORMATION: Codon optimized nucleic acid sequence for
      intermediate fragment of HisRS1

<400> SEQUENCE: 29

```
tgcctgaaaa tcatgtgtga gatcctgagt agtctgcaaa ttggcgactt tctggtcaaa    60
```

```
gtgaacgatc gccgtattct ggatggcatg ttcgccatct gtggtgttag cgactccaaa    120
ttccgtacaa tctgtagcag cgtggacaaa ctggataaag tgtcctggga agaggtgaaa    180
aacgaaatgg tgggtgaaaa aggtctggct ccggaggttg ctgaccgtat cggtgattat    240
gttcagcagc acggcggtgt tagtctggtt gaacaactgc tgcaagaccc gaaactgtct    300
cagaacaaac aggccctgga aggactggga gatctgaaac tgctgttcga gtatctgacg    360
ctgttcggca ttgatgacaa aatttctttc gacctgtcac tggcacgtgg actggactat    420
tataccggt                                                            429

<210> SEQ ID NO 30
<211> LENGTH: 315
<212> TYPE: DNA
<213> ORGANISM: Artificial Sequence
<220> FEATURE:
<223> OTHER INFORMATION: Codon optimized nucleic acid sequence for
      C-terminal fragment of HisRS1

<400> SEQUENCE: 30
cgtaccaccg aaacccaagt tctggttgcc tcagctcaga aaaaactgct ggaagaacgc     60
ctgaaactgg ttagcgaact gtgggatgct ggcattaaag ccgaactgct gtataaaaaa    120
aacccgaaac tgctgaatca gctgcagtat tgtgaggaag cgggtattcc tctggtggcc    180
attatcggag aacaggaact gaagacggc gttattaaac tgcgtagcgt gacctctcgt    240
gaagaagttg acgttcgccg tgaagatctg gtcgaggaaa tcaaacgtcg taccggtcaa    300
cctctgtgta tttgc                                                    315

<210> SEQ ID NO 31
<211> LENGTH: 810
<212> TYPE: DNA
<213> ORGANISM: Artificial Sequence
<220> FEATURE:
<223> OTHER INFORMATION: Codon optimized nucleic acid sequence for
      N-terminal fragment of HisRS1

<400> SEQUENCE: 31
atggcagaac gtgccgccct ggaagagctg gtaaaactgc aaggcgagcg tgttcgtggt     60
ctgaaacagc agaaagcaag cgctgaactg atcgaagaag aagtggcgaa actgctgaaa    120
ctgaaagcac agctgggtcc tgatgaatca aacaaaaat cgtcctgaa aactccgaaa    180 ggaacccgtg actattctcc tcgtcaaatg gccgtccgtg aaaaagtgtt cgacgtgatc    240
attcgctgct ttaaacgcca tggtgccgaa gtgattgata ccccggtgtt tgagctgaaa    300
gagacactga tgggcaaata tggtgaggac agcaaactga tctatgacct gaaagaccaa    360
ggcggtgaac tgctgtccct gcgttatgat ctgactgtgc gtttgcccg ttatctggcc    420 atgaataaac tgacgaacat taacgctat cacattgcca agtgtatcg ccgtgacaat    480 cctgctatga ctcgtggacg ttatcgtgaa ttctatcagt gtgacttcga tattgccggc    540
aacttcgacc ctatgattcc ggatgctgaa tgcctgaaaa tcatgtgtga tcctgagc    600 agcctgcaaa ttggtgactt cctggtgaaa gtgaatgacc gtcgtatcct ggatggcatg    660
tttgccattt gtggtgtgag cgattccaaa ttccgtacca tctgtagtag tgtggacaaa    720
ctggataaag tgggctatcc gtggtggaac tcttgtagcc gtattctgaa ctatcctaaa    780
accagccgcc gtggcgtgc ttgggaaact                                      810

<210> SEQ ID NO 32
```

<211> LENGTH: 1185
<212> TYPE: DNA
<213> ORGANISM: Artificial Sequence
<220> FEATURE:
<223> OTHER INFORMATION: Codon optimized nucleic acid sequence for
      C-terminal fragment of HisRS1

<400> SEQUENCE: 32

| | | | | |
|---|---|---|---|---|
| atggcagaac | gtgccgccct | ggaagagctg | gtaaaactgc | aaggcgagcg | tgttcgtggt | 60 |
| ctgaaacagc | agaaagcaag | cgctgaactg | atcgaagaag | aagtggcgaa | actgctgaaa | 120 |
| ctgaaagcac | agctgggtcc | tgatgaatca | aaacaaaaat | cgtcctgaa | actcccgaaa | 180 |
| gacttcgata | ttgccgggaa | ttttgaccct | atgatcccctg | atgccgaatg | tctgaaaatc | 240 |
| atgtgtgaga | tcctgagcag | tctgcagatt | ggtgacttcc | tggtgaaagt | gaacgatcgc | 300 |
| cgtattctgg | atggaatgtt | tgccattgt | ggcgtgtctg | acagcaaatt | cgtacgatc | 360 |
| tgtagcagcg | tggataaact | ggataaagtg | agctgggagg | aggtgaaaaa | tgagatggtg | 420 |
| ggcgaaaaag | gtctggcacc | tgaagtggct | gaccgtatcg | tgattatgt | tcagcaacat | 480 |
| ggcggtgttt | ctctggtcga | acagctgctg | caagacccaa | aactgagcca | gaacaaacag | 540 |
| gcactggaag | gactgggtga | tctgaaactg | ctgtttgagt | atctgacgct | gtttggcatc | 600 |
| gatgacaaaa | tctcgtttga | cctgagcctg | gcacgtggtc | tggattatta | taccggcgtg | 660 |
| atctatgaag | ccgtcctgct | gcaaactcca | gcacaagcag | gtgaagaacc | tctgggtgtt | 720 |
| ggtagtgtag | cggcaggcgg | acgttatgat | ggactggtgg | ggatgtttga | tccgaaaggc | 780 |
| cgtaaagttc | gtgtgtcgg | tctgagtatc | ggggttgagc | gtatctttag | cattgtggag | 840 |
| caacgtctgg | aagctctgga | ggaaaaaatc | cgtaccaccg | aaacccaagt | tctggttgcc | 900 |
| tcagctcaga | aaaaactgct | ggaagaacgc | ctgaaactgg | ttagcgaact | gtgggatgct | 960 |
| ggcattaaag | ccgaactgct | gtataaaaaa | aacccgaaac | tgctgaatca | gctgcagtat | 1020 |
| tgtgaggaag | cgggtattcc | tctggtggcc | attatcggag | aacaggaact | gaaagacggc | 1080 |
| gttattaaac | tgcgtagcgt | gacctctcgt | gaagaagttg | acgttcgccg | tgaagatctg | 1140 |
| gtcgaggaaa | tcaaacgtcg | taccggtcaa | cctctgtgta | tttgc | | 1185 |

<210> SEQ ID NO 33
<211> LENGTH: 1077
<212> TYPE: DNA
<213> ORGANISM: Artificial Sequence
<220> FEATURE:
<223> OTHER INFORMATION: Codon optimized nucleic acid sequence for
      C-terminal fragment of HisRS1

<400> SEQUENCE: 33

| | | | | |
|---|---|---|---|---|
| atggcagaac | gtgccgccct | ggaagagctg | gtaaaactgc | aaggcgagcg | tgttcgtggt | 60 |
| ctgaaacagc | agaaagcaag | cgctgaactg | atcgaagaag | aagtggcgaa | actgctgaaa | 120 |
| ctgaaagcac | agctgggtcc | tgatgaatca | aaacaaaaat | cgtcctgaa | actcccgaaa | 180 |
| gtgaatgatc | gccgtatcct | ggatggcatg | tttgccattt | gtggtgtgag | cgactcgaaa | 240 |
| ttccgtacga | tttgctctag | cgtcgataaa | ctggacaaag | tgtcctggga | agaggtgaaa | 300 |
| aacgagatgg | tgggtgagaa | aggtctggct | cctgaagttg | ccgaccgtat | tgtgattat | 360 |
| gttcagcagc | atggcggtgt | tcactggtt | gaacaactgc | tgcaagaccc | gaaactgtct | 420 |
| cagaataaac | aggcgctgga | aggactggga | gatctgaaac | tgctgtttga | gtatctgacc | 480 |
| ctgttcggca | ttgatgacaa | aatcagcttc | gacctgagcc | tggcacgtgg | tctggattat | 540 |
| tataccggcg | tgatctatga | agccgttctg | ctgcagacac | cagcacaagc | aggcgaagaa | 600 |

```
cctctgggtg ttggttctgt ggcagccggt ggtcgttatg atggactggt aggcatgttc      660
gatccgaaag gccgtaaagt tccgtgtgtg ggactgagta tcggtgttga gcgtatcttt      720
agcatcgtgg aacaacgtct ggaagcgctg gaggagaaaa ttcgtaccac cgaaacccaa      780
gttctggttg cctcagctca gaaaaaactg ctggaagaac gcctgaaact ggttagcgaa      840
ctgtgggatg ctggcattaa agccgaactg ctgtatataaa aaaacccgaa actgctgaat      900
cagctgcagt attgtgagga agcgggtatt cctctggtgg ccattatcgg agaacaggaa      960
ctgaaagacg gcgttattaa actgcgtagc gtgacctctc gtgaagaagt tgacgttcgc     1020
cgtgaagatc tggtcgagga aatcaaacgt cgtaccggtc aacctctgtg tatttgc        1077
```

<210> SEQ ID NO 34
<211> LENGTH: 1197
<212> TYPE: DNA
<213> ORGANISM: Artificial Sequence
<220> FEATURE:
<223> OTHER INFORMATION: Codon-optimized nucleic acid sequence for
      C-terminal fragment of HisRS1

<400> SEQUENCE: 34

```
atggcagaac gtgccgccct ggaagagctg gtaaaactgc aaggcgagcg tgttcgtggt       60
ctgaaacagc agaaagcaag cgctgaactg atcgaagaag aagtggcgaa actgctgaaa      120
ctgaaagcac agctgggtcc tgatgaatca aacaaaaat tcgtcctgaa actcccgaaa      180
ggaactcgtg attatagccc tcgccagatg gctgtccgtg aaaaagtgtt cgatgtgatc      240
attcgctgct tcaaacgtca tggtgccgaa gtcattgata ccccggtgtt cgagctgaaa      300
gtgaacgatc gccgtattct ggatggcatg ttcgccattt gtgtgttag cgatagcaaa      360 ttccgtacaa tctgctctag cgtggacaaa ctggacaaag tgagctggga gaggtgaaa       420 aacgagatgg tgggtgagaa aggcctggct cctgaagttg ccgaccgtat cggagattat      480
gttcagcagc atggcggagt tcactggtt gaacaactgc tgcaagaccc gaaactgtct      540
cagaacaaac aggcactgga aggtctggga gatctgaaac tgctgttcga gtatctgacg      600
ctgttcggta ttgacgacaa aatttccttc gacctgtcgc tggcacgtgg tctggattat      660
tatacaggcg tgatctatga ggctgtactg ctgcagacac cagcacaagc aggtgaagag      720
cctctgggtg ttggttcagt tgctgccggt ggacgttatg acggactggt agggatgttt      780
gacccaaaag gccgtaaagt cccgtgtgta ggactgtcta ttggcgttga gcgtatcttt      840
agcatcgtgg agcaacgtct ggaagctctg gaggagaaaa tccgtaccac cgaaacccaa      900
gttctggttg cctcagctca gaaaaaactg ctggaagaac gcctgaaact ggttagcgaa      960
ctgtgggatg ctggcattaa agccgaactg ctgtatataa aaaaacccgaa actgctgaat     1020 cagctgcagt attgtgagga agcgggtatt cctctggtgg ccattatcgg agaacaggaa     1080
ctgaaagacg gcgttattaa actgcgtagc gtgacctctc gtgaagaagt tgacgttcgc     1140
cgtgaagatc tggtcgagga aatcaaacgt cgtaccggtc aacctctgtg tatttgc        1197
```

<210> SEQ ID NO 35
<211> LENGTH: 1419
<212> TYPE: DNA
<213> ORGANISM: Artificial Sequence
<220> FEATURE:
<223> OTHER INFORMATION: Codon optimized nucleic acid sequence for
      C-terminal fragment of HisRS1

<400> SEQUENCE: 35

```
atggcagaac gtgccgccct ggaagagctg gtaaaactgc aaggcgagcg tgttcgtggt      60
ctgaaacagc agaaagcaag cgctgaactg atcgaagaag aagtggcgaa actgctgaaa     120
ctgaaagcac agctgggtcc tgatgaatca aaacaaaaat cgtcctgaa  aactccgaaa     180
ggaactcgtg attatagccc tcgccagatg gctgtccgtg aaaaagtgtt cgatgtgatc     240
attcgctgct tcaaacgtca tggtgccgaa gtcattgata ccccggtgtt cgagctgaaa     300
gaaaccctga tgggcaaata tgggaagat  tccaaactga tctatgacct gaaagaccag     360
ggaggtgaac tgctgtctct cgctatgac  ctgactgttc cttttgctcg ctatctggcc     420
atgaataaac tgaccaacat caaacgctat catatcgcca agtgtatcg  ccgtgacaat     480
ccagcaatga cccgtggtcg ttatcgtgaa ttttatcagt gtgtgaacga tcgccgtatt     540
ctggacggca tgttcgccat ttgtggtgtg tctgactcca aatttcgtac gatctgctca     600
agcgtggaca aactggacaa agtgagctgg gaagaggtga aaaacgagat ggtgggtgag     660
aaaggcctgg ctcctgaagt tgccgaccgt atcggagatt atgttcagca gcatggcgga     720
gtttcactgg ttgaacaact gctgcaagac ccgaaactgt cacagaacaa acaggcactg     780
gaaggtctgg gggatctgaa actgctgttc gagtatctga cgctgttcgg tattgacgac     840
aaaatcagct cgatctgag  cctggcacgt ggtctggact attataccgg cgtgattat     900
gaagccgttc tgctgcagac tccagcacaa gcaggtgaag agcctctggg tgttggaagt     960
gtggcagccg tgccgtta   tgatggtctg gttggcatgt tgacccgaa  aggccgtaaa    1020
gtcccgtgtg taggactgtc tatcggcgtg gagcgtattt ttagcatcgt ggaacaacgc    1080
ctggaagctc tggaagagaa aatccgtacc accgaaaccc aagttctggt tgcctcagct    1140
cagaaaaaac tgctggaaga acgcctgaaa ctggttagcg aactgtggga tgctggcatt    1200
aaagccgaac tgctgtataa aaaaaacccg aaactgctga atcagctgca gtattgtgag    1260
gaagcgggta ttcctctggt ggccattatc ggagaacagg aactgaaaga cggcgttatt    1320
aaactgcgta gcgtgacctc tcgtgaagaa gttgacgttc gccgtgaaga tctggtcgag    1380
gaaatcaaac gtcgtaccgg tcaacctctg tgtatttgc                           1419
```

<210> SEQ ID NO 36  
<211> LENGTH: 1407  
<212> TYPE: DNA  
<213> ORGANISM: Artificial Sequence  
<220> FEATURE:  
<223> OTHER INFORMATION: Codon optimized nucleic acid sequence for C-terminal fragment of HisRS1

<400> SEQUENCE: 36

```
atggcagaac gtgccgccct ggaagagctg gtaaaactgc aaggcgagcg tgttcgtggt      60
ctgaaacagc agaaagcaag cgctgaactg atcgaagaag aagtggcgaa actgctgaaa     120
ctgaaagcac agctgggtcc tgatgaatca aaacaaaaat cgtcctgaa  aactccgaaa     180
gaaaccctga tgggcaaata tggcgaagat tccaaactga tctatgacct gaaagaccaa     240
ggcggtgaac tgctgtcccct cgcttatgac ctgactgttc cgtttgctcg ttatctggcc    300
atgaataaac tgaccaacat taaacgctat cacattgcca agtgtatcg  ccgtgacaat     360
cctgctatga ctcgtggacg ttatcgtgaa ttctatcagt gtgacttcga tattgccggc     420
aacttcgacc ctatgattcc ggatgctgaa tgcctgaaaa tcatgtgtga tcctgagc      480
agcctgcaaa ttggtgactt cctggtgaaa gtgaatgacc gtcgtatcct ggatggcatg     540
ttcgccattt gtggtgttag cgattccaaa ttccgtacca tctgtagtag tgtggacaaa    600
```

| | |
|---|---|
| ctggataaag tgagctggga agaggtgaaa aacgaaatgg tgggcgaaaa aggtctggca | 660 |
| cctgaggttg ctgatcgtat cggtgactat gtccagcagc atggaggtgt ttcactggtt | 720 |
| gagcaactgc tgcaagatcc gaaactgtct cagaacaaac aggccctgga aggactgggt | 780 |
| gatctgaaac tgctgttcga gtatctgacg ctgttcggta ttgatgacaa aatctcgttc | 840 |
| gacctgtctc tggctcgtgg actggattat tatacgggcg taatctatga agctgtcctg | 900 |
| ctgcagacac cagcacaagc aggtgaagag cctctgggtg ttggaagtgt tgctgccggt | 960 |
| ggtcgctatg acggactggt tggcatgttc gatccgaaag gccgtaaagt tccgtgtgta | 1020 |
| ggactgagca ttggcgttga gcgtatcttt ccatcgttg agcaacgtct ggaagcactg | 1080 |
| gaagagaaaa tccgtaccac cgaaacccaa gttctggttg cctcagctca gaaaaaactg | 1140 |
| ctggaagaac gcctgaaact ggttagcgaa ctgtgggatg ctggcattaa agccgaactg | 1200 |
| ctgtataaaa aaacccgaa actgctgaat cagctgcagt attgtgagga agcgggtatt | 1260 |
| cctctggtgg ccattatcgg agaacaggaa ctgaaagacg gcgttattaa actgcgtagc | 1320 |
| gtgacctctc gtgaagaagt tgacgttcgc cgtgaagatc tggtcgagga aatcaaacgt | 1380 |
| cgtaccggtc aacctctgtg tatttgc | 1407 |

<210> SEQ ID NO 37
<211> LENGTH: 1305
<212> TYPE: DNA
<213> ORGANISM: Artificial Sequence
<220> FEATURE:
<223> OTHER INFORMATION: Codon optimized nucleic acid sequence from C-terminal of HisRS1

<400> SEQUENCE: 37

| | |
|---|---|
| atggcagaac gtgccgccct ggaagagctg gtaaaactgc aaggcgagcg tgttcgtggt | 60 |
| ctgaaacagc agaaagcaag cgctgaactg atcgaagaag aagtggcgaa actgctgaaa | 120 |
| ctgaaagcac agctgggtcc tgatgaatca aacaaaaat tcgtcctgaa actccgaaa | 180 |
| ggaactcgtg attatagccc tcgccagatg gctgtccgtg aaaaagtgtt cgatgtgatc | 240 |
| attcgctgct tcaaacgtca tggtgccgaa gtcattgata ccccggtgtt cgagctgaaa | 300 |
| gatttcgata ttgccggcaa ctttgatccg atgattccgg atgctgagtg tctgaaaatc | 360 |
| atgtgtgaga tcctgagtag tctgcagatt ggggatttcc tggtgaaagt gaacgatcgc | 420 |
| cgtattctgg acggcatgtt tgccatttgt ggcgttagcg atagcaaatt ccgtacgatc | 480 |
| tgtagcagtg tggacaaact ggataaagtc tcttgggaag aggtcaaaaa cgagatggtt | 540 |
| ggtgagaaag gcctggctcc tgaagtggct gaccgtattg tgattatgt ccagcagcat | 600 |
| ggtggtgttt cactggttga caactgctg caagacccga actgtctca gaacaaacag | 660 |
| gcactggaag gtctggtgta tctgaaactg ctgttcgagt atctgacgct gttcggtatt | 720 |
| gacgacaaaa tttccttcga cctgtcactg gcacgtggtc tggattatta tacaggcgta | 780 |
| atctatgagg ctgtactgct gcaaactcca gcacaagcag gtgaagaacc tctgggagtt | 840 |
| ggtagtgtag cggcagggg tcgttatgat gggctggtcg ggatgttcga tccaaaaggc | 900 |
| cgtaaagtcc cgtgtgttgg tctgtctatt ggcgttgagc gtatcttctc catcgtggag | 960 |
| caacgtctgg aagctctgga agaaaaaatc cgtaccaccg aaacccaagt tctggttgcc | 1020 |
| tcagctcaga aaaactgct ggaagaacgc ctgaaactgg ttagcgaact gtgggatgct | 1080 |
| ggcattaaag ccgaactgct gtataaaaaa acccgaaac tgctgaatca gctgcagtat | 1140 |
| tgtgaggaag cgggtattcc tctggtggcc attatcggag aacaggaact gaaagacggc | 1200 |

```
gttattaaac tgcgtagcgt gacctctcgt gaagaagttg acgttcgccg tgaagatctg    1260
gtcgaggaaa tcaaacgtcg taccggtcaa cctctgtgta tttgc                    1305
```

<210> SEQ ID NO 38

<400> SEQUENCE: 38

000

<210> SEQ ID NO 39
<211> LENGTH: 506
<212> TYPE: PRT
<213> ORGANISM: Homo sapiens

<400> SEQUENCE: 39

```
Met Pro Leu Leu Gly Leu Leu Pro Arg Arg Ala Trp Ala Ser Leu Leu
1               5                   10                  15

Ser Gln Leu Leu Arg Pro Pro Cys Ala Ser Cys Thr Gly Ala Val Arg
            20                  25                  30

Cys Gln Ser Gln Val Ala Glu Ala Val Leu Thr Ser Gln Leu Lys Ala
        35                  40                  45

His Gln Glu Lys Pro Asn Phe Ile Ile Lys Thr Pro Lys Gly Thr Arg
    50                  55                  60

Asp Leu Ser Pro Gln His Met Val Val Arg Glu Lys Ile Leu Asp Leu
65                  70                  75                  80

Val Ile Ser Cys Phe Lys Arg His Gly Ala Lys Gly Met Asp Thr Pro
                85                  90                  95

Ala Phe Glu Leu Lys Glu Thr Leu Thr Glu Lys Tyr Gly Glu Asp Ser
            100                 105                 110

Gly Leu Met Tyr Asp Leu Lys Asp Gln Gly Gly Glu Leu Leu Ser Leu
        115                 120                 125

Arg Tyr Asp Leu Thr Val Pro Phe Ala Arg Tyr Leu Ala Met Asn Lys
    130                 135                 140

Val Lys Lys Met Lys Arg Tyr His Val Gly Lys Val Trp Arg Arg Glu
145                 150                 155                 160

Ser Pro Thr Ile Val Gln Gly Arg Tyr Arg Glu Phe Cys Gln Cys Asp
                165                 170                 175

Phe Asp Ile Ala Gly Gln Phe Asp Pro Met Ile Pro Asp Ala Glu Cys
            180                 185                 190

Leu Lys Ile Met Cys Glu Ile Leu Ser Gly Leu Gln Leu Gly Asp Phe
        195                 200                 205

Leu Ile Lys Val Asn Asp Arg Arg Ile Val Asp Gly Met Phe Ala Val
    210                 215                 220

Cys Gly Val Pro Glu Ser Lys Phe Arg Ala Ile Cys Ser Ser Ile Asp
225                 230                 235                 240

Lys Leu Asp Lys Met Ala Trp Lys Asp Val Arg His Glu Met Val Val
                245                 250                 255

Lys Lys Gly Leu Ala Pro Glu Val Ala Asp Arg Ile Gly Asp Tyr Val
            260                 265                 270

Gln Cys His Gly Gly Val Ser Leu Val Glu Gln Met Phe Gln Asp Pro
        275                 280                 285

Arg Leu Ser Gln Asn Lys Gln Ala Leu Glu Gly Leu Gly Asp Leu Lys
    290                 295                 300

Leu Leu Phe Glu Tyr Leu Thr Leu Phe Gly Ile Ala Asp Lys Ile Ser
305                 310                 315                 320
```

```
Phe Asp Leu Ser Leu Ala Arg Gly Leu Asp Tyr Tyr Thr Gly Val Ile
            325                 330                 335

Tyr Glu Ala Val Leu Leu Gln Thr Pro Thr Gln Ala Gly Glu Glu Pro
        340                 345                 350

Leu Asn Val Gly Ser Val Ala Ala Gly Gly Arg Tyr Asp Gly Leu Val
        355                 360                 365

Gly Met Phe Asp Pro Lys Gly His Lys Val Pro Cys Val Gly Leu Ser
370                 375                 380

Ile Gly Val Glu Arg Ile Phe Tyr Ile Val Glu Gln Arg Met Lys Thr
385                 390                 395                 400

Lys Gly Glu Lys Val Arg Thr Thr Glu Thr Gln Val Phe Val Ala Thr
                405                 410                 415

Pro Gln Lys Asn Phe Leu Gln Glu Arg Leu Lys Leu Ile Ala Glu Leu
            420                 425                 430

Trp Asp Ser Gly Ile Lys Ala Glu Met Leu Tyr Lys Asn Asn Pro Lys
        435                 440                 445

Leu Leu Thr Gln Leu His Tyr Cys Glu Ser Thr Gly Ile Pro Leu Val
        450                 455                 460

Val Ile Ile Gly Glu Gln Glu Leu Lys Glu Gly Val Ile Lys Ile Arg
465                 470                 475                 480

Ser Val Ala Ser Arg Glu Glu Val Ala Ile Lys Arg Glu Asn Phe Val
                485                 490                 495

Ala Glu Ile Gln Lys Arg Leu Ser Glu Ser
            500                 505

<210> SEQ ID NO 40
<211> LENGTH: 198
<212> TYPE: DNA
<213> ORGANISM: Artificial Sequence
<220> FEATURE:
<223> OTHER INFORMATION: Codon optimized DNA endcoding resokine
      (N-terminal fragment of HisRS) for E. coli expression

<400> SEQUENCE: 40
atggcagaac gtgcggcatt ggaagaattg gttaaactgc aaggtgaacg tgttcgtggt      60
ctgaagcagc agaaggctag cgcggagctg atcgaagaag aggtggccaa actgctgaag     120
ctgaaggcgc agctgggccc ggacgagagc aaacaaaagt tcgtcctgaa accccgaaa     180 caccaccatc accatcac                                                   198

<210> SEQ ID NO 41
<211> LENGTH: 66
<212> TYPE: PRT
<213> ORGANISM: Artificial Sequence
<220> FEATURE:
<223> OTHER INFORMATION: Resokine (N-terminal fragment of HisRs) with
      His tag

<400> SEQUENCE: 41

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys His His His His
    50                  55                  60

His His
```

<210> SEQ ID NO 42
<211> LENGTH: 1563
<212> TYPE: DNA
<213> ORGANISM: Artificial Sequence
<220> FEATURE:
<223> OTHER INFORMATION: Codon optimized full length HisRS gene for E. coli expression

<400> SEQUENCE: 42

```
atggcggaac gtgccgcact ggaagaattg gttaaattac agggagaacg cgtacgtggt      60
cttaaacaac aaaaagcctc tgcggaattg attgaagaag aagttgccaa attactgaaa     120
ctgaaagctc aacttggacc cgatgaaagt aaacaaaaat ttgtgttgaa acgcccaaa      180
ggaacccgtg attatagtcc acgtcaaatg gccgttcgtg aaaaagtgtt cgacgttatt     240
attcgctgtt ttaaacgtca cggtgctgaa gtaatcgata cccccgtatt tgaattgaaa     300
gagactctga tgggcaaata tggtgaagat tctaaactga tttatgattt gaaagaccaa     360
ggaggtgaac tgctgagcct cgctacgac ttaactgtgc cttttgcccg ttacttagcc     420
atgaataaat taaccaacat caaacgttac catattgcaa agtatatcg ccgcgacaac     480
cctgcaatga ctcgtggacg ctatcgcgaa ttctatcagt gtgatttga tattgccgga     540
aatttcgacc cgatgatccc ggatgccgag tgtttgaaaa ttatgtgtga aattctgagt     600
tcgttgcaga tcggagactt tcttgtaaaa gttaatgacc gccgtattct ggatggtatg     660
tttgctattt gcggtgtttc tgattccaaa ttccgtacaa tctgctcaag cgtggacaaa     720
ttggataaag tgtcttggga agaagtaaaa atgaaatgg tgggagaaaa aggcctggct     780
ccagaagtag cagaccgtat tggtgactat gttcaacaac atggcggtgt gtccttagtc     840
gaacagttat tacaggatcc taaactgagc caaaataaac aagcacttga aggactggga     900
gatctgaaat actctttga atatctgacc ttatttggga ttgatgataa aattagcttt     960
gatctgagct tggcccgcgg tcttgattat tataccggcg tgatttacga agctgttctc    1020
ttgcaaaccc cagcccaggc gggcgaagag cctttgggag tcggcagtgt ggcagccggt    1080
ggtcgttatg atggtttggt aggaatgttt gaccctaaag gccgtaaagt accatgtgtg    1140
gggctttcta tcggtgtcga acgtatcttt tctattgttg aacaacgtct tgaagctttg    1200
gaggaaaaga tccgtaccac ggaaaccaa gtcttagttg caagtgccca aaaaaactg    1260
ttagaagaac gcctgaaact cgtatcagaa cttttgggacg ccggcatcaa ggccgaactg    1320
ctgtataaaa gaaccccgaa attgttaaac caactccagt attgtgaaga agctgggatc    1380
ccactcgtag ctattattgg tgagcaagaa ttaaaagatg gcgtgattaa actgcgttca    1440
gtaacaagcc gtgaagaggt agatgtacgt cgcgaagact tagtggaaga aattaaacgc    1500
cgcaccggtc aaccgttatg tatttgcgcg gccgcactcg agcaccacca ccaccaccac    1560
tga                                                                 1563
```

<210> SEQ ID NO 43
<211> LENGTH: 520
<212> TYPE: PRT
<213> ORGANISM: Artificial Sequence
<220> FEATURE:
<223> OTHER INFORMATION: Full length HisRS with His tag

<400> SEQUENCE: 43

```
Met Ala Glu Arg Ala Ala Leu Glu Glu Leu Val Lys Leu Gln Gly Glu
 1               5                  10                  15
```

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
        210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
        370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys Ala Ala Ala
            500                 505                 510

Leu Glu His His His His His His
        515                 520

<210> SEQ ID NO 44
<211> LENGTH: 41
<212> TYPE: DNA
<213> ORGANISM: Artificial Sequence
<220> FEATURE:
<223> OTHER INFORMATION: Primer designed to selectively mutate cysteine
      residue

<400> SEQUENCE: 44
gtttgacgta atcatccgtt gcttcaagcg ccacggtgca g                    41

<210> SEQ ID NO 45
<211> LENGTH: 41
<212> TYPE: DNA
<213> ORGANISM: Artificial Sequence
<220> FEATURE:
<223> OTHER INFORMATION: Primer designed to selectively mutate cysteine
      residue

<400> SEQUENCE: 45
ctgcaccgtg gcgcttgaag caacggatga ttacgtcaaa c                    41

<210> SEQ ID NO 46
<211> LENGTH: 44
<212> TYPE: DNA
<213> ORGANISM: Artificial Sequence
<220> FEATURE:
<223> OTHER INFORMATION: Primer designed to selectively mutate cysteine
      residue

<400> SEQUENCE: 46
gccgataccg ggaattctac cagtgtgatt ttgacattgc tggg                 44

<210> SEQ ID NO 47
<211> LENGTH: 44
<212> TYPE: DNA
<213> ORGANISM: Artificial Sequence
<220> FEATURE:
<223> OTHER INFORMATION: Primer designed to selectively mutate cysteine
      residue

<400> SEQUENCE: 47
cccagcaatg tcaaaatcac actggtagaa ttcccggtat cggc                 44

<210> SEQ ID NO 48
<211> LENGTH: 41
<212> TYPE: DNA
<213> ORGANISM: Artificial Sequence
<220> FEATURE:
<223> OTHER INFORMATION: Primer

<400> SEQUENCE: 48
ccatgatccc tgatgcagag tgcctgaaga tcatgtgcga g     41

<210> SEQ ID NO 49
<211> LENGTH: 41
<212> TYPE: DNA
<213> ORGANISM: Artificial Sequence
<220> FEATURE:
<223> OTHER INFORMATION: Primer

<400> SEQUENCE: 49
ctcgcacatg atcttcaggc actctgcatc agggatcatg g     41

<210> SEQ ID NO 50
<211> LENGTH: 43
<212> TYPE: DNA
<213> ORGANISM: Artificial Sequence
<220> FEATURE:
<223> OTHER INFORMATION: Primer

<400> SEQUENCE: 50
gcagagtgcc tgaagatcat gtgcgagatc ctgagttcac ttc     43

<210> SEQ ID NO 51
<211> LENGTH: 43
<212> TYPE: DNA
<213> ORGANISM: Artificial Sequence
<220> FEATURE:
<223> OTHER INFORMATION: Primere

<400> SEQUENCE: 51
gaagtgaact caggatctcg cacatgatct tcaggcactc tgc     43

<210> SEQ ID NO 52
<211> LENGTH: 45
<212> TYPE: DNA
<213> ORGANISM: Artificial Sequence
<220> FEATURE:
<223> OTHER INFORMATION: primer

<400> SEQUENCE: 52
ctagatggga tgtttgctat ctgtggtgtt tctgacagca agttc     45

<210> SEQ ID NO 53
<211> LENGTH: 45
<212> TYPE: DNA
<213> ORGANISM: Artificial Sequence
<220> FEATURE:
<223> OTHER INFORMATION: primer

<400> SEQUENCE: 53
gaacttgctg tcagaaacac cacagatagc aaacatccca tctag     45

<210> SEQ ID NO 54
<211> LENGTH: 41
<212> TYPE: DNA
<213> ORGANISM: Artificial Sequence
<220> FEATURE:
<223> OTHER INFORMATION: primier

<400> SEQUENCE: 54
cagcaagttc cgtaccatct gctcctcagt agacaagctg g     41

<210> SEQ ID NO 55
<211> LENGTH: 41
<212> TYPE: DNA

<213> ORGANISM: Artificial Sequence
<220> FEATURE:
<223> OTHER INFORMATION: primieer

<400> SEQUENCE: 55
ccagcttgtc tactgaggag cagatggtac ggaacttgct g                41

<210> SEQ ID NO 56
<211> LENGTH: 37
<212> TYPE: DNA
<213> ORGANISM: Artificial Sequence
<220> FEATURE:
<223> OTHER INFORMATION: primier

<400> SEQUENCE: 56
gggcgcaagg tgccatgtgt ggggctcagc attgggg                    37

<210> SEQ ID NO 57
<211> LENGTH: 37
<212> TYPE: DNA
<213> ORGANISM: Artificial Sequence
<220> FEATURE:
<223> OTHER INFORMATION: primier

<400> SEQUENCE: 57
ccccaatgct gagccccaca catggcacct tgcgccc                    37

<210> SEQ ID NO 58
<211> LENGTH: 38
<212> TYPE: DNA
<213> ORGANISM: Artificial Sequence
<220> FEATURE:
<223> OTHER INFORMATION: primer

<400> SEQUENCE: 58
ctgaaccagt tacagtactg tgaggaggca ggcatccc                   38

<210> SEQ ID NO 59
<211> LENGTH: 38
<212> TYPE: DNA
<213> ORGANISM: Artificial Sequence
<220> FEATURE:
<223> OTHER INFORMATION: primier

<400> SEQUENCE: 59
gggatgcctg cctcctcaca gtactgtaac tggttcag                   38

<210> SEQ ID NO 60
<211> LENGTH: 39
<212> TYPE: DNA
<213> ORGANISM: Artificial Sequence
<220> FEATURE:
<223> OTHER INFORMATION: primier

<400> SEQUENCE: 60
gagaacaggc cagcccctct gcatctgcta gaacccagc                  39

<210> SEQ ID NO 61
<211> LENGTH: 39
<212> TYPE: DNA
<213> ORGANISM: Artificial Sequenc
<220> FEATURE:
<223> OTHER INFORMATION: primeir

<400> SEQUENCE: 61
gctgggttct agcagatgca gaggggctgg cctgttctc                  39

<210> SEQ ID NO 62
<211> LENGTH: 37
<212> TYPE: DNA
<213> ORGANISM: Artificial Sequence
<220> FEATURE:
<223> OTHER INFORMATION: primeir

<400> SEQUENCE: 62
ccagcccctc tgcatctgct agaacccagc tttcttg                              37

<210> SEQ ID NO 63
<211> LENGTH: 37
<212> TYPE: DNA
<213> ORGANISM: Artificial Sequence
<220> FEATURE:
<223> OTHER INFORMATION: primer

<400> SEQUENCE: 63
caagaaagct gggttctagc agatgcagag gggctgg                              37

<210> SEQ ID NO 64
<211> LENGTH: 35
<212> TYPE: DNA
<213> ORGANISM: Artificial Sequence
<220> FEATURE:
<223> OTHER INFORMATION: primer

<400> SEQUENCE: 64
gaacaggcca gcccctctag aacccagctt tcttg                                35

<210> SEQ ID NO 65
<211> LENGTH: 35
<212> TYPE: DNA
<213> ORGANISM: Artificial Sequence
<220> FEATURE:
<223> OTHER INFORMATION: primier

<400> SEQUENCE: 65
caagaaagct gggttctaga ggggctggcc tgttc                                35

<210> SEQ ID NO 66
<211> LENGTH: 41
<212> TYPE: DNA
<213> ORGANISM: Artificial Sequence
<220> FEATURE:
<223> OTHER INFORMATION: primer

<400> SEQUENCE: 66
cgccgcaccg gtcaaccgtt acaccaccac caccaccact g                         41

<210> SEQ ID NO 67
<211> LENGTH: 41
<212> TYPE: DNA
<213> ORGANISM: Artificial Sequence
<220> FEATURE:
<223> OTHER INFORMATION: Primer

<400> SEQUENCE: 67
cagtggtggt ggtggtggtg taacggttga ccggtgcggc g                         41

<210> SEQ ID NO 68
<211> LENGTH: 39
<212> TYPE: DNA
<213> ORGANISM: Artificial Sequence
<220> FEATURE:

<223> OTHER INFORMATION: Primer

<400> SEQUENCE: 68
cgccgcaccg gtcaaccgtt atgagatccg gctgctaac         39

<210> SEQ ID NO 69
<211> LENGTH: 39
<212> TYPE: DNA
<213> ORGANISM: Artificial Sequence
<220> FEATURE:
<223> OTHER INFORMATION: Primer

<400> SEQUENCE: 69
gttagcagcc ggatctcata acggttgacc ggtgcggcg         39

<210> SEQ ID NO 70
<211> LENGTH: 506
<212> TYPE: PRT
<213> ORGANISM: Homo sapiens

<400> SEQUENCE: 70

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285
```

```
Leu Ser Gln Asn Lys Gln Ala Leu Glu Gly Leu Gly Asp Leu Lys Leu
    290                 295                 300
Leu Phe Glu Tyr Leu Thr Leu Phe Gly Ile Asp Asp Lys Ile Ser Phe
305                 310                 315                 320
Asp Leu Ser Leu Ala Arg Gly Leu Asp Tyr Tyr Thr Gly Val Ile Tyr
                325                 330                 335
Glu Ala Val Leu Leu Gln Thr Pro Ala Gln Ala Gly Glu Glu Pro Leu
            340                 345                 350
Gly Val Gly Ser Val Ala Ala Gly Arg Tyr Asp Gly Leu Val Gly
        355                 360                 365
Met Phe Asp Pro Lys Gly Arg Lys Val Pro Cys Val Gly Leu Ser Ile
    370                 375                 380
Gly Val Glu Arg Ile Phe Ser Ile Val Glu Gln Arg Leu Glu Ala Leu
385                 390                 395                 400
Glu Glu Lys Ile Arg Thr Thr Glu Thr Gln Val Leu Val Ala Ser Ala
                405                 410                 415
Gln Lys Lys Leu Leu Glu Glu Arg Leu Lys Leu Val Ser Glu Leu Trp
            420                 425                 430
Asp Ala Gly Ile Lys Ala Glu Leu Leu Tyr Lys Lys Asn Pro Lys Leu
        435                 440                 445
Leu Asn Gln Leu Gln Tyr Cys Glu Glu Ala Gly Ile Pro Leu Val Ala
    450                 455                 460
Ile Ile Gly Glu Gln Glu Leu Lys Asp Gly Val Ile Lys Leu Arg Ser
465                 470                 475                 480
Val Thr Ser Arg Glu Glu Val Asp Val Arg Arg Glu Asp Leu Val Glu
                485                 490                 495
Glu Ile Lys Arg Arg Thr Gly Gln Pro Leu
            500                 505

<210> SEQ ID NO 71
<211> LENGTH: 48
<212> TYPE: PRT
<213> ORGANISM: Homo sapiens

<400> SEQUENCE: 71

Met Ala Glu Arg Ala Ala Leu Glu Glu Leu Val Lys Leu Gln Gly Glu
1               5                   10                  15
Arg Val Arg Gly Leu Lys Gln Gln Lys Ala Ser Ala Glu Leu Ile Glu
            20                  25                  30
Glu Glu Val Ala Lys Leu Leu Lys Leu Lys Ala Gln Leu Gly Pro Asp
        35                  40                  45

<210> SEQ ID NO 72
<211> LENGTH: 1518
<212> TYPE: DNA
<213> ORGANISM: Artificial Sequence
<220> FEATURE:
<223> OTHER INFORMATION: Codon optimized nucleic acid sequence for
      N-terminal fragment of HisRS1

<400> SEQUENCE: 72
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat ttgtgctcaa aacccccaag     180
ggcacaagag actatagtcc ccggcagatg gcagttcgcg agaaggtgtt tgacgtaatc     240
```

```
atccgttgct tcaagcgcca cggtgcagaa gtcattgata cacctgtatt tgaactaaag    300
gaaacactga tgggaaagta tggggaagac tccaagctta tctatgacct gaaggaccag    360
ggcggggagc tcctgtccct tcgctatgac ctcactgttc cttttgctcg gtatttggca    420
atgaataaac tgaccaacat taaacgctac cacatagcaa aggtatatcg gcgggataac    480
ccagccatga cccgtggccg ataccgggaa ttctaccagt gtgattttga cattgctggg    540
aactttgatc ccatgatccc tgatgcagag tgcctgaaga tcatgtgcga gatcctgagt    600
tcacttcaga taggcgactt cctggtcaag gtaaacgatc gacgcattct agatgggatg    660
tttgctatct gtggtgtttc tgacagcaag ttccgtacca tctgctcctc agtagacaag    720
ctggacaagg tgtcctggga agaggtgaag aatgagatgg tgggagagaa gggccttgca    780
cctgaggtgg ctgaccgcat tgggactat gtccagcaac atggtggggt atccctggtg    840
gaacagctgc tccaggatcc taaactatcc caaacaagc aggccttgga gggcctggga    900
gacctgaagt tgctctttga gtacctgacc ctatttggca ttgatgacaa aatctccttt    960
gacctgagcc ttgctcgagg gctggattac tacactgggg tgatctatga ggcagtgctg    1020
ctacagaccc cagcccaggc agggaagag ccctgggtg tgggcagtgt ggctgctgga   1080
ggacgctatg atgggctagt gggcatgttc gaccccaaag gcgcaaggt gccatgtgtg    1140 gggctcagca ttggggtgga gcggattttc tccatcgtgg aacagagact agaggctttg    1200
gaggagaaga tacggaccac ggagacacag gtgcttgtgg catctgcaca aagaagctg    1260 ctagaggaaa gactaaagct tgtctcagaa ctgtgggatg ctgggatcaa ggctgagctg    1320
ctgtacaaga gaacccaaa gctactgaac cagttacagt actgtgagga ggcaggcatc    1380
ccactggtgg ctatcatcgg cgagcaggaa ctcaaggatg gggtcatcaa gctccgttca    1440
gtgacgagca gggaagaggt ggatgtccga agaagacc ttgtggagga atcaaaagg    1500 agaacaggcc agcccctc                                                1518
```

```
<210> SEQ ID NO 73
<211> LENGTH: 144
<212> TYPE: DNA
<213> ORGANISM: Artificial Sequence
<220> FEATURE:
<223> OTHER INFORMATION: Codon optimized nucleic acid fragment for
      N-terminal fragment of HisRS1

<400> SEQUENCE: 73
atggcagaac gtgccgccct ggaagagctg gtaaaactgc aaggcgagcg tgttcgtggt    60
ctgaaacagc agaaagcaag cgctgaactg atcgaagaag agtggcgaa actgctgaaa    120 ctgaaagcac agctgggtcc tgat                                          144
```

```
<210> SEQ ID NO 74
<211> LENGTH: 80
<212> TYPE: PRT
<213> ORGANISM: Homo sapiens

<400> SEQUENCE: 74

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
```

```
                    50                  55                  60

Tyr Ser Pro Arg Gln Met Ala Val Arg Glu Lys Val Phe Asp Val Ile
 65                  70                  75                  80

<210> SEQ ID NO 75
<211> LENGTH: 79
<212> TYPE: PRT
<213> ORGANISM: Homo sapiens

<400> SEQUENCE: 75

Met Ala Glu Arg Ala Ala Leu Glu Glu Leu Val Lys Leu Gln Gly Glu
  1               5                  10                  15

Arg Val Arg Gly Leu Lys Gln Gln Lys Ala Ser Ala Glu Leu Ile Glu
                 20                  25                  30

Glu Glu Val Ala Lys Leu Leu Lys Leu Lys Ala Gln Leu Gly Pro Asp
             35                  40                  45

Glu Ser Lys Gln Lys Phe Val Leu Lys Thr Pro Lys Gly Thr Arg Asp
         50                  55                  60

Tyr Ser Pro Arg Gln Met Ala Val Arg Glu Lys Val Phe Asp Val
 65                  70                  75

<210> SEQ ID NO 76
<211> LENGTH: 78
<212> TYPE: PRT
<213> ORGANISM: Homo sapiens

<400> SEQUENCE: 76

Met Ala Glu Arg Ala Ala Leu Glu Glu Leu Val Lys Leu Gln Gly Glu
  1               5                  10                  15

Arg Val Arg Gly Leu Lys Gln Gln Lys Ala Ser Ala Glu Leu Ile Glu
                 20                  25                  30

Glu Glu Val Ala Lys Leu Leu Lys Leu Lys Ala Gln Leu Gly Pro Asp
             35                  40                  45

Glu Ser Lys Gln Lys Phe Val Leu Lys Thr Pro Lys Gly Thr Arg Asp
         50                  55                  60

Tyr Ser Pro Arg Gln Met Ala Val Arg Glu Lys Val Phe Asp
 65                  70                  75

<210> SEQ ID NO 77
<211> LENGTH: 77
<212> TYPE: PRT
<213> ORGANISM: Homo sapiens

<400> SEQUENCE: 77

Met Ala Glu Arg Ala Ala Leu Glu Glu Leu Val Lys Leu Gln Gly Glu
  1               5                  10                  15

Arg Val Arg Gly Leu Lys Gln Gln Lys Ala Ser Ala Glu Leu Ile Glu
                 20                  25                  30

Glu Glu Val Ala Lys Leu Leu Lys Leu Lys Ala Gln Leu Gly Pro Asp
             35                  40                  45

Glu Ser Lys Gln Lys Phe Val Leu Lys Thr Pro Lys Gly Thr Arg Asp
         50                  55                  60

Tyr Ser Pro Arg Gln Met Ala Val Arg Glu Lys Val Phe
 65                  70                  75

<210> SEQ ID NO 78
<211> LENGTH: 76
<212> TYPE: PRT
<213> ORGANISM: Homo sapiens
```

```
<400> SEQUENCE: 78

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val
65                  70                  75

<210> SEQ ID NO 79
<211> LENGTH: 75
<212> TYPE: PRT
<213> ORGANISM: Homo sapiens

<400> SEQUENCE: 79

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys
65                  70                  75

<210> SEQ ID NO 80
<211> LENGTH: 74
<212> TYPE: PRT
<213> ORGANISM: Homo sapiens

<400> SEQUENCE: 80

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu
65                  70

<210> SEQ ID NO 81
<211> LENGTH: 73
<212> TYPE: PRT
<213> ORGANISM: Homo sapiens

<400> SEQUENCE: 81

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
```

-continued

```
            35                  40                  45
Glu Ser Lys Gln Lys Phe Val Leu Lys Thr Pro Lys Gly Thr Arg Asp
 50                  55                  60
Tyr Ser Pro Arg Gln Met Ala Val Arg
 65                  70
```

<210> SEQ ID NO 82
<211> LENGTH: 72
<212> TYPE: PRT
<213> ORGANISM: Homo sapiens

<400> SEQUENCE: 82

```
Met Ala Glu Arg Ala Ala Leu Glu Glu Leu Val Lys Leu Gln Gly Glu
 1               5                  10                  15
Arg Val Arg Gly Leu Lys Gln Gln Lys Ala Ser Ala Glu Leu Ile Glu
                20                  25                  30
Glu Glu Val Ala Lys Leu Leu Lys Leu Lys Ala Gln Leu Gly Pro Asp
            35                  40                  45
Glu Ser Lys Gln Lys Phe Val Leu Lys Thr Pro Lys Gly Thr Arg Asp
 50                  55                  60
Tyr Ser Pro Arg Gln Met Ala Val
 65                  70
```

<210> SEQ ID NO 83
<211> LENGTH: 71
<212> TYPE: PRT
<213> ORGANISM: Homo sapiens

<400> SEQUENCE: 83

```
Met Ala Glu Arg Ala Ala Leu Glu Glu Leu Val Lys Leu Gln Gly Glu
 1               5                  10                  15
Arg Val Arg Gly Leu Lys Gln Gln Lys Ala Ser Ala Glu Leu Ile Glu
                20                  25                  30
Glu Glu Val Ala Lys Leu Leu Lys Leu Lys Ala Gln Leu Gly Pro Asp
            35                  40                  45
Glu Ser Lys Gln Lys Phe Val Leu Lys Thr Pro Lys Gly Thr Arg Asp
 50                  55                  60
Tyr Ser Pro Arg Gln Met Ala
 65                  70
```

<210> SEQ ID NO 84
<211> LENGTH: 70
<212> TYPE: PRT
<213> ORGANISM: Homo sapiens

<400> SEQUENCE: 84

```
Met Ala Glu Arg Ala Ala Leu Glu Glu Leu Val Lys Leu Gln Gly Glu
 1               5                  10                  15
Arg Val Arg Gly Leu Lys Gln Gln Lys Ala Ser Ala Glu Leu Ile Glu
                20                  25                  30
Glu Glu Val Ala Lys Leu Leu Lys Leu Lys Ala Gln Leu Gly Pro Asp
            35                  40                  45
Glu Ser Lys Gln Lys Phe Val Leu Lys Thr Pro Lys Gly Thr Arg Asp
 50                  55                  60
Tyr Ser Pro Arg Gln Met
 65                  70
```

<210> SEQ ID NO 85

```
<211> LENGTH: 69
<212> TYPE: PRT
<213> ORGANISM: Homo sapiens

<400> SEQUENCE: 85

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln
65

<210> SEQ ID NO 86
<211> LENGTH: 68
<212> TYPE: PRT
<213> ORGANISM: Homo sapiens

<400> SEQUENCE: 86

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg
65

<210> SEQ ID NO 87
<211> LENGTH: 67
<212> TYPE: PRT
<213> ORGANISM: Homo sapiens

<400> SEQUENCE: 87

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro
65

<210> SEQ ID NO 88
<211> LENGTH: 66
<212> TYPE: PRT
<213> ORGANISM: Homo sapiens

<400> SEQUENCE: 88

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
```

```
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser
65

<210> SEQ ID NO 89
<211> LENGTH: 65
<212> TYPE: PRT
<213> ORGANISM: Homo sapiens

<400> SEQUENCE: 89

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr
65

<210> SEQ ID NO 90
<211> LENGTH: 64
<212> TYPE: PRT
<213> ORGANISM: Homo sapiens

<400> SEQUENCE: 90

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

<210> SEQ ID NO 91
<211> LENGTH: 63
<212> TYPE: PRT
<213> ORGANISM: Homo sapiens

<400> SEQUENCE: 91

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg
        50                  55                  60

<210> SEQ ID NO 92
<211> LENGTH: 62
<212> TYPE: PRT
<213> ORGANISM: Homo sapiens
```

<400> SEQUENCE: 92

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr
    50                  55                  60

<210> SEQ ID NO 93
<211> LENGTH: 61
<212> TYPE: PRT
<213> ORGANISM: Homo sapiens

<400> SEQUENCE: 93

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly
    50                  55                  60

<210> SEQ ID NO 94
<211> LENGTH: 60
<212> TYPE: PRT
<213> ORGANISM: Homo sapiens

<400> SEQUENCE: 94

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 95
<211> LENGTH: 59
<212> TYPE: PRT
<213> ORGANISM: Homo sapiens

<400> SEQUENCE: 95

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro
    50                  55

<210> SEQ ID NO 96
<211> LENGTH: 58
<212> TYPE: PRT

<213> ORGANISM: Homo sapiens

<400> SEQUENCE: 96

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr
    50                  55

<210> SEQ ID NO 97
<211> LENGTH: 57
<212> TYPE: PRT
<213> ORGANISM: Homo sapiens

<400> SEQUENCE: 97

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys
    50                  55

<210> SEQ ID NO 98
<211> LENGTH: 56
<212> TYPE: PRT
<213> ORGANISM: Homo sapiens

<400> SEQUENCE: 98

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu
    50                  55

<210> SEQ ID NO 99
<211> LENGTH: 55
<212> TYPE: PRT
<213> ORGANISM: Homo sapiens

<400> SEQUENCE: 99

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val
    50                  55

<210> SEQ ID NO 100
<211> LENGTH: 54

```
<212> TYPE: PRT
<213> ORGANISM: Homo sapiens

<400> SEQUENCE: 100

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe
    50

<210> SEQ ID NO 101
<211> LENGTH: 53
<212> TYPE: PRT
<213> ORGANISM: Homo sapiens

<400> SEQUENCE: 101

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys
    50

<210> SEQ ID NO 102
<211> LENGTH: 52
<212> TYPE: PRT
<213> ORGANISM: Homo sapiens

<400> SEQUENCE: 102

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln
    50

<210> SEQ ID NO 103
<211> LENGTH: 51
<212> TYPE: PRT
<213> ORGANISM: Homo sapiens

<400> SEQUENCE: 103

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys
    50

<210> SEQ ID NO 104
```

```
<211> LENGTH: 50
<212> TYPE: PRT
<213> ORGANISM: Homo sapiens

<400> SEQUENCE: 104

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser
    50

<210> SEQ ID NO 105
<211> LENGTH: 49
<212> TYPE: PRT
<213> ORGANISM: Homo sapiens

<400> SEQUENCE: 105

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu

<210> SEQ ID NO 106
<211> LENGTH: 48
<212> TYPE: PRT
<213> ORGANISM: Homo sapiens

<400> SEQUENCE: 106

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

<210> SEQ ID NO 107
<211> LENGTH: 47
<212> TYPE: PRT
<213> ORGANISM: Homo sapiens

<400> SEQUENCE: 107

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro
        35                  40                  45

<210> SEQ ID NO 108
<211> LENGTH: 46
<212> TYPE: PRT
<213> ORGANISM: Homo sapiens

<400> SEQUENCE: 108
```

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly
        35                  40                  45

<210> SEQ ID NO 109
<211> LENGTH: 45
<212> TYPE: PRT
<213> ORGANISM: Homo sapiens

<400> SEQUENCE: 109

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu
        35                  40                  45

<210> SEQ ID NO 110
<211> LENGTH: 44
<212> TYPE: PRT
<213> ORGANISM: Homo sapiens

<400> SEQUENCE: 110

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln
        35                  40

<210> SEQ ID NO 111
<211> LENGTH: 43
<212> TYPE: PRT
<213> ORGANISM: Homo sapiens

<400> SEQUENCE: 111

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala
        35                  40

<210> SEQ ID NO 112
<211> LENGTH: 42
<212> TYPE: PRT
<213> ORGANISM: Homo sapiens

<400> SEQUENCE: 112

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys
        35                  40

<210> SEQ ID NO 113

```
<211> LENGTH: 41
<212> TYPE: PRT
<213> ORGANISM: Homo sapiens

<400> SEQUENCE: 113

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu
        35                  40

<210> SEQ ID NO 114
<211> LENGTH: 40
<212> TYPE: PRT
<213> ORGANISM: Homo sapiens

<400> SEQUENCE: 114

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys
        35                  40

<210> SEQ ID NO 115
<211> LENGTH: 79
<212> TYPE: PRT
<213> ORGANISM: Homo sapiens

<400> SEQUENCE: 115

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
            20                  25                  30

Glu Val Ala Lys Leu Leu Lys Leu Lys Ala Gln Leu Gly Pro Asp Glu
        35                  40                  45

Ser Lys Gln Lys Phe Val Leu Lys Thr Pro Lys Gly Thr Arg Asp Tyr
    50                  55                  60

Ser Pro Arg Gln Met Ala Val Arg Glu Lys Val Phe Asp Val Ile
65                  70                  75

<210> SEQ ID NO 116
<211> LENGTH: 78
<212> TYPE: PRT
<213> ORGANISM: Homo sapiens

<400> SEQUENCE: 116

Glu Arg Ala Ala Leu Glu Glu Leu Val Lys Leu Gln Gly Glu Arg Val
1               5                   10                  15

Arg Gly Leu Lys Gln Gln Lys Ala Ser Ala Glu Leu Ile Glu Glu Glu
            20                  25                  30

Val Ala Lys Leu Leu Lys Leu Lys Ala Gln Leu Gly Pro Asp Glu Ser
        35                  40                  45

Lys Gln Lys Phe Val Leu Lys Thr Pro Lys Gly Thr Arg Asp Tyr Ser
    50                  55                  60

Pro Arg Gln Met Ala Val Arg Glu Lys Val Phe Asp Val Ile
65                  70                  75
```

```
<210> SEQ ID NO 117
<211> LENGTH: 77
<212> TYPE: PRT
<213> ORGANISM: Homo sapiens

<400> SEQUENCE: 117

Arg Ala Ala Leu Glu Glu Leu Val Lys Leu Gln Gly Glu Arg Val Arg
1               5                   10                  15

Gly Leu Lys Gln Gln Lys Ala Ser Ala Glu Leu Ile Glu Glu Glu Val
            20                  25                  30

Ala Lys Leu Leu Lys Leu Lys Ala Gln Leu Gly Pro Asp Glu Ser Lys
        35                  40                  45

Gln Lys Phe Val Leu Lys Thr Pro Lys Gly Thr Arg Asp Tyr Ser Pro
    50                  55                  60

Arg Gln Met Ala Val Arg Glu Lys Val Phe Asp Val Ile
65                  70                  75

<210> SEQ ID NO 118
<211> LENGTH: 76
<212> TYPE: PRT
<213> ORGANISM: Homo sapiens

<400> SEQUENCE: 118

Ala Ala Leu Glu Glu Leu Val Lys Leu Gln Gly Glu Arg Val Arg Gly
1               5                   10                  15

Leu Lys Gln Gln Lys Ala Ser Ala Glu Leu Ile Glu Glu Glu Val Ala
            20                  25                  30

Lys Leu Leu Lys Leu Lys Ala Gln Leu Gly Pro Asp Glu Ser Lys Gln
        35                  40                  45

Lys Phe Val Leu Lys Thr Pro Lys Gly Thr Arg Asp Tyr Ser Pro Arg
    50                  55                  60

Gln Met Ala Val Arg Glu Lys Val Phe Asp Val Ile
65                  70                  75

<210> SEQ ID NO 119
<211> LENGTH: 75
<212> TYPE: PRT
<213> ORGANISM: Homo sapiens

<400> SEQUENCE: 119

Ala Leu Glu Glu Leu Val Lys Leu Gln Gly Glu Arg Val Arg Gly Leu
1               5                   10                  15

Lys Gln Gln Lys Ala Ser Ala Glu Leu Ile Glu Glu Glu Val Ala Lys
            20                  25                  30

Leu Leu Lys Leu Lys Ala Gln Leu Gly Pro Asp Glu Ser Lys Gln Lys
        35                  40                  45

Phe Val Leu Lys Thr Pro Lys Gly Thr Arg Asp Tyr Ser Pro Arg Gln
    50                  55                  60

Met Ala Val Arg Glu Lys Val Phe Asp Val Ile
65                  70                  75

<210> SEQ ID NO 120
<211> LENGTH: 74
<212> TYPE: PRT
<213> ORGANISM: Homo sapiens

<400> SEQUENCE: 120

Leu Glu Glu Leu Val Lys Leu Gln Gly Glu Arg Val Arg Gly Leu Lys
1               5                   10                  15
```

```
Gln Gln Lys Ala Ser Ala Glu Leu Ile Glu Glu Val Ala Lys Leu
            20                  25                  30

Leu Lys Leu Lys Ala Gln Leu Gly Pro Asp Glu Ser Lys Gln Lys Phe
         35                  40                  45

Val Leu Lys Thr Pro Lys Gly Thr Arg Asp Tyr Ser Pro Arg Gln Met
 50                  55                  60

Ala Val Arg Glu Lys Val Phe Asp Val Ile
 65                  70

<210> SEQ ID NO 121
<211> LENGTH: 73
<212> TYPE: PRT
<213> ORGANISM: Homo sapiens

<400> SEQUENCE: 121

Glu Glu Leu Val Lys Leu Gln Gly Glu Arg Val Arg Gly Leu Lys Gln
 1               5                   10                  15

Gln Lys Ala Ser Ala Glu Leu Ile Glu Glu Val Ala Lys Leu Leu
            20                  25                  30

Lys Leu Lys Ala Gln Leu Gly Pro Asp Glu Ser Lys Gln Lys Phe Val
         35                  40                  45

Leu Lys Thr Pro Lys Gly Thr Arg Asp Tyr Ser Pro Arg Gln Met Ala
 50                  55                  60

Val Arg Glu Lys Val Phe Asp Val Ile
 65                  70

<210> SEQ ID NO 122
<211> LENGTH: 72
<212> TYPE: PRT
<213> ORGANISM: Homo sapiens

<400> SEQUENCE: 122

Glu Leu Val Lys Leu Gln Gly Glu Arg Val Arg Gly Leu Lys Gln Gln
 1               5                   10                  15

Lys Ala Ser Ala Glu Leu Ile Glu Glu Val Ala Lys Leu Leu Lys
            20                  25                  30

Leu Lys Ala Gln Leu Gly Pro Asp Glu Ser Lys Gln Lys Phe Val Leu
         35                  40                  45

Lys Thr Pro Lys Gly Thr Arg Asp Tyr Ser Pro Arg Gln Met Ala Val
 50                  55                  60

Arg Glu Lys Val Phe Asp Val Ile
 65                  70

<210> SEQ ID NO 123
<211> LENGTH: 71
<212> TYPE: PRT
<213> ORGANISM: Homo sapiens

<400> SEQUENCE: 123

Leu Val Lys Leu Gln Gly Glu Arg Val Arg Gly Leu Lys Gln Gln Lys
 1               5                   10                  15

Ala Ser Ala Glu Leu Ile Glu Glu Val Ala Lys Leu Leu Lys Leu
            20                  25                  30

Lys Ala Gln Leu Gly Pro Asp Glu Ser Lys Gln Lys Phe Val Leu Lys
         35                  40                  45

Thr Pro Lys Gly Thr Arg Asp Tyr Ser Pro Arg Gln Met Ala Val Arg
 50                  55                  60

Glu Lys Val Phe Asp Val Ile
```

65                    70

<210> SEQ ID NO 124
<211> LENGTH: 70
<212> TYPE: PRT
<213> ORGANISM: Homo sapiens

<400> SEQUENCE: 124

Val Lys Leu Gln Gly Glu Arg Val Arg Gly Leu Lys Gln Gln Lys Ala
1               5                   10                  15

Ser Ala Glu Leu Ile Glu Glu Val Ala Lys Leu Leu Lys Leu Lys
            20                  25                  30

Ala Gln Leu Gly Pro Asp Glu Ser Lys Gln Lys Phe Val Leu Lys Thr
        35                  40                  45

Pro Lys Gly Thr Arg Asp Tyr Ser Pro Arg Gln Met Ala Val Arg Glu
    50                  55                  60

Lys Val Phe Asp Val Ile
65                  70

<210> SEQ ID NO 125
<211> LENGTH: 69
<212> TYPE: PRT
<213> ORGANISM: Homo sapiens

<400> SEQUENCE: 125

Lys Leu Gln Gly Glu Arg Val Arg Gly Leu Lys Gln Gln Lys Ala Ser
1               5                   10                  15

Ala Glu Leu Ile Glu Glu Glu Val Ala Lys Leu Leu Lys Leu Lys Ala
            20                  25                  30

Gln Leu Gly Pro Asp Glu Ser Lys Gln Lys Phe Val Leu Lys Thr Pro
        35                  40                  45

Lys Gly Thr Arg Asp Tyr Ser Pro Arg Gln Met Ala Val Arg Glu Lys
    50                  55                  60

Val Phe Asp Val Ile
65

<210> SEQ ID NO 126
<211> LENGTH: 68
<212> TYPE: PRT
<213> ORGANISM: Homo sapiens

<400> SEQUENCE: 126

Leu Gln Gly Glu Arg Val Arg Gly Leu Lys Gln Gln Lys Ala Ser Ala
1               5                   10                  15

Glu Leu Ile Glu Glu Glu Val Ala Lys Leu Leu Lys Leu Lys Ala Gln
            20                  25                  30

Leu Gly Pro Asp Glu Ser Lys Gln Lys Phe Val Leu Lys Thr Pro Lys
        35                  40                  45

Gly Thr Arg Asp Tyr Ser Pro Arg Gln Met Ala Val Arg Glu Lys Val
    50                  55                  60

Phe Asp Val Ile
65

<210> SEQ ID NO 127
<211> LENGTH: 67
<212> TYPE: PRT
<213> ORGANISM: Homo sapiens

<400> SEQUENCE: 127

```
Gln Gly Glu Arg Val Arg Gly Leu Lys Gln Gln Lys Ala Ser Ala Glu
 1               5                  10                  15
Leu Ile Glu Glu Val Ala Lys Leu Leu Lys Leu Lys Ala Gln Leu
             20                  25                  30
Gly Pro Asp Glu Ser Lys Gln Lys Phe Val Leu Lys Thr Pro Lys Gly
             35                  40                  45
Thr Arg Asp Tyr Ser Pro Arg Gln Met Ala Val Arg Glu Lys Val Phe
 50                  55                  60
Asp Val Ile
 65

<210> SEQ ID NO 128
<211> LENGTH: 66
<212> TYPE: PRT
<213> ORGANISM: Homo sapiens

<400> SEQUENCE: 128

Gly Glu Arg Val Arg Gly Leu Lys Gln Gln Lys Ala Ser Ala Glu Leu
 1               5                  10                  15
Ile Glu Glu Val Ala Lys Leu Leu Lys Leu Lys Ala Gln Leu Gly
             20                  25                  30
Pro Asp Glu Ser Lys Gln Lys Phe Val Leu Lys Thr Pro Lys Gly Thr
             35                  40                  45
Arg Asp Tyr Ser Pro Arg Gln Met Ala Val Arg Glu Lys Val Phe Asp
 50                  55                  60
Val Ile
 65

<210> SEQ ID NO 129
<211> LENGTH: 64
<212> TYPE: PRT
<213> ORGANISM: Homo sapiens

<400> SEQUENCE: 129

Arg Val Arg Gly Leu Lys Gln Gln Lys Ala Ser Ala Glu Leu Ile Glu
 1               5                  10                  15
Glu Val Ala Lys Leu Leu Lys Leu Lys Ala Gln Leu Gly Pro Asp
             20                  25                  30
Glu Ser Lys Gln Lys Phe Val Leu Lys Thr Pro Lys Gly Thr Arg Asp
             35                  40                  45
Tyr Ser Pro Arg Gln Met Ala Val Arg Glu Lys Val Phe Asp Val Ile
 50                  55                  60

<210> SEQ ID NO 130
<211> LENGTH: 63
<212> TYPE: PRT
<213> ORGANISM: Homo sapiens

<400> SEQUENCE: 130

Val Arg Gly Leu Lys Gln Gln Lys Ala Ser Ala Glu Leu Ile Glu Glu
 1               5                  10                  15
Glu Val Ala Lys Leu Leu Lys Leu Lys Ala Gln Leu Gly Pro Asp Glu
             20                  25                  30
Ser Lys Gln Lys Phe Val Leu Lys Thr Pro Lys Gly Thr Arg Asp Tyr
             35                  40                  45
Ser Pro Arg Gln Met Ala Val Arg Glu Lys Val Phe Asp Val Ile
 50                  55                  60
```

```
<210> SEQ ID NO 131
<211> LENGTH: 62
<212> TYPE: PRT
<213> ORGANISM: Homo sapiens

<400> SEQUENCE: 131

Arg Gly Leu Lys Gln Gln Lys Ala Ser Ala Glu Leu Ile Glu Glu
1               5                   10                  15

Val Ala Lys Leu Leu Lys Leu Lys Ala Gln Leu Gly Pro Asp Glu Ser
            20                  25                  30

Lys Gln Lys Phe Val Leu Lys Thr Pro Lys Gly Thr Arg Asp Tyr Ser
        35                  40                  45

Pro Arg Gln Met Ala Val Arg Glu Lys Val Phe Asp Val Ile
    50                  55                  60

<210> SEQ ID NO 132
<211> LENGTH: 61
<212> TYPE: PRT
<213> ORGANISM: Homo sapiens

<400> SEQUENCE: 132

Gly Leu Lys Gln Gln Lys Ala Ser Ala Glu Leu Ile Glu Glu Val
1               5                   10                  15

Ala Lys Leu Leu Lys Leu Lys Ala Gln Leu Gly Pro Asp Glu Ser Lys
            20                  25                  30

Gln Lys Phe Val Leu Lys Thr Pro Lys Gly Thr Arg Asp Tyr Ser Pro
        35                  40                  45

Arg Gln Met Ala Val Arg Glu Lys Val Phe Asp Val Ile
    50                  55                  60

<210> SEQ ID NO 133
<211> LENGTH: 60
<212> TYPE: PRT
<213> ORGANISM: Homo sapiens

<400> SEQUENCE: 133

Leu Lys Gln Gln Lys Ala Ser Ala Glu Leu Ile Glu Glu Val Ala
1               5                   10                  15

Lys Leu Leu Lys Leu Lys Ala Gln Leu Gly Pro Asp Glu Ser Lys Gln
            20                  25                  30

Lys Phe Val Leu Lys Thr Pro Lys Gly Thr Arg Asp Tyr Ser Pro Arg
        35                  40                  45

Gln Met Ala Val Arg Glu Lys Val Phe Asp Val Ile
    50                  55                  60

<210> SEQ ID NO 134
<211> LENGTH: 59
<212> TYPE: PRT
<213> ORGANISM: Homo sapiens

<400> SEQUENCE: 134

Lys Gln Gln Lys Ala Ser Ala Glu Leu Ile Glu Glu Val Ala Lys
1               5                   10                  15

Leu Leu Lys Leu Lys Ala Gln Leu Gly Pro Asp Glu Ser Lys Gln Lys
            20                  25                  30

Phe Val Leu Lys Thr Pro Lys Gly Thr Arg Asp Tyr Ser Pro Arg Gln
        35                  40                  45

Met Ala Val Arg Glu Lys Val Phe Asp Val Ile
    50                  55
```

```
<210> SEQ ID NO 135
<211> LENGTH: 58
<212> TYPE: PRT
<213> ORGANISM: Homo sapiens

<400> SEQUENCE: 135

Gln Gln Lys Ala Ser Ala Glu Leu Ile Glu Glu Val Ala Lys Leu
1               5                   10                  15

Leu Lys Leu Lys Ala Gln Leu Gly Pro Asp Glu Ser Lys Gln Lys Phe
            20                  25                  30

Val Leu Lys Thr Pro Lys Gly Thr Arg Asp Tyr Ser Pro Arg Gln Met
        35                  40                  45

Ala Val Arg Glu Lys Val Phe Asp Val Ile
    50                  55

<210> SEQ ID NO 136
<211> LENGTH: 57
<212> TYPE: PRT
<213> ORGANISM: Homo sapiens

<400> SEQUENCE: 136

Gln Lys Ala Ser Ala Glu Leu Ile Glu Glu Val Ala Lys Leu Leu
1               5                   10                  15

Lys Leu Lys Ala Gln Leu Gly Pro Asp Glu Ser Lys Gln Lys Phe Val
            20                  25                  30

Leu Lys Thr Pro Lys Gly Thr Arg Asp Tyr Ser Pro Arg Gln Met Ala
        35                  40                  45

Val Arg Glu Lys Val Phe Asp Val Ile
    50                  55

<210> SEQ ID NO 137
<211> LENGTH: 56
<212> TYPE: PRT
<213> ORGANISM: Homo sapiens

<400> SEQUENCE: 137

Lys Ala Ser Ala Glu Leu Ile Glu Glu Val Ala Lys Leu Leu Lys
1               5                   10                  15

Leu Lys Ala Gln Leu Gly Pro Asp Glu Ser Lys Gln Lys Phe Val Leu
            20                  25                  30

Lys Thr Pro Lys Gly Thr Arg Asp Tyr Ser Pro Arg Gln Met Ala Val
        35                  40                  45

Arg Glu Lys Val Phe Asp Val Ile
    50                  55

<210> SEQ ID NO 138
<211> LENGTH: 55
<212> TYPE: PRT
<213> ORGANISM: Homo sapiens

<400> SEQUENCE: 138

Ala Ser Ala Glu Leu Ile Glu Glu Val Ala Lys Leu Leu Lys Leu
1               5                   10                  15

Lys Ala Gln Leu Gly Pro Asp Glu Ser Lys Gln Lys Phe Val Leu Lys
            20                  25                  30

Thr Pro Lys Gly Thr Arg Asp Tyr Ser Pro Arg Gln Met Ala Val Arg
        35                  40                  45

Glu Lys Val Phe Asp Val Ile
    50                  55
```

```
<210> SEQ ID NO 139
<211> LENGTH: 54
<212> TYPE: PRT
<213> ORGANISM: Homo sapiens

<400> SEQUENCE: 139

Ser Ala Glu Leu Ile Glu Glu Val Ala Lys Leu Leu Lys Leu Lys
1               5                   10                  15

Ala Gln Leu Gly Pro Asp Glu Ser Lys Gln Lys Phe Val Leu Lys Thr
            20                  25                  30

Pro Lys Gly Thr Arg Asp Tyr Ser Pro Arg Gln Met Ala Val Arg Glu
        35                  40                  45

Lys Val Phe Asp Val Ile
        50

<210> SEQ ID NO 140
<211> LENGTH: 53
<212> TYPE: PRT
<213> ORGANISM: Homo sapiens

<400> SEQUENCE: 140

Ala Glu Leu Ile Glu Glu Val Ala Lys Leu Leu Lys Leu Lys Ala
1               5                   10                  15

Gln Leu Gly Pro Asp Glu Ser Lys Gln Lys Phe Val Leu Lys Thr Pro
            20                  25                  30

Lys Gly Thr Arg Asp Tyr Ser Pro Arg Gln Met Ala Val Arg Glu Lys
        35                  40                  45

Val Phe Asp Val Ile
        50

<210> SEQ ID NO 141
<211> LENGTH: 52
<212> TYPE: PRT
<213> ORGANISM: Homo sapiens

<400> SEQUENCE: 141

Glu Leu Ile Glu Glu Val Ala Lys Leu Leu Lys Leu Lys Ala Gln
1               5                   10                  15

Leu Gly Pro Asp Glu Ser Lys Gln Lys Phe Val Leu Lys Thr Pro Lys
            20                  25                  30

Gly Thr Arg Asp Tyr Ser Pro Arg Gln Met Ala Val Arg Glu Lys Val
        35                  40                  45

Phe Asp Val Ile
        50

<210> SEQ ID NO 142
<211> LENGTH: 51
<212> TYPE: PRT
<213> ORGANISM: Homo sapiens

<400> SEQUENCE: 142

Leu Ile Glu Glu Val Ala Lys Leu Leu Lys Leu Lys Ala Gln Leu
1               5                   10                  15

Gly Pro Asp Glu Ser Lys Gln Lys Phe Val Leu Lys Thr Pro Lys Gly
            20                  25                  30

Thr Arg Asp Tyr Ser Pro Arg Gln Met Ala Val Arg Glu Lys Val Phe
        35                  40                  45

Asp Val Ile
```

50

<210> SEQ ID NO 143
<211> LENGTH: 50
<212> TYPE: PRT
<213> ORGANISM: Homo sapiens

<400> SEQUENCE: 143

Ile Glu Glu Glu Val Ala Lys Leu Leu Lys Leu Lys Ala Gln Leu Gly
1               5                   10                  15

Pro Asp Glu Ser Lys Gln Lys Phe Val Leu Lys Thr Pro Lys Gly Thr
            20                  25                  30

Arg Asp Tyr Ser Pro Arg Gln Met Ala Val Arg Glu Lys Val Phe Asp
        35                  40                  45

Val Ile
    50

<210> SEQ ID NO 144
<211> LENGTH: 49
<212> TYPE: PRT
<213> ORGANISM: Homo sapiens

<400> SEQUENCE: 144

Glu Glu Glu Val Ala Lys Leu Leu Lys Leu Lys Ala Gln Leu Gly Pro
1               5                   10                  15

Asp Glu Ser Lys Gln Lys Phe Val Leu Lys Thr Pro Lys Gly Thr Arg
            20                  25                  30

Asp Tyr Ser Pro Arg Gln Met Ala Val Arg Glu Lys Val Phe Asp Val
        35                  40                  45

Ile

<210> SEQ ID NO 145
<211> LENGTH: 48
<212> TYPE: PRT
<213> ORGANISM: Homo sapiens

<400> SEQUENCE: 145

Glu Glu Val Ala Lys Leu Leu Lys Leu Lys Ala Gln Leu Gly Pro Asp
1               5                   10                  15

Glu Ser Lys Gln Lys Phe Val Leu Lys Thr Pro Lys Gly Thr Arg Asp
            20                  25                  30

Tyr Ser Pro Arg Gln Met Ala Val Arg Glu Lys Val Phe Asp Val Ile
        35                  40                  45

<210> SEQ ID NO 146
<211> LENGTH: 47
<212> TYPE: PRT
<213> ORGANISM: Homo sapiens

<400> SEQUENCE: 146

Glu Val Ala Lys Leu Leu Lys Leu Lys Ala Gln Leu Gly Pro Asp Glu
1               5                   10                  15

Ser Lys Gln Lys Phe Val Leu Lys Thr Pro Lys Gly Thr Arg Asp Tyr
            20                  25                  30

Ser Pro Arg Gln Met Ala Val Arg Glu Lys Val Phe Asp Val Ile
        35                  40                  45

<210> SEQ ID NO 147
<211> LENGTH: 46
<212> TYPE: PRT

<213> ORGANISM: Homo sapiens

<400> SEQUENCE: 147

Val Ala Lys Leu Leu Lys Leu Lys Ala Gln Leu Gly Pro Asp Glu Ser
1               5                   10                  15

Lys Gln Lys Phe Val Leu Lys Thr Pro Lys Gly Thr Arg Asp Tyr Ser
            20                  25                  30

Pro Arg Gln Met Ala Val Arg Glu Lys Val Phe Asp Val Ile
        35                  40                  45

<210> SEQ ID NO 148
<211> LENGTH: 45
<212> TYPE: PRT
<213> ORGANISM: Homo sapiens

<400> SEQUENCE: 148

Ala Lys Leu Leu Lys Leu Lys Ala Gln Leu Gly Pro Asp Glu Ser Lys
1               5                   10                  15

Gln Lys Phe Val Leu Lys Thr Pro Lys Gly Thr Arg Asp Tyr Ser Pro
            20                  25                  30

Arg Gln Met Ala Val Arg Glu Lys Val Phe Asp Val Ile
        35                  40                  45

<210> SEQ ID NO 149
<211> LENGTH: 44
<212> TYPE: PRT
<213> ORGANISM: Homo sapiens

<400> SEQUENCE: 149

Lys Leu Leu Lys Leu Lys Ala Gln Leu Gly Pro Asp Glu Ser Lys Gln
1               5                   10                  15

Lys Phe Val Leu Lys Thr Pro Lys Gly Thr Arg Asp Tyr Ser Pro Arg
            20                  25                  30

Gln Met Ala Val Arg Glu Lys Val Phe Asp Val Ile
        35                  40

<210> SEQ ID NO 150
<211> LENGTH: 43
<212> TYPE: PRT
<213> ORGANISM: Homo sapiens

<400> SEQUENCE: 150

Leu Leu Lys Leu Lys Ala Gln Leu Gly Pro Asp Glu Ser Lys Gln Lys
1               5                   10                  15

Phe Val Leu Lys Thr Pro Lys Gly Thr Arg Asp Tyr Ser Pro Arg Gln
            20                  25                  30

Met Ala Val Arg Glu Lys Val Phe Asp Val Ile
        35                  40

<210> SEQ ID NO 151
<211> LENGTH: 42
<212> TYPE: PRT
<213> ORGANISM: Homo sapiens

<400> SEQUENCE: 151

Leu Lys Leu Lys Ala Gln Leu Gly Pro Asp Glu Ser Lys Gln Lys Phe
1               5                   10                  15

Val Leu Lys Thr Pro Lys Gly Thr Arg Asp Tyr Ser Pro Arg Gln Met
            20                  25                  30

Ala Val Arg Glu Lys Val Phe Asp Val Ile

<210> SEQ ID NO 152
<211> LENGTH: 41
<212> TYPE: PRT
<213> ORGANISM: Homo sapiens

<400> SEQUENCE: 152

Lys Leu Lys Ala Gln Leu Gly Pro Asp Glu Ser Lys Gln Lys Phe Val
1               5                   10                  15

Leu Lys Thr Pro Lys Gly Thr Arg Asp Tyr Ser Pro Arg Gln Met Ala
            20                  25                  30

Val Arg Glu Lys Val Phe Asp Val Ile
        35                  40

<210> SEQ ID NO 153
<211> LENGTH: 40
<212> TYPE: PRT
<213> ORGANISM: Homo sapiens

<400> SEQUENCE: 153

Leu Lys Ala Gln Leu Gly Pro Asp Glu Ser Lys Gln Lys Phe Val Leu
1               5                   10                  15

Lys Thr Pro Lys Gly Thr Arg Asp Tyr Ser Pro Arg Gln Met Ala Val
            20                  25                  30

Arg Glu Lys Val Phe Asp Val Ile
        35                  40

<210> SEQ ID NO 154
<211> LENGTH: 15
<212> TYPE: DNA
<213> ORGANISM: Homo sapiens

<400> SEQUENCE: 154
aaacaaaaca aaaca                                                    15

<210> SEQ ID NO 155
<211> LENGTH: 10
<212> TYPE: DNA
<213> ORGANISM: Homo sapiens

<400> SEQUENCE: 155
aaacaaaaca                                                          10

<210> SEQ ID NO 156
<211> LENGTH: 10
<212> TYPE: DNA
<213> ORGANISM: Homo sapiens

<400> SEQUENCE: 156
caaaacaaaa                                                          10

<210> SEQ ID NO 157
<211> LENGTH: 15
<212> TYPE: DNA
<213> ORGANISM: Homo sapiens

<400> SEQUENCE: 157
caaaacaaaa caaaa                                                    15

<210> SEQ ID NO 158
<211> LENGTH: 10

```
<212> TYPE: DNA
<213> ORGANISM: Homo sapiens

<400> SEQUENCE: 158
aaacaaaaca                                                                  10

<210> SEQ ID NO 159
<211> LENGTH: 10
<212> TYPE: DNA
<213> ORGANISM: Homo sapiens

<400> SEQUENCE: 159
acaaaacaaa                                                                  10

<210> SEQ ID NO 160
<211> LENGTH: 500
<212> TYPE: PRT
<213> ORGANISM: Homo sapiens

<400> SEQUENCE: 160
```

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

```
Leu Ser Gln Asn Lys Gln Ala Leu Glu Gly Leu Gly Asp Leu Lys Leu
290                 295                 300
Leu Phe Glu Tyr Leu Thr Leu Phe Gly Ile Asp Asp Lys Ile Ser Phe
305                 310                 315                 320
Asp Leu Ser Leu Ala Arg Gly Leu Asp Tyr Tyr Thr Gly Val Ile Tyr
                325                 330                 335
Glu Ala Val Leu Leu Gln Thr Pro Ala Gln Ala Gly Glu Glu Pro Leu
            340                 345                 350
Gly Val Gly Ser Val Ala Ala Gly Gly Arg Tyr Asp Gly Leu Val Gly
        355                 360                 365
Met Phe Asp Pro Lys Gly Arg Lys Val Pro Cys Val Gly Leu Ser Ile
370                 375                 380
Gly Val Glu Arg Ile Phe Ser Ile Val Glu Gln Arg Leu Glu Ala Leu
385                 390                 395                 400
Glu Glu Lys Ile Arg Thr Thr Glu Thr Gln Val Leu Val Ala Ser Ala
                405                 410                 415
Gln Lys Lys Leu Leu Glu Arg Leu Lys Leu Val Ser Glu Leu Trp
            420                 425                 430
Asp Ala Gly Ile Lys Ala Glu Leu Leu Tyr Lys Lys Asn Pro Lys Leu
            435                 440                 445
Leu Asn Gln Leu Gln Tyr Cys Glu Glu Ala Gly Ile Pro Leu Val Ala
450                 455                 460
Ile Ile Gly Glu Gln Glu Leu Lys Asp Gly Val Ile Lys Leu Arg Ser
465                 470                 475                 480
Val Thr Ser Arg Glu Glu Val Asp Val Arg Arg Glu Asp Leu Val Glu
                485                 490                 495
Glu Ile Lys Arg
            500

<210> SEQ ID NO 161
<211> LENGTH: 501
<212> TYPE: PRT
<213> ORGANISM: Homo sapiens

<400> SEQUENCE: 161

Met Ala Glu Arg Ala Ala Leu Glu Glu Leu Val Lys Leu Gln Gly Glu
1               5                   10                  15
Arg Val Arg Gly Leu Lys Gln Gln Lys Ala Ser Ala Glu Leu Ile Glu
                20                  25                  30
Glu Glu Val Ala Lys Leu Leu Lys Leu Lys Ala Gln Leu Gly Pro Asp
            35                  40                  45
Glu Ser Lys Gln Lys Phe Val Leu Lys Thr Pro Lys Gly Thr Arg Asp
        50                  55                  60
Tyr Ser Pro Arg Gln Met Ala Val Arg Glu Lys Val Phe Asp Val Ile
65                  70                  75                  80
Ile Arg Cys Phe Lys Arg His Gly Ala Glu Val Ile Asp Thr Pro Val
                85                  90                  95
Phe Glu Leu Lys Glu Thr Leu Met Gly Lys Tyr Gly Glu Asp Ser Lys
            100                 105                 110
Leu Ile Tyr Asp Leu Lys Asp Gln Gly Gly Glu Leu Leu Ser Leu Arg
        115                 120                 125
Tyr Asp Leu Thr Val Pro Phe Ala Arg Tyr Leu Ala Met Asn Lys Leu
    130                 135                 140
Thr Asn Ile Lys Arg Tyr His Ile Ala Lys Val Tyr Arg Arg Asp Asn
145                 150                 155                 160
```

```
Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
        290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
        370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg
            500

<210> SEQ ID NO 162
<211> LENGTH: 502
<212> TYPE: PRT
<213> ORGANISM: Homo sapiens

<400> SEQUENCE: 162

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
```

```
                20                  25                  30
Glu Glu Val Ala Lys Leu Leu Lys Leu Lys Ala Gln Leu Gly Pro Asp
                35                  40                  45

Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
                 85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
                115                 120                 125

Tyr Asp Leu Thr Val Pro Phe Ala Arg Tyr Leu Ala Met Asn Lys Leu
                130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
                180                 185                 190

Lys Ile Met Cys Glu Ile Leu Ser Ser Leu Gln Ile Gly Asp Phe Leu
                195                 200                 205

Val Lys Val Asn Asp Arg Arg Ile Leu Asp Gly Met Phe Ala Ile Cys
                210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
                290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
                370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
                435                 440                 445
```

```
Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr
            500
```

<210> SEQ ID NO 163
<211> LENGTH: 503
<212> TYPE: PRT
<213> ORGANISM: Homo sapiens

<400> SEQUENCE: 163

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
```

```
                             305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Arg Tyr Asp Gly Leu Val Gly
                355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
                435                 440                 445

Leu Asn Gln Leu Gln Tyr Cys Glu Glu Ala Gly Ile Pro Leu Val Ala
                450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly
                500

<210> SEQ ID NO 164
<211> LENGTH: 504
<212> TYPE: PRT
<213> ORGANISM: Homo sapiens

<400> SEQUENCE: 164

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
                35                  40                  45

Glu Ser Lys Gln Lys Phe Val Leu Lys Thr Pro Lys Gly Thr Arg Asp
                50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
                115                 120                 125

Tyr Asp Leu Thr Val Pro Phe Ala Arg Tyr Leu Ala Met Asn Lys Leu
                130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175
```

```
Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Glu Asp Leu Val Glu
                485                 490                 495

Glu Ile Lys Arg Arg Thr Gly Gln
            500

<210> SEQ ID NO 165
<211> LENGTH: 505
<212> TYPE: PRT
<213> ORGANISM: Homo sapiens

<400> SEQUENCE: 165

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45
```

```
Glu Ser Lys Gln Lys Phe Val Leu Lys Thr Pro Lys Gly Thr Arg Asp
 50                  55                  60

Tyr Ser Pro Arg Gln Met Ala Val Arg Glu Lys Val Phe Asp Val Ile
 65                      70                  75                  80

Ile Arg Cys Phe Lys Arg His Gly Ala Glu Val Ile Asp Thr Pro Val
                 85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460
```

```
Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro
                500                 505

<210> SEQ ID NO 166
<211> LENGTH: 505
<212> TYPE: PRT
<213> ORGANISM: Homo sapiens

<400> SEQUENCE: 166

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
                20                  25                  30

Glu Val Ala Lys Leu Leu Lys Leu Lys Ala Gln Leu Gly Pro Asp Glu
                35                  40                  45

Ser Lys Gln Lys Phe Val Leu Lys Thr Pro Lys Gly Thr Arg Asp Tyr
50                  55                  60

Ser Pro Arg Gln Met Ala Val Arg Glu Lys Val Phe Asp Val Ile Ile
65                  70                  75                  80

Arg Cys Phe Lys Arg His Gly Ala Glu Val Ile Asp Thr Pro Val Phe
                85                  90                  95

Glu Leu Lys Glu Thr Leu Met Gly Lys Tyr Gly Glu Asp Ser Lys Leu
                100                 105                 110

Ile Tyr Asp Leu Lys Asp Gln Gly Gly Glu Leu Leu Ser Leu Arg Tyr
                115                 120                 125

Asp Leu Thr Val Pro Phe Ala Arg Tyr Leu Ala Met Asn Lys Leu Thr
130                 135                 140

Asn Ile Lys Arg Tyr His Ile Ala Lys Val Tyr Arg Arg Asp Asn Pro
145                 150                 155                 160

Ala Met Thr Arg Gly Arg Tyr Arg Glu Phe Tyr Gln Cys Asp Phe Asp
                165                 170                 175

Ile Ala Gly Asn Phe Asp Pro Met Ile Pro Asp Ala Glu Cys Leu Lys
                180                 185                 190

Ile Met Cys Glu Ile Leu Ser Ser Leu Gln Ile Gly Asp Phe Leu Val
                195                 200                 205

Lys Val Asn Asp Arg Arg Ile Leu Asp Gly Met Phe Ala Ile Cys Gly
210                 215                 220

Val Ser Asp Ser Lys Phe Arg Thr Ile Cys Ser Ser Val Asp Lys Leu
225                 230                 235                 240

Asp Lys Val Ser Trp Glu Glu Val Lys Asn Glu Met Val Gly Glu Lys
                245                 250                 255

Gly Leu Ala Pro Glu Val Ala Asp Arg Ile Gly Asp Tyr Val Gln Gln
                260                 265                 270

His Gly Gly Val Ser Leu Val Glu Gln Leu Leu Gln Asp Pro Lys Leu
                275                 280                 285

Ser Gln Asn Lys Gln Ala Leu Glu Gly Leu Gly Asp Leu Lys Leu Leu
                290                 295                 300

Phe Glu Tyr Leu Thr Leu Phe Gly Ile Asp Asp Lys Ile Ser Phe Asp
305                 310                 315                 320

Leu Ser Leu Ala Arg Gly Leu Asp Tyr Tyr Thr Gly Val Ile Tyr Glu
                325                 330                 335
```

```
Ala Val Leu Leu Gln Thr Pro Ala Gln Ala Gly Glu Pro Leu Gly
            340                 345                 350

Val Gly Ser Val Ala Ala Gly Arg Tyr Asp Gly Leu Val Gly Met
            355                 360                 365

Phe Asp Pro Lys Gly Arg Lys Val Pro Cys Val Gly Leu Ser Ile Gly
370                 375                 380

Val Glu Arg Ile Phe Ser Ile Val Gln Arg Leu Glu Ala Leu Glu
385                 390                 395                 400

Glu Lys Ile Arg Thr Thr Glu Thr Gln Val Leu Val Ala Ser Ala Gln
                405                 410                 415

Lys Lys Leu Leu Glu Glu Arg Leu Lys Leu Val Ser Glu Leu Trp Asp
            420                 425                 430

Ala Gly Ile Lys Ala Glu Leu Leu Tyr Lys Lys Asn Pro Lys Leu Leu
            435                 440                 445

Asn Gln Leu Gln Tyr Cys Glu Glu Ala Gly Ile Pro Leu Val Ala Ile
    450                 455                 460

Ile Gly Glu Gln Glu Leu Lys Asp Gly Val Ile Lys Leu Arg Ser Val
465                 470                 475                 480

Thr Ser Arg Glu Glu Val Asp Val Arg Arg Glu Asp Leu Val Glu Glu
                485                 490                 495

Ile Lys Arg Arg Thr Gly Gln Pro Leu
    500                 505

<210> SEQ ID NO 167
<211> LENGTH: 507
<212> TYPE: PRT
<213> ORGANISM: Homo sapiens

<400> SEQUENCE: 167

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
```

```
                195                 200                 205
Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
                260                 265                 270

Gln His Gly Gly Val Ser Leu Val Glu Gln Leu Leu Gln Asp Pro Lys
                275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
                340                 345                 350

Gly Val Gly Ser Val Ala Ala Gly Arg Tyr Asp Gly Leu Val Gly
                355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
                420                 425                 430

Asp Ala Gly Ile Lys Ala Glu Leu Leu Tyr Lys Lys Asn Pro Lys Leu
                435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys
                500                 505

<210> SEQ ID NO 168
<211> LENGTH: 508
<212> TYPE: PRT
<213> ORGANISM: Homo sapiens

<400> SEQUENCE: 168

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
    50                  55                  60
```

-continued

Tyr Ser Pro Arg Gln Met Ala Val Arg Glu Lys Val Phe Asp Val Ile
 65                  70                  75                  80

Ile Arg Cys Phe Lys Arg His Gly Ala Glu Val Ile Asp Thr Pro Val
             85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu

```
                        485                 490                 495
Glu Ile Lys Arg Arg Thr Gly Gln Pro Leu Cys Ile
                    500                 505

<210> SEQ ID NO 169
<211> LENGTH: 509
<212> TYPE: PRT
<213> ORGANISM: Homo sapiens

<400> SEQUENCE: 169

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350
```

```
Gly Val Gly Ser Val Ala Ala Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
            405                 410                 415

Gln Lys Lys Leu Leu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Val Asp Val Arg Arg Glu Asp Leu Val Glu
            485                 490                 495

Glu Ile Lys Arg Arg Thr Gly Gln Pro Leu Cys Ile Cys
            500                 505
```

<210> SEQ ID NO 170
<211> LENGTH: 61
<212> TYPE: PRT
<213> ORGANISM: Artificial Sequence
<220> FEATURE:
<223> OTHER INFORMATION: Cysteine modified HRS polypeptide

<400> SEQUENCE: 170

```
Met Cys Ala Glu Arg Ala Ala Leu Glu Glu Leu Val Lys Leu Gln Gly
1               5                   10                  15

Glu Arg Val Arg Gly Leu Lys Gln Gln Lys Ala Ser Ala Glu Leu Ile
                20                  25                  30

Glu Glu Glu Val Ala Lys Leu Leu Lys Leu Lys Ala Gln Leu Gly Pro
            35                  40                  45

Asp Glu Ser Lys Gln Lys Phe Val Leu Lys Thr Pro Lys
        50                  55                  60
```

<210> SEQ ID NO 171
<211> LENGTH: 60
<212> TYPE: PRT
<213> ORGANISM: Artificial Sequence
<220> FEATURE:
<223> OTHER INFORMATION: Cysteine modified HRS polypeptide

<400> SEQUENCE: 171

```
Met Ala Glu Arg Ala Ala Leu Glu Glu Leu Val Lys Leu Gln Gly Glu
1               5                   10                  15

Arg Val Arg Gly Leu Lys Gln Gln Lys Cys Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys
        50                  55                  60
```

<210> SEQ ID NO 172
<211> LENGTH: 61
<212> TYPE: PRT
<213> ORGANISM: Artificial Sequence
<220> FEATURE:
<223> OTHER INFORMATION: Cysteine modified HRS polypeptide

<400> SEQUENCE: 172

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Cys
    50                  55                  60

<210> SEQ ID NO 173
<211> LENGTH: 183
<212> TYPE: DNA
<213> ORGANISM: Artificial Sequence
<220> FEATURE:
<223> OTHER INFORMATION: Polynucleotide encoding cyteine modified HRS

<400> SEQUENCE: 173
atgtgtgcag aaagagccgc cctggaagag ttagttaagt tgcaaggtga acgtgtccgt        60
ggtctgaagc agcagaaggc tagcgcggag ctgatcgaag aagaggtggc caaactgctg       120
aagctgaagg cgcagctggg cccggacgag agcaaacaaa agttcgtcct gaaaaccccg       180
aaa                                                                    183

<210> SEQ ID NO 174
<211> LENGTH: 180
<212> TYPE: DNA
<213> ORGANISM: Artificial Sequence
<220> FEATURE:
<223> OTHER INFORMATION: Polynucleotide encoding cyteine modified HRS

<400> SEQUENCE: 174
atggcagaac gtgcggcatt ggaagaattg gttaaactgc aaggtgaacg tgttcgtggt        60
ctgaagcagc agaagtgcag cgcggagctg atcgagaag aggtggccaa actgctgaag       120
ctgaaggcgc agctgggccc ggacgagagc aaacaaaagt tcgtcctgaa aaccccgaaa      180

<210> SEQ ID NO 175
<211> LENGTH: 183
<212> TYPE: DNA
<213> ORGANISM: Artificial Sequence
<220> FEATURE:
<223> OTHER INFORMATION: Polynucleotide encoding cyteine modified HRS

<400> SEQUENCE: 175
atggcagaac gtgcggcatt ggaagaattg gttaaactgc aaggtgaacg tgttcgtggt        60
ctgaagcagc agaaggctag cgcggagctg atcgaagaag aggtggccaa actgctgaag       120
ctgaaggcgc agctgggccc ggacgagagc aaacaaaagt tcgtcctgaa aaccccgaaa      180
tgc                                                                    183

<210> SEQ ID NO 176
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 176

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
            85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Ala Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
    275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
```

```
                420                 425                 430
Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
        450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
            485                 490                 495

Glu Ile Lys Arg Arg Thr Gly Gln Pro Leu
            500                 505

<210> SEQ ID NO 177
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 177

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Val Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
```

```
                    275                 280                 285
Leu Ser Gln Asn Lys Gln Ala Leu Glu Gly Leu Gly Asp Leu Lys Leu
    290                 295                 300
Leu Phe Glu Tyr Leu Thr Leu Phe Gly Ile Asp Asp Lys Ile Ser Phe
305                 310                 315                 320
Asp Leu Ser Leu Ala Arg Gly Leu Asp Tyr Tyr Thr Gly Val Ile Tyr
                325                 330                 335
Glu Ala Val Leu Leu Gln Thr Pro Ala Gln Ala Gly Glu Glu Pro Leu
            340                 345                 350
Gly Val Gly Ser Val Ala Ala Gly Gly Arg Tyr Asp Gly Leu Val Gly
        355                 360                 365
Met Phe Asp Pro Lys Gly Arg Lys Val Pro Cys Val Gly Leu Ser Ile
    370                 375                 380
Gly Val Glu Arg Ile Phe Ser Ile Val Glu Gln Arg Leu Glu Ala Leu
385                 390                 395                 400
Glu Glu Lys Ile Arg Thr Thr Glu Thr Gln Val Leu Val Ala Ser Ala
                405                 410                 415
Gln Lys Lys Leu Leu Glu Glu Arg Leu Lys Leu Val Ser Glu Leu Trp
            420                 425                 430
Asp Ala Gly Ile Lys Ala Glu Leu Leu Tyr Lys Lys Asn Pro Lys Leu
        435                 440                 445
Leu Asn Gln Leu Gln Tyr Cys Glu Glu Ala Gly Ile Pro Leu Val Ala
    450                 455                 460
Ile Ile Gly Glu Gln Glu Leu Lys Asp Gly Val Ile Lys Leu Arg Ser
465                 470                 475                 480
Val Thr Ser Arg Glu Glu Val Asp Val Arg Arg Glu Asp Leu Val Glu
                485                 490                 495
Glu Ile Lys Arg Arg Thr Gly Gln Pro Leu
            500                 505

<210> SEQ ID NO 178
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 178

Met Ala Glu Arg Ala Ala Leu Glu Glu Leu Val Lys Leu Gln Gly Glu
1               5                   10                  15
Arg Val Arg Gly Leu Lys Gln Gln Lys Ala Ser Ala Glu Leu Ile Glu
            20                  25                  30
Glu Glu Val Ala Lys Leu Leu Lys Leu Lys Ala Gln Leu Gly Pro Asp
        35                  40                  45
Glu Ser Lys Gln Lys Phe Val Leu Lys Thr Pro Lys Gly Thr Arg Asp
    50                  55                  60
Tyr Ser Pro Arg Gln Met Ala Val Arg Glu Lys Val Phe Asp Val Ile
65                  70                  75                  80
Ile Arg Cys Phe Lys Arg His Gly Ala Glu Val Ile Asp Thr Pro Val
                85                  90                  95
Phe Glu Leu Lys Glu Thr Leu Met Gly Lys Tyr Gly Glu Asp Ser Lys
            100                 105                 110
Leu Ile Tyr Asp Leu Lys Asp Gln Gly Gly Glu Leu Leu Ser Leu Arg
        115                 120                 125
Tyr Asp Leu Thr Val Pro Phe Ala Arg Tyr Leu Ala Met Asn Lys Leu
```

```
            130                 135                 140
Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ala Leu
            180                 185                 190

Lys Ile Met Cys Glu Ile Leu Ser Ser Leu Gln Ile Gly Asp Phe Leu
            195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505
```

<210> SEQ ID NO 179
<211> LENGTH: 506
<212> TYPE: PRT
<213> ORGANISM: Artificial Sequence
<220> FEATURE:
<223> OTHER INFORMATION: Cysteine mutated HRS polypeptide

```
<400> SEQUENCE: 179

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ser Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415
```

```
Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505

<210> SEQ ID NO 180
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 180

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Val Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270
```

```
Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
                355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
                435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505

<210> SEQ ID NO 181
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 181

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125
```

Tyr Asp Leu Thr Val Pro Phe Ala Arg Tyr Leu Ala Met Asn Lys Leu
        130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Ser
210                 215                 220

Gly Val Ser Asp Ser Lys Phe Arg Thr Ile Cys Ser Ser Val Asp Lys
225                 230                 235                 240

Leu Asp Lys Val Ser Trp Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505

<210> SEQ ID NO 182
<211> LENGTH: 506
<212> TYPE: PRT
<213> ORGANISM: Artificial Sequence
<220> FEATURE:

<223> OTHER INFORMATION: Cysteine mutated HRS polypeptide

<400> SEQUENCE: 182

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Ser Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400
```

```
Glu Glu Lys Ile Arg Thr Thr Glu Thr Gln Val Leu Val Ala Ser Ala
                405                 410                 415
Gln Lys Lys Leu Leu Glu Glu Arg Leu Lys Leu Val Ser Glu Leu Trp
            420                 425                 430
Asp Ala Gly Ile Lys Ala Glu Leu Leu Tyr Lys Lys Asn Pro Lys Leu
        435                 440                 445
Leu Asn Gln Leu Gln Tyr Cys Glu Glu Ala Gly Ile Pro Leu Val Ala
    450                 455                 460
Ile Ile Gly Glu Gln Glu Leu Lys Asp Gly Val Ile Lys Leu Arg Ser
465                 470                 475                 480
Val Thr Ser Arg Glu Glu Val Asp Val Arg Arg Glu Asp Leu Val Glu
                485                 490                 495
Glu Ile Lys Arg Arg Thr Gly Gln Pro Leu
                500                 505

<210> SEQ ID NO 183
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 183
```

| | | | | | |
|---|---|---|---|---|---|
| atggcggaac | gtgccgcact | ggaagaattg | gttaaattac | agggagaacg | cgtacgtggt | 60 |
| cttaaacaac | aaaaagcctc | tgcggaattg | attgaagaag | aagttgccaa | attactgaaa | 120 |
| ctgaaagctc | aacttggacc | cgatgaaagt | aaacaaaaat | tgtgttgaa | aacgcccaaa | 180 |
| ggaacccgtg | attatagtcc | acgtcaaatg | gccgttcgtg | aaaaagtgtt | cgacgttatt | 240 |
| attcgctgtt | ttaaacgtca | cggtgctgaa | gtaatcgata | ccccgtatt | tgaattgaaa | 300 |
| gagactctga | tgggcaaata | tggtgaagat | tctaaactga | tttatgattt | gaaagaccaa | 360 |
| ggaggtgaac | tgctgagcct | cgcgtacgac | ttaactgtgc | cttttgcccg | ttacttagcc | 420 |
| atgaataaat | taccaacat | caaacgttac | catattgcaa | aagtatatcg | ccgcgacaac | 480 |
| cctgcaatga | ctcgtggacg | ctatcgcgaa | ttctatcagg | ctgattttga | tattgccgga | 540 |
| aatttcgacc | cgatgatccc | ggatgccgag | tgtttgaaaa | ttatgtgtga | aattctgagt | 600 |
| tcgttgcaga | tcggagactt | tcttgtaaaa | gttaatgacc | gccgtattct | ggatggtatg | 660 |
| tttgctattt | gcggtgtttc | tgattccaaa | ttccgtacaa | tctgctcaag | cgtggacaaa | 720 |
| ttggataaag | tgtcttggga | agaagtaaaa | aatgaaatgg | tgggagaaaa | aggcctggct | 780 |
| ccagaagtag | cagaccgtat | tggtgactat | gttcaacaac | atggcggtgt | gtccttagtc | 840 |
| gaacagttat | tacaggatcc | taaactgagc | caaaataaac | aagcacttga | aggactggga | 900 |
| gatctgaaat | tactctttga | atatctgacc | ttatttggga | ttgatgataa | aattagcttt | 960 |
| gatctgagct | tggcccgcgg | tcttgattat | tataccggcg | tgatttacga | agctgttctc | 1020 |
| ttgcaaaccc | cagcccaggc | gggcgaagag | cctttgggag | tcggcagtgt | ggcagccggt | 1080 |
| ggtcgttatg | atggtttggt | aggaatgtttt | gaccctaaag | ccgtaaagt | accatgtgtg | 1140 |
| gggctttcta | tcggtgtcga | acgtatcttt | tctattgttg | aacaacgtct | tgaagctttg | 1200 |
| gaggaaaaga | tccgtaccac | ggaaacccaa | gtcttagttg | caagtgccca | aaaaaaactg | 1260 |
| ttagaagaac | gcctgaaact | cgtatcagaa | ctttgggacg | ccggcatcaa | ggccgaactg | 1320 |
| ctgtataaaa | agaacccgaa | attgttaaac | caactccagt | attgtgaaga | agctgggatc | 1380 |
| ccactcgtag | ctattattgg | tgagcaagaa | ttaaaagatg | gcgtgattaa | actgcgttca | 1440 |

```
gtaacaagcc gtgaagaggt agatgtacgt cgcgaagact tagtggaaga aattaaacgc    1500
cgcaccggtc aaccgtta                                                  1518

<210> SEQ ID NO 184
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 184
atggcggaac gtgccgcact ggaagaattg gttaaattac agggagaacg cgtacgtggt      60
cttaaacaac aaaaagcctc tgcggaattg attgaagaag aagttgccaa attactgaaa     120
ctgaaagctc aacttggacc cgatgaaagt aaacaaaaat ttgtgttgaa aacgcccaaa     180
ggaacccgtg attatagtcc acgtcaaatg gccgttcgtg aaaaagtgtt cgacgttatt     240
attcgctgtt ttaaacgtca cggtgctgaa gtaatcgata cccccgtatt tgaattgaaa     300
gagactctga tgggcaaata tggtgaagat tctaaactga tttatgattt gaaagaccaa     360
ggaggtgaac tgctgagcct gcgctacgac ttaactgtgc cttttgcccg ttacttagcc     420
atgaataaat taaccaacat caaacgttac catattgcaa agtatatcg ccgcgacaac     480 cctgcaatga ctcgtggacg ctatcgcgaa ttctatcagg ttgattttga tattgccgga     540
aatttcgacc cgatgatccc ggatgccgag tgtttgaaaa ttatgtgtga aattctgagt     600
tcgttgcaga tcggagactt tcttgtaaaa gttaatgacc gccgtattct ggatggtatg     660
tttgctattt gcggtgtttc tgattccaaa ttccgtacaa tctgctcaag cgtggacaaa     720
ttggataaag tgtcttggga agaagtaaaa atgaaatggt gggagaaaaa aggcctggct     780
ccagaagtag cagaccgtat tggtgactat gttcaacaac atggcggtgt gtccttagtc     840
gaacagttat tacaggatcc taaactgagc caaaataaac aagcacttga aggactggga     900
gatctgaaat tactctttga atatctgacc ttatttggga ttgatgataa aattagcttt     960
gatctgagct tggcccgcgg tcttgattat tataccggcg tgatttacga agctgttctc    1020
ttgcaaaccc cagcccaggc gggcgaagag cctttgggag tcggcagtgt ggcagccggt    1080
ggtcgttatg atggtttggt aggaatgttt gaccctaaag ccgtaaagt accatgtgtg     1140 gggctttcta tcggtgtcga acgtatcttt tctattgttg aacaacgtct tgaagctttg    1200
gaggaaaaga tccgtaccac ggaaacccaa gtcttagttg caagtgccca aaaaaaactg    1260
ttagaagaac gcctgaaact cgtatcagaa ctttgggacg ccggcatcaa ggccgaactg    1320
ctgtataaaa agaacccgaa attgttaaac caactccagt attgtgaaga agctgggatc    1380
ccactcgtag ctattattgg tgagcaagaa ttaaaagatg gcgtgattaa actgcgttca    1440
gtaacaagcc gtgaagaggt agatgtacgt cgcgaagact tagtggaaga aattaaacgc    1500
cgcaccggtc aaccgtta                                                  1518

<210> SEQ ID NO 185
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 185
```

| | |
|---|---|
| atggcggaac gtgccgcact ggaagaattg gttaaattac agggagaacg cgtacgtggt | 60 |
| cttaaacaac aaaaagcctc tgcggaattg attgaagaag aagttgccaa attactgaaa | 120 |
| ctgaaagctc aacttggacc cgatgaaagt aaacaaaaat ttgtgttgaa aacgcccaaa | 180 |
| ggaacccgtg attatagtcc acgtcaaatg gccgttcgtg aaaaagtgtt cgacgttatt | 240 |
| attcgctgtt ttaaacgtca cggtgctgaa gtaatcgata cccccgtatt tgaattgaaa | 300 |
| gagactctga tgggcaaata tggtgaagat tctaaactga tttatgattt gaaagaccaa | 360 |
| ggaggtgaac tgctgagcct cgcgctacgac ttaactgtgc cttttgcccg ttacttagcc | 420 |
| atgaataaat taaccaacat caaacgttac catattgcaa aagtatatcg ccgcgacaac | 480 |
| cctgcaatga ctcgtggacg ctatcgcgaa ttctatcagt gtgattttga tattgccgga | 540 |
| aatttcgacc cgatgatccc ggatgccgag gctttgaaaa ttatgtgtga aattctgagt | 600 |
| tcgttgcaga tcggagactt tcttgtaaaa gttaatgacc gccgtattct ggatggtatg | 660 |
| tttgctattt gcggtgtttc tgattccaaa ttccgtacaa tctgctcaag cgtggacaaa | 720 |
| ttggataaag tgtcttggga agaagtaaaa atgaaatgg tgggagaaaa aggcctggct | 780 |
| ccagaagtag cagaccgtat tggtgactat gttcaacaac atggcggtgt gtccttagtc | 840 |
| gaacagttat tacaggatcc taaactgagc caaaataaac aagcacttga aggactggga | 900 |
| gatctgaaat tactctttga atatctgacc ttatttggga ttgatgataa aattagcttt | 960 |
| gatctgagct tggcccgcgg tcttgattat tataccggcg tgatttacga agctgttctc | 1020 |
| ttgcaaaccc cagcccaggc gggcgaagag cctttgggag tcggcagtgt ggcagccggt | 1080 |
| ggtcgttatg atggtttggt aggaatgttt gaccctaaag gccgtaaagt accatgtgtg | 1140 |
| gggctttcta tcggtgtcga acgtatcttt tctattgttg aacaacgtct tgaagctttg | 1200 |
| gaggaaaaga tccgtaccac ggaaacccaa gtcttagttg caagtgccca aaaaaaactg | 1260 |
| ttagaagaac gcctgaaact cgtatcagaa cttttgggacg ccggcatcaa ggccgaactg | 1320 |
| ctgtataaaa agaacccgaa attgttaaac caactccagt attgtgaaga agctgggatc | 1380 |
| ccactcgtag ctattattgg tgagcaagaa ttaaagatg gcgtgattaa actgcgttca | 1440 |
| gtaacaagcc gtgaagaggt agatgtacgt cgcgaagact tagtggaaga aattaaacgc | 1500 |
| cgcaccggtc aaccgtta | 1518 |

<210> SEQ ID NO 186
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 186

| | |
|---|---|
| atggcggaac gtgccgcact ggaagaattg gttaaattac agggagaacg cgtacgtggt | 60 |
| cttaaacaac aaaaagcctc tgcggaattg attgaagaag aagttgccaa attactgaaa | 120 |
| ctgaaagctc aacttggacc cgatgaaagt aaacaaaaat ttgtgttgaa aacgcccaaa | 180 |
| ggaacccgtg attatagtcc acgtcaaatg gccgttcgtg aaaaagtgtt cgacgttatt | 240 |
| attcgctgtt ttaaacgtca cggtgctgaa gtaatcgata cccccgtatt tgaattgaaa | 300 |
| gagactctga tgggcaaata tggtgaagat tctaaactga tttatgattt gaaagaccaa | 360 |
| ggaggtgaac tgctgagcct cgcgctacgac ttaactgtgc cttttgcccg ttacttagcc | 420 |
| atgaataaat taaccaacat caaacgttac catattgcaa aagtatatcg ccgcgacaac | 480 |

```
cctgcaatga ctcgtggacg ctatcgcgaa ttctatcagt gtgattttga tattgccgga    540
aatttcgacc cgatgatccc ggatgccgag agtttgaaaa ttatgtgtga aattctgagt    600
tcgttgcaga tcggagactt tcttgtaaaa gttaatgacc gccgtattct ggatggtatg    660
tttgctattt gcggtgtttc tgattccaaa ttccgtacaa tctgctcaag cgtggacaaa    720
ttggataaag tgtcttggga agaagtaaaa aatgaaatgg tgggagaaaa aggcctggct    780
ccagaagtag cagaccgtat tggtgactat gttcaacaac atggcggtgt gtccttagtc    840
gaacagttat tacaggatcc taaactgagc caaataaaac aagcacttga aggactggga    900
gatctgaaat tactctttga atatctgacc ttatttggga ttgatgataa aattagcttt    960
gatctgagct tggcccgcgg tcttgattat tataccggcg tgatttacga agctgttctc   1020
ttgcaaaccc cagcccaggc gggcgaagag ccttttggga gtcggcagtgt ggcagccggt   1080 ggtcgttatg atggtttggt aggaatgttt gaccctaaag gccgtaaagt accatgtgtg   1140
gggctttcta cggtgtcga acgtatcttt tctattgttg aacaacgtct gaagctttg    1200 gaggaaaaga tccgtaccac ggaaacccaa gtcttagttg caagtgccca aaaaaaactg   1260
ttagaagaac gcctgaaact cgtatcagaa cttttgggacg ccggcatcaa ggccgaactg   1320 ctgtatataaaa agaaacccgaa attgttaaac caactccagt attgtgaaga agctgggatc   1380
ccactcgtag ctattattgg tgagcaagaa ttaaaagatg gcgtgattaa actgcgttca   1440
gtaacaagcc gtgaagaggt agatgtacgt cgcgaagact tagtggaaga aattaaacgc   1500
cgcaccggtc aaccgtta                                                 1518

<210> SEQ ID NO 187
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 187
atggcggaac gtgccgcact ggaagaattg gttaaattac agggagaacg cgtacgtggt     60
cttaaacaac aaaaagcctc tgcggaattg attgaagaag aagttgccaa attactgaaa    120
ctgaaagctc aacttggacc cgatgaaagt aaacaaaaat ttgtgttgaa aacgcccaaa    180
ggaacccgtg attatagtcc acgtcaaatg gccgttcgtg aaaaagtgtt cgacgttatt    240
attcgctgtt ttaaacgtca cggtgctgaa gtaatcgata ccccggtatt tgaattgaaa    300
gagactctga tgggcaaata tggtgaagat tctaaactga tttatgattt gaaagaccaa    360
ggaggtgaac tgctgagcct cgctacgac ttaactgtgc cttttgcccg ttacttagcc     420
atgaataaat taccaacat caaacgttac catattgcaa agtatatcg ccgcgacaac      480 cctgcaatga ctcgtggacg ctatcgcgaa ttctatcagt gtgattttga tattgccgga    540
aatttcgacc cgatgatccc ggatgccgag gtttttgaaaa ttatgtgtga aattctgagt    600
tcgttgcaga tcggagactt tcttgtaaaa gttaatgacc gccgtattct ggatggtatg    660
tttgctattt gcggtgtttc tgattccaaa ttccgtacaa tctgctcaag cgtggacaaa    720
ttggataaag tgtcttggga agaagtaaaa aatgaaatgg tgggagaaaa aggcctggct    780
ccagaagtag cagaccgtat tggtgactat gttcaacaac atggcggtgt gtccttagtc    840
gaacagttat tacaggatcc taaactgagc caaataaaac aagcacttga aggactggga    900
gatctgaaat tactctttga atatctgacc ttatttggga ttgatgataa aattagcttt    960
```

```
gatctgagct tggcccgcgg tcttgattat tataccggcg tgatttacga agctgttctc    1020
ttgcaaaccc cagcccaggc gggcgaagag cctttgggag tcggcagtgt ggcagccggt    1080
ggtcgttatg atggtttggt aggaatgttt gaccctaaag gccgtaaagt accatgtgtg    1140
gggctttcta tcggtgtcga acgtatcttt tctattgttg aacaacgtct tgaagctttg    1200
gaggaaaaga tccgtaccac ggaaacccaa gtcttagttg caagtgccca aaaaaaactg    1260
ttagaagaac gcctgaaact cgtatcagaa ctttgggacg ccggcatcaa ggccgaactg    1320
ctgtataaaa agaacccgaa attgttaaac caactccagt attgtgaaga agctgggatc    1380
ccactcgtag ctattattgg tgagcaagaa ttaaaagatg gcgtgattaa actgcgttca    1440
gtaacaagcc gtgaagaggt agatgtacgt cgcgaagact tagtggaaga aattaaacgc    1500
cgcaccggtc aaccgtta                                                  1518
```

<210> SEQ ID NO 188
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
        protein

<400> SEQUENCE: 188

```
atggcggaac gtgccgcact ggaagaattg gttaaattac agggagaacg cgtacgtggt      60
cttaaacaac aaaaagcctc tgcggaattg attgaagaag aagttgccaa attactgaaa     120
ctgaaagctc aacttggacc cgatgaaagt aaacaaaaat ttgtgttgaa acgcccaaa      180
ggaacccgtg attatagtcc acgtcaaatg gccgttcgtg aaaaagtgtt cgacgttatt     240
attcgctgtt ttaaacgtca cggtgctgaa gtaatcgata ccccgtatt tgaattgaaa      300
gagactctga tgggcaaata tggtgaagat tctaaactga tttatgattt gaaagaccaa     360
ggaggtgaac tgctgagcct cgcgtacgac ttaactgtgc ttttgcccg ttacttagcc      420
atgaataaat taaccaacat caaacgttac catattgcaa agtatatcg ccgcgacaac      480
cctgcaatga ctcgtggacg ctatcgcgaa ttctatcagt gtgattttga tattgccgga     540
aatttcgacc cgatgatccc ggatgccgag tgtttgaaaa ttatgtgtga aattctgagt     600
tcgttgcaga tcggagactt tcttgtaaaa gttaatgacc gccgtattct ggatggtatg     660
tttgctattt ccggtgtttc tgattccaaa ttccgtacaa tctgctcaag cgtggacaaa     720
ttggataaag tgtcttggga gaagtaaaa atgaaatgg tgggagaaaa aggcctggct      780
ccagaagtag cagaccgtat tggtgactat gttcaacaac atggcggtgt gtccttagtc     840
gaacagttat tacaggatcc taaactgagc caaaataaac aagcacttga aggactggga     900
gatctgaaat tactctttga atatctgacc ttatttggga ttgatgataa aattagcttt     960
gatctgagct tggcccgcgg tcttgattat tataccggcg tgatttacga agctgttctc    1020
ttgcaaaccc cagcccaggc gggcgaagag cctttgggag tcggcagtgt ggcagccggt    1080
ggtcgttatg atggtttggt aggaatgttt gaccctaaag gccgtaaagt accatgtgtg    1140
gggctttcta tcggtgtcga acgtatcttt tctattgttg aacaacgtct tgaagctttg    1200
gaggaaaaga tccgtaccac ggaaacccaa gtcttagttg caagtgccca aaaaaaactg    1260
ttagaagaac gcctgaaact cgtatcagaa ctttgggacg ccggcatcaa ggccgaactg    1320
ctgtataaaa agaacccgaa attgttaaac caactccagt attgtgaaga agctgggatc    1380
ccactcgtag ctattattgg tgagcaagaa ttaaaagatg gcgtgattaa actgcgttca    1440
```

-continued

```
gtaacaagcc gtgaagaggt agatgtacgt cgcgaagact tagtggaaga aattaaacgc      1500
cgcaccggtc aaccgtta                                                    1518
```

<210> SEQ ID NO 189
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 189

```
atggcggaac gtgccgcact ggaagaattg gttaaattac agggagaacg cgtacgtggt        60
cttaaacaac aaaaagcctc tgcggaattg attgaagaag aagttgccaa attactgaaa       120
ctgaaagctc aacttggacc cgatgaaagt aaacaaaaat tgtgtgttga aacgcccaaa       180
ggaacccgtg attatagtcc acgtcaaatg gccgttcgtg aaaaagtgtt cgacgttatt       240
attcgctgtt ttaaacgtca cggtgctgaa gtaatcgata ccccgtatt tgaattgaaa       300 gagactctga tgggcaaata tggtgaagat tctaaactga tttatgattt gaagaccaa       360 ggaggtgaac tgctgagcct cgctacgac ttaactgtgc cttttgcccg ttacttagcc       420
atgaataaat taccaacat caaacgttac catattgcaa agtatatcg ccgcgacaac        480 cctgcaatga ctcgtggacg ctatcgcgaa ttctatcagt gtgattttga tattgccgga       540
aatttcgacc cgatgatccc ggatgccgag tgtttgaaaa ttatgtgtga aattctgagt       600
tcgttgcaga tcggagactt tcttgtaaaa gttaatgacc gccgtattct ggatggtatg       660
tttgctattt gcggtgtttc tgattccaaa ttccgtacaa tctcctcaag cgtggacaaa       720
ttggataaag tgtcttggga agaagtaaaa aatgaaatgg tgggagaaaa aggcctggct       780
ccagaagtag cagaccgtat tggtgactat gttcaacaac atggcggtgt gtccttagtc       840
gaacagttat tacaggatcc taaactgagc caaataaaac aagcacttga aggactggga       900
gatctgaaat tactctttga atatctgacc ttatttggga ttgatgataa aattagcttt       960
gatctgagct tggcccgcgg tcttgattat tataccggcg tgatttacga agctgttctc      1020
ttgcaaaccc cagcccaggc gggcgaagag cctttgggag tcggcagtgt ggcagccggt      1080
ggtcgttatg atggtttggt aggaatgttt gaccctaaag ccgtaaagt accatgtgtg      1140 gggctttcta tcggtgtcga acgtatcttt tctattgttg aacaacgtct tgaagctttg      1200
gaggaaaaga tccgtaccac ggaaacccaa gtcttagttg caagtgccca aaaaaactg      1260 ttagaagaac gcctgaaact cgtatcagaa ctttgggacg ccggcatcaa ggccgaactg      1320
ctgtataaaa agaacccgaa attgttaaac caactccagt attgtgaaga agctgggatc      1380
ccactcgtag ctattattgg tgagcaagaa ttaaagatg gcgtgattaa actgcgttca      1440
gtaacaagcc gtgaagaggt agatgtacgt cgcgaagact tagtggaaga aattaaacgc      1500
cgcaccggtc aaccgtta                                                    1518
```

<210> SEQ ID NO 190
<211> LENGTH: 10
<212> TYPE: PRT
<213> ORGANISM: Homo sapiens

<400> SEQUENCE: 190

```
Val Phe Asp Val Ile Ile Arg Cys Phe Lys
1               5                   10
```

```
<210> SEQ ID NO 191
<211> LENGTH: 39
<212> TYPE: PRT
<213> ORGANISM: Homo sapiens

<400> SEQUENCE: 191

Val Tyr Arg Arg Asp Asn Pro Ala Met Thr Arg Gly Arg Tyr Arg Glu
1               5                   10                  15

Phe Tyr Gln Cys Asp Phe Asp Ile Ala Gly Asn Phe Asp Pro Met Ile
            20                  25                  30

Pro Asp Ala Glu Cys Leu Lys
        35

<210> SEQ ID NO 192
<211> LENGTH: 17
<212> TYPE: PRT
<213> ORGANISM: Homo sapiens

<400> SEQUENCE: 192

Ile Met Cys Glu Ile Leu Ser Ser Leu Gln Ile Gly Asp Phe Leu Val
1               5                   10                  15

Lys

<210> SEQ ID NO 193
<211> LENGTH: 20
<212> TYPE: PRT
<213> ORGANISM: Homo sapiens

<400> SEQUENCE: 193

Val Asn Asp Arg Arg Ile Leu Asp Gly Met Phe Ala Ile Cys Gly Val
1               5                   10                  15

Ser Asp Ser Lys
        20

<210> SEQ ID NO 194
<211> LENGTH: 10
<212> TYPE: PRT
<213> ORGANISM: Homo sapiens

<400> SEQUENCE: 194

Phe Arg Thr Ile Cys Ser Ser Val Asp Lys
1               5                   10

<210> SEQ ID NO 195
<211> LENGTH: 13
<212> TYPE: PRT
<213> ORGANISM: Homo sapiens

<400> SEQUENCE: 195

Phe Arg Thr Ile Cys Ser Ser Val Asp Lys Leu Asp Lys
1               5                   10

<210> SEQ ID NO 196
<211> LENGTH: 27
<212> TYPE: PRT
<213> ORGANISM: Homo sapiens

<400> SEQUENCE: 196

Val Pro Cys Val Gly Leu Ser Ile Gly Val Glu Arg Ile Phe Ser Ile
1               5                   10                  15

Val Glu Gln Arg Leu Glu Ala Leu Glu Glu Lys
            20                  25
```

```
<210> SEQ ID NO 197
<211> LENGTH: 25
<212> TYPE: PRT
<213> ORGANISM: Homo sapiens

<400> SEQUENCE: 197

Leu Leu Asn Gln Leu Gln Tyr Cys Glu Glu Ala Gly Ile Pro Leu Val
1               5                   10                  15

Ala Ile Ile Gly Glu Gln Glu Leu Lys
            20                  25

<210> SEQ ID NO 198
<211> LENGTH: 10
<212> TYPE: PRT
<213> ORGANISM: Homo sapiens

<400> SEQUENCE: 198

Arg Arg Thr Gly Gln Pro Leu Cys Ile Cys
1               5                   10

<210> SEQ ID NO 199
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 199
gtttgacgta atcatccgtt gcttcaagcg ccacggtgca g                          41

<210> SEQ ID NO 200
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 200
ctgcaccgtg gcgcttgaag caacggatga ttacgtcaaa c                          41

<210> SEQ ID NO 201
<211> LENGTH: 44
<212> TYPE: DNA
<213> ORGANISM: Artificial Sequence
<220> FEATURE:
<223> OTHER INFORMATION: Primer to selectively mutate cysteine residue

<400> SEQUENCE: 201
gccgataccg ggaattctac cagtgtgatt ttgacattgc tggg                       44

<210> SEQ ID NO 202
<211> LENGTH: 44
<212> TYPE: DNA
<213> ORGANISM: Artificial Sequence
<220> FEATURE:
<223> OTHER INFORMATION: Primer to selectively mutate cysteine residue

<400> SEQUENCE: 202
cccagcaatg tcaaaatcac actggtagaa ttcccggtat cggc                       44

<210> SEQ ID NO 203
<211> LENGTH: 41
<212> TYPE: DNA
<213> ORGANISM: Artificial Sequence
<220> FEATURE:
<223> OTHER INFORMATION: Primer to selectively mutate cysteine residue
```

<400> SEQUENCE: 203
ccatgatccc tgatgcagag tgcctgaaga tcatgtgcga g         41

<210> SEQ ID NO 204
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 204
ctcgcacatg atcttcaggc actctgcatc agggatcatg g         41

<210> SEQ ID NO 205
<211> LENGTH: 43
<212> TYPE: DNA
<213> ORGANISM: Artificial Sequence
<220> FEATURE:
<223> OTHER INFORMATION: Primer to selectively mutate cysteine residue

<400> SEQUENCE: 205
gcagagtgcc tgaagatcat gtgcgagatc ctgagttcac ttc       43

<210> SEQ ID NO 206
<211> LENGTH: 43
<212> TYPE: DNA
<213> ORGANISM: Artificial Sequence
<220> FEATURE:
<223> OTHER INFORMATION: Primer to selectively mutate cysteine residue

<400> SEQUENCE: 206
gaagtgaact caggatctcg cacatgatct tcaggcactc tgc       43

<210> SEQ ID NO 207
<211> LENGTH: 45
<212> TYPE: DNA
<213> ORGANISM: Artificial Sequence
<220> FEATURE:
<223> OTHER INFORMATION: Primer to selectively mutate cysteine residue

<400> SEQUENCE: 207
ctagatggga tgtttgctat ctgtggtgtt tctgacagca agttc     45

<210> SEQ ID NO 208
<211> LENGTH: 45
<212> TYPE: DNA
<213> ORGANISM: Artificial Sequence
<220> FEATURE:
<223> OTHER INFORMATION: Primer to selectively mutate cysteine residue

<400> SEQUENCE: 208
gaacttgctg tcagaaacac cacagatagc aaacatccca tctag     45

<210> SEQ ID NO 209
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 209
cagcaagttc cgtaccatct gctcctcagt agacaagctg g         41

<210> SEQ ID NO 210
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 210
ccagcttgtc tactgaggag cagatggtac ggaacttgct g           41

<210> SEQ ID NO 211
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 211
gggcgcaagg tgccatgtgt ggggctcagc attgggg               37

<210> SEQ ID NO 212
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 212
ccccaatgct gagccccaca catggcacct tgcgccc               37

<210> SEQ ID NO 213
<211> LENGTH: 38
<212> TYPE: DNA
<213> ORGANISM: Artificial Sequence
<220> FEATURE:
<223> OTHER INFORMATION: Primer to selectively mutate cysteine residue

<400> SEQUENCE: 213
ctgaaccagt tacagtactg tgaggaggca ggcatccc              38

<210> SEQ ID NO 214
<211> LENGTH: 38
<212> TYPE: DNA
<213> ORGANISM: Artificial Sequence
<220> FEATURE:
<223> OTHER INFORMATION: Primer to selectively mutate cysteine residue

<400> SEQUENCE: 214
gggatgcctg cctcctcaca gtactgtaac tggttcag              38

<210> SEQ ID NO 215
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 215
gagaacaggc cagcccctct gcatctgcta gaacccagc             39

<210> SEQ ID NO 216
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 216
gctgggttct agcagatgca gaggggctgg cctgttctc         39

<210> SEQ ID NO 217
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 217
ccagcccctc tgcatctgct agaacccagc tttcttg           37

<210> SEQ ID NO 218
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 218
caagaaagct gggttctagc agatgcagag gggctgg           37

<210> SEQ ID NO 219
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 219
gaacaggcca gcccctctag aacccagctt tcttg             35

<210> SEQ ID NO 220
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 220
caagaaagct gggttctaga ggggctggcc tgttc             35

<210> SEQ ID NO 221
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 221
cccggatgcc gaggctttga aaattatgtg                   30

<210> SEQ ID NO 222
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 222
cacataattt tcaaagcctc ggcatccggg                   30

```
<210> SEQ ID NO 223
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 223
gatcccggat gccgagagtt tgaaaattat gtgtg                              35

<210> SEQ ID NO 224
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 224
cacacataat tttcaaactc tcggcatccg ggatc                              35

<210> SEQ ID NO 225
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 225
gatcccggat gccgaggttt tgaaaattat gtgtg                              35

<210> SEQ ID NO 226
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 226
cacacataat tttcaaaacc tcggcatccg ggatc                              35

<210> SEQ ID NO 227
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 227
cgcgaattct atcaggctga ttttgatatt gccgg                              35

<210> SEQ ID NO 228
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 228
ccggcaatat caaaatcagc ctgatagaat tcgcg                              35

<210> SEQ ID NO 229
<211> LENGTH: 34
<212> TYPE: DNA
<213> ORGANISM: Artificial Sequence
<220> FEATURE:
<223> OTHER INFORMATION: Primer to selectively mutate cysteine residue
```

<400> SEQUENCE: 229
cgcgaattct atcaggttga ttttgatatt gccg                34

<210> SEQ ID NO 230
<211> LENGTH: 34
<212> TYPE: DNA
<213> ORGANISM: Artificial Sequence
<220> FEATURE:
<223> OTHER INFORMATION: Primer to selectively mutate cysteine residue

<400> SEQUENCE: 230
cggcaatatc aaaatcaacc tgatagaatt cgcg                34

<210> SEQ ID NO 231
<211> LENGTH: 33
<212> TYPE: DNA
<213> ORGANISM: Artificial Sequence
<220> FEATURE:
<223> OTHER INFORMATION: Primer to selectively mutate cysteine residue

<400> SEQUENCE: 231
ggtatgtttg ctatttccgg tgtttctgat tcc                 33

<210> SEQ ID NO 232
<211> LENGTH: 33
<212> TYPE: DNA
<213> ORGANISM: Artificial Sequence
<220> FEATURE:
<223> OTHER INFORMATION: Primer to selectively mutate cysteine residue

<400> SEQUENCE: 232
ggaatcagaa acaccggaaa tagcaaacat acc                 33

<210> SEQ ID NO 233
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 233
ccaaattccg tacaatctcc tcaagcgtgg acaaattgg           39

<210> SEQ ID NO 234
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 234
ccaatttgtc cacgcttgag gagattgtac ggaatttgg           39

<210> SEQ ID NO 235
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 235
cccggatgcc gaggctttga aaattatgtg                     30

```
<210> SEQ ID NO 236
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 236
cacataattt tcaaagcctc ggcatccggg                                     30
```